US00RE39679E

(19) United States
(12) Reissued Patent
Robichaud et al.

(10) Patent Number: US RE39,679 E
(45) Date of Reissued Patent: Jun. 5, 2007

(54) SUBSTITUTED HETEROCYCLE FUSED GAMMA-CARBOLINES

(75) Inventors: Albert J. Robichaud, Landenberg, PA (US); Taekyu Lee, Wilmington, DE (US); Wei Deng, Wilmington, DE (US); Ian S. Mitchell, Philadelphia, PA (US); Michael Guang Yang, Wilmington, DE (US); Simon Haydar, Niskayuna, NY (US); Wenting Chen, Exton, PA (US); Christopher D. McClung, Wilmington, DE (US); Emile J. B. Calvello, Bryn Mawr, PA (US); David M. Zawrotny, Moorestown, NJ (US); Parthasarathl Rajagopalan, Chennai (IN)

(73) Assignee: Bristol-Myers Squibb Pharma Company, Princeton, NJ (US)

(21) Appl. No.: 11/356,423

(22) Filed: Feb. 16, 2006

Related U.S. Patent Documents

Reissue of:
(64) Patent No.: 6,713,471
Issued: Mar. 30, 2004
Appl. No.: 09/594,954
Filed: Jun. 15, 2000

U.S. Applications:
(60) Provisional application No. 60/139,321, filed on Jun. 15, 1999.

(51) Int. Cl.

| | |
|---|---|
| ***C07D 267/22*** | (2006.01) |
| ***C07D 281/18*** | (2006.01) |
| ***C07D 267/02*** | (2006.01) |
| ***C07D 279/00*** | (2006.01) |
| ***C07D 265/34*** | (2006.01) |

(52) U.S. Cl. ..... 514/211.1; 514/215; 514/224.5; 514/287; 540/468; 540/546; 544/14; 544/99

(58) Field of Classification Search ..... 514/211.1, 514/215, 224.5, 287; 540/468, 546; 544/14, 544/99

See application file for complete search history.

(56) References Cited

U.S. PATENT DOCUMENTS

| | | | | |
|---|---|---|---|---|
| 3,299,078 | A | 1/1967 | Pachter | 260/296 |
| 3,914,421 | A | 10/1975 | Rajogopalan | 424/248 |
| 4,013,652 | A | 3/1977 | Rajagopalan | 260/244 R |
| 4,088,647 | A | 5/1978 | Glushkov et al. | 544/343 |
| 4,115,577 | A | 9/1978 | Rajagopalan | 424/256 |
| 4,183,936 | A | 1/1980 | Rajagopalan | 424/256 |
| 4,219,550 | A | 8/1980 | Rajagopalan | 424/246 |
| 4,238,607 | A | 12/1980 | Rajagopalan | 544/14 |
| 4,997,831 | A | 3/1991 | Bays et al. | 514/211 |
| 5,100,884 | A | 3/1992 | Hamminga et al. | 514/183 |
| 5,223,625 | A | 6/1993 | Van Wijngaarden et al. | 546/70 |
| 5,328,905 | A | 7/1994 | Hamminga et al. | 514/214 |
| 5,512,575 | A | 4/1996 | Jacobs et al. | 514/256 |
| 5,654,139 | A | 8/1997 | Lappalainen et al. | 435/6 |
| 5,902,815 | A | 5/1999 | Olney et al. | 514/285 |
| 5,908,830 | A | 6/1999 | Smith et al. | 514/12 |
| 6,107,324 | A | 8/2000 | Behan et al. | 514/406 |
| 6,140,509 | A | 10/2000 | Behan et al. | 548/365.7 |
| 6,407,092 | B1 | 6/2002 | Hester et al. | 514/215 |

FOREIGN PATENT DOCUMENTS

| | | |
|---|---|---|
| CA | 2011107 | 8/1991 |
| EP | 0725068 | 8/1996 |
| FR | 2213283 | 2/1974 |
| WO | WO 0064899 | 11/2000 |

OTHER PUBLICATIONS

Database Caplus 'Online! Chemical Abstracts Service; 84:59411, XP002153997 RN = 58121–96–3, 58121–97–4 & Khim. Geterotsikl. Soedin., No. 9, 1975, pp. 1262–1266, & Chemical Abstracts, vol. 84, No. 9, Mar. 1, 1976 Columbus, Ohio US; abstract No. 59411, Orlova et al.: "Synthesis of 2,3,4,5–tetrahydro–1,5–benzox(and thi)azepines and their use for synthesis of condensed indoles".

Bickerdike MJ, Vickers, SP, Dourish CT, (1999) S–HT2C receptor modulation and the treatment of obesity. Diabetes, Obesity and Metabolism 1:207–214.

Tecott LH, et al. (1995) Eating disorder and epilepsy in mice lacking 5–HT2C serotonin receptors. Nature (London) 374:542–546.

Cryan JF, Lucki I, (2000) Antidepressant–like behavioral effects mediated by 5–hydroxtryptamine2C receptors. J. Pharmacol. Exper. Ther. 295:1120–1126.

*Primary Examiner*—Bruck Kifle
(74) *Attorney, Agent, or Firm*—Sammy G. Duncan, Jr.

(57) ABSTRACT

The present invention is directed to certain novel compounds represented by structural Formula (I)

(I)

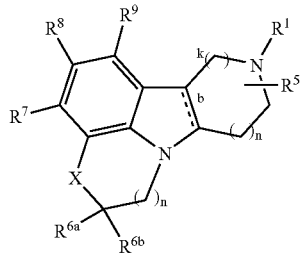

or pharmaceutically acceptable salt forms thereof, wherein $R^1$, $R^5$, $R^{6a}$, $R^{6b}$, $R^7$, $R^8$, $R^9$, X, b, k, m, and n, and the dashed lines are described herein. The invention is also concerned with pharmaceutical formulations comprising these novel compounds as active ingredients and the use of the novel compounds and their formulations in the treatment of certain disorders. The compounds of this invention are serotonin agonists and antagonists and are useful in the control or prevention of central nervous system disorders including obesity, anxiety, depression, psychosis, schizophrenia, sleep disorders, sexual disorders, migraine, conditions associated with cephalic pain, social phobias, and gastrointestinal disorders such as dysfunction of the gastrointestinal tract motility.

33 Claims, No Drawings

OTHER PUBLICATIONS

Millan MJ, Peglion JL, Lavielle G, Perrin–Monneyron S, (1997) 5–HT2C receptors mediate penile erection in rats: actions of novel and selective agonists and antagonists. Eur. J. Pharmacol. 325:9–12.

Martin JR, et al. (1998) 5–HT2C receptor agonists: Pharmacological characteristics and therapeutic potential. J. Pharmacol. Exper. Ther. 286:913–924.

Meltzer HY. (1999) The role of serotonin in antipsychotic drug action. Neuropsychopharmacology 21 (2) :106S115S.

Curzon et al, Appetite suppression by commonly used drugs depends on 5–HT receptors but not on 5–HT availability, TiPS, vol. 18, 1997; 21–25.

Mora et al, Role of 5–HT2A and 5–HT2C Receptor subtypes in the Two Types of Fear Generated by the Elevated T–Maze. Pharma. Biolchem. & Behavior, vol. 58, No. 4, 1997; 1051–1057.

Jenck et al, Antiaversive effects of 5HT2C receptor agonists and fluoxetine in a model of panic–like anxiety in rats, European Neuropsychopharmacology, 8, 1998; 161–168.

Leysen, Selective 5–HT2c agonists as potential antidepressants. Drugs, 1999, 2(2); 109–120.

Jenck et al, The role of 5–HT2c receptors in affective disorders. Exp. Opin. Invest. Drugs, 1998, 7(10); 1587–1599.

Kennett, 5–HT drugs and eating disorders, I Drugs, 1998, vol. 1, No. 4; 456–470.

Brewerton, Induction of migrainelike headaches by the serotonin agonist m–chlorophenylpiperazine, Clin. Pharmacol. Ther., 1988, 605–609.

Kahn et al, m–Chlorophenylpiperazine as a probe of serotonin function, Biol. Psychiatry, 1991; 30: 1139–1166.

Gibson et al, Evidence that mCPP–induced Anxiety in the Plus–maze is mediated by Postsynaptic 5–HT2c receptors but not by sympathomimetic effects, Neuropharmacology, vol. 33, No. 3, 4, 1994; 457–465.

SUBSTITUTED HETEROCYCLE FUSED GAMMA-CARBOLINES

Matter enclosed in heavy brackets [ ] appears in the original patent but forms no part of this reissue specification; matter printed in italics indicates the additions made by reissue.

This application claims the benefit of U.S. Provisional Application No. 60/139,321, filed Jun. 15, 1999.

FIELD OF THE INVENTION

The present invention is directed to certain novel compounds represented by structural Formula (I)

(I)

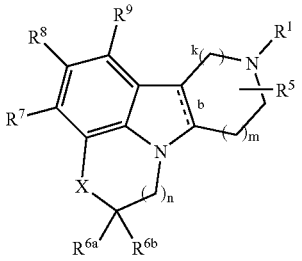

or pharmaceutically acceptable salt forms thereof, wherein $R^1$, $R^5$, $R^{6a}$, $R^{6b}$, $R^7$, $R^8$, $R^9$, X, b, k, m, and n, and the dashed lines are described herein. The invention is also concerned with pharmaceutical formulations comprising these novel compounds as active ingredients and the use of the novel compounds and their formulations in the treatment of certain disorders. The compounds of this invention are serotonin agonists and antagonists and are useful in the control or prevention of central nervous system disorders including obesity, anxiety, depression, psychosis, schizophrenia, sleep disorders, sexual disorders, migraine, conditions associated with cephalic pain, social phobias, and gastrointestinal disorders such as dysfunction of the gastrointestinal tract mobility.

BACKGROUND OF THE INVENTION

There exists a substantial correlation for the relationship between 5-HT2 receptor modulation and a variety of diseases and therapies. To date, three subtypes of the 5-HT2 receptor class have been identified, 5-HT2A, 5-HT2B, and 5-HT2C. Prior to the early 1990's the 5-HT2C and 5-HT2A receptors were referred to as 5-HT1C and 5-HT2, respectively.

The agonism or antagonism of 5-HT2 receptors, either selectively or nonselectively, has been associated with the treatment of various central nervous system (CNS) disorders. Ligands possessing affinity for the 5-HT2 receptors have been shown to have numerous physiological and behavioral effects (Trends in Pharmacological Sciences, 11, 181, 1990). In the recent past the contribution of serotonergic activity to the mode of action of antidepressant drugs has been well documented. Compounds that increase the overall basal tone of serotonin in the CNS have been successfully developed as antidepressants. The serotonin selective reuptake inhibitors (SSRI) function by increasing the amount of serotonin present in the nerve synapse. These breakthrough treatments, however, are not without side effects and suffer from delayed onset of action (Leonard, J. Clin. Psychiatry, 54(suppl), 3, 1993). Due to the mechanism of action of the SSRIs, they effect the activity of a number of serotonin receptor subtypes. This non-specific modulation of the serotonin family of receptors most likely plays a significant role in the side effect profile. In addition, these compounds often have a high affinity for a number of the serotonin receptors as well as a multitude of other monoamine neurotransmitters and nuisance receptors. Removing some of the receptor cross reactivity would allow for the examination and possible development of potent therapeutic ligands with an improved side effect profile.

There is ample evidence to support the role of selective 5-HT2 receptor ligands in a number of disease therapies. Modulation of 5-HT2 receptors has been associated with the treatment of schizophrenia and psychoses (Ugedo, L., et al., Psychopharmacology, 98, 45, 1989). Mood, behavior and hallucinogenesis can be affected by 5-HT2 receptors in the limbic system and cerebral cortex. 5-HT2 receptor modulation in the hypothalamus can influence appetite, thermoregulation, sleep, sexual behavior, motor activity, and neuroendocrine function (Hartig, P., et al., Annals New York Academy of Science, 149, 159). There is also evidence indicating that 5-HT2 receptors mediate hypoactivity, effect feeding in rats, and mediate penile erections (Pyschopharmacology, 101, 57, 1990).

Compounds exhibiting selectively for the 5-HT2B receptor are useful in treating conditions such as tachygastria, hypermotility associated with irritable bowel disorder, constipation, dyspepsia, and other peripherally mediated conditions.

5-HT2A antagonists have been shown to be effective in the treatment of schizophrenia, anxiety, depression, and migraines (Koek, W., Neuroscience and Behavioral reviews, 16, 95, 1996). Aside from the beneficial antipsychotic effects, classical neuroleptic are frequently responsible for eliciting acute extrapyramidal side effects and neuroendocrine disturbances. These compounds generally possess significant dopamine D2 receptor affinity (as well as other nuisance receptor affinity) which frequently is associated with extra pyramidal symptoms and tardive dyskinesia, thus detracting from their efficacy as front line treatments in schizophrenia and related disorders. Compounds possessing a more favorable selectively profile would represent a possible improvement for the treatment of CNS disorders.

U.S. Pat. Nos. 3,914,421; 4,013,652; 4,115,577; 4,183,936; and 4,238,607 disclose pyridopyrrolobenzheterocycles of formula:

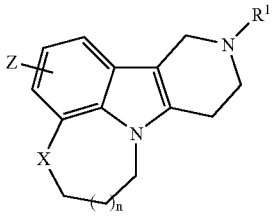

where X is O, S, S(=O), or $SO_2$; n is 0 or 1; $R^1$ is various carbon substituents, and Z is a monosubstituent of H. methyl, or chloro.

U.S. Pat. No. 4,219,550 discloses pyridopyrrolobenzheterocycles of formula:

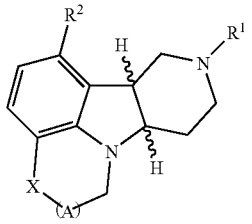

where X is O or S; $R^1$ is $C_{1-4}$ alkyl or cyclopropyl; $R^2$ is H, $CH_3$, $OCH_3$, Cl, Br, F, or $CF_3$; and (A) is —$CH_2$—, —$CH(CH_3)$—, or —$CH_2CH_2$—.

SUMMARY OF THE INVENTION

One object of the present invention is to provide novel compounds which are useful as agonists or antagonists of 5-HT2 receptors, more specifically 5-HT2A and 5-HT2C receptors, or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility comprising administering to a host in need of such treatment a therapeutically effective amount of at least one of the compounds of the present invention or a pharmaceutically acceptable salt or prodrug form thereof. More specifically, the present invention provides a method for treating obesity anxiety, depression, or schizophrenia.

These and other objects, which will become apparent during the following detailed description, have been achieved by the inventors' discovery that compounds of Formula (I):

(I)

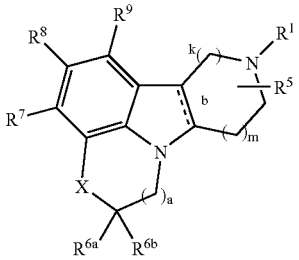

or pharmaceutically acceptable salt or prodrug forms thereof, wherein $R^1$, $R^5$, $R^{6a}$, $R^{6b}$, $R^7$, $R^8$, $R^9$, X, b, k, m, and n are defined below, are effective agonists or antagonists of 5-HT2 receptors.

DETAILED DESCRIPTION OF THE EMBODIMENTS

Thus, in a first embodiment, the present invention provides a novel compound of Formula (I):

(I)

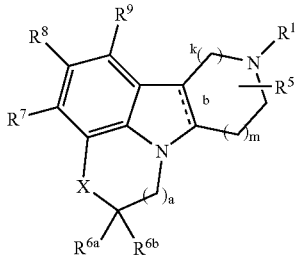

or stereoisomers or pharmaceutically acceptable salt forms thereof, wherein:

b is a single bond or a double bond;

X is —$CHR^{10}$—, —C(=O)—, —O—, —S—, —S(=O)—, —$S(=O)_2$—, —$NR^{10A}$—, —C(=O)$NR^{10A}$—, or —$NR^{10A}$C(=O)—;

$R^1$ is selected from

H

C(=O)$R^2$,

C(=O)O$R^2$, $C_{1-8}$ alkyl, $C_{2-8}$ alkenyl, $C_{2-8}$ alkynyl, $C_{3-7}$ cycloalkyl, $C_{1-6}$ alkyl substituted with Z, $C_{2-6}$ alkenyl substituted with Z, $C_{2-6}$ alkynyl substituted with Z, $C_{3-6}$ cycloalkyl substituted with Z, aryl substituted with Z, 5–6 membered heterocyclic ring system containing at least one heteroatom selected from the group consisting of N, O, and S, said heterocyclic ring system substituted with Z;

$C_{1-3}$ alkyl substituted with Y, $C_{2-3}$ alkenyl substituted with Y, $C_{2-3}$ alkynyl substituted with Y, $C_{1-6}$ alkyl substituted with 0–2 $R^2$, $C_{2-6}$ alkenyl substituted with 0–2 $R^2$, $C_{2-6}$ alkynyl substituted with 0–2 $R^2$, aryl substituted with 0–2 $R^2$, and 5–6 membered heterocyclic ring system containing at least one heteroatom selected from the group consisting of N, O, and S, said heterocyclic ring system substituted with 0–2 $R^2$;

Y is selected from $C_{3-6}$ cycloalkyl substituted with Z, aryl substituted with Z, 5–6 membered heterocyclic ring system containing at least one heteroatom selected from the group consisting of N, O, and S, said heterocyclic ring system substituted with Z;

$C_{3-6}$ cycloalkyl substituted with —($C_{1-3}$ alkyl)-Z, aryl substituted with —($C_{1-3}$ alkyl)-Z, and 5–6 membered heterocyclic ring system containing at least one heteroatom selected from the group consisting of N, O, and S, said heterocyclic ring system substituted with —($C_{1-3}$ alkyl)-Z;

Z is selected from H,

—CH(OH)$R^2$,

—C(ethylenedioxy)$R^2$,

—$OR^2$,

—$SR^2$,

—$NR^2R^3$,

—$C(O)R^2$,

—$C(O)NR^2R^3$,

—$NR^3C(O)R^2$,

—$C(O)OR^2$,

—$OC(O)R^2$,

—$CH(=NR^4)NR^2R^3$,

—$NHC(=NR^4)NR^2R^3$,

—$S(O)R^2$,

—$S(O)_2R^2$,

—$S(O)_2NR^2R^3$, and —$NR^3S(O)_2R^2$;

$R^2$, at each occurrence, is independently selected from $C_{1-4}$ alkyl, $C_{2-4}$ alkenyl, $C_{2-4}$ alkynyl, $C_{3-6}$ cycloalkyl, phenyl substituted with 0–5 $R^{42}$;

$C_{3-10}$ carbocyclic residue substituted with 0–3 $R^{41}$, and

5–10 membered heterocyclic ring system containing from 1–4 heteroatoms selected from the group consisting of N, O, and S substituted with 0–3 $R^{41}$;

$R^3$, at each occurrence, is independently selected from H, $C_{1-4}$ alkyl, $C_{2-4}$ alkenyl, and $C_{2-4}$ alkynyl;

alternatively, $R^2$ and $R^3$ join to form a 5- or 6-membered ring optionally substituted with —O— or —$N(R^4)$—;

$R^4$, at each occurrence, is independently selected from H and $C_{1-4}$ alkyl;

$R^5$ is H or $C_{1-4}$ alkyl;

$R^{6a}$ and $R^{6b}$, at each occurrence, are independently selected from

H, —OH, —$NR^{46}R^{47}$, —$CF_3$, $C_{1-4}$ alkyl, $C_{2-4}$ alkenyl, $C_{2-4}$ alkynyl, $C_{1-4}$ alkoxy, $C_{1-4}$ haloalkyl, $C_{3-6}$ cycloalkyl, and aryl substituted with 0–3 $R^{44}$;

$R^7$ and $R^9$, at each occurrence, are independently selected from

H, halo, —$CF_3$, —$OCF_3$, —OH, —CN, —$NO_2$, —$NR^{46}R^{47}$, $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy, $C_{3-10}$ cycloalkyl, substituted with 0–2 $R^{33}$, $C_{1-4}$ alkyl substituted with 0–2 $R^{11}$, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, $C(O)R^{13}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, and $NR^{14}S(O)_2R^{12}$;

$R^8$ is selected from

H, halo, —$CF_3$, —$OCF_3$, —OH, —CN, —$NO_2$, $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy, $C_{3-10}$ cycloalkyl, substituted with 0–2 $R^{33}$, $C_{1-4}$ alkyl substituted with 0–2 $R^{33}$, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, $C(O)R^{13}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, and $NR^{14}S(O)_2R^{12}$;

$R^{10}$ is selected from H, —OH, $C_{1-6}$ alkyl substituted with 0–1 $R^{10B}$, $C_{2-6}$ alkenyl substituted with 0–1 $R^{10B}$, $C_{2-6}$ alkynyl substituted with 0–1 $R^{10B}$, and $C_{1-6}$ alkoxy;

$R^{10A}$ is selected from H, $C_{1-6}$ alkyl substituted with 0–1 $R^{10B}$, $C_{2-6}$ alkenyl substituted with 0–1 $R^{10B}$, $C_{2-6}$ alkynyl substituted with 0–1 $R^{10B}$, and $C_{1-6}$ alkoxy;

$R^{10B}$ is selected from $C_{1-4}$ alkoxy, $C_{3-6}$ cycloalkyl, $C_{3-10}$ carbocyclic residue substituted with 0–3 $R^{33}$, phenyl substituted with 0–3 $R^{33}$, and 5–6 membered heterocyclic ring system containing 1, 2, or 3 heteroatoms selected from the group consisting of N, O, and S substituted with 0–2 $R^{44}$;

$R^{11}$ is selected from

H, halo, —$CF_3$, —CN, —$NO_2$, $C_{1-8}$ alkyl, $C_{2-8}$ alkenyl, $C_{2-8}$ alkynyl, $C_{1-4}$ haloalkyl, $C_{1-8}$ alkoxy, $C_{3-10}$ cycloalkyl, $C_{3-10}$ carboncyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{33}$, $OR^{12}$, $SR^{12}$, $NR^{12}R^{13}$, $C(O)R^{13}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, and $NR^{14}S(O)_2R^{12}$;

$R^{12}$, at each occurrence, is independently selected from $C_{1-4}$ alkyl, $C_{2-4}$ alkenyl, $C_{2-4}$ alkynyl, $C_{3-6}$ cycloalkyl, phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively,$R^{12}$ and $R^{13}$ join to form a 5- or 6-membered ring optionally substituted with —O— or —$N(R^{14})$—;

$R^{14}$, at each occurrence, is independently selected from H. and $C_{1-4}$ alkyl;

$R^{31}$, at each occurrence is independently selected from H, OH, halo, $CF_3$, $SO_2R^{45}$, $NR^{46}R^{47}$, and $C_{1-4}$ alkyl;

$R^{33}$, at each occurrence, is independently selected from H, OH, halo, CN, $NO_2$, $CF_3$, $SO_2R^{45}$, $NR^{46}R^{47}$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(═O)—, and $C_{1-4}$ alkyl-C(═O)NH—;

$R^{41}$, at each occurrence, is independently selected from

H, $CF_3$, halo, OH, $CO_2H$, $SO_2R^{45}$, $NR^{46}R^{47}$ , $NO_2$, CN;

$C_{2-8}$ alkenyl, $C_{2-8}$ alkynyl, $C_{1-4}$ alkoxy, $C_{1-4}$ haloalkyl $C_{1-4}$ alkyl substituted with 0–1 $R^{43}$, aryl substituted with 0–3 $R^{42}$, and 5–10 membered heterocyclic ring system containing from 1–4 heteroatoms selected from the group consisting of N, O, and S substituted with 0–3 $R^{44}$;

$R^{42}$, at each occurrence, is independently selected from

H, $CF_3$, halo, OH, $CO_2H$, $SO_2R^{45}$, $NR^{46}SO_2R^{45}$, $NR^{46}COR^{45}$, $NR^{46}R^{47}$, $NO_2$, CN, CH(═NH)$NH_2$, NHC(═NH)$NH_2$, $C_{2-6}$ alkenyl, $C_{2-6}$ alkynyl, $C_{1-4}$ alkoxy, $C_{1-4}$ haloalkyl, $C_{3-6}$ cycloaklyl, $C_{1-4}$ alkyl substituted with 0–1 $R^{43}$, aryl substituted with 0–3 $R^{44}$, and 5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H and $C_{1-4}$ alkyl;

k is 1 or 2;

m is 0, 1, 2, or 3;

n is 0, 1, or 2;

provided when m is 0, then k is 1;

provided that when b is a double bond; n is 1 or 2; m is 1; k is 1; X is —O—, —S—, —S(═O)—, or —$SO_2$—; and the three substituents of $R^7$, $R^8$, $R^9$, consist of i) three hydrogens, ii) two hydrogens and one chloro, or iii) two hydrogens and one methyl; then $R^1$ must contain the substituent Z or Y;

provided that when b is a double bond; n is 0 or 1; m is 1; k is 1; X is —$CH_2$—; and $R^1$ is hydrogen, $C_{1-6}$ alkyl or benzyl; then one of $R^7$, $R^8$, and $R^9$, must be other than hydrogen, halo, $C_{1-6}$ alkyl, $C_{1-6}$ alkoxy or trifluoromethyl;

provided that when b is a single bond; n is 1 or 2; m is 1; k is 1; X is O or S; and $R^1$ is $C_{1-4}$ alkyl or cyclopropyl, then $R^8$ is substituent other than H;

provided that when $R^6$ or $R^{6a}$ is $NH_2$, then X is not —CH($R^{10}$); and provided that when n=0, then $R^6$ or $R^{6a}$ is not $NH_2$ or —OH.

In another embodiment of the present invention,

X is —$CHR^{10}$—, —C(═O)—, —O—, —S—, —S(═O)—, —S(═O)$_2$—, —NH—, —C(═O)NH—, or —NHC(═O)—;

$R^1$ is selected from

H,

C(═O)$R^2$,

C(═O)O$R^2$, $C_{1-8}$ alkyl, $C_{2-8}$ alkenyl, $C_{2-8}$ alkynyl, $C_{3-7}$ cycloalkyl, $C_{1-6}$ alkyl substituted with Z, $C_{2-6}$ alkenyl substituted with Z, $C_{2-6}$ alkynyl substituted with Z, $C_{3-6}$ cycloalkyl substituted with Z, aryl substituted with Z, 5–6 membered heterocyclic ring system containing at least one heteroatom selected from the group consisting of N, O, and S, said heterocyclic ring system substituted with Z, $C_{1-3}$ alkyl substituted with Y, $C_{2-3}$ alkenyl substituted with Y, $C_{2-3}$ alkynyl substituted with Y, $C_{2-6}$ alkyl substituted with 0–2 $R^2$, $C_{2-6}$ alkenyl substituted with 0–2 $R_2$, $C_{2-6}$ alkynyl substituted with 0–2 $R^2$, aryl substituted with 0–2 $R^2$, and 5–6 membered heterocyclic ring system containing at least one heteroatom selected from the group consisting of N, O, and S, said heterocyclic ring system substituted with 0–2 $R^2$;

Y is selected from $C_{3-6}$ cycloalkyl substituted with Z, aryl substituted with Z, 5–6 membered heterocyclic ring system containing at least one heteroatom selected from the group consisting of N, O, and S, said heterocyclic ring system substituted with Z;

$C_{3-6}$ cycloalkyl substituted with —($C_{1-3}$ alkyl)-Z, aryl substituted with —($C_{1-3}$ alkyl)-Z, and 5–6 membered heterocyclic ring system containing at least one heteroatom selected from the group consisting of N, O, and S, said heterocyclic ring system substituted with —($C_{1-3}$ alkyl)-Z;

Z is selected from H,

—CH(OH)$R^2$,

—C(ethylenedioxy)$R^2$,

—O$R^2$,

—S$R^2$,

—$NR^2R^3$,

—C(O)$R^2$,

—C(O)$NR^2R^3$,

—$NR^3$C(O)$R^2$,

—C(O)O$R^2$,

—OC(O)$R^2$,

—CH(═$NR^4$)$NR^2R^3$,

—NHC(═$NR^4$)$NR^2R^3$,

—S(O)$R^2$,

—S(O)$_2R^2$,

—S(O)$_2NR^2R^3$, and —$NR^3$S(O)$_2R^2$;

$R^2$, at each occurrence, is independently selected from halo, $C_{1-3}$ haloalkyl, $C_{1-4}$ alkyl, $C_{2-4}$ alkenyl, $C_{2-4}$ alkynyl, $C_{3-6}$ cycloalkyl, aryl substituted with 0–5 $R^{42}$;

$C_{3-10}$ carboncyclic residue substituted with 0–3 $R^{41}$, and 5–10 membered heterocyclic ring system containing from 1–4 heteroatoms selected from the group consisting of N, O, and S substituted with 0–3 $R^{41}$;

$R^3$, at each occurrence, is independently selected from H, $C_{1-4}$ alkyl, $C_{2-4}$ alkenyl, $C_{2-4}$ alkynyl, and $C_{1-4}$ alkoxy;

alternatively, $R^2$ and $R^3$ join to form a 5- or 6-membered ring optionally substituted with —O— or —N($R^4$)—;

$R^4$, at each occurrence, is independently selected from H and $C_{1-4}$ alkyl;

$R^5$ is H or $C_{1-4}$ alkyl;

$R^{6a}$ and $R^{6b}$, at each occurrence, are independently selected from

H, —OH, —$NR^{46}R^{47}$, —$CF_3$, $C_{1-4}$ alkyl, $C_{2-4}$ alkenyl, $C_{2-4}$ alkynyl, $C_{1-4}$ alkoxy, $C_{1-4}$ haloalkyl, $C_{3-6}$ cycloalkyl, and aryl substituted with 0–3 $R^{44}$;

$R^7$ and $R^9$, at each occurrence, are independently selected from

H, halo, —$CF_3$, —$OCF_3$, —OH, —CN, —$NO_2$, —$NR^{46}R^{47}$, $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, C(O)H, C(O)$R^{12}$, C(O)$NR^{12}R^{13}$, $NR^{14}C(O)R^{12}$, C(O)$OR^{12}$, OC(O)$R^{12}$, OC(O)$OR^{12}$, CH(═$NR^{14}$)$NR^{12}R^{13}$, NHC(═$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^8$ is selected from

H, halo, —$CF_3$, —$OCF_3$, —OH, —CN, —$NO_2$, $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{2-4}$ alkenyl substituted with 0–2 $R^{11}$, $C^{2-4}$ alkynyl substituted with 0–1 $R^{11}$, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, C(O)H, C(O)$R^{12}$, C(O)$NR^{12}R^{13}$, $NR^{14}C(O)R^{12}$, C(O)$OR^{12}$, OC(O)$R^{12}$, OC(O)$OR^{12}$, CH(═$NR^{14}$)$NR^{12}R^{13}$, NHC(═$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}S(O)R^{12}$, $NR^{14}S(O)_2R^{12}$, $NR^{12}(O)R^{15}{}_1$, $NR^{12}C(O)OR^{15}$, $NR^{12}S(O)_2R^{15}$, and $NR^{12}C(O)NHR^{15}$;

$R^{11}$ is selected from

H, halo, —$CF_3$, —CN, —$NO_2$, $C_{1-8}$ alkyl, $C_{2-8}$ alkenyl, $C_{2-8}$ alkynyl, $C_{1-4}$ haloalkyl, $C_{1-8}$ alkoxy, $C_{3-10}$ cycloalkyl, $C_{3-10}$ carbocyclic residue substituted with 0–3 $R^{33}$, aryl substituted with 0–5 $R^{33}$, 5–10 membered heterocyclic ring system containing from 1-4 heteroatoms selected from the group consisting of N, O, and S substituted with 0–3 $R^{31}$;

$OR^{12}$, $SR^{12}$, $NR^{12}R^{13}$, C(O)H, C(O)$R^{12}$, C(O)$NR^{12}R^{13}$, $NR^{14}C(O)R^{12}$, C(O)$OR^{12}$, OC(O)$R^{12}$, OC(O)$OR^{12}$, CH(═$NR^{14}$)$NR^{12}R^{13}$, NHC(═$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$, $R^{12}$, at each occurrence, is independently selected from $C_{1-4}$ alkyl substituted with 0–1 $R^{12a}$, $C_{2-4}$ alkenyl substituted with 0–1 $R^{12a}$, $C_{2-4}$ alkynyl substituted with 0–1 $R^{12a}$, $C_{3-6}$ cycloalkyl substituted with 0–3 $R^{33}$, phenyl substituted with 0–5 $R^{33}$;

$C_{3-10}$ carbocyclic residue substituted with 0–3 $R^{33}$,and

5–10 membered heterocyclic ring system containing from 1–4 heteroatoms selected from the group consisting of N, O, and S substituted with 0–3 $R^{31}$;

$R^{12a}$, at each occurrence, is independently selected from phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively,$R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H and $C_{1-4}$ alkyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from H, OH, halo, CN, $NO_2$, $CF_3$,$SO_2R^{45}$, $NR^{46}R^{47}$, —C(═O)H, $C_{1-4}$ alkyl, $C_{2-4}$ alkenyl, $C_{2-4}$ alkynyl, $C_{1-4}$ haloalkyl, $C_{1-3}$ haloalkenyl-oxy-, and $C_{1-3}$ alkyloxy-;

$R^{31}$, at each occurrence, is independently selected from H, OH, halo, $CF_3$, $SO_2R^{45}$, $NR^{46}R^{47}$, and $C_{1-4}$ alkyl;

$R^{33}$, at each occurrence, is independently selected from

H, OH, halo, CN, $NO_2$, $CF_3$, $SO_2R^{45}$, $NR^{46}R^{47}$, —C(═O)H, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(═O)—, $C_{1-4}$ alkyl-C(═O)NH—, $C_{1-4}$ alkyl-OC(═O)—, $C_{1-4}$ alkyl-C(═O)O—, $C_{3-6}$ cycloalkyl-oxy-, $C_{3-6}$ cycloalkymethyl-oxy-;

$C_{1-6}$ alkyl substituted with OH, methoxy, ethoxy, propoxy, or butoxy; and $C_{2-6}$ alkenyl substituted with OH, methoxy, ethoxy, propoxy, or butoxy;

$R^{41}$, each occurrence, is independently selected from

H, $CF_3$, halo, OH, $CO_2H$, $SO_2R^{45}$, $NR^{46}R^{47}$, $NO_2$, CN, ═O;

$C_{2-8}$ alkenyl, $C_{2-8}$ alkynyl, $C_{1-4}$ alkoxy, $C_{1-4}$ haloalkyl $C_{1-4}$ alkyl substituted with 0–1 $R^{43}$, aryl substituted with 0–3 $R^{42}$, and 5–10 membered heterocyclic ring system containing from 1–4 heteroatoms selected from the group consisting of N, O, and S substituted with 0–3 $R^{44}$;

$R^{42}$, at each occurrence, is independently selected from H, $CF_3$, halo, OH, $CO_2H$, $SO_2R^{45}$, $SOR^{45}$, $SR^{45}$, $NR^{46}SO_2R^{45}$, $NR^{46}COR^{45}$, $NR^{46}R^{47}$, $NO_2$, CN, $CH(=NH)NH_2$, $NHC(=NH)NH_2$, $C_{2-6}$ alkenyl, $C_{2-6}$ alkynyl, $C_{1-4}$ alkoxy, $C_{1-4}$ haloalkyl, $C_{3-6}$ cycloalkyl, $C_{1-4}$ alkyl substituted with 0–1 $R^{43}$, aryl substituted with 0–3 $R^{44}$, and 5–10 membered heterocyclic ring system containing from 1–4 heteroatoms selected from the group consisting of N, O, and S substituted with 0—3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H, $C_{1-4}$ alkyl, —C(=O)NH($C_{1-4}$ alkyl), —$SO_2$($C_{1-4}$ alkyl), —C(=O)O($C_{1-4}$ alkyl), —C(=O)($C_{1-4}$ alkyl), and —C(=O)H;

k is 1 or 2;

m is 0, 1, or 2;

n is 1, 2, or 3;

provided when m is 0 or 1 then k is 1 or 2;

provided when m is 2 then k is 1;

provided that when b is a double bond; n is 1 or 2; m is 1; k is 1; X is —O—, —S—, —S(=O)—, or —$SO_2$—; and the three substituents of $R^7$, $R^8$, and $R^9$, consist of i) three hydrogens, ii) two hydrogens and one chloro, or iii) two hydrogens and one methyl; then $R^1$ must contain the substituent Z or Y;

provided that when b is a single bond; n is 1 or 2; m is 1; k is 1; X is O or S; and $R^1$ is $C_{1-4}$ alkyl or cyclopropyl, then $R^8$ is a substituent other than H; and provided that when n=0, then $R^6$ or $R^{6a}$ is not $NH_2$ or —OH.

[2] In a preferred embodiment of the present invention, X is —O—, —S—, —S(=O)—, or —S(=O)$_2$—;

$R^1$ is selected from

H,

C(=O)$R^2$,

C(=O)O$R^2$, $C_{1-8}$ alkyl, $C_{2-8}$ alkenyl, $C_{2-8}$ alkynyl, $C_{3-7}$ cycloalkyl, $C_{1-6}$ alkyl substituted with Z, $C_{2-6}$ alkenyl substituted with Z, $C_{2-6}$ alkynyl substituted with Z, $C_{3-6}$ cycloalkyl substituted with Z, aryl substituted with Z, 5–6 membered heterocyclic ring system containing at least one heteroatom selected from the group consisting of N, O, and S, said heterocyclic ring system substituted with z;

$C_{1-3}$ alkyl substituted with Y, $C_{2-3}$ alkenyl substituted with Y, $C_{2-3}$ alkynyl substituted with Y, $C_{1-6}$ alkyl substituted with 0–2 $R^2$, $C_{2-6}$ alkenyl substituted with 0–2 $R^2$, $C_{2-6}$ alkynyl substituted with 0–2 $R^2$, aryl substituted with 0–2 $R^2$, and 5–6 membered heterocyclic ring system containing at least one heteroatom selected from the group consisting of N, O, and S, said heterocyclic ring system substituted with 0–2 $R^2$;

Y is selected from $C_{3-6}$ cycloalkyl substituted with Z, aryl substituted with Z, 5–6 membered heterocyclic ring system containing at least one heteroatom selected from the group consisting of N, O, and S, said heterocyclic ring system substituted with Z;

$C_{3-6}$ cycloalkyl substituted with —($C_{1-3}$ alkyl)-Z, aryl substituted with —($C_{1-3}$ alkyl)-Z, and 5–6 membered heterocyclic ring system containing at least one heteroatom selected from the group consisting of N, O, and S, said heterocyclic ring system substituted with —($C_{1-3}$ alkyl)-Z;

Z is selected from H,

—CH(OH)$R^2$,

—C(ethylenedioxy)$R^2$,

—O$R^2$,

—S$R^2$,

—$NR^2R^3$,

—C(O)$R^2$,

—C(O)$NR^2R^3$,

—$NR^3$C(O)$R^2$,

—C(O)O$R^2$,

—OC(O)$R^2$,

—CH(=$NR^4$)$NR^2R^3$,

—NHC(=$NR^4$)$NR^2R^3$,

—S(O)$R^2$,

—S(O)$_2R^2$,

—S(O)$_2NR^2R^3$, and —$NR^3$S(O)$_2R^2$;

$R^2$, at each occurrence, is independently selected from halo,

—$C_{1-3}$ haloalkyl, $C_{1-4}$ alkyl, $C_{2-4}$ alkenyl, $C_{2-4}$ alkynyl, $C_{3-6}$ cycloalkyl, aryl substituted with 0–5 $R^{42}$;

$C_{3-10}$ carbocyclic residue substituted with 0–3 $R^{41}$, and

5–10 membered heterocyclic ring system containing from 1–4 heteroatoms selected from the group consisting of N, O, and S substituted with 0–3 $R^{41}$;

$R^3$, at each occurrence, is independently selected from H, $C_{1-4}$ alkyl, $C_{2-4}$ alkenyl, $C_{2-4}$ alkynyl, and $C_{1-4}$ alkoxy;

alteratively, $R^2$ and $R^3$ join to form a 5- or 6-membered ring optionally substituted with —O— or —N($R^4$)—;

$R^4$, at each occurrence, is independently selected from H and $C_{1-4}$ alkyl;

$R^5$ is H or $C_{1-4}$ alkyl;

$R^{6a}$ and $R^{6b}$, at each occurrence, are independently selected from

H, —OH, —$NR^{46}R^{47}$, —$CF_3$, $C_{1-4}$ alkyl, $C_{2-4}$ alkenyl, $C_{2-4}$ alkynyl, $C_{1-4}$ alkoxy, $C_{1-4}$ haloalkyl, $C_{3-6}$ cycloalkyl, and aryl substituted with 0–3 $R^{44}$;

$R^7$ and $R^9$, at each occurrence, are independently selected from

H, halo, —$CF_3$, —$OCF_3$, —OH, —CN, —$NO_2$, —$NR^{46}R^{47}$, $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{33}$, $OR^{12}$, $SR^{12}$, $NR^{12}R^{13}$, C(O)H, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^8$ is selected from

H, halo, —$CF_3$, —$OCF_3$, —OH, —CN, —$NO_2$, $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{2-4}$ alkenyl substituted with 0–2 $R^{11}$, $C_{2-4}$ alkynyl substituted with 0–1 $R^{11}$, $C_{3-10}$ carboncyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, C(O)H, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from

H, halo, —$CF_3$, —CN, —$NO_2$, $C_{1-8}$ alkyl, $C_{2-8}$ alkenyl, $C_{2-8}$ alkynyl, $C_{1-4}$ haloalkyl, $C_{1-8}$ alkoxy, $C_{3-10}$ cycloalkyl, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, C(O)H, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$,$NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{12}$, at each occurrence, is independently selected from $C_{1-4}$ alkyl substituted with 0–1 $R^{12a}$, $C_{2-4}$ alkenyl substituted with 0–1 $R^{12a}$, $C_{2-4}$ alkynyl substituted with 0–1 $R^{12a}$, $C_{3-6}$ cycloalkyl substituted with 0–3 $R^{33}$, phenyl substituted with 0–5 $R^{33}$, $C_{3-10}$ carbocyclic residue substituted with 0–3 $R^{33}$, and 5–10 membered heterocyclic ring system containing from 1–4 heteroatoms selected from the group consisting of N, O, and S substituted with 0–3 $R^{31}$;

$R^{12a}$, at each occurrence, is independently selected from phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H and $C_{1-4}$ alkyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from H, OH, halo, CN, $NO_2$, $CF_3$, $SO_2R^{45}$, $NR^{46}R^{47}$, —C(=O)H, $C_{1-4}$ alkyl, $C_{2-4}$ alkenyl, $C_{2-4}$ alkynyl, $C_{1-4}$ haloalkyl, $C_{1-3}$ haloalkyl-oxy-, and $C_{1-3}$ alkyloxy-;

$R^{31}$, at each occurrence, is independently selected from H, OH, halo, $CF_3$, $SO_2R^{45}$, $NR^{46}R^{47}$, and $C_{1-4}$ alkyl;

$R^{33}$, at each occurrence, is independently selected from H, OH, halo, CN, $NO_2$, $CF_3$, $SO_2R^{45}$, $NR^{46}R^{47}$, —C(=O)H, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-C(=O)NH—, $C_{1-4}$ alkyl-OC(=O)—, $C_{1-4}$ alkyl-C(=O)O—, $C_{3-6}$ cycloalkyl-oxy-, $C_{3-6}$ cycloalkylmethyl-oxy-;

$C_{1-6}$ alkyl substituted with OH, methoxy, ethoxy, propoxy, or butoxy; and $C_{2-6}$ alkenyl substituted with OH, methoxy, ethoxy, propoxy, or butoxy;

$R^{43}$, at each occurrence, is independently selected from

H, $CF_3$, halo, OH, $CO_2H$, $SO_2R^{45}$, $NR^{46}R^{47}$, $NO_2$, CN, =O;

$C_{2-8}$ alkenyl, $C_{2-8}$ alkynyl, $C_{1-4}$ alkoxy, $C_{1-4}$ haloalkyl $C_{1-4}$ alkyl substituted with 0–1 $R^{43}$, aryl substituted with 0–3 $R^{42}$, and 5–10 membered heterocyclic ring system containing from 1–4 heteroatoms selected from the group consisting of N, O, and S substituted with 0–3 $R^{44}$;

$R^{42}$, at each occurrence, is independently selected from

H, $CF_3$, halo, OH, $CO_2H$, $SO_2R^{45}$, $SOR^{45}$, $SR^{45}$, $NR^{46}SO_2R^{45}$, $NR^{46}COR^{45}$, $NR^{46}R^{47}$, $NO_2$, CN, $CH(=NH)NH_2$, $NHC(=NH)NH_2$, $C_{2-6}$ alkenyl, $C_{2-6}$ alkynyl, $C_{1-4}$ alkoxy, $C_{1-4}$ haloalkyl, $C_{3-6}$ cycloalkyl, $C_{1-4}$ alkyl substituted with 0–1 $R^{43}$, aryl substituted with 0–3 $R^{44}$, and 5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H, $C_{1-4}$ alkyl, —C(═O)NH($C_{1-4}$ alkyl), —$SO_2$($C_{1-4}$ alkyl), —C(═O)O($C_{1-4}$ alkyl), —C(═O)($C_{1-4}$ alkyl), and —C(═O)H;

k is 1 or 2;

m is 0, 1, or 2;

n is 1, 2, or 3;

provided when m is 0 or 1 then k is 1 or 2;

provided when m is 2 then k is 1;

provided that when b is a double bond; n is 1 or 2; m is 1; k is 1; X is —O—, —S—, —S(═O)—, or —$SO_2$—; and the three substituents of $R^7$, $R^8$, and $R^9$, consist of i) three hydrogens, ii) two hydrogens and one chloro, or iii) two hydrogens and one methyl; then $R^1$ must contain the substituent Z or Y;

provided that when b is a single bond; n is 1 or 2; m is 1; k is 1; X is O or S; and $R^1$ is $C_{1-4}$ alkyl or cyclopropyl, then $R^8$ is a substituent other than H; and provided that when n=0, then $R^6$ or $R^{6a}$ is not $NH_2$ or —OH.

[3] In a further preferred embodiment of the present invention,

X is —O—, —S—, —S(═O)—, or —S(═O)$_2$—;

$R^1$ is selected from

H,

C(═O)$R^2$,

C(═O)O$R^2$, $C_{1-8}$ alkyl, $C_{2-8}$ alkenyl, $C_{2-8}$ alkynyl, $C_{3-7}$ cycloalkyl, $C_{1-6}$ alkyl substituted with 0–2 $R^2$, $C_{2-6}$ alkenyl substituted with 0–2 $R^2$, $C_{2-6}$ alkynyl substituted with 0–2 $R^2$, aryl substituted with 0–2 $R^2$, and 5–10 membered heterocyclic ring system containing at least one heteroatom selected from the group consisting of N, O, and S, said heterocyclic ring system substituted with 0–2 $R^2$;

$R^2$, at each occurrence, is independently selected from

F, Cl, $CH_2F$, $CHF_2$, $CF_3$, $C_{1-4}$ alkyl, $C_{2-4}$ alkenyl, $C_{2-4}$ alkynyl, $C_{3-6}$ cycloalkyl, phenyl substituted with 0–5 $R^{42}$;

$C_{3-10}$ carbocyclic residue substituted with 0–3 $R^{43}$, and

5–10 membered heterocyclic ring system containing from 1–4 heteroatoms selected from the group consisting of N, O, and S substituted with 0–3 $R^{41}$;

$R^5$ is H, methyl, ethyl, propyl, or butyl;

$R^{6a}$ is selected from

H, —OH, —$NR^{46}R^{47}$, —$CF_3$, $C_{1-4}$ alkyl, $C_{1-4}$ alkoxy, $C_{1-4}$ haloalkyl, and aryl substituted with 0–3 $R^{44}$;

$R^7$ and $R^9$, at each occurrence, are independently selected from

H, halo, —$CF_3$, —$OCF_3$, —OH, —CN, —$NO_2$, —$NR^{46}R^{47}$, $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3$R^{31}$;

$OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)O$R^{12}$, OC(O)$R^{12}$, OC(O)O$R^{12}$, CH(═$NR^{14}$)$NR^{12}R^{13}$, NHC(═$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, $NR^{14}$S(O)$_2R^{12}$, $NR^{12}$C(O)$R^{15}$, $NR^{12}$C(O)O$R^{15}$, $NR^{12}$S(O)$_2R^{15}$, and $NR^{12}$C(O)NH$R^{15}$;

$R^8$ is selected from

H, halo, —$CF_3$, —$OCF_3$, —OH, —CN, —$NO_2$, $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{2-4}$ alkenyl substituted with 0–2 $R^{11}$, $C_{2-4}$ alkynyl substituted with 0–1 $R^{11}$, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)O$R^{12}$, OC(O)$R^{12}$, OC(O)O$R^{12}$, CH(═$NR^{14}$)$NR^{12}R^{13}$, NHC(═$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, $NR^{14}$S(O)$_2R^{12}$, $NR^{12}$C(O)$R^{15}$, $NR^{12}$C(O)O$R^{15}$, $NR^{12}$S(O)$_2R^{15}$, and $NR^{12}$C(O)NH$R^{15}$;

$R^{11}$ is selected from

H, halo, —$CF_3$, —CN, —$NO_2$, $C_{1-8}$ alkyl, $C_{2-8}$ alkenyl, $C_{2-8}$ alkynyl, $C_{1-4}$ haloalkyl, $C_{1-8}$ alkoxy, $C_{3-10}$ cycloalkyl, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$, $OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)O$R^{12}$, OC(O)$R^{12}$, OC(O)O$R^{12}$, CH(═$NR^{14}$)$NR^{12}R^{13}$, NHC(═$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, $NR^{14}$S(O)$_2R^{12}$, $NR^{12}$C(O)$R^{15}$, $NR^{12}$C(O)O$R^{15}$, $NR^{12}$S(O)$_2R^{15}$, and $NR^{12}$C(O)NH$R^{15}$;

$R^{12}$, at each occurrence, is independently selected from $C_{1-4}$ alkyl substituted with 0–1 $R^{12a}$, $C_{2-4}$ alkenyl substituted with 0–1 $R^{12a}$, $C_{2-4}$ alkynyl substituted with 0–1 $R^{12a}$, $C_{3-6}$ cycloalkyl substituted with 0–3 $R^{33}$, phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{12a}$, at each occurrence, is independently selected from phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, S and substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10- membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H and $C_{1-4}$ alkyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from H, OH, halo, CN, $NO_2$, $CF_3$, $SO_2R^{45}$, $NR^{46}R^{47}$, —C(═O)H, $C_{1-4}$ alkyl, $C_{2-4}$ alkenyl, $C_{2-4}$ alkynyl, $C_{1-4}$ haloalkyl, $C_{1-3}$ haloalkyl-oxy-, and $C_{1-3}$ alkyloxy-;

$R^{31}$, at each occurrence, is independently selected from H, OH, halo, $CF_3$, $SO_2R^{45}$, $NR^{46}R^{47}$, and $C_{1-4}$ alkyl;

$R^{33}$, at each occurrence, is independently selected from

H, OH, halo, CN, $NO_2$, $CF_3$, $SO_2R^{45}$, $NR^{46}R^{47}$, —C(═O)H, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(═O)—, $C_{1-4}$ alkyl-C(═O)NH—, $C_{1-4}$ alkyl-OC(═O)—, $C_{1-4}$ alkyl-C(═O)O—, $C_{3-6}$ cycloalkyl-oxy-, $C_{3-6}$ cycloalkylmethyl-oxy-;

$C_{1-6}$ alkyl substituted with OH, methoxy, ethoxy, propoxy, or butoxy; and $C_{2-6}$ alkenyl substituted with OH, methoxy, ethoxy, propoxy, or butoxy;

$R^{41}$, at each occurrence, is independently selected from

H, $CF_3$, halo, OH, $CO_2H$, $SO_2R^{45}$, $NR^{46}R^{47}$, $NO_2$, CN;

$C_{2-8}$ alkenyl, $C_{2-8}$ alkynyl, $C_{1-4}$ alkoxy, $C_{1-4}$ haloalkyl $C_{1-4}$ alkyl substituted with 0–1 $R^{43}$, aryl substituted with 0–3 $R^{42}$, and 5–10 membered heterocyclic ring system containing from 1–4 heteroatoms selected from the group consisting of N, O, and S substituted with 0–3 $R^{44}$;

$R^{42}$, at each occurrence, is independently selected from

H, $CF_3$, halo, OH, $CO_2H$, $SO_2R^{45}$, $NR^{46}R^{47}$, $NO_2$, CN, CH(═NH)$NH_2$, NHC(═NH)$NH_2$, $C_{2-6}$ alkenyl, $C_{2-6}$ alkynyl, $C_{1-4}$ alkoxy, $C_{1-4}$ haloalkyl, $C_{3-6}$ cycloalkyl, $C_{1-4}$ alkyl substituted with 0–1 $R^{43}$, aryl substituted with 0–3 $R^{44}$, and 5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H and $C_{1-4}$ alkyl;

k is 1 or 2;

m is 0, 1, or 2; and n is 1, 2, or 3.

[4] In a more preferred embodiment of the present invention,

X is —O— or —S—;

$R^1$ is selected from

H,

C(═O)$R^2$,

C(═O)O$R^2$, $C_{1-6}$ alkyl, $C_{2-6}$ alkenyl, $C_{2-6}$ alkynyl, $C_{3-6}$ cycloalkyl, $C_{1-4}$ alkyl substituted with 0–2 $R^2$, $C_{2-4}$ alkenyl substituted with 0–2 $R^2$, and $C_{2-4}$ alkynyl substituted with 0–2 $R^2$;

$R^2$, at each occurrence, is independently selected from $C_{1-4}$ alkyl, $C_{2-4}$ alkenyl, $C_{2-4}$ alkynyl, $C_{3-6}$ cycloalkyl, phenyl substituted with 0–5 $R^{42}$;

$C_{3-10}$ carbocyclic residue substituted with 0–3 $R^{41}$, and

5–10 membered heterocyclic ring system containing from 1–4 heteroatoms selected from the group consisting of N, O, and S substituted with 0–3 $R^{41}$;

$R^5$ is H, methyl, ethyl, propyl, or butyl;

$R^{6a}$ is selected independently from H, —OH, —$NR^{46}R^{47}$, —$CF_3$, $C_{1-3}$ alkyl, and $C_{1-3}$ alkoxy;

$R^{6b}$ is H;

$R^7$ and $R^9$, at each occurrence, are independently selected from

H, halo, —$CF_3$, —$OCF_3$, —OH, —CN, —$NO_2$, —$NR^{46}R^{47}$, $C_{1-6}$ alkyl, $C_{2-6}$ alkenyl, $C_{2-6}$ alkynyl, $C_{1-6}$ haloalkyl, $C_{1-6}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)O$R^{12}$, OC(O)$R^{12}$, OC(O)O$R^{12}$, CH(═$NR^{14}$)$NR^{12}R^{13}$, NHC(═$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, and $NR^{14}$S(O)$_2R^{12}$;

$R^8$ is selected from

H, halo, —$CF_3$, —$OCF_3$, —OH, —CN, —$NO_2$, $C_{1-6}$ alkyl, $C_{2-6}$ alkenyl, $C_{2-6}$ alkynyl, $C_{1-6}$ haloalkyl, $C_{1-6}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{2-4}$ alkenyl substituted with 0–2 $R^{11}$, $C_{2-4}$ alkynyl substituted with 0–1 $R^{11}$, $C_{1-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, C(O)H, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from

H, halo, —$CF_3$, —CN, —$NO_2$, $C_{1-6}$ alkyl, $C_{2-6}$ alkenyl, $C_{2-6}$ alkynyl, $C_{1-4}$ haloalkyl, $C_{16}$ alkoxy, $C_{3-10}$ cycloalkyl, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, C(O)H, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, and $NR^{14}S(O)_2R^{12}$;

$R^{12}$, at each occurrence, is independently selected from $C_{1-4}$ alkyl substituted with 0–1 $R^{12a}$, $C_{2-4}$ alkenyl substituted with 0–1 $R^{12a}$, $C_{2-4}$ alkynyl substituted with 0–1 $R^{12a}$, $C_{3-6}$ cycloalkyl substituted with 0–3 $R^{33}$, phenyl substituted with 0–5 $R^{33}$, $C_{3-10}$ carbocyclic residue substituted with 0–3 $R^{33}$, and 5–10 membered heterocyclic ring system containing from 1–4 heteroatoms selected from the group consisting of N, O, and S substituted with 0–3 $R^{31}$;

$R^{12a}$, at each occurrence, is independently selected from phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{15}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —$N(R^{14})$—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H, methyl, ethyl, propyl, and butyl;

$R^{15}$, at each occurrence, is independently selected from H, $C_{1-4}$ alkyl, $C_{2-4}$ alkenyl, and $C_{2-4}$ alkynyl;

$R^{16}$ at each occurrence, is independently selected from H, OH, F, Cl, CN, $NO_2$, $CF_3$, $SO_2R^{45}$, $NR^{46}R^{47}$, —C(=O)H, methyl, ethyl, methoxy, ethoxy, trifluoromethyl, and trifluoromethoxy;

$R^{31}$, at each occurrence, is independently selected from H, OH, halo, $CF_3$, $SO_2R^{45}$, $NR^{46}R^{47}$, and $C_{1-4}$ alkyl;

$R^{33}$, at each occurrence, is independently selected from

H, OH, halo, CN, $NO_2$, $CF_3$, $SO_2R^{45}$, $NR^{46}R^{47}$, —C(=O)H, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-C(=O)NH—, $C_{1-4}$ alkyl-OC(=O)—, $C_{1-4}$ alkyl-C(=O)O—, $C_{3-6}$ cycloalkyl-oxy-, $C_{3-6}$ cycloalkylmethyl-oxy-;

$C_{1-6}$ alkyl substituted with OH, methoxy, ethoxy, propoxy, or butoxy; and $C_{2-6}$ alkenyl substituted with OH, methoxy, ethoxy, propoxy, or butoxy;

$R^{41}$, at each occurrence, is independently selected from

H, $CF_3$, halo, OH, $CO_2H$, $SO_2R^{45}$, $NR^{46}R^{47}$, $NO_2$, CN, $C_{2-8}$ alkenyl, $C_{2-8}$ alkynyl, $C_{1-4}$ alkoxy, $C_{1-4}$ haloalkyl $C_{1-4}$ alkyl substituted with 0–1 $R^{43}$, aryl substituted with 0–3 $R^{42}$, and 5–10 membered heteroatoms ring system containing from 1–4 heteroatoms selected from the group consisting of N, O, and S substituted with 0–3 $R^{44}$;

$R^{42}$, at each occurrence, is independently selected from

H, $CF_3$, halo, OH, $CO_2H$, $SO_2R^{45}$, $NR^{46}R^{47}$, $NO_2$, CN, $CH(=NH)NH_2$, $NHC(=NH)NH_2$, $C_{2-6}$ alkenyl, $C_{2-6}$ alkynyl, $C_{1-4}$ alkoxy, $C_{1-4}$ haloalkyl, $C_{3-6}$ cycloalkyl, $C_{1-4}$ alkyl substituted with 0–1 $R^{43}$, aryl substituted with 0–3 $R^{44}$, and 5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H and $C_{1-4}$ alkyl;

k is 1 or 2;

m is 0 or 1; and n is 1 or 2.

[5] In an even more preferred embodiment of the present invention,

X is —S—;

$R^1$ is selected from

H, $C_{1-4}$ alkyl, $C_{2-4}$ alkenyl, $C_{2-4}$ alkynyl, $C_{3-4}$ cycloalkyl, $C_{1-3}$ alkyl substituted with 0–1 $R^2$, $C_{2-3}$ alkenyl substituted with 0–1 $R^2$, and $C_{2-3}$ alkynyl substituted with 0–1 $R^2$;

$R^2$, at each occurrence, is independently selected from $C_{1-4}$ alkyl, $C_{2-4}$ alkenyl, $C_{2-4}$ alkynyl, $C_{3-6}$ cycloalkyl, phenyl substituted with 0–5 $R^{42}$, $C_{3-6}$ carbocyclic residue substituted with 0–3 $R^{41}$, and 5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;

$R^{6a}$ is H, methyl, ethyl, methoxy, —OH, or —$CF_3$;

$R^{6b}$ is H;

$R^7$ and $R^9$, at each occurrence, are independently selected from

H, halo, —$CF_3$, —$OCF_3$, —OH, —CN, —$NO_2$, —$NR^{46}R^{47}$, $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{3-10}$ carbocyclic residue substituted with 0–3 $R^{33}$, aryl substituted with 0–5 $R^{33}$, and 5–6 membered heterocyclic ring system containing 1, 2, or 3 heteroatoms selected from the group consisting of N, O, and S substituted with 0–3 $R^{31}$;

$R^8$ is selected from

H, halo, —$CF_3$, —$OCF_3$, —OH, —CN, —$NO_2$, $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{2-4}$ alkenyl substituted with 0–2 $R^{11}$, $C_{2-4}$ alkynyl substituted with 0–1 $R^{11}$, $C_{3-10}$ carbocyclic residue substituted with 0–3 $R^{33}$, aryl substituted with 0–5 $R^{33}$, 5–6 membered heterocyclic ring system containing 1, 2, or 3 heteroatoms selected from the group consisting of N, O, and S substituted with 0–3 $R^{31}$;

$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from

H, halo, —$CF_3$, —CN, —$NO_2$, $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy, $C_{3-10}$ cycloalkyl substituted with 0–2 $R^{33}$, $C_{3-10}$ carbocyclic residue substituted with 0–3 $R^{33}$, aryl substituted with 0–5 $R^{33}$, and 5–6 membered heterocyclic ring system containing 1, 2, or 3 heteroatoms selected from the group consisting of N, O, and S substituted with 0–3 $R^{31}$;

$R^{12}$, at each occurrence, is independently selected from $C_{1-4}$ alkyl substituted with 0–1 $R^{12a}$, $C_{2-4}$ alkenyl substituted with 0–1 $R^{12a}$, $C_{2-4}$ alkynyl substituted with 0–1 $R^{12a}$, $C_{3-6}$ cycolalkyl substituted with 0–3 $R^{33}$, phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{12a}$, at each occurrence, is independently selected from phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of one N, two N, three N, one N one O, and one N one S; wherein said bicyclic heterocyclic ring system is unsaturated or partially saturated, wherein said bicyclic heterocyclic ring system is substituted with 0–2 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$, at each occurrence, is independently selected from H, OH, F, Cl, CN, $NO_2$, methyl, ethyl, methoxy, ethoxy, trifluoromethyl, and trifluromethoxy;

$R^{31}$, at each occurrence, is independently selected from H, OH, halo, $CF_3$, methyl, ethyl, and propyl;

$R^{33}$, at each occurrence, is independently selected from

H, OH, halo, CN, $NO_2$, $CF_3$, $SO_2R^{45}$, $NR^{46}R^{47}$, —O(═O)H, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(═O)—, $C_{1-4}$ alkyl-C(═O)NH—, $C_{1-4}$ alkyl-OC(═O)—, $C_{1-4}$ alkyl-C(═O)O—, $C_{3-6}$ cycloalkyl-oxy-, $C_{3-6}$ cycloalkylmethyl-oxy-;

$C_{1-6}$ alkyl substituted with OH, methoxy, ethoxy, propoxy, or butoxy; and $C_{2-6}$ alkenyl substituted with OH, methoxy, ethoxy, propoxy, or butoxy;

$R^{41}$, at each occurrence, is independently selected from

H, $CR_3$, halo, OH, $CO_2H$, $SO_2R^{45}$, $NR^{46}R^{47}$, $NO_2$, CN, $C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from

H, $CF_3$, halo, OH, $CO_2H$, $SO_2R^{45}$, $NR^{46}R^{47}$, $NO_2$, CN, CH(═NH)$NH_2$, NHC(═NH)$NH_2$, $C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

k is 1;

m is 1; and n is 1 or 2.

[6] In an even more preferred embodiment of the present invention,

X is —S—;

$R^1$ is selected from

H, $C_{1-4}$ alkyl, $C_{2-4}$ alkenyl, $C_{2-4}$ alkynyl, $C_{3-4}$ cycloalkyl, $C_{1-3}$ alkyl substituted with 0–1 $R^2$, $C_{2-3}$ alkenyl substituted with 0–1 $R^2$, and $C^{2-3}$ alkynyl substituted with 0–1 $R^2$;

$R^2$, at each occurrence, is independently selected from $C_{1-4}$ alkyl, $C_{2-4}$ alkenyl, $C_{2-4}$ alkynyl, $C_{3-4}$ cycloalkyl, $C_{1-3}$ alkyl substituted with 0–1 $R^2$, $C_{2-3}$ alkenyl substituted with 0–1 $R^2$, and $C_{2-3}$ alkynyl substituted with 0–1 $R^2$;

$R^2$, at each occurrence, is independently selected from $C_{1-4}$ alkyl, $C_{2-4}$ alkenyl, $C_{2-4}$ alkynyl, $C_{3-6}$ cycloalkyl, phenyl substituted with 0–5 $R^{42}$;

$C_{3-6}$ carbocyclic residue substituted with 0–3 $R^{41}$, and

5–6 membered heterocyclic ring system containing 1, 2, or 3 heteroatoms selected from the group consisting of N, O, and S substituted with 0–3 $R^{43}$;

$R^5$ is H, methyl, ethyl, propyl, or butyl;

$R^{6a}$ is H, methyl, ethyl, methoxy, —OH, or $CF_3$;

$R^{6b}$ is H;

$R^7$ and $R^9$, at each occurrence, are independently selected from H, F, Cl, —$CH_3$, —$OCH_3$, —$CF_3$, —$OCF_3$, —CN, and —$NO_2$, $R^8$ is selected from H, F, Cl, Br, —$CF_3$, —$OCF_3$, —OH, —CN, —$NO_2$, $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{2-4}$ alkenyl substituted with 0–2 $R^{11}$, $C_{2-4}$ alkynyl substituted with 0–1 $R^{11}$, $C_{3-10}$ carbocyclic residue substituted with 0–3 $R^{33}$, aryl substituted with 0–5 $R^{33}$, 5–6 membered heterocyclic ring system containing 1, 2, or 3 heteroatoms selected from the group consisting of N, O, and S substituted with 0–3 $R^{31}$;

$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from

H, halo, —$CF_3$, —CN, —$NO_2$, $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy, $C_{3-10}$ cycloalkyl substituted with 0–2 $R^{33}$, $C_{3-10}$ carbocyclic residue substituted with 0–3 $R^{33}$, aryl substituted with 0–5 $R^{33}$, and 5–6 membered heterocyclic ring system containing 1, 2, or 3 heteroatoms selected from the group consisting of N, O, and S substituted with 0–3 $R^{31}$;

$R^{12}$ at each occurrence, is independently selected from $C_{1-4}$ alkyl substituted with 0–1 $R^{12a}$, $C_{2-4}$ alkenyl substituted with 0–1 $R^{12a}$, $C_{2-4}$ alkynyl substituted with 0–1 $R^{12a}$, $C_{3-6}$ cycloalkyl substituted with 0–3 $R^{33}$, phenyl substituted with 0–5 $R^{33}$, $C_{3-10}$ carbocyclic residue substituted with 0–3 $R^{33}$, and 5–10 membered heterocyclic ring system containing from 1–4 heteroatoms selected from the group consisting of N, O, and S substituted with 0–3 $R^{31}$;

$R^{12a}$, at each occurrence, is independently selected from phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to from a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, and benztriazolyl; wherein said bicyclic heterocyclic ring system is substituted with 0–1 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{31}$, at each occurrence, is independently selected from H, OH, halo, $CF_3$, methyl, ethyl, and propyl;

$R^{33}$, at each occurrence, is independently selected from H, OH, halo, CN, $NO_2$, $CF_3$, $SO_2R^{45}$, $NR^{46}R^{47}$, —C(═O)H,

H, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(═O)—, $C_{1-4}$ alkyl-C(═O)NH—, $C_{1-4}$ alkyl-OC(═O)—, $C_{1-4}$ alkyl-C(═O)O—, $C_{3-6}$ cycloalkyl-oxy-, $C_{3-6}$ cycloalkylmethyl-oxy-;

$C_{1-6}$ alkyl substituted with OH, methoxy, ethoxy, propoxy, or butoxy; and $C_{2-6}$ alkenyl substituted with OH, methoxy, ethyoxy, propoxy, or butoxy;

$R^{41}$, at each occurrence, is independently selected from H, $CF_3$, halo, OH, $CO_2H$, $SO_2R^{45}$, $NR^{46}R^{47}$, $NO_2$, CN, $C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from

H, $CF_3$, halo, OH, $CO_2H$, $SO_2R^{45}$, $NR^{46}R^{47}$, $NO_2$, CN, CH(═NH)$NH_2$, NHC(═NH)$NH_2$, $C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

k is 1;

m is 1; and n is 1 or 2.

[7] In an even further more preferred embodiment of the present invention,

X is —S—;

$R^1$ is selected from H, $C_{1-5}$ alkyl substituted with 0–1 $R^2$, $C_{2-5}$ alkenyl substituted with 0–1 $R^2$, and $C_{2-3}$ alkynyl substituted with 0–1 $R^2$;

$R^2$ is $C_{3-6}$ cycloalkyl;

$R^5$ is H, methyl, ethyl, or propyl;

$R^{6a}$ is H, methyl, or ethyl;

$R^{6b}$ is H;

$R^7$ and $R^9$, at each occurrence, are independently selected from H, F, Cl, —$CH_3$, —$OCH_3$, —$CF_3$, —$OCF_3$, —CN, and —$NO_2$, $R^8$ is selected from methyl substituted with $R^{11}$;

ethenyl substituted with $R^{11}$;

$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from phenyl-substituted with 0–5 fluoro;

2-($H_3CCH_2C(=O)$)-phenyl-substituted with $R^{33}$;

2-($H_3CC(=O)$)-phenyl-substituted with $R^{33}$;

2-($HC(=O)$)-phenyl-substituted with $R^{33}$;

2-($H_3CCH(OH)$)-phenyl-substituted with $R^{33}$;

2-($H_3CCH_2CH(OH)$)-phenyl-substituted with $R^{33}$;

2-($HOCH_2$)-phenyl-substituted with $R^{33}$;

2-($HOCH_2CH_2$)-phenyl-substituted with $R^{33}$;

2-($H_3COCH_2$)-phenyl-substituted with $R^{33}$;

2-($H_3COCH_2CH_2$)-phenyl-substituted with $R^{33}$;

2-($H_3CCH(OMe)$)-phenyl-substituted with $R^{33}$;

2-($H_3COC(=O)$)-phenyl-substituted with $R^{33}$;

2-($HOCH_2CH=CH$)-phenyl-substituted with $R^{33}$;

2-($(MeOC=O)CH=CH$)-phenyl-substituted with $R^{33}$;

2-(methyl)-phenyl-substituted with $R^{33}$;

2-(ethyl)-phenyl-substituted with $R^{33}$;

2-(i-propyl)-phenyl-substituted with $R^{33}$;

2-($F_3C$)-phenyl-substituted with $R^{33}$;

2-(NC)-phenyl-substituted with $R^{33}$;

2-($H_3CO$)-phenyl-substituted with $R^{33}$;

2-(fluoro)-phenyl-substituted with $R^{33}$;

2-(chloro)-phenyl-substituted with $R^{33}$;

3-(NC)-phenyl-substituted with $R^{33}$;

3-($H_3CO$)-phenyl-substituted with $R^{33}$;

3-(fluoro)-phenyl-substituted with $R^{33}$;

3-(chloro)-phenyl-substituted with $R^{33}$;

4-(NC)-phenyl-substituted with $R^{33}$;

4-(fluoro)-phenyl-substituted with $R^{33}$;

4-(chloro)-phenyl-substituted with $R^{33}$;

4-($H_3CS$)-phenyl-substituted with $R^{33}$;

4-($H_3CO$)-phenyl-substituted with $R^{33}$;

4-(ethoxy)-phenyl-substituted with $R^{33}$;

4-(i-propoxy)-phenyl-substituted with $R^{33}$;

4-(i-butoxy)-phenyl-substituted with $R^{33}$;

4-($H_3CCH_2CH_2C(=O)$ )-phenyl-substituted with $R^{33}$;

4-($(H_3C)_2CHC(=O)$)-phenyl-substituted with $R^{33}$;

4-($H_3CCH_2C(=O)$)-phenyl-substituted with $R^{33}$;

4-($H_3CC(=O)$)-phenyl-substituted with $R^{33}$;

4-($H_3CCH_2CH_2CH(OH)$)-phenyl-substituted with $R^{33}$;

4-($(H_3C)_2CHCH(OH)$)-phenyl-substituted with $R^{33}$;

4-($H_3CCH_2CH(OH)$)-phenyl-substituted with $R^{33}$;

4-($H_3CCH(OH)$)-phenyl-substituted with $R^{33}$;

4-(cyclopropyloxy)-phenyl-substituted with $R^{33}$;

4-(cyclobutyloxy)-phenyl-substituted with $R^{33}$; and 4-(cyclopentyloxy)-phenyl-substituted with $R^{33}$;

$R^{12}$ is selected from phenyl-substituted with 0–5 fluoro;

2-($H_3CCH_2C(=O)$)-phenyl-substituted with $R^{33}$;

2-($H_3CC(=O)$)-phenyl-substituted with $R^{33}$;

2-($HC(=O)$)-phenyl-substituted with $R^{33}$;

2-($H_3CCH(OH)$)-phenyl-substituted with $R^{33}$;

2-($H_3CCH_2CH(OH)$)-phenyl-substituted with $R^{33}$;

2-($HOCH_2$)-phenyl-substituted with $R^{33}$;

2-($HOCH_2CH_2$)-phenyl-substituted with $R^{33}$;

2-($H_3COCH_2$)-phenyl-substituted with $R^{33}$;

2-($H_3COCH_2CH_2$)-phenyl-substituted with $R^{33}$;

2-($H_3CCH(OMe)$)-phenyl-substituted with $R^{33}$;

2-($H_3COC(=O)$)-phenyl-substituted with $R^{33}$;

2-($HOCH_2CH=CH$)-phenyl-substituted with $R^{33}$;

2-($(MeOC=O)CH=CH$)-phenyl-substituted with $R^{33}$;

2-(methyl)-phenyl-substituted with $R^{33}$;

2-(ethyl)-phenyl-substituted with $R^{33}$;

2-(i-propyl)-phenyl-substituted with $R^{33}$;

2-($F_3C$)-phenyl-substituted with $R^{33}$;

2-(NC)-phenyl-substituted with $R^{33}$;

2-($H_3CO$)-phenyl-substituted with $R^{33}$;

2-(fluoro)-phenyl-substituted with $R^{33}$;

2-(chloro)-phenyl-substituted with $R^{33}$;

3-(NC)-phenyl-substituted with $R^{33}$;

3-($H_3CO$)-phenyl-substituted with $R^{33}$;

3-(fluoro)-phenyl-substituted with $R^{33}$;

3-(chloro)-phenyl-substituted with $R^{33}$;

4-(NC)-phenyl-substituted with $R^{33}$;

4-(fluoro)-phenyl-substituted with $R^{33}$;

4-(chloro)-phenyl-substituted with $R^{33}$;

4-($H_3CS$)-phenyl-substituted with $R^{33}$;

4-($H_3CO$)-phenyl-substituted with $R^{33}$;

4-(ethoxy)-phenyl-substituted with $R^{33}$;

4-(i-propoxy)-phenyl-substituted with $R^{33}$;

4-(i-butoxy)-phenyl-substituted with $R^{33}$;

4-($H_3CCH_2CH_2C(=O)$)-phenyl-substituted with $R^{33}$;

4-($(H_3C)_2CHC(=O)$)-phenyl-substituted with $R^{33}$;

4-($H_3CCH_2C(=O)$)-phenyl-substituted with $R^{33}$;

4-($H_3CC(=O)$)-phenyl-substituted with $R^{33}$;

4-($H_3CCH_2CH_2CH(OH)$)-phenyl-substituted with $R^{33}$;

4-($(H_3C)_2CHCH(OH)$)-phenyl-substituted with $R^{33}$;

4-($H_3CCH_2CH(OH)$)-phenyl-substituted with $R^{33}$;

4-($H_3CCH(OH)$)-phenyl-substituted with $R^{33}$;

4-(cyclopropyloxy)-phenyl-substituted with $R^{33}$;

4-(cyclobutyloxy)-phenyl-substituted with $R^{33}$;

4-(cyclopentyloxy)-phenyl-substituted with $R^{33}$;

$R^{13}$ is H, methyl, or ethyl;

alternatively, $R^{12}$ and $R^{13}$ join to form a 5- or 6-membered ring selected from pyrrolyl, pyrrolidinyl, imidazolyl, piperidinyl, piperizinyl, methylpiperizinyl,and morpholinyl;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, and benztriazolyl; wherein said bicyclic heterocyclic ring system is substituted with 0–1 $R^{16}$;

$R^{15}$ is H, methyl, ethyl, propyl, or butyl;

$R^{16}$, at each occurrence, is independently selected from H, OH, F, Cl, CN, $NO_2$, methyl, ethyl, methoxy, ethoxy, trifluoromethyl, and trifluromethoxy;

$R^{33}$, at each occurrence, is independently selected from H, F, Cl, —$CH_3$, —$OCH_3$, —$CF_3$, —CN, and —$NO_2$;

k is 1;

m is 1; and n is 1 or 2.

[8] In another even more preferred embodiment of the present invention,

X is —O—;

$R^1$ is selected from

H, $C_{1-4}$ alkyl, $C_{2-4}$ alkenyl, $C_{2-4}$ alkynyl, $C_{3-4}$ cycloalkyl, $C_{1-3}$ alkyl substituted with 0–1 $R^2$, $C_{2-3}$ alkenyl substituted with 0–1 $R^2$, and $C_{2-3}$ alkynyl substituted with 0–1 $R^2$;

$R^2$, at each occurrence, is independently selected from $C_{1-4}$ alkyl, $C_{2-4}$ alkenyl, $C_{2-4}$ alkynyl, $C_{3-6}$ cycloalkyl, phenyl substituted with 0–5 $R^{42}$;

$C_{3-6}$ carbocyclic residue substituted with 0–3 $R^{41}$, and

5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;

$R^{6a}$ is H, methyl, ethyl, methoxy, —OH, or —$CF_3$;

$R^{6b}$ is H;

$R^7$ and $R^9$, at each occurrence, are independently selected from

H, halo, —$CF_3$, —$OCF_3$, —OH, —CN, —$NO_2$, —$NR^{46}R^{47}$, $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{3-10}$ carbocyclic residue substituted with 0–3 $R^{33}$, aryl substituted with 0–5 $R^{33}$, and 5–6 membered heterocyclic ring system containing 1, 2, or 3 heteroatoms selected from the group consisting of N, O, and S substituted with 0–3 $R^{31}$;

$R^8$ is selected from

H, halo, —$CF_3$, —$OCF_3$, —OH, —CN, —$NO_2$, $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{2-4}$ alkenyl substituted with 0–2 $R^{11}$, $C_{2-4}$ alkynyl substituted with 0–1 $R^{11}$, $C_{3-10}$ carbocyclic residue substituted with 0–3 $R^{33}$, aryl substituted with 0–5 $R^{33}$, 5–6 membered heterocyclic ring system containing 1, 2, or 3 heteroatoms selected from the group consisting of N, O, and S substituted with 0–3 $R^{31}$;

$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from

H, halo, —$CF_3$, —CN, —$NO_2$, $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy, $C_{3-10}$ cycloalkyl substituted with 0–2 $R^{33}$, $C_{3-10}$ carbocyclic residue substituted with 0–3 $R^{33}$, aryl substituted with 0–5 $R^{33}$, and 5–6 membered heterocyclic ring system containing 1, 2, or 3 heteroatoms selected from the group consisting of N, O, and S substituted with 0–3 $R^{31}$;

$R^{12}$, at each occurrence, is independently selected from $C_{1-4}$ alkyl substituted with 0–1 $R^{12a}$, $C_{2-4}$ alkenyl substituted with 0–1 $R^{12a}$, $C_{2-4}$ alkynyl substituted with 0–1 $R^{12a}$, $C_{3-6}$ cycloalkyl substituted with 0–3 $R^{33}$, phenyl substituted with 0–5 $R^{33}$;

$C_{1-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{12a}$, at each occurrence, is independently selected from phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3$R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- and 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of one N, two N, three N, one N one O, and one N one S; wherein said bicyclic heterocyclic ring system is unsaturated or partially saturated, wherein said bicyclic heterocyclic ring system is substituted with 0–2 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$ at each occurrence, is independently selected from H, OH, F, Cl, CN, $NO_2$, methyl, ethyl, methoxy, ethoxy, trifluoromethyl, and trifluoromethoxy;

$R^{31}$, at each occurrence, is independently selected from H, OH, halo, $CF_3$, methyl, ethyl, and propyl;

$R^{33}$, at each occurrence, is independently selected from

H, OH, halo, CN, $NO_2$, $CF_3$, $SO_2R^{45}$, $NR^{46}R^{47}$, —C(═O)H, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(═O)—, $C_{1-4}$ alkyl-C(═O)NH—, $C_{1-4}$ alkyl-OC(═O)—, $C_{1-4}$ alkyl-C(═O)O—, $C_{3-6}$ cycloalkyl-oxy-, $C_{3-6}$ cycloalkylmethyl-oxy-;

$C_{1-6}$ alkyl substituted with OH, methoxy, ethoxy, propoxy, or butoxy; and $C_{2-6}$ alkenyl substituted with OH, methoxy, ethoxy, propoxy, or butoxy;

$R^{41}$, at each occurrence, is independently selected from

H, $CF_3$, halo, OH, $CO_2H$, $SO_2R^{45}$, $NR^{46}R^{47}$, $NO_2$, CN, $C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from

H, $CF_3$, halo, OH, $CO_2H$, $SO_2R^{45}$, $NR^{46}R^{47}$, $NO_2$, CN, CH(═NH)$NH_2$, NHC(═NH)$NH_2$, $C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO^2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

k is 1;

m is 1; and n is 1 or 2.

[9] In another even more preferred embodiment of the present invention,

X is —O—;

$R^1$ is selected from

H, $C_{1-4}$ alkyl, $C_{2-4}$ alkenyl, $C_{2-4}$ alkynyl, $C_{3-4}$ cycloalkyl, $C_{1-3}$ alkyl substituted with 0–1 $R^2$, $C_{2-3}$ alkenyl substituted with 0–1 $R^2$, and $C_{2-3}$ alkynyl substituted with 0–1 $R^2$;

$R^2$, at each occurrence, is independently selected from $C_{1-4}$ alkyl, $C_{2-4}$ alkenyl, $C_{2-4}$ alkynyl, $C_{3-6}$ cycloalkyl, phenyl substituted with 0–5 $R^{42}$;

$C_{3-6}$ carbocyclic residue substituted with 0–3 $R^{41}$, and

5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;

$R^{6a}$ is H, methyl, ethyl, methoxy, —OH, or —$CF_3$;

$R^{6b}$ is H;

$R^7$ and $R^9$, at each occurrence, are independently selected from H, F, Cl, —$CH_3$, —$OCH_3$, —$CF_3$, —$OCF_3$, —CN, and —$NO_2$, $R^8$ is selected from H, F, Cl, Br, —$CF_3$, —$OCF_3$, —OH, —CN, —$NO_2$, $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{2-4}$ alkenyl substituted with 0–2 $R^{11}$, $C_{2-4}$ alkynyl substituted with 0–1 $R^{11}$, $C_{3-10}$ carbocyclic residue substituted with 0–3 $R^{33}$, aryl substituted with 0–5 $R^{33}$, 5–6 membered heterocyclic ring system containing 1, 2, or 3 heteroatoms selected from the group consisting of N, O, and S substituted with 0–3 $R^{33}$;

$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from

H, halo, —$CF_3$, —CN, —$NO_2$, $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy, $C_{3-10}$ cycloalkyl substituted with 0–2 $R^{33}$, $C_{3-10}$ carbocyclic residue substituted with 0–3 $R^{33}$, aryl substituted with 0–5 $R^{33}$, and 5–6 membered heterocyclic ring system containing 1, 2, or 3 heteroatoms selected from the group consisting of N, O, and S substituted with 0–3 $R^{33}$;

$R^{12}$, at each occurrence, is independently selected from $C_{1-4}$ alkyl substituted with 0–1 $R^{12a}$, $C_{2-4}$ alkenyl substituted with 0–1 $R^{12a}$, $C_{2-4}$ alkynyl substituted with 0–1 $R^{12a}$, $C_{3-6}$ cycloalkyl substituted with 0–3 $R^{33}$;

phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{12a}$, at each occurrence, is independently selected from phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, benztriazolyl, benzoxazolyl, benzoxazolinyl, benzthiazolyl, and dioxobenzthiazolyl; wherein said bicyclic heterocyclic ring system is substituted with 0–1 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$ at each occurrence, is independently selected from H, OH, F, Cl, CN, $NO_2$, methyl, ethyl, methoxy, ethoxy, trifluoromethyl, and trifluoromethoxy;

$R^{31}$, at each occurrence, is independently selected from H, OH, halo, $CF_3$, methyl, ethyl, and propyl;

$R^{33}$, at each occurrence, is independently selected from

H, OH, halo, CN, $NO_2$, $CF_3$, $SO_2R^{45}$, $NR^{46}R^{47}$, —C(═O)H, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(═O)—, $C_{1-4}$ alkyl-C(═O)NH—, $C_{1-4}$ alkyl-OC(═O)—, $C_{1-4}$ alkyl-C(═O)O—, $C_{3-6}$ cycloalkyl-oxy-, $C_{3-6}$ cycloalkylmethyl-oxy-;

$C_{1-6}$ alkyl substituted with OH, methoxy, ethoxy, propoxy, or butoxy; and $C_{2-6}$ alkenyl substituted with OH, methoxy, ethoxy, propoxy, or butoxy;

$R^{41}$, at each occurrence, is independently selected from

H, $CF_3$, halo, OH, $CO_2H$, $SO_2R^{45}$, $NR^{46}R^{47}$, $NO_2$, CN, $C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from

H, $CF_3$, halo, OH, $CO_2H$, $SO_2R^{45}$, $NR^{46}R^{47}$, $NO_2$, CN, CH(═NH)$NH_2$, NHC(═NH)$NH_2$, $C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

k is 1;

m is 1; and n is 1 or 2.

[10] In another even further more preferred embodiment of the present invention, X is —O—;

$R^1$ is selected from H, $C_{1-5}$ alkyl substituted with 0–1 $R^2$, $C_{2-5}$ alkenyl substituted with 0–1 $R^2$, and $C_{2-3}$ alkynyl substituted with 0–1 $R^2$;

$R^2$ is $C_{3-6}$ cycloalkyl;

$R^5$ is H, methyl, ethyl, or propyl;

$R^{6a}$ is H, methyl, or ethyl;

$R^{6b}$ is H;

$R^7$ and $R^9$, at each occurrence, are independently selected from H, F, Cl, —$CH_3$, —$OCH_3$, —$CF_3$, —$OCF_3$, —CN, and —$NO_2$, $R^8$ is selected from methyl substituted with $R^{11}$;

ethenyl substituted with $R^{11}$;

$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from phenyl-substituted with 0–5 fluoro;

2-($H_3CCH_2C$(═O)-phenyl-substituted with $R^{33}$;

2-($H_3CC$(═O))-phenyl-substituted with $R^{33}$;

2-(HC(═O))-phenyl-substituted with $R^{33}$;

2-($H_3CCH$(OH))-phenyl-substituted with $R^{33}$;

2-($H_3CCH_2CH$(OH))-phenyl-substituted with $R^{33}$;

2-($HOCH_2$)-phenyl-substituted with $R^{33}$;

2-($HOCH_2CH_2$)-phenyl-substituted with $R^{33}$;

2-($H_3COCH_2$)-phenyl-substituted with $R^{33}$;

2-($H_3COCH_2CH_2$)-phenyl-substituted with $R^{33}$;

2-($H_3CCH$(OMe))-phenyl-substituted with $R^{33}$;

2-($H_3COC$(═O))-phenyl-substituted with $R^{33}$;

2-($HOCH_2CH$═CH)-phenyl-substituted with $R^{33}$;

2-((MeOC═O)CH═CH)-phenyl-substituted with $R^{33}$;

2-(methyl)-phenyl-substituted with $R^{33}$;

2-(ethyl)-phenyl-substituted with $R^{33}$;

2-(i-propyl)-phenyl-substituted with $R^{33}$;

2-($F_3C$)-phenyl-substituted with $R^{33}$;

2-(NC)-phenyl-substituted with $R^{33}$;

2-($H_3CO$)-phenyl-substituted with $R^{33}$;

2-(fluoro)-phenyl-substituted with $R^{33}$;

2-(chloro)-phenyl-substituted with $R^{33}$;

3-(NC)-phenyl-substituted with $R^{33}$;

3-($H_3CO$)-phenyl-substituted with $R^{33}$;

3-(fluoro)-phenyl-substituted with $R^{33}$;

3-(chloro)-phenyl-substituted with $R^{33}$;

4-(NC)-phenyl-substituted with $R^{33}$;

4-(fluoro)-phenyl-substituted with $R^{33}$;

4-(chloro)-phenyl-substituted with $R^{33}$;

4-($H_3CS$)-phenyl-substituted with $R^{33}$;

4-($H_3CO$)-phenyl-substituted with $R^{33}$;

4-(ethoxy)-phenyl-substituted with $R^{33}$;

4-(i-propoxy)-phenyl-substituted with $R^{33}$;

4-(butoxy)-phenyl-substituted with $R^{33}$;

4-($H_3CCH_2CH_2C$(═O))-phenyl-substituted with $R^{33}$;

4-($(H_3C)_2CHC$(═O))-phenyl-substituted with $R^{33}$;

4-($H_3CCH_2C$(═O))-phenyl-substituted with $R^{33}$;

4-($H_3CC$(═O))-phenyl-substituted with $R^{33}$;

4-($H_3CCH_2CH_2CH$(OH))-phenyl-substituted with $R^{33}$;

4-($(H_3C)_2CHCH$(OH))-phenyl-substituted with $R^{33}$;

4-($H_3CCH_2CH$(OH))-phenyl-substituted with $R^{33}$;

4-($H_3CCH$(OH))-phenyl-substituted with $R^{33}$;

4-(cyclopropyloxy)-phenyl-substituted with $R^{33}$;

4-(cyclobutyloxy)-phenyl-substituted with $R^{33}$;

4-(cyclopentyloxy)-phenyl-substituted with $R^{33}$;

$R^{12}$ is selected from phenyl-substituted with 0–5 fluoro;

2-($H_3CCH_2C$(═O))-phenyl-substituted with $R^{33}$;

2-($H_3CC$(═O))-phenyl-substituted with $R^{33}$;

2-(HC(═O))-phenyl-substituted with $R^{33}$;

2-($H_3CCH$(OH))-phenyl-substituted with $R^{33}$;

2-($H_3CCH_2CH$(OH))-phenyl-substituted with $R^{33}$;

2-($HOCH_2$)-phenyl-substituted with $R^{33}$;

2-($HOCH_2CH_2$)-phenyl-substituted with $R^{33}$;

2-($H_3COCH_2$)-phenyl-substituted with $R^{33}$;

2-($H_3COCH_2CH_2$)-phenyl-substituted with $R^{33}$;

2-($H_3CCH$(OMe))-phenyl-substituted with $R^{33}$;

2-($H_3COC$(═O))-phenyl-substituted with $R^{33}$;

2-($HOCH_2CH$═CH)-phenyl-substituted with $R^{33}$;

2-((MeOC═O)CH═CH)-phenyl-substituted with $R^{33}$;

2-(methyl)-phenyl-substituted with $R^{33}$;

2-(ethyl)-phenyl-substituted with $R^{33}$;

2-(i-propyl)-phenyl-substituted with $R^{33}$;

2-($F_3C$)-phenyl-substituted with $R^{33}$;

2-(NC)-phenyl-substituted with $R^{33}$;

2-($H_3CO$)-phenyl-substituted with $R^{33}$;

2-(fluoro)-phenyl-substituted with $R^{33}$;

2-(chloro)-phenyl-substituted with $R^{33}$;

3-(NC)-phenyl-substituted with $R^{33}$;

3-($H_3CO$)-phenyl-substituted with $R^{33}$;

3-(fluoro)-phenyl-substituted with $R^{33}$;

3-(chloro)-phenyl-substituted with $R^{33}$;

4-(NC)-phenyl-substituted with $R^{33}$;

4-(fluoro)-phenyl-substituted with $R^{33}$;

4-(chloro)-phenyl-substituted with $R^{33}$;

4-($H_3CS$)-phenyl-substituted with $R^{33}$;

4-($H_3CO$)-phenyl-substituted with $R^{33}$;

4-(ethoxy)-phenyl-substituted with $R^{33}$;

4-(i-propoxy)-phenyl-substituted with $R^{33}$;

4-(i-butoxy)-phenyl-substituted with $R^{33}$;

4-($H_3CCH_2CH_2C(=O)$)-phenyl-substituted with $R^{33}$;

4-($(H_3C)_2CHC(=O)$)-phenyl-substituted with $R^{33}$;

4-($H_3CCH_2C(=O)$)-phenyl-substituted with $R^{33}$;

4-($H_3CC(=O)$)-phenyl-substituted with $R^{33}$;

4-($H_3CCH_2CH_2CH(OH)$)-phenyl-substituted with $R^{33}$;

4-($(H_3C)_2CHCH(OH)$)-phenyl-substituted with $R^{33}$;

4-($H_3CCH_2CH(OH)$)-phenyl-substituted with $R^{33}$;

4-($H_3CCH(OH)$)-phenyl-substituted with $R^{33}$;

4-(cyclopropyloxy)-phenyl-substitutued with $R^{33}$;

4-(cyclobutyloxy)-phenyl-substituted with $R^{33}$;

4-(cyclopentyloxy)-phenyl-substituted with $R^{33}$;

$R^{13}$ is H, methyl, or ethyl;

alternatively, $R^{12}$ and $R^{13}$ join to form a 5- or 6-membered ring selected from pyrrolyl, pyrrolidinyl, imidazolyl, piperidinyl, piperizinyl, methylpiperizinyl,and morpholinyl;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, benztriazolyl, benzoxazolyl, benzoxazolinyl, benzthiazolyl, and dioxobenzthiazolyl; wherein said bicyclic heterocyclic ring system is substituted with 0–1 $R^{16}$;

$R^{15}$ is H, methyl, ethyl, propyl, or butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{33}$, at each occurrence, is independently selected from H, F, Cl, —$CH_3$, —$OCH_3$, —$CF_3$, —$OCF_3$, —CN, and —$NO_2$;

k is 1;

m is 1; and n is 1 or 2.

[11] In another even more preferred embodiment of the present invention, the compound of Formula (I) is selected from Formula (I-a):

(I-a)

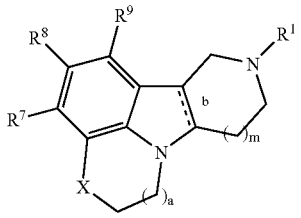

wherein:

b is a single bond or a double bond;

X is —S— or —O—;

$R^1$ is selected from hydrogen, methyl, ethyl, n-propyl, n-butyl, s-butyl, t-butyl, n-pentyl, n-hexyl, 2-propyl, 2-butyl, 2-pentyl, 2hexyl, 2-methylpropyl, 2-methylbutyl, 2-methylpentyl, 2-ethylbutyl, 3-methylpentyl, 3-methylbutyl, 4-methylpentyl, 2-fluoroethyl, 2,2-difluoroethyl, 2,2,2-trifluoroethyl, 2-propenyl, 2-methyl-2-propenyl, trans-2-butenyl, 3-methyl-butenyl, 3-butenyl, trans-2-pentenyl, cis-2-pentenyl, 4-pentenyl, 4-methyl-3-pentenyl, 3,3-dichloro-2-propenyl, trans-3-phenyl-2-propenyl, cyclopropyl, cyclobutyl, cyclopentyl, cyclohexyl, cyclopropylmethyl, cyclobutylmethyl, cyclopentylmethyl, cyclohexylmethyl, benzyl, 2-methylbenzyl, 3-methylbenzyl, 4-methylbenzyl, 2,5-dimethylbenzyl, 2,4-dimethylbenzyl, 3,5dimethylbenzyl, 2,4,6-trimethyl-benzyl, 3-methoxy-benzyl, 3,5-dimethoxy-benzyl, pentafluorobenzyl, 2-phenylethyl, 1-phenyl-2-propyl, 4-phenylbutyl, 4-phenylbenzyl, 2-phenylbenzyl, (2,3-dimethoxy-phenyl)C(=O)—, (2,5-dimethoxy-phenyl)C(=O)—, (3,4-dimethoxy-phenyl)C(=O)—, (3,5-dimethoxy-phenyl)C(=O)—, cyclopropyl-C(=O)—, isopropyl-C(=O)—, ethyl-$CO_2$—, propyl-$CO_2$—, 1-butyl-$CO_2$—, 2,6-dimethoxy-benzyl, 2,4-dimethoxy-benzyl, 2,4,6-trimethoxy-benzyl, 2,3-dimethoxy-benzyl, 2,4,5-trimethoxy-benzyl, 2,3,4-trimethoxy-benzyl, 3,4-dimethoxy-benzyl, 3,4,5-trimethoxy-benzyl, (4-fluoro-phenyl)ethyl, —CH=$CH_2$, —$CH_2$—CH=$CH_2$, —CH=CH—$CH_3$, —C≡CH, —C≡C—$CH_3$, and —$CH_2$—C≡CH;

$R^7$, $R^8$, and $R^9$, at each occurrence, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl, methylC(=O)—, ethylC(=O)—, propylC(=O)—, isopropylC(=O)—, butylC(=O)—, phenylC(=O)—, methyl$CO_2$—, ethyl$CO_2$—, propyl$CO_2$—, isopropyl$CO_2$—, butyl$CO_2$—, phenyl$CO_2$—, dimethylamino-S(=O)—, diethylamino-S(=O)—, dipropylamino-S(=O)—, di-isopropylamino-S(=O)—, dibutylamino-S(=O)—, diphenylamino-S(=O)—, dimethylamino-$SO_2$—, diethylamino-$SO_2$—, dipropylamino-$SO_2$—, di-isopropylamino-$SO_2$—, dibutylamino-$SO_2$—, diphenylamino-$SO_2$—, dimethylamino-C(═O)—, diethylamino-C(═O)—, dipropylamino-C(═O)—, di-isopropylamino-C(═O)—, dibutylamino-C(═O)—, diphenylamino-C(═O)—, 2-chlorophenyl, 2-fluorophenyl, 2-bromophenyl, 2-cyanophenyl, 2-methylphenyl, 2-trifluoromethylphenyl, 2-methoxyphenyl, 2-trifluoromethoxyphenyl, 3-chlorophenyl, 3-fluorophenyl, 3-bromophenyl, 3-cyanophenyl, 3-methylphenyl, 3-ethylphenyl, 3-propylphenyl, 3-isopropylphenyl, 3-butylphenyl, 3-trifluoromethylphenyl, 3-methoxyphenyl, 3-isopropoxyphenyl, 3-trifluoromethyoxyphenyl, 3-thiomethoxyphenyl, 4-chlorophenyl, 4-fluorophenyl, 4-bromophenyl, 4-cyanophenyl, 4-methylphenyl, 4-ethylphenyl, 4-propylphenyl, 4-isopropylphenyl, 4-butylphenyl, 4-trifluoromethylphenyl, 4-methoxyphenyl, 4-isopropoxyphenyl, 4-trifluoromethoxyphenyl, 4-thiomethoxyphenyl, 2,3-dichlorophenyl, 2,3-difluorophenyl, 2,3-dimethylphenyl, 2,3-ditrifluoromethylphenyl, 2,3-dimethoxyphenyl, 2,3-ditrifluoromethoxyphenyl, 2,4-dichlorophenyl, 2,4-difluorophenyl, 2,4-dimethylphenyl, 2,4-ditrifluoromethylphenyl, 2,4-dimethoxyphenyl, 2,4-ditrifluoromethoxyphenyl, 2,5-dichlorophenyl, 2,5-difluorophenyl, 2,5-dimethylphenyl, 2,5-ditrifluoromethylphenyl, 2,5-dimethoxyphenyl, 2,5-ditrifluoromethoxyphenyl, 2,6-dichlorophenyl, 2,6-difluorophenyl, 2,6-dimethylphenyl, 2,6-ditrifluoromethylphenyl, 2,6-dimethoxyphenyl, 2,6-ditrifluoromethoxyphenyl, 3,4-dichlorophenyl, 3,4-difluorophenyl, 3,4-dimethylphenyl, 3,4-ditrifluoromethylphenyl, 3,4-dimethoxyphenyl, 3,4-ditrifluoromethoxyphenyl, 2,4,6-trichlorophenyl, 2,4,6-trifluorophenyl, 2,4,6-trimethylphenyl, 2,4,6-tritrifluoromethylphenyl, 2,4,6-trimethoxyphenyl, 2,4,6-tritrifluoromethoxyphenyl, 2-chloro-4-$CF_3$-phenyl, 2-fluoro-3-chloro-phenyl, 2-chloro-4-$CF_3$-phenyl, 2-chloro-4-methoxy-phenyl, 2-methoxy-4-isopropyl-phenyl, 2-$CF_3$-4-methoxy-phenyl, 2-methyl-4-methoxy-5-fluoro-phenyl, 2-methyl-4-methoxy-phenyl, 2-chloro-4-$CF_3O$-phenyl, 2,4,5-trimethyl-phenyl, 2-methyl-4-chloro-phenyl, methyl-C(═O)NH—, ethyl-C(═O)NH—, propyl-C(═O)NH—, isopropyl-C(═O)NH—, butyl-C(═O)NH—, phenyl-C(═O)NH—, 4-acetylphenyl, 3-acetamidophenyl, 4-pyridyl, 2-furanyl, 2-thiophenyl, 2-naphthyl, 2-Me-5-F-phenyl, 2-F-5-Me-phenyl, 2-MeO-5-F-phenyl, 2-Me-3-Cl-phenyl, 3-$NO_2$-phenyl, 2-$NO_2$-phenyl, 2-Cl-3-Me-phenyl, 2-Me-4-EtO-phenyl, 2-Me-4-F-phenyl, 2-Cl-6-F-phenyl, 2-Cl-4-($CHF_2$)O-phenyl, 2,4-diMeO-6-F-phenyl, 2-$CF_3$-6-F-phenyl, 2-MeS-phenyl, 2,6-diCl-4-MeO-phenyl, 2,3,4-triF-phenyl, 2,6-diF-4-Cl-phenyl, 2,3,4,6-tetraF-phenyl, 2,3,4,5,6-pentaF-phenyl, 2-$CF_3$-4-EtO-phenyl, 2-$CF_3$-4-iPrO-phenyl, 2-$CF_3$-4-Cl-phenyl, 2-$CF_3$-4-F-phenyl, 2-Cl-4-EtO-phenyl, 2-Cl-4-iPrO-phenyl, 2-Et-4-MeO-phenyl, 2-CHO-4-MeO-phenyl, 2-CH(OH)Me-4-MeO-phenyl, 2-CH(OMe)Me-4-MeO-phenyl, 2-C(═O)Me-4-MeO-phenyl, 2-$CH_2$(OH)-4-MeO-phenyl, 2-$CH_2$(OMe)-4-MeO-phenyl, 2-CH(OH)Et-4-MeO-phenyl, 2-C(═O)Et-4-MeO-phenyl, (Z)-2-CH═$CHCO_2$Me-4-MeO-phenyl, 2-$CH_2CH_2CO_2$Me-4-MeO-phenyl, (Z)-2-CH═$CHCH_2$(OH)-4-MeO-phenyl, (E)-2-CH═$CHCO_2$Me-4-MeO-phenyl, (E)-2-CH═$CHCH_2$(OH)-4-MeO-phenyl, 2-$CH_2CH_2$OMe-4-MeO-phenyl, 2-F-4-MeO-phenyl, 2-Cl-4-F-phenyl, (2-Cl-phenyl)-CH═CH—, (3-Cl-phenyl)-CH═CH—, (2,6-diF-phenyl)-CH═CH—, —$CH_2$CH═$CH_2$, phenyl-CH═CH—, (2-Me-4-MeO-phenyl)-CH═CH—, cyclohexyl, cyclopentyl, cyclohexylmethyl, —$CH_2CH_2CO_2$Et, —$(CH_2)_3CO_2$Et, —$(CH_2)_4CO_2$Et, benzyl, 2-F-benzyl, 3-F-benzyl, 4-F-benzyl, 3-MeO-benzyl, 3-OH-benzyl, 2-MeO-benzyl, 2-OH-benzyl, 2-$CO_2$Me-3-MeO-phenyl, 2-Me-4-CN-phenyl, 2-Me-3-CN-phenyl, 2-$CF_3$-4-CN-phenyl, 3-CHO-phenyl, 3-$CH_2$(OH)-phenyl, 3-$CH_2$(OMe)-phenyl, 3-$CH_2$($NMe_2$)-phenyl, 3-CN-4-F-phenyl, 3-$CONH_2$-4-F-phenyl, 2-$CH_2$($NH_2$)-4-MeO-phenyl-, phenyl-NH—, (4-F-phenyl)-NH—, (2,4-diCl-phenyl)-NH—, phenyl-C(═O)NH—, benzyl-NH—, (2-Me-4-MeO-phenyl)-NH—, (2-F-4-MeO-phenyl)-NH—, (2-Me-4-F-phenyl)-NH—, phenyl-S—, —$NMe_2$, 1-pyrrolidinyl, and —N(tosylate)$_2$, provided that two of $R^7$, $R^8$, $R^9$, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy;

m is 1; and n is 1 of 2.

[12] In another even more preferred embodiment of the present invention, the compound of Formula (I) is selected from Formula (II):

(II)

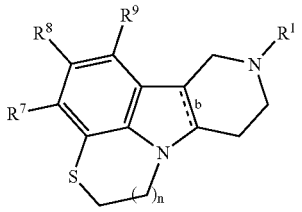

wherein:

b is a single bond, wherein the bridge hydrogens are in a cis position;

$R^1$ is selected from hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl, 4-methylpentyl, 2-fluoroethyl, 2,2-difluoroethyl, 2,2,2-trifluoroethyl, 2-propenyl, 2-methyl-2-propenyl, trans-2-butenyl, 3-methyl-butenyl, 3-butenyl, trans-2-pentenyl, cis-2-pentenyl, 4-pentenyl, 4-methyl-3-pentenyl, 3,3-dichloro-2-propenyl, trans-3-phenyl-2-propenyl, cyclopropyl, cyclobutyl, cyclopentyl, cyclohexyl, cyclopropylmethyl, cyclobutylmethyl, cyclopentylmethyl, cyclohexylmethyl, —CH═$CH_2$, —$CH_2$—CH═$CH_2$, —CH═CH—$CH_3$, —C≡CH, —C≡C—$CH_3$, and —$CH_2$—C≡CH;

$R^7$ and $R^9$, at each occurrence, are independently selected from hydrogen, fluoro, methyl, trifluoromethyl, and methoxy;

$R^8$ is selected from hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl, methylC(═O)—, ethylC(═O)—, propylC(═O)—, isopropylC(═O)—, butylC(═O)—, phenylC(═O)—, methyl$CO_2$—, ethyl$CO_2$—, propyl$CO_2$—, isopropyl$CO_2$—, butyl$CO_2$—, phenyl$CO_2$—, dimethylamino-S(═O)—, diethylamino-S(═O)—, dipropylamino-S(═O)—, di-isopropylamino-S(═O)—, dibutylamino-S(═O)—, diphenylamino-S(═O)—, dimethylamino-$SO_2$—, diethylamino-$SO_2$—, dipropylamino-$SO_2$—, di-isopropylamino-$SO_2$—, dibutylamino-$SO_2$—, diphenylamino-$SO_2$—, dimethylamino-C(═O)—, diethylamino-C(═O)—, dipropylamino-C(═O)—, di-isopropylamino-C(═O)—, dibutylamino-C(═O)—, diphenylamino-C(═O)—, 2-chlorophenyl, 2-fluorophenyl, 2-bromophenyl, 2-cyanophenyl, 2-methylphenyl, 2-trifluoromethylphenyl, 2-methoxyphenyl, 2-trifluoromethoxyphenyl, 3-chlorophenyl, 3-fluorophenyl, 3-bromophenyl, 3-cyanophenyl, 3-methylphenyl, 3-ethylphenyl, 3-propylphenyl, 3-isopropylphenyl, 3-butylphenyl, 3-trifluoromethylphenyl, 3-methoxyphenyl, 3-isopropoxyphenyl, 3-trifluoromethoxyphenyl, 3-thiomethoxyphenyl, 4-chlorophenyl, 4-fluorophenyl, 4-bromophenyl, 4-cyanophenyl, 4-methylphenyl, 4-ethylphenyl, 4-propylphenyl, 4-isopropylphenyl, 4-butylphenyl, 4-isopropoxyphenyl, 4-trifluoromethoxyphenyl, 4-thiomethoxyphenyl, 2,3-dichlorophenyl, 2,3-difluorophenyl, 2,3-dimethylphenyl, 2,3-ditrifluoromethylphenyl, 2,3-dimethoxyphenyl, 2,3-ditrifluoromethoxyphenyl, 2,4-dichlorophenyl, 2,4-difluorophenyl, 2,4-dimethylphenyl, 2,4-ditrifluoromethylphenyl, 2,4-dimethoxyphenyl, 2,4-ditrifluoromethoxyphenyl, 2,5dichlorophenyl, 2,5-difluorophenyl, 2,5-dimethylphenyl, 2,5-ditrifluoromethylphenyl, 2,5-dimethoxyphenyl, 2,5-ditrifluoromethoxyphenyl, 2,6-dichlorophenyl, 2,6-difluorophenyl, 2,6-dimethylphenyl, 2,6-ditrifluoromethylphenyl, 2,6-dimethoxyphenyl, 2,6-ditrifluoromethoxyphenyl, 3,4-dichlorophenyl, 3,4-difluorophenyl, 3,4-dimethylphenyl, 3,4-ditrifluoromethylphenyl, 3,4-dimethoxyphenyl, 3,4-ditrifluoromethoxyphenyl, 2,4,6-trichlorophenyl, 2,4,6-trifluorophenyl, 2,4,6-trimethylphenyl, 2,4,6-tritrifluoromethylphenyl, 2,4,6-trimethoxyphenyl, 2,4,6-tritrifluoromethoxyphenyl, 2-chloro-4-$CF_3$-phenyl, 2-fluoro-3-chloro-phenyl, 2-chloro-4-$CF_3$-phenyl, 2-chloro-4-methoxy-phenyl, 2-methoxy-4-isopropyl-phenyl, 2-$CF_3$-4-methoxy-phenyl, 2-methyl-4-methoxy-5-fluoro-phenyl, 2-methyl-4-methoxy-phenyl, 2-chloro-4-$CF_3O$-phenyl, 2,4,5-trimethyl-phenyl, 2-methyl-4-chloro-phenyl, methyl-C(═O)NH—, ethyl-C(═O)NH—, propyl-C(═O)NH—, isopropyl-C(═O)NH—, butyl-C(═O)NH—, phenyl-C(═O)NH—, 4-acetylphenyl, 3-acetamidophenyl, 4-pyridyl, 2-furanyl, 2-thiophenyl, 2-naphthyl;

2-Me-5-F-phenyl, 2-F-5-Me-phenyl, 2-MeO-5-F-phenyl, 2-Me-3-Cl-phenyl, 3-$NO_2$-phenyl, 2-$NO_2$-phenyl, 2-Cl-3-Me-phenyl, 2-Me-4-EtO-phenyl, 2-Me-4-F-phenyl, 2-Cl-6-F-phenyl, 2-Cl-4-($CHF_2$)O-phenyl, 2,4-diMeO-6-F-phenyl, 2-$CF_3$-6-F-phenyl, 2-MeS-phenyl, 2,6-diCl-4-MeO-phenyl, 2,3,4-triF-phenyl, 2,6-diF-4-Cl-phenyl, 2,3,4,6-tetraF-phenyl, 2,3,4,5,6-pentaF-phenyl, 2-$CF_3$-4-EtO-phenyl, 2-$CF_3$-4-iPrO-phenyl, 2-$CF_3$-4-Cl-phenyl, 2-$CF_3$-4-F-phenyl, 2-Cl-4-EtO-phenyl, 2-Cl-4-iPrO-phenyl, 2-Et-4-MeO-phenyl, 2-CHO-4-MeO-phenyl, 2-CH(OH)Me-4-MeO-phenyl, 2-CH(OMe)Me-4-MeO-phenyl, 2-C(═O)Me-4-MeO-phenyl, 2-$CH_2$(OH)-4-MeO-phenyl, 2-$CH_2$(OMe)-4-MeO-phenyl, 2-CH(OH)Et-4-MeO-phenyl, 2-C(═O)Et-4-MeO-phenyl, (Z)-2-CH═CH$CO_2$Me-4-MeO-phenyl, 2-$CH_2CH_2CO_2$Me-4-MeO-phenyl, (Z)-2-CH═CH$CH_2$(OH)-4-MeO-phenyl, (E)-2-CH═CH$CH_2$Me-4-MeO-phenyl, (E)-2-CH═CH$CH_2$(OH)-4-MeO-phenyl, 2-$CH_2CH_2$OMe-4-MeO-phenyl, 2-F-4-MeO-phenyl, 2-Cl-4-F-phenyl, (2-Cl-phenyl)-CH═CH—, (3-Cl-phenyl)-CH═CH—, (2,6-diF-phenyl)-CH═CH—, —$CH_2$CH═$CH_2$, phenyl-CH═CH—, (2-Me-4-MeO-phenyl)-CH═CH—, cyclohexyl, cyclopentyl, cyclohexylmethyl, —$CH_2CH_2CO_2$Et, —$(CH_2)_3CO_2$Et, —$(CH_2)_4CO_2$Et, benzyl, 2-F-benzyl, 3-F-benzyl, 4-F-benzyl, 3-MeO-benzyl, 3-OH-benzyl, 2-MeO-benzyl, 2-OH-benzyl, 2-$CO_2$Me-3-MeO-phenyl, 2-Me-4-CN-phenyl, 2-Me-3-CN-phenyl, 2-$CF_3$-4-CN-phenyl, 3-CHO-phenyl, 3-$CH_2$(OH)-phenyl, 3-$CH_2$(OMe)-phenyl, 3-$CH_2$($NMe_2$)-phenyl, 3-CN-4-F-phenyl, 3-$CONH_2$-4-F-phenyl, 2-$CH_2$($NH_2$)-4-MeO-phenyl, phenyl-NH—, (4-F-phenyl)-NH—, (2,4-diCl-phenyl)-NH—, phenyl-C(═O)NH—, benzyl-NH—, (2-Me-4-MeO-phenyl)-NH—, (2-F-4-MeO-phenyl)-NH—, (2-Me-4-F-phenyl)-NH—, phenyl-S—, —$NMe_2$, 1-pyrrolidinyl, and —N(tosylate)$_2$; and n is 1 or 2.

[13] In another even more preferred embodiment of the present invention, the compound of Formula (I) is selected from Formula (III):

(III)

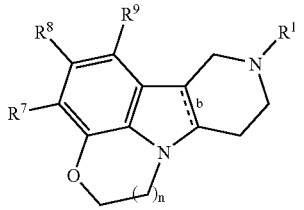

wherein:

b is a single bond, wherein the bridge hydrogens are in a cis position;

$R^1$ is selected from hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl, 4-methylpentyl, 2-fluoromethyl, 2,2-difluoroethyl, 2,2,2-trifluoroethyl, 2-propenyl, 2-methyl-2-propenyl, trans-2-butenyl, 3-methyl-butenyl, 3-butenyl, trans-2-pentenyl, cis-2-pentenyl, 4-pentenyl, 4-methyl-3-pentenyl, 3,3-dichloro-2-propenyl, trans-3-phenyl-2-propenyl, cyclopropyl, cyclobutyl, cyclopentyl, cyclohexyl, cyclopropylmethyl, cyclobutylmethyl, cyclopentylmethyl, cyclohexylmethyl, —CH═$CH_2$, —$CH_2$—CH═$CH_2$, —CH═CH—$CH_3$, —C≡CH, —C≡C—$CH_3$, and —$CH_2$—C≡CH;

$R^7$ and $R^9$, at each occurrence, are independently selected from hydrogen, fluoro, methyl, trifluoromethyl, and methoxy; and $R^8$ is selected from hydrogen, fluoro, chloro, bromo, cyano, methyl, ethyl, propyl, isopropyl, butyl, t-butyl, nitro, trifluoromethyl, methoxy, ethoxy, isopropoxy, trifluromethoxy, phenyl, methylC(═O)—, ethylC(═O)—, propylC(═O)—, isopropylC(═O)—, butylC(═O)—, phenylC(═O)—, methyl$CO_2$—, ethyl$CO_2$—, propyl$CO_2$—, isopropyl$CO_2$—, butyl$CO_2$—, phenyl$CO_2$—, dimethylamino-S(═O)—, diethylamino-S(═O)—, dipropylamino-S(═O)—, di-isopropylamino-S(═O)—, dibutylamino-S(═O)—, diphenylamino-S(═O)—, dimethylamino-$SO_2$—, diethylamino-$SO_2$—, dipropylamino-$SO_2$—, di-isopropylamino-$SO_2$—, dibutylamino-$SO_2$—, diphenylamino-$SO_2$—, dimethylamino-C(═O)—, diethylamino-C(═O)—, dipropylamino-C(═O)—, di-isopropylamino-C(═O)—, dibutylamino-C(═O)—, diphenylamino-C(═O)—, 2-chlorophenyl, 2-flurophenyl, 2-bromophenyl, 2-cyanophenyl, 2-methylphenyl, 2-trifluoromethylphenyl, 2-methoxyphenyl, 2-trifluoromethoxyphenyl, 3-chlorophenyl, 3-fluorophenyl, 3-bromophenyl, 3-cyanophenyl, 3-methylphenyl, 3-ethylphenyl, 3-propylphenyl, 3-isopropylphenyl, 3-butylphenyl, 3-trifluoromethylphenyl, 3-methoxyphenyl, 3-isopropoxyphenyl, 3-trifluoromethoxyphenyl, 3-thiomethoxyphenyl, 4-chlorophenyl, 4-fluorophenyl, 4-bromophenyl, 4-cyanophenyl, 4-methylphenyl, 4-ethylphenyl, 4-propylphenyl, 4-isopropylphenyl, 4-butylphenyl, 4-isopropoxyphenyl, 4-trifluoromethoxyphenyl, 4-thiomethoxyphenyl, 2,3-dichlorophenyl, 2,3-difluorophenyl, 2,3-dimethylphenyl, 2,3-ditrifluoromethylphenyl, 2,3-dimethoxyphenyl, 2,3-ditrifluoromethoxyphenyl, 2,4-dichlorophenyl, 2,4-difluorophenyl, 2,4-dimethylphenyl, 2,4-ditrifluoromethylphenyl, 2,4-dimethoxyphenyl, 2,4-ditrifluoromethyoxyphenyl, 2,5-dichlorophenyl, 2,5-difluorophenyl, 2,5-dimethylphenyl, 2,5-ditrifluoromethylphenyl, 2,5-dimethoxyphenyl, 2,5-ditrifluoromethyoxyphenyl, 2,6-dichlorophenyl, 2,6-difluorophenyl, 2,6-dimethylphenyl, 2,6-ditrifluoromethylphenyl, 2,6-dimethoxyphenyl, 2,5-ditrifluoromethyoxyphenyl, 3,4-dichlorophenyl, 3,4-difluorophenyl, 3,4-dimethylphenyl, 3,4-ditrifluoromethylphenyl, 3,4-dimethoxyphenyl, 3,4-ditrifluoromethyoxyphenyl, 2,4,6-trichlorophenyl, 2,4,6-trifluorophenyl, 2,4,6-trimethylphenyl, 2,4,6-tritrifluoromethylphenyl, 2,4,6-trimethyoxyphenyl, 2,4,6-tritrifluoromethoxyphenyl, 2-chloro-4-$CF_3$-phenyl, 2-fluoro-3-chloro-phenyl, 2-chloro-4-$CF_3$-phenyl, 2-chloro-4-methoxy-phenyl, 2-methoxy-4-isopropyl-phenyl, 2-$CF^3$-4-methoxy-phenyl, 2-methyl-4-methoxy-5-fluoro-phenyl, 2-methyl-4-methoxy-phenyl, 2-chloro-4-$CF_3O$-phenyl, 2,4,5-trimethyl-phenyl, 2-methyl-4-chloro-phenyl, methyl-C(═O)NH—, ethyl-C(═O)NH—, propyl-C(═O)NH—, isopropyl-C(═O)NH—, butyl-C(═O)NH—, phenyl-C(═O)NH—, 4-acetylphenyl, 3-acetamidophenyl, 4-pyridyl, 2-furanyl, 2-thiophenyl, 2-naphthyl;

2-Me-5-F-phenyl, 2-F-5-Me-phenyl, 2-MeO-5-F-phenyl, 2-Me-3-Cl-phenyl, 3-$NO_2$-phenyl, 2-$NO_2$-phenyl, 2-Cl-3-Me-phenyl, 2-Me-4-EtO-phenyl, 2-Me-4-F-phenyl, 2-Cl-6-F-phenyl, 2-Cl-4-($CHF_2$)O-phenyl, 2,4-diMeO-6-F-phenyl, 2-$CF_3$-6-F-phenyl, 2-MeS-phenyl, 2,6-diCl-4-MeO-phenyl, 2,3,4-triF-phenyl, 2,6-diF-4-Cl-phenyl, 2,3,4,6-tetraF-phenyl, 2,3,4,5,6-pentaF-phenyl, 2-$CF_3$-4-EtO-phenyl, 2-$CF_3$-4-iPrO-phenyl, 2-$CF_3$-4-Cl-phenyl, 2-$CF_3$-4-F-phenyl, 2-Cl-4-EtO-phenyl, 2-Cl-4-iPrO-phenyl, 2-Et-4-MeO-phenyl, 2-CHO-4-MeO-phenyl, 2-CH(OH)Me-4-MeO-phenyl, 2-CH(OMe)Me-4-MeO-phenyl, 2-C(═O)Me-4-MeO-phenyl, 2-$CH_2$(OH)-4-MeO-phenyl, 2-$CH_2$(OMe)-4-MeO-phenyl, 2-CH(OH)Et-4-MeO-phenyl, 2-C(═O)Et-4-MeO-phenyl, (Z)-2-CH═CH$CO_2$Me-4-MeO-phenyl, 2$CH_2CH_2CO_2$Me-4-MeO-phenyl, (Z)-2-CH═CH$CH_2$(OH)-4-MeO-phenyl, (E)-2-CH═CH$CO_2$Me-4-MeO-phenyl, (E)-2-CH═CH$CH_2$(OH)-4-MeO-phenyl, 2-$CH_2CH_2$OME-4-MeO-phenyl, 2-F-4-MeO-phenyl, 2-Cl-4-F-phenyl, (2-Cl-phenyl)-CH═CH—, (3-Cl-phenyl)-CH═CH—, (2,6-diF-phenyl)-CH═CH—, —$CH_2$CH═$CH_2$, phenyl-CH═CH—, (2-Me-4-MeO-phenyl)-CH═CH—, cyclohexyl, cyclopentyl, cyclohexylmethyl, —$CH_2CH_2CO_2$Et, —$(CH_2)_3CO_2$Et, —$(CH_2)_4CO_2$Et, benzyl, 2-F-benzyl, 3-F-benzyl, 4-F-benzyl, 3-MeO-benzyl, 3-OH-benzyl, 2-MeO-benzyl, 2-OH-benzyl, 2-$CO_2$Me-3-MeO-phenyl, 2-Me-4-CN-phenyl, 2-Me-3-CN-phenyl, 2-$CF_3$-4-CN-phenyl, 3-CHO-phenyl, 3-$CH_2$(OH)-phenyl, 3-$CH_2$(OMe)-phenyl, 3-$CH_2$($NMe_2$)-phenyl, 3-CN-4-F-phenyl, 3-$CONH_2$-4-F-phenyl, 2-$CH_2$($NH_2$)-4-MeO-phenyl-, phenyl-NH—, (4-F-phenyl)-NH—, (2,4-diCl-phenyl)-NH—, phenyl-C(═O)NH—, benzyl-NH—, (2-MeO-phenyl)-NH—, (2-F-4-MeO-phenyl)-NH—, (2-Me-4-F-phenyl)-NH—, phenyl-S—, —$NMe_2$, 1-pyrrolidinyl, and —N(tosylate)$_2$; and n is 1 or 2.

[14] In another preferred embodiment of the present invention,

X is —O—, —S—, —S(═O)—, or —S(═O)$_2$—;

$R^1$ is selected from $C_{1-6}$ alkyl substituted with Z, $C_{2-6}$ alkenyl substituted with Z, $C_{2-6}$ alkynyl substituted with Z, $C_{3-6}$ cycloalkyl substituted with Z, aryl substituted with Z, 5–6 membered heterocyclic ring system containing at least one heteroatom selected from the group consisting of N, O, and S, said heterocyclic ring system substituted with Z;

$C_{1-6}$ alkyl substituted with 0–2 $R^2$, $C_{2-6}$ alkenyl substituted with 0–2 $R^2$, $C_{2-6}$ alkynyl substituted with 0–2 $R^2$, aryl substituted with 0–2 $R^2$, and 5–6 membered heterocyclic ring system containing at least one heteroatom selected from the group consisting of N, O, and S, said heterocyclic ring system substituted with 0–2 $R^2$;

Z is selected from H,

—CH(OH)$R^2$,

—C(ethylenedioxy)$R^2$,

—O$R^2$,

—S$R^2$,

—N$R^2R^3$,

—C(O)$R^2$,

—C(O)N$R^2R^3$,

—N$R^3$C(O)$R^2$,

—C(O)OR$^2$,
—OC(O)R$^2$,
—CH(═NR$^4$)NR$^2$R$^3$,
—NHC(═NR$^4$)NR$^2$R$^3$,
—S(O)R$^2$,
—S(O)$_2$R$^2$,
—S(O)$_2$NR$^2$R$^3$, and —NR$^3$S(O)$_2$R$^2$;

R$^2$, at each occurrence, is independently selected from
C$_{1-4}$ alkyl,
C$_{2-4}$ alkenyl,
C$_{2-4}$ alkynyl,
C$_{3-6}$ cycloalkyl,
aryl substituted with 0–5 R$^{42}$;
C$_{3-10}$ carbocyclic residue substituted with 0–3 R$^{41}$, and
5–10 membered heterocyclic ring system containing from 1–4 heteroatoms selected from the group consisting of N, O, and S substituted with 0–3 R$^{41}$;

R$^3$, at each occurrence, is independently selected from H, C$_{1-4}$ alkyl, C$_{2-4}$ alkenyl, C$_{2-4}$ alkynyl, and C$_{1-4}$ alkoxy;

alternatively, R$^2$ and R$^3$ join to form a 5- or 6-membered ring optionally substituted with —O— or —N(R$^4$)—;

R$^4$, at each occurrence, is independently selected from H, methyl, ethyl, propyl, and butyl;

R$^5$ is H, methyl, ethyl, propyl, or butyl;

R$^{6a}$ is selected from
H, —OH, —NR$^{46}$R$^{47}$, —CF$_3$,
C$_{1-4}$ alkyl, C$_{2-4}$ alkenyl, C$_{2-4}$ alkynyl, C$_{1-4}$ alkoxy, C$_{1-4}$ haloalkyl, C$_{3-6}$ cycloalkyl, and
aryl substituted with 0–3 R$^{44}$;

R$^{6b}$ is H;

R$^7$, R$^8$, and R$^9$, at each occurrence, are independently selected from
H, halo, —CF$_3$, —OCF$_3$, —OH, —CN, —NO$_2$, —NR$^{46}$R$^{47}$,
C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
C$_{1-4}$ alkyl substituted with 0–2 R$^{11}$,
C$_{3-10}$ carbocyclic residue substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(═NR$^{14}$)NR$^{12}$R$^{13}$, NHC(═NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

R$^{11}$ is selected from
H, halo, —CF$_3$, —CN, —NO$_2$,
C$_{1-8}$ alkyl, C$_{2-8}$ alkenyl, C$_{2-8}$ alkynyl, C$_{1-4}$ haloalkyl, C$_{1-8}$ alkoxy, C$_{3-10}$ cycloalkyl,
C$_{3-10}$ carbocyclic residue substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(═NR$^{14}$)NR$^{12}$R$^{13}$, NHC(═NR$^{14}$)NR$^{12}$R$^{13}$, S(O)R$^{12}$, S(O)R$^{12}$, S(O)$_2$R$^{12}$, S(O)NR$^{12}$R$^{13}$, S(O)$_3$NR$^{12}$R$^{13}$, NR$^{14}$S(O)R$^{12}$, and NR$^{14}$S(O)$_2$R$^{12}$;

R$^{12}$, at each occurrence, is independently selected from
C$_{1-4}$ alkyl,
C$_{2-4}$ alkenyl,
C$_{2-4}$ alkynyl,
C$_{3-6}$ cycloalkyl,
phenyl substituted with 0–5 R$^{33}$;
C$_{3-10}$ carbocyclic residue substituted with 0–3 R$^{33}$, and
5–10 membered heterocyclic ring system containing from 1–4 heteroatoms selected from the group consisting of N, O, and S substituted with 0–3 R$^{31}$;

R$^{13}$, at each occurrence, is independently selected from H, C$_{1-4}$ alkyl, C$_{2-4}$ alkenyl, and C$_{2-4}$ alkynyl;

alternatively, R$^{12}$ and R$^{13}$ join to form a 5- or 6-membered ring optionally substituted with —O— or —N(R$^{14}$)—;

R$^{14}$, at each occurrence, is independently selected from H and C$_{1-4}$ alkyl;

R$^{31}$, at each occurrence, is independently selected from H, OH, halo, CF$_3$, SO$_2$R$^{45}$, NR$^{46}$R$^{47}$, methyl, ethyl, and propyl;

R$^{33}$, at each occurrence, is independently selected from H, OH, halo, CN, NO$_2$, CF$_3$, SO$_2$R$^{45}$, NR$^{46}$R$^{47}$, C$_{1-3}$ alkyl, C$_{2-3}$ alkenyl, C$_{2-3}$ alkynyl, C$_{3-5}$ cycloalkyl, C$_{1-3}$ haloalkyl, C$_{1-3}$ haloalkyl-oxy-, C$_{1-3}$ alkyloxy-, C$_{1-3}$ alkylthio-, C$_{1-3}$ alkyl-C(═O)—, and C$_{1-3}$ alkyl-C(═O)NH—;

R$^{41}$, at each occurrence, is independently selected from H, CF$_3$, halo, OH, CO$_2$H, SO$_2$R$^{45}$, NR$^{46}$R$^{47}$, NO$_2$, CN, ═O,
C$_{2-8}$ alkenyl, C$_{2-8}$ alkynyl, C$_{1-4}$ alkoxy, C$_{1-4}$ haloalkyl
C$_{1-4}$ alkyl substituted with 0–1 R$^{43}$,
aryl substituted with 0–3 R$^{42}$, and
5–10 membered heterocyclic ring system containing from 1–4 heteroatoms selected from the group consisting of N, O, and S substituted with 0–3 R$^{44}$;

R$^{42}$, at each occurrence, is independently selected from H, CF$_3$, halo, OH, CO$_2$H, SO$_2$R$^{45}$, SR$^{45}$, NR$^{46}$R$^{47}$, OR$^{48}$, NO$_2$, CN, CH(═NH)NH$_2$, NHC(═NH)NH$_2$,
C$_{2-6}$ alkenyl, C$_{2-6}$ alkynyl, C$_{1-4}$ alkoxy, C$_{1-4}$ haloalkyl, C$_{3-6}$ cycloalkyl,
C$_{1-4}$ alkyl substituted with 0–1 R$^{43}$,
aryl substituted with 0–3 R$^{44}$, and
5–10 membered heterocyclic ring system containing from 1–4 heteroatoms selected from the group consisting of N, O, and S substituted with 0–3 R$^{44}$;

R$^{43}$ is C$_{3-6}$ cycloalkyl or aryl substituted with 0–3 R$^{44}$;

R$^{44}$, at each occurrence, is independently selected from H, halo, —OH, NR$^{46}$R$^{47}$, CO$_2$H, SO$_2$R$^{45}$, —CF$_3$, —OCF$_3$, —CN, —NO$_2$, C$_{1-4}$ alkyl, and C$_{1-4}$ alkoxy;

R$^{45}$ is C$_{1-4}$ alkyl;

R$^{46}$, at each occurrence, is independently selected from H and C$_{1-4}$ alkyl;

R$^{47}$, at each occurrence, is independently selected from H, C$_{1-4}$ alkyl, —C(═O)NH(C$_{1-4}$ alkyl), —SO$_2$(C$_{1-4}$ alkyl), —SO$_2$(phenyl), —C(═O)O(C$_{1-4}$ alkyl), —C(═O)(C$_{1-4}$ alkyl), and —C(═O)H;

R$^{48}$, at each occurrence, is independently selected from H, C$_{1-4}$ alkyl, —C(═O)NH(C$_{1-4}$ alkyl), —C(═O)O(C$_{1-4}$ alkyl), —C(═O)(C$_{1-4}$ alkyl), and —C(═O)H;

k is 1 or 2;

m is 0, 1, or 2; and n is 1 or 2.

[15] In another more preferred embodiment of the present invention,

X is —O— or —S—;

$R^1$ is selected from
- $C_{2-5}$ alkyl substituted with Z,
- $C_{2-5}$ alkenyl substituted with Z,
- $C_{2-5}$ alkynyl substituted with Z,
- $C_{3-6}$ cycloalkyl substituted with Z,
- aryl substituted with Z,
- 5–6 membered heterocyclic ring system containing at least one heteroatom selected from the group consisting of N, O, and S, said heterocyclic ring system substituted with Z;
- $C_{1-5}$ alkyl substituted with 0–2 $R^2$,
- $C_{2-5}$ alkenyl substituted with 0–2 $R^2$, and
- $C_{2-5}$ alkynyl substituted with 0–2 $R^2$;

Z is selected from H,
- —CH(OH)$R^2$,
- —C(ethylenedioxy)$R^2$,
- —$OR^2$,
- —$SR^2$,
- —$NR^2R^3$,
- —C(O)$R^2$,
- —C(O)$NR^2R^3$,
- —$NR^3$C(O)$R^2$,
- —C(O)$OR^2$,
- —OC(O)$R^2$,
- —CH(═$NR^4$)$NR^2R^3$,
- —NHC(═$NR^4$)$NR^2R^3$,
- —S(O)$R^2$,
- —$S(O)_2R^2$,
- —$S(O)_2NR^2R^3$, and —$NR^3S(O)_2R^2$;

$R^2$, at each occurrence, is independently selected from
- $C_{1-4}$ alkyl,
- $C_{2-4}$ alkenyl,
- $C_{2-4}$ alkynyl,
- $C_{3-6}$ cycloalkyl,
- aryl substituted with 0–5 $R^{42}$;
- $C_{3-10}$ carbocyclic residue substituted with 0–3 $R^{41}$, and
- 5–10 membered heterocyclic ring system containing from 1–4 heteroatoms selected from the group consisting of N, O, and S substituted with 0–3 $R^{41}$;

$R^3$, at each occurrence, is independently selected from H, $C_{1-4}$ alkyl, $C_{2-4}$ alkenyl, $C_{2-4}$ alkynyl, and $C_{1-4}$ alkoxy;

alternatively, $R^2$ and $R^3$ join to form a 5- or 6-membered ring optionally substituted with —O— or —N($R^4$)—;

$R^4$, at each occurrence, is independently selected from H, methyl, ethyl, propyl, and butyl;

$R^5$ is H, methyl, or ethyl;

$R^{6a}$ is selected from
- H, —OH, —$NR^{46}R^{47}$, —$CF_3$,
- $C_{1-4}$ alkyl, $C_{2-4}$ alkenyl, $C_{2-4}$ alkynyl, $C_{1-4}$ alkoxy, $C_{1-4}$ haloalkyl, $C_{3-6}$ cycloalkyl;

$R^{6b}$ is H;

$R^7$, $R^8$, and $R^9$, at each occurrence, are independently selected from
- H, halo, —$CF_3$, —$OCF_3$, —OH, —$OCH_3$, —CN, —$NO_2$, —$NR^{46}R^{47}$,
- $C_{1-6}$ alkyl, $C_{2-6}$ alkenyl, $C_{2-6}$ alkynyl, $C_{1-4}$ haloalkyl, $C_{1-6}$ alkoxy, ($C_{1-4}$ haloalkyl)oxy,
- $C_{1-4}$ alkyl substituted with 0–2 $R^{11}$,
- $C_{3-10}$ carbocyclic residue substituted with 0–3 $R^{33}$,
- aryl substituted with 0–5 $R^{33}$,
- 5–10 membered heterocyclic ring system containing from 1–4 heteroatoms selected from the group consisting of N, O, and S substituted with 0–3 $R^{31}$;
- $OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, CH(═$NR^{14}$)$NR^{12}R^{13}$, NHC(═$NR^{14}$)$NR^{12}R^{13}$, S(O)$R^{12}$, $S(O)_2R^{12}$, S(O)$NR^{12}R^{13}$, $NR^{14}S(O)_2R^{12}$, $NR^{14}$S(O)$R^{12}$, $NR^{14}S(O)_2R^{12}$, $NR^{12}$C(O)$R^{15}$, $NR^{12}$C(O)$OR^{15}$, $NR^{12}S(O)_2R^{15}$, and $NR^{12}$C(O)$NHR^{15}$;

$R^{11}$ is selected from
- H, halo, —$CF_3$, —$OCF_3$, —OH, —$OCH_3$, —CN, —$NO_2$, —$NR^{46}R^{47}$,
- $C_{1-6}$ alkyl, $C_{2-6}$ alkenyl, $C_{2-6}$ alkynyl, $C_{1-4}$ haloalkyl, $C_{1-6}$ alkoxy, ($C_{1-4}$ haloalkyl)oxy,
- $C_{3-10}$ carbocyclic residue substituted with 0–3 $R^{33}$,
- aryl substituted with 0–5 $R^{33}$,
- 5–10 membered heterocyclic ring system containing from 1–4 heteroatoms selected from the group consisting of N, O, and S substituted with 0–3 $R^{31}$;
- $OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, CH(═$NR^{14}$)$NR^{12}R^{13}$, NHC(═$NR^{14}$)$NR^{12}R^{13}$, S(O)$R^{12}$, $S(O)_2R^{12}$, S(O)$NR^{12}R^{13}$, and $NR^{14}S(O)_2R^{12}$;

$R^{12}$, at each occurrence, is independently selected from
- $C_{1-4}$ alkyl,
- $C_{2-4}$ alkenyl,
- $C_{2-4}$ alkynyl,
- $C_{3-6}$ cycloalkyl,
- phenyl substituted with 0–5 $R^{33}$;
- $C_{3-10}$ carbocyclic residue substituted with 0–3 $R^{33}$, and
- 5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

$R^{14}$, at each occurrence, is independently selected from H and $C_{1-4}$ alkyl;

$R^{31}$, at each occurrence, is independently selected from H, OH, halo, $CF_3$, methyl, and ethyl;

$R^{33}$, at each occurrence, is independently selected from H, OH, halo, CN, $NO_2$, $CF_3$, methyl, and ethyl;

$R^{41}$, at each occurrence, is independently selected from H, $CF_3$, halo, OH, $CO_2H$, $SO_2R^{45}$, $NR^{46}R^{47}$, $NO_2$, CN, ═O,
- $C_{2-8}$ alkenyl, $C_{2-8}$ alkynyl, $C_{1-4}$ alkoxy, $C_{1-4}$ haloalkyl,
- $C_{1-4}$ alkyl substituted with 0–1 $R^{43}$,
- aryl substituted with 0–3 $R^{42}$, and
- 5–10 membered heterocyclic ring system containing from 1–4 heteroatoms selected from the group consisting of N, O, and S substituted with 0–3 $R^{44}$;

$R^{42}$, at each occurrence, is independently selected from H, $CF_3$, halo, OH, $CO_2H$, $SO_2R^{45}$, $SR^{45}$, $NR^{46}R^{47}$, $OR^{48}$, $NO_2$, CN, CH(═NH)$NH_2$, NHC(═NH)$NH_2$,
- $C_{2-6}$ alkenyl, $C_{2-6}$ alkynyl, $C_{1-4}$ alkoxy, $C_{1-4}$ haloalkyl, $C_{3-6}$ cycloalkyl,
- $C_{1-4}$ alkyl substituted with 0–1 $R^{43}$,
- aryl substituted with 0–3 $R^{44}$, and
- 5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-3}$ alkyl;

$R^{47}$, at each occurrence, is independently selected from H, $C_{1-4}$ alkyl, —C(═O)NH($C_{1-4}$ alkyl), —$SO_2$($C_{1-4}$ alkyl), —$SO_2$(phenyl), —C(═O)O($C_{1-4}$ alkyl), —C(═O)($C_{1-4}$ alkyl), and —C(═O)H;

$R^{48}$, at each occurrence, is independently selected from H, $C_{1-4}$ alkyl, —C(═O)NH($C_{1-4}$ alkyl), —C(═O)O($C_{1-4}$ alkyl), —C(═O)($C_{1-4}$ alkyl), and —C(═O)H;

k is 1 or 2;

m is 0, 1, or 2; and n is 1 or 2.

[16] In another even more preferred embodiment of the present invention,

X is —O—;

$R^1$ is selected from $C_{2-4}$ alkyl substituted with Z, $C_{2-4}$ alkenyl substituted with Z, $C_{2-4}$ alkynyl substituted with Z, $C_{3-6}$ cycloalkyl substituted with Z, aryl substituted with Z, 5–6 membered heterocyclic ring system containing at least one heteroatom selected from the group consisting of N, O, and S, said heterocyclic ring system substituted with Z;

$C_{2-4}$ alkyl substituted with 0–2 $R^2$, and $C_{2-4}$ alkenyl substituted with 0–2 $R^2$;

Z is selected from H,

—CH(OH)$R^2$,

—C(ethylenedioxy)$R^2$,

—$SR^2$,

—$NR^2R^3$,

—C(O)$R^2$,

—C(O)$NR^2R^3$,

—$NR^3$C(O)$R^2$,

—C(O)O$R^2$,

—S(O)$R^2$,

—$S(O)_2R^2$,

—$S(O)_2NR^2R^3$, and —$NR^3S(O)_2R^2$;

$R^2$, at each occurrence, is independently selected from phenyl substituted with 0–5 $R^{42}$;

$C_{3-10}$ carbocyclic residue substituted with 0–3 $R^{41}$, and

5–10 membered heterocyclic ring system containing from 1–4 heteroatoms selected from the group consisting of N, O, and S substituted with 0–3 $R^{41}$;

$R^3$, at each occurrence, is independently selected from H, $C_{1-4}$ alkyl, $C_{2-4}$ alkenyl, $C_{2-4}$ alkynyl, and $C_{1-4}$ alkoxy;

alternatively, $R^2$ and $R^3$ join to form a 5- or 6-membered ring optionally substituted with —O— or —N($R^4$)—;

$R^4$, at each occurrence, is independently selected from H, methyl, ethyl, propyl, and butyl;

$R^5$ is H;

$R^{6a}$ is selected from H, —OH, —$CF_3$, methyl, ethyl, propyl, butyl, methoxy, and, ethoxy;

$R^{6b}$ is H;

$R^7$, $R^8$, and $R^9$, at each occurrence, are independently selected from

H, halo, —$CF_3$, —$OCF_3$, —OH, —$OCH_3$, —CN, —$NO_2$, $C_{1-4}$ alkyl, $C_{1-4}$ haloalkyl, $C_{1-4}$ alkoxy, ($C_{1-3}$ haloalkyl)oxy, and $C_{1-4}$ alkyl substituted with 0–2 $R^{11}$;

$R^{11}$ is selected from

H, halo, —$CF_3$, —$OCF_3$, —OH, —$OCH_3$, —CN, —$NO_2$, $C_{1-4}$ alkyl, $C_{1-4}$ haloalkyl, $C_{1-4}$ alkoxy, and ($C_{1-3}$ haloalkyl)oxy;

$R^{33}$, at each occurrence, is independently selected from H, OH, halo, $CF_3$, and methyl;

$R^{41}$, at each occurrence, is independently selected from H, $CF_3$, halo, OH, $CO_2H$, $SO_2R^{45}$, $NR^{46}R^{47}$, $NO_2$, CN, ═O, $C_{2-8}$ alkenyl, $C_{2-8}$ alkynyl, $C_{1-4}$ alkoxy, $C_{1-4}$ haloalkyl, $C_{1-4}$ alkyl substituted with 0–1 $R^{43}$, aryl substituted with 0–3 $R^{42}$, and 5–10 membered heterocyclic ring system containing from 1–4 heteroatoms selected from the group consisting of N, O, and S substituted with 0–3 $R^{44}$;

$R^{42}$, at each occurrence, is independently selected from H, $CF_3$, halo, OH, $CO_2H$, $SO_2R^{45}$, $SR^{45}$, $NR^{46}R^{47}$, $OR^{48}$, $NO_2$, CN, CH(═NH)$NH_2$, NHC(═NH)$NH_2$, $C_{2-6}$ alkenyl, $C_{2-6}$ alkynyl, $C_{1-4}$ alkoxy, $C_{1-4}$ haloalkyl, $C_{3-6}$ cycloalkyl, $C_{1-4}$ alkyl substituted with 0–1 $R^{43}$, aryl substituted with 0–3 $R^{44}$, and 5–10 membered heterocyclic ring system containing from 1–4 heteroatoms selected from the group consisting of N, O, and S substituted with 0–3 $R^{44}$;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from H, methyl, ethyl, n-propyl, i-propyl, n-butyl, i-butyl, —C(═O)NH(methyl), —C(═O)NH(ethyl), —$SO_2$(methyl), —$SO_2$(ethyl), —$SO_2$(phenyl), —C(═O)O(methyl), —C(═O)O(ethyl), —C(═O)(methyl), —C(═O)(ethyl), and —C(═O)H;

$R^{48}$, at each occurrence, is independently selected from H, methyl, ethyl, n-propyl, i-propyl, —C(═O)NH(methyl), —C(═O)NH(ethyl), —C(═O)O(methyl),—C(═O)O(ethyl), —C(═O)(methyl), —C(═O)(ethyl), and —C(═O)H;

k is 1;

m is 0, 1, or 2; and n is 1 or 2.

[17] In another even more preferred embodiment of the present invention,

X is —O—;

$R^1$ is selected from ethyl substituted with Z, propyl substituted with Z, butyl substituted with Z, propenyl substituted with Z, butenyl substituted with Z, ethyl substituted with $R^2$, propyl substituted with $R^2$, butyl substituted with $R^2$, propenyl substituted with $R^2$, and butenyl substituted with $R^2$;

Z is selected from H,

—CH(OH)$R^2$,

—O$R^2$,

—$SR^2$,

—$NR^2R^3$,

—C(O)$R^2$,

—C(O)$NR^2R^3$,

—$NR^3C(O)R^2$,
—$C(O)OR^2$,
—$S(O)_2R^2$,
—$S(O)_2NR^2R^3$, and —$NR^3S(O)_2R^2$;

$R^2$, at each occurrence, is independently selected from
phenyl substituted with 0–3 $R^{42}$;
naphthyl substituted with 0–3 $R^{42}$;
cyclopropyl substituted with 0–3 $R^{41}$;
cyclobutyl substituted with 0–3 $R^{41}$;
cyclopentyl substituted with 0–3 $R^{41}$;
cyclohexyl substituted with 0–3 $R^{41}$;
pyridyl substituted with 0–3 $R^{41}$;
indolyl substituted with 0–3 $R^{41}$;
indolinyl substituted with 0–3 $R^{41}$;
benzimidazolyl substituted with 0–3 $R^{41}$;
benzotriazolyl substituted with 0–3 $R^{41}$;
benzothienyl substituted with 0–3 $R^{41}$;
benzofuranyl substituted with 0–3 $R^{41}$;
phthalimid-1-yl substituted with 0–3 $R^{41}$;
inden-2-yl substituted with 0–3 $R^{41}$;
2,3-dihydro-1H-inden-2-yl substituted with 0–3 $R^{41}$;
indazolyl substituted with 0–3 $R^{41}$;
tetrahydroquinolinyl substituted with 0–3 $R^{41}$; and
tetrahydro-isoquinolinyl substituted with 0–3 $R^{41}$;

$R^3$, at each occurrence, is independently selected from H, methyl, and ethyl;

$R^5$ is H;

$R^{6a}$ is selected from H, —OH, methyl, and methoxy;

$R^{6b}$ is H;

$R^7$, $R^8$, and $R^9$, at each occurrence, are independently selected from H, F, Cl, methyl, ethyl, methoxy, —$CF_3$, and —$OCF_3$;

$R^{41}$, at each occurrence, is independently selected from H, F, Cl, Br, OH, $CF_3$, $NO_2$, CN, =O, methyl, ethyl, propyl, butyl, methoxy, and ethoxy;

$R^{42}$, at each occurrence, is independently selected from H, F, Cl, Br, OH, $CF_3$, $SO_2R^{45}$, $SR^{45}$, $NR^{46}R^{47}$, $OR^{48}$, $NO_2$, CN, =O, methyl, ethyl, propyl, butyl, methoxy, and ethoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from H, methyl, ethyl, n-propyl, i-propyl, n-butyl, i-butyl, —C(=O)NH(methyl), —C(=O)NH(ethyl), —$SO_2$(methyl), —$SO_2$(ethyl), —$SO_2$(phenyl), —C(=O)O(methyl), —C(=O)O(ethyl), —C(=O)(methyl), —C(=O)(ethyl), and —C(=O)H;

$R^{48}$, at each occurrence, is independently selected from H, methyl, ethyl, n-propyl, i-propyl, —C(=O)NH(methyl), —C(=O)NH(ethyl), —C(=O)O(methyl), —C(=O)O(ethyl), —C(=O)(methyl), —C(=O)(ethyl), and —C(=O)H;

k is 1;

m is 0, 1, or 2; and n is 1 or 2.

[18] In another even more preferred embodiment of the present invention,

X is —S—;

$R^1$ is selected from
$C_{2-4}$ alkyl substituted with Z,
$C_{2-4}$ alkenyl substituted with Z,
$C_{2-4}$ alkynyl substituted with Z,
$C_{3-6}$ cycloalkyl substituted with Z,
aryl substituted with Z,
5–6 membered heterocyclic ring system containing at least one heteroatom selected from the group consisting of N, O, and S, said heterocyclic ring system substituted with z;
$C_{2-4}$ alkyl substituted with 0–2 $R^2$, and
$C_{2-4}$ alkenyl substituted with 0–2 $R^2$;

Z is selected from H,
—$CH(OH)R^2$,
—C(ethylenedioxy)$R^2$,
—$OR^2$,
—$SR^2$,
—$NR^2R^3$,
—$C(O)R^2$,
—$S(O)R^2$,
—$S(O)_2R^2$,
—$S(O)_2NR^2R^3$, and —$NR^3S(O)_2R^2$;

$R^2$, at each occurrence, is independently selected from
phenyl substituted with 0–5 $R^{42}$;
$C_{3-10}$ carbocyclic residue substituted with 0–3 $R^{41}$, and
5–10 membered heterocyclic ring system containing from 1–4 heteroatoms selected from the group consisting of N, O, and S substituted with 0–3 $R^{41}$;

$R^3$, at each occurrence, is independently selected from H, $C_{1-4}$ alkyl, $C_{2-4}$ alkenyl, $C_{2-4}$ alkynyl, and $C_{1-4}$ alkoxy;

alternatively, $R^2$ and $R^3$ join to form a 5- or 6-membered ring optionally substituted with —O— or —$N(R^4)$—;

$R^4$, at each occurrence, is independently selected from H, methyl, ethyl, propyl, and butyl;

$R^5$ is H;

$R^{6a}$ is selected from H, —OH, —$CF_3$, methyl, ethyl, propyl, butyl, methoxy, and, ethoxy;

$R^{6b}$ is H;

$R^7$, $R^8$, and $R^9$, at each occurrence, are independently selected from
H, halo, —$CF_3$, —$OCF_3$, —OH, —$OCH_3$, —CN, —$NO_2$,
$C_{1-4}$ alkyl, $C_{1-4}$ haloalkyl, $C_{1-4}$ alkoxy, ($C_{1-3}$ haloalkyl)oxy, and
$C_{1-4}$ alkyl substituted with 0–2 $R^{11}$;

$R^{11}$ is selected from
H, halo, —$CF_3$, —$OCF_3$, —OH, —$OCH_3$, —CN, —$NO_2$,
$C_{1-4}$ alkyl, $C_{1-4}$ haloalkyl, $C_{1-4}$ alkoxy, and ($C_{1-3}$ haloalkyl)oxy;

$R^{33}$, at each occurrence, is independently selected from H, OH, halo, $CF_3$, and methyl;

$R^{41}$, at each occurrence, is independently selected from
H, $CF_3$, halo, OH, $CO_2H$, $SO_2R^{45}$, $NR^{46}R^{47}$, $NO_2$, CN, =O,
$C_{2-8}$ alkenyl, $C_{2-8}$ alkynyl, $C_{1-4}$ alkoxy, $C_{1-4}$ haloalkyl,
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2H$, $SO_2R^{45}$, $SR^{45}$, $NR^{46}R^{47}$, $OR^{48}$, $NO_2$, CN, $CH(=NH)NH_2$, $NHC(=NH)NH_2$,
$C_{2-6}$ alkenyl, $C_{2-6}$ alkynyl, $C_{1-4}$ alkoxy, $C_{1-4}$ haloalkyl, $C_{1-4}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from H, methyl, ethyl, n-propyl, i-propyl, n-butyl, i-butyl, —C(═O)NH(methyl), —C(═O)NH(ethyl), —$SO_2$(methyl), —$SO_2$(ethyl), —$SO_2$(phenyl), —C(═O)O(methyl), —C(═O)O(ethyl), —C(═O)(methyl), —C(═O)(ethyl), and —C(═O)H;

$R^{48}$, at each occurrence, is independently selected from H, methyl, ethyl, n-propyl, i-propyl, —C(═O)NH(methyl), —C(═O)NH(ethyl), —C(═O)O(methyl), —C(═O)O(ethyl), —C(═O)(methyl), —C(═O)(ethyl), and —C(═O)H;

k is 1;

m is 0, 1, or 2; and n is 1 or 2.

[19] In another even more preferred embodiment of the present invention,

X is —O—;

$R^1$ is selected from
ethyl substituted with Z;
propyl substituted with Z;
butyl substituted with Z;
propenyl substituted with Z;
butenyl substituted with Z;
ethyl substituted with $R^2$;
propyl substituted with $R^2$;
butyl substituted with $R^2$;
propenyl substituted with $R^2$; and
butenyl substituted with $R^2$;

Z is selected from H,
—$CH(OH)R^2$,
—$OR^2$,
—$SR^2$,
—$NR^2R^3$,
—$C(O)R^2$,
—$C(O)NR^2R^3$,
—$NR^3C(O)R^2$,
—$C(O)OR^2$,
—$S(O)R^2$,
—$S(O)_2R^2$,
—$S(O)_2NR^2R^3$, and —$NR^3S(O)_2R^2$;

$R^2$, at each occurrence, is independently selected from
phenyl substituted with 0–3 $R^{42}$;
naphthyl substituted with 0–3 $R^{42}$;
cyclopropyl substituted with 0–3 $R^{41}$;
cyclobutyl substituted with 0–3 $R^{41}$;
cyclopentyl substituted with 0–3 $R^{41}$;
cyclohexyl substituted with 0–3 $R^{41}$;
pyridyl substituted with 0–3 $R^{41}$;
indolyl substituted with 0–3 $R^{41}$;
benzimidazolyl substituted with 0–3 $R^{41}$;
benzotriazolyl substituted with 0–3 $R^{41}$;
benzothienyl substituted with 0–3 $R^{41}$;
benzofuranyl substituted with 0–3 $R^{41}$;
phthalimid-1-yl substituted with 0–3 $R^{41}$;
inden-2-yl substituted with 0–3 $R^{41}$;
2,3-dihydro-1H-inden-2-yl substituted with 0–3 $R^{41}$;
indazolyl substituted with 0–3 $R^{41}$;
tetrahydroquinolinyl substituted with 0–3 $R^{41}$; and
tetrahydro-isoquinolinyl substituted with 0–3 $R^{41}$;

$R^3$, at each occurrence, is independently selected from H, methyl, and ethyl;

$R^5$ is H;

$R^{6a}$ is selected from H, —OH, methyl, and methoxy;

$R^{6b}$ is H;

$R^7$, $R^8$, and $R^9$, at each occurrence, are independently selected from H, F, Cl, methyl, ethyl, methoxy, —$CF_3$, and $OCF_3$;

$R^{41}$, at each occurrence, is independently selected from H, F, Cl, Br, OH, $CF_3$, $NO_2$, CN, ═O, methyl, ethyl, propyl, butyl, methoxy, and ethoxy;

$R^{42}$, at each occurrence, is independently selected from H, F, Cl, Br, OH, $CF_3$, $SO_2R^{45}$, $SR^{45}$, $NR^{46}R^{47}$, $OR^{48}$, $NO_2$, CN, ═O, methyl, ethyl, propyl, butyl, methoxy, and ethoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from H, methyl, ethyl, n-propyl, i-propyl, n-butyl, i-butyl, —C(═O)NH(methyl), —C(═O)NH(ethyl), —$SO_2$(methyl), —$SO_2$(ethyl), —$SO_2$(phenyl), —C(═O)O(methyl), —C(═O)O(ethyl), —C(═O)(methyl), —C(═O)(ethyl), and —C(═O)H;

$R^{48}$, at each occurrence, is independently selected from H, methyl, ethyl, n-propyl, i-propyl, —C(═O)NH(methyl), —C(═O)NH(ethyl), —C(═O)O(methyl), —C(═O)O(ethyl), —C(═O)(methyl), —C(═O)(ethyl), and —C(═O)H;

k is 1;

m is 0, 1, or 2; and n is 1 or 2.

[20] In another even more preferred embodiment of the present invention, the compound of Formula (I) is selected from Formula (I-a):

(I-a)

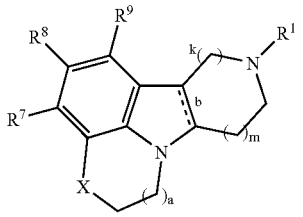

wherein:

b is a single bond or a double bond;

X is —S— or —O—;

$R^1$ is selected from
—$(CH_2)_3C(═O)$(4-fluoro-phenyl),
—$(CH_2)_3C(═O)$(4-bromo-phenyl),
—$(CH_2)_3C(═O)$(4-methyl-phenyl),
—$(CH_2)_3C(═O)$(4-methoxy-phenyl),
—$(CH_2)_3C(═O)$(4-(3,4-dichloro-phenyl)phenyl),
—$(CH_2)_3C(═O)$(3-methyl-4-fluoro-phenyl),
—$(CH_2)_3C(═O)$(2,3-dimethoxy-phenyl),
—$(CH_2)_3C(═O)$(phenyl),
—$(CH_2)_3C(═O)$(4-chloro-phenyl), —$(CH_2)_3C(=O)$(3-methyl-phenyl),
—$(CH_2)_3C(=O)$(4-t-butyl-phenyl),
—$(CH_2)_3C(=O)$(3,4-difluoro-phenyl),
—$(CH_2)_3C(=O)$(2-methoxy-5-fluoro-phenyl),
—$(CH_2)_3C(=O)$(4-fluoro-1-naphthyl),
—$(CH_2)_3C(=O)$(benzyl),
—$(CH_2)_3C(=O)$(4-pyridyl),
—$(CH_2)_3C(=O)$(3-pyridyl),
—$(CH_2)_3CH(OH)$(4-fluoro-phenyl),
—$(CH_2)_3CH(OH)$(4-pyridyl),
—$(CH_2)_3CH(OH)$(2,3-dimethoxy-phenyl),
—$(CH_2)_3S$(3-fluoro-phenyl),
—$(CH_2)_3S$(4-fluoro-phenyl),
—$(CH_2)_3S(=O)$(4-fluoro-phenyl),
—$(CH_2)_3SO_2$(3-fluoro-phenyl),
—$(CH_2)_3SO_2$(4-fluoro-phenyl),
—$(CH_2)_3O$(4-fluoro-phenyl),
—$(CH_2)_3O$(phenyl),
—$(CH_2)_3O$(3-pyridyl),
—$(CH_2)_3O$(4-pyridyl),
—$(CH_2)_3O$(2-$NH_2$-phenyl),
—$(CH_2)_3O$(2-$NH_2$-5-F-phenyl),
—$(CH_2)_3O$(2-$NH_2$-4-F-phenyl),
—$(CH_2)_3O$(2-$NH_2$-3-F-phenyl),
—$(CH_2)_3O$(2-$NH_2$-4-Cl-phenyl)
—$(CH_2)_3O$(2-$NH_2$-4-OH-phenyl),
—$(CH_2)_3O$(2-$NH_2$-4-Br-phenyl),
—$(CH_2)_3O$(2-NHC(=O)Me-4-F-phenyl)
—$(CH_2)_3O$(2-NHC(=O)Me-phenyl),
—$(CH_2)_3NH$(4-fluoro-phenyl),
—$(CH_2)_3N$(methyl)(4-fluoro-phenyl),
—$(CH_2)_3CO_2$(ethyl),
—$(CH_2)_3C(=O)N$(methyl)(methoxy),
—$(CH_2)_3C(=O)NH$(4-fluoro-phenyl),
—$(CH_2)_2NHC(=O)$(phenyl),
—$(CH_2)_2NMeC(=O)$(phenyl),
—$(CH_2)_2NHC(=O)$(2-fluoro-phenyl),
—$(CH_2)_2NMeC(=O)$(2-fluoro-phenyl),
—$(CH_2)_2NHC(=O)$(4-fluoro-phenyl),
—$(CH_2)_2NMeC(=O)$(4-fluoro-phenyl),
—$(CH_2)_2NHC(=O)$(2,4-difluoro-phenyl),
—$(CH_2)_2NMeC(=O)$(2,4-difluoro-phenyl),
—$(CH_2)_3$(3-indolyl),
—$(CH_2)_3$(1-methyl-3-indolyl),
—$(CH_2)_3$(1-indolyl),
—$(CH_2)_3$(1-indolinyl),
—$(CH_2)_3$(1-benzimidazolyl),
—$(CH_2)_3$(1H-1,2,3-benzotriazol-1-yl),
—$(CH_2)_3$(1H-1,2,3-benzotriazol-2-yl),
—$(CH_2)_2$(1H-1,2,3-benzotriazol-1-yl),
—$(CH_2)_2$(1H-1,2,3-benzotriazol-2-yl),
—$(CH_2)_3$(3,4-dihydro-1(2H)-quinolinyl),
—$(CH_2)_2C(=O)$(4-fluoro-phenyl),
—$(CH_2)_2C(=O)NH$(4-fluoro-phenyl),
—$CH_2CH_2$(3-indolyl),
—$CH_2CH_2$(1-phthalimidyl),
—$(CH_2)_4C(=O)N$(methyl)(methoxy),
—$(CH_2)_4CO_2$(ethyl),
—$(CH_2)_4C(=O)$(phenyl),
—$(CH_2)_4$(cyclohexyl),
—$(CH_2)_3CH(phenyl)_2$,
—$CH_2CH_2CH=C(phenyl)_2$,
—$CH_2CH_2CH=CMe$(4-F-phenyl),
—$(CH_2)_3CH$(4-fluoro-phenyl)$_2$,
—$CH_2CH_2CH=C$(4-fluoro-phenyl)2,
—$(CH_2)_2$(2,3-dihydro-1H-inden-2-yl),
—$(CH_2)_3C(=O)$(2-$NH_2$-phenyl),
—$(CH_2)_3C(=O)$(2-$NH_2$-5-F-phenyl),
—$(CH_2)_3C(=O)$(2-$NH_2$-4-F-phenyl),
—$(CH_2)_3C(=O)$(2-$NH_2$-3-F-phenyl),
—$(CH_2)_3C(=O)$(2-$NH_2$-4-Cl-phenyl),
—$(CH_2)_3C(=O)$(2-$NH_2$-4-OH-phenyl),
—$(CH_2)_3C(=O)$(2-$NH_2$-4-Br-phenyl),
—$(CH_2)_3$(1H-indazol-3-yl),
—$(CH_2)_3$(5-F-1H-indazol-3-yl),
—$(CH_2)_3$(7-F-1H-indazol-3-yl),
—$(CH_2)_3$(6-Cl-1H-indazol-3-yl),
—$(CH_2)_3$(6-Br-1H-indazol-3-yl),
—$(CH_2)_3C(=O)$(2-NHMe-phenyl),
—$(CH_2)_3$(1-benzothien-3-yl),
—$(CH_2)_3$(6-F-1H-indol-1-yl),
—$(CH_2)_3$(5-F-1H-indol-1-yl),
—$(CH_2)_3$(6-F-2,3-dihydro-1H-indol-1-yl),
—$(CH_2)_3$(5-F-2,3-dihydro-1H-indol-1-yl),
—$(CH_2)_3$(6-F-1H-indol-3-yl),
—$(CH_2)_3$(5-F-1H-indol-3-yl),
—$(CH_2)_3$(5-F-1H-indol-3-yl),
—$(CH_2)_3$(9H-purin-9-yl),
—$(CH_2)_3$(7H-purin-7-yl),
—$(CH_2)_3$(6-F-1H-indazol-3-yl),
—$(CH_2)_3C(=O)$(2-$NHSO_2$-Me-4-F-phenyl),
—$(CH_2)_3C(=O)$(2-NHC(=O)Me-4-F-phenyl),
—$(CH_2)_3C(=O)$(2-NHC(=O)Me-phenyl),
—$(CH_2)_3C(=O)$(2-$NHCO_2$Et-4-F-phenyl),
—$(CH_2)_3C(=O)$(2-NHC(=O)NHEt-4-F-phenyl),
—$(CH_2)_3C(=O)$(2-NHCHO-4-F-phenyl),
—$(CH_2)_3C(=O)$(2-OH-4-F-phenyl),
—$(CH_2)_3C(=O)$(2-MeS-4-F-phenyl),
—$(CH_2)_3C(=O)$(2-$NHSO_2$Me-4-F-phenyl),
—$(CH_2)_2C(Me)CO_2Me$,
—$(CH_2)_2C(Me)CH(OH)$(4-F-phenyl)$_2$,
—$(CH_2)_2C(Me)CH(OH)$(4-Cl-phenyl)$_2$,
—$(CH_2)_2C(Me)C(=O)$(4-F-phenyl),
—$(CH_2)_2C(Me)C(=O)$(2-MeO-4-F-phenyl),
—$(CH_2)_2C(Me)C(=O)$(3-Me-4-F-phenyl),
—$(CH_2)_2C(Me)C(=O)$(2-Me-phenyl),
—$(CH_2)_2C(Me)C(=O)$phenyl,

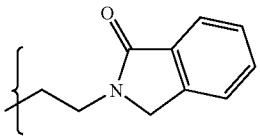

,
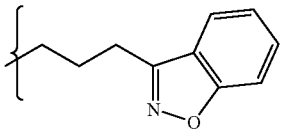

,

-continued

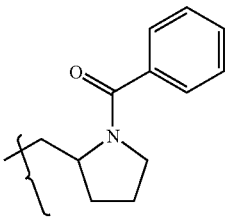

,

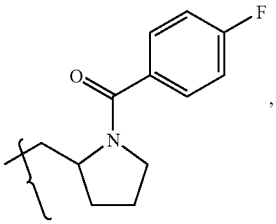

,

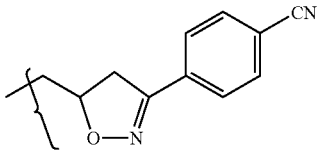

, and

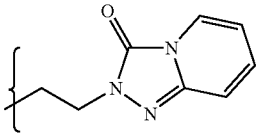

;

$R^7$, $R^8$, and $R^9$, at each occurrence, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl, benzyl, HC(═O)—, methylC(═O)—, ethylC(═O)—, propylC(═O)—, isopropylC(═O)—, n-butylC(═O)—, isobutylC(═O)—, secbutylC(═O)—, tertbutylC(═O)—, phenylC(═O)—, methylC(═O)NH—, ethylC(═O)NH—, propylC(═O)NH—, isopropylC(═O)NH—, n-butylC(═O)NH—, isobutylC(═O)NH—, secbutylC (═O)NH—, tertbutylC(═O)NH—, phenylC(═O)NH—, methylamino-, ethylamino-, propylamino-, isopropylamino-, n-butylamino-, isobutylamino-, secbutylamino-, tertbutylamino-, phenylamino-, provided that two of substituents $R^7$, $R^8$, and $R^9$, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy;

k is 1 or 2;

m is 1 or 2; and n is 1 or 2.

[21] In another even more preferred embodiment of the present invention, the compound of Formula (I) is selected from Formula (II-a):

(II-a)

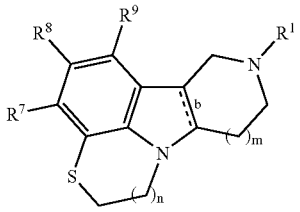

wherein:

b is a single bond, wherein the bridge hydrogens are in a cis position;

$R^1$ is selected from

—$(CH_2)_3C(═O)$(4-fluoro-phenyl),

—$(CH_2)_3C(═O)$(4-bromo-phenyl),

—$(CH_2)_3C(═O)$(4-methyl-phenyl),

—$(CH_2)_3C(═O)$(4-methoxy-phenyl),

—$(CH_2)_3C(═O)$(4-(3,4-dichloro-phenyl)phenyl),

—$(CH_2)_3C(═O)$(3-methyl-4-fluoro-phenyl),

—$(CH_2)_3C(═O)$(2,3-dimethoxy-phenyl),

—$(CH_2)_3C(═O)$(phenyl),

—$(CH_2)_3C(═O)$(4-chloro-phenyl),

—$(CH_2)_3C(═O)$(3-methyl-phenyl),

—$(CH_2)_3C(═O)$(4-t-butyl-phenyl),

—$(CH_2)_3C(═O)$(3,4-difluoro-phenyl),

—$(CH_2)_3C(═O)$(2-methoxy-5-fluoro-phenyl),

—$(CH_2)_3C(═O)$(4-fluoro-1-naphthyl),

—$(CH_2)_3C(═O)$(benzyl),

—$(CH_2)_3C(═O)$(4-pyridyl),

—$(CH_2)_3C(═O)$(3-pyridyl),

—$(CH_2)_3CH(OH)$(4-fluoro-phenyl),

—$(CH_2)_3CH(OH)$(4-pyridyl),

—$(CH_2)_3CH(OH)$(2,3-dimethoxy-phenyl),

—$(CH_2)_3S$(3-fluoro-phenyl),

—$(CH_2)_3S$(4-fluoro-phenyl),

—$(CH_2)_3S(═O)$(4-fluoro-phenyl),

—$(CH_2)_3SO_2$(3-fluoro-phenyl),

—$(CH_2)_3SO_2$(4-fluoro-phenyl),

—$(CH_2)_3O$(4-fluoro-phenyl),

—$(CH_2)_3O$(phenyl),

—$(CH_2)_3NH$(4-fluoro-phenyl),

—$(CH_2)_3N$(methyl)(4-fluoro-phenyl),

—$(CH_2)_3CO_2$(ethyl),

—$(CH_2)_3C(═O)N$(methyl)(methoxy),

—$(CH_2)_3C(═)NH$(4-fluoro-phenyl),

—$(CH_2)_2NHC(═O)$(phenyl),

—$(CH_2)_2NMeC(═O)$(phenyl),

—$(CH_2)_2NHC(═O)$(2-fluoro-phenyl),

—$(CH_2)_2NMeC(═O)$(2-fluoro-phenyl),

—$(CH_2)_2NHC(═O)$(4-fluoro-phenyl),

—$(CH_2)_2NMeC(═O)$(4-fluoro-phenyl),

—$(CH_2)_2NHC(═O)$(2,4-difluoro-phenyl),

—$(CH_2)_2NMeC(═O)$(2,4-difluoro-phenyl),

—$(CH_2)_3$(3-indolyl),

—$(CH_2)_3$(1-methyl-3-indolyl),

—$(CH_2)_3$(1-indolyl),

—$(CH_2)_3$(1-indolinyl),

—$(CH_2)_3$(1-benzimidazolyl),

—$(CH_2)_3$(1H-1,2,3-benzotriazol-1-yl),

—$(CH_2)_3$(1H-1,2,3-benzotriazol-2-yl),

—$(CH_2)_2$(1H-1,2,3-benzotriazol-1-yl),

—$(CH_2)_2$(1H-1,2,3-benzotriazol-2-yl),

—$(CH_2)_3$(3,4 dihydro-1(2H)-quinolinyl),

—$(CH_2)_2C(═O)$(4-fluoro-phenyl),

—$(CH_2)_2C(═O)NH$(4-fluoro-phenyl),

—$CH_2CH_2$(3-indolyl),

—$CH_2CH_2$(1-phthalimidyl),

—$(CH_2)_4C(═O)N$(methyl)(methoxy),

—$(CH_2)_4CO_2$(ethyl),

—$(CH_2)_4C(═O)$(phenyl),

—$(CH_2)_4$(cyclohexyl),
—$(CH_2)_3CH(phenyl)_2$,
—$CH_2CH_2CH{=}C(phenyl)_2$,
—$CH_2CH_2CH{=}CMe$(4-F-phenyl),
—$(CH_2)_3CH$(4-fluoro-phenyl)$_2$,
—$CH_2CH_2CH{=}C$(4-fluoro-phenyl)$_2$,
—$(CH_2)_2$(2,3-dihydro-1H-inden-2-yl),
—$(CH_2)_3C(=O)$(2-$NH_2$-phenyl),
—$(CH_2)_3C(=O)$(2-$NH_2$-5-F-phenyl),
—$(CH_2)_3C(=O)$(2-$NH_2$-4-F-phenyl),
—$(CH_2)_3C(=O)$(2-$NH_2$-3-F-phenyl),
—$(CH_2)_3C(=O)$(2-$NH_2$-4-Cl-phenyl),
—$(CH_2)_3C(=O)$(2-$NH_2$-4-OH-phenyl),
—$(CH_2)_3C(=O)$(2-$NH_2$-4-Br-phenyl),
—$(CH_2)_3$(1H-indazol-3-yl),
—$(CH_2)_3$(5-F-1H-indazol-3-yl),
—$(CH_2)_3$(7-F-1H-indazol-3-yl),
—$(CH_2)_3$(6-Cl-1H-indazol-3-yl),
—$(CH_2)_3$(6-Br-1H-indazol-3-yl),
—$(CH_2)_3C(=O)$(2-NHMe-phenyl),
—$(CH_2)_3$(1-benzothien-3-yl),
—$(CH_2)_3$(6-F-1H-indol-1-yl),
—$(CH_2)_3$(5-F-1H-indol-1-yl),
—$(CH_2)_3$(6-F-2,3-dihydro-1H-indol-1-yl),
—$(CH_2)_3$(5-F-2,3-dihydro-1H-indol-1-yl),
—$(CH_2)_3$(6-F-1H-indol-3-yl),
—$(CH_2)_3$(5-F-1H-indol-3-yl),
—$(CH_2)_3$(5-F-1H-indol-3-yl),
—$(CH_2)_3$(9H-purin-9-yl),
—$(CH_2)_3$(7H-purin-7-yl),
—$(CH_2)_3$(6-F-1H-indazol-3-yl),
—$(CH_2)_3C(=O)$(2-$NHSO_2$Me-4-F-phenyl),
—$(CH_2)_3C(=O)$(2-NHC(=O)Me-4-F-phenyl),
—$(CH_2)_3C(=O)$(2-NHC(=O)Me-4-F-phenyl),
—$(CH_2)_3C(=O)$(2-$NHCO_2$Et-4-F-phenyl),
—$(CH_2)_3C(=O)$(2-NHCHO-4-F-phenyl),
—$(CH_2)_3C(=O)$(2-OH-4-F-phenyl),
—$(CH_2)_3C(=O)$(2-MeS-4-F-phenyl),
—$(CH_2)_3C(=O)$(2-$NHSO_2$-Me-4-F-phenyl),
—$(CH_2)_2C(Me)CO_2Me$,
—$(CH_2)_2C(Me)CH(OH)$(4-F-phenyl)$_2$,
—$(CH_2)_2C(Me)CH(OH)$(4-Cl-phenyl)$_2$,
—$(CH_2)_2C(Me)C(=O)$(4-F-phenyl),
—$(CH_2)_2C(Me)C(=O)$(2-MeO-4-F-phenyl),
—$(CH_2)_2C(Me)C(=O)$(3-Me-4-F-phenyl),
—$(CH_2)_2C(Me)C(=O)$(2-Me-phenyl),
—$(CH_2)_2C(Me)C(=O)$phenyl,

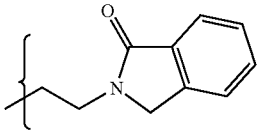
,
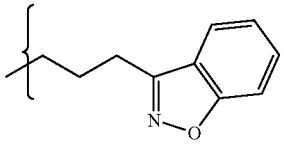
,

-continued

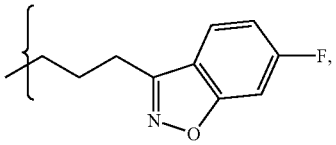
,

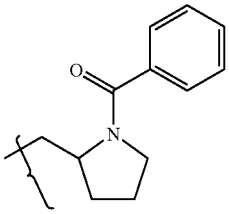
,

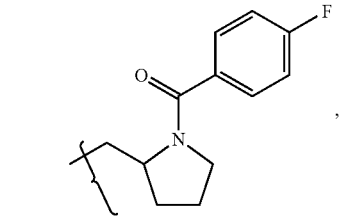
, and

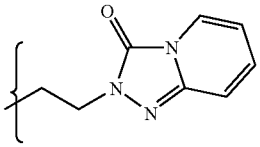
;

$R^7$, $R^8$, and $R^9$, at each occurrence, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, methylC(=O)—, ethylC(=O)—, propylC(=O)—, isopropylC(=O—, methylC(=O)NH—, ethylC(=O)NH—, propylC(=O)NH—, isopropylC(=O)NH, methylamino-, ethylamino-, propylamino-, and isopropylamino-, provided that two of substituents $R^7$, $R^8$, and $R^9$, are independently selected from hydrogen, fluoro, chloro, methyl, trifluoromethyl, methoxy, and trifluoromethoxy;

m is 1 or 2; and n is 1 or 2.

[22] In another even more preferred embodiment of the present invention, the compound of Formula (I) is selected from Formula (III-a):

(III-a)

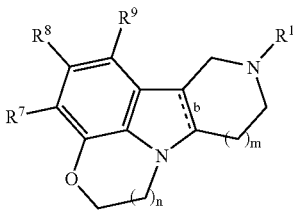

wherein:

b is a single bond, wherein the bridge hydrogens are in a cis position;

$R^1$ is selected from

—$(CH_2)_3C(=O)$(4-fluoro-phenyl),
—$(CH_2)_3C(=O)$(4-bromo-phenyl),
—$(CH_2)_3C(=O)$(4-methyl-phenyl),
—$(CH_2)_3C(=O)$(4-methoxy-phenyl),
—$(CH_2)_3C(=O)$(4-(3,4-dichloro-phenyl)phenyl),
—$(CH_2)_3C(=O)$(3-methyl-4-fluoro-phenyl),
—$(CH_2)_3C(=O)$(2,3-dimethoxy-phenyl),
—$(CH_2)_3C(=O)$(phenyl),
—$(CH_2)_3C(=O)$(4-chloro-phenyl),
—$(CH_2)_3C(=O)$(3-methyl-phenyl),
—$(CH_2)_3C(=O)$(4-t-butyl-phenyl),
—$(CH_2)_3C(=O)$(3,4-difluoro-phenyl),
—$(CH_2)_3C(=O)$(2-methoxy-5-fluoro-phenyl),
—$(CH_2)_3C(=O)$(4-fluoro-1-naphthyl),
—$(CH_2)_3C(=O)$(benzyl),
—$(CH_2)_3C(=O)$(4-pyridyl),
—$(CH_2)_3C(=O)$(3-pyridyl),
—$(CH_2)_3CH(OH)$(4-fluoro-phenyl),
—$(CH_2)_3CH(OH)$(4-pyridyl),
—$(CH_2)_3CH(OH)$(2,3-dimethoxy-phenyl),
—$(CH_2)_3S$(3-fluoro-phenyl),
—$(CH_2)_3S$(4-fluoro-phenyl),
—$(CH_2)_3S(=O)$(4-fluoro-phenyl),
—$(CH_2)_3SO_2$(3-fluoro-phenyl),
—$(CH_2)_3SO_2$(4-fluoro-phenyl),
—$(CH_2)_3O$(4-fluoro-phenyl),
—$(CH_2)_3O$(phenyl),
—$(CH_2)_3NH$(4-fluoro-phenyl),
—$(CH_2)_3N$(methyl)(4-fluoro-phenyl),
—$(CH_2)_3CO_2$(ethyl),
—$(CH_2)_3C(=O)N$(methyl)(methoxy),
—$(CH_2)_3C(=)NH$(4-fluoro-phenyl),
—$(CH_2)_2NHC(=O)$(phenyl),
—$(CH_2)_2NMeC(=O)$(phenyl),
—$(CH_2)_2NHC(=O)$(2-fluoro-phenyl),
—$(CH_2)_2NMeC(=O)$(2-fluoro-phenyl),
—$(CH_2)_2NHC(=O)$(4-fluoro-phenyl),
—$(CH_2)_2NMeC(=O)$(4-fluoro-phenyl),
—$(CH_2)_2NHC(=O)$(2,4-difluoro-phenyl),
—$(CH_2)_2NMeC(=O)$(2,4-difluoro-phenyl),
—$(CH_2)_3$(3-indolyl),
—$(CH_2)_3$(1-methyl-3-indolyl),
—$(CH_2)_3$(1-indolyl),
—$(CH_2)_3$(1-indolinyl)
—$(CH_2)_3$(1-benzimidazolyl),
—$(CH_2)_3$(1H-1,2,3-benzotriazol-1-yl),
—$(CH_2)_3$(1H-1,2,3-benzotriazol-2-yl),
—$(CH_2)_2$(1H-1,2,3-benzotriazol-1-yl),
—$(CH_2)_2$(1H-1,2,3-benzotriazol-2-yl),
—$(CH_2)_3$(3,4 dihydro-1(2H)-quinolinyl),
—$(CH_2)_2C(=O)$(4-fluoro-phenyl),
—$(CH_2)_2C(=O)NH$(4-fluoro-phenyl),
—$CH_2CH_2$(3-indolyl),
—$CH_2CH_2$(1-phthalimidyl),
—$(CH_2)_4C(=O)N$(methyl)(methoxy),
—$(CH_2)_4CO_2$(ethyl),
—$(CH_2)_4C(=O)$(phenyl),
—$(CH_2)_4$(cyclohexyl),
—$(CH_2)_3CH(\text{phenyl})_2$,
—$CH_2CH_2CH=C(\text{phenyl})_2$,
—$CH_2CH_2CH=CMe$(4-F-phenyl),
—$(CH_2)_3CH(\text{4-fluoro-phenyl})_2$,
—$CH_2CH_2CH=C(\text{4-fluoro-phenyl})_2$,
—$(CH_2)_2$(2,3-dihydro-1H-inden-2-yl),
—$(CH_2)_3C(=O)$(2-$NH_2$-phenyl),
—$(CH_2)_3C(=O)$(2-$NH_2$-5-F-phenyl),
—$(CH_2)_3C(=O)$(2-$NH_2$-4-F-phenyl),
—$(CH_2)_3C(=O)$(2-$NH_2$-3-F-phenyl),
—$(CH_2)_3C(=O)$(2-$NH_2$-4-Cl-phenyl),
—$(CH_2)_3C(=O)$(2-$NH_2$-4-OH-phenyl),
—$(CH_2)_3C(=O)$(2-$NH_2$-4-Br-phenyl),
—$(CH_2)_3$(1H-indazol-3-yl),
—$(CH_2)_3$(5-F-1H-indazol-3-yl),
—$(CH_2)_3$(7-F-1H-indazol-3-yl),
—$(CH_2)_3$(6-Cl-1H-indazol-3-yl),
—$(CH_2)_3$(6-Br-1H-indazol-3-yl),
—$(CH_2)_3C(=O)$(2-NHMe-phenyl),
—$(CH_2)_3$(1-benzothien-3-yl),
—$(CH_2)_3$(6-F-1H-indol-1-yl),
—$(CH_2)_3$(5-F-1H-indol-1-yl),
—$(CH_2)_3$(6-F-2,3-dihydro-1H-indol-1-yl),
—$(CH_2)_3$(5-F-2,3-dihydro-1H-indol-1-yl),
—$(CH_2)_3$(6-F-1H-indol-3-yl),
—$(CH_2)_3$(5-F-1H-indol-3-yl),
—$(CH_2)_3$(5-F-1H-indol-3-yl),
—$(CH_2)_3$(9H-purin-9-yl),
—$(CH_2)_3$(7H-purin-7-yl),
—$(CH_2)_3$(6-F-1H-indazol-3-yl),
—$(CH_2)_3C(=O)$(2-$NHSO_2$Me-4-F-phenyl),
—$(CH_2)_3C(=O)$(2-NHC(=O)Me-4-F-phenyl),
—$(CH_2)_3C(=O)$(2-NHC(=O)Me-4-F-phenyl),
—$(CH_2)_3C(=O)$(2-$NHCO_2$Et-4-F-phenyl),
—$(CH_2)_3C(=O)$(2-NHC(=O)NHEt-4-F-phenyl),
—$(CH_2)_3C(=O)$(2-NHCHO-4-F-phenyl),
—$(CH_2)_3C(=O)$(2-OH-4-F-phenyl),
—$(CH_2)_3C(=O)$(2-MeS-4-F-phenyl),
—$(CH_2)_3C(=O)$(2-$NHSO_2$-Me-4-F-phenyl),
—$(CH_2)_2C(Me)CO_2Me$,
—$(CH_2)_2C(Me)CH(OH)(\text{4-F-phenyl})_2$,
—$(CH_2)_2C(Me)CH(OH)(\text{4-Cl-phenyl})_2$,
—$(CH_2)_2C(Me)C(=O)$(4-F-phenyl),
—$(CH_2)_2C(Me)C(=O)$(2-MeO-4-F-phenyl),
—$(CH_2)_2C(Me)C(=O)$(3-Me-4-F-phenyl),
—$(CH_2)_2C(Me)C(=O)$(2-Me-phenyl),
—$(CH_2)_2C(Me)C(=O)$phenyl,

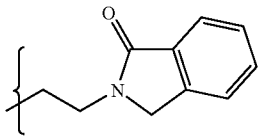

,
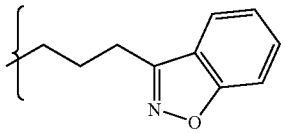

,

-continued

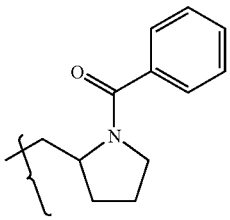

,

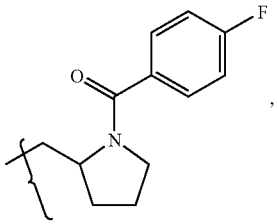

,

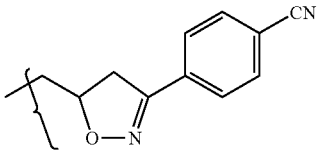

, and

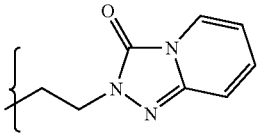

; and $R^7$, $R^8$, and $R^9$, at each occurrence, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, methylC(═O)—, ethylC(═O)—, propylC(═O)—, isopropylC(═O—, methylC(═O)NH—, ethylC(═O)NH—, propylC(═O)NH—, isopropylC(═O)NH, methylamino-, ethylamino-, propylamino-, and isopropylamino-, provided that two of substituents $R^7$, $R^8$, and $R^9$, are independently selected from hydrogen, fluoro, chloro, methyl, trifluoromethyl, methoxy, and trifluoromethoxy;

m is 1 or 2; and n is 1 or 2.

In an even further more preferred embodiment of the present invention, are compounds of Formula (I) selected from Table 1.

In an even further more preferred embodiment of the present invention, are compounds of Formula (I) selected from Table 1A.

In an even further more preferred embodiment of the present invention, are compounds of Formula (I) selected from Table 2.

In an even further more preferred embodiment of the present invention, are compounds of Formula (I) selected from Table 2A.

In an even further more preferred embodiment of the present invention, are compounds of Formula (I) selected from Table 3.

In an even further more preferred embodiment of the present invention, are compounds of Formula (I) selected from Table 3A.

In an even further more preferred embodiment of the present invention, are compounds of Formula (I) selected from Table 4.

In an even further more preferred embodiment of the present invention, are compounds of Formula (I) selected from Table 4A.

In an even further more preferred embodiment of the present invention, are compounds of Formula (I) selected from Table 5.

In a second embodiment, the present invention provides a pharmaceutical composition comprising a compound of Formula (I) and a pharmaceutically acceptable carrier.

In a third embodiment, the present invention provides a method for the treatment a central nervous system disorder comprising administering to a host in need of such treatment a therapeutically effective amount of a compound of Formula (I), or a pharmaceutically acceptable salt thereof, wherein the compound is a 5HT2a antagonist or a 5HT2c agonist.

In a preferred embodiment the compound is a 5HT2a antagonist.

In another preferred embodiment the compound is a 5HT2c agonist.

In a more preferred embodiment the present invention provides a method for the treatment central nervous system disorders including obesity, anxiety, depression, psychosis, schizophrenia, sleep disorders, sexual disorders, migraine, conditions associated with cephalic pain, social phobias, and gastrointestinal disorders such as dysfunction of the gastrointestinal tract motility comprising administering to a host in need of such treatment a therapeutically effective amount of a compound of Formula (I).

In a further preferred embodiment the central nervous system disorder comprises obesity.

In another further preferred embodiment the central nervous system disorder comprises schizophrenia.

In another further preferred embodiment the central nervous system disorder comprises depression.

In another further preferred embodiment the central nervous system disorder comprises anxiety.

In a fourth embodiment the present invention provides novel compounds of Formula (I) or pharmaceutically acceptable salt forms thereof for use in therapy.

In a fifth embodiment the present invention provides the use of novel compounds of Formula (I) or pharmaceutically acceptable salt forms thereof for the manufacture of a medicament for the treatment of central nervous system disorders including obesity, anxiety, depression, psychosis, schizophrenia, sleep disorders, sexual disorders, migraine, conditions associated with cephalic pain, social phobias, and gastrointestinal disorders.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C═N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The numbering of the tetracyclic ring-system present in the compounds of Formula (I), as defined by nomenclature known to one skilled in the art, is shown for two examples in Formula (I'), when k is 1, m is 1, and n is 1; and in Formula (I"), when k is 1, m is 1, and n is 2:

(I')

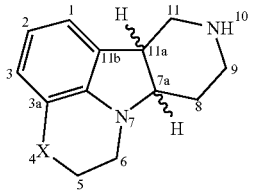

(I")

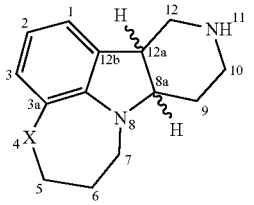

The tetracyclic ring-system present in compounds of Formula (I) occur as "cis" or "trans" isomers when the carbon-carbon bond b in Formula (I) is a single bond. As such, the terms "cis" and "trans", in conjunction with the tetracyclic ring structure, refer to the configuration of hydrogen atoms on carbon atoms 7a and 11a in Formula (I') or, for example, on carbon atoms 8a and 12a in Formula (I"), above. When both hydrogens are on the same side of the mean plane determined by the octahydro tetracyclic moiety then the configuration is designated "cis", if not, the configuration is designated "trans". It is understood that the above example is for demonstrative puproses only and not intended to limit the scope of the tetracyclic ring-system present in compounds of Formula (I). As such, it is understood that one skilled in the art of organic chemistry can apply the above numbering system to other values of k, m, and n in the scope of compounds of Formula (I) to deterine the appropriate numbering. Additional Examples of the numbering of the tetracyclic ring-system are further provided below in the synthetic Examples. Lastly, it is understood that the use of "cis" or "trans" in the identification of the tetracyclic ring-system is not meant to construe the configuration of any other cis or trans geometric isomer in the molecule, for example, cis or trans butene.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^2$) occurs more than one time in any constituent or formula for a compound, its definition at each occurrence is independent of its definition at every other occurrence. Thus, for example, if a group is shown to be substituted with 0–2 $R^2$, then said group may optionally be substituted with up to two $R^2$ groups and $R^2$ at each occurrence is selected independently from the definition of $R^2$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms; for example, "$C_1$–$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms and one or more unsaturated carbon-carbon bonds which may occur in any stable point along the chain. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain, such as ethynyl, propynyl, butynyl, pentynyl, hexynyl and the like.

"Cycloalkyl" is intended to include saturated ring groups, having the specified number of carbon atoms. For example, "$C_3$–$C_6$ cycloalkyl" denotes such as cyclopropyl, cyclobutyl, cyclopentyl, or cyclohexyl.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" is represents an alkyl group as defined above with the indicated number of carbon atoms attached through a sulpher bridge.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, heptafluoropropyl, and heptachloropropyl.

As used herein, "carbocycle" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic ring" is intended to mean a stable 5- to 7-membered monocyclic or bicyclic or 7- to 14-membered bicyclic heterocyclic ring which is saturated partially unsaturated or unsaturated (aromatic), and which consists of carbon atoms and 1, 2, 3 or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quanternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro [2,3-b[tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred heterocycles includes, but are not limited to, pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, and pyrazolopyridinyl. Preferred 5 to 6 membered heterocycles include but are not limited to, pyridinyl, furanyl, thienyl, pyrrolyl, pyrazolyl, pyrazinyl, piperazinyl, imidazolyl, and oxazolidinyl. Also included are fused ring and spiro compounds containing, for example, the above heterocycles.

As used herein, the term "bicyclic heterocyclic ring system" is intended to mean a stable 9- to 10-membered bicyclic heterocyclic ring formed from the substituent $NR^{12}R^{13}$, which is partially unsaturated or unsaturated (aromatic), and which consists of carbon atoms, a nitrogen atom, and 1 or 2 additional heteroatoms independently selected from the group consisting of N, O and S. The additional nitrogen or sulfur heteroatoms may optionally be oxidized. The heterocyclic ring is attached to its pendant group by the nitrogen atom of the group $NR^{12}R^{13}$ and for which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. The term "bicyclic heterocyclic ring system" is intended to be a subset of the term "heterocyclic ring system". Preferred examples of a 9- to 10-membered bicyclic heterocyclic ring system are benzimidazolyl, benzimidazolinyl, benzoxazolinyl, dihydrobenzthiazolyl, dihydrodioxobenzthiazolyl, benzisoxazolinyl, 1H-indazolyl, indolyl, indolinyl, isoindolinyl, tetrahydro-isoquinolinyl, tetrahydro-quinolinyl, and benzotriazolyl.

Additionally, a subclass of preferred heterocycles are heterocycles which function as an isostere of a cyclic but non-heterocyclic substituent such as $—CH_2—C(=O)$-phenyl. Preferred examples of such heterocycles include, but are not limited to, benzimidazolyl, benzofuranyl, benzothiophenyl, benzoxazolyl, benzthiazolyl, benzisoxazolyl, furanyl, imidazolinyl, 1H-indazolyl, indolinyl, isoindolinyl, isoquinolinyl, oxazolyl, piperidinyl, pyrazinyl, pyridinyl, pyrimidinyl, quinolinyl, thiazolyl, thiophenyl, and 1,2,3-triazolyl.

As used herein, the term "aryl", or aromatic residue, is intended to mean an aromatic moiety containing the specified number of carbon atoms, such as phenyl, pyridinyl and naphthyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of Formula (I), and the like.

"Stable compound" and "stable structure" are meant to indicate a compound that is sufficiently robust to survive isolation to a useful degree of purity from a reaction mixture, and formulation into an efficacious therapeutic agent.

Synthesis

Throughout the details of the invention, the following abbreviations are used with the following meanings:

| | |
|---|---|
| **Reagents** | |
| MCPBA | m-chloroperoxybenzoic acid |
| DIBAL | diisobutyl aluminum hydride |
| $Et_3N$ | triethylamine |
| TFA | trifluoroacetic acid |
| LAH | lithium aluminum hydride |
| NBS | N-bromo succinimide |
| Red-Al | Sodium bis(2-methoxyethoxy)aluminum hydride |
| $Pd_2dho_3$ | Tris(dibenzylideneacetone)dipalladium(0) |
| ACE-Cl | 2-chloroethylchloroformate |
| **Solvents** | |
| THF | tetrahydrofuran |
| MeOH | methanol |
| EtOH | ethanol |
| EtOAc | ethyl acetate |
| HOAc | acetic acid |
| DMF | dimethyl formamide |
| DMSO | dimethyl sulfoxide |
| DME | dimethoxyethane |
| $Et_2O$ | diethylether |
| iPrOH | isopropanol |
| MEK | methyl ethyl ketone |
| **Others** | |
| Ar | aryl |
| Ph | phenyl |
| Me | methyl |
| Et | ethyl |
| NMR | nuclear magnetic resonance |
| MHz | megahertz |
| BOC | tert-butoxycarbonyl |
| CBZ | benzyloxycarbonyl |
| Bn | benzyl |
| Bu | butyl |
| Pr | propyl |

-continued

| | |
|---|---|
| cat. | catalytic |
| mL | milliliter |
| nM | nanometer |
| ppm | part per million |
| mmol | millimole |
| mg | milligram |
| g | gram |
| kg | kilogram |
| TLC | thin layer chromatography |
| HPLC | high pressure liquid chromatography |
| RPM | revolutions per minute |
| rt | room temperature |
| aq. | aqueous |
| sat. | saturated |

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformation being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

The preparation of compounds of Formula (I) of the present invention may be carried out in a convergent or sequential synthetic manner. Detailed synthetic preparations of the compounds of Formula (I) are shown in the following reaction schemes. The skills required in preparation and purification of the compounds of Formula (I) and the intermediates leading to these compounds are known to those in the art. Purification procedures include, but are not limited to, normal or reverse phase chromatography, crystallization, and distillation.

Several methods for the preparation of the compounds of the present invention are illustrated in the schemes and examples shown below. The substitutions are as described and defined above.

Compounds of Formula (I) of this invention may be prepared as shown in Scheme 1. Thus, preparation of an aryl hydrazine (III) is accomplished, for example, by treatment of a corresponding substituted aniline (II) with $NaNO_2$ followed by reduction of the N-nitroso intermediate with a reducing agent such as LAH or zinc and an organic acid, such as acetic acid or trifluoroacetic acid at low temperature. Assembly of the core tetracyclic intermediate indole (V) is accomplished by Fischer indole cyclization of the aryl hydrazine and a suitably substituted ketone (i.e. (IV)) by methods described by, but not limited to, R. J. Sundberg, "Indoles, Best Synthetic Methods" 1996, Academic Press, San Diego, Calif. For example, treatment of the aryl hydrazine (III) as the free base or the corresponding mineral acid salt with the ketone (IV) ($R^1$=H, Bn, CBZ, $CO_2Et$, etc) in an alcoholic solvent in the presence of mineral acid affords the indoles (V) as the free bases (after treatment with aq. NaOH). Reduction of the indoles to the corresponding cis- or trans substituted dihydroindoles is accomplished by, for example, treatment with hydrogen in the presence of a catalyst such as platinum oxide or palladium on carbon, or with a metal such as zinc and a mineral acid such as hydrochloric acid, or with sodium and liquid ammonia, or with borane-amine complex such as borane-triethylamine in tetrahydrofuran, or preferably by treatment with $NaCNBH_3$ in an acid such as acetic or trifluoroacetic acid.

The corresponding enantiomers can be isolated by separation of the racemic mixture of (I) on a chiral stationary phase column utilizing normal or reverse phase HPLC techniques, the details of which are described in the examples. Alternatively, a diastereomeric mixture of (I) can be prepared by treatment of (I, $R^1$=H) with an appropriate chiral acid (or suitably activated derivative), for example dibenzoyl tartrate or the like (see, for example, Kinbara, K., et al., J. Chem. Soc., Perkin Trans. 2, 1996, 2615; and Tomori, H., et al., Bull. Chem. Soc. Jpn., 1996, 3581). The diastereomers would then be separated by traditional techniques (i.e. silica chromatography, crystallization, HPLC, etc) followed by removal of the chiral auxiliary to afford enantiomerically pure (I).

In the cases where the carboline nitrogen has been protected (VI) (i.e. $R^1$=Boc, Bn, CBZ, $CO_2R$), it may be removed under a variety of conditions as described in Greene, T. W., Wuts, P. G. W., "Protective Groups in Organic Synthesis, 2nd Edition", John Wiley and Sons, Inc., New York, pages 309–405, 1991. The free secondary amine could then be alkylated, for example, by treatment with a suitably substituted alkyl halide ($R^1Cl$, or $R^1I$) and a base to afford additional compounds of type (I), as described, for example, by Glennon, R. A., et al., Med. Chem. Res., 1996, 197.

SCHEME 1

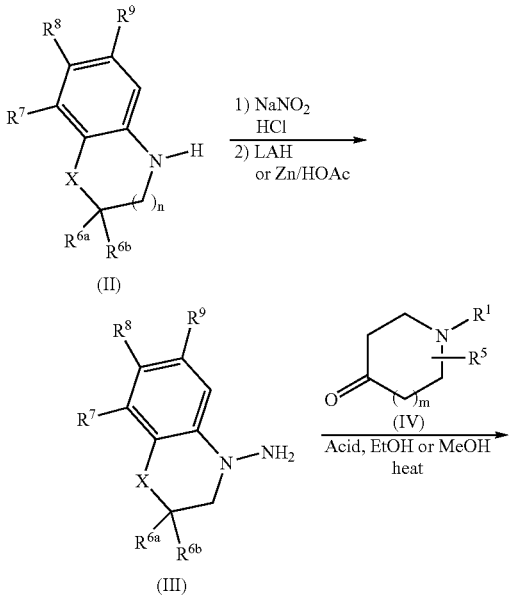

-continued

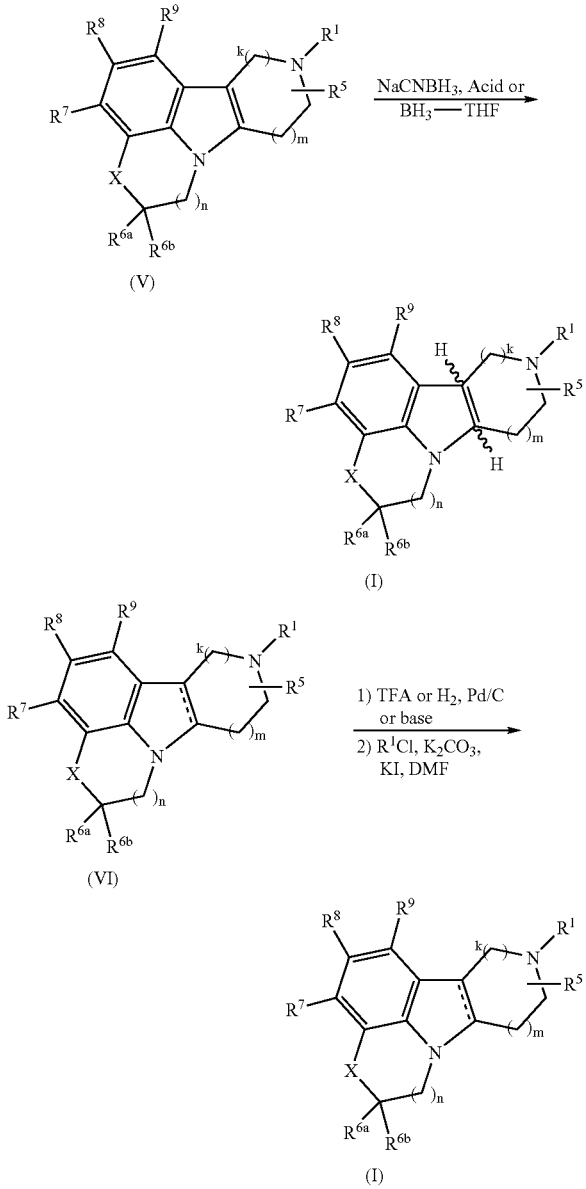

Alternatively, compounds of Formula (I) can be prepared as described in Scheme 2. Treatment of an ortho halonitrobenzene compound (VII) with a nucleophilic alkyl halide (X=OH, SH, NHR, (VIII)) (as described by Kharasch, N., Langford, R. B., J. Org. Chem., 1963, 1903) and a suitable base followed by subsequent reduction of the corresponding nitroaryl derivative to the aniline (IX). The reduction may be accomplished with a variety of reducing agents, for example, LAH, $SnCl_2$, $NaBH_4$, $N_2H_4$, etc. or with hydrogen in the presence of a suitable catalyst, such as palladium on carbon, or platinum oxide, etc., (see Hudlicky, M., "Reductions in Organic Chemistry", Ellis Horwood, Ltd., Chichester, UK, 1984). Formation of the aryl hydrazine (X) may be accomplished as described previously in Scheme 1 or more directly by treatment of the aniline (IX) with aq. hydrochloric acid, stannous chloride and $NaNO_2$ at room temperature (see, Buck, J. S., Ide, W. S., Org. Syn., Coll. Vol., 2, 1943, 130). This primary aryl hydrazine (X) can then be cyclized under Fischer indole cyclization conditions as detailed above for compound (V), to afford the indole (XI)

as the corresponding salt. Upon treatment of the indole (XI) with a base such potassium hydroxide or potassium t-butoxide in a solvent such as DME or THF affords the tetracyclic indole intermediates (V). These indoles can also be reduced to the corresponding cis- or trans indolines (I) as described previously in Scheme 1.

SCHEME 2

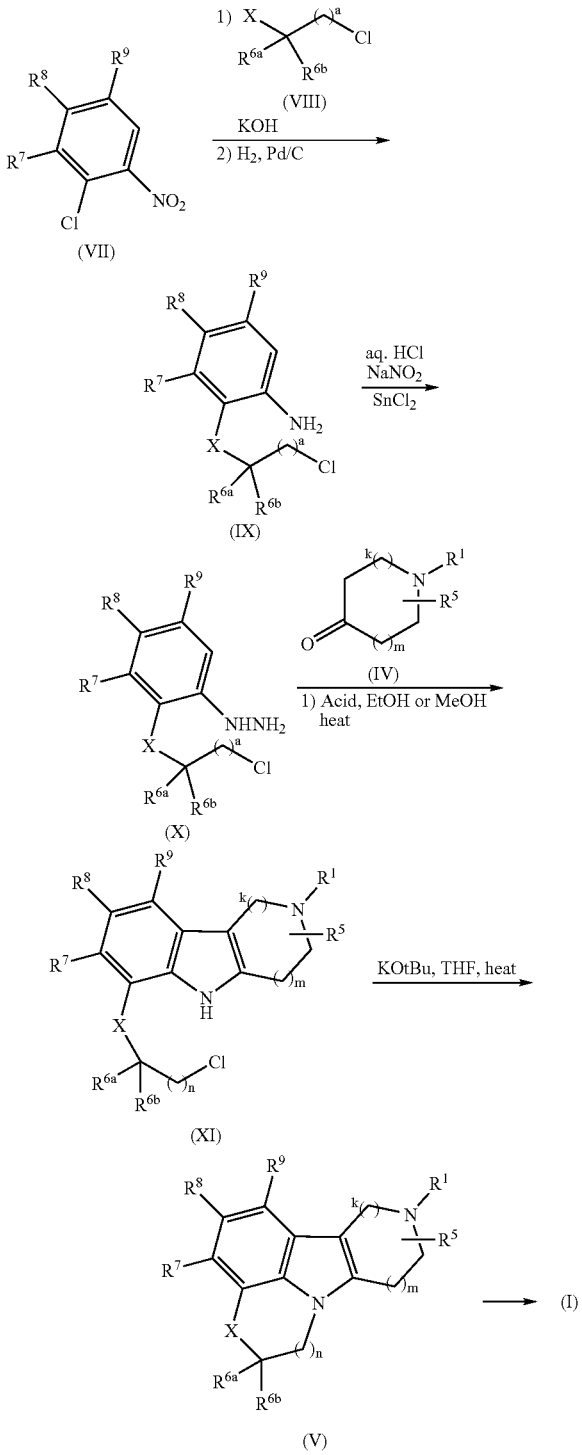

Still another related route to compounds of Formula (I) is shown in Scheme 3. Initiating the synthesis with a nitrobenzene derivative such as (XII), this approach allows for a variety of derivatization. More highly substituted nitrobenzenes can be obtained by traditional synthetic manipulation (i.e. aromatic substitution) and are known by those in the art (see Larock, R. C., Comprehensive Organic Transformations, VCH Publishers, New York, 1989). Treatment of nitrobenzene derivative with a reducing agent such as LAH, etc., as described previously (see Hudlicky, et. al.), affords the corresponding aniline intermediate. Subsequent formation of the hydrazine followed by Fischer indole cyclization with a suitably functionalized ketone as described above (i.e. Scheme 1, (III) to (V)) affords the g-carboline indole (XIII). At this point the fused ring may be appended by condensation of a haloalkyl carboxylic acid or a related activated carboxylic acid (i.e. acid chloride, mixed anhydride, etc.) such as (XIV). Reduction of the resultant heterocyclic carbonyl may be effected with various reducing agents, for example, sodium borohydride, diisobutyl aluminum hydride and the like (see Larock, R. C., Comprehensive Organic Transformations, VCH Publishers, New York, 1989 and/or Hudlicky, M., "Reductions in Organic Chemistry", Ellis Horwood, Ltd., Chichester, UK, 1984) to afford the tetracyclic indoles (V). Further reduction of the indole (V) to the indolines (I) is as described previously in Scheme 1.

SCHEME 3

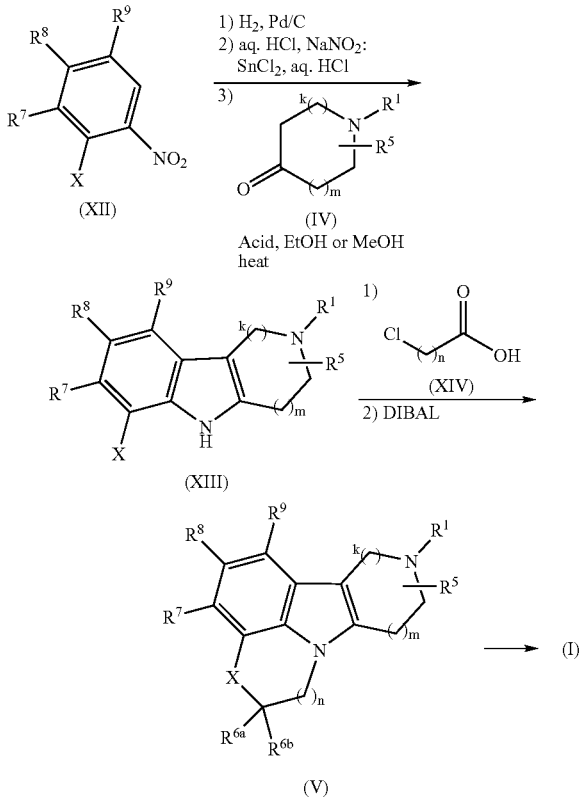

Preparation of the aniline precursors (II) to the Fischer indole cyclizations is shown in Scheme 4. Treatment of a suitably ortho-functionalized aniline (XVI) with a chloroalkyl carboxylic acid or ester (or equivalent substrate, i.e. acrylic acid, acryloyl chloride, etc.) and concomitant condensation, followed by reduction of the resultant heterocyclic carbonyl with a reducing agent such as LAH, DIBAL, or Red-Al affords the fused heterocyclic benzene derivatives (II). More diverse intermediates of (II) may be obtained by formation of the ortho substituted aniline from the corresponding ortho substituted nitobenzenes and concomitant reduction of the nitro moiety as described above. Furthermore, aromatic substitution of the fluoro (or other halo derived nitrobenzene) functionality of (XV) for an oxygen, or sulphur moiety is accomplished, for example, by treatment of (XV) with a nucleophile, such as sodium sulfide or an alcohol, followed by formation of the requisite thiophenol or phenol, respectively, using standard techniques known by those in the art (see Larock, R. C., Comprehensive Organic Transformations, VCH Publishers, New York, 1989, page 481). Reduction of the nitro as before affords the substituted anilines (XVI).

SCHEME 4

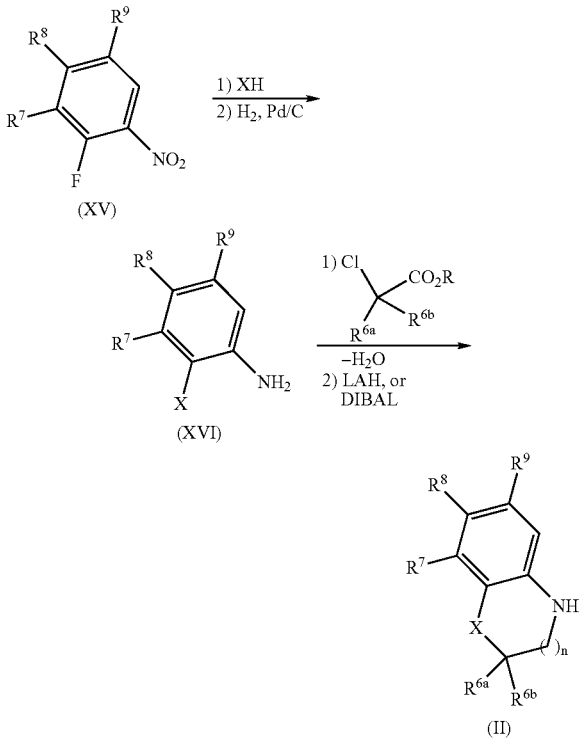

An alternate approach to the substituted fused anilines (II) is shown in Scheme 5. Treatment of the phenol (X=OH), thiophenol (X=SH), or other nucleophilically aromatic substituted derivative (XVII) with, for example, a haloalkyl carboxylic acid (or equivalent activated haloalkylcarboxylic acid, (i.e. acid halide, mixed anhydride, acrylic acid, acryloyl chloride, etc.), affords the derivative (XVIII) which when treated under Friedel-Crafts acylation conditions (see Ed. G. A. Olah, "Friedel-Crafts and Related Reactions", J. Wiley and Sons, New York, 1964, Vol 3, Pts 1 and 2 or Chem. Rev., 1955, 229, or Olah, G. A., "Friedel-Crafts Chemistry", Wiley Interscience, New York, 1973, for varying conditions and protocols), i.e. strong Lewis acids ($AlCl_3$, $FeCl_3$, etc.), affords the cyclic alkylphenones (XIX). Incorporation of the nitrogen functionality can be accomplished in several ways. For example, Schmidt rearrangement (as described by Smith, P. A. S., J. Am. Chem. Soc., 1948, 320) is effected by treatment of the carbonyl derivative (XIX) with $NaN_3$ and methanesulfonic acid to afford the bicyclic lactam (XX). Alternatively, this transformation may be carried out under Hoffmann rearrangement protocol (see, for example, Dike, S. Y., et al., Bioorg. Med. Chem. Lett., 1991, 383), by initial formation of the oxime derivative of (XXI) by treatment with hydroxylamine hydrochloride. Subsequent rearrangement to the lactam is efficiently accomplished by heating in polyphosphoric acid to afford the lactam (XX). Reduction of the lactam (XX) can be accomplished with a variety of reducing agents, for example, DIBAL, Red-Al and the like to afford the aniline (II).

SCHEME 5

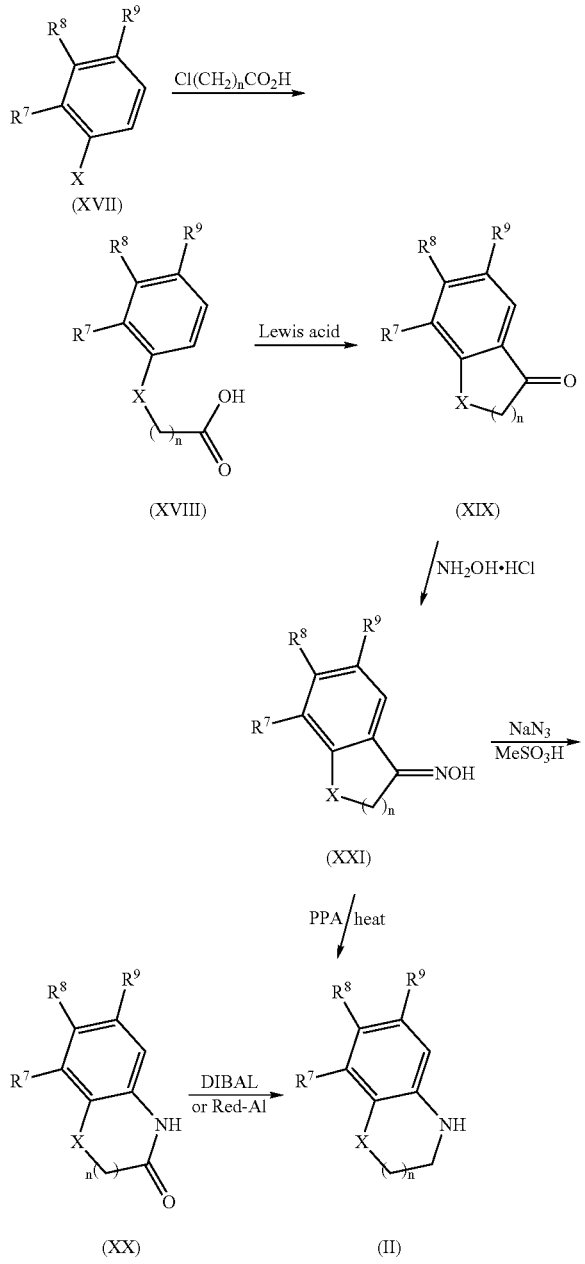

The preparation of compounds of Formula (I) with additional diversity of functionalization of the aromatic A ring of the tetracycle is shown in Scheme 6 and Scheme 7 and described here. Due to the nature of the synthetic route of Scheme 1 to derivatives of Formula (I), compounds with halogen substituents on the A-ring are difficult to prepare. However, bromination of the indolines (I, $R^8$=H) when the amine is protected, for example, with the Boc or CBZ protecting groups, with, for example, NBS in DMF affords the $R^8$ brominated derivatives (XXII). These activated aryl derivatives (XXII) act as excellent counterparts for a number of important synthetic transformations.

For example, biaryl coupling is accomplished under Suzuki coupling protocol. For a review and leading references of palladium catalyzed cross coupling reactions, see Miyaura, N., Suzuki, A., Chem. Rev., 1995, 2457. One such procedure entails treatment of the aryl bromide (XXII) with a functionalized aryl boronic acid (XXIII) in the presence of a catalytic Pd(0) species, such as $Pd(PPh_3)_4$, $Pd(PPh_3)_2Cl_2$, $Pd(OAc)_2$, $Pd_2(dba)_3$ and a suitable ligand such as $PPh_3$, $AsPh_3$, etc., or other such Pd(0) catalyst, and a base such as $Na_2CO_3$ or $Et_3N$ in a suitable solvent such as DMF, toluene, THF, DME or the like, to afford the indolines (XXIV). Alternatively formation of the indole boronic acid from the bromine derivative (XXII) (i.e. (I, $R^8$=$B(OH)_2$)) would allow for greater diversity in the subsequent coupling of this indole boronic acid with commercially available haloaromatic derivatives in a similar Suzuki coupling strategy as described above to afford the indolines (XXIV).

SCHEME 6

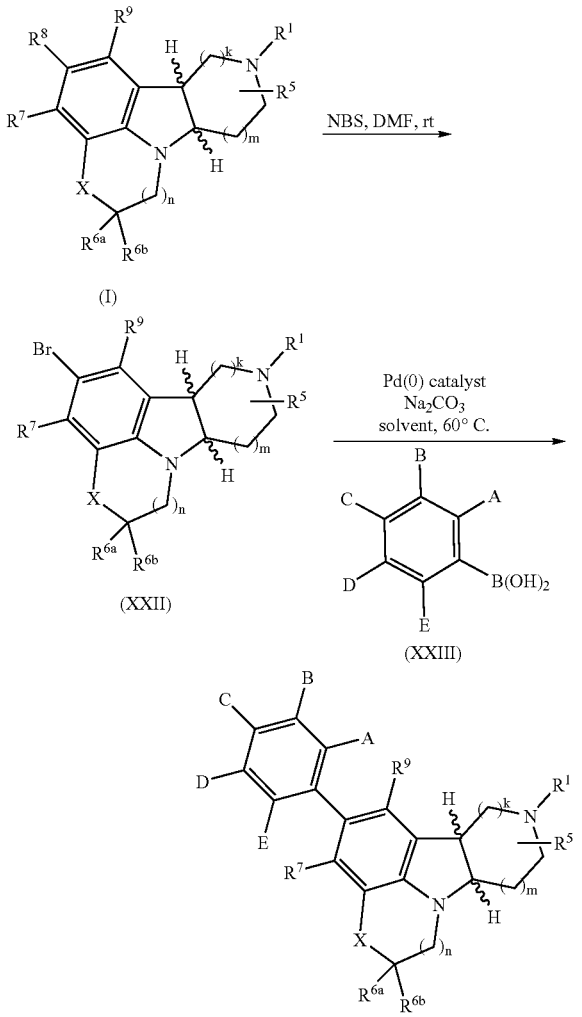

(I)

(XXII)

(XXIII)

(XXIV)

Similarly biaryl coupling of the bromine derivatives (XXV), readily obtained by the synthetic sequence exemplified in Scheme 2, (starting with the suitably functionalized bromo nitrobenzenes (II)), is shown in Scheme 7. This approach allows for the preparation of biaryl indoles as well as the corresponding indoline derivatives. Protection of the amine functionality must be carried out if $R^1$=H (Greene et. al for protections of amines). This is readily accomplished, for example, by treatment of bromo derviatives (XXV) with $(Boc)_2O$ in aqueous sodium hydroxide and dioxane. Subsequent Suzuki coupling with a variety of aryl boronic acids is carried out as described above in Scheme 6, to afford the biaryl adducts (XXVI). This protocol is amenable to $R^7$, $R^8$, and $R^9$ bromide, iodide, triflates, and/or diazo derivatives (see Miyaura, N., Suzuki, A., Chem. Rev., 1995, 2457, for a review of aryl couplings).

SCHEME 7

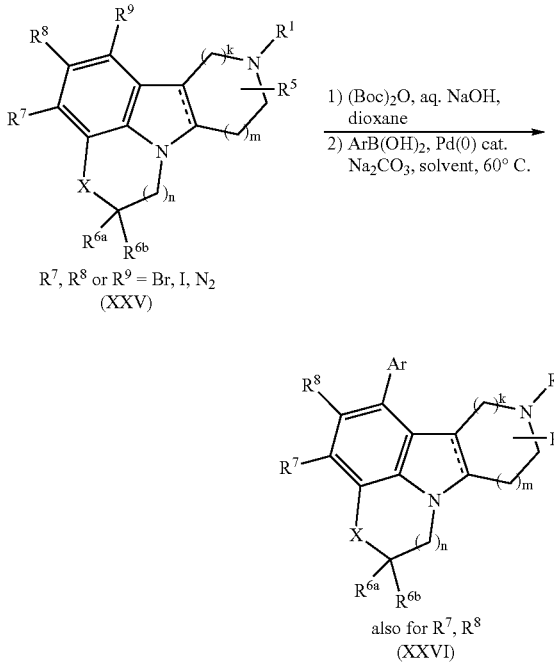

$R^7$, $R^8$ or $R^9$ = Br, I, $N_2$
(XXV)

also for $R^7$, $R^8$
(XXVI)

Furthermore and as an extension of this approach to a rapid preparation of a large array of biaryl indole and indoline derivatives, these bromide derivatives (XXV) can be bound to a solid support and the Suzuki couplings can be carried out on solid support (see XXVIII) as illustrated in Scheme 8. Towards that end treatment of indoline (XXV) with TFA in $CH_2Cl_2$, to remove the Boc protecting group, followed extraction from aqueous base provides the free amine (XXXVII). The free amine can be loaded onto a suitable solid support such as (XXVIII) using conditions well known to those skilled in the art. Thus, p-nitrophenylchloroformate Wang resin (XXVIII) which can be obtained commercially from sources such as Novabiochem, Inc. is swollen in a suitable solvent such as N-methyl pyrrolidinone and treated with 1.5 equiv. of amine to afford the functionalized resin (XXIX). Suzuki couplings are then carried out in array format by treatment of resins (XXIX) with a suitable palladium source such as $Pd(PPh_3)_4$ or $Pd(dppf)Cl_2$ and a suitable base such as 2M aqueous $K_2CO_3$ or $Na_2CO_3$ or triethylamine with an excess (typically 5 equivalents) of an aryl boronic acid (procedures for solid-phase Suzuki and other palladium couplings are well-known by those in the art, see for instance L. A. Thompson and J. A. Ellman, Chem. Rev. 1996, 96, (1), 555–600). The coupling may be repeated to ensure complete conversion to the desired coupled product. Cleavage from the solid support by treatment with TFA affords the corresponding indoles and indolines (XXX) as their TFA salts.

SCHEME 8

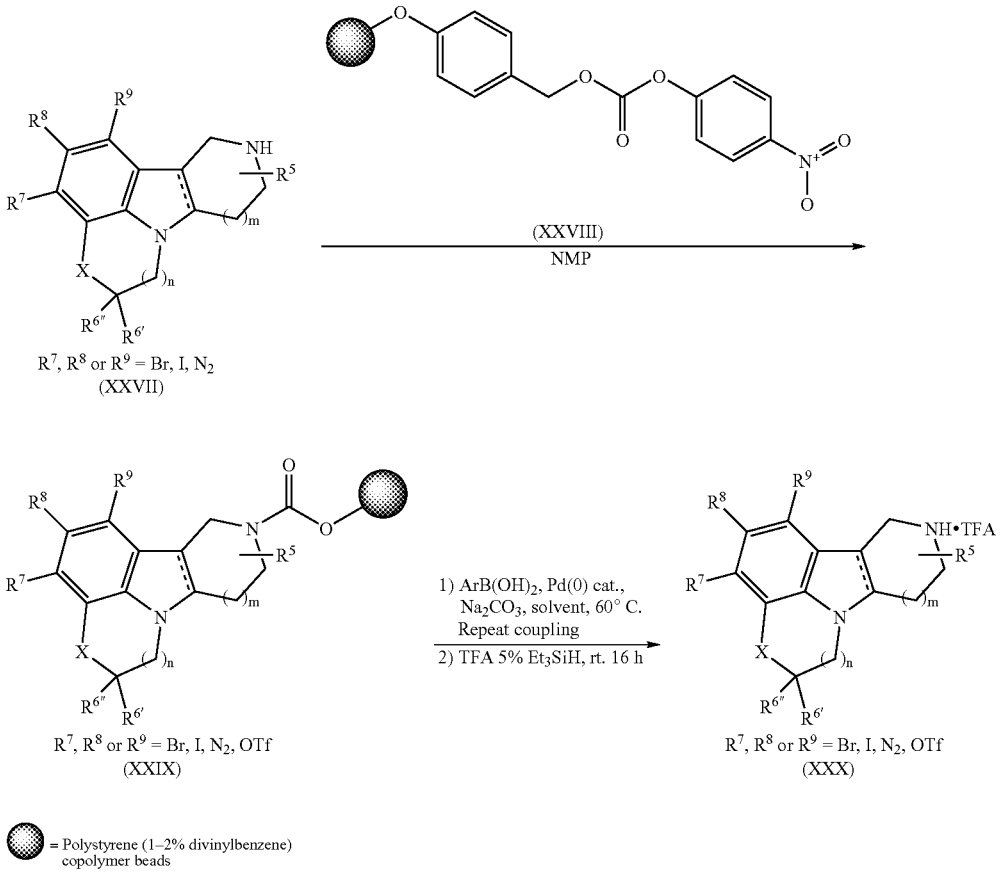

In addition, there exists a wide range of procedures and protocols for functionalizing haloaromatics, aryldiazonium and aryltriflate compounds. These procedures are well known by those in the art and described, for example, by Stanforth, S. P., Tetrahedron, 1998, 263; Buchwald, S. L., et. al., J. Am. Chem. Soc., 1998, 9722; Stille, J. K., et al., J. Am. Chem. Soc., 1984, 7500. Among these procedures are biaryl couplings, alkylations, acylations, aminations, and amidations. The power of palladium catalyzed functionalization of aromatic cores has been explored in depth in the last decade. An excellent review of this field can be found in J. Tsuji, "Palladium Reagents and Catalysts, Innovations in Organic Synthesis", J. Wiley and Sons, New York; 1995.

One such method to prepare compounds of Formula (I) with substituted $R^1$ sidechains in a more direct manner is shown in Scheme 9. Alkylation of the indole or indoline derivatives (I, $R^1$=H) with a haloalkyl ester, such as $ClCH_2(CH_2)pCO_2Me$, in the presence of NaI or KI and a base such as $K_2CO_3$, $Na_2CO_3$ or the like, in dioxane or THF or other such solvent while heating (see Glennon, R. A., et al., Med. Chem. Res., 1996, 197) affords the $R^1$ alkylated esters. Subsequent formation of the activated amides (XXXI) is accomplished by treatment of the ester with N, O-dimethylhydroxylamine hydrochloride and a Lewis acid such as trimethylaluminum or triethylaluminum in toluene (see, for example, Golec, J. M. C., et. al., Tetrahedron, 1994, 809) at 0° C. Treatment of the amide (XXXI) with a variety or organometallic agents, such as Grignard reagents $R^{1a}MgBr$, alkyl and aryl lithium reagents etc. (see Sibi, M. P., et. al., Tetrahedron Lett., 1992, 1941; and more generally House, H. O., Modern Synthetic Reactions, W. A. Benjamin, Inc., Menlo Park, Calif., 1972), in a suitable solvent such as THF, ether, etc. at low temperatures affords the substituted ketones (XXXII).

SCHEME 9

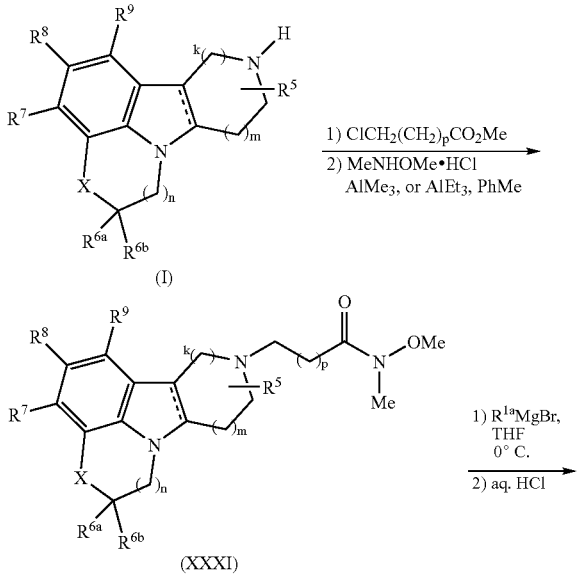

-continued

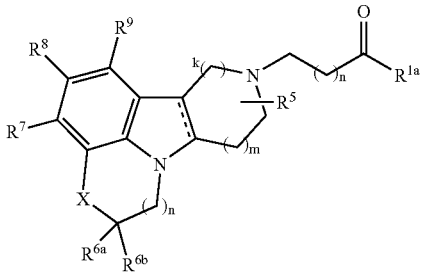

(XXXII)

Preparation of compounds of Formula (I) where m=0, k=1 is outlined in Scheme 10 and described here. Fischer indole cyclization of the previously described hydrazine (III) with a known protected 2,3-dioxopyrolidine (Carlson, E. H., et. al., J. Org. Chem., 1956, 1087) under a variety of typical cyclization conditions affords the tetracyclic indole (XXXIII). The reduction may be accomplished with a variety of reducing agents, for example, LAH, DIBAL, etc., to yield the pyrole fused indole (XXXIV). This derivative can then be deprotected and subsequently alkylated as described previously (see Greene, T. W., Wuts, P. G. W., "Protective Groups in Organic Synthesis, 2nd Edition", John Wiley and Sons, Inc., New York, 1991, and Scheme 1), to give the $R^1$ alkylated indole analogs (XXXV). Alternatively, reduction of the indole to the indoline, as described previously (see Scheme 1), followed by deprotection of the benzyl group to give (XXXVI) and alkylation gives access to the corresponding $R^1$ alkylated indoline derivatives (XXXVII). All the previously described methods to functionalize the aromatic ring, and to afford derivatives of varying $R^1$ sidecahins are applicable to these cores.

SCHEME 10

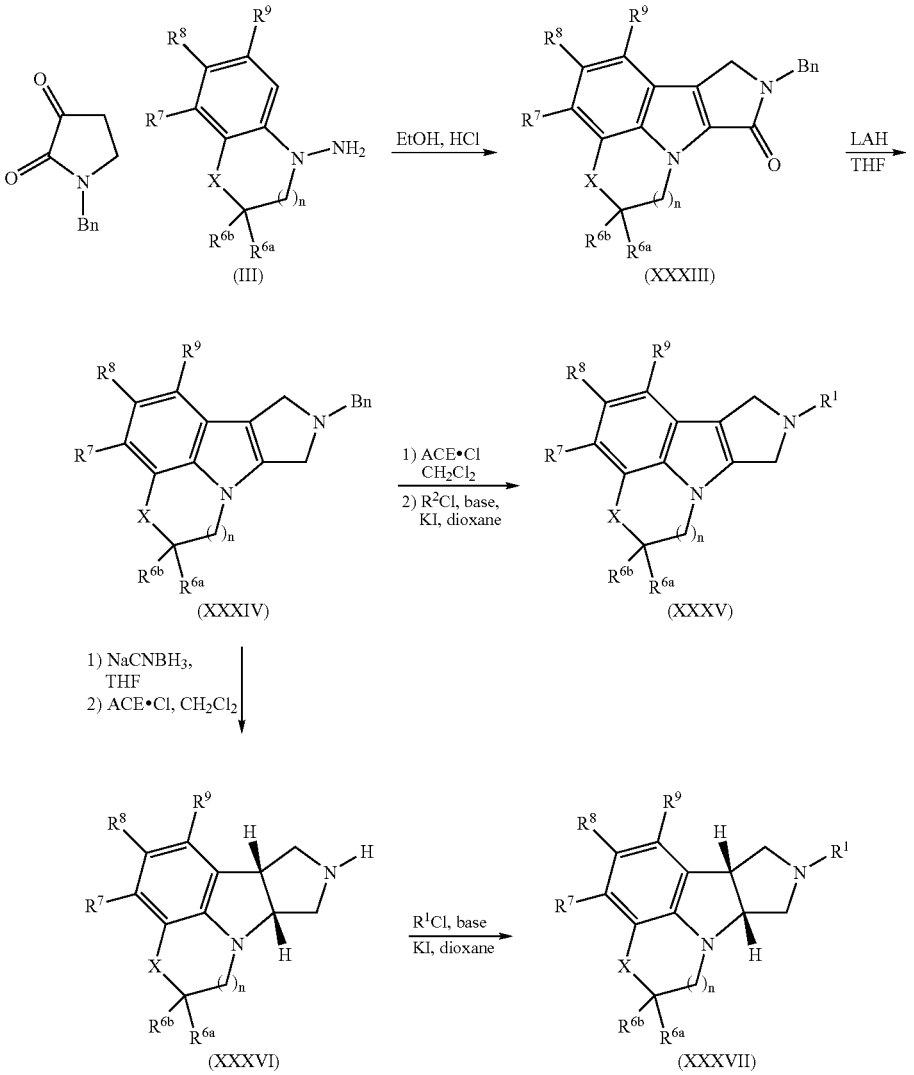

EXAMPLES

Chemical abbreviations used in the Examples are defined above. The detailed processes for preparing the compounds of Formula (I) are illustrated by the following Examples. It is, however, understood that this invention is not limited to the specific details of these examples. The Examples as set forth below are intended to demonstrate the scope of the invention but are not intended to limit the scope of the invention. Proton nuclear magnetic resonance spectra ($^1$H NMR) were measured in chloroform-d ($CDCl_3$) unless otherwise specified and the peaks are reported in parts per million (ppm) downfield from tetramethylsilane (TMS). The coupling patterns are reported as follows: s, singlet; d, doublet; dd, doublet of doublets; t, triplet; q, quartet; m, multiplet; bs, broad singlet; bm, broad multiplet.

Example 4 ethyl 1-fluoro-6,7,9,12-tetrahydro-5H-pyrido[4,3-b][1,4]thiazepino[2,3,4-hi]indole-11(10H)-carboxylate Step A p-Fluorothiophenol (5 g, 40 mmol) and β-propiolactone (2.8 g, 40 mmol) were dissolved in THF (36 mL of freshly distilled) and then placed in an ice bath. 95% sodium hydride (1 g, 42.9 mmol) was added in small portions over 1 hour. The reation was allowed to stir at 0° C. for 2 hours, then placed in the freezer overnight. The reaction was quenched with ice chips and then acidified with concentrated hydrogen chloride until a pH of 2. The product was extracted with ethyl acetate (1×200 mL) and dichloromethane (2×200 mL), dried (sodium sulfate) and concentrated to give 3-(4-fluorophenylthio)propanoic acid (7.08 g, 89%). $^1$H NMR ($CDCl_3$, 300 MHz): δ7.42–7.35 (m, 2H), 7.02 (t, 2H, J=8.6 Hz), 4.35 (t, 1H, J=6.2 Hz), 3.10 (t, 2H, J=7.3 MHz), 2.63 (t, 2H, J=7.3 Hz) ppm.

Step B 3-(4-Fluorophenylthio)propanoic acid (3 g, 15 mmol) was dissloved in dichloromethane (30 mL) and cooled to 0° C. in an ice bath. Oxalyl chloride (10 mL) was added slowly, dimethyl formamide (1 drop) was added and the reaction mixture was stirred at 0° C. for 0.5 hours. At which point the reaction was concentrated under reduced pressure to a residue, then resuspended in dichloromethane and cooled to 0° C. in an ice bath, $Cs_2$ (1 mL) was added and $AlCl_3$ (4 g, 15 mmol) was added slowly. The reaction mixture was then allowed to warm to room temperature and stirred over night. Ice chips and water (250 mL) were added and stirred. Concentrated hydrogen chloride was added until pH of 2, and extracted with dichloromethane (3×150 mL). Organics were combined, washed with brine (1×100 mL) and water (1×100 mL), dried (sodium sulfate), and concentrated to a yellow solid. The solid was purified by flash column chromatography on 100 g silica gel, eluting 10% ethyl acetate in hexanes to give 6-fluoro-2,3-dihydro-4H-1-benzothiopyran-4-one (2.55 g, 93%). $^1$H NMR ($CDCl_3$, 300 MHz): δ7.80–7.76 (m, 1H), 7.27–7.23 (m, 2H), 7.15–7.09 (m, 1H), 3.23 (t, 2H, J=6.4 Hz), 2.97 (t, 2H, J=6.4 Hz) ppm.

Step C

6-Fluoro-2,3-dihydro-4H-1-benzothiopyran-4-one (100 mg, 0.54 mmol) was dissolved in acetic acid (0.5 mL, 1.1 eq), sodium azide (71.2 mg, 1.1 mmol) was added and mixture was heated to 50° C. Sulfuric acid (0.13 mL, 4.3 eq) was added slowly and stirred at 50° C. for 1.5 hours. Ice chips (150 mg) were added and a green solid percipitated, this was filtered, washed with water and dried to 7-fluoro-2,3-dihydro-1,5-benzothiazepin-4(5H)-one (80 mg, 24%). $^1$H NMR ($CDCl_3$, 300 MHz): δ7.77 (s-broad, 1H) 7.69 (t, 1H, J=7.3 Hz), 6.94–6.82 (m, 2H), 3.42 (t, 2H, J=7 Hz), 2.63 (t, 2H, J=6.7 Hz) ppm.

Step D

7-Fluoro-2,3-dihydro-1,5-benzothiazepin-4(5H)-one (76 mg, 0.38 mmol) dissolved in toluene (1 mL) and cooled to 0° C. in an ice bath. Red-Al (275 mL, 0.91 mmol) was added and then the reaction allowed to warm to room temperature. The reaction was heated at reflux for 1.5 hours. 1 N sodium hydoxide was added slowly until pH>10, this was stirred for 10 minutes, extracted with dichloromethane (3×25 mL), washed with water, and dried (sodium sulfate). The concentrated organics were purified by preperative thin layer chromatography on silica gel and eluted with 50% ethyl acetate in hexanes to 7-fluoro-2,3,4,5-tetrahydro-1,5-benzothiazepine (30.8 mg, 93%). $^1$H NMR ($CDCl_3$, 300 MHz): δ7.32 (t, 1H, J=7.5 Hz), 6.53–6.42 (m, 2H), 4.09 (s-broad, 1H), 3.31–3.27 (m, 2H), 2.83–2.79 (m, 2H), 2.11–2.04 (m, 2H) ppm.

Step E

7-Fluoro-2,3,4,5-tetrahydro-1,5-benzothiazepine (423 mg, 2.3 mmol) was dissolved in acetic acid (1.15 mL)at 0° C. in an ice bath. 2.7 M aqueous sodium nitrite (1 mL) was added and this was stirred over night. Water was added (100 mL) and extracted with dichloromethane (3×50 mL), the organics were combined and concentrated to give 7-fluoro-5-nitroso-2,3,4,5-tetrahydro-1,5-benzothiazepine (449 mg, 92%). $^1$H NMR ($CDCl_3$, 300 MHz): δ7.43 (t, 1H, J=7.1 Hz), 7.30 (dd, 1H, J=9.1 Hz, J=9.2 MHz), 7.26–7.00 (m, 1H), 4.18 (t, 2H, J=5.8 Hz), 2.86 (t, 2H, J=7.2 Hz), 2.17–2.04 (m, 2H) ppm.

Step F 7-fluoro-5-nitroso-2,3,4,5-tetrahydro-1,5-benzothiazepine (449 mg, 2.11 mmol) was suspended in THF (1 mL of freshly distilled) and cooled to 0° C. in an ice bath. Lithium aluminum hydride (80 mg, 2.11 mmol) was added in a portion wise fashion. The flask was removed from the ice bath and allowed to warm to room temperature and was stirred for 2 hours. Water (0.08 mL) was added and stirred for 10 minutes. 15% sodium hydroxide (0.08 mL) was added stirred for 10 minutes. Water (0.024 mL) was added and stirred for 10 minutes. The reaction was extracted with dichloromethane (2×25 mL). The organics were concentrated to a residue, then taken up in minimal amount of dichloromethane and then hydrogen chloride in ether (1 M) was added until percipatation formed, the precipatate was filtered off to 7-fluoro-3,4-dihydro-1,5-benzothiazepine-5(2H)-amine (471 mg, 95%). $^1$H NMR ($CD_3OD$, 300 MHz): δ7.59 (t, 1H, J=7.5 Hz), 7.28 (d, 1H, J=9.9 Hz), 7.00 (t, 1H, J=8.2 Hz), 3.52 (t, 1H, J=7.5 Hz), 2.92–2.86 (m, 1H), 2.72–2.70 (m, 2H), 2.40–2.31 (m, 1H), 2.2–2.18 (m, 2H) ppm.

Step G to 7-fluoro-3,4-dihydro-1,5-benzothiazepine-5(2H)-amine (470 mg, 2 mmol), 1-carbethoxy-4-piperidone (0.3 mL, 2 mmol), and ethanol (11 mL) were all combined and heated to reflux overnight. The reaction was concentrated to a residue and purified by flash column chromatography on 20 g of silica, eluting with (1%, 2%, 3%, and 10%) methanol in dichloromethane to give the title compound (115 mg, 54%). $^1$H NMR ($CDCl_3$, 300 MHz): δ6.84 (t, 1H, J=6.4 Hz), 6.50 (t, 1H, J=6 Hz), 4.72 (s-broad, 2H), 4.47 (t, 2H, J=5.8 Hz), 4.20–4.13 (m, 2H), 3.82 (s-broad, 2H), 3.27 (t, 2H, J=6.7 Hz), 2.69 (s-broad, 2H), 2.27 (q, 2H, J=6.1 Hz), 1.36 (t, 3H, J=6.9 Hz) ppm. Mass Spec (ESI): 335 (base M+H).

Example 5

1-fluoro-6,7,9,10,11,12-hexahydro-5H-pyrido[4,3-b][1,4]thiazepino[2,3,4-hi]indole Ethyl-1-fluoro-6,7,9,12-tetrahydro-5H-pyrido[4,3-b][1,4]thiazepino[2,3,4-hi]indole-11(10H)-carboxylate (26 mg, 0.079 mmol), ethylene glycol (0.7 mL), hydrazine hydrate (19.5 mg, 0.39 mmol), and potassium hydroxide (11.2 mg, 0.2 mmol) were combined and heated at reflux 1.5 hours. Water (15 mL) was added and then extracted with dichloromethane (2×15 mL), dried (sodium sulfate) and concentrated to a residue. The residue was taken up in ether (2 mL) and 1 M hydrogen chloride in ether (0.1 mL) was added until a solid crashed out. The solid was filtered to give the title compound (5.6 mg, 26.7%). $^1$H NMR ($CD_3OD$, 300 MHz): δ6.92 (q, 1H, J=4.8 Hz), 6.57 (q, 1H, J=6.1 Hz), 5.46 (s, 2H), 4.69 (t, 2H, J=5.9 Hz), 4.46 (s, 2H), 3.59 (t, 2H, J=6.2 Hz), 3.07 (t, 2H, J=6.2 Hz), 2.33 (q, 2H, J=5.8 Hz) ppm.

Example 6

1-methyl-6,7,9,10,11,12-hexahydro-5H-pyrido[4,3-b][1,4]thiazepino[2,3,4-hi]indole Step A The corresponding acid, 3-[(4-methylphenyl)sulfanyl] propanoic acid, was prepared by the method of Example 4 Step A, using p-thiocresol to afford (7.84 g, 43.9%). $^1$H NMR ($CDCl_3$, 300 MHz): δ7.30 (d, 2H, J=8.1 Hz), 7.11 (d, 2H, J=7.7 Hz), 3.10 (t, 2H, J=7.3 Hz), 2.64 (t, 2H, J=7.3 Hz), 2.32 (s, 3H) ppm.

Step B

The 6-methyl-2,3-dihydro-4H-1-benzothiopyran-4-one was prepared by the method of Example 4 Step B, to afford (3.44 g, 100%). $^1$H NMR ($CDCl_3$, 300 MHz): δ7.92 (s, 1H), 7.26–7.18 (m, 2H), 3.23 (t, 2H, J=6.4 Hz), 2.96 (m, 2H, J=6.4 Hz), 2.32 (s, 3H) ppm.

Step C

6-Methyl-2,3-dihydro-4H-1-benzothiopyran-4-one (2g, 10.9 mmol) was dissolved in 80% ethanol (73 mL) and to this was added hydroxylamine hydrochloride (840 mg, 12.05 mmol) and sodium acetate (990 mg, 12.03 mmol). This mixture was heated at reflux for 3 hours. Water (150 mL) was added and then extracted with dichloromethane (3×100 mL), washed with brine (75 mL), water (75 mL), dried (sodium sulfate) and concentrated to residue. The residue was taken up in polyphosphoric acid (10 mL) and heated at reflux for 1 hour. Ice chips were added and water was added (100 mL) this was stirred for 1 hour. A solid formed and was filtered and purified by flashcolumn chromatography on 20 g of silica gel, eluting with (50%, 60%, and 70%) ethyl acetate in hexanes to give 7-methyl-2,3,4,5-tetrahydrobenzo[b]1,4-thiazepin-4-one (500 mg, 30%). $^1$H NMR ($CDCl_3$, 300 MHz): δ7.87 (s-broad, 1H), 7.47 (d, 1H, J=7.7 Hz), 6.98 (d, 1H, J=8.1 Hz), 6.91 (s, 1H), 3.42 (t, 2H, J=6.9 Hz), 2.62 (t, 2H, J=6.9 Hz), 2.35 (s, 3H) ppm.

Step D

The 7-methyl-2,3,4,5-tetrahydro-1,5-benzothiazepine was prepared by the method of Example 4 Step D, to afford (939 mg, 100%). $^1$H NMR ($CDCl_3$, 300 MHz): δ7.26 (d, 1H, J=4.8 Hz), 6.44 (d, 1H, J=8.4 Hz), 6.58 (s, 1H), 4.00–3.75 (s-broad, 1H), 3.22 (t, 2H, J=5.3 Hz), 2.77 (t, 2H, J=5.8 Hz), 2.25 (s, 3H, 2.09–2.03 (m, 2H) ppm.

Step E

The 7-methyl-5-nitroso-2,3,4,5-tetrahydro-1,5-benzothiazepine was prepared by the method of Example 4 Step E, to afford (1.06 g, 98%). $^1$H NMR ($CDCl_3$, 300 MHz): δ7.37–7.34 (m, 2H), 7.12–7.10 (d, 1H, 9.2 Hz), 4.17–4.14 (t, 2H, 5.9 Hz), 2.87–2.83 (t, 2H, 6 Hz), 2.38 (s, 3H), 2.17–2.10 (m, 2H), ppm. Mass Spec (ESI): U/A (base M+H).

Step F

The 7-methyl-3,4-dihydro-1,5-benzothiazepin-5(2H)-amine was prepared by the method of Example 4, Step F to afford (292 mg, 30%). $^1$H NMR ($CDCl_3$, 300 MHz): δ7.68 (d, 1H, J=7.7 Hz), 7.31–7.26 (m, 2H), 3.46 (t, 2H, J=5.6 Hz), 2.88 (t, 2H, J=5.7 Hz), 2.38 (s, 3H) ppm.

Step G

7-Methyl-3,4-dihydro-1,5-benzothiazepin-5(2H)-amine (50 mg, 0.24 mmol) and 4-piperidone monohydrate (37 mg, 0.24 mmol) were dissolved in a 1:1 mixture of ethanol/acetic acid (0.4 mL) and cooled to 0° C. in an ice bath. To this was added zinc dust (94 mg, 1.44 mmol) slowly monitoring addition rate to keep internal temperature<20° C. The reaction was stirred at 0° C. for 1 hour. The reaction was allowed to warm to room temperature and stirred for an additional 0.5 hours. The reaction was then filtered, and the filter cake washed with ethanol. The filtrate was heated to reflux for 2 hours, then concentrated to a residue. The residue was dissolved in a minimum amount of water and to it added cold ammonium hydroxide unit pH>11. This was extracted with dichloromethane (2×50 mL) and dried (sodium sulfate), then concentrated to a residue. The residue was dissolved in a minimum amount of dichloromethane and the hydrochloride salt made using hydrogen chloride in ether (1M). The salt was then refluxed in 2-propaonal (10 mL) for 24 hours. Product purified by preperative thin layer chromatography on silica gel, and eluted with dichloromethane/methanol (9:1) to give the title compound (18 mg, 50%). $^1$H NMR ($CD_3OD$, 300 MHz): δ7.14 (d, 1H, J=7.7 Hz), 6.77 (d, 1H, J=7.7 Hz), 4.66 (s, 2H), 3.57 (t, 2H, J=6.2 Hz), 3.00 (t, 2H, J=7.7 Hz), 2.90 (t, 2H, J=6.95 Hz), 2.54 (s, 3H) ppm.

Example 7 tert-butyl1-methyl-6,7,9,12-tetrahydro-5H-pyrido[4,3-b][1,4-thiazepino[2,3,4-hi]indole-11(10H)-carboxylate 1-Methyl-6,7,9,10,11,12-hexahydro-5H-pyrido[4,3-b][1,4]thiazepino[2,3,4-hi]indole (47 mg, 0.18 mmol) was heated at 90° with di-tert-butyl dicarbonate (90 mg, 0.9 mmol) for 4 hours. Then purified by preperative thin layer chromatography on silica gel, and eluted with hexanes/ethyl acetate (3:1) to give the title compound (18.7 mg, 29%). $^1$H NMR ($CDCl_3$, 300 MHz) δ6.91–6.89 (m, 1H), 6.63–6.61 (m, 1H), 4.77 (s, 2H), 4.46 (t, 2H, J=5.8 Hz), 3.71 (s, 1H), 3.33 (t, 2H, J=5.7 Hz), 2.76–2.71 (m, 2H), 2.53 (s, 3H), 2.44–2.30 (m, 2H): 2.28–2.26 (m, 2H), 1.49 (s, 12H) ppm.

Example 8 cis-(8a,12a)-1-methyl-6,7,8a, 9,10,11,12,12a-octahydro-5H-pyrido[4,3-b][1,4]thiazepino [2,3,4-hi]indole Tert-butyl-1-methyl-6,7,9,12-tetrahydro-5H-pyrido[4,3-b][1,4]thiazepino[2,3,4-hi]indole-11(10H)-carboxylate (59 mg, 0.23 mmol) was dissolved in trifluoroacetic acid (1.6 mL) and cooled to 0° C. in an ice bath. Sodium cyanoborohydride (45 m, 0.72 mmol) was added slowly over 10 minutes, this was stirred at 0° C. for 1.5 hours. Then 6N hydrogen chloride (0.5 mL) was added and the reaction heated at reflux for 1 hour. 1N Sodium hydroxide was added until pH>12 and extracted with dichloromethane (2×25 mL), dried (sodium sulfate) and concentrated to give the title compound. $^1$H NMR ($CDCl_3$, 300 MHz): δ6.84 (d, 1H, J=8.1 Hz), 6.43 (d, 1H, J=7.9 Hz), 3.96–3.83 (m, 1H), 3.62–3.57 (m, 1H), 3.31–3.20 (m, 1H), 3.11–2.83 (m, 4H), 2.80–2.63 (m, 2H), 2.41–2.38 (m, 1H), 2.168 (s, 3H), 1.97–1.91 (m, 1H), 1.80–1.75 (m, 1H), 1.63–1.58 (s-broad, 2H) ppm. Mass Spec (ESI): 261 (base M+H).

Example 9 trans-(8a,12a)-6,7,8a, 9,10,11,12,12a-octahydro-5H-pyrido[4,3-b][1,4]thiazepino[2,3,4-hi]indole To a solution of 6,7,9,10,11,12-hexahydro-5H-pyrido[4,3-b][1,4]thiazepino[2,3,4-hi]indole, from Example 128 Step B (90 mg, 0.37 mmol) was added an excess of borane-THF (3 mL) at 0° C. in an ice bath. The solution was diluted carefully with water (29 mL), followed by the addition of trifluoroacetic acid (4.3mL). The reaction was stirred at 0° C. and followed by TLC (10% methanol in dichloromethane) until the starting material dissappeared. The reaction was basified with ammonium hydroxide until pH>12 and extracted with dichloromethane (3×20 mL). Extracts were collected washed with brine (1×20 mL), water, and dried (magnesium sulfate). Then concentrated to give the title compound (78 mg, 84%). $^1$H NMR ($CDCl_3$, 300 MHz): δ7.10 (dd, 1H, J=8 Hz, J=7.7 Hz), 7.00 (dd, 1H, J=7.7 Hz, J=7.3 Hz), 6.85 (t, 1H, J=7.7 Hz), 4.59–4.50 (m, 1H), 4.39–4.34 (m, 1H), 4.24 (dd, 1H, J=15.4 Hz, J=15.4 Hz), 3.83 (t, 1H, J=10.6 Hz, J=13.2 Hz), 3.79–3.60 (m, 2H), 3.42–3.2 (m, 2H), 3.07–2.92 (m, 1H), 2.87–2.73 (m, 2H), 2.30–2.19 (m, 2H) ppm.

Example 10

1-nitro-6,7,9,10,11,12-hexahydro-5H-pyrido[4,3-b][1,4]thiazepino[2,3,4-hi]indole Step A 2-amino-4-nitro-fluorbenzene (500 mg, 3.2 mmol), 3-chloro-1 propanethiol (354 mg, 3.2 mmol), and potassium hydroxide (269 mg, 4.8 mmol) were mixed together in ethylene glycol dimethyl ether (6.4 mL) and heated at reflux for 72 hours. The reaction was filtered and the filtercake washed with chloroform. The filtrate was concentrated and purified by flash column chromatography on 10 g if silica gel and eluted with 3% methanol in chloroform to give 2-[(3-chloropropyl)sulfanyl]-5-nitrophenylamine (130 mg, 17%). $^1$H NMR ($CDCl_3$, 300 MHz): δ7.49–7.48 (m, 2H), 7.38 (dd, 1H, J=7.7 Hz, J=7.7 Hz), 4.55 (s-broad, 2H), 3.64 (t, 2H, J=6.2 Hz), 3.03 (t, 2H, J=7 Hz), 2.00 (q, 2H, J=7 Hz) ppm. Mass Spec (ESI):264 (base M+H).

Step B

2-[(3-Chloropropyl)sulfanyl]-5-nitrophenylamine (100 mg, 0.44 mmol) was dissolved in hydrochloric acid (1.8 mL) in an ice bath, 1 M aqueous sodium nitrate (0.5 mL) was added dropwise. This was stirred at 0° C. for 1.5 hours. 0.25 M tin (II) chloride in hydrogen chloride (3.28 mL) was added dropwise. After addition the reaction was allowed to warm to room temperature, and stirred for 1.5 hours. The reaction was basified with 50% sodium hydroxide until pH of 14 and extracted with ethylacetate (3×50 mL). The solution was concentrated to a residue, taken up in minimal chloroform and 1 M hydrogen chloride in ether was added until percipitation. The solution was filtered and dried to give 1-{2-[(3-chloropropyl)sulfanyl]-5-nitrophenyl}hydrazine (100 mg, 85%). $^1$H NMR ($CDCl_3$, 300 MHz): δ7.94 (d, 1H, J=2.5 Hz), 7.3 (dd, 1H, J=8.5 Hz, J=8.4 Hz), 7.38 (d, 1H, J=8.4 Hz), 6.28 (s-broad, 1H), 3.73 (s-broad, 2H), 3.63 (t, 2H, J=6.3 Hz), 3.00 (t, 2H, J=7 Hz), 2.01 (q, 2H, J=6.5 Hz) ppm.

Step C

1-{2-[(3-Chloropropyl)sulfanyl]-5-nitrophenyl}hydrazine (100 mg, 0.38 mmol) and 4-piperidone mono hydrate (58 mg, 0.38 mmol) were dissolved in trifluoroethanol (1 mL) andheated at reflux for 1 hour. To this was added 12 N HCl (3 mL) and the reaction allowed to heat at reflux for 2 hours. The product percipatated out upon cooling to room temperature, it was filtered off and washed with cold 2-propanol to give 3-chloropropyl9-nitro-2,3,4,5-tetrahydro-1H-pyrido[4,3-b]indol-6-yl sulfide (120 mg, 75.4%). $^1$H NMR ($CD_3OD$, 300 MHz): δ8.00 (d, 1H, J=8.4 Hz), 7.30 (d, 1H, J=8.4 Hz), 4.68 (s, 2H), 3.69 (t, 2H, J=6.2 Hz), 3.60 (t, 2H, J=6 Hz), 3.23 (t, 2H, J=6.2 Hz), 2.08 (q, 2H, J=6.2 Hz) ppm.

Step D

3-Chloropropyl 9-nitro-2,3,4,5-tetrahydro-1H-pyrido[4,3-b]indol-6-yl sulfid (100 mg, 0.38 mmol) and 4-piperidone mono hydrate (58 mg, 0.38 mmol) were dissolved in trifluoroethanol (1 mL) and heated at reflux for 1 hour. To this was added 12 N HCl (3 mL) and the reaction allowed to heat at reflux for 2 hours. The product percipatated out upon cooling to room temperature, it was filtered off and washed with cold 2-propanol to give the title compound (160 mg, 63%). $^1$H NMR ($CD_3OD$, 300 MHz): δ7.79 (d, 1H, J=8.4 Hz), 7.11 (d, 1H, J=8.4 Hz), 4.65 (t, 2H, J=6.1 Hz), 4.58 (s, 2H), 3.61 (t, 2H, J=6.3 Hz), 3.17 (t, 2H, J=6.3 Hz), 2.36 (q, 2H, J=6.2 Hz) ppm.

Example 11 cis-(8a,12a)-1-nitro-6,7,8a,9,10,11,12,12a-octahydro-5H-pyrido[4,3-b][1,4]thiazepino[2,3,4-hi]indole 1-Nitro-6,7,9,10,11,12-hexahydro-5H-pyrido[4,3-b][1,4]thiazepino[2,3,4-hi]indole (0.04 mg, 0.13 mmol) was dissolved in tirfluoroacetic acid (0.86 mL) at 0° C. Sodium cyanoborohydride (40.1 mg, 0.66 mmol) was added slowly so internal temperature<8° C. After addition the reaction was allowed to stir at 0° C. for 5 hours. Then basified with sodium hydroxide (50%) until pH of 12–14. The solution was extracted with dichloromethane (3×10 mL) and concentrated to a residue. To the residue was added concentrated hydrogen chloride (0.5 mL) and heated to reflux for 1.5 hours. Then basified with ammonium hydroxide to pH 12–14, then extracted with dichloromethane (3×10 mL) and concentrated. The residue was purified by preperative thin layer chromatography, eluting with 10% methanol in dichloromethane to give the title compound (5 mg, 13%). $^1$H NMR ($CD_3OD$, 300 MHz): δ7.40 (d, 1H, J=8.4 Hz), 7.04 (d, 1H, J=8.4 Hz), 4.09–3.70 (m, 5H), 3.51–3.48 (m, 2H), 3.12–2.92 (m, 2H), 2.83–2.78 (m, 1H), 2.20–2.18 (m, 1H), 2.02–1.89 (m, 3H) ppm.

Example 12

3-chloro-6,7,9,10,11,12-hexahydro-5H-pyrido[4,3-b][1,4]thiazepino[2,3,4-hi]indole Step A To a dry THF (Aldrich anhydrous grade, 70 mL) solution of 2,3-dichloronitrobenzene (9.61 g, 50.1 mmol) and 3-chloropropanethiol (5.0 g, 45.5 mmol) was added in one portion at 23° C. KOH pellets. The resulting mixture was vigorously stirred at 23° C. for 3.5 h. The reaction mixture was filtered through a Celite plug to remove remaining KOH. The plug was washed with THF (2×50 mL). The filtrate was concentrated in vacuo to give crude 1-chloro-2-[(3-chloropropyl)sulfanyl]-3-nitrobenzene (12 g, ~100%).

Step B

The crude 1-chloro-2-[(3-chloropropyl)sulfanyl]-3-nitrobenzene was dissolved in MeOH (150 mL) and degassed with $N_2$. Palladium hydroxide (1.8 g) was added in four portions to this solution in a Parr apparatus. The resulting heterogeneous solution was shaken under hydrogenation conditions (55 psi) at room temp for 18 h. The catalyst was removed via filtration in the same manner as above and the filtrate was concentrated in vacuo. to afford 3-chloro-2-[(3-chloropropyl)sulfanyl]aniline (9.94 g, 93%) as a dark oil: $^1$H NMR ($CHCl_3$, 300 MHz) δ7.03 (t, 1H, J=8.1 Hz), 6.82 (t, 1H, J=8.1 Hz), 6.63 (t, 1H, J=8.0 Hz), 4.62 (br s, 1H), 3.68 (t, 2H, J=6.4 Hz), 2.92 (t, 2H, J=6.9 Hz), 1.98 (quintet, 2H, J=6.6 Hz) ppm.

Step C

3-Chloro-2-[(3-chloropropyl)sulfanyl]aniline (4.2 g, 15.4 mmol) was dissolved in TFA (24 mL) at 23° C. With stirring concentrated HCl (24 mL) was added. This mixture was cooled in an ice bath. A solution of $NaNO_2$ (1.17 g, 10 mmol) in water (6 mL) was added dropwise over 10 min. The internal temperature of the reaction was maintained at 21 5° C. during this addition, and then maintained at 0° C. for 1 h at which time it was transferred via cannula over 10 min to a stirred solution (8 mL) of $SnCl_2.2H_2O$ (7.65 g, 34 mmol) in concentrated HCl cooled in. an ice bath. The cooling bath was then removed and the reaction was allowed to warm to 23° C. for 1 h. It was recooled in an ice bath. Aqueous NaOH solution (50%) was added dropwise until pH>12 affording a heterogeneous product which was treated with $CH_2Cl_2$-MeOH (20:1, 250 mL). This mixture was filtered and the resulting two-phase filtrate was extracted with $CH_2Cl_2$ (2×200 mL). The combined organic extracts were dried ($MgSO_4$) and concentrated in vacuo. to afford 3-Chloro-2-(3'-chloropropylthio)phenyl hydrazine (4.0 g, 90%) as a brown oil. The resulting oil was dissolved in $CH_2Cl_2$ (100 mL),and a stream of HCl gas was bubbled into this solution for 5 min. The resultant purple solid was isolated after evaporation of the solvent to afford 1-{3-chloro-2-[(3-chloropropyl)sulfanyl]phenyl}hydrazine hydrochloride and used without further purification. $^1H$ NMR ($CD_3OD$, 300 MHz) δ7.37 (t, 1H, J=8.0 Hz), 7.15 (dd, 1H, J=8.1, 1.1 Hz), 6.95 (dd, 1H, J=8.5, 1.1 Hz), 3.67 (t, 2H, J=6.3 Hz), 2.95 (t, 2H, J=7.0 Hz), 1.90 (quintet, 2H, J=6.6 Hz) ppm Step D 1-{3-Chloro-2-[(3-chloropropyl)sulfanyl]phenyl}hydrazine hydrochloride (700 mg, 2.4 mmol) and 4-piperidone monohydrate hydrochloride (373 mg, 2.4 mmol) were added to 2,2,2-trifluoroethanol (6 mL) at 23° C. This suspension was heated at reflux for 18 h at which time a solid was formed. The solid was collected via vacuum filtration after cooling to 23° C. It was dried over 12 h to 7-chloro-6-[(3-chloropropyl)sulfanyl]-2,3,4,5-tetrahydro-1H-pyrido[4,3-b]indole hydrochloride (506 mg, 59%) as a brown powder. The filtrate concentrated and to afford a second crop of product (140 mg, 16%). $^1H$ NMR ($CD_3OD$, 300 MHz) δ11.09 (br s, 1H), 7.41 (t, 1H, J=8.4 Hz), 7.17 (d, 1H, J=8.4 Hz), 4.40 (br s, 2H), 3.67–3.59 (m, 4H), 3.17 (t, 2H, J=5.9 Hz), 3.00 (t, 2H, J=7.0 Hz), 1.84 (quintet, 2H, J=6.9 Hz) ppm.

Step E

To 7-chloro-6-[(3-chloropropyl)sulfanyl]-2,3,4,5-tetrahydro-1H-pyrido[4,3-b]indole hydrochloride (2.0 g, 5.7 mmol) and KI (850 mg) were suspended in anhydrous DME (200 mL). KOH powder (3.2 g, 57 mmol) was added in four portions with stirring. This mixture was heated at reflux for 3 h. The reaction mixture was cooled and filtered. The filtrate was concentrated to afford the title compound as an oil (1.13 g, 71%). $^1H$ NMR ($CHCl_3$, 300 MHz) δ7.07 (d, 1H, J=8.4 Hz), 6.99 (d, 1H, J=8.4 Hz), 4.50 (t, 2H, J=5.9 Hz), 3.92 (br s, 2H), 3.40 (t, 2H, J=6.6 Hz), 3.24 (t, 2H, J=5.7 Hz), 2.65 (t, 2H, J=5.5 Hz), 1.28 (quintet, 2H, J=6.3 Hz) ppm.

Example 13 cis-(8a,12a)-3-chloro-6,7,8a,9,10,11,12,12a-octahydro-5H-pyrido[4,3-b][1,4]thiazepino[2,3,4-hi]indole To a TFA solution (40 mL) of 3-chloro-6,7,9,10,11,12-hexahydro-5H-pyrido[4,3-b][1,4]thiazepino[2,3,4-hi]indole (1.0 g, 3.6 mmol) cooled in an ice bath was added in ten portions over 20 min $NaBH_4$ (684 mg, 18.0 mmol). The internal temperature of reaction mixture was maintained at <8° C. during this addition. The heterogeneous solution was allowed to stir at 2° C. for an additional 1.5 h. It was then poured on to ice chips, and aqueous NaOH solution (50%) was added until pH>12 (by pH paper). The resultant mixture was extracted with $CH_2Cl_2$ (3×200 mL). The extracts were combined, dried ($MgSO_4$) and concentrated in vacuo. The title compound was isolated as a tan powder (350 mg, 35%). $^1H$ NMR ($CHCl_3$, 300 MHz) δ6.72 (s, 2H), 4.01–3.91 (m, 1H), 3.72–3.62 (m, 2H), 3.38–3.33 (m, 1H), 3.14–3.30 (m, 4H), 2.91 (dd, 1H, J=8.3, 4.4 Hz), 2.56 (dd, 1H, J=12.1, 2.2 Hz), 2.17–1.79 (m, 4H) ppm. MS (CI, $NH_3$): 281 (base, M+H).

Example 14

3-methyl-6,7,9,10,11,12-hexahydro-5H-pyrido[4,3-b][1,4]thiazepino[2,3,4-hi]indole Step A A solution of acetonitrile (30 mL) and o-thiocresol (5.0 g, 40 mmol) was heated to reflux. Next β-propiolactone (2.8 mL, 40 mmol) was added dropwise over 5 min. Heating was continued at reflux for 20 h at which time additional β-propiolactone (2.8 mL, 40 mmol) was added in one portion. After heating for an additional 24 h, the reaction mixture was concentrated in vacuo. The resulting solid-oil mixture was treated at 23° C. with 2N aqueous NaOH (150 mL). This basic solution was washed with $Et_2O$ (2×200 mL). The separated aqueous layer was acidified with conc. aqueous HCl unit pH<1. This heterogeneous solution was concentrated in vacuo to half of its original volume. Then it was allowed to stand at 23° C. for 2 h. The solid product was collected by vacuum filtration, washed with $H_2O$ (20 mL), and dried under vacuum at 65° C. for 2 h to afford 3-[(2-methylphenyl)sulfanyl]propanoic acid (4.62 g, 59%) as a white powder. $^1H$ NMR ($CHCl_3$, 300 MHz) δ7.31 (d, 1H, J=7.0 Hz), 7.20–7.15 (m, 3H), 3.14 (t, 2H, J=7.3 Hz), 2.69 (t, 2H, J=7.4 Hz), 2.39 (s, 3H) ppm.

Step B

To heated (at 105° C.) polyphosphoric acid (PPA, 7.5 g) was added in one portion 3-[(2-methylphenyl)sulfanyl]propanoic acid (4.5 g, 23.0 mmol). This mixture was maintained at 105° C. for 1.5 h at which time it was poured onto ice-$H_2O$ (250 mL) to afford a heterogeneous mixture. The reaction vessel was rinsed with $H_2O$ (3×50 mL) and the rinses were combined. After the PPA was completely dissolved in water, the reaction mixture was filtered by vacuum. The isolated solid was washed with $H_2O$ (3×50 mL), and dried under vacuum for 18 h to yield 8-methyl-2,3-dihydro-4H-1-benzothiopyran-4-one (3.52 g, 86%) as a pink solid. $^1H$ NMR ($CHCl_3$, 300 MHz) δ8.00 (d, 1H, J=8.0 Hz), 7.28 (d, 1H, J=8.0 Hz), 7.09 (t, 1H, J=8.0 Hz), 3.22 (t, 2H, J=6.6 Hz), 2.95 (t, 2H, J=6.6 Hz), 2.30 (s, 3H) ppm.

Step C

To a solution of 8-methyl-2,3-dihydro-4H-1-benzothiopyran-4-one (2.24 g, 12.6 mmol) and $NaN_3$ (1.64 g, 25.2 mmol) in AcOH (7.6 mL) was added dropwise at 50° C. conc. $H_2SO_4$ (1.9 mL). The reaction was maintained at 50° C. for 2 h and poured onto ice chips. The solid was collected by vacuum filtration and dried under vacuum at 23° C. This crude sample was a mixture of starting material, desired product and regioisomeric product with a ratio of 1:11:7 (by $^1H$ NMR). Purification of the crude solid by column silica gel chromatography eluting with 20:1 $CHCl_3$-MeOH provided a mixture 9-methyl-2,3-dihydro-1,5-benzothiazepin-4(5H)-one and its regioisomer (500 mg, 4:1, by $^1H$ NMR). This sample was used without further purification. $^1$H NMR ($CHCl_3$, 300 MHz) δ7.22 (t, 1H, J=7.7 Hz), 7.15 (d, 1H, J=7.3 Hz), 6.94 (d, 1H, J=7.4 Hz), 3.39 (t, 2H, J=7.3 Hz), 2.59 (t, 2H, J=7.0 Hz), 2.54 (s, 3H) ppm.

Step D

To a suspension of 9-methyl-2,3-dihydro-1,5-benzothiazepin-4(5H)-one (4:1 regioisomers, 500 mg, 2.6 mmol) in toluene (10 mL) was added dropwise over 3 min Red-Al (65% w. in toluene, 1.6 mL). This solution was heated at 85° C. for 1.5 h. After it was allowed to cool to 23° C., aqueous 1N NaOH solution (2 mL) was added cautiously. Then, $CHCl_3$ (50 mL) and aqueous saturated Rochelle salt solution (50 mL) were added sequentially. This two-phase mixture was stirred vigorously at 23° C. for 1 h. The layers were separated, and the aqueous layer was back-extracted with $CHCl_3$ (2×50 mL). The extracts were combined, dried ($MgSO_4$) and concentrated in vacuo. to give 9-methyl-2,3,4,5-tetrahydro-1,5-benzothiazepine (500 mg, >100%) as a yellow oil. $^1$H NMR ($CDCl_3$, 300 MHz): δ6.92 (t, 1H, J=7.3 Hz), 6.75 (d, 1H, J=7.4 Hz), 6.58 (d, 1H, J=8.1 Hz), 3.34 (t, 1H, J=5.2 Hz), 2.92 (t, 2H, J=5.8 Hz), 2.48 (s, 3H), 2.25 (s, 3H), 2.04 (quintet, 2H, J=3.0 Hz) ppm.

Step E

To a solution of 9-methyl-2,3,4,5-tetrahydro-1,5-benzothiazepine (500 mg, 2.6 mmol) and AcOH (2 mL) cooled to ~9° C. was added a solution of $NaNO_2$ (212 mg, 3.1 mmol) and water (1 mL) dropwise over 4 min (internal temperature<12° C.). The cooling bath was removed and the reaction was maintained at 23° C. for 2 h. It was diluted with $H_2O$ (50 mL). 9-methyl-5-nitroso-2,3,4,5-tetrahydro-1,5-benzothiazepine was obtained (470 mg, 87%) as a yellow solid after it was collected by vacuum filtration and air-dried at 23° C.

Step F

To a 1.0 M THF solution of $LiAlH_4$ (2.3 mL, 2.3 mmol) cooled to ~10° C. was added dropwise via cannula over 3 min (internal temperature <25° C.) a THF solution (2.3 mL) of 9-methyl-5-nitroso-2,3,4,5-tetrahydro-1,5-benzothiazepine (crude, 470 mg, 2.3 mmol). The cooling bath was removed once the addition was finished, and the reaction was maintained at 25° C. to 32° C. for 1.5 h. $H_2O$ (0.1 mL) was added cautiously over 5 min, followed by THF (40 mL), aqueous NaOH solution (15%, 0.1 mL), and again $H_2O$ (0.3 mL). The resulting mixture was vigorously stirred at 23° C. for 1 h and dried ($MgSO_4$). The drying agent was removed by filtration and the filtrate was concentrated to afford a residue which was dissolved in EtOAc (4 mL). To this solution was added a 1M HCl.$Et_2O$ solution dropwise over 1 min. The solid was isolated by concentrated in vacuo to yield 9-methyl-3,4-dihydro-1,5-benzothiazepin-5(2H)-amine hydrochloride (477 mg, 80%) as a brown powder. $^1$H NMR ($CDCl_3$, 300 MHz): δ7.13 (m, 2H), 6.91 (m, 1H), 4.00–3.80 (br s, 2H), 3.36 (t, 2H, J=5.7 Hz), 2.87 (t, 2H, J=5.7 Hz), 2.42 (s, 3H), 2.05 (m, 2H) ppm.

Step G

To 9-methyl-3,4-dihydro-1,5-benzothiazepin-5(2H)-amine hydrochloride (477 mg, 2.1 mmol) and 4-piperidone monohydrate hydrochloride (307 mg, 2.1 mmol) were suspended in 2,2,2-trifluoroethanol (5 mL) at 23° C. This suspension was heated at 70° C. for 1.5 h. The product was collected by vacuum filtration after the reaction mixture was allowed to cool to 23° C. to afford the title compound (312 mg, 35%) as a pale yellow powder. $^1$H NMR ($CD_3OD$, 300 MHz): δ7.09 (d, 1H, J=8.0 Hz), 6.83 (d, 1H, J=8.0 Hz), 4.56 (t, 2H, J=6.1 Hz), 4.33 (br s, 2H), 3.60 (t, 2H, J=6.2 Hz), 3.18 (t, 2H, J=5.9 Hz), 3.06 (t, 2H, J=6.0 Hz), 2.34 (s, 3H), 2.29 (m, 2H) ppm.

Example 15 cis-(8a,12a)-3-methyl-6,7,8a,9,10,11,12,12a-octahydro-5H-pyrido[4,3-b][1,4]thiazepino[2,3,4-hi]indole To a TFA solution (10 mL) of 3-methyl-6,7,9,10,11,12-hexahydro-5H-pyrido[4,3-b][1,4]thiazepino[2,3,4-hi]indole (295 mg, 1.0 mmol) cooled in an ice bath was added in 4 portions over 4 min $NaBH_4$ (122 mg, 3.2 mmol. The cooling bath was removed after this addition and the heterogeneous solution was allowed to stir at 23° C. for 24 h. It was then poured on to ice chips,and 50% aqueous NaOH solution was added slowly (internal temperature <8° C.) until pH>12 (by pH paper). The resulting mixture was extracted with $CHCl_3$ (6×100 mL). The extracts were combined, dried ($MgSO_4$) and concentrated in vacuo. to afford the crude title compound (225 mg, 87%) as a yellow oil. $^1$H NMR ($CDCl_3$, 300 MHz): δ6.75 (d, 1H, J=8.1 Hz), 6.59 (d, 1H, J=7.9 Hz), 4.08–3.92 (m, 1H), 3.72–3.60 (m, 1H), 3.39–3.30 (m, 1H), 3.20–2.92 (m, 6H), 2.64–2.52 (m, 1H), 2.25 (s, 3H), 2.19–1.90 (m, 4H) ppm. The oil was recrystallized as its fumarate salt to afford the title compound.

Example 18

1-bromo-6,7,9,10,11,12-hexahydro-5H-pyrido[4,3-b][1,4]thiazepino[2,3,4-hi]indole Step A 2,5-Dibromonitrobenzene (6.32 g, 22.5 mmol) and 3-bromopropane-1-thiol (2 mL, 20 mmol) were dissolved in THF (35 mL) at rt. The reaction flask was cooled to 0° C. Powdered KOH (1.72 g, 30.7 mmol) was added at once. The reaction was then warmed to rt and stirred for 4 hrs. Water (20 mL) and EtOAc (20 mL) were added. The layers were separated. The aqeuous layer was extracted with EtOAc (2×20 mL). The combined organic layers were washed with brine, dried, and concentrated. 5.40 g of a crude, yellow, oily solid were isolated. The crude product was purified by column chromatography (10–30% acetone-hexane) to afford 4-bromo-1-[(3-chloropropyl)sulfanyl]-2-nitrobenzene (3.56 g, 64%) as a pale-yellow solid. $^1$H NMR ($CDCl_3$, 300 Mhz) δ8.35 (d, 1H, 2.2 Hz), 7.67 (dd, 1H, 2.2, 8.5 Hz Hz), 7.32 (d, 1H, 8.0 Hz), 3.70 (t, 2H, 5.9 Hz), 3.13 (t, 2H, 7.3 Hz), 2.14–2.21 (m, 2H) ppm.

Step B

4-Bromo-1-[(3-chloropropyl)sulfanyl]-2-nitrobenzene (1.97 g, 7.1 mmol) was dissolved in MeOH (25 mL). The reaction flask was evacuated with nitrogen, and $Pd(OH)_2$ on carbon (400 mg) was added. The reaction flask was evacuated with nitrogen several time before being subjected to an atmosphere of H2 (50 psi). The flask was shaken on a parr apparatus for 72 hrs. The reaction was filtered over a bed of celite and the residue was washed with MeOH (5 mL). The supernatant was concentrated, and the crude, black residue was purified by column chromatography (50–20% hexanes-$CH_2Cl_2$), to afford 5-bromo-2-[(3-chloropropyl)sulfanyl]aniline (1.28 g, 73%) as a clear oil. $^1$H NMR ($CDCl_3$, 300 Mhz) δ7.20 (d, 1H, 8.0 Hz), 6.88 (d, 1H, 2.0 Hz), 6.79 (dd, 1H, 2.0 Hz, 8.0 Hz), 4.41 (s, 2H), 3.64 (t, 2H, 6.6 Hz), 2.86 (t, 2H, 7.0 Hz), 1.94–1.99 (m, 2H) ppm.

Step C

5-Bromo-2-[(3-chloropropyl)sulfanyl]aniline (0.938 g, 3.3 mmol) was dissolved in TFA (4 mL). The reaction flask was cooled to 0° C. and HCl (15 mL) was added. To the resulting suspension, an aqueous solution of $NaNO_2$ (0.25 g, 3.7 mmol, 3 mL $H_2O$) was slowly added. The flask was warmed to rt and stirred for 2 hrs. The flask was re-cooled to 0° C. and was transferred via cannula to an aqueous solution of $SnCl_2.2H_2O$ (1.49 g, 6.6 mmol, 3 mL of $H_2O$). The solution was stirred for 3 hours. The precipitate was collected by filtration and the residue was air-dried overnight. 1-{5-bromo-2-[(3-chloropropyl)sulfanyl]phenyl}hydrazine hydrochloride was isolated (0.800 g, 73%) was a light-brown powder. $^1$H NMR ($CD_3OD$, 300 Mhz) δ7.42 (d, 1H, 8.0 Hz), 7.14–7.21 (m, 2H), 3.66 (t, 2H, 6.2 Hz), 2.97 (t, 2H, 6.9 Hz), 1.90–1.99 (m, 2H) ppm. MS (CI, NH3): 297 (base, M+H).

Step D

1-{5-Bromo-2-[(3-chloropropyl)sulfanyl]phenyl}hydrazine hydrochloride (784 mg, 2.4 mmol) and 4-piperidone monohydrate.HCl (398 mg, 2.6) were dissolved in EtOH (5mL). Conc. Hcl (0.2 mL, 2.4 mmol) were added. The reaction was refluxed for 18 hrs and then cooled to rt. The ppt was collected by filtration and the residue was washed with EtOH (3mL). 9-bromo-6-[(3-chloropropyl) sulfanyl]-2,3,4,5-tetrahydro-1H-pyrido[4,3-b]indole hydrochloroide (500.4 mg, 58%) was isolated as a white powder. $^1$H NMR ($CD_3OD$, 300 Mhz) δ7.18 (d, 1H, 8.0 Hz), 7.12 (d, 1H, 8.0 Hz), 4.73 (s, 2H), 3.64 (t, 2H, 6.6 Hz), 3.58 (t, 2H, 6.3 Hz), 3.16 (t, 2H, 6.3 Hz), 3.02 (t, 2H, 6.6 Hz), 1.87–1.96 (m, 2H) ppm.

Step E

9-Bromo-6-[(3-chloropropyl)sulfanyl]-2,3,4,5-tetrahydro-1H-pyrido[4,3-b]indole hydrochloroide (297 mg, 0.82 mmol) was dissolved in DME (50 mL). KOH (460 mg, 8.2 mmol) and KI (1360 mg, 0.82 mmol) were added. The solution was refluxed for 18 hours and then cooled to rt. The reaction was concentrated. Water (20 mL) and $CH_2Cl_2$ (20 mL) were added. The layers were separated and the aqueous was extracted with $CH_2Cl_2$ (2×20 mL). The combined organic layers were washed with brine, dried, and concentrated to afford 5 (209 mg, 92%) was a pale-white amorphous solid. $^1$H NMR ($CDCl_3$, 300 Mhz) δ6.97 (d, 1H, 7.9 Hz), 6.82 (d, 1H, 7.9 Hz), 4.55 (t, 2H, 5.9 Hz), 4.37 (s, 2H), 3.34 (t, 2H, 7.0 Hz), 3.21 (t, 2H, 5.9 Hz), 2.65 (t, 2H, 5.8 Hz), 2.25–2.33 (m, 2H) ppm.

Example 19

(8aS, 12aR)-1-bromo-6,7,8a,9,10,11,12,12a-octahydro-5H-pyrido[4,3-b][1,4]thiazepino[2,3,4-hi]indole 1-Bromo-6,7,9,10,11,12-hexahydro-5H-pyrido[4,3-b][1,4]thiazepino[2,3,4-hi]indole (53.0 mg, 0.17 mmol) was dissolved in TFA (2 mL). The reaction was cooled to 0° C. $NaCNBH_3$ (32.3 mg, 0.51 mmol) was added. The reaction was stirred at 0° C. for 2 hr. Ice (2 chips) were added. The reaction was basified with 50% NaOH until a pH of 14, keeping the temperature less than 7° C. The reaction mixture was extracted with CH2Cl2 (3×10 mL). The combined organic layers were washed with brine, dried, and concentrated to afford the title compound (53 mg, 100%) as a pure, white, amorphous solid. The enantiomers were separated by preparative HPLC on a Chiracel OD column using isocratic 10% IPA/hexane as the eluent. $^1$H NMR (CDCl3, 300 Mhz) δ6.79 (d, 1H, 8.4 Hz), 6.72 (d, 1H, 8.4 Hz), 3.89–3.99 (m, 1H), 3.55–3.65 (m, 1H), 3.30–3.40 (m, 1H), 3.10–3.30 (m, 2H), 2.80–3.10 (m, 3H), 3.34 (t, 1H, 11.7 Hz), 1.60–2.30 (m, 5H) ppm. MS (CI, $NH_3$): 325 (base, M+H).

Example 25 cis-(8a,12a)-11-(3,4-dimethoxybenzoyl)-6,7,8a,9,10,11,12,12a-octahydro-5H-pyrido[4,3-b][1,4]thiazepino[2,3,4-hi]indole Cis-(8a,12a)-6,7;8a,9,10,11,12,12a-octahydro-5H-pyrido[4,3-b][1,4]thiazepino[2,3,4-hi]indole(44 mg, 0.16) was dissolved in $CH_2Cl_2$ (3 mL). $Et_3N$ (0.067 mL, 0.48 mmol) and 3,4-dimethoxybenzoyl chloride (47 mg, 0.23 mmol) were added. The reaction was stirred for 18 hr. Brine (5 mL) was added. The layers were separated. The aqueous phase was extracted (2×5 mL) with $CH_2Cl_2$. The combined organic layers were washed with brined, dried, and concentrated to afford a crude brown amorphous solid (138 mg). The residue was purified by column chromatography (1–5% MeOH/$CH_2Cl_2$) to afford the title compound (691 mg, 100%) as a white amorphous solid. $^1$H NMR ($CDCl_3$ 300 MHz) δ6.80–7.10 (m, 5H), 6.62 (m, 1H), 3.75–4.10 (m, 8H), 3.42–3.70 (M, 4H), 2.80–3.40 (m, 4H), 1.80–2.25 (m, 4H) ppm. MS (ESI): 411 (base, M+H).

Example 26 cis-(8a,12a)-11-(2,5-dimethoxybenzoyl)-6,7,8a,9,10,11,12,12a-octahydro-5H-pyrido[4,3-b][1,4]thiazepino[2,3,4-hi]indole The title compound was prepared by the method of Example 25 from cis-(8a,12a)-6,7,8a,9,10,11,12,12a-octahydro-5H-pyrido[4,3-b][1,4]thiazepino[2,3,4-hi]indole (44 mg, 0.16 mmol), 2,5-dimethoxybenzoyl chloride (47 mg, 0.23 mmol), and $Et_3N$ (0.067 mL, 0.48 mmol) to afford after chromatographic purification the title compound (32 mg, 49%) as a white amorphous solid. $^1$H NMR ($CDCl_3$ 300 MHz) δ6.90–7.05 (m, 1H), 6.75–6.90 (m, 2H), 6.60–6.75 (m, 1H), 6.50–6.60 (m, 1H), 4.20–4.60 (m, 1H), 3.95–4.10 (m, 1H), 3.65–3.94 (m, 6H), 3.20–3.60 (M, 4H), 2.80–3.25 (m, 4H), 1.60–2.20 (m, 4H) ppm. MS (ESI): 411 (base, M+H).

Example 27 cis-(8a,12a)-11-(3,5-dimethoxybenzoyl)-6,7,8a,9,10,11,12,12a-octahydro-5H-pyrido[4,3-b][1,4]thiazepino[2,3,4-hi]indole The title compound was prepared by the method of Example 25 from cis-(8a,12a)-6,7,8a,9,10,11,12,12a-octahydro-5H-pyrido[4,3-b][1,4]thiazepino[2,3,4-hi]indole (44 mg, 0.16 mmol), 3,5-dimethoxybenzoyl chloride (47 mg, 0.23 mmol), and $Et_3N$ (0.067 mL, 0.48 mmol) to afford after chromatographic purification the title compound (44 mg, 99%) as a white amorphous solid. $^1$H NMR ($CDCl_3$ 300 MHz) δ6.90–7.10 (m, 1H), 6.30–6.80 (m, 4H), 3.80–4.20 (m, 2H), 3.79 (s, 6H), 3.25–3.90 (M, 4H), 2.80–3.20 (m, 4H), 1.70–2.20 (m, 4H) ppm. MS (ESI): 411 (base, M+H).

Example 28

(8aS,12aR)-11-2,6-dimethoxybenzyl)-6,7,8a,9,10,11,12,12a-octahydro-5H-pyrido[4,3-b][1,4]thiazepino[2,3,4-hi]indole Cis-(8a,12a)-6,7,8a;9,10,11,12,12a-octahydro-5H-pyrido[4,3-b][1,4]thiazepino[2,3,4-hi]indole was dissolved in 1:1 THF/MeOH (4 mL). 2,6-dimethoxybenzaldehyde (34 mg, 0.20 mmol), molecular sieves (20 mg), and two drops of acetic acid were added. The solution was stirred at rt four hours. $NaCNBH_3$ was added (45mg, 0.72 mmol), and the reaction was stirred for 18 hours. The suspension was filtered over a pad of celite, and the residue was washed with EtOAc. Saturated aqueous $NaHCO_3$ (5 mL) was added to the supernant. The bi-phasic mixture was stirred for 10 min. The layers were separated. The aqueous layer was extracted with EtOAc (2×5 mL). The combined organic layers were washed with brine, dried, and concentrated. 94 mg of a crude, brown, amorphous solid were isolated. The residue was purified by column chromatography (5–10% MeOH-$CH_2Cl_2$). The title compound (56 mg, 78%) was isolated as an amorphous, white solid. $^1$H NMR ($CDCl_3$, 300 MHz) δ7.22 (t, 1H, 8.4 Hz), 6.93 (dd, 1H, 1.1 Hz, 7.7 Hz), 6.83 (d, 1H, 6.6 Hz), 6.60 (t, 1H, 7.3 Hz), 6.56 (d, 2H, 8.4 Hz), 3.80 (s, 6H), 3.69 (s, 2H), 3.47–3.62 (m, 2H), 3.18–3.38 (m, 2H), 2.77–3.10 (m, 4H), 2.30–2.60 (m, 1H), 1.80–2.20 (m, 5H) ppm. MS (ESI): 397.3 (base, M+H).

Example 29

(8aS,12aR)-11-(2,4-dimethoxybenzyl)-6,7,8a,9,10,11,12,12a-octahydro-5H-pyrido[4,3-b][1,4]thiazepino[2,3,4-hi]indole The title compound were prepared by the method of Example 28 from cis-(8a,12a)-6,7,8a,9,10,11,12,12a-octahydro-5H-pyrido[4,3-b][1,4]thiazepino[2,3,4-hi]indole (63 mg, 0.22 mmol), 2,4-dimethoxybenzaldehyde (41 mg, 0.25 mmol), and $NaCNBH_3$ (56 mg, 0.89 mmol) to afford after chromatographic purification the title compound (49 mg, 56%) as a white amorphous solid. $^1H$ NMR ($CDCl_3$, 300 MHz) δ7.23 (d, 1H, 7.7 Hz), 6.93 (dd, 1H, 1.1 Hz, 7.7 Hz), 6.81 (d, 1H, 7.3 Hz), 6.60 (t, 1H, 7.5 Hz), 3.81 (s, 3H), 3.78 (s, 3H), 3.51–3.61 (m, 2H), 3.43 (d, 2H, 5.1 Hz), 3.21–3.35 (m, 1H), 3.01–3.20 (m, 1H), 2.85–3.00 (m, 1H), 2.72–2.81 (m, 1H), 2.60–2.70 (m, 1H), 2.22–2.38 (m, 1H), 1.92–2.20 (m, 3H), 1.82–1.90 (m, 2H) ppm. MS (ESI): 397.3 (base, M+H).

Example 30

(8aS,12aR)-11-(2,4,6-trimethoxybenzyl)-6,7,8a,9,10,11,12,12a-octahydro-5H-pyrido[4,3-b ][1,4]thiazepino[2,3,4-hi]indole The title compound was prepared by the method of Example 28 from cis-(8a,12a)-6,7,8a,9,10,11,12,12a-octahydro-5H-pyrido[4,3-b][1,4]thiazepino[2,3,4-hi]indole (48 mg, 0.17 mmol), 2,3,6-trimethoxybenzaldehyde (37 mg, 0.19 mmol), and $NaCNBH_3$ (43 mg, 0.68 mmol) to afford after chromatographic purification the title compound (60 mg, 83%) as a white amorphous solid. $^1H$ NMR ($CDCl_3$, 300 MHz) δ6.93 (dd, 1H, 1.1 Hz, 7.7 Hz), 6.83 (dd, 1H, 1.1 Hz, 7.0 Hz), 6.60 (t, 1H, 7.6 Hz), 6.12 (s, 2H), 3.81 (s, 3H), 3.78 (s, 6H), 3.42–3.70 (m, 4H), 3.10–3.40 (m, 2H), 2.92–3.08 (m, 1H), 2.70–2.90 (m, 3H), 2.30–2.50 (m, 1H), 1.70–2.20 (m, 5H), ppm. MS (ESI): 427.3 (base, M+H).

Example 31

(8aS,12aR)-11-(2,3-dimethoxybenzyl)-6,7,8a,9,10,11,12,12a-octahydro-5H-pyrido[4,3-b][1,4]thiazepino[2,3,4-hi]indole The title compound was prepared by the method of Example 28 from cis-(8a,12a)-6,7,8a,9,10,11,12,12a-octahydro-5H-pyrido[4,3-b][1,4]thiazepino[2,3,4-hi]indole (57 mg, 0.20 mmol), 2,3-dimethoxybenzaldehyde (37 mg, 0.22 mmol), and $NaCNBH_3$ (50 mg, 0.80 mmol) to afford after chromatographic purification the title compound (47 mg, 59%) as a white amorphous solid. $^1H$ NMR ($CDCl_3$, 300 MHz) δ6.99–7.07 (m, 2H), 6.93 (dd, 1H, 1.1 Hz, 7.0 Hz), 6.80–6.86 (m, 2H), 6.59 (t, 1H, 7.7 Hz), 3.87 (s, 3H), 3.81 (s, 3H), 3.41–3.70 (m, 4H), 3.21–3.35 (m, 1H), 3.01–3.21 (m, 2H), 2.87–3.01 (m, 1H), 2.75–2.82 (m, 1H), 2.60–2.72 (m, 1H), 2.24–2.42 (m, 1H), 1.80–2.20 (m, 5H) ppm. MS (ESI): 397.3 (base, M+H).

Example 32 cis-(8a,12a)-11-(2,4,5-trimethoxybenzyl)-6,7,8a,9,10,11,12,12a-octahydro-5H-pyrido[4,3-b][1,4]thiazepino[2,3,4-hi]indole The title compound was prepared by the method of Example 28 from cis-(8a,12a)-6,7,8a,9,10,11,12,12a-octahydro-5H-pyrido[4,3-b][1,4]thiazepino[2,3,4-hi]indole (56 mg, 0.20 mmol), 2,4,5-trimethoxybenzaldehyde(47 mg, 0.23 mmol), and $NaCNBH_3$ (50 mg, 0.80 mmol) to afford after chromatographic purification the title compound (18 mg, 41%) as a white amorphous solid. $^1H$ NMR ($CDCl_3$, 300 MHz) δ7.02 (s, 1H), 6.94 (d, 1H, 7.7 Hz), 6.81 (d, 1H, 7.0 Hz), 6.60 (t, 1H, 7.7 Hz), 6.51 (s, 1H), 3.89 (s, 3H), 3.87 (s, 3H), 3.77 (s, 3H), 3.40–3.70 (m, 4H), 3.15–3.35 (m, 2H), 3.05–3.15 (m, 1H), 2.90–3.05 (m, 1H), 2.60–2.90 (m, 2H), 2.25–2.50 (m, 1H), 1.80–2.20 (m, 5H). MS. (ESI): 427.3 (base, M+H).

Example 33 cis-(8a,12a)-11-(cyclohexylmethyl)-6,7,8a,9,10,11,12,12a-octahydro-5H-pyrido[4,3-b][1,4]thiazepino[2,3,4-hi]indole To a solution of cis-(8a,12a)-6,7,8a,9,10,11,12,12a-octahydro-5H-pyrido[4,3-b][1,4]thiazepino[2,3,4-hi]indole (50 mg, 0.18 mmol) in MeOH (2 mL) was added cyclohexane carboxaldehyde (19.8 mg, 0.18 mmol) and 3 Å Mol sieves, and this mixture was stirred at room temperature for 1.5 hours. After which time sodium cyanoborohydride (45.2 mg, 0.72 mmol) was added and reaction allowed to stir overnight. The reaction mixture was filtered through celite and the filtrate was extracted with EtOAc (3×50 mL), washed with sat. Potassium carbonate (1×50 mL) and brine (1×50 mL) and dried (sodium sulfate). Concentrated to a residue and purified by column chromatography (gradient: 1%, 2.5%, and 5% MeOH in $CH_2Cl_2$) to give the title compound (35 mg, 58%). $^1H$ NMR ($CDCl_3$, 300 MHz): δ6.93 (dd, H, J=7.7 Hz, J=7.6 Hz), 6.85 (d, 1H, J=7.3 Hz), 6.61 (t, 1H, J=7.3 Hz), 3.81–3.77 (m, 1H), 3.61–3.48 (m, 1H), 3.31–3.3.22 (m, 1H), 3.21–3.11 (m, 1H), 3.10–3.02 (m, 1H), 2.98–2.88 (m, 1H), 2.79–2.70 (m, 1H), 2.69–2.59 (m, 1H), 2.25–2.17 (m, 1H), 2.12–1.97 (m, 3H), 1.93–182 (m, 2H), 1.80–1.61 (m, 4H), 1.58–1.43 (m, 1H), 1.33–1.09 (m, 3H), 0.94–0.81 (m, 2H) ppm. Mass Spec (ESI): 343 (base M+H).

Example 34 cis-(8a,12a)-11-(2,3,4-trimethoxybenzyl)-6,7,8a,9,10,11,12,12a-octahydro-5H-pyrido[4,3-b][1,4]thiazepino[2,3,4-hi]indole The above compound was prepared by the method of Example 33 using 2,3,4-trimethoxybenzaldehyde. Purified by column chromatography (gradient: 1%, 2.5%, and 5% MeOH in $CH_2Cl_2$) to give the title compound (15.7 mg, 42%). $^1H$ NMR ($CDCl_3$, 300 MHz): δ7.03 (d, 1H, J=8.4 Hz), 6.93 (dd, 1H, J=8 Hz, J=8.1 Hz), 6.81 (d, 1H, J=6.6 Hz), 6.8–6.6 (m, 3H), 4.16 (q, 1H, J=7.1 Hz), 3.93–3.90 (m, 1H), 3.8–3.75 (m, 1H), 3.6–3.53 (m, 1H), 3.4 (m, 2H), 3.3–3.25 (m, 1H), 3.2–3.12 (m, 2H), 3.1–2.9 (m, 1H), 2.7–2.59 (m, 2H), 2.3–2.22 (m, 1H), 2.1–2.07 (m, 1H), 2.04 (s, 2H), 2.01 (s, 1H), 1.98–1.88 (m, 3H), 1.25 (t, 1H, J=7.1 Hz) ppm.

Example 35 cis-(8a,12a)-11-(3,4-dimethoxybenzyl)-6,7,8a,9,10,11,12,12a-octahydro-5H-pyrido[4,3-b][1,4]thiazepino[2,3,4-hi]indole The above compound was prepared by the method of Example 33 using 4,5-dimethoxybenzaldehyde. Purified by column chromatography (gradient: 1%, 2.5%, and 5% MeOH in $CH_2Cl_2$) to give the title compound (26 mg, 37%).

$^1$H NMR ($CDCl_3$, 300 MHz): δ6.97–6.87 (m, 2H), 6.82–6.79 (m, 2H), 6.91 (t, 1H, J=7.4 Hz ), 4.15 (q, 1H, J=7.1 Hz), 3.8–3.75 (m, 1H), 3.6–3.48 (m, 1H), 3.4 (s, 2H), 3.37–3.25 (m, 2H), 3.2–3.3.08 (m, 1H), 2.73–2.67 (m, 1H), 2.63–2.59 (m, 1H), 2.32–2.23 (m, 1H), 2.17–2.07 (m, 1H), 2.04 (s, 2H), 1.95–1.88 (m, 3H), 1.25 (t, 1H, J=7.1 Hz) ppm.

Example 36 cis-(8a,12a)-11-(3,4,5-trimethoxybenzyl)-6,7,8a,9,10,11,12,12a-octahydro-5H-pyrido[4,3-b][1,4]thiazepino[2,3,4-hi]indole The above compound was prepared by the method of Example 33 using 3,4,5-trimethoxybenzaldehyde. Purified by column chromatography (gradient: 1%, 2.5%, and 5% MeOH in $CH_2Cl_2$) to give the title compound (30 mg, 49%). $^1$H NMR ($CDCl_3$, 300 MHz): δ6.95 (dd, 1H, J=7.7 Hz, J=7.7 Hz), 6.80 (d, 1H, J=6.6 Hz), 6.63–6.56 (m, 3H), 4.15 (q, 1H, J=8 Hz), 3.92 (d, 1H, J=2.2 Hz), 3.8–3.75 (m, 1H), 3.6–3.53 (m, 1H), 3.39 (d, 2H, J=2.2 Hz), 3.3–3.25 (m, 1H), 3.2–3.12 (m, 2H), 3.1–2.9 (m, 1H), 2.7–2.59 (m, 2H), 2.3–2.22 (m, 1H), 2.1–2.07 (m, 1H), 2.04 (s, 2H),2.01 (s, 1H), 1.98–1.88 (m, 3H), 1.25 (t, 1H, J=7.1 Hz) ppm. Mass Spec (ESI): 427 (base M+H).

Example 39 cis-(8a,12a)-6,7,9,10,12,12a-hexahydro-5H-pyrido[4,3-b][1,4]thiazepino[2,3,4-hi]indole-11(8aH)-carboxylate Cis-(8a,12a)-6,7,8a,9,10,11,12,12a-octahydro-5H-pyrido[4,3-b][1,4]thiazepino[2,3,4-hi]indole (0.320 g, 1.3 mmol) was dissolved in $CH_2Cl_2$ (15 mL) with 1M aqueous $K_2CO_3$ (15.6 mL) of at 0° C. Ethylchloroformate (0.423 g, 3.92 mmol) was then added slowly and the reaction brought to room temperature for 2 hours. The aqueous and organic layers were separated. The aqueous layer was extracted with $CHCl_3$ (3×15 mL). THe combined extracts were washed with water and dried ($Na_2SO_4$) and evaporated affording the title compound (0.480 g, 100%). $^1$H NMR ($CD_3OD$, 300 MHz) δ6.87 (d, 2H, J=7.3 Hz), 6.58 (t, 1H, J=7.3 Hz), 4.0–4.17 (m, 2H), 3.55–3.82 (m, 3H), 3.28–3.47 (m, 4H), 3.15–3.28 (m, 3H), 2.81–1.93 (m, 1H), 1.92–2.19 (m, 2H), 1.82–1.9 (m, 2H), 1.19 (t, 3H, J=6.6 Hz) ppm.

Example 40 ethyl-cis-(8a,12a)-2-acetyl-6,7,9,10,12,12a-hexahydro-5H-pyrido[4,3-b][1,4]thiazepino[2,3,4-hi]indole-11(8aH)-carboxylate To a solution of $AlCl_3$ (0.359 g, 2.7 mmol) in $CH_2Cl_2$ (1.7 mL) was added acetylchloride (0.133 g, 1.78 mmol) and allowed to stir for 30 minutes. This solution was then added to a solution of cis-(8a,12a)-6,7,9,10,12,12a-hexahydro-5H-pyrido[4,3-b][1,4]thiazepino[2,3,4-hi]indole-11(8aH)-carboxylate from Example 39 (0.285 g, 0.89 mmol) in $CH_2Cl_2$ (0.8 mL) and brought to reflux for 2 hours. Ice was added and the aqueous and organic layers were separated. The aqueous layer was extracted with $CHCl_3$ (3×20 mL). The combined extracts were washed with brine and dried ($Na_2SO_4$) and evaporated leaving an oil which was purified by preparatory silica gel TLC (2% MeOH/$CH_2Cl_2$). The title compound was afforded in 27% (87 mg) yield. $^1$H NMR ($CD_3OD$, 300 MHz) δ7.56 (d, 1H, J=1.5 Hz), 7.51(d, 1H, J=1.5 Hz), 3.92–4.16 (m, 3H), 3.52–3.81 (m, 4H), 3.29–3.52 (m, 4H), 2.98–3.08 (m, 1H), 2.21 (s, 3H), 2.02–2.18 (m, 2H), 1.83–1.95 (m, 2H), 1.12–1.20 (m, 3H) ppm.

Example 41 ethyl-cis-(8a,12a)-2-(acetylamino)-6,7,9,10,12,12a-hexahydro-5H-pyrido[4,3-b][1,4]thiazepino[2,3,4-hi]indole-11(8aH)-carboxylate Cis-(8a,12a)-6,7,9,10,12,12a-hexahydro-5H-pyrido[4,3-b][1,4]thiazepino[2,3,4hi]indole-11(8aH)-carboxylate (0.088 g, 0.24 mmol) was dissolved in methanesulfonic acid (1.2 mL). $NaN_3$ (0.031 g, 0.48 mmol) was added slowly. The reaction was stirred at room temperature for one hour. Ice was added and the aqueous layer extracted with $CHCl_3$ (3×10 mL). The combined organic extracts were washed with brine, water and dried ($Na_2SO_4$) and evaporated giving the title compound (0.063 g, 69%). $^1$H NMR ($CD_3OD$, 300 MHz) δ6.95–7.19 (m, 2H), 4.0–4.13 (m, 2H), 3.95 (br. s, 1H), 3.56–3.65 (m, 2H), 3.32–3.48 (m, 4H), 3.10–3.23 (m 3H), 2.82–2.92 (m, 1H), 2.0–2.18 (m, 2H), 2.03 (s, 3H), 2.84–2.96 (m, 2H), 1.98 (t, 3H, J=6.5 Hz) ppm.

Example 42 cis-(8a,12a)-11-[2-(4-fluorophenyl)ethyl]-6,7,8a,9,10,11,12,12a-octahydro-5H-pyrido[4,3-b][1,4]thiazepino[2,3,4-hi]indole Step A 4-Fluorophenethyl alcohol (2.0 g, 14.2 mmol) was dissolved in $CH_2Cl_2$ (12 mL) with cat. amount DMAP and triethylamine (2.2 g, 21.3 mmol). The reaction was cooled to 0° C. and methane sulfonylchloride (1.9 g, 17.0 mmol) was added slowly. The reaction was brought to room temperature and allowed to stir for 2 hours. The reaction was partitioned between water and EtOAc. The aqueous layer was extracted with EtOAc (3×50 mL) and the combined extracts were washed with brine, water and dried ($Na_2SO_4$) and evaporated affording 4-fluorophenethylmethanesulfonate (2.5 g, 89%) as a light yellow oil. $^1$H NMR ($CDCl_3$, 300 MHz) δ7.21 (d, 1H, J=5.2 Hz), 7.18 (d, 1H, J=5.1 Hz), 7.01 (t, 2H, J=8.8 Hz), 4.41 (t, 2H, J=6.6 Hz), 3.03 (t, 2H, J=6.7 Hz), 2.88 (s, 3H) ppm.

Step B

The cis-(8a,12a)-6,7,8a,9,10,11,12,12a-octahydro-5H-pyrido[4,3-b][1,4]thiazepino[2,3,4-hi]indole (0.100 g, 0.408 mmol) was dissolved in 1,4 dioxane (3 mL) with 4-fluorophenethylmethanesulfonate (0.106 g, 0.489 mmol) and $K_2CO_3$ (0.281 g, 2.04 mmol) and brought to reflux overnight. The reaction was cooled and the inorganics filtered off. The filtrate was diluted with $CHCl_3$ (10 mL) and washed with brine, water and dried ($Na_2SO_4$) and evaporated. The residue was purified by preparatory silica gel TLC (10% MeOH/$CHCl_3$) affording the title compound (0.047 g, 31%). $^1$H NMR ($CDCl_3$, 300 MHz) δ7.14 (m, 2H), 6.95–7.02 (m, 3H), 6.87 (d, 1H, J=7 Hz), 6.63 (t, 1H, J=7.3 Hz), 3.78–3.92 (m, 1H), 3.56–3.63 (m, 1H), 3.25–3.33 (m, 1H), 3.17–3.22 (m, 1H), 3.03–3.17 (m, 1H), 2.89–3.0 (m, 1H), 2.65–2.90 (m, 4H), 2.45–2.63 (m, 2H), 2.32 (d.t., 1H, J=6.6, 4.4 Hz), 1.91–2.20 (m, 5H) ppm.

Example 43

General Procedure

To a solution of cis-(8a,12a)-6,7,8a,9,10,11,12,12a-octahydro-5H-pyrido[4,3-b][1,4]thiazepino[2,3,4-hi]indole (1.0 mole equivalent) in 1,4-dioxane was added an alkyl halides or mesylate (1.3–2.0 mole equivalent), KI (catalytic amount) and $K_2CO_3$ (1.5 mole equivalent. The reaction mixture was heated at 100° C. for 1.5–2.5 days. The reaction mixture was cooled to 20° C. then diluted with $CHCl_3$. The solution was filtered to remove excess $K_2CO_3$ and the filterate was concentrated in vacuo and chromatographed on a silica gel column by elution with $CHCl_3$/MeOH to give the title compound.

General Procedure for Mesylation

To a solution of alcohol (1.0 mole equivalent) in $CH_2Cl_2$ and $Et_3N$ (2.0 mole equivalent) was added methan sulfonyl chloride (1.5 mole equivalent) at 0° C. under $N_2$ atmosphere. The reaction mixture was stirred at 0° C. for 1–4 h and quenchen by addition of 1 N HCl. The layer was separated and the aqueous layer was extracted with $Et_2O$. The combined organic solution was washed with $H_2O$ and brine. The organic layer was then dried over $MgSO_4$, filtered and concentrated in vacuo and chromatographed on a silica gel column by elution with EtOAc/Hexanes to give the title compound.

General Procedure for Bromination

To a solution of alcohol (1.0 mole equivalent) and $Ph_3P$ (1.05 mole equivalent) in DMF was added $Br_2$ dropwise until color of the solution remain orange at 0° C. under $N_2$ atmosphere. The reaction mixture was stirred at 20° C. for 30 min and quenchen by addition of $H_2O$. The layer was separated and the aqueous layer was extracted with hexanes. The combined organic solution was washed with $H_2O$ and brine. The organic layer was then dried over $MgSO_4$, filtered and concentrated in vacuo and chromatographed on a silica gel column by elution with EtOAc/Hexanes to give the title compound.

cis-(8a,12a)-11-ethyl-6,7,8a,9,10,11,12,12a-octahydro-5H-pyrido[4,3-b][1,4]thiazepino[2,3,4-hi] indole The title compound was prepared, by following the general coupling procedure of Example 43, as a pale yellow oil (20 mg, 73%) from cis-(8a,12a)-6,7,8a,9,10,11,12,12a-octahydro-5H-pyrido[4,3-b][1,4]thiazepino[2,3,4-hi]indole (25 mg, 0.10 mmol) and bromoethane (25 mg, 0.23 mmol). $^1$H NMR ($CDCl_3$, 300 MHz) δ1.11 (t, 3H, J=6.9 Hz), 1.87 (t, 1H, J=10.6 Hz), 1.94–2.20 (m, 4H), 2.22–2.35 (m, 1H), 2.43 (dq, 2H J=2.2, 7.0 Hz), 2.72–2.80 (m, 1H), 2.83 (ddd, 1H J=1.8, 5.9, 11.7 Hz), 2.93 (ddd, 1H, J=3.3, 5.9, 14.3 Hz), 3.04 (ddd, 1H, J=2.6, 5.5, 13.6 Hz), 3.20–3.30 (m, 2H), 3.55 (ddd, 1H, J=5.5, 10.5, 16.1 Hz), 3.83 (ddd, 1H, J=4.4, 10.7, 15.3 Hz), 6.62 (t, 1H, J=7.7 Hz), 6.87 (dd, 1H, J=0.8, 7.4 Hz), 6.95 (dd,1H, J=1.5, 8.1 Hz) ppm.

Example 44 cis-(8a,12a)-11-propyl-6,7,8a,9,10,11,12,12a-octahydro-5H-pyrido[4,3-b][1,4]thiazepino[2,3,4-hi] indole The title compound was prepared by following the general coupling procedure of Example 43 as a pale yellow oil (20 mg, 74%) from cis-(8a,12a)-6,7,8a,9,10,11,12,12a-octahydro-5H-pyrido[4,3-b][1,4]thiazepino[2,3,4-hi]indole (23 mg, 0.093 mmol) and 1-bromopropane (23 mg, 0.19 mmol). $^1$H NMR ($CDCl_3$, 300 MHz) δ0.89 (t, 3H, J=7.4 Hz), 1.55 (se, 1H, J=8.4 Hz), 1.85–2.20 (m, 5H), 2.22–2.40 (m, 3H), 2.72–2.77 (m, 1H), 2.83 (ddd, 1H, J=1.8, 6.0, 11.6 Hz), 2.93 (ddd, 1H, J=3.7, 5.5, 14.3 Hz), 3.05 (ddd, 1H, J=2.6, 5.1, 13.5 Hz), 3.17–3.30 (m, 2H), 3.55 (ddd, 1H, J=5.6, 10.6, 16.1 Hz), 3.82 (ddd, 1H, J=4.0, 11.0, 15.0 Hz), 6.62 (t, 1H, J=7.7 Hz), 6.86 (d, 1H, J=7.0 Hz), 6.95 (dd, 1H, J=1.1, 7.7 Hz) ppm.

Example 45 cis-(8a,12a)-11-butyl-6,7,8a,9,10,11,12,12a-octahydro-5H-pyrido[4,3-b][1,4]thiazepino[2,3,4-hi] indole The title compound was prepared by following the general coupling procedure of Example 43 as a pale yellow oil (5.0 mg, 32%) from cis-(8a,12a)-6,7,8a,9,10,11,12,12a-octahydro-5H-pyrido[4,3-b][1,4]thiazepino[2,3,4hi]indole (11 mg, 0.047 mmol) and 1-bromobutane (9.6 mg, 0.071 mmol). $^1$H NMR ($CDCl_3$, 300 MHz) δ0.92 (t, 3H, J=7.3 Hz), 1.32 (se, 1H, J=7.7 Hz), 1.57 (qu, 2H, J=7.7 Hz), 1.90–2.22 (m, 5H), 2.35–2.50 (m, 3H), 2.80–3.00 (m, 3H), 3.02–3.10 (m, 1H), 3.30–3.40 (m, 2H), 3.55 (ddd, 1H, J=5.5, 10.7, 16.2 Hz), 3.83 (ddd, 1H, J=4.0, 11.0, 15.0 Hz), 6.63 (t, 1H, J=7.3 Hz), 6.87 (dd, 1H, J=0.8, 7.0 Hz), 6.96 (dd, 1H, J=1.1, 7.7 Hz) ppm.

Example 46 cis-(8a,12a)-11-pentyl-6,7,8a,9,10,11,12,12a-octahydro-5H-pyrido[4,3-b][1,4]thiazepino[2,3,4-hi] indole The title compound was prepared by following the general coupling procedure of Example 43 as a pale yellow oil (30 mg, 90%) from cis-(8a,12a)-6,7,8a,9,10,11,12,12a-octahydro-5H-pyrido[4,3-b][1,4]thiazepino[2,3,4-hi]indole (26 mg, 0.11 mmol) and 1-bromopentane (32 mg, 0.21 mmol). $^1$H NMR ($CDCl_3$, 300 MHz) δ0.88 (t, 3H, J=6.9 Hz), 1.20–1.37 (m, 4H), 1.54 (qu, 2H, J=7.7 Hz), 1.85–2.20 (m, 5H), 2.22–2.40 (m, 3H), 2.70–2.85 (m, 2H), 2.93 (ddd, 1H, J=3.3, 5.5, 14.2 Hz), 3.04 (ddd, 1H, J=2.2, 5.1, 13.6 Hz), 3.18–3.30 (m, 2H), 3.55 (ddd, 1H, J=5.2, 10.7, 15.8 Hz), 3.82 (ddd, 1H, J=4.4, 11.4, 15.4 Hz), 6.62 (t, 1H, J=7.4 Hz), 6.86 (d, 1H, J=6.2 Hz), 6.95 (dd, 1H, J=1.1, 7.7 Hz) ppm.

Example 47 cis-(8a,12a)-11-hexyl-6,7,8a,9,10,11,12,12a-octahydro-5H-pyrido[4,3-b][1,4]thiazepino[2,3,4-hi] indole The title compound was prepared by following the general coupling procedure of Example 43 as a pale yellow oil (32 mg, 82%) from cis-(8a,12a)-6,7,8a,9,10,11,12,12a-octahydro-5H-pyrido[4,3-b][1,4]thiazepino[2,3,4-hi]indole (29 mg, 0.12 mmol) and 1-bromohexane (40 mg, 0.24 mmol). $^1$H NMR ($CDCl_3$, 300 MHz) δ0.87 (t, 3H, J=6.9 Hz), 1.22–1.37 (m, 6H), 1.54–0.64 (m, 2H), 1.90–2.20 (m, 5H), 2.33–2.50 (m, 3H), 2.80–2.97 (m, 3H), 3.04 (ddd, 1H, J=2.6, 5.1, 13.5 Hz), 3.16–3.40 (m, 2H), 3.54 (ddd, 1H, J=5.5, 10.6, 15.8 Hz), 3.83 (ddd, 1H, J=4.4, 11.3, 15.4 Hz), 6.64 (t, 1H, J=7.7 Hz), 6.87 (dd, 1H, J=1.1, 7.3 Hz), 6.96 (dd, 1H, J=1.1, 7.7 Hz) ppm.

Example 48 cis-(8a,12a)-11-(2-propyl)-6,7,8a,9,10,11,12,12a-octahydro-5H-pyrido[4,3-b][1,4]thiazepino[2,3,4-hi] indole The title compound was prepared by following the general coupling procedure of Example 43 as a pale yellow oil (13 mg, 71%) from cis-(8a,12a)-6,7,8a,9,10,11,12,12a-octahydro-5H-pyrido[4,3-b][1,4]thiazepino[2,3,4-hi]indole (15.7 mg, 0.064 mmol) and 2-bromopropane (12 mg, 0.10 mmol). $^1$H NMR ($CDCl_3$, 300 MHz) δ0.98 (d, 3H, J=2.6 Hz), 1.00 (d, 3H, J=2.6 Hz), 1.87–2.15 (m, 5H), 2.35–2.45 (m, 1H), 2.60–2.80 (m, 3H), 2.86 (ddd, 1H, J=3.3, 5.4, 14.2 Hz), 2.97 (ddd, 1H, J=2.6, 5.5, 13.2 Hz), 3.13–3.25 (m, 2H), 3.50 (ddd, 1H, J=5.5, 11.0, 16.1 Hz), 3.76 (ddd, 1H, J=4.0, 10.9, 15.3 Hz), 6.56 (t, 1H, J=7.3 Hz), 6.81 (dd, 1H, J=1.1, 7.3 Hz), 6.89 (dd, 1H, J=1.1, 7.6 Hz) ppm.

Example 49 cis-(8a,12a)-11-sec-butyl-6,7,8a,9,10,11,12,12a-octahydro-5H-pyrido[4,3-b][1,4]thiazepino[2,3,4-hi] indole The title compound was prepared by following the general coupling procedure of Example 43 as a pale yellow oil (9.0 mg, 32%) from cis-(8a,12a)-6,7,8a, 9,10,11,12,12a-octahydro-5H-pyrido[4,3-b][1,4]thiazepino[2,3,4-hi]indole (23 mg, 0.93 mmol) and 2-bromobutane (21 mg, 0.19 mmol). $^1$H NMR ($CDCl_3$, 300 MHz) δ0.86–0.98 (m, 6H), 1.21–1.37 (m, 1H), 1.55–1.70 (m, 1H), 1.85–2.22 (m, 6H), 2.42–2.77 (m, 3H), 2.87–2.97 (m, 1H), 3.00–3.13 (m, 1H), 3.15–3.31 (m, 2H), 3.50–3.63 (m, 1H), 3.78–3.87 (m, 1H), 6.62 (t, 1H, J=7.4 Hz), 6.86 (d, 1H, J=7.4 Hz), 6.95 (dd, 1H, J=1.1, 8.1 Hz) ppm.

Example 50 cis-(8a,12a)-11-(1-methylbutyl)-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (23 mg, 61%) cis-(8a,12a)-6,7,8a,9,10,11,12,12a-octahydro-5H-pyrido[4,3-b][1,4]thiazepino[2,3,4-hi]indole (30 mg, 0.12 mmol) and 2-bromopantane (37 mg, 0.24 mmol). $^1$H NMR ($CDCl_3$, 300 MHz) δ0.91 (t, 3H, J=6.8 Hz), 1.01 (t, 3H, J=5.9 Hz), 1.21–1.40 (m, 3H), 1.55–1.70 (m, 1H), 1.85–2.22 (m, 6H), 2.52–2.80 (m, 3H), 2.85–2.96 (m, 1H), 3.02–3.13 (m, 1H), 3.29 (m, 2H), 3.52–3.65 (m, 1H), 3.78–3.87 (m, 1H), 6.64 (t, 1H, J=7.7 Hz), 6.86 (d, 1H, J=6.9 Hz), 6.96 (d, 1H, J=7.7 Hz) ppm.

Example 51 cis-(8a,12a)-11-(1-methylpentyl)-6,7,8a,9,10,11,12,12a-octahydro-5H-pyrido[4,3-b][1,4]thiazepino[2,3,4-hi]indole Step A 2-Hexyl methanesulfonate. The title compound was prepared by following the general procedure of Example 43 for mesylation as a colorless oil (408 mg, 68%) from 2-hexanol (312 mg, 2.90 mmol) and methanesulfonyl chloride (500 mg, 4.40 mmol). $^1$H NMR ($CDCl_3$, 300 MHz) δ0.89–0.94 (m, 3H), 1.31–1.43 (m, 5H), 1.57–1.71 (m, 4H), 2.99 (s, 3H), 4.76–4.82 (m, 1H) ppm.

Step B

The title compound was prepared by following the general coupling procedure of Example 43 as a pale yellow oil (25 mg, 62%) from cis-(8a,12a)-6,7,8a,9,10,11,12,12a-octahydro-5H-pyrido[4,3-b][1,4]thiazepino[2,3,4-hi]indole (30 mg, 0.12 mmol) and 2-(methylsulfonyl)hexane (66 mg, 0.37 mmol). $^1$H NMR ($CDCl_3$, 300 MHz) δ0.80–0.90 (m, 6H), 1.13–1.25 (m, 5H), 1.45–1.60 (m, 2H), 1.85–2.20 (m, 6H), 2.50–2.70 (m, 2H), 2.84–2.89 (m, 1H), 2.96–3.05 (m, 1H), 3.14–3.24 (m, 2H), 3.44–3.54 (m, 1H), 3.69–3.79 (m, 1H), 6.56 (t, 1H, J=7.7 Hz), 6.80 (d, 1H, J=6.9 Hz), 6.88 (d, 1H, J=7.6 Hz) ppm.

Example 52 cis-(8a,12a)-11-isobutyl-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (23 mg, 75%) from cis-(8a,12a)-6,7,8a,9,10,11,12,12a-octahydro-5H-pyrido[4,3-b][1,4thiazepino[2,3,4-hi]indole (25 mg, 0.10 mmol) and 1-bromo-2-methylpropane (28 mg, 0.20 mmol). $^1$H NMR ($CDCl_3$, 300 MHz) δ0.88–0.92 (m, 6H), 1.75–1.93 (m, 3H), 1.95–2.23 (m, 6H), 2.55–2.62 (m, 1H), 2.68 (dd, 1H, J=6.2, 11.3 Hz), 2.95 (ddd, 1H, J=3.6, 5.8, 14.6 Hz), 3.02–3.19 (m, 2H), 3.26 (qu, 1H, J=3.3 Hz), 3.54 (ddd, 1H, J=5.1, 10.2, 14.3 Hz), 3.81 (ddd, 1H, J=4.4, 11.0, 14.0 Hz), 6.61 (t, 1H, J=7.3 Hz), 6.85 (d, 1H, J=6.9 Hz), 6.93 (dd, 1H, J=1.1, 7.7 Hz) ppm.

Example 53 cis-(8a,12a)-11-[(1S)-1-methylpropyl]-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (26 mg, 68%) from cis-(8a,12a)-6,7,8a,9,10,11,12,12a-octahydro-5H-pyrido[4,3-b][1,4]thiazepino[2,3,4-hi]indole (30 mg, 0.12 mmol) and (S)-(+)-1-bromo-2-methylbutane (36, 0.24 mmol). $^1$H NMR ($CDCl_3$, 300 MHz) δ0.84–0.92 (m, 6H), 1.01–1.17 (m, 1H), 1.38–50 (m, 1H), 1.52–1.67 (m, 1H), 1.79–1.93 (m, 3H), 1.95–2.22 (m, 5H), 2.55–2.63 (m, 1H), 2.62–2.73 (m, 1H), 2.88–2.99 (m, 1H), 3.02–3.19 (m, 2H), 3.21–3.29 (m, 1H), 3.50–3.61 (m, 1H), 3.78–3.85 (m, 1H), 6.61 (t, 1H, J=7.4 Hz), 6.85 (d, 1H, J=6.9 Hz), 6.94 (dd, 1H, J=1.1, 8.1 Hz) ppm.

Example 54 cis-(8a,12a)-11-(2-methylpentyl)-6,7,8a,9,10,11,12,12a-octahydro-5H-pyrido[4,3-b][1,4]thiazepino[2,3,4-hi]indole.

Step A

2-Methyl-1-pentyl methanesulfonate. The title compound was prepared by following the general procedure of Example 43 for mesylation as a colorless oil (856 mg, 89%) from 2-methyl-1-pentanol (497 mg, 4.90 mmol) and methanesulfonyl chloride (821 mg, 7.30 mmol). $^1$H NMR ($CDCl_3$, 300 MHz) δ0.89–0.93 (m, 3H), 0.98 (d, 3H, J=6.6 Hz), 1.15–1.43 (m, 4H), 1.88–1.90 (m, 1H), 3.00 (s, 3H), 3.98–4.11 (m, 2H) ppm.

Step B

The title compound was prepared by following the general coupling procedure of Example 43 as a pale yellow oil (60 mg, 89%) from cis-(8a,12a)-6,7,8a,9,10,11,12,12a-octahydro-5H-pyrido[4,3-b][1,4]thiazepino[2,3,4-hi]indole (52 mg, 0.20 mmol) and and 2-methyl-1-(methylsulfonyl) pentane (73 mg, 0.40 mmol). $^1$H NMR ($CDCl_3$, 300 MHz) δ0.87–0.92 (m, 6H), 1.00–1.06 (m, 2H), 1.21–1.38 (m, 3H), 1.55–1.65 (m, 2H), 1.77–1.88 (m, 2H), 1.95–2.19 (m, 4H), 2.51–2.59 (m, 1H), 2.62–2.68 (m, 1H), 2.91–2.98 (m, 1H), 3.05–3.16 (m, 2H), 3.24–3.27 (m, 1H), 3.49–3.59 (m, 1H), 3.76–3.85 (m, 1H), 6.61 (t, 1H, J=7.7), 6.85 (d, 1H, J=7.4), 6.93 (dd, 1H, J=1.1, 7.7) ppm.

Example 55 cis-(8a,12a)-11-(2-ethylbutyl)-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (24 mg, 61%) from cis-(8a,12a)-6,7,8a,9,10,11,12,12a-octahydro-5H-pyrido[4,3-b][1,4]thiazepino[2,3,4-hi]indole (30 mg, 0.12 mmol) and 1-bromo-2-ethylbutane (40 mg, 0.24 mmol). $^1$H NMR ($CDCl_3$, 300 MHz) δ0.78–0.92 (m, 6H), 1.25–1.43 (m, 5H), 1.77–1.93 (m, 3H), 1.95–2.23 (m, 5H), 2.55–2.61 (m, 1H), 2.68 (dd, 1H, J=6.6, 11.3 Hz), 2.95 (ddd, 1H, J=3.6, 5.8, 14.6 Hz), 3.02–3.19 (m, 2H), 3.26 (qu, 1H, J=3.3 Hz), 3.55 (ddd, 1H, J=5.2, 10.3, 15.8 Hz), 3.81 (ddd, 1H, J=4.1, 10.7, 14.0 Hz), 6.61 (t, 1H, J=7.7 Hz), 6.85 (d, 1H, J=7.0 Hz), 6.94 (dd, 1H, J=1.1, 7.7 Hz) ppm.

Example 56 cis-(8a,12a)-11-(2-methylpentyl)-6,7,8a,9,10,11,12,12a-octahydro-5H-pyrido[4,3-b][1,4]thiazepino[2,3,4-hi]indole Step A 3-Methyl-1-pentyl methanesulfonate. The title compound was prepared by following the general procedure of Example 43 for mesylation as a colorless oil (384 mg, 67%) from 3-methyl-1-pentanol (300 mg, 2.90 mmol) and methanesulfonyl chloride (500 mg, 4.40 mmol). $^1$H NMR ($CDCl_3$, 300 MHz) δ0.86–0.95 (m, 6H), 1.15–1.25 (m, 1H), 1.33–1.42 (m, 1H), 1.51–1.60 (m, 2H), 1.76–1.84 (m, 1H), 3.00 (s, 3H), 4.23–4.31 (m, 2H) ppm.

Step B

The title compound was prepared by following the general coupling procedure of Example 43 as a pale yellow oil (29 mg, 72%) from cis-(8a,12a)-6,7,8a,9,10,11,12,12a-octahydro-5H-pyrido[4,3-b][1,4]thiazepino[2,3,4-hi]indole (30 mg, 0.12 mmol) and 3-methyl-1-(methylsulfonyl) pentane (68 mg, 0.36 mmol). $^1$H NMR ($CDCl_3$, 300 MHz) δ0.84–0.88 (m, 6H), 1.12–1.18 (m, 1H), 1.28–1.38 (m, 2H), 1.50–1.60 (m, 3H), 1.84–1.99 (m, 3H), 2.01–2.14 (m, 2H), 2.25–2.34 (m, 2H), 2.66–2.70 (m, 1H), 2.76–2.80 (m, 1H), 2.90–2.97 (m, 1H), 3.02–3.08 (m, 1H), 3.13–3.18 (m, 1H), 3.25–3.29 (m, 1H), 3.51–3.61 (m, 1H), 3.78–3.88 (m, 1H), 6.62 (t, 1H, J=7.6 Hz), 6.86 (d, 1H, J=6.9 Hz), 6.95 (dd, 1H, J=1.1, 7.7 Hz).

Example 57 cis-(8a,12a)-11-(3-methylbutyl)-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (27 mg, 73%) from cis-(8a,12a)-6,7,8a,9,10,11,12,12a-octahydro-5H-pyrido[4,3-b][1,4]thiazepino[2,3,4-hi]indole (29 mg, 0.12 mmol) and 1-bromo-3-methylbutane (36 mg, 0.24 mmol). $^1$H NMR ($CDCl_3$, 300 MHz) δ0.88 (d, 3H, J=6.6 Hz), 0.89 (d, 3H, J=6.6 Hz), 1.38–1.47 (m, 2H), 1.43 (he, 1H, J=4.4), 1.84–2.17 (m, 5H), 2.23–2.40 (m, 3H), 2.70–2.78 (m, 1H), 2.81 (dd, 1H, J=5.8, 11.0 Hz), 2.93 (ddd, 1H, J=3.6, 5.8, 14.6 Hz), 3.04 (ddd, 1H, J=2.5, 5.1, 13.5), 3.19–3.29 (m, 2H), 3.55 (ddd, 1H, J=5.5, 11.0, 16.1 Hz), 3.83 (ddd, 1H, J=4.4, 11.0, 15.4 Hz), 6.62 (t, 1H, J=7.7 Hz), 6.86 (d, 1H, J=6.6 Hz), 6.95 (dd, 1H, J=1.1, 7.7 Hz) ppm.

Example 58 cis-(8a,12a)-11-(4-methylpentyl)-6,7,8a,9,10,11,12,12a-octahydro-5H-pyrido[4,3-b][1,4]thiazepino[2,3,4-hi]indole Step A 4-Methyl-1-pentyl methanesulfonate. The title compound was prepared by following the general procedure of Example 43 for mesylation as a colorless oil (620 mg, 63%) from 4-methyl-1-pentanol (511 mg, 5.00 mmol) and methanesulfonyl chloride (844 mg, 7.50 mmol). $^1$H NMR ($CDCl_3$, 300 MHz) δ0.88 (d, 6H, J=4.7 Hz), 1.23–1.31 (m, 2H), 1.53–1.62 (m, 1H), 1.70–1.80 (m, 2H), 3.00 (s, 3H), 4.21 (t, 2H, J=6.6 Hz) ppm.

Step B

The title compound was prepared by following the general coupling procedure of Example 43 as a pale yellow oil (46 mg, 69%) from cis-(8a,12a)-6,7,8a,9,10,11,12,12a-octahydro-5H-pyrido[4,3-b][1,4]thiazepino[2,3,4-hi]indole (53 mg, 0.20 mmol) and 4-methyl-1-(methylsulfonyl) pentane (77 mg, 0.40 mmol). $^1$H NMR ($CDCl_3$, 300 MHz) δ0.87 (d, 6H, J=6.6 Hz), 1.15 (m, 3H), 1.44–1.56 (m, 3H), 1.81–1.94 (m, 3H), 2.00–2.13 (m, 2H), 2.23–2.30 (m, 2H), 2.66–2.69 (m, 1H), 2.74–2.80 (m, 1H), 2.93 (m, 1H), 3.05 (m, 1H), 3.14–3.18 (m, 1H), 3.25–3.28 (m, 1H), 3.56 (ddd, 1H, J=5.5, 10.6, 15.7 Hz), 3.82 (ddd, 1H, J=4.0, 11.0, 15.0 Hz), 6.62 (t, 1H, J=7.7 Hz), 6.86 (d, 1H, J=7.0 Hz), 6.94 (dd, 1H, J=1.1, 7.7 Hz) ppm.

Example 59 cis-(8a,12a)-11-(cyclopropylmethyl)-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (26 mg, 72%) from cis-(8a,12a)-6,7,8a,9,10,11,12,12a-octahydro-5H-pyrido[4,3-b][1,4]thiazepino[2,3,4-hi]indole (30 mg, 0.12 mmol) and (bromomethyl)cyclopropane (25 mg, 0.19 mmol). $^1$H NMR ($CDCl_3$, 300 MHz) δ0.18 (d, 2H, J=5.8 Hz), 0.60 (dd, 2H, J=1.5, 8.5), 0.97–1.06 (m, 1H), 1.98–2.27 (m, 5H), 2.41 (d, 2H, J=6.6 Hz), 2.48 (t, 1H, J=11.7 Hz), 2.92 (ddd, 1H, J=3.3, 5.5, 14.2 Hz), 3.01–3.15 (m, 3H), 3.31–3.37 (m, 1H), 3.38–3.47 (m, 1H), 3.54 (ddd, 1H, J=5.1, 10.6, 15.8 Hz), 3.83 (ddd, 1H, J=4.0, 11.0, 15.3 Hz), 6.65 (t, 1H, J=7.7 Hz), 6.89 (dd, 1H, J=0.7, 7.3 Hz), 6.97 (dd, 1H, J=1.5, 8.0 Hz) ppm.

Example 60 cis-(8a,12a)-11-(cyclobutylmethyl)-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (14 mg, 82%) from cis-(8a,12a)-6,7,8a,9,10,11,12,12a-octahydro-5H-pyrido[4,3-b][1,4]thiazepino[2,3,4-hi]indole (14 mg, 0.054 mmol) and (bromomethyl)cyclopropane (13 mg, 0.084 mmol). $^1$H NMR ($CDCl_3$, 300 MHz) δ1.62–1.95 (m, 7H), 1.97–2.27 (m, 5H), 2.37 (d, 2H, J=6.7 Hz), 2.48–2.75 (m, 3H), 2.95 (ddd, 1H, J=3.2, 5.7, 14.3 Hz), 3.06 (ddd, 1H, J=2.3, 5.6, 14.5), 3.11–3.20 (m, 1H), 3.23 (qu, 1H, J=3.3 Hz), 3.55 (ddd, 1H, J=5.4, 10.6, 15.7 Hz), 3.81 (ddd, 1H, J=4.4, 11.0, 15.0 Hz), 6.61 (t, 1H, J=7.4 Hz), 6.84 (d, 1H, J=7.3 Hz), 6.94 (dd, 1H, J=1.1, 7.7 Hz) ppm.

Example 61 cis-(8a,12a)-11-(cyclohexylmethyl)-6,7,8a,9,10,11,12,12a-octahydro-5H-pyrido[4,3-b][1,4]thiazepino[2,3,4-hi]indole The title compound was prepared by following the general coupling precedure of Example 43 as a pale yellow oil (24 mg, 78%) from cis-(8a,12a)-6,7,8a,9,10,11,12,12a-octahydro-5H-pyrido[4,3-b][1,4]thiazepino[2,3,4-hi]indole (22 mg, 0.089 mmol) and (bromomethyl)cyclohexene (18 mg, 0.10 mmol). $^1$H NMR ($CDCl_3$, 300 MHz) δ0.86 (q, 2H, J=11.0 Hz), 1.13–1.30 (m, 3H), 1.42–1.57 (m, 1H), 1.60–1.93 (m, 9H), 1.95–2.20 (m, 4H), 2.55–2.60 (m, 1H), 2.63–2.73 (m, 1H), 2.94 (ddd, 1H, J=3.6, 5.8, 14.2 Hz), 3.02–3.20 (m, 2H), 3.24 (qu, 1H, J=3.3 Hz), 3.55 (ddd, 1H, J=5.5, 10.6, 15.8 Hz), 3.81 (ddd, 1H, J=4.1, 11.0, 13.6 Hz), 6.61 (t, 1H, J=7.3 Hz), 6.86 (d, 1H, J=6.6 Hz), 6.93 (dd, 1H, J=1.1, 7.7 Hz) ppm.

Example 62 cis-(8a,12a)-11-allyl-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (10 mg, 45%) from cis-(8a,12a)-6,7,8a,9,10,11,12,12a-octahydro-5H-pyrido[4,3-b][1,4]thiazepino[2,3,4-hi]indole (19 mg, 0.077 mmol) and allyl bromide (14 mg, 0.12 mmol). $^1$H NMR ($CDCl_3$, 300 MHz) δ1.84 (t, 1H, J=11 Hz), 1.89–2.17 (m, 4H), 2.24 (dt, 1H, J=4.4, 8.4 Hz), 2.63–2.74 (m, 1H), 2.78 (ddd, 1H, J=1.8, 6.2, 12.1 Hz), 2.90–3.00 (m, 3H), 3.02–3.10 (m, 1H), 3.12–3.20 (m, 1H), 3.27 (qu, 1H, J=2.8 Hz), 3.56 (ddd, 1H, J=5.1, 10.6, 15.7 Hz), 3.83 (ddd, 1H, J=4.4, 11.3, 15.0 Hz), 5.12 (d, 1H, J=1.1 Hz), 5.17 (dd, 1H, J=1.1, 4.8 Hz), 5.80–5.95 (m, 1H), 6.62 (t, 1H, J=7.7 Hz), 6.86 (d, 1H, J=7.4 Hz), 6.95 (dd, 1H, J=1.1, 7.7 Hz) ppm.

Example 63 cis-(8a,12a)-11-(2-methyl-2-propenyl)-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (23 mg, 77%) from cis-(8a,12a)-6,7,8a,9,10,11,12,12a-octahydro-5H-pyrido[4,3-b][1,4]thiazepino[2,3,4-hi]indole (25 mg, 0.10 mmol) and 3-bromo-2-methylpropene (21 mg, 0.16 mmol) $^1$H NMR ($CDCl_3$, 300 MHz) δ1.76 (s, 3H), 1.79–1.95 (m, 3H), 2.00–2.21 (m, 3H), 2.50–2.61 (m, 1H), 2.68 (dd, 1H, J=6.2, 12.3 Hz), 2.82 (s, 2H), 2.95 (ddd, 1H, J=3.3, 5.5, 14.3 Hz), 3.02–3.20 (m, 3H), 3.27 (qu, 1H, J=3.3 Hz), 3.55 (ddd, 1H, J=5.5, 10.6, 15.7 Hz), 3.82 (ddd, 1H, J=4.0, 10.6, 15.0 Hz), 4.84 (s, 2H), 6.61 (t, 1H, J=7.4 Hz), 6.85 (d, 1H, J=7.3 Hz), 6.94 (dd, 1H, J=1.5, 8.1 Hz) ppm.

Example 64 cis-(8a,12a)-11-[(2E)-2-butenyl]-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (14 mg, 61%) from cis-(8a,12a)-6,7,8a,9,10,11,12,12a-octahydro-5H-pyrido[4,3-b][1,4]thiazepino[2,3,4-hi]indole (19 mg, 0.077 mmol) and trans-1-chloro-2-pentene (7.1 mg, 0.078 mmol). $^1$H NMR ($CDCl_3$, 300 MHz) δ1.69 (d, 3H, J=5.1 Hz), 1.80–2.25 (m, 6H), 2.68–2.75 (m, 1H), 2.76–2.85 (m, 1H), 2.86–3.05 (m, 4H), 3.10–3.21 (m, 1H), 3.27 (qu, 1H, J=3.6 Hz), 3.55–3.63 (m, 1H), 3.78–3.88 (m, 1H), 5.43–5.72 (m, 2H), 6.62 (t, 1H, J=7.4 Hz), 6.86 (d, 1H, J=7.0 Hz), 6.95 (dd, 1H, J=1.7, 7.7 Hz) ppm.

Example 65 cis-(8a,12a)-11-(3-methyl-2-butenyl)-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (66 mg, 85%) from cis-(8a,12a)-6,7,8a,9,10,11,12,12a-octahydro-5H-pyrido[4,3-b][1,4]thiazepino[2,3,4-hi]indole (61 mg, 0.25 mmol) and 4-bromo-2-methyl-2-butene (55 mg, 0.37 mmol). $^1$H NMR ($CDCl_3$, 300 MHz) δ1.61 (s, 3H), 1.74 (s, 3H), 1.81 (t, 1H, J=11.0 Hz), 1.90–1.97 (m, 2H), 2.00–2.23 (m, 3H), 2.65–2.73 (m, 1H), 2.78 (ddd, 1H, J=1.8, 6.2, 11.4 Hz), 2.86–2.97 (m, 3H), 3.02–3.10 (m, 1H), 3.15 (dt, 1H, J=6.9, 10.6 Hz), 3.26 (qu, 1H, J=3.6 Hz), 3.57 (ddd, 1H, J=5.2, 9.6, 16.1 Hz), 3.83 (ddd, 1H, J=4.1, 11.0, 13.6 Hz), 5.24–5.28 (m, 1H), 6.62 (t, 1H, J=7.7 Hz), 6.86 (dd, 1H, J=0.7, 7.3 Hz), 6.95 (dd, 1H, J=1.1, 7.7 Hz) ppm.

Example 66 cis-(8a,12a)-11-(3-butenyl)-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (18 mg, 67%) from cis-(8a,12a)-6,7,8a,9,10,11,12,12a-octahydro-5H-pyrido[4,3-b][1,4]thiazepino[2,3,4-hi]indole (22 mg, 0.089 mmol) and 4-bromo-1-butene (19 mg, 0.14 mmol). $^1$H NMR ($CDCl_3$, 300 MHz) δ1.84–1.95 (m, 3H), 2.01–2.20 (m, 2H), 2.24–2.33 (m, 3H), 2.37–2.44 (m, 2H), 2.63–2.74 (m, 1H), 2.70–2.82 (m, 1H), 2.90–2.99 (m, 1H), 3.02–3.20 (m, 2H), 3.27 (qu, 1H, J=2.9 Hz), 3.56 (ddd, 1H, J=5.5, 10.7, 16.1 Hz), 3.83 (ddd, 1H, J=4.0, 11.0, 15.0 Hz), 5.01 (dd, 1H, J=1.1, 10.2 Hz), 5.08 (dd, 1H, J=1.1, 15.4 Hz), 5.75–5.85 (m, 1H), 6.62 (t, 1H, J=7.3 Hz), 6.86 (d, 1H, J=6.6 Hz), 6.95 (dd, 1H, J=1.1, 7.7 Hz) ppm.

Example 67 cis-(8a,12a)-11-[(2E)-2-pentenyl]-6,7,8a,9,10,11,12,12a-octahydro-5H- pyrido[4,3-b][1,4]thiazepino[2,3,4-hi]indole The title compound was prepared by following the general coupling procedure of Example 43 as a pale yellow oil (20 mg, 58%) from cis-(8a,12a)-6,7,8a,9,10,11,12,12a-octahydro-5H-pyrido[4,3-b][1,4]thiazepino[2,3,4-hi]indole (27 mg, 0.11 mmol) and trans-1-bromo-2-pentene (25 mg, 0.17 mmol). $^1$H NMR ($CDCl_3$, 300 MHz) δ0.99 (t, 3H, J=7.7 Hz), 1.81 (t, 1H, J=9.0 Hz), 1.87–2.22 (m, 7H), 2.67–2.75 (m, 1H), 2.76–2.83 (m, 1H), 2.85–3.00 (m, 3H), 3.02–3.10 (m, 1H), 3.10–3.21 (m, 1H), 3.27 (qu, 1H, J=3.0 Hz), 3.56 (ddd, 1H, J=5.1, 10.1, 15.8 Hz), 3.83 (ddd, 1H, J=4.0, 11.0, 13.5 Hz), 5.43–5.72 (m, 2H), 6.62 (t, 1H, J=7.3 Hz), 6.86 (d, 1H, J=6.6 Hz), 6.94 (dd, 1H, J=1.1, 6.7 Hz) ppm.

Example 68 cis-(8a,12a)-11-[(2Z)-2-pentenyl]-6,7,8a,9,10,11,12,12a-octahydro-5H- pyrido[4,3-b][1,4]thiazepino[2,3,4-hi]indole The title compound was prepared by following the general coupling procedure of Example 43 as a pale yellow oil (20 mg, 63%) from cis-(8a,12a)-6,7,8a,9,10,11,12,12a-octahydro-5H-pyrido[4,3-b][1,4]thiazepino[2,3,4-hi]indole (25 mg, 0.10 mmol) and cis-1-bromo-2-pentene (30 mg, 0.20 mmol). $^1$H NMR ($CDCl_3$, 300 MHz) δ0.94 (t, 3H, J=7.4 Hz), 1.83 (t, 1H, J=11.0 Hz), 1.89–2.28 (m, 7H), 2.67–2.75 (m, 1H), 2.76–2.82 (m, 1H), 2.85–3.10 (m, 4H), 3.12–3.23 (m, 1H), 3.27 (qu, 1H, J=3.0 Hz), 3.56 (ddd, 1H, J=5.2, 10.7, 15.8 Hz), 3.82 (ddd, 1H, J=4.0, 11.0, 13.5 Hz), 5.40–5.65 (m, 2H), 6.62 (t, 1H, J=7.7 Hz), 6.86 (d, 1H, J=6.7 Hz), 6.94 (dd, 1H, J=0.7, 7.7 Hz) ppm.

Example 69 cis-(8a,12a)-11-(4-pentenyl)-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (68 mg, 85%) from cis-(8a,12a)-6,7,8a,9,10,11,12,12a-octahydro-5H-pyrido[4,3-b][1,4 ]thiazepino[2,3,4-hi]indole (63 mg, 0.26 mmol) and 5-bromo-1-pentene (57 mg, 0.39 mmol). $^1$H NMR ($CDCl_3$, 300 MHz) δ1.62 (qu, 2H, J=8.0 Hz), 1.85–2.20 (m, 7H), 2.22–2.38 (m, 3H), 2.66–2.74 (m, 1H), 2.73–2.82 (m, 1H), 2.85–2.95 (m, 1H), 3.02–3.13 (m, 1H), 3.15–3.23 (m, 1H), 3.27 (qu, 1H, J=3.3 Hz), 3.55 (ddd, 1H, J=5.5, 10.6, 15.7 Hz), 3.82 (ddd, 1H, J=4.3, 11.0, 13.9 Hz), 4.93–5.07 (m, 2H), 5.75–5.85 (m; 1H), 6.62 (t, 1H, J=7.3 Hz), 6.86 (d, 1H, J=6.6 Hz), 6.95 (dd, 1H, J=1.1, 7.7 Hz) ppm.

Example 70 cis-(8a,12a)-11-(4-methyl-3-pentenyl)-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (23 mg, 74%) from cis-(8a,12a)-6,7,8a,9,10,11,12,12a-octahydro-5H-pyrido[4,3-b][1,4]thiazepino[2,3,4-hi]indole (24 mg, 0.097 mmol) and 5-bromo-2-methyl-2-pentene (18 mg, 0.11 mmol). $^1$H NMR ($CDCl_3$, 300 MHz) δ1.61 (s, 3H), 1.68 (s, 3H), 1.83–2.38 (m, 10H), 2.67–2.76 (m, 1H), 2.79 (ddd, 1H, J=1.4, 6.2, 11.3 Hz), 2.85–2.97 (m, 1H), 3.02–3.12 (m, 1H), 3.18 (dt, 1H, J=6.2, 10.6 Hz), 3.27 (qu, 1H, J=3.3 Hz), 3.57 (ddd, 1H, J=5.5, 9.0, 14.6 Hz), 3.83 (ddd, 1H, J=4.0, 10.8, 13.6 Hz), 5.04–5.15 (m, 1H), 6.62 (t, 1H, J=7.3 Hz), 6.86 (d, 1H, J=7.3 Hz), 6.95 (dd, 1H, J=1.1, 7.7 Hz) ppm.

Example 71 cis-(8a,12a)-11-(3,3-dichloro-2-propenyl)-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (7.0 mg, 17%) from cis-(8a,12a)-6,7,8a,9,10,11,12,12a-octahydro-5H-pyrido[4,3-b][1,4]thiazepino[2,3,4-hi]indole (29 mg, 0.12 mmol) and 1,1,3-trichloropropene (34 mg, 0.23 mmol). $^1$H NMR ($CDCl_3$, 300 MHz) δ1.81–2.20 (m, 5H), 2.34 (dt, 1H, J=3.6, 11.0 Hz), 2.60–2.68 (m, 1H), 2.73 (ddd, 1H, J=1.8, 6.2, 11.4 Hz), 2.86–2.97 (m, 1H), 3.02–3.18 (m, 4H), 3.26 (qu, 1H, J=4.0 Hz), 3.56 (ddd, 1H, J=5.1, 10.6, 15.7 Hz), 3.82 (ddd, 1H, J=4.0, 11.0, 13.7 Hz), 6.00 (t, 1H, J=6.6 Hz), 6.63 (t, 1H, J=7.3 Hz), 6.87 (d, 1H, J=7.6 Hz), 6.95 (dd, 1H, J=1.1, 7.7 Hz) ppm.

Example 72 cis-(8a,12a)-11-benzyl-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (22 mg, 63%) from cis-(8a,12a)-6,7,8a,9,10,11,12,12a-octahydro-5H-pyrido[4,3-b][1,4]thiazepino[2,3,4-hi ]indole (26 mg, 0.11 mmol) and benzyl bromide (36 mg, 0.21 mmol). $^1$H NMR ($CDCl_3$, 300 MHz) δ1.87–1.98 (m, 3H), 1.99–2.20 (m, 2H), 2.25–2.35 (m, 1H), 2.60–2.68 (m, 1H), 2.70–2.79 (m, 1H), 2.93–3.01 (m, 1H), 3.04–3.19 (m, 2H), 3.28 (qu, 1H, J=3.3 Hz), 3.45 (s, 2H), 3.55 (ddd, 1H, J=5.5, 10.6, 14.4 Hz), 3.81 (ddd, 1H, J=4.0, 10.6, 13.6 Hz), 6.60 (t, 1H, J=7.3 Hz), 6.79 (d, 1H, J=6.9 Hz), 6.94 (dd, 1H, J=1.1, 7.7 Hz), 7.24–7.35 (m, 5H) ppm.

Example 73 cis-(8a,12a)-11-(2-methylbenzyl)-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (28 mg, 67%) from cis-(8a,12a)-6,7,8a,9,10,11,12,12a-octahydro-5H-pyrido[4,3-b][1,4]thiazepino[2,3,4-hi]indole (30 mg, 0.12 mmol) and 2-methylbenzyl bromide (44 mg, 0.24 mmol). $^1$H NMR ($CDCl_3$, 300 MHz) δ1.84–2.20 (m, 5H), 2.25–2.35 (m, 1H), 2.35 (s, 3H), 2.55–2.63 (m, 1H), 2.67–2.77 (m, 1H), 2.93–3.01 (m, 1H), 3.04–3.17 (m, 2H), 3.27 (qu, 1H, J=3.3 Hz), 3.40 (d, 2H, J=7.4 Hz), 3.56 (ddd, 1H, J=5.5, 10.6, 13.6 Hz), 3.75 (ddd, 1H, J=4.0, 11.0, 13.6 Hz), 6.60 (t, 1H, J=7.3 Hz), 6.79 (d, 1H, J=6.7 Hz), 6.94 (dd, 1H, J=1.1, 7.7 Hz), 7.11–7.20 (m, 3H), 7.25–7.30 (m, 1H) ppm.

Example 74 cis-(8a,12a)-11-(3-methylbenzyl)-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (40 mg, 95%) from cis-(8a,12a)-6,7,8a,9,10,11,12,12a-octahydro-5H-pyrido[4,3-b][1,4]thiazepino[2,3,4-hi]indole (30 mg, 0.12 mmol) and 3-methylbenzyl bromide (44 mg, 0.24 mmol). $^1$H NMR ($CDCl_3$, 300 MHz) δ1.84–1.95 (m, 3H), 2.00–2.20 (m, 2H), 2.25–2.34 (m, 1H), 2.35 (s, 3H), 2.58–2.67 (m, 1H), 2.69–2.77 (m, 1H), 2.93–3.01 (m, 1H), 3.04–3.19 (m, 2H), 3.28 (qu, 1H, J=3.3 Hz), 3.41 (s, 2H), 3.56 (ddd, 1H, J=5.5, 10.6, 14.6 Hz), 3.80 (ddd, 1H, J=4.0, 10.6, 13.5 Hz), 6.60 (t, 1H, J=7.7 Hz), 6.80 (d, 1H, J=7.0 Hz), 6.94 (dd, 1H, J=1.1, 8.1 Hz), 7.05–7.24 (m, 4H) ppm.

Example 75 cis-(8a,12a)-11-(4-methylbenzyl)-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (35 mg, 85%) from cis-(8a,12a)-6,7,8a,9,10,11,12,12a-octahydro-5H-pyrido[4,3-b][1,4]thiazepino[2,3,4-hi]indole (33 mg, 0.12 mmol) and 4-methylbenzyl bromide (44 mg, 0.24 mmol). $^1$H NMR ($CDCl_3$, 300 MHz) δ1.84–1.95 (m, 3H), 1.98–2.15 (m, 2H), 2.22–2.34 (m, 1H), 2.35 (s, 3H), 2.58–2.67 (m, 1H), 2.69–2.77 (m, 1H), 2.90–3.01 (m, 1H), 3.04–3.19 (m, 2H), 3.26 (qu, 1H, J=3.3 Hz), 3.41 (s, 2H), 3.55 (ddd, 1H, J=5.1, 10.3, 14.3 Hz), 3.80 (ddd, 1H, J=4.4, 11.0, 13.9 Hz), 6.59 (t, 1H, J=7.3 Hz), 6.80 (d, 1H, J=6.5 Hz), 6.94 (dd, 1H, J=1.1, 7.7 Hz), 7.12 (d, 2H, J=8.1 Hz), 7.20 (d, 2H, J=8.1 Hz) ppm.

Example 76 cis-(8a,12a)-11-(2,5-dimethylbenzyl)-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (22 mg, 51%) from cis-(8a,12a)-6,7,8a,9,10,11,12,12a-octahydro-5H-pyrido[4,3-b][1,4]thiazepino[2,3,4-hi]indole (29 mg, 0.12 mmol) and 2,5-dimethylbenzyl bromide (36 mg, 0.24 mmol). $^1$H NMR ($CDCl_3$, 300 MHz) δ1.82–2.20 (m, 5H), 2.22–2.34 (m, 7H), 2.55–2.63 (m, 1H), 2.67–2.74 (m, 1H), 2.93–3.02 (m, 1H), 3.06–3.17 (m, 2H), 3.27 (qu, 1H, J=3.3 Hz), 3.36 (d, 2H, J=6.2 Hz), 3.56 (ddd, 1H, J=5.5, 10.2, 15.3 Hz), 3.80 (ddd, 1H, J=4.4, 10.6, 14.7 Hz), 6.60 (t, 1H, J=7.7 Hz), 6.80 (d, 1H, J=7.0 Hz), 6.94 (dd, 1H, J=1.1, 8.1 Hz), 6.96–7.08 (m, 3H) ppm.

Example 77 cis-(8a,12a)-11-(2,4-dimethylbenzyl)-6,7,8a,9,10,11,12,12a-octahydro-5H-pyrido[4,3-b][1,4]thiazepino[2,3,4-hi]indole Step A 2,4-Dimethylbenzyl bromide. The title compound was prepared by following the general procedure of Example 43 for bromination as a colorless oil (180 mg, 41%) from 2,4-dimethylbenzyl alcohol (300 mg, 2.20 mmol). $^1$H NMR ($CDCl_3$, 300 MHz) δ2.31–2.38 (m, 6H), 4.52 (s, 2H), 6.98–7.02 (m, 2H), 7.20 (d, 1H, J=7.3 Hz) ppm.

Step B

The title compound was prepared by following the general coupling procedure of Example 43 as a pale yellow oil (34 mg, 79%) from cis-(8a,12a)-6,7,8a,9,10,11,12,12a-octahydro-5H-pyrido[4,3-b][1,4]thiazepino[2,3,4-hi]indole (30 mg, 0.12 mmol) and 2,4-dimethylbenzyl bromide (73 mg, 0.36 mmol). $^1$H NMR ($CDCl_3$, 300 MHz) δ1.86–1.96 (m, 3H), 2.03–2.13 (m, 2H), 2.28–2.38 (m, 7H), 2.57–2.68 (m, 1H), 2.70–2.74 (m, 1H), 2.93–3.00 (m, 1H), 3.06–3.12 (m, 2H), 3.25–3.42 (m, 3H), 3.51–3.61 (m, 1H), 3.75–3.83 (m, 1H), 6.59 (t, 1H, J=7.4 Hz), 6.79 (d, 1H, J=7.3 Hz), 6.92–6.98 (m, 3H), 7.13 (d, 1H, J=7.3 Hz) ppm.

Example 78 cis-(8a,12a)-11-(3,5-dimethylbenzyl)-6,7,8a,9,10,11,12,12a-octahydro-5H-pyrido[4,3-b][1,4]thiazepino[2,3,4-hi]indole Step A 3, 5-Dimethylbenzyl bromide. The title compound was prepared by following the general procedure of Example 43 for bromination as a colorless oil (122 mg, 28%) from 3,5-dimethylbenzyl alcohol (300 mg, 2.20 mmol). $^1$H NMR ($CDCl_3$, 300 MHz) δ2.31 (s, 6H), 4.44 (s, 2H), 6.93 (s, 1H), 7.01 (s, 2H) ppm.

Step B

The title compound was prepared by following the general coupling procedure of Example 43 as a pale yellow oil (39 mg, 88%) from cis-(8a,12a)-6,7,8a,9,10,11,12,12a-octahydro-5H-pyrido[4,3-b][1,4]thiazepino[2,3,4-hi]indole (30 mg, 0.11 mmol) and 3,5-dimethylbenzyl bromide (122 mg, 0.61 mmol). $^1$H NMR ($CDCl_3$, 300 MHz) δ1.87–1.94 (m, 3H), 2.00–2.14 (m, 2H), 2.22–2.35 (s, 7H), 2.62–2.70 (m, 1H), 2.72–2.76 (m, 1H), 2.92–3.00 (m, 1H), 3.06–3.19 (m, 2H), 3.26–3.33 (m, 1H), 3.38 (s, 2H), 3.51–3.61 (m, 1H), 3.76–3.85 (m, 1H), 6.60 (t, 1H, J=7.4 Hz), 6.81 (d, 1H, J=6.5 Hz), 6.90–6.99 (m, 4H) ppm.

Example 79 cis-(8a,12a)-11-(2,4,6-trimethylbenzyl)-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (27 mg, 60%) from cis-(8a,12a)-6,7,8a,9,10,11,12,12a-octahydro-5H-pyrido[4,3-b][1,4]thiazepino[2,3,4-hi]indole (30 mg, 0.12 mmol) and 2,4,6-trimethylbenzyl chloride (41 mg, 0.24 mmol). $^1$H NMR ($CDCl_3$, 300 MHz) δ1.75–1.90 (m, 2H), 1.97–2.20 (m, 3H), 2.27 (s, 3H), 2.33–2.39 (m, 7H), 2.47–2.55 (m, 1H), 2.63–2.72 (m, 1H), 2.93–3.17 (m, 3H), 3.20–3.30 (m, 1H), 3.38 (s, 2H), 3.56 (ddd, 1H, J=5.5, 10.3, 15.4 Hz), 3.71–3.80 (m, 1H), 6.60 (t, 1H, J=7.4 Hz), 6.78 (d, 1H, J=7.0 Hz), 6.83 (s, 2H), 6.94 (dd, 1H, J=1.1, 8.1 Hz) ppm.

Example 80 cis-(8a,12a)-11-(3-methoxybenzyl)-6,7,8a,9,10,11,12,12a-octahydro-5H-pyrido[4,3-b][1,4]thiazepino[2,3,4-hi]indole Step A 3-Methoxybenzyl methanesulfonate. The title compound was prepared by following the general procedure of Example 43 for mesylation as a colorless oil (292 mg, 93%) from 3-methoxybenzyl alcohol (200 mg, 1.45 mmol) and methanesulfonyl chloride (249 mg, 2.17 mmol). $^1$H NMR ($CDCl_3$, 300 MHz) δ2.92 (s, 3H), 3.83 (s, 3H), 5.22 (s, 2H), 6.90–7.03 (m, 3H), 7.32 (t, 1H, J=7.7 Hz) ppm.

Step B

The title compound was prepared by following the general coupling procedure of Example 43 as a pale yellow oil (13 mg, 30%) from cis-(8a,12a)-6,7,8a,9,10,11,12,12a-octahydro-5H-pyrido[4,3-b][1,4]thiazepino[2,3,4-hi]indole (30 mg, 0.12 mmol) and 3-methoxybenzyl methanesulfonate (52 mg, 0.24 mmol). $^1$H NMR ($CDCl_3$, 300 MHz) δ1.85–2.20 (m, 5H), 2.25–2.34 (m, 1H), 2.58–2.67 (m, 1H), 2.68–2.77 (m, 1H), 2.90–3.00 (m, 1H), 3.04–3.19 (m, 2H), 3.27–3.32 (m, 1H), 3.43 (s, 2H), 3.50–3.61 (m, 1H), 3.76–3.83 (m, 4H), 6.59 (t, 1H, J=7.4 Hz), 6.79–6.83 (m, 2H), 6.85–6.94 (m, 3H), 7.22 (t, 1H, J=8.0 Hz) ppm.

Example 81 cis-(8a,12a)-11-(3,5-dimethoxybenzyl)-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (42 mg, 88%) from cis-(8a,12a)-6,7,8a,9,10,11,12,12a-octahydro-5H-pyrido[4,3-b][1,4]thiazepino[2,3,4-hi]indole (30 mg, 0.12 mmol) and 3,5-dimethoxybenzyl bromide (56 mg, 0.24 mmol). $^1$H NMR ($CDCl_3$, 300 MHz) δ1.85–2.20 (m, 5H), 2.25–2.34 (m, 1H), 2.58–2.67 (m, 1H), 2.70–2.77 (m, 1H), 2.92–3.01 (m, 1H), 3.06–3.19 (m, 2H), 3.24–3.32 (m, 1H), 3.39 (s, 2H), 3.50–3.61 (m, 1H), 3.78–3.88 (m, 7H), 6.37 (t, 1H, J=2.2 Hz), 6.51 (d, 2H, J=2.2 Hz), 6.60 (t, 1H, J=7.7 Hz), 6.81 (d, 1H, J=7.3 Hz), 6.94 (d, 1H, J=7.5 Hz) ppm.

Example 82 cis-(8a,12a)-11-(2,3,4,5,6-pentafluorobenzyl)-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (21 mg, 42%) from cis-(8a,12a)-6,7,8a,9,10,11,12,12a-octahydro-5H-pyrido[4,3-b][1,4]thiazepino[2,3,4-hi]indole (29 mg, 0.12 mmol) and 2,3,4,5,6-pentafluorobenzyl bromide (62 mg, 0.24 mmol). $^1$H NMR ($CDCl_3$, 300 MHz) δ1.80–2.20 (m, 5H), 2.28–2.40 (m, 1H), 2.61–2.69 (m, 1H), 2.71–2.81 (m, 1H), 2.89–2.99 (m, 1H), 3.01–3.11 (m, 1H), 3.12–3.20 (m, 1H), 3.20–3.27 (m, 1H), 3.53 (ddd, 1H, J=5.1, 10.6, 14.7 Hz), 3.67 (s, 2H), 3.79 (ddd, 1H, J=4.4, 10.4, 13.7 Hz), 6.63 (t, 1H, J=7.3 Hz), 6.85 (d, 1H, J=7.3 Hz), 6.95 (dd, 1H, J=1.1, 7.7 Hz) ppm.

Example 83 cis-(8a,12a)-11-(2-phenylethyl)-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (28 mg, 60%) from cis-(8a,12a)-6,7,8a,9,10,11,12,12a-octahydro-5H-pyrido[4,3-b][1,4]thiazepino[2,3,4-hi]indole (33 mg, 0.13 mmol) and (2-bromoethyl)benzene (50 mg, 0.27 mmol). $^1$H NMR ($CDCl_3$, 300 MHz) δ190–2.20 (m, 5H), 2.34 (dt, 1H, J=4.4, 7.3 Hz), 2.55–2.65 (m, 2H), 2.71–2.98 (m, 5H), 3.02–3.15 (m, 1H), 3.18–3.23 (m, 1H), 3.28 (qu, 1H, J=3.8 Hz), 3.56 (ddd, 1H, J=5.1, 10.6, 14.3 Hz), 3.84 (ddd, 1H, J=4.0, 11.0, 13.5 Hz), 6.63 (t, 1H, J=7.6 Hz), 6.88 (d, 1H, J=6.7 Hz), 6.96 (dd, 1H, J=1.1, 7.7 Hz), 7.17–7.31 (m, 5H) ppm.

Example 84 cis-(8a,12a)-11-(1-methyl-2-phenylethyl)-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (11 mg, 30%) from cis-(8a,12a)-6,7,8a,9,10,11,12,12a-octahydro-5H-pyrido[4,3-b][1,4]thiazepino[2,3,4-hi]indole (25 mg, 0.10 mmol) and 2-bromo-1-phenylpropane (40 mg, 0.20 mmol). $^1$H NMR ($CDCl_3$, 300 Mhz) δ0.92 (d, 3H, J=5.1 Hz), 1.90–2.26 (m, 5H), 2.30–2.45 (m, 1H), 2.55–2.72 (m, 3H), 2.75–3.03 (m, 5H), 3.07–3.23 (m, 1H), 3.27–3.35 (m, 1H), 3.56–3.65 (m, 1H), 3.79–3.90 (m, 1H), 6.60–6.70 (m, 1H), 6.89 (t, 1H, J=7.3 Hz), 6.93–6.98 (m, 1H), 7.14–7.29 (m, 5H) ppm.

Example 85 cis-(8a,12a)-11-[(2E)-3-phenyl-2-propenyl]-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (17 mg, 47%) from cis-(8a,12a)-6,7,8a,9,10,11,12,12a-octahydro-5H-pyrido[4,3-b][1,4]thiazepino[2,3,4-hi]indole (25 mg, 0.10 mmol) and trans-3-bromo-1-phenyl-1-propene (40 mg, 0.20 mmol). $^1$H NMR ($CDCl_3$, 300 MHz) δ1.90–2.20 (m, 5H), 2.29 (dt, 1H, J=4.3, 7.3 Hz), 2.70–2.80 (m, 1H), 2.81–2.90 (m, 1H), 2.91–2.99 (m, 1H), 3.03–3.21 (m, 4H), 3.28 (qu, 1H, J=3.7 Hz), 3.56–3.63 (m, 1H), 3.79–3.89 (m, 1H), 6.29 (dt, 1H, J=6.6, 16.1 Hz), 6.49 (d, 1H, J=15.8 Hz), 6.61 (t, 1H, J=7.7 Hz), 6.85 (d, 1H, J=6.6 Hz), 6.95 (dd, 1H, J=1.1, 7.7 Hz), 7.21–7.40 (m, 5H) ppm.

Example 86 cis-(8a,12a)-11-(4-phenylbutyl)-6,7,8a,9,10,11,12,12a-octahydro-5H-pyrido[4,3-b][1,4]thiazepino[2,3,4-hi]indole Step A 1-Bromo-4-phenylbutane. The title compound was prepared by following the general procedure of Example 43 for bromination as a colorless oil (202 mg, 71%) from 4-phenyl-1-butanol (200 mg, 1.33 mmol). $^1$H NMR ($CDCl_3$, 300 MHz) δ1.72–1.95 (m, 4H), 2.65 (t, 2H, J=7.4 Hz), 3.42 (t, 2H, J=7.0 Hz), 7.16–7.32 (m, 5H) ppm.

Step B

The title compound was prepared by following the general coupling procedure of Example 43 as a pale yellow oil (32 mg, 70%) from cis-(8a,12a)-6,7,8a,9,10,11,12,12a-octahydro-5H-pyrido[4,3-b][1,4]thiazepino[2,3,4-hi]indole (30 mg, 0.12 mmol) and 1-bromo-4-phenylbutane (39 mg, 0.18 mmol). $^1$H NMR ($CDCl_3$, 300 MHz)) δ1.55–1.70 (m, 4H). 1.90–2.20 (m, 5H), 2.27–2.47 (m, 3H), 2.58–2.65 (m, 2H), 2.71–2.90 (m, 2H), 2.92–2.99 (m, 1H), 3.02–3.10 (m, 1H), 3.20–3.30 (m, 2H), 3.54 (ddd, 1H, J=5.0, 10.8, 14.1 Hz), 3.82 (ddd, 1H, J=3.9, 10.7, 13.6 Hz), 6.63 (t, 1H, J=7.7 Hz), 6.86 (dd, 1H, J=1.1, 7.3 Hz), 6.96 (dd, 1H, J=1.1, 8.1 Hz), 7.15–7.30 (m, 5H) ppm.

Example 87 cis-(8a,12a)-11-([1,1'-biphenyl]-4-ylmethyl)-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (19 mg, 50%) from cis-(8a,12a)-6,7,8a,9,10,11,12,12a-octahydro-5H-pyrido[4,3-b][1,4]thiazepino[2,3,4-hi]indole (23 mg, 0.093 mmol) and 4-phenylbenzyl chloride (38 mg, 0.19 mmol). $^1$H NMR ($CDCl_3$, 300 MHz) δ1.87–1.98 (m, 3H), 1.99–2.20 (m, 2H), 2.25–2.35 (m, 1H), 2.62–2.71 (m, 1H), 2.73–2.81 (m, 1H), 2.92–3.01 (m, 1H), 3.04–3.20 (m, 2H), 3.29 (qu, 1H, J=3.3 Hz), 3.49 (s, 2H), 3.56 (ddd, 1H, J=5.4, 10.7, 13.6 Hz), 3.78–3.88 (m, 1H), 6.60 (t, 1H, J=7.3 Hz), 6.82 (d, 1H, J=6.9 Hz), 6.95 (dd, 1H, J=1.1, 7.7 Hz), 7.31–7.47 (m, 5H), 7.54–7.62 (m, 4H) ppm.

Example 88 cis-(8a,12a)-11-([1,1'-biphenyl]-2-ylmethyl)-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (35 mg, 71%) from cis-(8a,12a)-6,7,8a,9,10,11,12,12a-octahydro-5H-pyrido[4,3-b][1,4]thiazepino[2,3,4-hi]indole (30 mg, 0.12 mmol) and 2-phenylbenzyl bromide (59 mg, 0.24 mmol). $^1$H NMR ($CDCl_3$, 300 MHz) δ1.80–1.90 (m, 3H), 1.95–2.15 (m, 2H), 2.19–2.28 (m, 1H), 2.50–2.58 (m, 1H), 2.62–2.75 (m, 1H), 2.89–2.98 (m, 1H), 3.05–3.15 (m, 2H), 3.24–3.30 (m, 1H), 3.36 (d, 2H, J=8.4 Hz), 3.42–3.56 (m, 1H), 3.75–3.82 (m, 1H), 6.59 (t, 1H, J=7.4 Hz), 6.78 (d, 1H, J=6.6 Hz), 6.92 (dd, 1H, J=1.5, 8.1 Hz), 7.20–7.41 (m, 8H), 7.58 (d, 1H, J=7.0 Hz) ppm.

Example 115 tert-butyl-bromo-6,7,9,12-tetrahydro-5H-pyrido[4,3-b][1,4]thiazepino[2,3,4-hi]indole-11(10H)-carboxylate The title compound was prepared by the method of Example 107 from 1-bromo-6,7,9,10,11,12-hexahydro-5H-pyrido[4,3-b][1,4]thiazepino[2,3,4-hi]indole (339 mg, 1.10 mmol) and $Boc_2O$ (263 mg, 1.20 mmol) after chromatographic purification (404 mg, 90%) as a white amorphous solid. $^1$H NMR ($CDCl_3$, 300 MHz) δ7.00 (d, 1H, J=7.9 Hz), 6.83 (d, 1H, J=7.9 Hz), 4.94 (s, 2H), 4.54 (t, 2H, J=5.9 Hz), 3.80 (bt, 2H), 3.33 (t, 2H, J=7.0 Hz), 2.71 (bt, 2H), 2.25–2.31 (m, 2H), 1.50 (s, 9H) ppm. MS (CI, $NH_3$): 425 (base, M+H).

Example 116 tert-butyl-1-(2,3-dichlorophenyl)-6,7,9,12-tetrahydro-5H-pyrido[4,3-b][1,4]thiazepino[2,3,4-hi]indole-11(10H)-carboxylate Tert-butyl 1-bromo-6,7,9,12-tetrahydro-5H-pyrido[4,3-b][1,4]thiazepino[2,3,4-hi]indole-11(10H)-carboxylate (55 mg, 0.13 mmol) was dissolved in DME (3 mL) 2M sodium carbonate (0.55 mL) was added. 2,3-dichlorophenyl boronic acid (51.3 mg, 0.27 mmol) was added, followed by $Pd_2dba_3$ (7.0 mg, 0.0007 mmol). $P(Ph)_3$ (6.8 mg, 0.026 mmol) was added. The reaction flask was degassed and kept under a nitrogen atmosphere. The suspension was refluxed for 18 hrs cooled in rt. The reaction was concentrated in vacuo, after which water (10 mL) and EtOAc (10 mL) were added. The layers were separated and the aqueous phase was extracted with EtOAc (2×10 mL). The combined organic layers were washed with brine (2×10 mL), dried, and concentrated to afford a crude brown amorphous solid (214 mg). The residue was purified by column chromatography (20–40% EtOAc/Hexane) to afford the title compound (63.1 mg, 99%) as a white amorphous solid. δ7.3–7.5 (m, 1H), 7.2–7.3 (m, 2 H), 7.01 (d, 1H, J=7.2 Hz), 6.65 (d, 1H, J=7.2 Hz), 4.4–4.6 (m, 2H), 3.5–3.9 (m, 4H), 3.2–3.4 (m, 2H), 2.5–2.7 (m, 2H), 2.1–2.4 (m, 2H), 1.30 (s, 9H) ppm.

Example 117

1-(3,4-dichlorophenyl)-6,7,9,10,11,12-hexahydro-5H-pyrido[4,3-b][1,4]thiazepino[2,3,4-hi]indole The title compound was prepared by the method of Example 116 from tert-butyl 1-bromo-6,7,9,12-tetrahydro-5H-pyrido[4,3-b][1,4]thiazepino[2,3,4-hi]indole-11(10H)-carboxylate (72 mg, 0.18 mmol) and 3,4-dichlorophenyl boronic acid (67.1 mg, 0.35 mmol), after chromatographic purification (65.7 mg, 74.6%) as a white amorphous solid. $^1$H NMR ($CDCl_3$, 300 MHz) δ7.39 (s, 1H), 7.1–7.3 (m, 2H), 6.99 (d, 1H, J=7.8 Hz), 6.68 (d, 1H, J=7.5 Hz), 4.52 (t, 2H, J=6.0 Hz), 3.68 (t, 2H, 6.0 Hz), 3.34 (t, 2H, J=6.9 Hz), 2.66 (t, 2H, J=6.00 Hz), 2.2–2.3 (m, 2H), 1.49 (s, 9H) ppm.

Example 118 tert-butyl 1-[2-chloro-4-(trifluoromethyl)phenyl]-6,7,9,12-tetrahydro-5H-pyrido[4,3-b][1,4]thiazepino[2,3,4-hi]indole-11(10H)-carboxylate The title compound was prepared by the method of Example 116 from tert-butyl 1-bromo-6,7,9,12-tetrahydro-5H-pyrido[4,3-b][1,4]thiazepino[2,3,4-hi]indole-11(10H)-carboxylate (60 mg, 0.15 mmol) and 2-chloro-4-trifluoromethylphenyl boronic acid (62.3 mg, 0.29 mmol), after chromatographic purification (60.0 mg, 95%) as a white amorphous solid. $^1$H NMR ($CDCl_3$, 300 MHz) δ7.73 (s, 1H), 7.49 (d, 1H, J=8.1 Hz), 7.43 (d, 1H, J=8.1 Hz), 7.07 (d, 1H, J=7.2 Hz), 6.7 (d, 1H, 7.2 Hz), 4.4–4.7 (m, 2H), 3.5–4.0 (m, 4H), 3.41 (dt, 2H, J=2.4, 6.6 Hz), 2.6–2.8 (m, 2H), 2.2–2.4 (m, 2H), 1.54 (s, 9H) ppm.

Example 119

1-(2,3-dichlorophenyl)-6,7,9,10,11,12-hexahydro-5H-pyrido[3',4':4,5]pyrrolo[1,2,3-ef][1,5]benzothiazepine Tert-butyl-1-(2,3-dichlorophenyl)-6,7,9,10,11,12-hexahydro-5H-pyrido[3',4':4,5]pyrrolo[1,2,3-ef][1,5]benzothiazepinyl-11-carboxylate (63.1 mg, 0.13 mmol) was dissolved in 20% TFA in methylene chloride (4 mL) and was stirred at rt for 2 hrs. The reaction was solution was cooled to 0° C. and basified with 1M aqueous NaOH until pH>14. The layers were separated. The aqueous phase was extracted the methylene chloride (2×10 mL). The organic layers were washed with brine and dried. Concentration afforded the title compound (50 mg, 99%) as a pale yellow amorphous solid. $^1$H NMR ($CDCl_3$, 300 MHz) δ7.40 (m, 1H), 7.14 (d, 1H, J=3.3 Hz), 7.12 (s, 1H), 6.98 (d, 1H, J=7.5 Hz), 6.63 (d, 1H, J=7.8 Hz), 4.51 (m, 2H), 3.2–3.4 (m, 3H), 3.0–3.2 (m, 3H), 2.59 (t, 2H, J=5.7 Hz), 2.26 (m, 2H) ppm. MS (CI, NH3): 389 (base, M+H).

Example 120

1-(3,4-dichlorophenyl)-6,7,9,10,11,12-hexahydro-5H-pyrido[4,3-b][1,4]thiazepino[2,3,4-hi]indole The title compound (44.5 mg, 100%) was prepared by the method of Example 119 from tert-butyl 1-(3,4-dichlorophenyl)-6,7,9,12-tetrahydro-5H-pyrido[4,3-b][1,4]thiazepino[2,3,4-hi]indole-11(10H)-carboxylate (67.5 mg, 0.14 mmol) as pale yellow amorphous solid. $^1$H NMR ($CDCl_3$, 300 MHz) δ7.46 (s, 1H), 7.43 (d, 1H, J=8.1 Hz), 7.20 (dd, 1H, J=1.8, 8.1 Hz), 7.04 (d, 1H, J=7.8 Hz), 6.73 (d, 1H, J=7.2 Hz), 4.60 (t, 2H, J=6.00 Hz), 3.44 (s, 2H), 3.40 (s, 2H, J=6.60 Hz), 3.19 (t, 2H, J=6.00 Hz), 2.69 (t, 2H, J=6.00 Hz), 2.33 (m, 2H) ppm. MS (CI, NH3): 389 (base, M+H).

Example 121

1-[2-chloro-4-(trifluoromethyl)phenyl]-6,7,9,10,11,12-hexahydro-5H-pyrido[4,3-b][1,4]thiazepino[2,3,4-hi]indole The title compound (46.9 mg, 92%) was prepared by the method of Example 119 from tert-butyl 1-[2-chloro-4-(trifluoromethyl)phenyl]-6,7,9,12-tetrahydro-5H-pyrido[4,3-b][1,4]thiazepino[2,3,4-hi]indole-11(10H)-carboxylate (64.4 mg, 0.12 mmol) as pale yellow amorphous solid. $^1$H NMR ($CDCl_3$, 300 MHz) δ7.72 (s, 1H), 7.51 (d, 1H, J=7.5 Hz), 7.06 (d, 1H, J=7.5 Hz), 6.70 (d, 1H, J=7.2 Hz), 4.4–4.7 (m, 2H), 3.3–3.5 (m, 3H), 3.1–3.3 (m, 3H),2.67 (t, 2H, J=5.1 Hz), 2.2–2.4 (m, 2H) ppm. MS (CI, $NH_3$): 423 (base, M+H).

Example 122

(8aS,12aR)-1-(2,3-dichlorophenyl)-6,7,8a,9,10,11,12,12a-octahydro-5H-pyrido[4,3-b][1,4]thiazepino[2,3,4-hi]indole 1-(2,3-Dichlorophenyl)-6,7,9,10,11,12-hexahydro-5H-pyrido[4,3-b][1,4]thiazepino[2,3,4-hi]indole (47.0 mg, 0.12 mmol) was dissolved in TFA (2 mL). The reaction was cooled to 0° C. $NaCNBH_3$ (22.7 mg, 0.36 mmol) was added. The reaction was stirred at 0° C. for 2 hr. Ice (2 chips) were added. The reaction was basified with 50% NaOH until a pH of 14, keeping the temperature less than 7° C. The reaction mixture was extracted with $CH_2Cl_2$ (3×10 mL). The combined organic layers were washed with brine, dried, and concentrated to afford the title compound (40.5 mg, 86%) as a pure, white, amorphous solid. $^1$H NMR ($CDCl_3$, 300 MHz) δ7.43 (d, 1H, 7.3 Hz), 7.23–7.30 (m, 2H), 7.00 (d, 1H, 8.1 Hz), 6.48 (d, 1H, 8.1 Hz), 3.94–4.03 (m, 1H), 3.62–3.70 (m, 1H), 3.21–3.40 (m, 1H), 2.80–3.07, m, 5H), 2.50–2.55 (m, 1H), 1.94–2.48 (m, 4H), 1.68–1.76 (m, 1H) ppm. MS (CI, $NH_3$): 391 (base, M+H).

Example 123

(8aS,12aR)-1-(3,4-dichlorophenyl)-6,7,8a,9,10,11,12,12a-octahydro-5H-pyrido[4,3-b][1,4]thiazepino[2,3,4,-hi]indole The title compound (28.8 mg, 73%) was prepared by the method of Example 122 from 1-(3,4-dichloropheny)-6,7,9,10,11,12-hexahydro-5H-pyrido[4,3-b][1,4]thiazepino[2,3,4-hi]indole (39.2 mg, 0.10 mmol) and $NaCNBH_3$ (28.8 mg, 0.30 mmol), as a white, amorphous solid. $^1$lH NMR ($CDCl_3$, 300 MHz) δ7.25–7.45 (m, 2H), 7.21 (dd, 1H, 2.4 Hz, 8.1 Hz), 7.00 (d, 1H, 7.8 Hz), 6.55 (d, 1H, 8.1 Hz), 4.0 (ddd, 1H, 4.0 Hz, 12.1 Hz, 13.6 Hz), 3.65 (ddd, 1H, 5.1 Hz, 11.3 Hz, 14.3 Hz), 3.37–3.41 (m, 1H), 3.20 (dt, 1H, 6.6 Hz, 17.7 Hz), 3.04 (b dd, 1H, 4.5 Hz, 13.5 Hz), 2.93 (ddd, 1H, 2.1 Hz, 5.7 Hz, 14.4 Hz), 2.84 (dd, 2H, 2.4 Hz, 9.9 Hz), 2.6 (dd, 1H, 6.3 Hz, 12.2 Hz), 1.8–2.3 (m, 4H), 1.7–1.8 (m, 1H) ppm. MS (CI, $NH_3$): 391 (base, M+H).

Example 124

(8aS,12aR)-1-[2-chloro-4-(trifluoromethyl)phenyl]-6,7,8a,9,10,11,12,12a-octahydro-5H-pyrido[4,3-b][1,4]thiazepino[2,3,4-hi]indole The title compound (44.3 mg, 95%) was prepared by the method of Example 122 from 1-[2-chloro-4-(trifluoromethyl)phenyl]-6,7,9,10,11,12-hexahydro-5H-pyrido[4,3-b][1,4]thiazepino[2,3,4-hi]indole (46.8 mg, 0.11 mmol) and $NaCNBH_3$ (21.0 mg, 0.33 mmol), as a white, amorphous solid. The enantiomers of the title compound were separated by preparative HPLC on a Chriacel OD column using isocratic 6% IPA/hexane as the eluent. $^1H$ NMR ($CDCl_3$, 300 MHz) δ7.70 (s, 1H), 7.52 (d, 1H, 7.7 Hz), 7.34 (bd, 1H), 7.01 (d, 1H, 8.1 Hz), 6.46 (bd, 1H), 3.95–4.05 (m, 1H), 3.58–3.78 (m, 1H), 3.30–3.41 (m, 1H), 2.81–3.07, m, 5H), 1.9–2.4 (m, 5H), 1.68–1.76 (m, 1H) ppm. MS (CI, $NH_3$): 425 (base, M+H).

Example 125 tert-butyl cis-(8a,12a)-1-bromo-6,7,9,10,12,12a-hexahydro-5H-pyrido[4,3-b][1,4]thiazepino[2,3,4-hi]indole-11(8aH)-carboxylate The title compound was prepared by the method of Example 107 from cis-(8a,12a)-1-bromo-6,7,8a,9,10,11,12,12a-octahydro-5H-pyrido[4,3-b][1,4]thiazepino[2,3,4-hi]indole (157 mg, 0.48 mmol) and $BOC_2O$ (116 mg, 0.53 mmol) after chromatographic purification (152 mg, 75%) as a white amorphous solid. $^1H$ NMR ($CDCl_3$, 300 MHz) δ7.73 (d, 1H, J=8.3 Hz), 6.66 (d, 1H, J=8.3 Hz), 3.35–4.1 (m, 5H), 2.70–3.35 (m, 5H), 1.75–2.20 (m, 4H), 1.33 (s, 9H) ppm.

Example 126 tert-butyl cis-(8a,12a)-1-(2,6-difluorophenyl)-6,7,9,10,12,12a-hexahydro-5H-pyrido[4,3-b][1,4]thiazepino[2,3,4-hi]indole-11(8aH)-carboxylate Tert-butyl cis-(8a,12a)-1-bromo-6,7,9,10,12,12a-hexahydro-5H-pyrido[4,3-b][1,4]thiazepino[2,3,4-hi]indole-11(8aH)-carboxylate (70 mg, 0.16 mmol) was dissolved in DME (3 mL). TEA (0.3 mL) was added. Boronic acid 2 (52 mg, 0.33 mmol) was added, followed by Pd(dppf)$Cl_2$ (6.7 mg, 0.0082 mmol). The reaction flask was degassed and kept under a nitrogen atmosphere. The suspension was refluxed for 18 hrs cooled to rt. The reaction was concentrated in vacuo, after which water (10 mL) and EtOAc (10 mL) were added. The layers were separated and the aqueous phase was extracted with EtOAc (2×10 mL). The combined organic layers were washed with brine (2×10 mL), dried, and concentrated to afford a crude brown amorphous solid (214 mg). The residue was purified by column chromatography (20–40% EtOAc/Hexane) to afford the title compound (29.5 mg, 40%) as a white amorphous solid. $^1H$ NMR ($CDCl_3$, 300 Mhz) δ7.20–7.25 (m, 1H). 6.97 (d, 1H, 7.7 Hz), 6.51 (d, 1H, 7.7 Hz), 3.90–3.99 (m, 1H), 3.60–3.75 (m, 1H), 3.43–3.59 (m, 1H), 3.35–3.42 (m, 2 H), 2.81–3.04 (m, 4H), 2.40–2.60 (m, 1H), 1.60–2.20 (m, 4H), 1.21 (bs, 9H) ppm.

Example 127 cis-(8a,12a)-1-(2,6-difluorophenyl)-6,7,8a,9,10,11,12,12a-octahydro-5H-pyrido[4,3-b][1,4]thiazepino[2,3,4-hi]indole Tert-butyl-cis-(8a,12a)-1-(2,6-difluorophenyl)-6,7,9,10,12,12a-hexahydro-5H-pyrido[4,3-b][1,4]thiazepino[2,3,4-hi]indole-11(8aH)-carboxylate (18.2 mg, 0.04 mmol) was dissolved in 20% TFA in methylene chloride (4 mL) and was stirred at rt for 2 hrs. The reaction was solution was cooled to 0° C. and basified with 1M NaOH until pH>14. The layers were separated. The aqueous phase was extracted the methylene chloride (2×10 mL). The organic layers were washed with brine and dried. Concentration afforded the title compound (14 mg, 100%) as a pale yellow amorphous solid. The enantiomers of the title compound were separated by preparative HPLC on a chiracel OD column using isocratic 5% IPA/hexane as the eluent. $^1H$ NMR ($CDCl_3$, 300 MHz) δ7.15–7.26 (m, 2H), 6.95 (d, 1H, 8.1 Hz), 6.81–6.81 (m, 1H), 6.48 (d, 1H, 7.7 Hz), 3.94 (ddd, 1H, 4.1 Hz, 11.8 Hz, 13.5 Hz), 3.62 (ddd, 1H, 5.1 Hz, 11.3 Hz, 14.6 Hz), 3.29–3.33 (m, 1H), 2.95 (bdd, 1H, 4.8 Hz, 13.6 Hz), 2.75–2.90 (m, 3H), 2.50 (dd, 1H, 6.6 Hz, 12.5 Hz), 2.28 (t, 1H, 11.7 Hz), 1.80–2.20 (m, 3H), 1.45–1.80 (m, 2H) ppm. MS (CI, NH3): 359 (base, M+H).

Example 128 cis-(8a,12a)-2-(2,4-dichlorophenyl)-6,7,8a,9,10,11,12,12a-octahydro-5H-pyrido[4,3-b][1,4]thiazepino[2,3,4-hi]indole Step A A solution of 5-nitroso-2,3,4,5-tetrahydro-1,5-benzothiazepine (32.21 g, 0.166 mol) in THF (650 mL) was added dropwise to LAH (1.0M in THF, 166 mL) under $N_2$ such that the temperature did not rise above 27–29° C. Once the addition was complete, the mixture was stirred at room temperature for 1 hr. It was cooled in an ice bath and treated with $H_2O$ (7.3 mL) added dropwise, followed by 1N NaOH (32.4 mL). Once at room temperature, the mixture was filtered and the filtrate was evaporated under reduced pressure. The residue was taken up in $CH_2Cl_2$ (200 mL) washed with $H_2O$, and dried over $MgSO_4$, and stripped of solvent under reduced pressure to yield 29.42 g (98%) of the crude product. Purification by column chromatography (EtOAc) afforded 17.69 g (59% yield) of 3,4-dihydro-1,5-benzothiazepin-5(2H)-amine as a liquid which was converted to the HCl salt, m.p. 202° C. (decomposition). $(M+H)^+$ 180.

Step B

4-Piperidone monohydrate HCl (4.55 g, 29.62 mmol) was added to a vigorously stirred solution of 2H,3H,4H-benzo[b]1,4-thiazepine-5-ylamine (6.42 g, 29.62 mmol) in i-PrOH (250 mL). The mixture was refluxed for 2 hrs. The white precipitate was collected and converted to the free base using 1N NaOH followed by extraction with $CH_2Cl_2$ (3×25 mL). The combined extracts were dried over $MgSO_4$ and stripped of the solvent using reduced pressure to yield 4.66 g (64%) of 6,7,9,10,11,12-hexahydro-5H-pyrido[4,3-b][1,4]thiazepino[2,3,4-hi]indole as an oil. $(M+H)^+$ 244.

Step C

To a stirred solution (0–5° C.) of 6,7,9,10,11,12-hexahydro-5H-pyrido[4,3-b][1,4]thiazepino[2,3,4-hi]indole (4.66 g, 19.07 mmol) in TFA (42 mL) under $N_2$ was added sodium cyanoborohydride (3.78 g, 60.07 mmol) in small portions. After stirring for 4 hrs at room temperature, the mixture was carefully treated with 6N HCl (44 mL) and refluxed for 1 hr. The mixture was basified with 25% NaOH and extracted with $CHCl_3$ (3×50 mL). The combined extracts were dried over $MgSO_4$ and stripped of the solvent under reduced pressure to yield 4.08 g (87%) of cis-(8a,12a)-6,7,8a,9,10,11,12,12a-octahydro-5H-pyrido[4,3-b][1,4]thiazepino[2,3,4-hi]indole. $^1H$ NMR ($CDCl_3$ 300 MHz) δ6.93 (dd, 1H), 6.84 (dd, 1H), 6.60 (t, 1H), 3.78 (qd, 1H), 3.64 (dq, 1H), 3.32–3.40 (m, 1H), 3.19 (dt, 1H), 2.86 (tt, 2H), 2.59 (td, 1H), 2.27 (s, 1H), 2.00–2.20 (m, 2H), 1.80 (qq, 2H) ppm. $(M+H)^+$ 246.

Step D

Di-tert-butyldicarbonate (9.04 g, 41.40 mmol) was added to a solution of cis-(8a,12a)-6,7,8a,9,10,11,12,12a-octahydro-5H-pyrido[4,3-b][1,4]thiazepino[2,3,4-hi]indole. (4.08 g, 16.56 mmol) in of $CH_2Cl_2$ (50 mL) and stirred at room temperature for 2 hours. The solvent was stripped under reduced pressure. The residue was taken up in 1% NaOH (50 mL) and extracted with $CH_2Cl_2$ (3×30 mL). The combined extracts were dried over $MgSO_4$ and stripped of solvent under reduced pressure, and the residue was purified by flash chromatography (66% hexanes in EtOAc) to yield 3.59 g (68%) of tert-butyl cis-(8a,12a)-6,7,9,10,12,12a-hexahydro-5H-pyrido[4,3-b][1,4]thiazepino[2,3,4-hi]indole-11(8aH)-carboxylate. $^1H$ NMR ($CDCl_3$ 300 MHz) δ6.98 (d, 1H), 6.90 (d, 1H), 6.61 (t, 1H), 3.80 (qd, 1H), 3.61 (dq, 1H), 3.40–3.58 (m, 2H), 3.14–3.40 (m, 4H), 2.98 (dt, 2H), 2.00–2.19 (m, 1H), 1.82–1.91 (m, 2H), 1.22 (s, 9H) ppm. $(M+H)^+$ 347, 247.

Step E

Bromine (0.462 g, 2.89 mmol) in $CHCl_3$ (5 mL) was added dropwise to a cold solution (0–5° C.) of tert-butyl cis-(8a,12a)-2-bromo-6,7,9,10,12,12a-hexahydro-5H-pyrido[4,3-b][1,4]thiazepino[2,3,4-hi]indole-11(8aH)-carboxylate (1.0 g, 2.89 mmol) in $CHCl_3$ (60 mL). The mixture was stirred at room temperature for 20 hrs after which time it was washed with aq. $NaHCO_3$, dried over $MgSO_4$ and stripped of solvent under reduced pressure to yield 1.12 g (91%) of tert-butyl cis-(8a,12a)-2-bromo-6,7,9,10,12,12a-hexahydro-5H-pyrido[4,3-b][1,4]thiazepino[2,3,4-hi]indole-11(8aH)-carboxylate as a reddish-brown liquid. $^1H$ NMR ($CDCl_3$ 300 MHz) δ7.08 (d, 1H), 6.98 (d, 1H), 3.78 (qd, 1H), 3.39–3.53 (m, 4H), 3.17–3.24 (m, 3H), 2.92–3.01 (m, 2H), 2.02–2.17 (m, 2H), 1.80–1.88 (m, 2H), 1.42 (s, 9H) ppm. $(M+H)^+$ 425, 369, 325.

Step F

To a solution of tert-butyl cis-(8a,12a)-2-bromo-6,7,9,10,12,12a-hexahydro-5H-pyrido[4,3-b][1,4]thiazepino[2,3,4-hi]indole-11(8aH)-carboxylate (0.800 g, 1.88 mmol) in benzene (40 mL) was added 2,4-dichlorobenzeneboronic acid (0.717 g, 3.76 mmol), Bis(triphenylphosphine)palladium (II) chloride (0.072 g), and 2M $Na_2CO_3$ (3.04 mL) The combined mixture was refluxed for 24 hrs and then evaporated to dryness under reduced pressure. The residue was taken up in $H_2O$ (80 mL) and extracted with EtOAc (3×10 mL). The combined extracts were dried over $MgSO_4$ and stripped of the solvent under reduced pressure to yield a mixture of 85% product and 15% unreacted starting material. Purification of the resinous product on normal phase HPLC (75% hexanes in EtOAc) afforded 0.612 g (66%) of tert-butyl(8a,12a)-2-(2,4-dichlorophenyl)-6,7,9,10,12,12a-hexahydro-5H-pyrido[4,3-b][1,4]thiazepino[2,3,4-hi]indole-11(8aH)-carboxylate as a foam. $^1NMR$ ($CDCl_3$ 300 MHz) δ7.44 (s, 1H), 7.18–7.24 (m, 2H), 7.04 (s, 1H), 7.00 (s, 1H), 3.79–3.88 (m, 2H), 3.60–3.80 (m, 2H), 3.40–3.59 (m, 2H), 3.20–3.40 (m, 2H), 3.00–3.18 (m, 1H), 2.10–2.21 (m, 2H), 1.82–1.96 (m, 2H), 1.38 (s, 9H), 1.61 (t, 1H) ppm. $(M+H)^+$ 492, 436, 392.

Step G

A solution of of tert-butyl(8a,12a)-2-(2,4-dichlorophenyl)-6,7,9,10,12,12a-hexahydro-5H-pyrido[4,3-b][1,4]thiazepino[2,3,4-hi]indole-11(8aH)-carboxylate (0.612 g, 1.25 mmol) in $CH_2Cl_2$ (10 mL) was treated with TFA (3 mL) and stirred at room temperature for 18 hrs. in a closed vial. The solution was basified with 1N NaOH (20 mL) and extracted with $CH_2Cl_2$ (3×10 mL). The combined extracts were dried over $MgSO_4$, and stripped of the solvent under reduced pressure to yield 0.380 g (78%) of cis-(8a,12a)-2-(2,4-dichlorophenyl)-6,7,8a,9,10,11,12,12a-octahydro-5H-pyrido[4,3-b][1,4]thiazepino[2,3,4-hi]indole as a foam. $^1H$ NMR ($CDCl_3$ 300 MHz) δ7.42 (d, 1H), 7.21–7.27 (m, 2H), 7.01 (dd, 1H), 6.97 (s, 1H), 3.90 (qd, 1H), 3.58 (dq, 1H), 3.42–3.50 (m, 1H), 3.22–3.41 (m, 1H), 2.98–3.21 (m, 5H), 2.91–2.93 (m, 1H), 2.62–2.74 (m, 1H), 2.00–2.20 (m, 4H) ppm. $(M+H)^+$ 392.

Example 129 cis-(8a,12a)-2-phenyl-6,7,8a,9,10,11,12,12a-octahydro-5H-pyrido[4,3-b][1,4]thiazepino[2,3,4-hi]indole The title compound was prepared by the method of Example 128, Step F and the corresponding aryl boronic acid followed by hydrolysis of the resultant BOC protected amine adduct by the procedure of Example 128, Step G. $^1H$ NMR ($CDCl_3$ 300 MHz) δ7.42 (dd, 2H), 7.36–7.40 (m, 2H), 7.26–7.31 (m, 1H), 7.24 (d, 1H), 7.16 (d, 1H), 3.96 (qd, 1H), 3.59 (dq, 1H), 3.31–3.44 (m, 4H), 3.19 (td, 1H), 2.96–3.09 (m, 2H), 2.72 (dd, 1H), 2.20–2.39 (m, 1H), 2.16–2.20 (m, 2H) ppm. $(M+H)^+$ 323.

Example 130 cis-(8a,12a)-2-(4-fluorophenyl)-6,7,8a,9,10,11,12,12a-octahydro-5H-pyrido[4,3-b][1,4]thiazepino[2,3,4-hi]indole The title compound was prepared by the method of Example 128, Step F and the corresponding aryl boronic acid followed by hydrolysis of the resultant BOC protected amine adduct by the procedure of Example 128, Step G. $(M+H)^+$ 341.

Example 131 cis-(8a,12a)-2-(4-chlorophenyl)-6,7,8a,9,10,11,12,12a-octahydro-5H-pyrido[4,3-b][1,4]thiazepino[2,3,4-hi]indole The title compound was prepared by the method of Example 128, Step F and the corresponding aryl boronic acid followed by hydrolysis of the resultant BOC protected amine adduct by the procedure of Example 128, Step G. $(M+H)^+$ 357.

Example 132 cis-(8a,12a)-2-(2-chlorophenyl)-6,7,8a,9,10,11,12,12a-octahydro-5H-pyrido[4,3-b][1,4]thiazepino[2,3,4-hi]indole The title compound was prepared by the method of Example 128, Step F and the corresponding aryl boronic acid followed by hydrolysis of the resultant BOC protected amine adduct by the procedure of Example 128, Step G. $^1H$ NMR ($CDCl_3$ 300 MHz) δ7.38 (dd, 2H), 7.10–7.18 (m, 2H), 7.00 (dd, 1H), 6.91 (d, 1H), 3.84 (qd, 1H), 3.57 (dq, 1H), 3.38 (m, 2H), 2.80–3.25 (m, 8H), 2.62 (dd, 1H), 2.01–2.18 (m, 2H) ppm. $(M+H)^+$ 357.

Example 133 cis-(8a,12a)-2-(2-methoxyphenyl)-6,7,8a,9,10,11,12,12a-octahydro-5H-pyrido[4,3-b][1,4]thiazepino[2,3,4-hi]indole The title compound was prepared by the method of Example 128, Step F and the corresponding aryl boronic acid followed by hydrolysis of the resultant BOC protected amine adduct by the procedure of Example 128, Step G. $(M+H)^+$353.

Example 134 cis-(8a,12a)-2-[2-chloro-4-(trifuloromethyl)phenyl]-6,7,8a,9,10,11,12,12a-octahydro-5H-pyrido[4,3-b][1,4]thiazepino[2,3,4-hi]indole The title compound was prepared by the method of Example 128, Step F and the corresponding aryl boronic acid followed by hydrolysis of the resultant BOC protected amine adduct by the procedure of Example 128, Step G. $(M+H)^+$425.

Example 135 cis-(8a,12a)-2-(2,4-dimethylphenyl)-6,7,8a,9,10,11,12,12a-octahydro-5H-pyrido[4,3-b][1,4]thiazepino[2,3,4-hi]indole The title compound was prepared by the method of Example 128, Step F and the corresponding aryl boronic acid followed by hydrolysis of the resultant BOC protected amine adduct by the procedure of Example 128, Step G. $^1H$ NMR ($CDCl_3$ 300 MHz) δ6.99–7.10 (m, 3H), 6.94 (d, 1H), 6.80 (d, 1H), 3.80 (qd, 1H), 3.58 (dq, 1H), 3.40–3.43 (m, 1H), 2.80–3.21 (m, 6H), 2.66 (dd, 1H), 2.37–2.42 (m, 1H), 2.37 (s, 3H), 2.22 (s, 3H), 2.01–2.21 (m, 2H), 1.83–1.91 (m, 2H), 1.26–1.28 (m, 1H) ppm. $(M+H)^+$ 351.

Example 136 cis-(8a,12a)-2-(2-chloro-4-methoxyphenyl)-6,7,8a,9,10,11,12,12a-octahydro-5H-pyrido[4,3-b][1,4]thiazepino[2,3,4-hi]indole The title compound was prepared by the method of Example 128, Step F and the corresponding aryl boronic acid followed by hydrolysis of the resultant BOC protected amine adduct by the procedure of Example 128, Step G. $^1H$ NMR ($CDCl_3$ 300 MHz) δ7.28 (dd, 2H), 7.18 (dd, 1H), 7.04 (d, 1H), 6.94 (d, 1H), 3.92 (qd, 1H), 3.59 (dq, 1H), 3.41–3.51 (m, 1H), 2.97–3.30 (m, 5H), 2.72 (dd, 1H), 2.01–2.19 (m, 4H) ppm. $(M+H)^+$ 387.

Example 137 cis-(8a,12a)-2-(4-isopropylphenyl)-6,7,8a,9,10,11,12,12a-octahydro-5H-pyrido[4,3-b][1,4]thiazepino[2,3,4-hi]indole The title compound was prepared by the method of Example 128, Step F and the corresponding aryl boronic acid followed by hydrolysis of the resultant BOC protected amine adduct by the procedure of Example 128, Step G. $^1H$ NMR ($CDCl_3$ 300 MHz), δ7.42 (d, 1H), 7.39 (d, 1H), 7.22 (d, 1H), 7.19 (d, 1H), 7.08 (s, 1H), 3.78 (qd, 1H), 3.51–3.60 (m, 1H), 3.39–3.45 (m, 1H), 2.80–3.22 (m, 8H), 2.68 (dd, 1H), 2.38 (s, 1H), 2.01–2.23 (m, 2H), 1.80–1.96 (m, 2H), 1.28 (d, 6H) ppm. $(M+H)^+$ 365.

Example 138 cis-(8a,12a)-2-(4-butylphenyl)-6,7,8a,9,10,11,12,12a-octahydro-5H-pyrido[4,3-b][1,4]thiazepino[2,3,4-hi]indole The title compound was prepared by the method of Example 128, Step F and the corresponding aryl boronic acid followed by hydrolysis of the resultant BOC protected amine adduct by the procedure of Example 128, Step G. $(M+H)^+$379.

Example 139 cis-(8a,12a)-2-(2-fluoro-4-methoxy-6-methylphenyl)-6,7,8a,9,10,11,12,12a-octahydro-5H-pyrido[4,3-b][1,4]thiazepino[2,3,4-hi]indole The title compound was prepared by the method of Example 128, Step F and the corresponding aryl boronic acid followed by hydrolysis of the resultant BOC protected amine adduct by the procedure of Example 128, Step G. $^1H$ NMR ($CDCl_3$ 300 MHz) δ6.92 (dd, 2H), 6.80 (dd, 2H), 3.92 (s, 3H), 3.90 (qd, 1H), 3.79 (dq, 1H), 3.43 (m, 1H), 2.98–3.36 (m, 8H), 2.69 (dd, 1H), 2.21 (s, 3H), 2.00–2.20 (m, 4H) ppm. $(M+H)^+$ 385.

Example 140 cis-(8a,12a)-2-(4-methoxy-2-methylphenyl)-6,7,8a,9,10,11,12,12a-octahydro-5H-pyrido[4,3-b][1,4]thiazepino[2,3,4-hi]indole The title compound was prepared by the method of Example 128, Step F and the corresponding aryl boronic acid followed by hydrolysis of the resultant BOC protected amine adduct by the procedure of Example 128, Step G. $^1H$ NMR ($CDCl_3$ 300 MHz) δ7.10 (d, 1H), 6.92 (d, 1H), 6.75–6.80 (m, 3H), 3.84 (qd, 1H), 3.81 (s, 3H), 3.59 (dq, 1H), 3.41 (m, 1H), 2.97–3.31 (m, 7H), 2.68 (dd, 1H), 2.22 (s, 3H), 2.00–2.20 (m, 4H) ppm. $(M+H)^+$ 367.

Example 141 cis-(8a,12a)-2-[2-chloro-4-(trifluoromethoxy)phenyl]-6,7,8a,9,10,11,12,12a-octahydro-5H-pyrido[4,3-b][1,4]thiazepino[2,3,4-hi]indole The title compound was prepared by the method of Example 128, Step F and the corresponding aryl boronic acid followed by hydrolysis of the resultant BOC protected amine adduct by the procedure of Example 128, Step G. $(M+H)^+$441.

Example 142 cis-(8a,12a)-2-mesityl-6,7,8a,9,10,11,12,12a-octahydro-5H-pyrido[4,3-b][1,4]thiazepino[2,3,4-hi]indole The title compound was prepared by the method of Example 128, Step F and the corresponding aryl boronic acid followed by hydrolysis of the resultant BOC protected amine adduct by the procedure of Example 128, Step G. $(M+H)^+$365.

Example 143 cis-(8a,12a)-2-(3-chlorophenyl)-6,7,8a,9,10,11,12,12a -octahydro-5H-pyrido[4,3-b][1,4]thiazepino[2,3,4-hi]indole The title compound was prepared by the method of Example 128, Step F and the corresponding aryl boronic acid followed by hydrolysis of the resultant BOC protected amine adduct by the procedure of Example 128, Step G. $(M+H)^+$357.

Example 144 cis-(8a,12a)-2-(4-methylphenyl)-6,7,8a,9,10,11,12,12a-octahydro-5H-pyrido[4,3-b][1,4]thiazepino[2,3,4-hi]indole The title compound was prepared by the method of Example 128, Step F and the corresponding aryl boronic acid followed by hydrolysis of the resultant BOC protected amine adduct by the procedure of Example 128, Step G. $(M+H)^+$337.

Example 145 cis-(8a,12a)-2-(4-chloro-2-methylphenyl)-6,7,8a,9,10,11,12,12a-octahydro-5H-pyrido[4,3-b][1,4]thiazepino[2,3,4-hi]indole The title compound was prepared by the method of Example 128, Step F and the corresponding aryl boronic acid followed by hydrolysis of the resultant BOC protected amine adduct by the procedure of Example 128, Step G. $(M+H)^+$371.

Example 146 cis-(8a,12a)-2-(2,5-dichlorophenyl)-6,7,8a,9,10,11,12,12a-octahydro-5H-pyrido[4,3-b][1,4]thiazepino[2,3,4-hi]indole The title compound was prepared by the method of Example 128, Step F and the corresponding aryl boronic acid followed by hydrolysis of the resultant BOC protected amine adduct by the procedure of Example 128, Step G. $(M+H)^+$391.

Example 147 cis-(8a,12a)-2-(4-isopropyl-2-methoxyphenyl)-6,7,8a,9,10,11,12,12a-octahydro-5H-pyrido[4,3-b][1,4]thiazepino[2,3,4-hi]indole The title compound was prepared by the method of Example 128, Step F and the corresponding aryl boronic acid followed by hydrolysis of the resultant BOC protected amine adduct by the procedure of Example 128, Step G. $(M+H)^+$395.

Example 148 cis-(8a,12a)-2-(2,6-dichlorophenyl)-6,7,8a,9,10,11,12,12a-octahydro-5H-pyrido[4,3-b][1,4]thiazepino[2,3,4-hi]indole Step A To a solution of tert-butyl cis-(8a,12a)-2-bromo-6,7,9,10,12,12a-hexahydro-5H-pyrido[4,3-b][1,4]thiazepino[2,3,4-hi]indole-11(8aH)-carboxylate (0.100 g, 0.24 mmol), from Step E of Example 128, in 1,2-dimethoxyethane (5mL) was added 2,6-dichlorophenylboronic acid (0.092 g, 0.48 mmol), 1,1'-bis(diphenyl-phosphino)ferrocene palladium (II) chloride complex with dichloromethane (0.005 g), and triethylamine (0.34 mL). The mixture was refluxed for 24 hrs which led to 55% conversion of the starting material into product. Another 0.48 mmol of 2,6-dichlorobenzeneboronic acid, 0.005 g of Pd(dppf), and 0.34 mL of TEA were added to the mixture which was refluxed for 24 hrs and then evaporated to dryness under reduced pressure. The residue was taken up in $H_2O$ (20 mL) and extracted with EtOAc (3×5 mL). The combined extracts were dried over $MgSO_4$ and stripped of the solvent under reduced pressure to yield a mixture of 95% product and 5% unreacted starting material which was purified by normal phase HPLC (75% hexanes in EtOAc) to yield 0.088 g (76%) of tert-butyl(8aS,12aR)-2-(2,6-dichlorophenyl)-6,7,9,10,12,12a-hexahydro-5H-pyrido[4,3-b][1,4]thiazepino[2,3,4-hi]indole-11(8aH)-carboxylate as a foam. $(M+H)^+$ 491, 435, 391.

Step B

Cis-(8a,12a)-2-(2,6-dichlorophenyl)-6,7,8a,9,10,11,12,12a-octahydro-5H-pyrido[4,3-b][1,4]thiazepino[2,3,4-hi]indole was prepared from tert-butyl cis-(8a,12a)-2-(2,6-dichlorophenyl)-6,7,9,10,12,12a-hexahydro-5H-pyrido[4,3-b][1,4]thiazepino[2,3,4-hi]indole-11(8aH)-carboxylate as exemplified in Step G of Example 128 to afford 0.034 g (49%) as a foam. $(M+H)^+$ 391.

Example 149 cis-(8a,12a)-2-(2,6-difluorophenyl)-6,7,8a,9,10,11,12,12a-octahydro-5H-pyrido[4,3-b][1,4]thiazepino[2,3,4-hi]indole The title compound was prepared by the method of Example 148, Step A, utilizing tert-butyl cis-(8a,12a)-2-bromo-6,7,9,10,12,12a-hexahydro-5H-pyrido[4,3-b][1,4]thiazepino[2,3,4-hi]indole-11(8aH)-carboxylate from Example 128, Step E and the corresponding aryl boronic acid followed by hydrolysis of the resultant BOC protected amine adduct by the procedure of Example 148, Step B. $(M+H)^+$358.

Example 150 cis-(8a,12a)-2-[4-methoxy-2-(trifluoromethyl)phenyl]-6,7,8a,9,10,11,12,12a-octahydro-5H-pyrido[4,3-b][1,4]thiazepino[2,3,4-hi]indole The title compound was prepared by the method of Example 148, Step A, utilizing tert-butyl cis-(8a,12a)-2-bromo-6,7,9,10,12,12a-hexahydro-5H-pyrido[4,3-b][1,4]thiazepino[2,3,4-hi]indole-11(8aH)-carboxylate from Example 128, Step E and the corresponding aryl boronic acid followed by hydrolysis of the resultant BOC protected amine adduct by the procedure of Example 148, Step B. $^1H$ NMR ($CDCl_3$ 300 MHz) δ7.20 (dd, 2H), 7.04 (dd, 1H), 6.90 (d, 1H), 6.79 (d, 1H), 3.84 (s, 3H), 3.82 (qd, 1H), 3.58 (dq, 1H), 3.42 (m, 1H), 2.94–3.21 (m, 5H), 2.63 (dd, 2H), 2.38 (s, 1H), 2.01–2.21 (m, 2H), 1.80–1.97 (m, 2H) ppm. $(M+H)^+$ 421.

Example 151 cis-(8a,12a)-2-[2-trifluoromethyl)phenyl]-6,7,8a,9,10,11,12,12a-octahydro-5H-pyrido[4,3-b][1,4]thiazepino[2,3,4-hi]indole The title compound was prepared by the method of Example 148, Step A, utilizing tert-butyl cis-(8a,12a)-2-bromo-6,7,9,10,12,12a-hexahydro-5H-pyrido[4,3-b][1,4]thiazepino[2,3,4-hi]indole-11(8aH)-carboxylate from Example 128, Step E and the corresponding aryl boronic acid followed by hydrolysis of the resultant BOC protected amine adduct by the procedure of Example 148, Step B. $(M+H)^+$391.

Example 152 cis-(8a,12a)-2-(4-pyridinyl)-6,7,8a,9,10,11,12,12a-octahydro-5H-pyrido[4,3-b][1,4]thiazepino[2,3,4-hi]indole Step A To a solution of tert-butyl cis-(8a,12a)-2-bromo-6,7,9,10,12,12a-hexahydro-5H-pyrido[4,3-b][1,4]thiazepino[2,3,4-hi]indole-11(8aH)-carboxylate (0.100 g, 0.24 mmol), from Step E of Example 128, in toluene (3 mL) was added pyridine-4-trimethylstannane (0.058 g, 0.24 mmol), $(Ph_3P)_2PdCl_2$ (0.005 g) and a couple of crystals of 2,6-di-tert-butyl-4-methylphenol. The combined mixture was refluxed for 13 hrs. and then evaporated to dryness under reduced pressure. The residue was taken up in $H_2O$ (20 mL) and extracted with EtOAc (3×5 mL). The combined extracts were dried over $MgSO_4$ and stripped of the solvent under reduced pressure to yield a mixture of product and unreacted starting material tert-butyl (8aS,12aR)-2-(4-pyridinyl)-6,7,9,10,12,12a-hexahydro-5H-pyrido[4,3-b][1,4]thiazepino[2,3,4-hi]indole-11(8aH)-carboxylate was purified on a prep TLC silica plate (50% EtOAc/Hexanes) and was isolated as a viscous liquid. Yield 0.017 g (17%). $(M+H)^+$ 423, 367, 323.

Step B cis-(8a,12a)-2-(4-pyridinyl)-6,7,8a,9,10,11,12,12a-octahydro-5H-pyrido[4,3-b][1,4]thiazepino[2,3,4-hi]indole was prepared from tert-butyl(8aS,12aR)-2-(4-pyridinyl)-6,7,9,10,12,12a-hexahydro-5H-pyrido[4,3-b][1,4]thiazepino[2,3,4-hi]indole-11(8aH)-carboxylate as exemplified in Step G of Example 128 to afford 5.0 mg (38%) as a foam. $(M+H)^+$ 323.

Example 153 cis-(8a,12a)-2-(4-furyl)-6,7,8a,9,10,11,12,12a-octahydro-5H-pyrido[4,3-b][1,4]thiazepino[2,3,4-hi]indole The title compound was prepared by the method of Example 152, Step A, utilizing tert-butyl cis-(8a,12a)-2-(2,3-dihydro-2-furanyl)-6,7,9,10,12,12a-hexahydro-5H-pyrido[4,3-b][1,4]thiazepino[2,3,4-hi]indole-11(8aH)-carboxylate from Example 128, Step E and the corresponding aryl boronic acid followed by hydrolysis of the resultant BOC protected amine adduct by the procedure of Example 128, Step G. $^1H$ NMR ($CDCl_3$ 300 MHz) δ7.38 (d, 1H), 7.31 (d, 1H), 7.18 (d, 1H), 6.41–6.44 (m, 2H), 3.80 (qd, 2H), 3.54 (dq, 2H), 3.40–3.48 (m, 1H), 2.98–3.24 (m, 5H), 2.68 (dd, 2H), 2.00–2.21 (m, 2H), 1.89–1.99 (m, 1H) ppm. $(M+H)^+$ 312.

Example 154 cis-(8a,12a)-2-(4-thienyl)-6,7,8a,9,10,11,12,12a-octahydro-5H-pyrido[4,3-b][1,4]thiazepino[2,3,4-hi]indole The title compound was prepared by the method of Example 152, Step A, utilizing tert-butyl cis-(8a,12a)-2-bromo-6,7,9,10,12,12a-hexahydro-5H-pyrido[4,3-b][1,4]thiazepino[2,3,4-hi]indole-11(8aH)-carboxylate from Example 128, Step E and the corresponding aryl boronic acid followed by hydrolysis of the resultant BOC protected amine adduct by the procedure of Example 128, Step G. $^1H$ NMR ($CDCl_3$ 300 MHz) δ7.26 (d, 1H), 7.10–7.18 (m, 3H), 7.00 (m, 1H), 3.82 (qd, 1H), 3.57 (dq, 1H), 3.41 (m, 1H), 3.10–3.30 (m, 2H), 2.96–3.06 (m, 2H), 2.70–2.92 (m, 1H), 2.68 (dd, 1H), 2.02–2.10 (m, 2H), 1.99 (m, 2H) ppm. $(M+H)^+$ 329.

Example 155 cis-(8a,12a)-2-(4-fluorophenyl)-6,7,8a,9,10,11,12,12a-octahydro-5H-pyrido[4,3-b][1,4]thiazepino[2,3,4-hi]indole Step A TFA (3 mL) was added to a solution of tert-butyl cis-(8a,12a)-2-bromo-6,7,9,10,12,12a-hexahydro-5H-pyrido[4,3-b][1,4]thiazepino[2,3,4-hi]indole-11(8aH)-carboxylate (1.50 g, 3.53 mmol), from Step E of Example 128, in $CH_2Cl_2$ (30 mL) and the resulting mixture was stirred at room temperature for 18 hrs. It was then basified with 1N aqueous NaOH (50 mL) and extracted with $CH_2Cl_2$ (3×30 mL). The combined extracts were washed with $H_2O$, dried over $MgSO_4$, and stripped of solvent under reduced pressure. The residue (0.900 mg, 2.8 mmol) was dissolved in NMP (15 mL), to which was added p-Nitrophenyl-carbonate Wang Resin (1.50 g, 1.40 mmol). The mixture was shaken at 180 RPM for 20 hrs. The resin was filtered and washed with 2×DMF, 2×DMF/$H_2O$, 2×$H_2O$, 2×DMF, 2×$CH_2Cl_2$, 1×diethyl ether and dried in vacuo for 18 hrs. to yield 1.50 g of the benzothiazepinylamine linked Wang resin as a yellow resin.

Step B

A 13 mm glass tube was charged with the amine linked resin (0.050 g), o-tolylbenzeneboronic acid 0.054 g, 0.4 mmol), 2M aqueous $Na_2CO_3$ (200 μL), $(PPh_3)_4Pd(0)$ (0.005 g), and THF (1 mL) and shaken at 70° C., 180 RPM, for 20 hrs. The resin was washed with 3×DMF, 2×$H_2O$, 1×DMF, 2×$CH_2Cl_2$, and 1×diethyl ether. The dry the resin was shaken at room temperature with TFA (1 mL) for 2 hrs. The resin was filtered off and washed with $CH_2Cl_2$ (3×3 mL). The filtrate was stripped of the solvent and dried in vacuo. Purification of the residue by Reverse Phase HPLC (20% $CH_5CN/H_2O$) afforded cis-(8a,12a)-2-(4-fluorophenyl)-6,7,8a,9,10,11,12,12a-octahydro-5H-pyrido[4,3-b][1,4]thiazepino[2,3,4-hi]indole (0.008 g, 44% yield) as an oil that solidified. $(M+H)^+$ 341.

Example 156 cis-(8a,12a)-2-(2,3-dichlorophenyl)-6,7,8a,9,10,11,12,12a-octahydro-5H-pyrido[4,3-b][1,4]thiazepino[2,3,4-hi]indole The title compound was prepared by the method of Example 155 and the corresponding aryl boronic acid. $(M+H)^+$ 391.

Example 157 cis-(8a,12a)-2-(4-ethylphenyl)-6,7,8a,9,10,11,12,12a-octahydro-5H-pyrido[4,3-b][1,4]thiazepino[2,3,4-hi]indole The title compound was prepared by the method of Example 155 and the corresponding aryl boronic acid. $(M+H)^+$ 351.

Example 158 cis-(8a,12a)-2-(2,4-dimethoxyphenyl)-6,7,8a,9,10,11,12,12a-octahydro-5H-pyrido[4,3-b][1,4]thiazepino[2,3,4-hi]indole The title compound was prepared by the method of Example 155 and the corresponding aryl boronic acid. $(M+H)^+$ 383.

Example 159 cis-(8a,12a)-2-(3-chloro-2-fluorophenyl)-6,7,8a,9,10,11,12,12a-octahydro-5H-pyrido[4,3-b](1,4-thiazepino[2,3,4-hi]indole The title compound was prepared by the method of Example 155 and the corresponding aryl boronic acid. $(M+H)^+$ 375.

Example 160 cis-(8a,12a)-2-(4-methoxyphenyl)-6,7,8a,9,10,11,12,12a-octahydro-5H-pyrido[4,3-b][1,4]thiazepino[2,3,4-hi]indole The title compound was prepared by the method of Example 155 and the corresponding aryl boronic acid. $(M+H)^+$ 353.

Example 161 cis-(8a,12a)-2-[4-(methylsulfanyl)phenyl]-6,7,8a,9,10,11,12,12a-octahydro-5H-pyrido[4,3-b][1,4]thiazepino[2,3,4-hi]indole The title compound was prepared by the method of Example 155 and the corresponding aryl boronic acid. $(M+H)^+$ 369.

Example 162

4-[cis-(8a,12a)-6,7,8a,9,10,11,12,12a-octahydro-5H-pyrido[4,3-b][1,4]thiazepino[2,3,4-hi]indol-2-yl] benzonitrile The title compound was prepared by the method of Example 155 and the corresponding aryl boronic acid. $(M+H)^+$ 348.

Example 163 cis-(8a,12a)-2-[3-(trifluoromethyl)phenyl]-6,7,8a,9,10,11,12,12a-octahydro-5H-pyrido[4,3-b][1,4]thiazepino[2,3,4-hi]indole The title compound was prepared by the method of Example 155 and the corresponding aryl boronic acid. $(M+H)^+$ 391.

Example 164 cis-(8a,12a)-2-(2-methoxyphenyl)-6,7,8a,9,10,11,12,12a-octahydro-5H-pyrido[4,3-b][1,4]thiazepino[2,3,4-hi]indole The title compound was prepared by the method of Example 155 and the corresponding aryl boronic acid. $(M+H)^+$ 353.

Example 165 cis-(8a,12a)-2-(2-naphthyl)-6,7,8a,9,10,11,12,12a-octahydro-5H-pyrido[4,3-b][1,4]thiazepino[2,3,4-hi]indole The title compound was prepared by the method of Example 155 and the corresponding aryl boronic acid. $(M+H)^+$ 373.

Example 166

1-{4-[cis-(8a,12a)-6,7,8a,9,10,11,12,12a-octahydro-5H-pyrido[4,3-b][1,4]thiazepino[2,3,4-hi]indol-2-yl] phenyl}ethanone The title compound was prepared by the method of Example 155 and the corresponding aryl boronic acid. $(M+H)^+$ 265.

Example 167

N-{4-[cis-(8a,12a)-6,7,8a,9,10,11,12,12a-octahydro-5H-pyrido[4,3-b][1,4]thiazepino[2,3,4-hi]indol-2-yl] phenyl}acetamide The title compound was prepared by the method of Example 155 and the corresponding aryl boronic acid. $(M+H)^+$ 380.

Example 168 cis-(8a,12a)-2-(2,4-dichlorophenyl)-11-methyl-6,7,8a,9,10,11,12,12a-octahydro-5H-pyrido[4,3-b][1,4]thiazepino[2,3,4-hi]indole Cis-(8a,12a)-2-(2,4-dichlorophenyl)-11-methyl-6,7,8a,9,10,11,12,12a-octahydro-5H-pyrido[4,3-b][1,4]thiazepino[2,3,4-hi]indole was prepared by following Example 128 Steps A–G, using 1-methyl-4-piperidone hydrochloride in Step B instead of 4-piperidone monohydrate, to yield 0.204 g (68%) as an oil. 1H NMR ($CDCl_3$ 300 MHz) δ7.42 (d, 1H), 7.23 (m, 2H), 7.01 (d, 1H), 6.98 (d, 1H), 3.90 (qd, 1H), 3.58 (dq, 1H), 3.38–3.50 (m, 1H), 2.82–3.17 (m, 5H), 2.04 (s, 3H), 2.0–2.10 (m, 6H) ppm. $(M+H)^+$ 405.

Example 169 cis-(8a,12a)-2-methyl-6,7,8a,9,10,11,12,12a-octahydro-5H-pyrido[4,3-b][1,4]thiazepino[2,3,4-hi]indole To a solution of tert-butyl cis-(8a,12a)-2-bromo-6,7,9,10,12,12a-hexahydro-5H-pyrido[4,3-b][1,4]thiazepino[2,3,4-hi]indole-11(8aH)-carboxylate (0.100 g, 0.24 mmol), from Step E of Example 128, and $(PPh_3)_2PdCl_2$ (0.005 g) in anhydrous THF (2 mL) under $N_2$ was added 2M trimethylaluminum in hexanes (0.17 mL, 0.34 mmol). The mixture was reluxed for 3 hrs, cooled to room temperature, and treated with a small amount of $H_2O$ carefully to destroy any unreacted $Al(CH_3)_3$. The mixture was then taken up in $H_2O$ (50 mL) and extracted with EtOAc (3×10 mL). The combined extracts were dried over $MgSO_4$ and stripped of the solvent under reduced pressure to yield a mixture of the expected and hydrolyzed products. The mixture was hydrolyzed as exemplified in Step G of Example 128, to the title compound yielding 0.027 g (44%) as an oil that solidified. $(M+H)^+$ 261.

Example 170 cis-(8a,12a)-6,7,8a,9,10,11,12,12a-octahydro-5H-pyrido[4,3-b][1,4]thiazepino[2,3,4-hi]indole-2-carbonitrile Copper cyanide (0.161 g, 1.8 mmol) was added to a solution of tert-butyl cis-(8a,12a)-2-bromo-6,7,9,10,12,12a-hexahydro-5H-pyrido[4,3-b][1,4]thiazepino[2,3,4-hi]indole-11(8aH)-carboxylate (0.425 g, 1.0 mmol) from Step E of Example 128, in anhydrous DMF (5 mL) under $N_2$ gas and refluxed for 5 hrs. The mixture was stirred at room temperature for 14 hrs, and stripped of the solvent under reduced pressure. The residue was taken up in ammonium hydroxide and extracted with EtOAc (3×5 mL). The combined extracts were dried over $MgSO_4$ and stripped of the solvent under reduced pressure to yield 0.260 g (81%) of a mixture of the expected and hydrolyzed products. The mixture was hydrolyzed to the the title compound using TFA and dichloromethane. The product was purified by flash chromatography using a solution of 9% methanol, 1% TEA in THF to yield 0.070 g (54%) of the title compound as an oil. $(M+H)^+$ 271.

Example 171 cis-(8a,12a)-2-ethyl-6,7,8a,9,10,11,12,12a-octahydro-5H-pyrido[4,3-b][1,4]thiazepino[2,3,4-hi]indole Step A To a solution of tert-butyl cis-(8a,12a)-2-bromo-6,7,9,10,12,12a-hexahydro-5H-pyrido[4,3-b][1,4]thiazepino[2,3,4-hi]indole-11(8aH)-carboxylate (0.680 g, 1.60 mmol) from Step E of Example 128, in toluene (7 mL) was added bis-(triphenylphosphine)palladium dichloride (0.032 g, 0.045 mmol) and a few crystals of 2,6-di-tert-butyl-4-methylphenol. The mixture was refluxed for 3 hours and then evaporated to dryness under reduced pressure. The residue was taken up in $H_2O$ (50 mL) and extracted with EtOAc (3×15 mL). The combined extracts were dried over $MgSO_4$ and stripped of the solvent under reduced pressure to yield a mixture of of product and unreacted starting material. The product was purified by flash chromatography (66% Hexanes in EtOAc) and tert-butyl (8aS,12aR)-2-vinyl-6,7,9,10,12,12a-hexahydro-5H-pyrido[4,3-b][1,4]thiazepino[2,3,4-hi]indole-11(8aH)-carboxylate was isolated as an oil. Yield 0.080 g (14%). $^1$H NMR ($CDCl_3$ 300 MHz) δ6.94 (d, 2H), 6.48 (dd, 1H), 5.49 (d, 1H), 5.01 (d, 1H), 3.61–3.75 (m, 2H), 3.30–3.46 (m, 4H), 3.06–3.31 (m, 3H), 2.98–3.01 (m, 1H), 2.05 (s, 2H), 1.77–1.82 (m, 2H), 1.36 (s, 9H) ppm. $(M+H)^+$ 273.

Step B

To a solution of tert-butyl cis-(8a,12a)-2-vinyl-6,7,9,10,12,12a-hexahydro-5H-pyrido[4,3-b][1,4]thiazepino[2,3,4-hi]indole-11(8aH)-carboxylate (0.080 g, 0.21 mmol) in EtOH (50 mL) was added Pd on Carbon 10% (0.020 g). The mixture was hydrogenated at 50 psi for 24 hrs. At this time, another equivalent of Pd on Carbon 10% (0.020 g) was added and hydrogenated at 48 psi for 48 hrs. The mixture was filtered through celite and evaporated to dryness under reduced pressure to yield 0.038 g of foam. The resulting foam was dissolved in $CH_2Cl_2$ (3 mL), to which was added TFA (0.5 mL). The mixture was stirred for 24 hrs, and then taken up in 1N NaOH (5 mL). The product was extracted with $CH_2Cl_2$ (3×3 mL), dried over $MgSO_4$, evaporated to dryness under reduced pressure, and collected over ether to afford the title compound as a white powder. Yield 0.012 g (43%). $^1$H NMR ($CDCl_3$ 300 MHz) δ6.78 (d, 1H), 6.62 (d, 1H), 3.68 (qd, 1H), 3.44 (dq, 1H), 3.21–3.28 (m, 1H), 2.80–3.20 (m, 7H), 2.56 (m, 1H), 2.40 (q, 2H), 1.80–2.10 (m, 4H), 1.18 (t, 3H), 0.78–0.84 (m, 2H) ppm. $(M+H)^+$ 275.

Example 172 cis-(8a,12a)-6,7,8a,9,10,11,12,12a-octahydro-5H-[1,4]oxazepino[2,3,4-hi]pyrido[4,3-b]indole Step A To a slurry of sodium methoxide (37.8 g, 0.70 mol) in EtOH (800 mL) was added 2-benzoxazoline (94.0 g, 0.70 mol). The mixture was refluxed for 1 hour followed by addition of 1-bromo-3-chloropropane (220.42 g, 1.40 mol). The mixture was refluxed for 18 hours, cooled to room temperature, filtered , and stripped to dryness under reduced pressure. The residue was taken up in 10% KOH (500 mL) and extracted with ether (3×200 mL). The combined extracts were washed with water, dried over $MgSO_4$, and stripped of solvent under reduced pressure to yield 35.75 g (32%) of 3-(3-chloropropyl)-1,3-benzoxazol-2(3H)-one, m.p. 62–64° C. $(M+H)^+$ 212.

Step B

Powdered KOH (37.60 g, 0.67 mol) was added to a slurry of 3-(3-chloropropyl)-1,3-benzoxazol-2(3H)-one (35.75 g, 0.169 mol) in n-butanol (450 mL) under $N_2$ gas and refluxed for 52 hours. The mixture was filtered and reduced to dryness under reduced pressure. The residue was taken up in $H_2O$ (500 mL) and extracted with ether (3×200 mL). The organic was washed with 10% HCl (2×200 mL), dried over $MgSO_4$, and stripped of solvent under reduced pressure. Purification by flash chromatography (50% EtOAc in hexanes) yielded 13.72 g (54%) of 2,3,4,5-tetrahydro-1,5-benzoxazepine as a powder, m.p. 50–51° C. $(M+H)^+$ 149.

Step C

To a stirred, cold slurry of 2,3,4,5-tetrahydro-1,5-benzoxazepine (13.72 g, 91.96 mmol) in 2N aqueous HCl (105 mL) was added dropwise a solution of $NaNO_2$ (7.30 g, 105.75 mmol) in $H_2O$ (16 mL) and stirred at room temperature for 2 hrs. The mixture was taken up in $H_2O$ (800 mL), extracted with ether (3×200 mL), dried over $MgSO_4$, and stripped of the solvent under reduced pressure to yield 15.59 g (95%) of 5-nitroso-2,3,4,5-tetrahydro-1,5-benzoxazepine as a tan powder. $(M+H)^+$ 178.

Step D

The title compound was prepared via Example 128 Steps A–C utilizing 5-nitroso-2,3,4,5-tetrahydro-1,5-benzoxazepine as the starting material to afford 36% of a powder, m.p. 94–98° C. $^1$H NMR ($CDCl_3$ 300 MHz) δ6.78 (m, 2H), 6.72 (d, 1H), 4.40 (dt, 1H), 3.78–3.82 (m, 1H), 3.30–3.41 (m, 3H), 3.18 (dt, 1H), 3.04 (dd, 1H), 2.82–2.94 (m, 2H), 2.42–2.61 (m, 2H), 2.08–2.14 (m, 2H), 1.90–2.01 (m, 1H), 1.74–1.82 (m, 1H) ppm. $(M+H)^+$ 230.

Example 173 cis-(6b,10a)-5-(2,4-dichlorophenyl)-1,2,6b,7,8,9,10,10a-octahydro-[1,4]oxazino[2,3,4-hi]pyrido[4,3-b]indole The title compound was prepared by following the procedures set forth in Example 128, Steps D–G utilizing the amine cis-(8a,12a)-2-bromo-6,7,8a,9,10,11,12,12a-octahydro-5H-[1,4]oxazepino[2,3,4,-hi]pyrrido[4,3-b]indole and the corresponding boronic acid. $^1$H NMR ($CDCl_3$ 300 MHz) δ7.39 (dd, 1H), 7.15–7.17 (m, 2H), 6.68 (dd, 1H), 6.64 (dd, 1H), 4.38–4.42 (m, 2H), 3.20–3.40 (m, 4H), 3.09–3.21 (m, 1H), 2.82–3.06 (m, 2H), 2.70–2.81 (m, 2H), 1.84–2.38 (m, 2H) ppm. $(M+H)^+$ 361.

Example 174 cis-(6b,10a)-5-(2-chloro-4-methoxyphenyl)-1,2,6b,7,8,9,10,10a-octahydro[1,4]oxazino[2,3,4-hi]pyrido[4,3-b]indole The title compound was prepared by following the procedures set forth in Example 128, Steps D–G utilizing cis-(8a,12a)-2-bromo-6,7,8a,9,10,11,12,12a-octahydro-5H-[1,4]oxazepino[2,3,4-hi]pyrido[4,3-b]indole and the corresponding boronic acid. $(M+H)^+$ 357.

Example 175

11-methyl-6,7,9,10,11,12-hexahydro-5H-pyrido[4,3-b][1,4]thiazepino[2,3,4-hi]indole The title compound was prepared via Example 128 Step B as modified by Example 168. $^1$H NMR ($CDCl_3$ 300 MHz) δ7.18 (dd, 1H), 7.01 (dd, 1H), 6.88 (m, 1H), 4.52 (t, 2H), 3.61 (S, 2H), 3.38 (t, 2H), 2.79–2.84 (m, 4H), 2.58 (s, 3H), 2.25–2.34 (m, 2H) ppm. $(M+H)^+$ 258.

Example 176 trans(8a,12a)-11-methyl-6,7,8a,9,10,11,12,12a-octahydro-5H-pyrido[4,3-b][1,4]thiazepino[2,3,4-hi]indole To a solution of 11-methyl-6,7,9,10,11,12-hexahydro-5H-pyrido[4,3-b][1,4]thiazepino[2,3,4-hi]indole (2.41 g, 9.33 mmol) in THF (30 mL) was added $BH_3$-THF (1.0 M, 20 mL) dropwise under $N_2$ gas. The mixture was then refluxed for 90 minutes. Once at room temperature, 6N HCl was added dropwise to destroy the excess borane then saturated with 6N HCl (35 mL) and glacial acetic acid (12 mL). The acidic mixture was refluxed for 1 hr then stirred overnight at room temperature. The solvent was stripped under reduced pressure and the residue was taken up in $H_2O$ (10 mL) and NaOH (80 mL) and extracted with EtOAc (3×50 mL). The combined extracts were dried over $MgSO_4$, stripped of solvent under reduced pressure, and purified by flash chromatography (9% methanol, 1% TEA in THF) to afford 1.42 g (58%) of the title compound as a colorless crystalline solid, m.p. 75–78° C. $^1$H NMR ($CDCl_3$ 300 MHz) δ6.98 (dd, 1H), 6.80 (dd, 1H), 6.64 (t, 1H), 3.76–3.78 (m, 1H), 3.58–3.62 (m, 1H), 3.40 (dd, 1H), 3.00–3.08 (m, 2H), 2.78–2.91 (m, 2H), 2.40 (m, s, 4H), 2.20–2.26 (m, 1H), 2.10–2.19 (m, 2H), 1.99–2.06 (m, 2H) ppm.

Example 177 trans(8a,12a)-6,7,8a,9,10,11,12,12a-octahydro-5H-pyrido[4,3-b][1,4]thiazepino[2,3,4-hi]indole Methylchloroformate (0.374 g, 3.96 mmol) in benzene (9 mL) was added to a solution of trans(8a,12a)-11-methyl-6,7,8a,9,10,11,12,12a-octahydro-5H-pyrido[4,3-b][1,4]thiazepino[2,3,4-hi]indole (1.03 g, 3.96 mmol) in benzene (20 mL) and refluxed for 3 hrs. The mixture was filtered while hot and the filtrate was stripped of solvent under reduced pressure. The residue was dissolved in n-butanol (20 mL) to which powdered KOH (3.0 g) was added and the mixture was refluxed for 1 hr. The solvent was stripped under reduced pressure and the residue was taken up in ice water (80 mL) and extracted with CHCl (3×20 mL). The combined extracts were dried over $MgSO_4$, and stripped of the solvent under reduced pressure. The title compound was collected over ether to afford 0.032 g (4% ) as a pure powder, m.p. 234° C. (decomposition). $^1$H NMR ($CDCl_3$ 300 MHz) δ7.00 (d, 1H), 6.78 (d, 1H), 6.74 (t, 1H), 3.80–3.98 (m, 2H), 3.57–3.64 (m, 2H), 2.94–3.09 (m, 4H), 2.62–2.76 (m, 1H), 2.20–2.36 (m, 2H), 1.98–2.14 (m, 1H), 1.30–1.42 (m, 2H) ppm. $(M+H)^+$ 246.

Example 178

4-(cis-(8a,12a)-3-chloro-6,7,9,10,12,12a-hexahydro-5H-pyrido[4,3-b][1,4]thiazepino[2,3,4-hi]indol-11(8aH)-yl)-1-(4-fluorophenyl)-1-butanone Cis-(8a,12a)-3-chloro-6,7,8a,9,10,11,12,12a-octahydro-5H-pyrido[4,3-b][1,4]thiazepino[2,3,4-hi]indole (90 mg, 0.32 mmol), 4-chloro-4'-fluorobutyrobenzophenone (161 mg, 0.8 mmol), KI (10 mg) and $K_2CO_3$ (132, 0.96 mmol) were suspended in dioxane (0.6 mL). The resulting mixture was heated at reflux for 24 h. After it was cooled to 23° C. the reaction mixture was partitioned between $H_2O$—$CHCl_3$ (1:1, 40 mL). The layers were separated and the aqueous layer was back-extracted with $CHCl_3$ (2×30 mL). The extracts were combined, dried ($MgSO_4$) and concentrated in vacuo. Purification of this residue by column silica gel chromatography eluting with $CHCl_3$ (100%), then 50:1 $CHCl_3$-MeOH provided the title compound as a semi-solid (90 mg, 25%). $^1$H NMR ($CD_3OD$, 300 MHz) δ8.99 (dd, 2H, J=8.8, 5.5 Hz), 7.12 (t, 2H, J=8.4 Hz), 6.72 (s, 2H), 4.03–3.91 (m, 1H), 3.77–3.62 (m, 1H), 3.27–3.00 (m, 1H), 3.09–2.81 (m, 7H), 2.78–2.69 (m, 3H), 2.42–2.32 (m, 2H), 2.30–2.19 (m, 1H), 2.16–1.76 (m, 4H) ppm.

Example 179

4-(cis-(8a,12a)-3-methyl-6,7,9,10,12,12a-hexahydro-5H-pyrido[4,3-b][1,4]thiazepino[2,3,4-hi]indol-11(8aH)-yl)-1-(4-fluorophenyl)-1-butanone The cis-(8a,12a)-3-methyl-6,7,8a,9,10,11,12,12a-octahydro-5H-pyrido[4,3-b][1,4]thiazepino[2,3,4-hi]indole (0.033 g, 0.09 mmol) was combined with 4-chloro-4'-fluorobutyrophenone (0.0176 g, 0.09 mmol) of KI (0.0179 g, 0.108 mmol), $K_2CO_3$ (0.062 g, 0.45 mmol) and 1,2-dioxane (0.7 mL). This mixture was refluxed for 4 days. Water was added and the layers were separated. The aqueous layer was extracted with $CHCl_3$ (3×15 mL) and the combined organics were washed with brine, water and dried ($Na_2SO_4$) and evaporated. The yellow oil was purified by preparatory silica gel TLC (70% EtOAc/Hexanes) affording the title compound (0.017 g, 45%) as a clear colorless oil. $^1$H NMR ($CD_3OD$, 300 MHz) δ8.02 (q, 2H, J=5.5, 3.7 Hz), 7.16 (t, 2H, J=2.9 Hz), 6.73 (d, 1H, J=7.7 Hz), 6.53 (d, 1H, J=8 Hz), 3.94–4.05 (m, 1H), 4.6–4.78 (m, 1H), 3.18–3.24 (m, 1H), 3.05–3.16 (m, 3H), 2.97 (t, 2H, J=7.3 Hz), 2.65–2.81 (m, 2H), 2.28–2.48 (m, 2H), 2.15 (s, 3H), 2.0–2.18 (m, 1H), 1.82–2.0 (m, 5H) ppm.

Example 180 cis-(8a,12a)-11-{3-[(4-fluorophenyl)sulfanyl]propyl}-6,7,8a,9,10,12,12a-octahydro-5H-pyrido[4,3-b][1,4]thiazepino[2,3,4-hi]indole To a solution of cis-(8a,12a)-6,7,8a,9,10,11,12,12a-octahydro-5H-pyrido[4,3-b][1,4]thiazepino[2,3,4-hi]indole (100 mg, 0.32 mmol) in 1,4-dioxane (2 mL) was added 3-chloro-1-(3-fluorophenylthio)propane (65.4 mg, 0.32 mmol), potassium iodide (64 mg, 0.38 mmol), and potassium carbonate (133 mg, 0.96 mmol). This mixture was heated at reflux with stirring for 60 hours. At which point 1 equivalent (32.4 mg, 0.32 mmol) of TEA was added and then heated at reflux for another 3 days, followed by thin layer chromatography (9:1 $CH_2Cl_2$:MeOH). After 132 hours water was added and organic layer was extracted with EtOAc (3×50 mL), and the extracts combined and concentrated to yield 170 mg of crude oil. Column chromatography (gradient: 1% and 10% MeOH in $CH_2Cl_2$) was used to purify cis-(8a,12a)-11-{3-[(4-fluorophenyl)sulfanyl]propyl}-6,7,8a,9,10,12,12a-octahydro-5H-pyrido[4,3-b][1,4]thiazepino[2,3,4-hi]indole (20 mg, 16%). $^1$H NMR ($CDCl_3$, 300 MHz): δ7.26–7.21 (m, 2H), 7.08–7.00 (m, 1H), 6.94 (dd, 1H, J=7.7 Hz, J=7.7 Hz), 6.87–6.81 (m, 2H), 6.5 (t, 1H, J=7.3 Hz), 3.86–3.76 (m, 1H), 3.59–3.49 (m, 1H), 3.27–3.25 (m, 1H), 3.17–2.91 (m, 4H), 2.75–2.72 (m, 1H), 2.61–2.58 (m, 1H), 2.45–2.39 (m, 2H), 2.31–2.2.2 (m, 1H), 2.18–2.02 (m, 3H), 1.99–1.82 (m, 3H), 1.50 (s-broad, 1H), 1.25 (s, 2H) ppm. Mass Spec (ESI): 415 (base M+H).

Example 181

4-(cis-(8a,12a)-6,7,9,10,12,12a-hexahydro-5H-pyrido[4,3-b][1,4]thiazepino[2,3,4-hi]indol-11(8aH)-yl)-1-(4-fluorophenyl)-1-butanol To 4-(cis-(8a,12a)-6,7,9,10,12,12a-hexahydro-5H-pyrido[4,3-b][1,4]thiazepino[2,3,4-hi]indol-11(8aH)-yl)-1-(4-fluorophenyl)-1-butanone (25 mg, 0.06 mmol) was added methanol (1 mL). The flask was cooled to 0° C. in an ice bath. Sodium cyanoborohydride was added (38 mg, 0.35 mmol) slowly portionwise. The reaction mixture was allowed to warm to room temperature over a 1 hour. Acetic acid was added (5 drops), then concentrated under reduced pressure to yield a residue. The residue was extracted with dichloromethane (1×50 mL), washed with sodium bicarbonate (1×25 mL) and brine (1×25 mL), then dried (sodium sulfate), and concentrated to an oil under reduced pressure. The hydrochloride salt was formed by taking oil up in minimal amount of chloroform, then adding hydrogen chloride in ether (1M) until precipitation. The solid was filtered off to give the title compound (21.1 mg, 81%). $^1$H NMR ($CD_3OD$, 300 MHz): δ7.40–7.37 (m, 2H), 7.06 (t, 2H, J=8.7 Hz), 6.95 (d, 2H, J=8.1 Hz), 6.66 (t, 1H, J=7.4 Hz), 4.8–4.7 (m, 1H), 3.83 (m, 1H), 3.1–3.53 (m, 3H), 3.45–3.30 (m, 2H), 3.22–3.18 (m, 3H), 3.18 (m, 1 H), 2.91 (m, 1 H), 2.59 (m, 1H), 2.37 (m, 1 H), 2.0–2.2 (m, 5H) ppm. Mass Spec (ESI): 399 (base M+H).

Example 182 cis-4-((6b,10a)-1,2,6b,9,10,10a-hexahydro[1,4]oxazino[2,3,4-hi]pyrido[4,3-b]indol-8(7H)-yl)-1-(4-fluorophenyl)-1-butanone The title compound was prepared from addition of 3-chloro-4'-fluorobutyrophenone to cis-(8a,12a)-6,7,8a,9,10,11,12,12a-octahydro-5H-[1,4]oxazepino[2,3,4-hi]pyrido[4,3-b]indole following General procedure A of Example 197. $^1$H NMR (300 MHz, $CDCl_3$) δ7.94–8.00 (m, 2H), 7.08–7.11 (m, 2H), 6.58–6.70 (m, 3H), 4.39–4.43 (m, 2H), 3.17–3.23 (m, 4H), 2.97–3.09 (m, 4H), 2.66–2.80 (m, 2H), 2.37–2.52 (m, 2H), 1.90–2.10 (m, 4H). MS-ESI: 381 $[MH]^+$ Example 183

1-(4-(fluorophenyl)-4-(6-(trifluoromethyl)-1,2,9,10,-tetrahydropyrido[4,3-b][1,4]thiazino[2,3,4-hi]indol-8(7H)-yl)-1-butanol 1-(4-Fluorophenyl)-4-(6-(trifluoromethyl)-1,2,9,10-tetrahydro[1,4]oxazino[2,3,4-hi]pyrido[4,3-b]indol-8(7H)-yl)-1-butanone (20 mg, 0.04 mmol) was dissolved in MeOH (0.8 mL) and cooled to 0° C. in an ice bath. Sodium borohydride (9.8 mg, 0.25 mmol) was added slowly and the reaction allowed to warm to room temperature, this was stirred for 2 hours. Acetic acid (4 drops) was added and the reaction mixture concentrated to give the title compound. $^1$H NMR ($CD_3OD$, 300 MHz): δ7.39–7.32 (m, 3H), 7.07–7.01 (m, 3H), 4.72 (m, 1H), 4.63–4.57 (m, 1H), 4.42–4.31 (m, 2H), 3.99–3.85 (m, 1H), 3.53 (t, 2H, J=6.4 Hz), 3.40–3.30 (m, 2H), 3.29–3.20 (m, 2H), 2.11–1.92 (m, 1H), 1.84–1.40 (m, 4H) ppm.

Example 184

8-{3-[2-(4-fluorophenyl)-1,3-dioxolan-2-yl]propyl}-6-(trifluoromethyl)-1,2,7,8,9,10-hexahydropyrido[4,3-b][1,4]thiazino[2,3,4-hi]indole 1-(4-Fluorophenyl)-4-(6-(trifluoromethyl)-1,2,9,10-tetrahydro[1,4]oxazino[2,3,4-hi]pyrido[4,3-b]indol-8(7H)-yl)-1-butanone (70 mg, 0.15 mmol) and ethylene glycol (10.4 mg, 0.17 mmol) were mixed together in anhydrous toluene (5 mL) in a round bottom flask equipped with a Dean-Stark apparatus and 3 Å molecular sieves. A few crystals of p-TsOH were added and reaction was heated to reflux for 5 hours. The reaction mixture was concentrated under reduced pressure and then extracted with dichloromethane (2×25 mL), washed with saturated sodium carbonate (1×15 mL) and brine (1×15 mL), dried (sodium sulfate) and concentrated. Product was purified by preparative thin layer chromatography on silica gel, and eluted with 10% MeOH in dichloromethane to give the title compound. $^1$H NMR ($CDCl_3$, 300 MHz): δ8.00–7.95 (m, 2H), 7.10–6.92 (m, 4H), 4.30–4.26 (m, 2H), 4.03–4.00 (m, 1H), 3.79–3.71 (m, 3H), 3.28–3.23 (m, 2H), 2.92–2.82 (m, 5H), 2.73 (t, 2H, J=7.1 Hz), 2.60 (t, 1H, J=7.5 Hz), 2.10–2.05 (m, 2H) ppm.

Example 185 cis-(6b,10a)-8-[4-(4-fluorophenyl)butyl]-6-(trifluoromethyl)-1,2,6b,7,8,9,10,10a-octahydropyrido[4,3-b][1,4]thiazino[2,3,4-hi]indole 1-(4-Fluorophenyl)-4-(6-(trifluoromethyl)-1,2,9,10-tetrahydro[1,4]oxazino[2,3,4-hi]pyrido[4,3-b]indol-8(7H)-yl)-1-butanone (34.5 mg, 0.07 mmol) was dissolved in trifluoroacetic acid (0.5 mL) and cooled to 0° C. in an ice bath. Sodium cyanoborohydride (14 mg, 0.22 mmol) was added slowly then stirred at 0° C. for 1 hour. 1N aqueous HCl (0.5 mL) was added and reaction heated at reflux for 0.5 hours. 50% Sodium hydroxide was added until pH>11 and extracted with dichloromethane (2×20 mL), dried (sodium sulfate) and concentrated to give the title compound. $^1$H NMR ($CD_3OD$, 300 MHz): δ7.18–7.15 (m, 2H), 7.12–6.91 (m, 3H), 6.81 (d, 1H, J=6.8 Hz), 3.69–3.65 (m, 1H), 3.56–3.28 (m,4H),3.12–3.10 (m, 1H), 2.93–2.87 (m, 1H), 2.71–2.56 (m, 2H), 2.35–2.22 (m, 1H), 2.21–2.01 (m, 1H), 1.95–1.78 (m, 1H), 1.75–1.47 (m, 4H), 1.37–1.13 (m,2H), 0.87–0.71 (m, 1H) ppm.

Example 186

4-(trans-(8a,12a)-6,7,9,10,12,12a-hexahydro-5H-pyrido[4,3-b][1,4]thiazepino[2,3,4-hi]indol-11(8aH)-yl)-1-(4-fluorophenyl)-1-butanone 4-(Cis-(8a,12a)-6,7,9,10,12,12a-hexahydro-5H-pyrido[4,3-b][1,4]thiazepino[2,3,4-hi]indol-11(8aH)-yl)-1-(4-fluorophenyl)-1-butanone (70 mg, 0.282 mmol), potassium iodide (28.2 mg, 0.17 mmol), potassium carbonate (84.5 mg, 0.61 mmol), and 4-chloro-4'fluorobutyrophenone (57 mg, 0.28 mmol) were combined in 1,4-dioxane (4 mL) and heated at reflux for 48 hours. The reaction was diluted with water (15 mL) and extracted with diethyl ether (3×25 mL), and concentrated to a residue. The residue was purified on a chiralcel OD column (8% 2-propanol in hexanes) to give (1 mg, 0.5%) of each enantiomer of the title compound. $^1$H NMR ($CD_3OD$, 300 MHz): δ8.07 (t, 2H, J=7.4 Hz), 7.19 (t, 2H, J=7.5 Hz), 6.84 (dd, 2H, J=8 Hz, J=7.7 Hz), 6.64 (t, 1H, J=7.7 Hz), 3.70–3.61 (m, 1H), 3.52–3.45 (m, 2H), 3.18–3.01 (m, 3H), 2.90–2.82 (m, 1H), 2.63–2.58 (m, 3H), 2.21–1.96 (m, 7H), 1.73–1.63 (m, 1H), 0.91–0.80 (m, 1H) ppm.

Example 187

4-(cis-(8a,12a)-2-methoxy-6,7,9,10,12,12a-hexahydro-5H-pyrido[4,3-b][1,4]thiazepino[2,3,4-hi]indol-11(8aH)-yl)-1-(4-fluorophenyl)-1-butanone Cis-(8a,12a)-2-methoxy-6,7,8a,9,10,11,12,12a-octahydro-5H-pyrido[4,3-b][1,4]thiazepino[2,3,4-hi]indole (43 mg, 0.16 mmol) was dissolved in 1.2 mL of MEK. KI (27 mg, 0.16 mmol) and $K_2CO_3$ (66 mg, 0.48 mmol), and 2a (112 mg, 0.56 mmol) were added. The suspension was refluxed for 48 hrs and then cooled to rt. The suspension was filtered and the residue was washed with $CH_2Cl_2$ (5ml). The solution was concentrated in vacuo. The residue was pruified by column chromatography (10% MeOH-$CH_2Cl_2$) to afford the title compound (67 mg, 95%) as a white amorphous solid. $^1$H NMR ($CDCl_3$, 300 MHz) δ7.95–8.02 (m, 2 H), 7.08–7.12 (m, 2H), 6.42 (dd, 2H, 2.2 Hz, 8.8 Hz), 3.60–3.80 (m, 5H), 3.40–3.58 (m, 2H), 3.15–3.25 (m, 1H), 2.90–3.10 (m, 4H), 2.70–2.88 (m, 2H), 2.50–2.68 (m, 1H), 2.39 (dt, 2H, 3.7 Hz, 7.4 Hz), 2.24 (dt, 1H, 4.1 Hz, 11.0 Hz), 1.70–2.10 (m, 5H) ppm. MS (ESI): 441.1 (M+H).

Example 188 cis-4-(6b,10a)-1,2,6b,9,10,10a-hexahydropyrido[4,3-b][1,4]thiazino[2,3,4-hi]indol-8(7H)-yl)-1-(4-fluorophenyl)-1-butanone The title compound (55.9 mg, 50%) was prepared by the method of Example 187 from cis-(6b,10a)-1,2,6b,7,8,9,10, 10a-octahydropyrido[4,3-b][1,4]thiazino[2,3,4-hi]indole (99 mg, 0.43 mmol), 4-chloro-4'-fluorobutyrophenone (112 mg, 0.56 mmol), KI (71 mg, 0.43 mmol), and $K_2CO_3$ (177 mg, 1.28 mmol) after chromatographic purification as a white amorphous solid. The enantiomers of the title compound were separated on a Chiracel OD column using isocratic 6% IPA/hexane as the eluent. $^1$H NMR ($CDCl_3$, 300 MHz) δ7.26–8.01 (m, 2 H), 7.12 (t, 2H, 8.4 Hz), 6.81 (t, 2H, 7.7 Hz), 6.19 (t, 1H, 7.6 Hz), 3.38–3.62 (m, 2H), 3.25–3.37 (m, 1H), 2.85–3.20 (m, 5H), 2.70–2.85 (m, 1H), 2.50–2.70 (m, 1H), 2.45–2.68 (m, 2H), 2.20 (dt, 1H, 3.0 Hz, 11.4 Hz), 1.70–2.10 (m, 5H) ppm. MS (ESI): 397.2 (base, M+H).

Example 192

4-(cis-(8a,12a)-6,7,9,10,12,12a-hexahydro-5H-pyrido[4,3-b][1,4]thiazepino[2,3,4-hi]indol-11(8aH)-yl)-1-(4-bromophenyl)-1-butanone The title compound (932 mg, 81%) was prepared by the method of Example 187 from cis-(8a,12a)-6,7,8a,9,10,11,12,12a-octahydro-5H-pyrido[4,3-b][1,4]thiazepino[2,3,4-hi]indole (594.00 mg, 2.44 mmol), 4-chloro-4'-fluorobutyrophenone (831.00 mg, 3.18 mmol), KI (406.00 mg, 2.44 mmol), and $K_2CO_3$ (638.00 mg, 7.33 mmol) after chromatographic purification as a white amorphous solid. $^1$H NMR ($CDCl_3$, 300 MHz) δ7.87–7.92 (m, 2 H), 7.64–7.68 (m, 2H), 6.94–6.99 (m, 2H), 6.67 (t, 1H, 7.4 Hz), 3.70–3.90 (m, 2H), 3.41–3.68 (m, 4H), 2.30–3.40 (m, 1H), 3.00–3.29 (m, 5H), 2.80–2.98 (m, 1H), 2.61–2.68 (t, 1H, 11.7 Hz), 1.90–2.50 (m, 5H) ppm. MS (CI, NH3): 473 (base, M+H).

Example 193

(8aS,12aR)-11-{3-[(4-fluorophenyl)sulfonyl]propyl}-6,7,8a,9,10,12,12a-octahydro-5H-pyrido[4,3-b][1,4]thiazepino[2,3,4-hi]indole The title compound (188.00 mg, 86%) was prepared by the method of Example 187 from (8aS,12aR)-6,7,8a-9,10,11,12,12a-octahydro-5H-pyrido[4,3-b][1,4]thiazepino[2,3,4-hi]indole (139.00 mg, 0.49 mmol), 3-(3-fluorophenylsulfonyl)propyl chloride (116.00 mg, 0.49 mmol), KI (48.00 mg, 0.29 mmol), and $K_2CO_3$ (135.00 mg, 0.98 mmol) after chromatographic purification as a white amorphous solid. $^1$H NMR ($CDCl_3$, 300 MHz) δ7.71 (bd, 1H, 6.6 Hz), 7.54–7.65 (m, 2H), 7.36–7.40 (m, 1H), 6.93 (dd, 1H, 1.1 Hz, 7.7 Hz), 6.62 (m, 1H), 3.73–3.76 (m, 1H), 3.45–3.52 (m, 1H), 3.18–3.30 (m, 3H), 2.90–3.18 (m, 3H), 2.57–2.62 (m, 1H), 2.41–2.55 (m, 1H), 2.17–2.41 (m, 3H), 1.95–2.17 (m, 2H), 1.65–1.94 (m, 5H) ppm. MS(ESI): 447.2 (base, M+H).

Example 194

4-(cis-(8a,12a)-6,7,9,10,12,12a-hexahydro-5H-pyrido[4,3-b][1,4]thiazepino[2,3,4-hi]indol-11(8aH)-yl)-1-(3',4'-dichloro[1,1'biphenyl]-4-yl)-1-butanone 4-(Cis-(8a,12a)-6,7,9,10,12,12a-hexahydro-5H-pyrido[4,3-b][1,4]thiazepino[2,3,4-hi]indol-11(8aH)-yl)-1-(4-bromophenyl)-1-butanone (123.9 mg, 0.26 mmol) was dissolved in DME (4 mL). 2M aqueous sodium carbonate (0.75 mL) was added. The 3,4-dichlorophenylboronic acid (100.4 mg, 0.53 mmol) was added, followed by $Pd_2(dba)_3$ (13.5 mg, 0.013 mmol). $PPh_3$ (13.8 mg, 0.053 mmol) was added. The reaction flask was degassed and kept under a nitrogen atmosphere. The suspension was refluxed for 18 hrs cooled to rt. The reaction was concentrated in vacuo, after which water (10 mL) and EtOAc (10 mL) were added. The layers were separated and the aqueous phase was extracted with EtOAc (2×10 mL). The combined, organic layers were washed with brine (2×10 mL), dried, and concentrated to afford a crude brown amorphous solid (187 mg). The residue was purified by column chromatography (20–40% EtOAc/Hexane) to afford the title compound (140.0 mg, 100%) as a white amorphous solid. $^1$H NMR ($CDCl_3$, 300 MHz) δ8.03–8.06 (m, 1 H), 7.43–7.71 (m, 6H), 6.93 (dd, 1H, 1.1 Hz), 6.84 (bd, 1H, 6.6 Hz), 6.58–6.63 (m, 1H), 3.70–3.90 (m, 1H), 3.50–3.60 (m, 1H), 3.15–3.30 (m, 1H), 2.90–3.18 (m, 4H), 2.50–2.80 (m, 2H), 2.20–2.50 (m, 3H), 1.50–2.20 (m, 8H) ppm. MS (ESI): 537.2 (base, M+H).

Example 195

1-(4-fluorophenyl)-4-(6-(trifluoromethyl)-1,2,9,10-tetrahydropyrido[4,3-b][1,4]thiazino[2,3,4-hi]indol-8(7H)-yl)-1-butanone 6-(Trifluoromethyl)-1,2,7,8,9,10-hexahydropyrido[4,3-b][1,4]thiazino[2,3,4-hi]indole (60 mg, 0.20 mmol) was dissolved in 1.2 mL of MEK. KI (33 mg, 0.20 mmol) and $K_2CO_3$ (52 mg, 0.60 mmol), and4-chloro-4'-fluorobutyrophenone (52.5 mg, 0.26 mmol) were added. The suspension was refluxed for 48 hrs and then cooled to rt. The suspension was filtered and the residue was washed with $CH_2Cl_2$ (5 ml). The solution was concentrated in vacuo. The residue was purified by column chromatography (10% MeOH-$CH_2Cl_2$) to afford the title compound (33 mg, 37%) as a white amorphous solid. $^1$H NMR ($CDCl_3$, 300 MHz) δ7.94–8.02 (m, 2 H), 7.29 (d, 1H, 8.4 Hz), 7.05–7.10 (m, 2H), 6.95 (d, 1H, 7.7 Hz), 4.27–4.30 (m, 2H), 3.81 (s, 2H), 3.25–3.29 (m, 2H), 3.07 (t, 2H, 7.0 Hz), 2.95 (m, 2H), 2.86 (m, 2H), 2.78 (t, 2H, 6.9 Hz), 2.06–2.19 (m, 2H) ppm. MS (ESI): 463.2 (base, M+H).

Example 197

4-((8aS,12aR)-6,7,9,10,12,12a-hexahydro-5H-pyrido[4,3-b][1,4]thiazepino[2,3,4-hi]indol-11(8aH)-yl)-1-(4-methylphenyl)-1-butanone General Procedure A To a suspension of (8aS,12aR)-6,7,8a,9,10,11,12,12a-octahydro-5H-pyrido[4,3-b][1,4]thiazepino[2,3,4-hi]indole 0.5 mmol) in 1,4-dioxane (3 mL) was added the corresponding chlorobutyrophenone (0.5–1.0 mmol), potassium iodine (100 mg) and potassium carbonate (300 mg). The reaction mixture was heated at reflux for 2 days. The solvent was removed under reduced pressure. The residue was treated with water (50 mL) and extracted with diethyl ether (3×50 mL). The ether extract was washed with brine (150 mL), dried over $MgSO_4$, filtered and concentrated to a residue. The residue was purified by flash column chromatography (Silica gel, $CH_2Cl_2$:$CH_3OH$9:1). The product was dissolved in ether (2 mL) and stirred at 0° C. for 10 minutes, added 1N HCl in ether (0.5 mL) at 0° C. The white crystalline solid was collected by filtration to give the title compound in 50–90% yield.

General Procedure B

To a suspension of (8aS,12aR)-6,7,8a,9,10,11,12,12a-octahydro-5H-pyrido[4,3-b][1,4]thiazepino[2,3,4-hi]indole 0.5 mmol) in 1,4-dioxane (3 mL) was added the corresponding alkyl halide (0.5–1.0 mmol), potassium iodine (100 mg) and triethylamine (1.5 mmol). The reaction mixture was heated at reflux for 2 days. The solvent was removed under reduced pressure. The residue was treated with water (50 mL) and extracted with diethyl ether (3×50 mL). The ether extract was washed with brine (150 mL), dried over $MgSO_4$, filtered and concentrated to a residue. The residue was purified by flash column chromatography (Silica gel, $CH_2Cl_2$:$CH_3OH$9:1). The product was dissolved in ether (2 mL) and stirred at 0° C. for 10 minutes, added 1N HCl in ether (0.5 mL) at 0° C. The white crystalline solid was collected by filtration to give the title compound in 50–90% yield.

The title compound was prepared from addition of 4-chloro-4'-methylbutyrophenone to (8aS,12aR)-6,7,8a,9,10,11,12,12a-octahydro-5H-pyrido[4,3-b][1,4]thiazepino[2,3,4-hi]indole following General procedure A above. $^1H$ NMR (300 MHz, $CDCl_3$) δ7.86 (d, J=8.0 Hz, 2H), 7.25 (d, J=8.0 Hz, 2H), 6.94 (d, J=7.7 Hz, 1H), 6.84 (d, J=7.3 Hz, 1H), 6.61 (dd, J=7.7 Hz, 7.3 Hz, 1H), 3.72–3.86 (m, 2H), 3.44–3.59 (m, 2H), 3.22–3.27 (m, 1H), 2.98–3.14 (m, 7H), 2.41 (s, 3H), 2.68–2.84 (m, 2H), 1.89–2.16 (m, 6H) ppm. MS-ESI: 407 $[MH]^+$ Example 198

4-((8aS,12aR)1-6,7,9,10,12,12a-hexahydro-5H-pyrido[4,3-b][1,4]thiazepino[2,3,4-hi]indol-11(8aH)-yl)-1-(4-fluorophenyl)-1-butanone The title compound was prepared from addition of 4-chloro-4'-fluorobutyrophenone to (8aS,12aR)-6,7,8a,9,10,11,12,12a-octahydro-5H-pyrido[4,3-b][1,4]thiazepino[2,3,4-hi]indole following General procedure A of Example 197. $^1H$ NMR (300 MHz, $CDCl_3$) δ7.97–8.02 (m, 2H), 7.10–7.16 (m, 2H), 6.95 (d, J=8.0 Hz, 1H), 6.85 (d, J=7.3 Hz, 1H), 6.62 (dd, J=7.2 Hz, 7.3 Hz, 1H), 3.76–3.86 (m, 1H), 3.44–3.59 (m, 2H), 3.24–3.30 (m, 1H), 2.90–3.14 (m, 4H) 2.68–2.84 (m, 4H), 2.24–2.58 (m, 4H), 1.99–2.11(m, 4H) ppm. MS-ESI: 411 $[MH]^+$ Example 199

4-((8aS,12aR)-6,7,9,10,12,12a-hexahydro-5H-pyrido[4,3-b][1,4]thiazepino[2,3,4-hi]indol-11(8aH)-yl)-1-(4-methoxyphenyl)-1-butanone The title compound was prepared from addition of 4-chloro-4'-methoxybutyrophenone to (8aS,12aR)-6,7,8a,9,10,11,12,12a-octahydro-5H-pyrido[4,3-b][1,4]thiazepino[2,3,4-hi]indole following General procedure A of Example 197. $^1H$ NMR (300 MHz, $CDCl_3$) δ7.93–7.99 (m, 2H), 6.88–6.98 (m, 3H), 6.84 (d, J=7.0 Hz, 1H), 6.61 (dd, J=8.0 Hz, 7.3 Hz, 1H), 3.87 (s, 3H), 3.70–3.90 (m, 2H), 3.48–3.58 (m, 1H), 3.22–3.27 (m, 1H), 2.90–2.99 (m, 4H), 2.62–2.80 (m, 4H), 2.27–2.42(m, 4H), 1.90–2.13 (m, 4H) ppm. MS-ESI: 423 $[MH]^+$ Example 200

3-((8aS,12aR)-6,7,9,10,12,12a-hexahydro-5H-pyrido[4,3-b][1,4]thiazepino[2,3,4-hi]indol-11(8aH)-yl)-1-(4-fluorophenyl)-1-propanone The title compound was prepared from addition of 3-chloro-4'-fluoropropiophenone to (8aS,12aR)-6,7,8a,9,10,11,12,12a-octahydro-5H-pyrido[4,3-b][1,4]thiazepino[2,3,4-hi]indole following General procedure A of Example 197. $^1H$ NMR (300 MHz, $CDCl_3$) δ7.98–8.03 (m, 2H), 7.12–7.18 (m, 2H), 6.88 (d, J=7.6 Hz, 1H), 6.87 (d, J=6.2 Hz, 1H), 6.65 (dd, J=7.7 Hz, 7.3 Hz, 1H), 3.79–3.88 (m, 1H), 3.7 (s, 2H), 3.50–3.60 (m, 1H), 3.25–3.38 (m, 3H), 2.89–3.01 (m, 7H), 1.90–2.15 (m, 4H). MS-ESI: 397 $[MH]^+$ Example 201

(8aS,12aR)-11-{3-[(4-fluorophenyl)sulfonyl]propyl}-6,7,8a,9,10,11,12,12a-octahydro-5H-pyrido[4,3-b][1,4]thiazepino[2,3,4-hi]indole The title compound was prepared from addition of 3-chloro-1-(4-fluorophenyl)sulfonyl)propane to (8aS,12aR)-6,7,8a,9,10,11,12,12a-octahydro-5H-pyrido[4,3-b][1,4]thiazepino[2,3,4-hi]indole following General procedure A of Example 197. $^1H$ NMR (300 MHz, $CDCl_3$) δ7.90–7.96 (m, 2H), 7.22–7.28 (m, 2H), 9.38 (d, J=7.7 Hz, 1H), 6.82 (d, J=6.6 Hz, 1H), 6.61 (dd, J=7.7 Hz, 7.3 Hz, 1H), 3.72–3.81 (m, 1H), 3.45–3.55 (m, 1H), 3.15–3.29 (m, 4H), 3.02–3.12 (m, 2H), 2.92–2.99 (m, 1H), 2.57–2.62 (m, 1H), 2.46–2.09 (m, 2H), 2.20–2.37 (m, 2H), 2.18–2.27 (m, 1H), 1.94–2.09 (m, 2H), 1.78–1.92 (m, 4H) ppm. MS (CI, $NH_3$) m/e 446 (base, $M+H^+$).

Example 202

(8aS,12aR)-11-{3-[(4-fluorophenyl)sulfinyl]propyl}-6,7,8a,9,10,11,12,12a-octahydro-5H-pyrido[4,3-b][1,4]thiazepino[2,3,4-hi]indole The title compound was prepared from addition of 3-chloro-1-[(4-fluorophenyl)sulfinyl]propane to (8aS,12aR)-6,7,8a,9,10,11,12,12a-octahydro-5H-pyrido[4,3-b][1,4]thiazepino[2,3,4-hi]indole following General procedure A of Example 197. $^1H$ NMR (300 MHz, $CD_3OD$) δ7.65–7.80 (m, 2H), 7.27–7.31 (m, 2H), 6.95 (d, J=8.1 Hz, 2H), 6.63 (dd, J=8.1 Hz, 7.7 Hz, 1H), 3.63–3.93 (m, 1H), 3.38–3.62 (m, 4H), 3.10–3.25 (m, 4H), 3.26–3.36 (m, 2H), 2.92–3.09 (m, 3H), 2.50–2.62 (m, 1H), 2.30–2.42 (m, 1H), 1.94–2.28 (m, 4H) ppm. MS (CI, $NH_3$) m/e 430 (base, 287).

Example 203

(8aS,12aR)-11-[3-(4-fluorophenoxy)propyl]-6,7,8a,9,10,12,12a-octahydro-5H-pyrido[4,3-b][1,4]thiazepino[2,3,4-hi]indole The title compound was prepared from addition of 3-chloro-1-(4-fluorophenoxy)propane (8aS,12aR)-6,7,8a,9,10,11,12,12a-octahydro-5H-pyrido[4,3-b][1,4]thiazepino[2,3,4-hi]indole following General procedure A of Example 197. $^1H$ NMR (300 MHz, $CDCl_3$) δ6.91–7.00 (m, 3H), 6.79–6.87 (m, 3H), 6.62 (dd, J=7.7 Hz, 7.3 Hz, 1H), 3.97 (t, J=6.2, 2H), 3.70–3.87 (m, 1H), 3.50–3.60 (m, 1H), 3.18–3.31 (m, 2H), 2.90–3.12 (m, 2H), 2.70–2.80 (m, 2H), 2.40–2.62 (m, 2H), 2.22–2.38 (m, 1H), 1.90–2.11 (m, 7H) ppm. MS-ESI: 399 $[MH]^+$ Example 204

(8aS,12aR)-11-(3-phenoxypropyl)-6,7,8a,9,10,12,12a-octahydro-5H-pyrido[4,3-b][1,4]thiazepino[2,3,4-hi]indole The title compound was prepared from addition of 3-chloro-1-phenoxypropane (8aS,12aR)-6,7,8a,9,10,11,12,12a-octahydro-5H-pyrido[4,3-b][1,4]thiazepino[2,3,4-hi]indole following General procedure B of Example 197. $^1H$ NMR (300 MHz, $CDCl_3$) δ7.25–7.30 (m, 2H), 6.85–6.97 (m, 5H), 6.62 (dd, J=7.7 Hz, 7.3 Hz, 1H), 4.02 (t, J=6.2 Hz, 2H), 3.78–3.88 (m, 1H), 3.50–3.60 (m, 1H), 3.17–3.31 (m, 2H), 2.90–3.10 (m, 2H), 2.72–2.86 (m, 2H), 2.51–2.58 (m, 2H), 2.30–2.37 (m, 1H), 1.92–2.15 (m, 7H) ppm. MS (CI, $NH_3$) m/e 380 (base, $M+H^+$).

Example 205

(8aS,12aR)-11-{3-[(4-fluorophenyl)sulfonyl]propyl}-6,7,8a,9,10,12,12a-octahydro-5H-pyrido[4,3-b][1,4]thiazepino[2,3,4-hi]indole The title compound was prepared from addition of 3-chloro-1-(4-fluorophenylthio)propane to (8aS,12aR)-6,7, 8a,9,10,11,12,12a-octahydro-5H-pyrido[4,3-b][1,4]thiazepino[2,3,4-hi]indole following General procedure B of Example 197. $^1$H NMR (300 MHz, $CDCl_3$) δ7.31–7.36 (m, 2H), 6.93–7.02 (m, 4H), 6.84 (d, J=7.3 Hz, 1H), 6.2 (dd, J=7.3 Hz, 7.3 Hz, 1H), 3.76–3.84 (m, 1H), 3.48–3.59 (m, 1H), 3.24–3.28 (m, 2H), 2.88–3.17 (m, 6H), 2.60–2.74 (m, 2H), 2.25–2.45 (m, 2H), 2.00–2.11 (m, 2H), 1.77–1.93 (m, 4H) ppm. MS (CI, $NH_3$) m/e 414 (base, M+H$^+$).

Example 206

N-[3-((8aS,12aR)-6,7,9,10,12,12a-hexahydro-5H-pyrido[4,3-b][1,4]thiazepino[2,3,4-hi]indol-11(8aH)-yl)propyl]-4-fluoroaniline The title compound was prepared from addition of 3-chloropropyl-4-fluorophenylamine to (8aS,12aR)-6,7,8a,9,10,11,12,12a-octahydro-5H-pyrido[4,3-b][1,4]thiazepino[2,3,4-hi]indole following General procedure B of Example 197. $^1$H NMR (300 MHz, $CDCl_3$) δ6.97 (d, J=8.1 Hz, 1H), 6.93–7.02 (m, 3H), 6.64 (dd, J=7.7 Hz, 7.3 Hz, 1H), 6.47–6.52 (m, 2H), 3.75–3.85 (m, 1H), 3.46–3.56 (m, 1H), 3.25–3.35 (m, 2H), 2.91–3.20 (m, 6H), 2.60–2.74 (m, 2H), 1.91–2.17 (m, 8H) ppm. MS (CI, $NH_3$) m/e 397 (base, M+H$^+$).

Example 207

N-[3-((8aS,12aR)-6,7,9,10,12,12a-hexahydro-5H-pyrido[4,3-b][1,4]thiazepino[2,3,4-hi]indol-11(8aH)-yl)propyl]-4-fluoro-N-methylaniline The title compound was prepared from addition of 3-chloropropyl-4-fluorophenylmethylamine to (8aS,12aR)-6,7,8a,9,10,11,12,12a-octahydro-5H-pyrido[4,3-b][1,4]thiazepino[2,3,4-hi]indole following General procedure B of Example 97. $^1$H NMR (300 MHz, $CDCl_3$) δ6.84–6.99 (m, 4H), 6.59–6.67 (m, 3H), 3.77–3.90 (m, 1H), 3.47–3.59 (m, 1H), 3.19–3.33 (m, 4H), 2.67–3.09 (m, 4H), 2.87 (s, 3H), 2.33–2.37 (m, 3H), 1.76–2.17 (m, 7H) ppm. MS (CI, $NH_3$) m/e 411 (base, M+H$^+$).

Example 208

4-((8aS,12aR)-6,7,9,10,12,12a-hexahydro-5H-pyrido[4,3-b][1,4]thiazepino[2,3,4-hi]indol-11(8aH)-yl)-1-(4-pyridinyl)-1-butanone The title compound was prepared from addition of 4-chloro-1-(4-pyridyl)butan-1-one to (8aS,12aR)-6,7,8a,9,10,11,12,12a-octahydro-5H-pyrido[4,3-b][1,4]thiazepino[2,3,4-hi]indole following General procedure A of Example 197. $^1$H NMR (300 MHz, $CDCl_3$) δ8.79 (dd, J=5.9 Hz, 1.5 Hz, 2H), 7.73 (dd, J=6.2 Hz, 1.8 Hz, 2H), 6.93 (d, J=7.7 Hz, 1H), 6.82 (d, J=7.4 Hz, 1H), 6.59 (dd, J=7.7 Hz, 7.4 Hz, 1H), 3.64–3.82 (m, 4H), 3.46–3.56 (m, 2H), 3.19–3.24 (m, 2H), 2.88–3.06 (m, 4H), 2.60–2.75 (m, 2H), 2.28–2.42 (m, 2H), 1.87–2.09 (m, 4H) ppm. MS (CI, $NH_3$) m/e 393 (base, M+H$^+$).

Example 209

4-((8aS,12aR)-6,7,9,10,12,12a-hexahydro-5H-pyrido[4,3-b][1,4]thiazepino[2,3,4-hi]indol-11(8aH)-yl)-1-(3-pyridinyl)-1-butanone The title compound was prepared from addition of 4-chloro-1-(3-pyridyl)butan-1-one to (8aS,12aR)-6,7,8a,9,10,11,12,12a-octahydro-5H-pyrido[4,3-b][1,4]thiazepino[2,3,4-hi]indole following General procedure A of Example 197. $^1$H NMR (300 MHz, $CDCl_3$) δ9.18 (d, J=2.2 Hz, 1H), 8.76 (dd, J=4.7 Hz, 1.8 Hz, 1H), 8.23 (dt, J=8.1 Hz, 1.8 Hz, 1H), 7.40 (dd, J=8.1 Hz, 4.8 Hz, 1H), 6.91–6.95 (m, 1H), 6.82–6.87 (m, 1H), 6.57–6.63 (m, 1H), 3.49–3.83 (m, 4H), 3.06–3.25 (m, 2H), 3.01 (t, J=7.0 Hz, 2H), 2.52–2.94 (m, 4H), 2.26–2.39 (m, 2H), 1.83–2.10 (m, 6H) ppm. MS (CI, $NH_3$) m/e 393 (base, M+H$^+$).

Example 210 cis-4-((6b,10a)-3-methyl-2,3,6b,9,10,10a-hexahydro-1H-pyrido[3',4':4,5]pyrrolo[1,2,3-de]quinoxalin-8(7H)-yl)-1-(4-pyridinyl)-1-butanone The title compound was prepared from addition of the of 4-chloro-1-(4-pyridyl)butan-1-one to cis-(6b,10a)-3-methyl-2,3,6b,7,8,9,10,10a-octahydro-1H-pyrido[3',4':4,5]pyrrolo[1,2,3-de quinoxaline following General procedure A of Example 197. $^1$H NMR (300 MHz, $CDCl_3$) δ8.79 (dd, J=4.4 Hz, 1.8 Hz, 2H), 7.74 (dd, J=4.4 Hz, 1.4 Hz, 2H), 6.64 (dd, J=7.4 Hz, 7.6 Hz, 1H), 6.49 (d, J=6.9 Hz, 1H), 6.39 (d, J=7.7 Hz, 1H), 3.54–3.62 (m, 1H), 3.23–3.31 (m, 2H), 3.13–3.17 (m, 1H), 2.95–3.03 (m, 2H), 2.85 (s, 3H), 2.76–2.84 (m, 2H), 2.57–2.60 (m, 1H), 2.31–2.41 (m, 1H), 2.22 (td, J=11.7 Hz, 2.9 Hz, 1H), 1.92–2.02 (m, 3H), 1.83–1.88 (m, 1H), 1.66–1.76 (m, 2H) ppm. MS (CI, $NH_3$) m/e 376 (base, M+H$^+$).

The title compound was separated into the corresponding enantiomers by chiral chromatographic separation. (Chiralpak AD column, methanol/ethanol:50/50): $^1$H NMR (300 MHz, $CDCl_3$) δ8.79 (dd, J=4.4 Hz, 1.8 Hz, 2H), 7.74 (dd, J=4.4 Hz, 1.4 Hz, 2H), 6.64 (dd, J=7.4 Hz, 7.6 Hz, 1),6.49 (d, J=6.9 Hz, 1H), 6.39 (d, J=7.7 Hz, 1H), 3.54–3.62 (m, 1H), 3.23–3.31 (m, 2H), 3.13–3.17 (m, 1H), 2.95–3.03 (m, 2H), 2.85 (s, 3H), 2.76–2.84 (m, 2H), 2.57–2.60 (m, 1H), 2.31–2.41 (m, 1H), 2.22 (td, J=11.7 Hz, 2.9 Hz, 1H), 1.92–2.02 (m, 3H),1.83–1.88 (m, 1H), 1.66–1.76 (m, 2H) ppm. MS (CI, $NH_3$) m/e 376 (base, M+H$^+$).

Example 211 cis-(6b,10a)-2,3,6b,7,8,9,10,10a-octahydro-1H-pyrido[3',4':4,5]pyrrolo[1,2,3-de]quinoxaline Step A The procedure described in Example 4, Steps E through G, was utilized to prepare ethyl 2-oxo-2,3,9,10-tetrahydro-1H-pyrido[3',4':4,5]pyrrolo[1,2,3-de]quinoxaline-8(7H)-carboxylate from the corresponding amine, 1,3,4-trihydroquinoxalin-2-one, and ethyl 4-oxopiperidinecarboxylate. This indole (5.74 g, 19.2 mmol) was dissolved in TFA (100 mL). The reaction was cooled to 0° C. $NaCNBH_3$ (3.96 g, 63.0 mmol) was added in small portions over 30 min, keeping the temperature less than 5° C. The reaction was stirred at r.t. for 4 hr. Ice was added to the reaction flask, and the reaction was basified with 50% NaOH until pH=12. Water (80 mL) was added to dissolved the precipitate. The reaction was extracted with $CHCl_3$ (3×200 mL). The combined organic layers were washed with brine, dried, and concentrated to afford cis-ethyl(6b,10a)-2-oxo-2,3,6b,9,10,10a-hexahydro-1H-pyrido[3',4':4,5]pyrrolo[1,2,3-de]quinoxaline-8(7H)-carboxylate (4.41 g, 77%). $^1$H NMR ($CDCl_3$, 300 MHz) δ8.45 (bs, 1H), 6.86 (d, J=7.4 Hz, 1H), 6.74 (dd, J=7.7 Hz, 7.7 Hz, 1H), 6.63 (d, J=7.3 Hz, 1H), 4.15 (q, J=7.0 Hz, 2H), 3.89–3.993 (m, 2H), 3.41–3.47 (m, 2H), 3.33–3.41 (m, 2H), 3.12–3.31 (m, 1H), 2.69–2.75 (m, 2H), 1.90–1.92 (m, 2H), 1.28 (t, J=7.3 Hz, 3H) ppm. MS-APcI: 302 [MH]$^+$ Step B To cis-ethyl(6b,10a)-2-oxo-2,3,6b,9,10,10a-hexahydro-1H-pyrido[3',4':4,5]pyrrolo[1,2,3-de]quinoxaline-8(7H)-carboxylate (4.41 g, 14.6 mmol) was added 1M $BH_3$ THF complex solution (36.6 mL). The reaction was heated under reflux for 5 hr. After the reaction cooled down to r.t, 6N HCl (40 mL) was added dropwise with chill. The reaction solution was heated under reflux for 30 minutes. After cooled down to r.t., 1N NaOH was added to adjust the pH to 8. The reaction was extracted with $CH_2Cl_2$ (2×200 mL). The combined organic layers were washed with brine, dried over $MgSO_4$, and concentrated to afford cis-ethyl (6b,10a)-2,3,6b,9,10,10a-hexahydro-1H-pyrido[3',4':4,5]pyrrolo[1,2,3-de]quinoxaline-8(7H)-carboxylate (4.10 g, 98%). The product was used in next step without further purification. MS-APcI: 288 $[MH]^+$ To cis-ethyl(6b,10a)-2,3,6b,9,10,10a-hexahydro-1H-pyrido[3',4':4,5]pyrrolo[1,2,3-de]quinoxaline-8(7H)-carboxylate (4.10 g, 14.3 mmol) was added n-butanol (18.0 mL) and KOH powder (3.0 g). The reaction was heated at 119° C. in a sealed tube for 18 hr. The solvent was removed under reduced pressure. To the residue was added water (30 mL) extracted with $CH_2Cl_2$ (3×50 mL). The combined organic layers were washed with brine, dried over $MgSO_4$, and concentrated to afford the title compound as a pale yellow oil (2.70 g, 78%). MS-ESI: 216 $[MH]^+$ Example 212 cis-4-((6b,10a)-2,3,6b,9,10,10a-hexahydro-1H-pyrido[3',4':4,5 pyrrolo[1,2,3-de]quinoxalin-8(7H)-yl)-1-(4-fluorophenyl)-1-butanone Step A To cis-(6b,10a)-2,3,6b,7,8,9,10,10a-octahydro-1H-pyrido[3',4':4,5]pyrrolo[1,2,3-de]quinoxaline (2.70 g, 10.8 mmol) was added 1N NaOH (40.0 mL) and dioxane (40.0 mL). $Boc_2O$ was added in small portions in 30 minute at 0° C. The reaction was stirred at r.t. for 18 hr. The reaction was extracted with $CH_2Cl_2$ (3×150 mL). The combined organic layers were washed with brine, dried over $MgSO_4$, and concentrated to afford a residue which was purified by flash column chromatography (Hexane/Ethyl acetate: 50/50) to afford cis-tert-butyl-2,3,6b,7,8,9,10,10a-octahydro-1H-pyrido[3',4':4,5]pyrrolo[1,2,3-de]-quinoxalin-8-yl-carboxylate. The racemate could be separated by Chiralcel OD column (5 cm×50 cm, 20u; IPA/Hexane: 8%) to afford the corresponding enantiomers.

Step B

To either of the enantiomers of cis-tert-butyl-2,3,6b,7,8,9,10,10a-octahydro-1H-pyrido[3',4':4,5]pyrrolo[1,2,3-de]-quinoxalin-8-yl-carboxylate (790 mg, 2.25 mmol) were added 20% TFA/$CH_2Cl_2$ (5 mL), stirred at r.t. overnight. The solution was concentrated to a residue to afford the TFA salt in 99% yield. To this indoline TFA salt (493.5 mg, 1.5 mmol) was added triethylamine (0.4 mL), $K_2CO_3$ (300 mg) KI (100 mg) and 1,4-dioxane (6 mL). The reaction was heated at 103° C. in a sealed tube for 24 hr. The solvent was removed under reduced pressure. To the residue was added water (30 mL) extracted with $CH_2Cl_2$ (3×50 mL). The combined organic layers were washed with brine, dried over $MgSO_4$, and concentrated to a residue. The residue was purified by flash column chromatography to afford the title compound (280 mg, 53% yield). $^1H$ NMR ($CDCl_3$, 300 MHz) δ7.97–8.02 (m, 2H), 7.09–7.15 (m, 2H), 6.51–6.61 (m, 2H), 6.38 (dd, J=7.3 Hz, J=1.4 Hz, 1H), 3.64–3.72 (m, 2H), 3.26–3.49 (m, 2H), 3.13–3.24 (m, 2H), 2.99–3.04 (m, 2H), 2.91–2.97 (m, 1H), 2.61–2.79 (m, 2H), 2.43–2.53 (m, 2H), 2.34–2.43 (m, 1H), 1.95–2.13 (m, 4H) ppm. MS-ESI: 380 $[MH]^+$ Example 213 cis-4-((6b,10a)-5-methyl-1,2,6b,9,10,10a-hexahydropyrido[4,3-b][1,4]thiazino[2,3,4-hi]indol-8(7H)-yl)-1-(4-fluorophenyl)-1-butanone The title compound was prepared from addition of the 4-chloro-4'-fluorobutyrophenone to cis-(6b,10a)-5-methyl-1,2,6b,7,8,9,10,10a-octahydropyrido[4,3-b][1,4]thiazino[2,3,4-hi]indole following General procedure A of Example 197. $^1H$ NMR (300 MHz, $CDCl_3$) δ7.90–8.03 (m, 2H), 6.81–7.16 (m, 4H), 3.75–3.80 (m, 1H), 3.39–3.52 (m, 2H), 3.18–3.24 (m, 2H), 3.06–3.13 (m, 2H), 2.84–2.94 (m, 1H), 1.92–2.52 (m, 10H), 2.24 (s, 3H) ppm. MS-ESI: 411 $[MH]^+$ Example 214

(8aS,12aR)-11-[3-(6-fluoro-1,2-benzisoxazol-3-yl) propyl]-6,7,8a,9,10,12,12a-octahydro-5H-pyrido[4,3-b][1,4]thiazepino[2,3,4-hi]indole The title compound was prepared from addition of 3-(3-chloropropyl)-6-fluorobenzo[d]isoxazole to (8aS,12aR)-6,7,8a-9,10,11,12,12a-octahydro-5H-pyrido[4,3b-][1,4]thiazepino[2,3,4-hi]indole benzothiazepine following General procedure A of Example 197. $^1H$ NMR (300 MHz, $CDCl_3$) δ7.66 (dd, J=8.4 Hz, 5.1 Hz, 1H), 7.23 (dd, J=8.5 Hz, 1.8 Hz, 1H), 7.06 (ddd, J=8.7 Hz, 8.8 Hz, 2.2 Hz, 1H), 6.93 (dd, J=7.7 Hz, 0.9 Hz, 1H), 6.84 (d, J=6.6 Hz, 1H), 6.61 (dd, J=7.7 Hz, 7.3 Hz, 1H), 3.70–3.83 (m, 1H), 3.48–3.56 (m, 1H), 3.23–3.27 (m, 1H), 2.91–3.12 (m, 5H), 2.71–2.77 (m, 1H), 2.61–2.65 (m, 1H), 2.39–2.46 (m, 2H), 2.24–2.28 (m, 1H), 1.90–2.11 (m, 4H), 1.84–1.88 (m, 3H) ppm. MS-ESI: 424 $[MH]^+$ Example 215

(8aS,12aR)-11-[3-(1,2-benzisoxazol-3-yl)propyl]-6,7,8a,9,10,12,12a-octahydro-5H-pyrido[4,3-b][1,4] thiazepino[2,3,4-hi]indole The title compound was prepared from addition of 3-(3-chloropropyl)benzo[d]isoxazole to (8aS,12aR)-6,7,8a-9,10,11,12,12a-octahydro-5H-pyrido[4,3b-][1,4]thiazepino[2,3,4-hi]indole following General procedure A of Example 197. $^1H$ NMR (300 MHz, $CDCl_3$) δ7.67 (dd, J=7.7 Hz, 1.1 Hz, 1H), 7.53–7.55 (m, 2H), 7.27–7.33 (m, 1H), 6.94 (dd, J=7.7 Hz, 1.1 Hz, 1H), 6.84 (d, J=6.6 Hz, 1H), 6.61 (dd, J=7.6 Hz, 7.4 Hz, 1H), 3.76–3.84 (m, 1H), 3.48–3.58 (m, 1H), 3.23–3.27 (m, 1H), 2.91–3.17 (m, 5H), 2.67–2.82 (m, 2H), 2.45–2.51 (m, 2H), 2.24–2.38 (m, 1H), 1.89–2.14 (m, 7H) ppm. MS (CI, $NH_3$) m/e 405 (base, $M+H^+$).

Example 217 cis-(6b,10a)-8-[3-(6-fluoro-1,2-benzisoxazol-3-yl) propyl]-3-methyl-2,3,6b,7,8,9,10,10a-octahydro-1H-pyrido[3',4':4,5]pyrrolo[1,2,3-de]quinoxaline Step A To a cold boron trifluoride etherate (280 mmol) solution was added 3-Fluorophenol or phenol (89 mmol) and 4-chlorobutyryl chloride (178 mmol). The resulting solution was stirred at 130° C. for 18 hours. The reaction mixture was cooled and poured into ice water (100 mL). After stirring for 10 minutes, the water mixture was extracted with ether (3×100 mL). The ether layer was washed with brine (100 mL), dried over $MgSO_4$, filtered and concentrated to a residue to afford 4-chloro-1-(4-fluoro-2-hydroxyphenyl) butan-1-one and 4-chloro-1-(2-hydroxyphenyl)butan-1-one in 52%–67% yield, which was used in the following step without further purification.

Step B

To pyridine (25 mL) was added the corresponding ketone from Step A (46.5 mmol) and hydroxylamine hydrochloride (53.5 mmol). The resultant mixture was stirred at ambient temperature overnight and then poured into dilute HCl (100 mL). The mixture was stirred for 5 minutes and extracted with ether (3×50 mL). The ether layer is dried over $MgSO_4$, filtered and concentrated to a residue to afford the corresponding oximes in 99% yield, which were used in the following step without further purification.

Step C

To acetic anhydride (10 mL) was added the corresponding oximes from Step B (40.0 mmol). The reaction mixture was heated at 60° C. for 2 hours, then poured into ether (10 mL). The mixture was washed with sat. $NaHCO_3$ solution (4×10 mL), then with brine (10 mL). The organic layer was separated, dried over $MgSO_4$, filtered and concentrated to afford the bis-acylated derivatives in 61%–75% yield.

Step D

To the corresponding bis-acylated derivatives from Step C (5.2 mmol) in ethanol (4 mL) was added KOH (14.4 mmol). The reaction mixture was refluxed for 2 hours, cooled down to rt, added ethyl acetate (10 mL), washed with brine (10 mL), dried over $MgSO_4$, filtered and concentrated to a residue. The residue was purified by silica gel flash column chromatography (Ethyl acetate/Hexane: 3:7) to afford 3-(3-chloropropyl)-6-fluorobenzo[d]isoxazole and 3-(3-chloropropyl)benzo[d]isoxazole in 32% yield.

Step E

The title compound was prepared from addition of 3-(3-Chloropropyl)-6-fluorobenzo[d]isoxaole from Step D to cis-(6b,10a)-3-methyl-2,3,6b,7,8,9,10,10a-octahydro-1H-pyrido[3',4':4,5]pyrrolo[1,2,3-de]quinoxaline following General procedure A, Example 97. $^1$H NMR (300 MHz, $CDCl_3$) δ7.63 (dd, J=8.8 Hz, 4.7 Hz, 1H), 7.20–7.24 (m, 1H), 7.03–7.10 (m, 1H), 6.65 (dd, J=7.7 Hz, 7.7 Hz, 1H), 6.50 (d, J=7.3 Hz, 1H), 6.41 (d, J=7.3 Hz), 3.73–3.77 (m, 1H), 3.55–3.62 (m, 1H), 3.21–3.32 (m, 3H), 2.91–3.10 (m, 3H), 2.86 (s, 3H), 2.75–2.82 (m, 2H), 2.54–2.63 (m, 1H), 2.41–2.48 (m, 1H), 1.95–2.11 (m, 6H) ppm. MS (CI, $NH_3$) m/e 407 (base, $M+H^+$).

Example 218 cis-(6b,10a)-8-[3-(1,2-benzisoxazol-3-yl)propyl]-3-methyl-2,3,6b,7,8,9,10,10a-octahydro-1H-pyrido[3',4':4,5]pyrrolo[1,2,3-de]quinoxaline The title compound was prepared from addition of 3-(3-chloropropyl)benzo[d]isoxazole from Step D Example 22 cis-(6b,10a)-3-methyl-2,3,6b,7,8,9,10,10a-octahydro-1H-pyrido[3',4':4,5]pyrrolo[1,2,3-de]quinoxaline following the General procedure A of Example 197. $^1$H NMR (300 MHz, $CDCl_3$) δ7.59–7.62 (m, 1H), 7.46–7.50 (m, 2H), 7.20–7.25 (m, 1H), 6.57 (dd, J=7.7 Hz, 7.3 Hz, 1H), 6.43 (d, J=6.9 Hz, 1H), 6.33 (d, J=7.3 Hz), 3.48–3.52 (m, 1H), 3.06–3.25 (m, 4H), 2.94–2.99 (m, 2H), 2.70–2.89 (m, 4H), 2.79 (s, 3H), 2.20–2.65 (m, 3H), 1.92–2.07 (m, 4H) ppm. MS (CI, $NH_3$) m/e 389 (base, $M+H^+$).

Example 219 ethyl 4-((8aS,12aR)-6,7,9,10,12,12a-hexahydro-5H-pyrido[4,3-b](1,4]thiazepino(2,3,4-hi]indol-11(8aH)-yl)butanoate General Procedure To a suspension of to (8aS,12aR)-6,7,8a,9,10,11,12,12a-octahydro-5H-pyrido[4,3-b][1,4]thiazepino[2,3,4-hi]indole (3 mmol) in 1,4-dioxane (18 mL) was added the corresponding alkyl halide (3.3 mmol), potassium iodine (100 mg) and potassium carbonate (900 mg), the reaction mixture was heated at reflux for 2 days. The solvent was removed under reduced pressure. The residue was treated with water (50 mL) and extracted with diethyl ether (3×50 mL). The ether extract was washed with brine (150 mL), dried over $MgSO_4$, filtered and concentrated to a residue. The residue was purified by flash column chromatography (Silica gel, $CH_2Cl_2$:$CH_3OH$9:1) to give the title compound in 47%–64% yields.

The title compound was prepared from addition of ethyl 4-chlorobutanoate to (8aS,12aR)-6,7,8a,9,10,11,12,12a-octahydro-5H-pyrido[4,3-b][1,4]thiazepino[2,3,4-hi]indole following the General procedure above. $^1$H NMR (300 MHz, $CDCl_3$) δ6.94 (bd, J=7.7 Hz, 1H), 6.86 (bd, J=6.9 Hz, 1H), 6.62 (dd, J=7.4 Hz, 7.3 Hz, 1H), 4.08–4.15 (m, 2H), 3.77–3.86 (m, 1H), 3.47–3.59 (m, 2H), 3.10–3.29 (m, 2H), 2.89–3.08 (m, 2H), 2.64–2.82 (m, 2H), 2.31–2.44 (m, 4H), 1.83–2.12 (m, 7H), 1.23–1.27 (m, 3H) ppm. MS-ESI: 361 $[MH]^+$ Example 220 ethyl 5-((8aS,12aR)-6,7,9,10,12,12a-hexahydro-5H-pyrido[4,3-b][1,4]thiazepino[2,3,4-hi]indol-11(8aH)-yl)pentanoate The title compound was prepared from addition of ethyl 5-chloropentanoate to to (8aS,12aR)-6,7,8a,9,10,11,12,12a-octahydro-5H-pyrido[4,3-b][1,4]thiazepino[2,3,4-hi]indole following the General procedure of Example 219. $^1$H NMR (300 MHz, $CDCl_3$) δ6.95 (bd, J=7.7 Hz, 1H), 6.86 (bd, J=7.4 Hz, 1H), 6.62 (dd, J=7.7 Hz, 7.3 Hz, 1H), 4.08–4.15 (m, 2H), 3.77–3.87 (m, 1H), 3.47–3.59 (m, 1H), 3.21–3.28 (m, 2H), 2.89–3.08 (m, 2H), 2.64–2.84 (m, 2H), 2.29–2.34 (m, 5H), 1.90–2.16 (m, 5H), 1.55–1.64 (m, 4H), 1.22–1.27 (m, 3H) ppm. MS-ESI: 375 $[MH]^+$ Example 221

4-((8aS,12aR)-6,7,9,10,12,12a-hexahydro-5H-pyrido[4,3-b][1,4]thiazepino[2,3,4-hi]indol-11(8aH)-yl)-N-methoxy-N-methylbutanamide General Procedure A solution of 2M trimethylaluminium in toluene (6.0 mmol) was added to a stirred mixture of N,O-dimethyl hydroxyamine hydrochloride (2.0 mmol) in dry toluene (20 mL) at 0° C. The resultant mixture was stirred at room temperature for 1 hour and added to a solution of ethyl 4-((8aS,12aR)-6,7,9,10,12,12a-hexahydro-5H-pyrido[4,3-b][1,4]thiazepino[2,3,4-hi]indol-11(8aH)-yl)butanoate or ethyl 5-((8aS,12aR)-6,7,9,10,12,12a-hexahydro-5H-pyrido[4,3-b][1,4]thiazepino[2,3,4-hi]indol-11(8aH)-yl) pentanoate from Example 219 and Example 220 in toluene (1 mL) at 0° C. The mixture was stirred at 0° C. for 2 hours, then at room temperature for 3 hours. 1M tartaric acid (27 mL) was added slowly to the reaction at 0° C. and stirred at 0° C. for 30 minutes. The reaction mixture was extracted with $CHCl_3$ (3×50 mL). The organic layer was washed with brine, dried over $Na_2SO_4$, filtered and concentrated to a residue. The residue was purified by flash column chromatography (Silica gel, $CH_2Cl_2$:$CH_3OH$9:1) to obtain the title compound in 70%–90% yields.

The title compound was prepared from the corresponding ester ethyl 4-((8aS,12aR)-6,7,9,10,12,12a-hexahydro-5H-pyrido[4,3-b][1,4]thiazepino[2,3,4-hi]indol-11(8aH)-yl)-butanoate following the General procedure above. $^1$H NMR (300 MHz, $CDCl_3$) δ6.94 (bd, J=7.7 Hz, 1H), 6.85 (bd, J=6.6 Hz, 1H), 6.61 (dd, J=7.6 Hz, 7.4 Hz, 1H), 3.77–3.86 (m, 1H), 3.67 (s, 3H), 3.48–3.59 (m, 1H), 3.21–3.28 (m, 2H), 3.17 (s, 3H), 2.89–3.08 (m, 2H), 2.71–2.84 (m, 2H), 2.29–2.52 (m, 5H), 1.84–2.16 (m, 7H) ppm. MS-ESI: 376 $[MH]^+$ Example 222

4-((8aS,12aR)-6,7,9,10,12,12a-hexahydro-5H-pyrido[4,3-b][1,4]thiazepino[2,3,4-hi]indol-11(8aH)-yl)-N-methoxy-N-methylpentanamide The title compound was prepared from the corresponding ester ethyl 5-((8aS,12aR)-6,7,9,10,12,12a-hexahydro-5H-pyrido[4,3-b][1,4]thiazepino[2,3,4-hi]indol-11(8aH)-yl) pentanoate following the General procedure of Example 221. $^1$H NMR (300 MHz, $CDCl_3$) δ6.95 (bd, J=7.7 Hz, 1H), 6.86 (bd, J=7.4 Hz, 1H), 6.62 (dd, J=7.7 Hz, 7.4 Hz, 1H), 3.77–3.87 (m, 1H), 3.67 (s, 3H), 3.47–3.59 (m, 1H), 3.23–3.29 (m, 2H), 3.16 (s, 3H), 2.77–3.06 (m, 4H), 2.33–2.44 (m, 5H), 1.91–2.13 (m, 5H), 1.61–1.65 (m, 4H) ppm. MS (CI, $NH_3$) m/e 389 (base, M+H$^+$).

Example 223

4-((8aS,12aR)-6,7,9,10,12,12a-hexahydro-5H-pyrido[4,3-b][1,4]thiazepino[2,3,4-hi]indol-11(8aH)-yl)-1-(4-fluoro-3-methylphenyl)-1-butanone General Procedure To a solution of 4-((8aS,12aR)-6,7,9,10,12,12a-hexahydro-5H-pyrido[4,3b][1,4]thiazepino[2,3,4-hi]indol-11(8aH)-yl)-N-methoxy-N-methylbutanamide or 5-((8aS,12aR)-6,7,9,10,12,12a-hexahydro-5H-pyrido[4,3-b][1,4]thiazepino[2,3,4-hi]indol-11(8aH)-yl)-N-methoxy-N-methylpentanamide from Example 221 and Example 222 (0.1 mmol) in THF (2 mL) or diethyl ether (2 mL) at ambient temperature, was added the corresponding aryl magnesium bromide (0.5 mmol) in THF (or diethyl ether) dropwise. The resultant mixture was stirred at room temperature for 2 to 5 hours. Added several drops of conc. HCl, extracted with $CH_2Cl_2$ (15 mL). The organic layer was washed with sat. $NaHCO_3$ (15 mL), brine (15 mL), dried over $Na_2SO_4$, filtered and concentrated to a residue. The result residue was purified by preparative TLC (Silica gel; $CH_2Cl_2$:$CH_3OH$ 9:1) to afford the title compounds in 70%–90% yields.

The title compound was prepared from addition of 4-((8aS,12aR)-6,7,9,10,12,12a-hexahydro-5H-pyrido[4,3-b][1,4]thiazepino[2,3,4-hi]indol-11(8aH)-yl)-N-methoxy-N-methylbutanamide following the General procedure above. $^1$H NMR (300 MHz, $CD_3OD$) δ7.84–7.94 (m, 2H), 7.08–7.16 (m, 1H), 6.92–6.99 (m, 2H), 6.64–6.72 (m, 1H), 3.79–3.93 (m, 1H), 3.48–3.70 (m, 3H), 3.36–3.47 (m, 1H), 2.98–3.14 (m, 7H), 2.84–2.94 (m, 1H), 2.58–2.68 (m, 1H), 2.31 (bs, 3H), 1.89–2.21 (m, 6H) ppm. MS (CI, $NH_3$) m/e 424 (base, M+H$^+$).

Example 224

4-((8aS,12aR)-6,7,9,10,12,12a-hexahydro-5H-pyrido[4,3-b][1,4]thiazepino[2,3,4-hi]indol-11(8aH)-yl)-1-phenyl-1-butanone The title compound was prepared from addition of phenyl magnesium bromide to 4-((8aS,12aR)-6,7,9,10,12,12a-hexahydro-5H-pyrido[4,3-b][1,4]thiazepino[2,3,4-hi]indol-11(8aH)-yl)-N-methoxy-N-methylbutanamide following the General procedure of Example 223. $^1$H NMR (300 MHz, $CDCl_3$) δ7.96 (d, J=7.3 Hz, 2H), 7.55–7.97 (m, 1H), 7.44–7.49 (m, 2H), 7.18–7.33 (m, 3H), 4.72–4.82 (m, 1H), 4.25–4.50 (m, 2H), 3.90–4.06 (m, 3H), 3.60–3.76 (m, 3H), 2.99–3.24 (m, 7H), 2.54–2.60 (m, 1H), 2.28–2.40 (m, 2H), 2.11–2.26 (m, 1H) ppm. MS (CI, $NH_3$) m/e 392 (base, M+H$^+$).

Example 225

4-((8aS,12aR)-6,7,9,10,12,12a-hexahydro-5H-pyrido[4,3-b][1,4]thiazepino[2,3,4-hi]indol-11(8aH)-yl)-1-(4-chlorophenyl)-1-butanone The title compound was prepared from addition of 4-chlorophenyl magnium bromide to 4-((8aS,12aR)-6,7,9,10,12,12a-hexahydro-5H-pyrido[4,3-b][1,4]thiazepino[2,3,4-hi]indol-11(8aH)-yl)-N-methoxy-N-methylbutanamide following the General procedure of Example 223. $^1$H NMR (300 MHz, $CD_3OD$) δ7.97–8.02 (m, 2H), 7.50–7.56 (m, 2H), 6.95–7.02 (m, 2H), 6.62–6.72 (m, 1H), 3.80–3.90 (m, 1H), 3.40–3.59 (m, 8H), 2.99–3.24 (m, 6H), 2.85–2.95 (m, 1H), 1.96–2.21(m, 4H) ppm. MS (CI, $NH_3$) m/e 426 (base, M+H$^+$).

Example 226

4-((8aS,12aR)-6,7,9,10,12,12a-hexahydro-5H-pyrido[4,3-b][1,4]thiazepino[2,3,4-hi]indol-11(8aH)-yl)-1-(3-methylphenyl)-1-butanone The title compound was prepared from addition of m-tolyl magnesium chloride to 4-((8aS,12aR)-6,7,9,10,12,12a-hexahydro-5H-pyrido[4,3-b][1,4]thiazepino[2,3,4-hi]indol-11(8aH)-yl)-N-methoxy-N-methylbutanamide following the General procedure of Example 223. $^1$H NMR (300 MHz, $CD_3OD$) δ7.79–7.84 (m, 2H), 7.38–7.44 (m, 2H), 6.95–7.05 (m, 2H), 6.62–6.72 (m, 1H), 3.80–3.90 (m, 1H), 3.40–3.59 (m, 8H), 2.99–3.24 (m, 6H), 2.85–2.95 (m, 1H), 2.38 (s, 3H), 1.96–2.21 (m, 4H) ppm. MS (CI, $NH_3$) m/e 406 (base, M+H$^+$).

Example 227

4-((8aS,12aR)-6,7,9,10,12,12a-hexahydro-5H-pyrido[4,3-b][1,4]thiazepino[2,3,4-hi]indol-11(8aH)-yl)-1-(4-tert-butylphenyl)-1-butanone The title compound was prepared from addition of 4-tert-butylphenyl magnesium bromide to 4-((8aS,12aR)-6,7,9,10,12,12a-hexahydro-5H-pyrido[4,3-b][1,4]thiazepino[2,3,4-hi]indol-11(8aH)-yl)-N-methoxy-N-methylbutanamide following the General procedure of Example 223. $^1$H NMR (300 MHz, $CD_3OD$) δ7.97–8.02 (m, 2H), 7.50–7.56 (m, 2H), 6.92–7.00 (m, 2H), 6.65–6.75 (m, 1H), 3.80–3.90 (m, 1H), 3.40–3.59 (m, 4H), 3.26–3.38 (m, 4H), 2.99–3.24 (m, 6H), 2.85–2.95 (m, 1H), 1.96–2.21(m, 4H), 1.32 (s, 9H) ppm. MS (CI, $NH_3$) m/e 448 (base, M+H$^+$).

Example 228

4-((8aS,12aR)-6,7,9,10,12,12a-hexahydro-5H-pyrido[4,3-b][1,4]thiazepino[2,3,4-hi]indol-11(8aH)-yl)-1-(3,4-difluorophenyl)-1-butanone The title compound was prepared from addition of 3,4-difluorophenyl magnesium bromide to 4-((8aS,12aR)-6,7,9,10,12,12a-hexahydro-5H-pyrido[4,3-b][1,4]thiazepino[2,3,4-hi]indol-11(8aH)-yl)-N-methoxy-N-methylbutanamide following the General procedure of Example 223. $^1$H NMR (300 MHz, $CD_3OD$) δ7.88–7.94 (m, 2H), 7.38–7.44 (m, 1H), 6.92–7.00 (m, 2H), 6.65–6.75 (m, 1H), 3.80–3.90 (m, 1H), 3.40–3.59 (m, 4H), 3.26–3.38 (m, 4H), 2.99–3.24 (m, 6H), 2.85–2.95 (m, 1H), 1.96–2.21(m, 4H) ppm. MS (CI, $NH_3$) m/e 428 (base, M+H$^+$).

Example 229

4-((8aS,12aR)-6,7,9,10,12,12a-hexahydro-5H-pyrido[4,3-b][1,4]thiazepino[2,3,4-hi]indol-11(8aH)-yl)-1-(5-fluoro-2-methoxyphenyl)-1-butanone The title compound was prepared from addition of 3-fluoro-6-methoxyphenyl magnesium bromide to 4-((8aS,12aR)-6,7,9,10,12,12a-hexahydro-5H-pyrido[4,3-b][1,4]thiazepino[2,3,4-hi]indol-11(8aH)-yl)-N-methoxy-N-methylbutanamide following the General procedure of Example 223. $^1$H NMR (300 MHz, $CD_3OD$) δ7.40–7.48 (m, 1H), 7.24–7.34 (m, 1H), 7.10–7.18 (m, 1H), 6.92–7.00 (m, 2H), 6.65–6.75 (m, 1H), 3.74–3.92 (m, 2H), 3.90 (s, 3H), 3.36–3.59 (m, 4H), 3.26–3.34 (m, 4H), 3.05–3.20 (m, 6H), 2.85–2.95 (m, 1H), 1.96–2.21(m, 4H) ppm. MS (CI, $NH_3$) m/e 440 (base, M+H$^+$).

Example 230

5-cis-((8a,12a)-6,7,9,10,12,12a-hexahydro-5H-pyrido[4,3-b][1,4]thiazepino[2,3,4-hi]indol-11(8aH)-yl)-1-phenyl-1-pentanone The title compound was prepared from addition of phenyl magnesium bromide to 5-((8aS,12aR)-6,7,9,10,12,12a-hexahydro-5H-pyrido[4,3-b][1,4]thiazepino[2,3,4-hi]indol-11(8aH)-yl)-N-methoxy-N-methylpentanamide following the General procedure of Example 223. $^1$H NMR (300 MHz, $CDCl_3$) δ7.84–7.94 (m, 2H), 7.50–7.58 (m, 1H), 7.44–7.50 (m, 2H), 6.92–7.00 (m, 2H), 6.70–6.79 (m, 1H), 3.76–3.82 (m, 1H), 3.58–3.68 (m, 2H), 3.45–3.56 (m, 1H), 3.18–3.21 (m, 2H), 2.64–2.98 (m, 7H), 2.30–2.35 (m, 1H), 1.80–1.92 (m, 4H), 1.60–1.72 (m, 4H) ppm. MS (CI, $NH_3$) m/e 406 (base, M+H$^+$).

Example 231

4-((8aS,12aR)-6,7,9,10,12,12a-hexahydro-5H-pyrido[4,3-b][1,4]thiazepino[2,3,4-hi]indol-11(8aH)-yl)-1-(4-fluoro-1-naphthyl)-1-butanone General Procedure To a solution of 4-((8aS,12aR)-6,7,9,10,12,12a-hexahydro-5H-pyrido[4,3-b][1,4]thiazepino[2,3,4-hi]indol-11(8aH)-yl)-N-methoxy-N-methylbutanamide from Example 26 (0.1 mmol) in THF (1 mL) at room temperature, was added the corresponding aryl magnesium bromide (0.5 mmol) in THF dropwise. The reaction mixture was stirred at ambient temperature for 18–20 hours, then heated at 72° C. for 1 hour. The reaction was concentrated to a residue. The residue was purified by prep. TLC (Silica gel; $CH_2Cl_2$:$CH_3OH$9:1) to afford the title compounds in 36%–40% yields.

The title compound was prepared from addition of 4-fluoro-1-naphthyl magnesium bromide to 4-((8aS,12aR)-6,7,9,10,12,12a-hexahydro-5H-pyrido[4,3-b][1,4]thiazepino[2,3,4-hi]indol-11(8aH)-yl)-N-methoxy-N-methylbutanamide following the General procedure above. $^1$H NMR (300 MHz, $CD_3OD$) δ8.72–8.80 (m, 1H), 8.10–8.18 (m, 2H), 7.62–7.68 (m, 2H), 7.24–7.30 (m, 1H), 6.92–7.00 (m, 2H), 6.64–6.70 (m, 1H), 3.82–3.92 (m, 1H), 3.52–3.64 (m, 2H), 3.24–3.44 (m, 7H), 2.90–3.14 (m, 2H), 2.68–2.84 (m, 2H), 2.30–2.44 (m, 2H), 1.99–2.11(m, 4H) ppm. MS-ESI: 461 [MH]$^+$ Example 232

5-((8aS,12aR)-6,7,9,10,12,12a-hexahydro-5H-pyrido[4,3-b][1,4]thiazepino[2,3,4-hi]indol-11(8aH)-yl)-1-phenyl-2-pentanone The title compound was prepared from addition of benzyl magnesium bromide to 4-((8aS,12aR)-6,7,9,10,12,12a-hexahydro-5H-pyrido[4,3-b][1,4]thiazepino[2,3,4-hi]indol-11(8aH)-yl)-N-methoxy-N-methylbutanamide following the General procedure of Example 231. $^1$H NMR (300 MHz, $CD_3OD$) δ7.22–7.28 (m, 5H), 6.92–6.98 (m, 2H), 6.62–6.68 (m, 1H), 4.88 (s, 2H), 3.82–3.92 (m, 1H), 3.52–3.64 (m, 2H), 3.24–3.44 (m, 7H), 2.82–3.18 (m, 4H), 2.32–2.44 (m, 2H), 1.92–2.30 (m, 4H) ppm. MS (CI, $NH_3$) m/e 406 (base, M+H$^+$).

Example 233

3-((8aS,12aR)-6,7,9,10,12,12a-hexahydro-5H-pyrido[4,3-b][1,4]thiazepino[2,3,4-hi]indol-11(8aH)-yl)-N-(4-fluorophenyl)propanamide General Procedure To 3-((8aS,12aR)-6,7,9,10,12,12a-hexahydro-5H-pyrido[4,3-b][1,4]thiazepino[2,3,4-hi]indol-11(8aH)-yl)-N-methoxy-N-methylpropanamide or 4-((8aS,12aR)-6,7,9,10,12,12a-hexahydro-5H-pyrido[4,3-b][1,4]thiazepino[2,3,4-hi]indol-11(8aH)-yl)-N-methoxy-N-methylbutanamide (0.06–0.1 mmol) in methanesulfonic acid (0.5 mL), was added $NaN_3$ (1.5 equiv.). The resultant mixture was stirred at ambient temperature for 1 hour, then was added water (5 mL). Ammonium hydroxide solution was added to adjust the pH to 11. Extracted with $CH_2Cl_2$(20 mL). The organic layer was dried over $MgSO_4$, filtered and concentrated to a residue. The residue was purified by prep. TLC (Silica gel; $CH_2Cl_2$:$CH_3OH$9/1). The product was dissolved in ether (1 mL) and stirred at 0° C. for 10 minutes, added 1N HCl in ether (0.5 mL) at 0° C. The white crystalline solid was collected by filtration to afford the title compounds in 50%–52% yields.

The title compound was prepared from 3-((8aS,12aR)-6,7,9,10,12,12a-hexahydro-5H-pyrido[4,3-b]1,4]thiazepino[2,3,4-hi]indol-11(8aH)-yl)-N-methoxy-N-methylpropanamide following the General procedure above: $^1$H NMR (300 MHz, $CDCl_3$) δ7.30–7.35 (m, 2H), 6.90–7.15 (m, 3H), 6.87 (d, J=7.0 Hz, 1H), 6.59 (dd, J=7.7 Hz, 7.3 Hz, 1H), 3.62–3.72 (m, 1H), 3.22–3.48 (m, 5H), 3.04–3.12 (m, 1H), 2.55–2.86 (m, 7H), 2.07–2.15 (m, 2H), 1.97–2.00 (m, 2H) ppm. MS (CI, $NH_3$) m/e 411 (base, M+H$^+$).

Example 234

4-((8aS,12aR)-6,7,9,10,12,12a-hexahydro-5H-pyrido[4,3-b][1,4]thiazepino[2,3,4-hi]indol-11(8aH)-yl)-N-(4-fluorophenyl)butanamide The title compound was prepared from 4-((8aS,12aR)-6,7,9,10,12,12a-hexahydro-5H-pyrido[4,3-b][1,4]thiazepino[2,3,4-hi]indol-11(8aH)-yl)-N-methoxy-N-methylbutanamide following the General procedure of Example 233. $^1$H NMR (300 MHz, $CDCl_3$) δ7.33–7.37 (m, 2H), 6.88–6.97 (m, 3H), 6.78 (d, J=7.0 Hz, 1H), 6.54 (dd, J=7.7 Hz, 7.3 Hz, 1H), 3.64–3.74 (m, 1H), 3.37–3.48 (m, 1H), 3.21–3.26 (m, 1H), 3.00–3.17 (m, 2H), 2.86–2.94 (m, 1H), 2.70–2.76 (m, 1H), 2.58–2.62 (m, 1H), 2.33–2.45 (m, 4H), 1.94–2.09 (m, 4H), 1.83–1.90 (m, 4H) ppm. MS (CI, $NH_3$) m/e 425 (base, M+H$^+$).

Example 235

4-((8aS,12aR)-6,7,9,10,12,12a-hexahydro-5H-pyrido[4,3-b][1,4]thiazepino[2,3,4-hi]indol-11(8aH)-yl)-1-(4-fluorophenyl)-1-butanol To 4-((8aS,12aR)1-6,7,9,10,12,12a-hexahydro-5H-pyrido[4,3-b][1,4]thiazepino[2,3,4-hi]indol-11(8aH)-yl)-1-(4-fluorophenyl)-1-butanone or 1-(4-pyridyl)-4-(2,3,6b,7,8,9,10,10a-octahydro-3-methyl-1H-pyrido[3',4':4,5]pyrrolo[1,2,3-de]quinoxalin-8-yl)-1-butanone (0.06 mmol) in methanol (1 mL) was added sodium borohydride (0.36 mmol) in three portions at 0° C. The reaction mixture was stirred at ambient temperature for 2 hours, followed by addition of two drops of conc. HCl to destroy the excess of $NaBH_4$. The $NH_4OH$ (1 mL) was added and extracted with $CH_2Cl_2$ (10 mL). The organic layer was dried over $MgSO_4$, filtered and concentrated to a residue. The residue was dissolved in ether (1 mL), added 1N HCl in ether. Concentrated to a residue to afford the title compounds in 60%–65% yields.

To the title compound was prepared from 4-((8aS,12aR)-6,7,9,10,12,12a-hexahydro-5H-pyrido[4,3-b][1,4]thiazepino[2,3,4-hi]indol-11(8aH)-yl)-1-(4-fluorophenyl)-1-butanone following the General procedure above: $^1$H NMR (300 MHz, $CD_3OD$) δ7.34–7.40 (m, 2H), 6.98–7.10 (m, 2H), 6.90–6.95 (m, 2H), 6.62–6.70 (m, 1H), 4.70 (m, 1H), 3.76–3.86 (m, 1H), 3.44–3.59 (m, 4H), 3.24–3.30 (m, 1H), 2.90–3.14 (m, 4H), 2.05–2.45 (m, 4H), 1.80–2.02 (m, 4H) ppm. MS-ESI: 413 $[MH]^+$ Example 236

4-((8aS,12aR)-6,7,9,10,12,12a-hexahydro-5H-pyrido[4,3-b][1,4]thiazepino[2,3,4-hi]indol-11(8aH)-yl)-1-(4-pyridinyl)-1-butanol The title compound was prepared from 1-(4-pyridyl)-4-(2,3,6b,7,8,9,10,10a-octahydro-3-methyl-1H-pyrido[3',4':4,5]-pyrrolo[1,2,3-de]quinoxalin-8-yl)-1-butanone following the General procedure of Example 235. $^1$H NMR (300 MHz, $CDCl_3$) δ8.53–8.57 (m, 2H), 7.32–7.36 (m, 2H), 6.90–6.98 (m, 1H), 6.84–6.87 (m, 1H), 6.60–6.66 (m, 1H), 4.66–4.72 (m, 1H), 3.80–3.92 (m, 1H), 3.55–3.71 (m, 3H), 3.22–3.30 (m, 2H), 2.64–3.02 (m, 4H), 2.31–2.54 (m, 3H), 1.69–2.03 (m, 8H) ppm. MS (CI, $NH_3$) m/e 395 (base, $M+H^+$).

Example 237

4-((8aS,12aR)-6,7,9,10,12,12a-hexahydro-5H-pyrido[4,3-b][1,4]thiazepino[2,3,4-hi]indol-11(8aH)-yl)-1-(2,3-dimethoxyphenyl)-1-butanol Step A Oxalyl chloride (55 mmol) was dissolved in $CH_2Cl_2$ (25 mL), cooled down to −60° C., DMSO (120 mmol) in $CH_2Cl_2$ (10 mL) solution was added dropwise. The reaction mixture was stirred at −60° C. for 10 minutes. 1-chlorobutan-4-ol (50 mmol) in $CH_2Cl_2$ (10 mL) was added slowly in 10 minutes. The reaction mixture was stirred at same temperature for 15 minute. Added $Et_3N$ in approximately 5 minutes at −60° C. The cooling bath was removed and water was added at rt, stirring was continued for 10 minutes. The organic layer was separated. The aqueous phase was extracted with $CH_2Cl_2$ (3×50 mL). Combined the organic layer, dried over $MgSO_4$, filtered, and concentrated to a residue to afford 1-chlorobutan-4-al in 64% yield. This product was distilled under reduced pressure to afford the aldehyde in 60% yield (5 mm Hg, 88–90° C.).

Step B

To a solution of TMEDA (6.6 mmol) in dry THF (15 mL), was added Sec-BuLi (6.6 mmol) slowly at −78° C. The reaction mixture was stirred at −78° C. for 10 minute, veratrole (6.0 mmol) in THF (3 mL) was added slowly. The reaction was stirred at −78° C. for 30 minutes, 1-chlorobutan-4-al (6.6 mmol) was added and stirred at −78° C. for 2 hr. The reaction mixture was warmed to rt, added brine (1 mL), and filtered. The filtrate was dried over $MgSO_4$, filtered and concentrated to a residue. The residue was purified by flash column chromatography (Silica gel; Ethyl acetate/Hexane: 3/7) to afford 1-(2,3-dimethoxyphenyl)-4-chlorobutan-1-ol in 20% yield. $^1$H NMR (300 MHz, $CDCl_3$) δ7.05 (dd, J=8.0 Hz, 7.7 Hz, 1H), 6.94 (bd, J=7.7 Hz, 1H), 6.85 (bd, J=8.1 Hz, 1H), 4.91–4.97 (m, 1H), 3.88 (s, 3H), 3.84 (s, 3H), 3.56–3.60 (m, 2H), 2.44–2.45 (m, 1H), 1.81–2.00 (m, 4H) ppm. MS (CI, $NH_3$) m/e 244 (base, $M+H^+$).

Step C

To a suspension of (8aS,12aR)-6,7,8a,9,10,11,12,12a-octahydro-5H-pyrido[4,3-b][1,4]thiazepino[2,3,4-hi]indole (1.17 mmol) in 1,4-dioxane (4 mL) was added the alcohol from Step B 1-(2,3-dimethoxyphenyl)-4-chlorobutan-1-ol (0.78 mmol), potassium iodine (100 mg) and potassium carbonate (300 mg). The reaction mixture was heated at reflux for 2 days. The solvent was removed under reduced pressure. The residue was treated with water (50 mL) and extracted with methylene chloride (3×50 mL). The $CH_2Cl_2$ extract was washed with brine (150 mL), dried over $MgSO_4$, filtered and concentrated to a residue. The residue was purified by flash column chromatography (Silica gel, $CH_2Cl_2$:$CH_3OH$9:1). The product was dissolved in ether (2 mL) and stirred at 0° C. for 10 minutes, added 1N HCl in ether (0.5 mL) at 0° C. The white crystalline solid was collected by filtration to give the title compound in 62% yield. $^1$H NMR (300 MHz, $CDCl_3$) δ7.07 (d, J=7.6 Hz, 1H), 6.99 (dd, J=7.7 Hz, 8.1 Hz, 1H), 6.89 (dd, J=1.5 Hz, 8.0 Hz, 1H), 6.83 (dd, J=1.1 Hz, 7.4 Hz, 1H), 6.75 (dd, J=1.5 Hz, 7.7 Hz, 1H), 6.57 (dd, J=7.3 Hz, 7.7 Hz, 1H), 4.92 (m, 1H), 3.79 (s, 6H), 3.46–3.56 (m, 1H), 3.16–3.20 (m, 2H), 2.67–2.95 (m, 4H), 2.31–2.34 (m, 3H), 1.80–2.05 (m, 5H), 1.64–1.76 (m, 6H) ppm. MS (CI, $NH_3$) m/e 455 (base, $M+H^+$).

Example 238

4-((8aS,12aR)-6,7,9,10,12,12a-hexahydro-5H-pyrido[4,3-b][1,4]thiazepino[2,3,4-hi]indol-11(8aH)-yl)-1-(2,3-dimethoxyphenyl)-1-butanone To a solution of the alcohol 4-((8aS,12aR)-6,7,9,10,12,12a-hexahydro-5H-pyrido[4,3-b][1,4]thiazepino[2,3,4hi]indol-11(8aH)-yl)-1-(2,3-dimethoxyphenyl)-1-butanol (0.11 mmol) and N-methylmorpholine N-oxide (0.17 mmol) in $CH_2Cl_2$ (2 mL) with powder 4 A molecular sieves at rt, was added solid tetrapropyl ammonium perruthenate (0.006 mmol) in one portion. The reaction mixture was stirred at rt for 4 hr., filtered and concentrated to a residue. The residue was purified by flash column chromatography (Silica gel; $CH_2Cl_2$/$CH_3OH$: 9:1) to afford the title compound in 94% yield. $^1$H NMR (300 MHz, $CDCl_3$) δ7.04 (d, J=7.3 Hz, 1H), 7.02 (d, J=7.4 Hz, 1H), 6.97 (dd, J=6.9 Hz, 7.7 Hz, 1H), 6.87 (d, J=7.7 Hz, 1H), 6.77 d, J=6.6 Hz, 1H), 6.53 (dd, J=7.7 Hz, 7.3 Hz, 1H), 3.82 (s, 3H), 3.80 (s, 3H), 3.70–3.80 (m, 1H), 3.43–3.56 (m, 1H), 3.17–3.22 (m, 1H), 2.82–3.05 (m, 5H), 2.56–2.76 (m, 2H), 2.10–2.30 (m, 3H), 1.80–2.05 (m, 7H) ppm.

Example 239 cis-(8a,12a)-11-(4-cyclohexylbutyl)-6,7,8a,9,10,11,12,12a-octahydro-5H-pyrido[4,3-b][1,4]thiazepino[2,3,4-hi]indole Step A 4-Cyclohexyl-1-butyl methanesulfonate was prepared by following the general procedure of Example 43 for mesylation as a colorless oil (734 mg, 95%) from 4-cyclohexyl-1-butanol (515 mg, 3.20 mmol) and methanesulfonyl chloride (540 mg, 4.80 mmol). $^1$H NMR ($CDCl_3$, 300 MHz) δ0.83–0.90 (m, 2H), 1.13–1.25 (m, 5H), 1.34–1.44 (m, 2H), 1.60–1.76 (m, 8H), 2.99 (s, 3H), 4.21 (t, 2H, J=6.5 Hz) ppm.

Step B

The title compound was prepared by following the general coupling procedure of Example 43 as a pale yellow oil (29 mg, 62%) from cis-(8a,12a)-6,7,8a,9,10,11,12,12a-octahydro-5H-pyrido[4,3-b][1,4]thiazepino[2,3,4-hi]indole (30 mg, 0.12 mmol) and 4-cyclohexylbutyl methylsulfonate (86 mg, 0.37 mmol). $^1$H NMR ($CDCl_3$, 300 MHz) δ0.81–0.85 (m, 2H), 1.09–1.18 (m, 9H), 1.52–1.69 (m, 8H), 1.98–2.13 (m, 4H), 2.37–2.43 (m, 2H), 2.81–3.07 (m, 3H), 3.28–3.32 (m, 2H), 3.54–3.64 (m, 2H), 3.78–3.87 (m, 1H), 6.63 (t, 1H, J=7.7Hz), 6.87 (dd, 1H, J=1.1, 7.3 Hz), 6.96 (dd, 1H, J=1.1, 7.7 Hz) ppm.

Example 240 cis-(8a,12a)-11-(4,4-diphenylbutyl)-6,7,8a,9,10,11,12,12a-octahydro-5H-pyrido[4,3-b][1,4]thiazepino[2,3,4-hi]indole Step A To a solution of 4-chloro-1,1-diphenyl-1-butene (200 mg, 0.82 mmol) in EtOAc (8.0 mL) was added Pd/C (10%, 50 mg). The reaction mixture was stirred under $H_2$ atmosphere for 15 h at 20° C. The reaction mixture was filtered through celite and the filterate was concentrated to give the analytically pure 4-Chloro-1,1-diphenylbutane (201 mg, 99%) as a colorless oil. $^1$H NMR ($CDCl_3$, 300 MHz) δ1.70–1.81 (m, 2H), 2.16–2.25 (m, 2H), 3.54 (t, 2H, J=6.5 Hz), 3.91 (t, 1H, J=7.8 Hz), 7.15–7.31 (m, 10H) ppm.

Step B

The title compound was prepared by following the general coupling procedure of Example 43 as a pale yellow oil (48 mg, 88%) cis-(8a,12a)-6,7,8a,9,10,11,12,12a-octahydro-5H-pyrido[4,3-b][1,4]thiazepino[2,3,4-hi]indole (30 mg, 0.12 mmol) and 4-chloro-1,1-diphenylbutane (44 mg, 0.18 mmol). $^1$H NMR ($CDCl_3$, 300 MHz) δ1.42–1.53 (m, 2H), 1.78 (t, 1H, J=12.0 Hz), 1.82–1.92 (m, 2H), 1.95–2.20 (m, 5H), 2.25–2.37 (m, 2H), 2.56–2.63 (m, 1H), 2.65–2.73 (m, 1H), 2.88–2.97 (m, 1H), 3.00–3.17 (m, 2H), 3.22–3.28 (m, 1H), 3.50–3.63 (m, 1H), 3.76–3.85 (m, 1H), 3.89 (t, 1H, J=7.9 Hz), 6.60 (t, 1H, J=7.7 Hz), 6.82 (d, 1H, J=7.3 Hz), 6.93 (d, 1H, J=7.7 Hz), 7.13–7.35 (m, 10H) ppm.

Example 241 cis-(8a,12a)-11-(4,4-diphenyl-3-butenyl)-6,7,8a,9,10,11,12,12a-octahydro-5H-pyrido[4,3-b][1,4]thiazepino[2,3,4-hi]indole Step A Cyclopropyldiphenylmethanol (500 mg, 2.23 mmol) was dissolved in 1M HCl in i-PrOH (4.0 mL). The reaction mixture was then heated at 60° C. for 1 h. The reaction was cooled 20° C. and diluted with $Et_2O$ (100 mL). The organic solution was successively washed with $H_2O$ $NaHCO_3$ saturated aqueous solution and brine. It was then dried over MgSO4, filtered, concentrated in vacuo and chromatographed on a silica gel column by elution with Hexanes to give 4-Chloro-1,1-diphenyl-1-butene (506 mg, 93%) as a colorless oil. $^1$H NMR ($CDCl_3$, 300 MHz) δ2.59 (q, 2H, J=6.9 Hz), 3.58 (t, 2H, J=6.9 Hz), 6.12 (t, 1H, J=7.3 Hz), 7.16–7.42 (m, 10H) ppm.

Step B

The title compound was prepared by following the general coupling procedure of Example 43 as a pale yellow oil (33 mg, 61%) from cis-(8a,12a)-6,7,8a,9,10,11,12,12a-octahydro-5H-pyrido[4,3-b][1,4]thiazepino[2,3,4-hi]indole (30 mg, 0.12 mmol) and 4-chloro-1,1-diphenyl-1-butene (44 mg, 0.18 mmol). $^1$H NMR ($CDCl_3$, 300 MHz) δ1.79–1.92 (m, 3H), 1.94–2.17 (m, 2H), 2.20–2.37 (m, 3H), 2.40–2.49 (m, 2H), 2.55–2.63 (m, 1H), 2.65–2.73 (m, 1H), 2.88–2.97 (m, 1H), 3.00–3.17 (m, 2H), 3.23–3.29 (m, 1H), 3.50–3.62 (m, 1H), 3.76–3.87 (m, 1H), 6.06 (t, 1H, J=7.3 Hz), 6.61 (t, 1H, J=7.3 Hz), 6.82 (d, 1H, J=6.6 Hz), 6.94 (dd, 1H, J=1.1, 7.7 Hz), 7.17–7.41 (m, 10H) ppm.

Example 242 cis-(8a,12a)-11-[4,4-bis(4-fluorophenyl)butyl]-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (89 mg, 51%) from cis-(8a,12a)-6,7,8a,9,10,11,12,12a-octahydro-5H-pyrido[4,3-b][1,4]thiazepino[2,3,4-hi]indole (68 mg, 0.27 mmol) and 1,1-bis-(4'-fluorophenyl)-4-chlorobutane (90 mg, 0.32 mmol). $^1$H NMR ($CDCl_3$, 300 MHz) δ1.38–1.48 (m, 2H), 1.79 (t, 1H, J=11.2 Hz), 1.83–1.91 (m, 2H), 1.95–2.21 (m, 5H), 2.23–2.35 (m, 2H), 2.53–2.62 (m, 1H), 2.63–2.75 (m, 1H), 2.89–2.99 (m, 1H), 3.01–3.16 (m, 2H), 3.22–3.27 (m, 1H), 3.52–3.62 (m, 1H), 3.76–3.85 (m, 1H), 3.86 (m, 1H, J=8.1 Hz), 6.61 (t, 1H, J=7.3 Hz), 6.82 (d, 1H, J=6.6 Hz), 6.90–6.99 (m, 5H), 7.13–7.22 (m, 4H) ppm.

Example 243 cis-(8a,12a)-11-4,4-bis(4-fluorophenyl)-3-butenyl]-6,7,8a,9,10,11,12,12a-octahydro-5H-pyrido[4,3-b][1,4]thiazepino[2,3,4-hi]indole Step A To a solution of cyclopropyl-(4-fluorophenyl)ketone (520 mg, 3.17 mmol) in THF (10 mL) was added 4-fluorophenyl magnesium bromide dropwise at 0° C. under $N_2$ atmosphere. The reaction mixture was stirred for 1 h at 0° C., quenched by addition of brine and extracted with $Et_2O$. The organic layer was then washed with $NaHCO_3$ saturated aqueous solution and brine. It was then dried over $MgSO_4$, filtered, concentrated in vacuo to give crude bis(4-fluorophenyl)-cyclopropylmethanol. It was used for ring opening reaction by following the procedure for formation of 4-chloro-1,1-diphenyl-1-butene without further purification. 1,1-Bis(4-fluorophenyl)-4-chloro-1-butene (780 mg, 88%) was obtained as a colorless oil $^1$H NMR ($CDCl_3$, 300 MHz) δ2.57 (q, 2H, J=6.9 Hz), 3.58 (t, 2H, J=6.9 Hz), 6.04 (t, 1H, J=7.3 Hz), 6.92–7.21 (m, 8H) ppm.

Step B

The title compound was prepared by following the general coupling procedure of Example 43 as a pale yellow oil (40 mg, 68%) from cis-(8a,12a)-6,7,8a,9,10,11,12,12a-octahydro-5H-pyrido[4,3-b][1,4]thiazepino[2,3,4-hi]indole (30 mg, 0.12 mmol) and 1,1-bis-(4'-fluorophenyl)-4-chloro-1-butene (51 mg, 0.18 mmol). $^1$H NMR ($CDCl_3$, 300 MHz) δ1.79–1.93 (m, 3H), 1.98–2.18 (m, 2H), 2.19–2.37 (m, 3H), 2.38–2.48 (m, 2H), 2.55–2.63 (m, 1H), 2.63–2.73 (m, 1H), 2.90–2.99 (m, 1H), 3.01–3.18 (m, 2H), 3.22–3.28 (m, 1H), 3.48–3.60 (m, 1H), 3.75–3.86 (m, 1H), 5.98 (t, 1H, J=7.3 Hz), 6.61 (t, 1H, J=7.3 Hz), 6.83 (d, 1H, J=7.3 Hz), 6.88–7.01 (m, 3H), 7.01–7.20 (m, 6H) ppm.

Example 244

N-[2-(cis-(8a,12a)-6,7,9,10,12,12a-hexahydro-5H-pyrido[4,3-b][1,4]thiazepino[2,3,4-hi]indol-11(8aH)-yl)ethyl]benzamide Step A To a solution of ethanolamine (1.09 g, 17.8 mmol) in THF was added benzoyl chloride (520 mg, 3.60 mmol) dropwise at 0° C. under $N_2$ atmosphere. The reaction mixture was stirred for 10 min and then quenched with 1M HCl. The mixture was then diluted with EtOAc and washed with sat. aq. $NaHCO_3$ and brine. The organic layer was dried over $MgSO_4$, filtered and concentrated in vacuo. The residue was crystallized to give N-(2-hydroxyethyl)benzamide (593 mg, 97%) as a white crystalline solid. $^1$H NMR ($CDCl_3$, 300 MHz) δ3.41 (s, 1H), 3.49–3.59 (m, 2H), 3.75 (t, 2H, J=5.2 Hz), 7.10 (s, 1H), 7.32–7.38 (m, 2H), 7.42–7.48 (m, 1H), 7.72–7.76 (m, 2H) ppm.

2-Benzamidoethyl methanesulfonate was prepared by following the general procedure of Example 43 for mesylation as a colorless oil (291 mg, 84%) from N-(2-hydroxyethyl)

benzamide (245 mg, 1.30 mmol) and methanesulfonyl chloride (223 mg, 1.94 mmol). $^1$H NMR ($CDCl_3$, 300 MHz) δ2.85 (s, 3H), 4.48 (t, 2H, J=9.5 Hz), 5.10 (t, 2H, J=10.2 Hz), 7.58–7.63 (m, 2H), 7.74–7.80 (m, 1H), 8.20–8.23 (m, 2H) ppm.

Step B

The title compound was prepared by following the general coupling procedure of Example 43 as a pale yellow oil (38 mg, 79%) from cis-(8a,12a)-6,7,8a,9,10,11,12,12a-octahydro-5H-pyrido[4,3-b][1,4]thiazepino[2,3,4-hi]indole (30 mg, 0.12 mmol) and 2-benzamidoethyl methanesulfonate (119 mg, 0.49 mmol). $^1$H NMR ($CDCl_3$, 300 MHz) δ1.87–1.92 (m, 2H), 2.05–2.12 (m, 2H), 2.16–2.23 (m, 1H), 2.40–2.50 (m, 1H), 2.55–2.60 (m, 2H), 2.77–2.84 (m, 2H), 2.92–3.05 (m, 1H), 3.15–3.24 (m, 1H), 3.31–3.34 (m, 1H), 3.44–3.57 (m, 2H), 3.69–3.78 (m, 2H), 4.45–4.51 (m, 1H), 6.59 (t, 1H, J=7.7 Hz), 6.83–6.86 (m, 1H), 6.91–6.97 (m, 1H), 7.15–7.23 (m, 1H), 7.35–7.5 (m, 2H), 7.61 (dd, 1H, J=1.1, 8.4 Hz) ppm.

Example 245

N-[2-(cis-(8a,12a)-6,7,9,10,12,12a-hexahydro-5H-pyrido[4,3-b][1,4]thiazepino[2,3,4-hi]indol-11(8aH)-yl)ethyl]-2-fluorobenzamide Step A Ethanolamine (1.00 mg, 15.8 mmol) and 2-fluorobenzoyl chloride (504 mg, 3.15 mmol) were coupled to give N-(2-hydroxyethyl)-2'-fluorobenzamide (460 mg, 79%) by following the procedure for preparation of N-(2-hydroxyethyl) benzamide. $^1$H NMR ($CD_3OD$, 300 MHz) δ3.49 (t, 2H, J=5.9 Hz), 3.68 (t, 2H, J=2.9 Hz), 7.15–7.28 (m, 2H), 7.47–7.55 (m, 1H), 7.72–7.78 (m, 1H) ppm. N-(2-Chloroethyl)-2'-fluorobenzamide was prepared by following the chlorination procedure in synthesis of 2-(2-chloroethyl) isoindolinone as a colorless oil (130 mg, 70%) from N-(2-hydroxyethyl)-2'-fluorobenzamide (130 mg, 0.71 mmol) and methanesulfonyl chloride (122 mg, 1.06 mmol). $^1$H NMR ($CDCl_3$, 300 MHz) $^1$H NMR ($CDCl_3$) δ3.72–3.76 (m, 2H), 3.82–3.87 (m, 2H), 7.11–7.18 (m, 2H), 7.25–7.28 (m, 1H), 7.46–7.53 (m, 1H), 8.08–8.13 (m, 1H) ppm.

Step B

The title compound was prepared by following the general coupling procedure of Example 43 as a pale yellow oil (56 mg, 90%) from cis-(8a,12a)-6,7,8a,9,10,11,12,12a-octahydro-5H-pyrido[4,3-b][1,4]thiazepino[2,3,4-hi]indole (30 mg, 0.12 mmol) and N-(2-chloroethyl)-2'-fluorobenzamide (74 mg, 0.37 mmol). $^1$H NMR ($CDCl_3$, 300 MHz) δ1.92–2.15 (m, 6H), 2.37–2.39 (m, 1H), 2.55–2.58 (m, 1H), 2.61–2.65 (m, 1H), 2.75–2.80 (m, 1H), 2.91–2.99 (m, 1H), 3.11–3.18 (m, 2H), 3.27–3.31 (m, 1H), 3.49–3.60 (m, 4H), 3.78–3.82 (m, 1H), 6.59 (t, 1H, J=7.3 Hz), 6.85 (d, 1H, J=7.0 Hz), 6.94 (dd, 1H, J=1.5, 8.1 Hz), 7.08, 7.15 (m, 1H), 7.24–7.29 (m, 1H), 7.43–7.51 (m, 1H), 8.08–8.14 (dt, 1H, J=1.8, 8.1 Hz) ppm.

Example 246

N-[2-(cis-(8a,12a)-6,7,9,10,12,12a-hexahydro-5H-pyrido[4,3-b][1,4]thiazepino[2,3,4-hi]indol-11(8aH)-yl)ethyl]-4-fluorobenzamide Step A Ethanolamine (0.96 mg, 15.8 mmol) and 4-fluorobenzoyl chloride were coupled to give N-(2-hydroxyethyl)-4'-fluorobenzamide (482 mg, 81%) by following the procedure for preparation of N-(2-hydroxyethyl)benzamide. $^1$H NMR ($CD_3OD$, 300 MHz) δ3.47 (t, 2H, J=5.9 Hz), 3.68 (t, 2H, J=5.7), 7.13–7.20 (m, 2H), 7.82–7.92 (m, 2H) ppm. 2-(4'-Fluorobenamido)ethyl methanesulfonate was prepared by following the general procedure of Example 43 for mesylation as a white crystal (130 mg, 70%) from N-(2-hydroxyethyl)-4'-fluorobenzamide (130 mg, 0.71 mmol) and methanesulfonyl chloride (122 mg, 1.06 mmol). $^1$H NMR ($CDCl_3$, 300 MHz) δ2.85 (s, 3H), 4.48 (t, 2H, J=9.5 Hz), 5.10 (t, 2H, J=10.2 Hz), 7.08–7.18 (m, 2H), 7.70–7.82 (m, 3H) ppm.

Step B

The title compound was prepared by following the general coupling procedure of Example 43 as a pale yellow oil (45 mg, 91%) from cis-(8a,12a)-6,7,8a,9,10,11,12,12a-octahydro-5H-pyrido[4,3-b][1,4]thiazepino[2,3,4-hi]indole (30 mg, 0.12 mmol) and N-[2-(methylsulfonyl)ethyl]-4-fluorobenzamide (63 mg, 0.24 mmol). $^1$H NMR ($CDCl_3$, 300 MHz) δ1.85–1.93 (m, 2H), 2.05–2.15 (m, 2H), 2.24 (dd, 1H, J=8.7, 11.3 Hz), 2.39–2.47 (m, 1H), 2.52–2.61 (m, 3H), 2.71–2.80 (m, 1H), 2.98–3.07 (m, 1H), 3.10–3.20 (m, 1H), 3.20–3.30 (m, 1H), 3.31–3.39 (m, 1H), 3.40–3.50 (m, 1H), 3.54 (q, 2H, J=6.2 Hz), 3.65–3.76 (m, 1H), 6.58 (t, 1H, J=7.7 Hz), 6.82–6.92 (m, 2H), 6.95 (dd, 1H, J=1.1, 8.1 Hz), 7.05–7.17 (m, 2H), 7.70–7.80 (m, 2H) ppm.

Example 247 cis-(8a,12a)-11-[3-(1H-indol-3-yl)propyl]-6,7,8a,9,10,11,12,12a-octahydro-5H-pyrido[4,3-b][1,4]thiazepino[2,3,4-hi]indole Step A 3-(3-Indolyl)-1-propyl methanesulfonate was prepared by following the general procedure of Example 43 for mesylation as a colorless oil (170 mg, 81%) from 3-(3-indolyl)-1-propanol (145 mg, 0.83 mmol) and methanesulfonyl chloride (142 mg, 1.24 mmol). $^1$H NMR ($CDCl_3$, 300 MHz) δ2.17 (qu, 2H, J=7.3 Hz), 2.92 (t, 2H, J=7.0 Hz), 2.99 (s, 3H), 4.27 (t, 2H, J=6.4 Hz), 7.04 (d, 1H, J=2.2 Hz), 7.12 (dt, 1H, J=1.1, 7.0 Hz), 7.21 (dt, 1H, J=1.1, 7.0 Hz), 7.38 (d, 1H, J=8.1 Hz), 7.59 (d, 1H, J=7.3 Hz), 8.00 (br, 1H) ppm.

Step B

The title compound was prepared by following the general coupling procedure of Example 43 as a pale yellow oil (20 mg, 59%) cis-(8a,12a)-6,7,8a,9,10,11,12,12a-octahydro-5H-pyrido[4,3-b][1,4]thiazepino[2,3,4-hi]indole (21 mg, 0.084 mmol) and 3-(3-indolyl)propyl methylsulfonate (32 mg, 0.13 mmol). $^1$H NMR ($CDCl_3$, 300 MHz) δ1.93–2.22 (m, 7H), 2.40–2.53 (m, 1H), 2.55–2.65 (m, 2H), 2.77–2.95 (m, 5H), 2.97–3.07 (m, 1H), 3.26–3.40 (m, 2H), 3.48–3.60 (m, 1H), 3.77–3.88 (m, 1H), 6.63 (t, 1H, J=7.7 Hz), 6.85 (d, 1H, J=7.3 Hz), 6.96 (dd, 1H, J=1.1, 8.1 Hz), 7.01 (d, 1H, 1.8 Hz), 7.10 (t, 1H, J=7.3 Hz), 7.19 (t, 1H, J=7.4 Hz), 7.36 (d, 1H, J=8.1 Hz), 7.58 (d, 1H, J=7.7 Hz), 8.00 (s, 1H) ppm.

Example 248 cis-(8a,12a)-11-[3-(1-methyl-1H-indol-3-yl)propyl]-6,7,8a,9,10,11,12,12a-octahydro-5H-pyrido[4,3-b][1,4]thiazepino[2,3,4-hi]indole Step A To a solution of KOH (2.24 g, 40.0 mmol), in dry DMSO (10 mL) was added 3-indolpropionic acid (946 mg, 5.0 mmol) followed immediately by MeI (3.0 g, 4.0 mmol). The reaction mixture was stirred for 1.5 h at 20° C., quenched by pouring into water and extracted with $CHCl_3$ (3×20 mL). The organic layer was then washed with brine, dried over MgSO4, filtered, concentrated in vacuo and chromatographed on a silica gel column by elution with EtOAc/Hexanes to give methyl 3-(1-methyl-3-indolyl)propionate (1.00 g, 92%) as a colorless oil. $^1$H NMR ($CDCl_3$, 300 MHz)

δ2.71 (t, 2H, J=8.1 Hz), 3.09 (t, 2H, J=7.0 Hz), 3.68 (s, 3H), 3.74 (s, 3H), 6.87 (s, 1H), 7.11 (dt, 1H, J=1.1, 6.8 Hz), 7.22 (dt, 1H, J=1.1, 8.0 Hz), 7.29 (d, 1H, J=8.1 Hz), 7.59 (d, 1H, J=7.7 Hz) ppm.

To a solution of methyl 3-(1-methyl-3-indolyl)propionate (300 mg, 1.38 mmol) in $Et_2O$ (3.0 mL) was added $LiAlH_4$ at 0° C. under $N_2$ atmosphere. The reaction mixture was stirred for 30 min at 0° C. and quenched by careful addition of $H_2O$. EtOAc was added to the quenched reaction mixture. The organic layer was separated, washed with brine and dried over $MgSO_4$. It was then concentrated in vacuo and chromatographed on a silica gel column by elution with EtOAc/Hexanes to give 3-(1-methyl-3-indolyl)-1-propanol (250 mg, 96%) as a colorless oil. $^1H$ NMR ($CDCl_3$, 300 MHz) δ1.28 (t, 1H, J=6.2 Hz), 1.98 (qu, 2H, J=7.7 Hz), 2.85 (t, 2H, J=7.3 Hz), 3.70–3.78 (m, 4H), 6.86 (s, 1H), 7.10 (dt, 1H, J=1.1, 7.0 Hz), 7.22 (dt, 1H, J=1.1, 7.5 Hz), 7.29 (d, 1H, J=8.1 Hz), 7.60 (d, 1H, J=7.7 Hz) ppm.

3-(1-methyl-3-indolyl)-1-propyl methanesulfonate was prepared by following the general procedure of Example 43 for mesylation as a colorless oil (291 mg, 84%) from 3-(1-methyl-3-indolyl)-1-propanol (245 mg, 1.30 mmol) and methanesulfonyl chloride (223 mg, 1.94 mmol). $^1H$ NMR ($CDCl_3$, 300 MHz) δ2.15 (qu, 2H, J=7.0 Hz), 2.90 (t, 2H, J=7.0 Hz), 2.99 (s, 3H), 3.76 (s, 3H), 4.27 (t, 2H, J=6.2 Hz), 6.88 (s, 1H), 7.11 (dt, 1H, J=1.1, 6.9 Hz), 7.23 (dt, 1H, J=1.1, 7.0 Hz), 7.29 (d, 1H, J=8.5 Hz), 7.57 (d, 1H, J=8.1 Hz) ppm.

Step B

The title compound was prepared by following the general coupling procedure of Example 43 as a pale yellow oil (36 mg, 86%) from cis-(8a,12a)-6,7,8a,9,10,11,12,12a-octahydro-5H-pyrido[4,3-b][1,4]thiazepino[2,3,4-hi]indole (25 mg, 0.10 mmol) and 3-(1-methyl-3-indolyl)propyl methylsulfonate (32 mg, 0.12 mmol). $^1H$ NMR ($CDCl_3$, 300 MHz) δ1.92–2.18 (m, 7H), 2.35–2.46 (m, 1H), 2.48–2.60 (m, 2H), 2.74–2.95 (m, 5H), 2.96–3.07 (m, 1H), 3.25–3.35 (m, 2H), 3.46–3.58 (m, 1H), 3.74 (s, 3H), 3.77–3.87 (m, 1H), 6.63 (t, 1H, J=7.3 Hz), 6.82–6.88 (m, 2H), 6.96 (d, 1H, J=7.7 Hz), 7.09 (t, 1H, J=7.0 Hz), 7.20–7.32 (m, 2H), 7.57 (d, 1H, J=7.7 Hz) ppm.

Example 249 cis-(8a,12a)-11-[2-(1H-indol-3-yl)ethyl]-6,7,8a,9,10,11,12,12a-octahydro-5H-pyrido[4,3-b][1,4]thiazepino[2,3,4-hi]indole The title compound was prepared by following the general coupling procedure of Example 43 as a pale yellow oil (33 mg, 71%) from cis-(8a,12a)-6,7,8a,9,10,11,12,12a-octahydro-5H-pyrido[4,3-b][1,4]thiazepino[2,3,4-hi]indole (30 mg, 0.12 mmol) and 3-(2-bromoethyl)indole (54 mg, 0.24 mmol). $^1H$ NMR ($CDCl_3$, 300 MHz) δ1.93–2.20 (m, 5H), 2.35–2.43 (m, 1H), 2.64–2.77 (m, 2H), 2.78–2.87 (m, 1H), 2.89–3.15 (m, 5H), 3.20–3.35 (m, 2H), 3.49–3.61 (m, 1H), 3.77–3.87 (m, 1H), 6.64 (t, 1H, J=7.7 Hz), 6.90 (d, 1H, J=7.3 Hz), 6.97 (dd, 1H, J=1.1, 8.1 Hz), 7.02 (d, 1H, 2.2 Hz), 7.08–7.21 (m, 2H), 7.35 (d, 1H, J=8.0 Hz), 7.61 (d, 1H, J=8.1 Hz), 7.98 (s, 1H) ppm.

Example 250 cis-(8a,12a)-11-[3-(1H-indol-1-yl)propyl]-6,7,8a,9,10,11,12,12a-octahydro-5H-pyrido[4,3-b][1,4]thiazepino[2,3,4-hi]indole Step A To a solution of 1-bromo-3-chloropropane (2.00 g, 12.7 mmol) in DMF (7.0 mL) was added indole (500 mg, 4.24 mmol) followed by powdered KOH (262 mg, 4.66 mmol) at 20° C. The reaction mixture was then stirred for 15 h at 20° C. The reaction was quenched by addition of $H_2O$ and the product was extracted with $Et_2O$. The organic solution was washed with $H_2O$ and brine, dried over $MgSO_4$, filtered and concentrated in vacuo. 1-(3-Chloro-1-propyl)indole (580 mg, 71%) was isolated by flash chromatography on a silica gel column by elution with EtOAc/Hexanes a pale yellow oil. $^1H$ NMR ($CDCl_3$, 300 MHz) δ2.28 (qu, 2H, J=6.3 Hz), 3.46 (t, 2H, J=6.2 Hz), 4.36 (t, 2H, J=6.6 Hz), 6.51 (d, 1H, J=3.3 Hz), 7.09–7.18 (m, 2H), 7.20–7.25 (m, 1H), 7.38 (d, 1H, J=8.5 Hz), 7.64 (d, 1H, J=7.7 Hz) ppm.

Step B

The title compound was prepared by following the general coupling procedure of Example 43 as a pale yellow oil (46 mg, 95%) from cis-(8a,12a)-6,7,8a,9,10,11,12,12a-octahydro-5H-pyrido[4,3-b][1,4]thiazepino[2,3,4-hi]indole (30 mg, 0.12 mmol) and 1-(3-chloropropyl)indole (46 mg, 0.24 mmol). $^1H$ NMR ($CDCl_3$, 300 MHz) δ1.90–2.15 (m, 7H), 2.18–2.33 (m, 3H), 2.52–2.60 (m, 1H), 2.66–2.75 (m, 1H), 2.89–2.98 (m, 1H), 3.02–3.18 (m, 2H), 3.26–3.33 (m, 1H), 3.48–3.59 (m, 1H), 3.77–3.87 (m, 1H), 4.21 (t, 2H, J=7.0 Hz), 6.62 (t, 1H, J=7.3 Hz), 6.85 (d, 1H, J=6.6 Hz), 6.95 (dd, 1H, J=1.1, 7.7 Hz), 7.05–7.16 (m, 2H), 7.20 (dt, 1H, J=1.1, 7.0 Hz), 7.38 (d, 1H, J=8.4 Hz), 7.63 (d, 1H, J=8.1 Hz) ppm.

Example 251 cis-(8a,12a)-11-[3-(2,3-dihydro-1H-indol-1-yl)propyl]-6,7,8a,9,10,11,12,12a-octahydro-5H-pyrido[4,3-b][1,4]thiazepino[2,3,4-hi]indole Step A To a solution of 1-bromo-3-chloropropane (1.98 g, 12.6 mmol) and indoline (500 mg, 4.20 mmol) in 1,4-dioxane (6.0 mL) was added $Et_3N$ (2.12 g, 21.0 mmol) at 20° C. The reaction mixture was then stirred for 15 h at 70° C. The reaction mixture was cooled to 20° C. and quenched by addition of $H_2O$. The product was extracted with $Et_2O$. The organic solution was then washed with $H_2O$ and brine, dried over $MgSO_4$, filtered and concentrated in vacuo. 1-(3-Chloro-1-propyl)indoline (373 mg, 45%) was isolated by flash chromatography on a silica gel column by elution with EtOAc/Hexanes a pale yellow oil. $^1H$ NMR ($CDCl_3$, 300 MHz) δ2.07 (qu, 2H, J=6.2 Hz), 2.97 (t, 2H, J=8.2 Hz), 3.24 (t, 2H, J=6.6 Hz), 3.35 (t, 2H, J=8.3 Hz), 3.68 (t, 2H, J=6.2 Hz), 6.50–6.56 (m, 1H), 6.66 (t, 1H, J=6.6 Hz), 7.04–7.10 (m, 2H) ppm.

Step B

The title compound was prepared by following the general coupling procedure of Example 43 as a pale yellow oil (36 mg, 74%) from (±)-cis-6,7,8a,9,10,11,12,12a-octahydro-5H-pyrido[3',4':4,5]pyrrolo[1,2,3-ef][1,5]benzothiazepine (30 mg, 0.12 mmol) and 1-(3-chloropropyl)indoline (47 mg, 0.24 mmol). $^1H$ NMR ($CDCl_3$, 300 MHz) δ1.80–2.18 (m, 7H), 2.23–2.35 (m, 2H), 2.43–2.55 (m, 1H), 2.70–2.85 (m, 2H), 2.89–2.98 (m, 3H), 3.02–3.19 (m, 4H), 3.28–3.38 (m, 3H), 3.48–3.61 (m, 1H), 3.78–3.90 (m, 1H), 6.45–6.52 (m, 1H), 6.59–6.70 (m, 2H), 6.82–6.90 (m, 1H), 6.92–6.98 (m, 1H), 7.02–7.13 (m, 2H) ppm.

Example 252 cis-(8a,12a)-11-[3-(1H-benzimidazol-1-yl)propyl]-6,7,8a,9,10,11,12,12a-octahydro-5H-pyrido[4,3-b][1,4]thiazepino[2,3,4-hi]indole Step A To a solution of benzimidazol (355 mg, 3.00 mmol) in dry DMF (10 mL) was added NaH (83 mg, 3.3 mmol) at 20° C.

under $N_2$ atmosphere. The reaction mixture was stirred for 30 min, and then 1,3-dibromopropane (1.82 g, 9.00 mmol) was added and stirres for additional 15 h at 20° C. The reaction was quenched by addition H2O, and the product was extracted with EtOAc. The organic solution was then washed with $H_2O$ and brine, dried over $MgSO_4$, filtered and concentrated in vacuo. 1-(3-Bromo-1-propyl)benzimidazole (530 mg, 74%) was isolated by flash chromatography on a silica gel column by elution with EtOAc/Hexanes a pale yellow oil. $^1$H NMR ($CDCl_3$, 300 MHz) δ2.40 (qu, 2H, J=6.6 Hz), 3.33 (t, 2H, J=6.2 Hz), 4.42 (t, 2H, J=6.6 Hz), 7.12–7.20 (m, 1H), 7.27–7.48 (m, 2H), 7.43–7.49 (m, 1H), 7.78–7.86 (m, 1H) ppm.

Step B

The title compound was prepared by following the general coupling procedure of Example 43 as a pale yellow oil (21 mg, 43%) from (±)-cis-6,7,8a,9,10,11,12,12a-octahydro-5H-pyrido[3',4':4,5]pyrrolo[1,2,3-ef][1,5] benzothiazepine (30 mg, 0.12 mmol) and 1-(3-chloropropyl) benzimidazole (58 mg, 0.24 mmol). $^1$H NMR ($CDCl_3$, 300 MHz) δ1.83–1.95 (m, 3H), 2.00–2.17 (m, 4H), 2.20–2.33 (m, 3H), 2.50–2.60 (m, 1H), 2.64–2.72 (m, 1H), 2.90–2.99 (m, 1H), 3.05–3.18 (m, 2H), 3.29–3.35 (m, 1H), 3.50–3.59 (m, 1H), 3.77–3.87 (m, 1H), 4.28 (dt, 2H, J=2.2, 6.2 Hz), 6.63 (t, 1H, J=7.7 Hz), 6.85 (d, 1H, J=6.6 Hz), 6.95 (dd, 1H, J=1.1, 7.7 Hz), 7.27–7.35 (m, 2H), 7.40–7.47 (m, 1H), 7.78–7.85 (m, 1H), 7.92 (s, 1H) ppm.

Example 253

2-[2-(cis-(8a,12a)-6,7,9,10,12,12a-hexahydro-5H-pyrido[4,3-b][1,4]thiazepino[2,3,4-hi]indol-11(8aH)-yl)ethyl]-1H-isoindole-1,3(2H)-dione The title compound was prepared by following the general coupling procedure of Example 43 as a pale yellow oil (40 mg, 79%) from (±) -cis-6,7,8a,9,10,11,12,12a-octahydro-5H-pyrido[3',4':4,5]pyrrolo[1,2,3-ef][1.5] benzothiazepine (30 mg, 0.12 mmol) and N-(2-bromoethyl) phthalimide (61 mg, 0.24 mmol). $^1$H NMR ($CDCl_3$, 300 MHz) δ1.80–2.20 (m, 5H), 2.25–2.39 (m, 1H), 2.58 (t, 2H, J=6.6 Hz), 2.69–2.77 (m, 1H), 2.79–2.89 (m, 1H), 2.90–2.98 (m, 1H), 3.02–3.13 (m, 2H), 3.17–3.27 (m, 1H), 3.50–3.61 (m, 1H), 3.77–3.87 (m, 3H), 6.57 (t, 1H, J=7.7 Hz), 6.84 (d, 1H, J=7.0 Hz), 6.92 (dd, 1H, J=1.1, 7.7 Hz), 7.68–7.78 (m, 2H), 7.82–7.89 (m, 2H) ppm.

Example 254

2-[2-(cis-(8a,12a)-6,7,9,10,12,12a-hexahydro-5H-pyrido[4,3-b][1,4]thiazepino[2,3,4-hi]indol-11(8aH)-yl)ethyl]-1-isoindolinone Step A Ethanolamine (4.78 g, 78.3 mmol) and phthalide (10.0 g, 74.6 mmol) were placed in a round-bottom flask equipped with a Dean-stark trap. The reaction mixture was heated at 150° C. for 4 h then 18 h at 205° C. The product was solidified upon cooling. Pure 2-(2-hydroxyethyl) isoindolinone (10.8 g, 82% was isolated by recrystallization in CHCl3/hexanes as a white crystal. $^1$H NMR ($CDCl_3$, 300 MHz) δ3.02–3.15 (br, 1H), 3.78 (t, 2H, J=5.0 Hz), 3.93 (t, 2H, J=4.4 Hz), 4.52 (s, 2H), 7.42–7.58 (m, 3H), 7.84 (d, 1H, J=7.4 Hz) ppm.

To a solution of 2-(2-hydroxyethyl)isoindolinone (1.0 g, 5.64 mmol) in toluene (3.5 mL) was added thionyl chloride (1.34 g, 11.3 mmol). The reaction mixture was stirred at 20° C. for 3 h then 4 h at 60° C. The reaction mixture was concentrated in vacuo to remove excess thionyl chloride and toluene. 2-(2-Chloroethyl)isoindolinone (1.01 g, 92%) was obtained by flash chromatography on a silica gel column by elution with EtOAc/Hexanes a white solid. $^1$H NMR ($CDCl_3$, 300 MHz) δ3.81 (t, 2H, J=5.5 Hz), 3.97 (t, 2H, J=5.9 Hz), 4.59 (s, 2H), 7.44–7.58 (m, 3H), 7.86 (d, 1H, J=6.9 Hz) ppm.

Step B

The title compound was prepared by following the general coupling procedure of Example 43 as a pale yellow oil (42 mg, 86%) from (±)-cis-6,7,8a,9,10,11,12,12a-octahydro-5H-pyrido[3',4':4,5]pyrrolo[1,2,3-ef][1,5] benzothiazepine (30 mg, 0.12 mmol) and 2-(2-chloroethyl) isoindolinone (47 mg, 0.24 mmol). $^1$H NMR ($CDCl_3$, 300 MHz) δ1.80–1.95 (m, 3H), 2.00–2.18 (m, 3H), 2.37 (dt, 1H, J=3.6, 11 Hz), 2.60 (t, 2H, J=6.6 Hz), 2.63–2.72 (m, 1H), 2.75–2.82 (m, 1H), 2.89–2.98 (m, 1H), 3.05–3.18 (m, 2H), 3.26–3.33 (m, 1H), 3.48–3.59 (m, 1H), 3.73–3.84 (m, 3H), 4.49 (s, 2H), 6.58 (t, 1H, J=7.3 Hz), 6.83 (d, 1H, J=6.6 Hz), 6.94 (dd, 1H, J=1.1, 7.7 Hz), 7.42–7.55 (m, 3H), 7.85 (d, 1H, J=7.3 Hz) ppm.

Example 255 cis-(6b,10a)-3-methyl-2,3,6b,7,8,9,10,10a-octahydro-1H-pyrido[3',4':4,5]pyrrolo[1,2,3-de] quinoxaline The procedure described in Example 4, Steps E through G, was utilized to prepare ethyl 2-oxo-2,3,9,10-tetrahydro-1H-pyrido[3',4':4,5]pyrrolo[1,2,3-de]quinoxaline-8(7H)-carboxylate from the corresponding amine, 1,3,4-trihydroquinoxalin-2-one, and ethyl 4-oxopiperidinecarboxylic.

Step A

Sodium cyanoborohydride (4.0 g, 65 mmol) was added, in small portions, to a vigorously stirred solution of ethyl 2-oxo-2,3,9,10-tetrahydro-1H-pyrido[3',4':4,5]pyrrolo[1,2,3-de]quinoxaline-8(7H)-carboxylate (11.97 g, 40 mmol) in trifluoroacetic acid (125 mL) cooled in an ice-water bath, under nitrogen. After the addition was complete, the mixture was stirred for 30 min and then poured slowly into ammonium hydroxide (300 mL) containing ice followed by the addition of enough 1N sodium hydroxide to make the mixture basic. The mixture was extracted with dichloromethane (2×) and the extract was washed with water, dried over magnesium sulfate, and evaporated to dryness to yield 10.89 g (90%) of cis-ethyl(6b,10a)-2-oxo-2,3,6b,9,10,10a-hexahydro-1H-pyrido[3',4':4,5]pyrrolo[1,2,3-de] quinoxaline-8(7H)-carboxylate as an off-white powder, m.p. 167–168° C. (dec. sinters at 70° C.). $^1$H NMR ($CDCl_3$, 300 MHz) δ1.28 (t, J=7 Hz, 3H), 1.81–1.95 (m, 2H), 3.13–3.22 (m,1H), 3.23–3.39 (m, 1H), 3.44 (d, J=14.7 Hz, 1H), 3.41–3.51(m, 1H), 3.80–3.95 (m, 1H), 3.98 (d, J=14.7 Hz, 2H), 4.16 (q, 2H), 6.59 (d, J=7.7 Hz, 1H), 6.74 (t, J=7.7 Hz, 1H), 6.93 (d, J=7.7 Hz, 1H), 8.17 (s, 1H) ppm. MS (CI): 302 ($M+H^+$).

Step B

Sodium hydride (900 mg of 60% dispersion in oil; 22.5 mmol) was washed with hexane, and suspended in anhydrous dimethylformamide (5 mL). The suspension was added to a stirred solution of cis-ethyl(6b,10a)-2-oxo-2,3,6b,9,10,10a-hexahydro-1H-pyrido[3',4':4,5]pyrrolo[1,2,3-de]quinoxaline-8(7H)-carboxylate (6.02 g, 20 mmol) in anhydrous dimethylformamide (50 mL) under nitrogen. After gas evolution had subsided, the mixture was cooled in ice-water bath and treated with iodomethane (3.55 g, 25 mmol). The mixture was stirred at room temperature for 1 h and then concentrated. The residue was treated with water and extracted with dichloromethane (2×) and the extract was washed with brine, dried over magnesium sulfate and evaporated to dryness to yield 5.48 g (87%) of cis-ethyl(6b,10a)-3-methyl-2-oxo-2,3,6b,9,10,10a-hexahydro-1H-pyrido[3',4':4,5]pyrrolo[1,2,3-de]quinoxaline-8(7H)-carboxylate as a tan solid, m.p. 149–151° C. (dec.). [M+H] calc. 316; found 316. $^1$H NMR ($CDCl_3$, 300 MHz) δ1.28 (t, J=7.3 Hz, 3H), 1.85 tol.93 (m,1H), 2.65 to 2.82 (m, 1H),3.08 to 3.25 (m, 1H), 3.25 to 3.40 (m, 1H),3.30–3.50 (m, 1H), 3.34 (s, 3H), 3.42 (d, J=14.3 Hz, 1H), 3.85 to 4.0 (m,1H), 4.02 (d, J=14.3 Hz, 1H, 4.15 (q, J=7.2 Hz, 4H), 6.76 (d, J=8.1 Hz, 1H), 6.83 (t, J=7.3 Hz, 1H), 6.90 (d, J=7.3 Hz, 1H). MS (CI): 316 (M+H$^+$).

Step C

A solution of borane in tetrahydrofuran (1M, 33 mL, 33 mmol) was added dropwise to a stirred solution of cis-ethyl (6b,10a)-3-methyl-2-oxo-2,3,6b,9,10,10a-hexahydro-1H-pyrido[3',4':4,5]pyrrolo[1,2,3-de]quinoxaline-8(7H)-carboxylate (5.24 g, 16.6 mmol) in anhydrous tetrahydrofuran (25 mL) under nitrogen. After the addition was complete, the mixture was stirred and heated at reflux for 1 h, cooled and treated with 6N hydrochloric acid (15 mL). It was then heated under reflux for 30 min, cooled and evaporated to dryness under reduced pressure. The residue was dissolved in a minimum quantity of water and the solution basified with 1N sodium hydroxide and extracted with dichloromethane (2×). The extract was washed with water, dried over magnesium sulfate, and concentrated to yield, 4.65 g (93%) of cis-ethyl(6b,10a)-3-methyl-2,3,6b,9,10,10a-hexahydro-1H-pyrido[3',4':4,5]pyrrolo[1,2,3-de] quinoxaline-8(7H)-carboxylate as a viscous liquid. $^1$H NMR ($CDCl_3$, 300 MHz) δ1.28 (t, J=7 Hz, 3H), 1.68–1.78 (m, 1H), 1.78–1.93 (m,2H), 2.81–2.90 (m, 2H), 2.86 (s, 3H), 3.05–3.26 (m, 2H), 3.26–3.38 (m, 2H), 3.56–3.75 (m, 2H), 3.79–3.87 (m, 1H), 4.16 (q, J=7 Hz, 2H), 6.41 (d, J=8.1 Hz, 1H), 6.61 (d, J=8.1 Hz, 1H), 6.67 (t, J=8.1 Hz, 1H) ppm. MS (CI): 302 (M+H$^+$).

Step D

Powdered potassium hydroxide (10.0 g) was added to a stirred solution of cis-ethyl(6b,10a)-3-methyl-2,3,6b,9,10,10a-hexahydro-1H-pyrido[3',4':4,5]pyrrolo[1,2,3-de] quinoxaline-8(7H)-carboxylate (4.52 g, 15.0 mmol) in warm 1-butanol (50 mL) and the resulting mixture was heated under reflux for 5 h. It was then evaporated under reduced pressure and the residue treated with water and extracted with dichloromethane (2×). The extract was washed with water, dried over magnesium sulfate and concentrated to yield 3.27 g (95%) of the title compound as a viscous liquid. $^1$H NMR ($CDCl_3$, 300 MHz) δ1.74–1.93 (m, 4H), 2.57–2.71 (m, 1H), 2.80–2.95 (m, 3H), 2.87 (s, 3H), 2.95–3.12 (m, 2H), 3.26–3.38 (m, 3H), 3.55–3.64 (m, 1H), 6.41 (d, J=7.3 Hz, 1H), 6.51 (d, J=7.3 Hz, 1H), 6.65 (t, J=7.3 Hz, 1H), ppm. MS (CI): 230 (M+H$^+$).

Example 256 cis-(6b,10a)-3-ethyl-2,3,6b,7,8,9,10,10a-octahydro-1H-pyrido[3',4':4,5]pyrrolo[1,2,3-de]quinoxaline Utilizing the material from Example 255 Step A, the title compound was prepared in analogous fashion using ethyl iodide as the alkyl halide and following the procedure of Step B–D of Example 255, as a light brown amorphous solid. $^1$H NMR ($CDCl_3$, 300 MHz) δ1.15 (t, 3H), 1.70–2.01 (m, 3H), 2.65–2.70 (t, J=9.6 Hz, 3H), 2.70–2.95 (m,2H), 2.95–3.13 (m, 2H), 3.13–3.72 (m, 5H), 3.60–3.95 (m, 1H), 6.39 (d, J=8.0 Hz, 1H), 6.47 (d, J=7.4 Hz, 1H), 6.64 (t, J=7.3 Hz), 1H) ppm. MS (CI): 244 (M+H$^+$).

Step B

Cis-ethyl(6b,10a)-3-ethyll-2-oxo-2,3,6b,9,10,10a-hexahydro-1H-pyrido[3',4':4,5]pyrrolo[1,2,3-de] quinoxaline-8(7H)-carboxylate. Viscous brown liquid. Yield 70%. MS (CI) 330 (M+H$^+$).

Step C

Cis-ethyl(6b,10a)-3-ethyl-2,3,6b,9,10,10a-hexahydro-1H-pyrido[3',4':4,5]pyrrolo[1,2,3-de]quinoxaline-8(7H)-carboxylate. Viscous brown liquid. Yield 70%. MS (CI): 316 (M+H$^+$).

Example 257 cis-(6b,10a)-3-propyl-2,3,6b,7,8,9,10,10a-octahydro-1H-pyrido[3',4':4,5]pyrrolo[1,2,3-de]quinoxaline Utilizing the material from Example 255 Step A, the title compound was prepared in analogous fashion using propyl iodide as the alkyl halide and following the procedure of Step B–D of Example 255, as an amorphous tan solid. $^1$H NMR ($CDCl_3$, 300 MHz) δ0.94 (t, 2H), 1.40–2.01 (m, 6H), 2.65–2.70 (t, J=9.6 Hz, 2H),2.70–2.95 (m, 2H), 2.95–3.45 (m, 7H), 3.3.60–3.95 (m, 1H), 6.37(d, J=7.7 Hz, 1H), 6.46 (d, J=7.0 Hz, 1H), 6.64 (t, J=7.6 Hz) ppm. MS (CI): 258 (M+H$^+$).

Step B

Cis-ethyl(6b,10a)-3-propyl-2-oxo-2,3,6b,9,10,10a-hexahydro-1H-pyrido[3',4':4,5]pyrrolo[1,2,3-de] quinoxaline-8(7H)-carboxylate. Viscous brown liquid. Yield 72%. MS (CI) 344 (M+H$^+$).

Step C

Cis-ethyl(6b,10a)-3-propyl-2,3,6b,9,10,10a-hexahydro-1H-pyrido[3',4':4,5]pyrrolo[1,2,3-de]quinoxaline-8(7H)-carboxylate. Light brown viscous liquid. Yield 69%. MS (CI): 330 (M+H$^+$).

Example 258 cis-(6b,10a)-3-isopropyl-2,3,6b,7,8,9,10,10a-octahydro-1H-pyrido[3',4':4,5]pyrrolo[1,2,3-de] quinoxaline Utilizing the material from Example 255 Step A, the title compound was prepared in analogous fashion using propyl iodide as the alkyl halide and following the procedure of Step B–D of Example 255, as a viscous brown liquid. $^1$H NMR ($CDCl_3$, 300 MHz) δ1.18 (d, 6H), 1.60–1.67 (m, 1H), 1.71–1.94 (m, 2H), 2.63–2.75 (m, 2H), 2.81–2.95 (m, 2H), 2.99–3.20 (m, 2H), 3.30–3.55 (m, 3H), 3.99–4.12 (m, 1H), 6.45 (d, J=7.4 Hz, 2H), 6.65 (t, J=7.3 Hz, 1H) ppm. MS (CI): 258 (M+H$^+$).

Step B

Cis-ethyl(6b,10a)-3-isopropyl-2-oxo-2,3,6b,9,10,10a-hexahydro-1H-pyrido[3',4':4,5]pyrrolo[1,2,3-de] quinoxaline-8(7H)-carboxylate. Viscous brown liquid. Yield 69%. MS (CI) 344 (M+H$^+$).

Step C

Cis-ethyl(6b,10a)-3-isopropyl-2,3,6b,9,10,10a-hexahydro-1H-pyrido[3',4':4,5]pyrrolo[1,2,3-de] quinoxaline-8(7H)-carboxylate. Viscous brown liquid. Yield 97%. MS (CI): 330 (M+H$^+$).

Example 259 cis-(6b,10a)-3-butyl-2,3,6b,7,8,9,10,10a-octahydro-1H-pyrido[3',4':4,5]pyrrolo[1,2,3-de]quinoxaline Utilizing the material from Example 255 Step A, the title compound was prepared in analogous fashion using n-butyl iodide as the alkyl halide and following the procedure of Step B–D of Example 255, as a viscous brown liquid. $^1$H NMR ($CDCl_3$, 300 MHz) δ0.95 (t, 3H), 1.30–1.45 (m, 2H), 1.50–1.65 (m, 2H), 1.95–2.15 (m, 2H), 2.65–2.80 (m, 2H), 2.65–2.80 (m, 2H), 2.85–3.08 (m, 1H), 3.08–3.22 (m, 3H), 3.22–3.40 (m, 6H), 3.68–3.78 (m, 1H), 6.38 (d, J=7.1 Hz), 6.46 (d, J=7.1 Hz, 1H), 6.66 (t, J=7.7 Hz, 1H) ppm. MS (CI): 436 ($M+H^+$).

Step B

Cis-ethyl(6b,10a)-3-butyl-2-oxo-2,3,6b,9,10,10a-hexahydro-1H-pyrido[3',4':4,5]pyrrolo[1,2,3-de]quinoxaline-8(7H)-carboxylate. Viscous brown liquid. Yield 82%. MS (CI): 358 ($M+H^+$).

Step C

Cis-ethyl(6b,10a)-3-butyl-2,3,6b,9,10,10a-hexahydro-1H-pyrido[3',4':4,5]pyrrolo[1,2,3-de]quinoxaline-8(7H)-carboxylate. Viscous brown liquid. Yield 92%. MS (CI): 344 ($M+H^+$).

Example 260 cis-(6b,10a)-3-benzyl-2,3,6b,7,8,9,10,10a-octahydro-1H-pyrido[3',4':4,5]pyrrolo[1,2,3-de]quinoxaline Utilizing the material from Example 255 Step A, the title compound was prepared in analogous fashion using benzyl iodide as the alkyl halide and following the procedure of Step B–D of Example 255, as a viscous liquid. $^1$H NMR ($CDCl_3$, 300 MHz) δ1.60–2.0 (m, 2H), 2.55–2.95(m, 4H), 2.95–3.15 (m, 2H), 3.20–3.45 (m, 3H), 4.40 (q, J=16.1 Hz, 2H), 6.41 (d, J=7.1 Hz, 1H), 6.51 (d, J=7.1 Hz, 1H), 6.62 (t, J=7.1 Hz, 1H), 7.20–7.40 (m, 5H) ppm. MS (CI): 306 ($M+H^+$).

Step B

Cis-ethyl(6b,10a)-3-benzyl-2-oxo-2,3,6b,9,10,10a-hexahydro-1H-pyrido[3',4':4,5]pyrrolo[1,2,3-de]quinoxaline-8(7H)-carboxylate. Viscous brown liquid. Yield 80%. MS (CI) 392 ($M+H^+$).

Step C

Cis-ethyl(6b,10a)-3-benzyl-2,3,6b,9,10,10a-hexahydro-1H-pyrido[3',4':4,5]pyrrolo[1,2,3-de]quinoxaline-8(7H)-carboxylate. Viscous brown liquid. Yield 85%. MS (CI): 378 ($M+H^+$).

Example 261 cis-4-((6b,10a)-3-methyl-2,3,6b,9,10,10a-hexahydro-1H-pyrido[3',4':4,5]pyrrolo[1,2,3-de]quinoxaline-8(7H)-yl)-1-(4-fluorophenyl)-1-butanone A mixture of cis-(6b,10a)-3-methyl-2,3,6b,7,8,9,10,10a-octahydro-1H-pyrido[3',4':4,5]pyrrolo[1,2,3-de]quinoxaline (3.20 g, 14 mmol), 4-chloro-4'-fluoro-butyrophenone (4.21 g, 21 mmol), triethylamine (3 mL), potassium iodide (3.48 g, 21 mmol), dioxane (25 mL), and toluene (25 mL) was stirred and refluxed for 15 h under an atmosphere of nitrogen and then evaporated under reduced pressure to remove the volatiles. The residue was triturated with a small volume of dichloromethane and decanted from the insoluble material. The process was repeated two more times and the combined dichloromethane solutions was added to 0.5N solution of hydrogen chloride in ether(200 mL). The salt that separated was filtered off, washed with ether, dissolved immediately in a minimum quantity of water and the solution extracted with ether. The ether extract was discarded and aqueous layer basified with 10% aqueous sodium hydroxide. The resulting mixture was extracted with dichloro-methane (2×) and the extract dried over magnesium sulfate and stripped of the solvent under reduced pressure to yield 4.15 g (75%) of a highly viscous brown liquid. $^1$H NMR ($CDCl_3$, 300 MHz) δ1.79–2.13 (m, 6H), 2.21–2.32 (m, 1H), 2.32–2.44 (m, 2H), 2.60–2.71 (m, 1H), 2.75–2.92 (m, 2H), 2.86 (s, 3H), 2.98 (t, J=7.3Hz, 2H), 3.04–3.16 (m, 1H), 3.16–3.35 (m, 2H), 3.55–3.64 (m, 1H), 6.39 (d, J=8.1 Hz, 1H), 6.50 (d, J=8.1 Hz, 1H), 6.64 (t, J=7.7 Hz, 1H), 7.12 (t, 2H), 8.01 (m, 2H) ppm. MS (CI): 394 ($M+H^+$).

The above compound was resolved into its enatiomers on chiral HPLC column. 4-((6bR,10aS)-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone. Viscous tan liquid. $[a]^D$=−36.8° (c=0.886, $CHCl_3$). MS (CI): 384 ($M+H^+$).

4-((6bS,10aR)-3-methyl-2,3,6b,9,10,10a-hexahydro-1H-pyrido[3',4':4,5]-pyrrolo[1,2,3-de]quinoxalin-8(7H)-yl)-1-(4-fluorophenyl)-1-butanone. Viscous tan liquid. $[a]^D$=+33.6° (c=0.646, $CHCl_3$). MS (CI): 394 ($M+H^+$).

Example 262 cis-4-((6b,10a)-3-ethyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone Treatment of cis-(6b,10a)-3-ethyl-2,3,6b,7,8,9,10,10a-octahydro-1H-pyrido[3',4':4,5]pyrrolo[1,2,3-de]quinoxaline according to the procedure of Example 261 afforded the title compound in good yield as a viscous brown liquid. $^1$H NMR (300 MHz, $CDCl_3$) δ1.15 (t, J=7.0 Hz, 3H), 1.75–2.03 (m, 5H), 2.20 to 2.30 (m, 1H), 2.30–2.42 (m, 2H), 2.63 to 2.77 (m, 3H), 2.77 to 2.87 (m,1H), 2.98 (t, J=7.0 HZ, 2H), 3.04–3.43 (m, 5H), 3.64–3.72 (m, 1H0, 6.30 (d, J=7.7 Hz, 1H), (6.47 d, J=7.7 Hz, 1H), 6.64 (d, J=7.7 Hz, 1H), 7.12 (t, J=8.5 Hz, 2H), 7.98 to 8.03 (m, 2H) ppm. MS (CI): 408 ($M+H^+$).

Example 263 cis-4-((6b,10a)-3-isopropyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone Treatment of cis-(6b,10a)-3-isopropyl-2,3,6b,7,8,9,10,10a-octahydro-1H-pyrido[3',4':4,5]pyrrolo[1,2,3-de]quinoxaline according to the procedure of Example 261 afforded the title compound in good yield as a viscous, brown liquid. $^1$H NMR ($CDCl_3$, 300 MHz) δ1.18 (d, J=6.6 Hz, 6H), 1.82–1.84 (m, 5H), 2.21–2.29 (m, 1H), 2.29–2.41 (m, 2H), 2.64–2.68 (m, 2H), 2.79–2.87 (m, 1H), 2.98 (t, J=7.3 Hz, 2H), 3.03–3.17 (m, 2H), 3.21–3.45 (m, 3H), 4.03 (d, J=6.6, 2.3 Hz, 1H), 6.45 (d, J=6.2 Hz, 2H), 6.64 (t, J=7.7 Hz, 1H), 7.12 (t, J=8.3 Hz, 2H), 8.0–8.03 (m, 2H) ppm. MS (CI): 422 ($M+H^+$).

Example 264 cis-4-((6b,10a)-3-benzyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone Treatment of cis-(6b,10a)-3-benzyl-2,3,6b,7,8,9,10,10a-octahydro-1H-pyrido[3',4':4,5]pyrrolo[1,2,3-de]quinoxaline according to the procedure of Example 261 afforded the title compound in good yield as a viscous brown liquid. Yield 23%. $^1$H NMR ($CDCl_3$, 300 MHz) δ1.84–2.05 (m, 5H), 2.20–2.31 (m, 1H), 2.31–2.43 (m, 2H), 2.64–2.72 (m, 1H), 2.72–2.80 (m, 1H), 2.80–2.89 (m, 1H), 2.99 (t, J=7.3 Hz, 2H), 3.06–3.14 (m, 1H), 3.14–3.26 (m, 1H), 3.26–3.34 (m, 2H), 3.65–3.74 (m, 1H), 4.43 (q, J=16.5 Hz, 2H), 6.40 (d, J=8.0 Hz, 1H), 6.50 (d, J=7.0 Hz, 1H),) 6.61 (t, J=8.1 Hz, 1H), 7.13 (t, J=8.5 Hz, 2H), 7.20–7.35 (m, 5H), 8.00–8.03 (m, 2H) ppm. MS (CI): 470 ($M+H^+$).

Example 266 cis-4-((6b,10a)-6-methyl-1,2,6b,9,10,10a-hexahydro-[1,4]oxazino[2,3,4-hi]pyrido[4,3-b]indol-8(7H)-yl)-1-(4-fluorophenyl)-1-butanone Treatment of cis-(6b,10a)-6-methyl-1,2,6b,7,8,9,10,10a-octahydro [1,4] oxazino[2,3,4-hi]pyrido[4,3-b]indole according to the procedure of Example 261 afforded the title compound in good yield as a viscous light brown liquid. Yield 53%. $^1H$ NMR ($CDCl_3$, 300 MHz) δ1.82–2.10 (m, 5H), 2.18 (s, 3H), 2.20–2.35 (m, 1H), 2.43 (t, J=6.9 Hz, 2H), 2.60–2.80 (m, 2H), 2.88–3.05 (m,1H), 2.99 (t, J=7.3 Hz, 2H), 3.07–3.20 (m, 2H), 3.25 (d, J=11 Hz, 1H), 4.35–4.45 (m, 2H), 6.44 (d, J=8.1 Hz, 1H), 6.53 (d, J=8.1 Hz, 1H), 7.13 (t, 8.4 Hz, 2H), 7.99–8.04 (m, 2H) ppm. MS (CI): 395 ($M+H^+$).

Example 268

4-(cis-(8a,12a)-2-fluoro-6,7,9,10,12,12a-hexahydro-5H-pyrido[4,3-b][1,4]thiazepino[2,3,4-hi]indol-11 (8aH)-yl)-1-(4-fluorophenyl)-1-butanone Treatment of cis-(8a,12a)-2-fluoro-6,7,8a,9,10,11,12,12a-octahydro-5H-pyrido[4,3-b][1,4]thiazepino[2,3,4-hi]indole according to the procedure of Example 261 afforded the title compound in good yield as a viscous oil, M.P. 226–227° C. Yield 27%. $^1H$ NMR ($CDCl_3$, 300 MHz) δ1.50–2.20 (m, 8H), 2.20–2.32 (m, 1H), 2.32–2.50 (m, 1H), 2.50–2.63 (m, 1H), 2.63–2.78 (m, 1H), 2.78–3.30 (m,6H), 3.45–3.60 (m, 1H), 3.60–3.77 (m,1H), 6.57 (d, J=7.7 Hz, 1H), 6.67 (t, J=6.2 Hz, 1H), 7.13 (t, J=7.8 Hz, 2H), 7.97–8.02 (m, 2H), ppm. MS (CI): 429 ($M+H^+$).

Example 269 cis-(6b,10a)-8-[3-(4-fluorophenoxy)propyl]-3-methyl-2,3,6b,7,8,9,10,10a-octahydro-1H-pyrido[3',4':4,5]pyrrolo[1,2,3-de]quinoxaline Treatment of cis-(6b,10a)-3-methyl-2,3,6b,7,8,9,10,10a-octahydro-1H-pyrido[3',4':4,5]pyrrolo[1,2,3-de]quinoxaline according to the procedure of Example 203 afforded the title compound in good yield as a viscous liquid. Yield 30%. $^1H$ NMR ($CDCl_3$, 300 MHz): δ1.85–2.10 (m, 5H), 2.20–2.40 (m, 1H)2.40–2.60 (m, 2H), 2.66–2.78 (m, 1H), 2.78–2.95 (m, 2H), 2.87 (t, 3H), 3.10–3.35 (m, 4H), 3.55–3.70 (m, 1H), 3.97 (t, J=6.2 Hz, 2H), 6.40 (d, J=7.7 Hz, 1H), 6.52 (d, J=7.3 Hz, 1H), 6.65 (t, J=7.7 Hz, 1H), 6.79–6.90 (m, 2H), 6.96 (t, J=8.5 Hz, 2H) ppm. MS (CI): 382 ($M+H^+$).

Example 270 cis-(6b,10a)-8-[3-(4-fluorophenoxy)propyl]-1,2,6b,7,8,9,10,10a-octahydro-[1,4]oxazino[2,3,4-hi]pyrido [4,3-b]indole Treatment of cis-(6b,10a)-1,2,6b,7,8,9,10,10a-octahydro [1,4]oxazino[2,3,4-hi]pyrido[4,3-b]indole according to the procedure of Example 203 afforded the title compound in good yield as a viscous liquid. Yield 32%. $^1H$ NMR ($CDCl_3$, 300 MHz) δ1.91–2.02 (m, 3H), 2.06 (t, J=11.4 Hz, 1H), 2.26–2.40 (m, 2H), 2.40–2.60 (m, 2H), 2.65–2.80 (m, 2H), 2.80–2.95 (m, 1H), 3.05–3.22 (m, 1H), 3.22–3.32 (m, 2H), 3.98 (t, J=6.3, Hz, 2H), 4.40–4.50 (m, 2H), 6.60–6.65 (m, 2H), 6.65–6.75 (m, 1H), 6.75–6.85 (m, 2H), 6.85–7.0 (m, 2H) ppm. MS (CI): 369 ($M+H^+$).

Example 271 cis-(8a,12a)-6,7,8a,9,10,11,12,12a-octahydro-5H-pyrido[4,3-b][1,4]thiazepino[2,3,4-hi]indole Powdered, fresh sodium cyanoborohydride (49.92 g, 0.8 mol) was added in small portions to a vigorously stirred and cooled solution of 6,7,9,10,11,12-hexahydro-5H-4,3-b][1,4] thiazepino[2,3,4-hi]indole (48.8 g, 0.2 pyrido[mol) in trifluoroacetic acid (300 mL) under nitrogen. After the addition was complete, the mixture was stirred at room temperature for 4 hrs and then treated carefully with 6N aqueous HCl (350 mL) with vigorous stirring. The mixture was then heated under reflux for 30 mins. cooled, basified with 20% aqueous sodium hydroxide, and extracted with chloroform (3×). The extract was washed with water, dried over magnesium sulfate, and evaporated to dryness under reduced pressure to furnish a colorless solid which was recrystallized from hexanes to yield 42.8 g (87%) of the product as colorless crystals, m.p. 72–73° C. $^1H$ NMR ($CDCl_3$, 300 MHz) δ1.30 (s, 1H), 1.68–1.85 (m, 2H), 1.95–2.20 (m, 2H), 2.53–2.65 (m, 1H), 2.73–2.93 (m, 2H), 2.93–3.10 (m, 3H), 3.10–3.28 (m, 1H), 3.33–3.45 (m, 1H),3.45–3.58 (m, 1H), 3.68–3.83 (m, 1H), 6.63 (t, 1H, J=7.3 Hz), 6.85 (d, 1H, J=7.3 Hz), 6.95 (d, 1H, J=7.3 Hz) ppm. MS (CI): 247 ($M+H^+$).

The resolution of Example 271 into its enantiomers was carried out by High Performance Liquid Chromatography using a chiral column and the enantiomers thus obtained were converted into their hydrochloride salts by dissolving each of them individually in a small volume of tetrahydrofuran and adding the resulting solution to an excess of a solution of hydrogen chloride in ether, filtering off the salt, washing with ether, and drying it in vacuo at 45° C. for 4 hrs.

(8aS,12aR)-6,7,8a,9,10,11,12,12a-octahydro-5H-pyrido [4,3-b][1,4]thiazepino[2,3,4-hi]indole hydrochloride. Colorless solid, m.p. 268–269° C. (dec.). $[a]^D$=−127.48° (c=0.644, MeOH). $^1H$ NMR ($Me_2SO$-$d_6$, 300 MHz) δ1.85–2.15 (m, 4H), 2.91–3.08 (m, 2H), 3.08–3.20 (m, 2H), 3.20–3.31 (m,1H), 3.31–3.41 (m, 3H), 3.41–3.55 (m, 1H), 3.55–3.65 (m,1H), 6.65 (t, 1H, J=7.3 Hz), 6.90 d, 1H, J=7.3 Hz), 6.98 (d, 1H, J=7.3 Hz), 9.08 (bs, 1H), 9.15 (bs, 1H) ppm.

Cis-(8aR,12aS)-6,7,8a,9,10,11,12,12a-octahydro-5H-pyrido[4,3-b][1,4]thiazepino[2,3,4-hi]indole hydrochloride. Colorless solid. m.p. 269–270° C. (dec.). $[a]^D$=+127.91° (c=0.634, MeOH).

Example 272 cis-(6b,10a)-1,2,6b,7,8,9,10,10a-octahydro-[1,4] oxazino[2,3,4-hi]pyrido[4,3-b]indole Treatment of benzo[b]morpholine according to the procedure of Example 4, Step E, followed by the procedure of Example 128, Steps A–C, afforded the title compound as colorless crystals, m.p.100–101° C. $^1H$ NMR ($CDCl_3$, 300 MHz) δ1.77–1.95 (m, 2H), 2.15 (s, 1H), 2.61–2.85 (m,2H), 2.85–3.00 (m, 2H), 3.03–3.21 (m, 2H), 3.28–3.41 (m, 2H), 4.40–4.51 (m,2H), 6.60–6.68 (m, 2H), 6.68–6.73 (m, 1H) ppm. MS (CI): 217 ($M+H^+$).

Example 273 cis-(8a,12a)-2-fluoro-6,7,8a,9,10,11,12,12a-octahydro-5H-pyrido[4,3-b][1,4]thiazepino[2,3,4-hi] indole Treatment of p-fluoroaniline according to the procedure of Example 10, Steps A–D, followed by the procedure of Example 11, afforded the title compound as colorless crystals, m.p.67–68° C. $^1$H NMR ($CDCl_3$, 300 MHz) δ1.65 (s, 1H), 1.65–1.93 (m, 2H), 1.95–2.20 (m,2H), 2.53–2.63 (m, 1H), 2.78–2.93 (m, 2H), 2.93–3.05 m, 3H), 3.08–3.21 (m, 1H), 3.30–3.40 (m, 1H), 3.48–3.60 (m, 1H), 3.60–3.73 (m, 1H), ppm. MS (CI): 265 ($M+H^+$).

Example 274

(8aS,12aR)-3-bromo-6,7,8a,9,10,11,12,12a-octahydro-5H-pyrido[4,3-b][1,4]thiazepino[2,3,4-hi] indole hydrochloride Step A A mixture of 2-chloro-3-nitrobenzoic acid (15 g, 74.4 mmol), red mercury oxide (24.2 g, 112 mmol), and carbon tetrachloride (350 mL) were irradiated with a 100 W light bulb and heated at reflux. Bromine (5.75 mL, 112 mmol) was added dropwise over 30 minutes. This was stirred at reflux for 3.5 hours. After cooling to room temperature, aqueous saturated sodium bicarbonate (250 mL) was added and stirred vigorously for 20 minutes. The mixture was filtered and the solids were washed with excess chloroform. This two-phase solution was separated and the aqueous layer back extracted with chloroform (2×200 mL). The organic layers were collected and washed with brine (150 mL), water (150 mL) and dried (magnesium sulfate) and concentrated to give 3-bromo-2-chloronitrobenzene (10.6 g, 60.4%). $^1$H NMR ($CDCl_3$, 300 MHz): δ7.86 (dd, 1H, J=8.1, 1.5), 7.73 (dd, 1H, J=8.1, 1.5 Hz), 7.31 (t, 1H, J=8.1 Hz) ppm.

Step B

3-Bromo-2-chloronitrobenzene (9 g, 38.1 mmol) and 3-chloro-1-propanethiol were dissolved in anhydrous tetrahydrofuran (75 mL) and cooled to 0° C. in an ice bath. Potassium hydroxide (3.2 g, 57.2 mmol) was added slowly. The reaction mixture was then allowed to warm to room temperature and stirred over night. Reaction was filtered, and filtrate was concentrated to the 1-bromo-2-[(3-chloropropyl)thio]-3-nitrobenzene (11.18 g, 94.6%). $^1$H NMR ($CDCl_3$, 300 MHz): δ7.84 (dd, 1H, J=8.1, 1.1 Hz), 7.51 (dd, 1H, J=8, 1.4 Hz), 7.3–7.267 (m, 1H), 3.63 (t, 2H, J=6.2 Hz), 3.09 (t, 2H, J=6.95 Hz), 2.04–1.95 (m, 2H) ppm.

Step C

1-Bromo-2-[(3-chloropropyl)thio]-3 -nitrobenzene (6.78 g, 21.9 mmol) was dissolved in ethyl alcohol (125 mL) and cooled in an ice bath to 0° C. Tin (II) chloride dihydrate (7.4 g, 32.8 mmol) was dissolved in concentrated hydrochloric acid (25 mL) and then added to the first solution over 20 minutes. The reaction was then allowed to warm to room temperature and stirred over night. Reaction mixture was cooled to 0° C. in an ice bath and another (1.5 eq, 7.4 g) of tin (II) chloride dihydrate in concentrated hydrochloric acid (25 mL) was added. This was stirred at 0° C. for 30 minutes and then allowed to warm to room temperature and stirred until loss of starting material. Reaction was then basified to pH 12 with ammonium hydroxide and then filtered. The filtrate was then concentrated to a aqueous slurry, the slurry was then diluted with water (100 mL) and extracted with ethyl acetate (3×300 mL). Organic extracts were dried over magnesium sulfate and filtered. The filtrate was concentrated to give 1-bromo-2-[(3-chloropropyl)thio]-benzenamine (5.7 g, 93.2%). $^1$H NMR ($CDCl_3$, 300 MHz): δ7.02–60.87 (m, 2H), 6.65 (dd, 1H, J=7.7, 1.9 Hz), 4.63 (s-broad, 2H), 3.68 (t, 2H, J=6.4 Hz), 2.92 (t, 2H, J=6.95 Hz), 2.04–1.95 (m, 2H) ppm.

Step D

1-Bromo-2-[(3-chloropropyl)thio]-benzenamine (5.7 g, 20.4 mmol) was dissolved in trifluoroacetic acid (52 mL), then concentrated hydrochloric acid (48 mL) was added and cooled to 0° C. in an ice bath. Sodium nitrite (1.69 g, 24.48 mmol) in water (6 mL) was added slowly to reaction mixture over 20 minutes, maintaining reaction temperature below 8° C. This was stirred at 0° C. for 1 hour. Tin (II) chloride dihydrate (10.1 g, 44.79 mmol) was dissolved in concentrated hydrochloric acid (12 mL) and cooled to 0° C. in an ice bath, then added slowly to the reaction mixture over 20 minutes. After addition the reaction was allowed to warm to room temperature and stir for 14 hours. The reaction was filtered and the filter cake was dissolved in water and basified to pH=10 with saturated potassium carbonate and then extracted with chloroform (3×200 mL). The organic extracts were washed with water (100 mL), and dried over magnesium sulfate. The organics were concentrated to give 1-[3-bromo-2-[(3-chloropropyl)thio]phenyl]-hydrazine (4.5 g, 75.3%). $^1$H NMR ($CDCl_3$, 300 MHz): δ7.16–7.01 (m, 3H), 6.70 (s-broad, 1H), 3.68 (t, 2H, J=6.25 Hz), 3.61 (s-broad, 2H), 2.89 (t, 2H, J=7 Hz), 2.01–1.92 (m, 2H) ppm.

Step E

1-[3-Bromo-2-[(3-chloropropyl)thio]phenyl]-hydrazine (2.4 g, 7.25 mmol) was suspended in isopropyl alcohol (14 mL) then hydrogen chloride gas was bubbled through and the suspension became a solution after 15 minutes. The reaction was sealed in pressure flask and heated at 80° C. for 14 hours. It was cooled to room temperature and filtered to give 7-bromo-6-[(3-chloropropyl)sulfanyl]-2,3,4,5-tetrahydro-1H-pyrido[4,3b]indole hydrochloride as a tan solid (1.9 g, 66%). $^1$H NMR ($CD_3OD$, 300 MHz): δ7.34–7.29 (m, 2H), 4.40 (s, 2H), 3.67–3.58 (m, 4H), 3.18–3.16 (m, 2H), 3.01 (t, 2H, J=6.95), 1.87–1.82 (m, 2H) ppm.

Step F

7-Bromo-6-[(3-chloropropyl)sulfanyl]-2,3,4,tetrahydro-1H-pyrido[4,3b]indole hydrochloride (2.06 g, 5.75 mmol), potassium hydroxide (3.2 g, 57.5 mmol), and potassium iodide (1.14 g, 6.9 mmol) were dissolved in diethylene glycol dimethyl ether (192 mL) and heated at reflux for 13 hours. Reaction was cooled to room temperature and filtered. The filtrate was concentrated under reduced pressure to give a brown oil. This oil was mostly dissolved in chloroform and re-filtered, the filtrate was again concentrated under reduced pressure to give a brown oil. The oil was purified by silica gel column chromatography, eluting with (0%, 10%, and 25%) methanol in chloroform to afford 3-bromo-6,7,9,10,11,12-hexahydro-5H-pyrido[4,3-b][1,4] thiazepino[2,3,4-hi]indole as an oil (210 mg, 12%). $^1$H NMR ($CDCl_3$, 300 MHz): δ7.12 (d, 1H, J=8.1 Hz), 6.94 (d, 1H, J=8.1 Hz), 4.42 (t, 2H, J=5.85 Hz), 4.01 (s, 2H), 3.37–3.28 (m, 4H), 2.71 (t, 2H, J=5.5), 2.28–2.20 (m, 2H) ppm.

Step G

3-Bromo-6,7,9,10,11,12-hexahydro-5H-pyrido[4,3-b][1,4]thiazepino[2,3,4-hi]indole (480 mg, 1.5 mmol) was dissolved in trifluoroacetic acid (8 mL) at room temperature, and then cooled to 0° C. in an ice bath. Sodium cyanoborohydride (408 mg, 6.0 mmol) was added in portions over 30 minutes. This mixture was stirred at 0° C. for an additional 6 hours. This solution was transferred via cannula to a saturated solution of potassium carbonate (aqueous) and ice chips (200 mL total volume) over 10 minutes. This mixture was stirred at ambient temperature for 3 minutes, tetrahydrofuran (200 mL) was added, followed by 4-(dimethylamino)pyridine (20 mg, 0.163 mmol) and di-tert-butyl di-carbonate (330 mg, 1.5 mmol). The two phased mixture was vigorously stirred for 1.5 hours at room temperature, starting at and warming to room temperature.

The reaction was extracted with ethyl acetate (3×100 mL) and the combined extracts were washed with brine (200 mL), water (200 mL) and dried over magnesium sulfate, and concentrated under reduced pressure to give an oil. The oil was purified by silica gel column chromatography (5 g) eluting with (20%) ethyl acetate in hexanes to afford the tert-butyl(8aS,12aR)-3-bromo-6,7,9,10,12,12a-hexahydro-5H-pyrido[4,3-b][1,4]thiazepino[2,3,4-hi]indole-11(8aH)-carboxylate (235 mg, 35%). $^1$H NMR ($CDCl_3$, 300 MHz): δ6.93 (d, 1H, J=7.7 Hz), 6.84 (d, 1H, J=7.7 Hz), 3.87–3.83 (m, 1H), 3.59–3.40 (m, 3H), 3.39–2.93 (m, 4H), 2.10–1.98 (m, 2H), 1.81–1.76 (m, 2H), 1.52 (s-broad, 2H), 1.34 (s-broad, 9H) ppm. Mass Spec (CI): 426 (base M+H).

Step H

Tert-butyl(8aS,12aR)-3-bromo-6,7,9,10,12,12a-hexahydro-5H-pyrido[4,3-b][1,4]thiazepino[2,3,4-hi]indole-11(8aH)-carboxylate (23 mg, 0.054 mmol) was dissolved in chloroform (2 mL) and methyl alcohol (0.5 mL) at room temperature. Then hydrogen chloride gas was bubbled through for 10 minutes. Reaction was then concentrated under reduced pressure to give the title compound (15 mg, 77%). $^1$H NMR ($CD_3OD$, 300 MHz): δ6.96 (d, 1H, J=8 Hz); 6.83 (d, 1H, J=8.1 Hz); 4.92–3.98 (m, 1H); 3.17–3.60 (m, 1H); 3.39–3.11 (m, 6H); 3.09–2.99 (m, 1H); 2.78–2.70 (m, 1H); 2.23–1.87 (m, 4H) ppm. Mass Spec (ApCI): 326 (base M+H).

Example 275

(8aS,12aR)-3-(2,6-Difluorophenyl)-6,7,8a,9,10,11,12,12a-octahydro-5H-pyrido[4,3-b][1,4]thiazepino[2,3,4-hi]indole, trifluoroacetate salt Step A Tert-butyl(8aS,12aR)-3-bromo-6,7,9,10,12,12a-hexahydro-5H-pyrido[4,3-b][1,4]thiazepino[2,3,4-hi]indole-11(8aH)-carboxylate (40 mg, 0.094 mmol), triphenyl phosphine (5 mg, 0.019 mmol), copper (II) bromide (3 mg, 0.019 mmol) and dichlorobis(triphenylphosphine)palladium (II) (7 mg, 0.0094 mmol) were dissolved N,N-dimethylformamide (1.0 mL). This solution was degassed for 10 minutes, then (2, 6-difluoro-phenyl)trimethylstannane (40 mg, 0.141 mmol) in degassed N,N-dimethylformamide (0.5 mL) and heated to 60° C. stirred for 45 min. Another (20 mg, 0.071 mmol) then (2,6-difluoro-phenyl) trimethylstannane in degassed N,N-dimethylformamide (0.4 mL) was added and reaction heated to 140° C. for 10 minutes. A final (20 mg, 0.071 mmol) of then (2,6-difluorophenyl)trimethylstannane in degassed N,N-dimethylformamide (0.4 mL) was added and reaction heated at 140° C. for 1.25 hours. The reaction temperature was then raised to 154° C. for 2 hours, then cooled to room temperature and diluted with ethyl acetate (10 mL) and water (10 mL). Organics were separated and washed with water (3×20 mL) and dried over magnesium sulfate and concentrated under reduced pressure to give an oil. The oil was purified by silica gel column chromatography, eluting with (10%) ethyl acetate in hexanes. The isolated oil was purified further by high pressure liquid chromatography on a Chiralcel OD column, eluted with 2% ethyl alcohol in hexanes (0.05% diethyl amine modifier) at 7 mL/min to afford of tert-butyl (8aS,12aR)-3-(2,6-difluorophenyl)-6,7,9,10,12,12a-hexahydro-5H-pyrido[4,3-b][1,4]thiazepino[2,3,4-hi]indole-11(8aH)-carboxylate as an oil (9.3 mg, 21%). $^1$H NMR ($CDCl_3$, 300 MHz): δ7.35–7.7.27 (m, 1H), 6.98–6.90 (m, 3H), 6.64 (d, 1H, J=7.3 Hz), 4.10–4.01 (m, 1H), 3.68–3.51 (m, 4H), 3.38–3.22 (m, 2H), 3.20–3.09 (m, 1H), 2.98–2.81 (m, 1H), 2.18–2.00(m, 2H), 1.91–1.86 (m, 2H), 1.60–1.55 (m, 1H), 1.43 (s-broad, 9H) ppm. MS (ApCI): 459 (base, M+H).

Step B

Tert-butyl(8aS,12aR)-3-(2,6-difluorophenyl)-6,7,9,10,12,12a-hexahydro-5H-pyrido[4,3-b][1,4]thiazepino[2,3,4-hi]indole-11(8aH)-carboxylate (9.3 mg, 0.0203 mmol) was dissolved in chloroform (5 mL) and cooled to 0° C. in an ice bath and trifluoroacetic acid (1 mL) was added and stirred for 3 hours, during which time reaction warmed to room temperature. The reaction was concentrated under reduced pressure to a residue then kept at reduced pressure for 13 hours to give the title compound as an amorphous solid (10 mg, 83%) $^1$H NMR ($CD_3OD$, 300 MHz): δ7.41–7.31 (m, 1H), 7.08–6.91 (m, 3H), 6.60 (d, 1H, J=7.7 Hz), 4.07–3.91 (m, 1H), 3.63–3.34 (m, 4H), 3.22–3.13 (m, 2H), 2.92–2.78 (m, 2H), 2.31–1.85 (m, 5H) ppm. MS (ApCI): 359 (base, M+H)

Example 276

(8aS,12aR)-3-(4-methoxy-2-methylphenyl)-6,7,8a,9,10,11,12,12a-octahydro-5H-pyrido[4,3-b][1,4]thiazepino[2,3,4-hi]indole Tert-butyl(8aS,12aR)-3-bromo-6,7,9,10,12,12a-hexahydro-5H-pyrido[4,3-b][1,4]thiazepino[2,3,4-hi]indole-11(8aH)-carboxylate (100 mg, 0.235 mmol), 2-methyl-4-methoxyphenyl boronic acid (125 mg, 0.282 mmol) and barium hydroxide (112 mg, 0.353 mmol) were dissloved in ethylene glycol dimethyl ether (3.2 mL) and water (1.1 mL). This solution was degassed for 3 minutes, then tetrakis(triphenylphosphine)palladium(0) (6 mg, 0.0047 mmol) was added and reaction heated at 90° C. for 14 hours. Reaction was cooled to room temperature and then an additional (125 mg, 0.282 mmol) 2-methyl-4-methoxyphenyl boronic acid and (6 mg, 0.0047 mmol) tetrakis(triphenylphosphine)palladium(0) were added, then heated at 90° C. for 14 hours. Reaction was cooled and diluted with ethyl acetate (25 mL) and water (5 mL). Organics were separated and washed with brine (25 mL) and dried over magnesium sulfate. Concentrated under reduced pressure to give an oil, which was purified by silica gel column chromatography, eluting with (14%) ethyl acetate in hexanes to give an oil. The oil was dissolved in chloroform (10 mL) and cooled to 0° C. in an ice bath and trifluoroacetic acid (2 mL) was added and stirred for 3 hours, during which time reaction warmed to room temperature. This was basified with concentrated ammonium hydroxide to pH=12, then extracted with chloroform (3×20 mL). Organics were filtered and then concentrated under reduced pressure to give a brown oil. This oil was purified further by high pressure liquid chromatography on a Chiralcel OD column, eluted with 6% ethyl alcohol in hexanes (0.05% diethyl amine modifier) at 7 mL/min to afford title compound as an oil. $^1$H NMR ($CDCl_3$, 300 MHz): δ7.07–7.03 (m, 1H), 6.86–6.72 (m, 3H), 6.50–6.46 (m, 1H), 4.08–3.83 (m, 1H), 3.81 (s, 3H), 3.60–3.51 (m, 1H), 3.44–3.37 (m, 1H), 3.29–2.80 (m, 5H), 2.77–2.51 (m, 1H), 2.14(d, 3H, J=10.6), 2.10–1.70 (m, 5H) ppm. MS (ApCI): 367 (base, M+H).

Example 277

(8aS,12aR)-3-[4-(Trifluoromethyl)phenyl]6,7,8a,9,10,11,12,12a-octahydro-5H-pyrido[4,3-b][1,4]thiazepino[2,3,4-hi]indole Tert-butyl(8aS,12aR)-3-bromo-6,7,9,10,12,12a-hexahydro-5H-pyrido[4,3-b][1,4]thiazepino[2,3,4-hi]indole-11(8aH)-carboxylate (86 mg, 0.202 mmol), 4-trifluoromethylphenyl boronic acid (46 mg, 0.243 mmol) and barium hydroxide (96 mg, 0.304 mmol) were dissloved in ethylene glycol dimethyl ether (3.2 mL) and water (1.1 mL). This solution was degassed for 3 minutes, then tetrakis (triphenylphosphine)palladium(0) (5 mg, 0.00405 mmol) was added and reaction heated at 90° C. for 14 hours. Reaction was cooled to room temperature and then an additional (46 mg, 0.243 mmol) 4-trifluoromethylphenyl boronic acid and (5 mg, 0.00405 mmol) tetrakis (triphenylphosphine)palladium(0) were added, then heated at 90° C. for 14 hours. Reaction was cooled and diluted with ethyl acetate (10 mL) and water (10 mL). Organics were separated and washed with brine and dried over magnesium sulfate. Then, filtered and the filtrate was concentrated under reduced pressure to give an oil, which was purified by silica gel column chromatography, eluting with (14%) ethyl acetate in hexanes to give an oil. The oil was dissolved in chloroform (10 mL) and cooled to 0° C. in an ice bath and trifluoroacetic acid (2 mL) was added and stirred for 3 hours, during which time reaction warmed to room temperature. This was basified with concentrated ammonium hydroxide to pH 12, then extracted with chloroform (3×25 mL).). Organics were separated and washed with brine and dried over magnesium sulfate. Organics were filtered and then concentrated under reduced pressure to give a brown oil. This oil was purified further by high pressure liquid chromatography on a Chiralcel OD column, eluted with 6% ethyl alcohol in hexanes (0.05% diethyl amine modifier) at 7 mL/min to afford the title compound (5.6 mg, 7%) as an oil. $^1$H NMR ($CDCl_3$, 300 MHz): δ7.63 (d, 2H, J=8.1 Hz), 7.48 (d, 2H, J=8 Hz), 6.89 (d, 1H, J=7.3 Hz), 6.60 (d, 1H, J=7.3 Hz), 4.07–3.98 (m, 1H), 3.59–3.49 (m, 1H), 3.47–3.42 (m, 1H), 3.27–3.20 (m, 1H), 3.09–3.01 (m, 2H), 2.97–2.81(m, 3H), 2.72–2.63 (m, 1H), 2.15–1.58 (m, 4H) ppm. MS (ApCI): 391 (base, M+H).

Example 278

(8aS,12aR)-3-(2,3-Dichlorophenyl)-6,7,8a,9,10,11,12,12a-octahydro-5H-pyrido[4,3-b][1,4]thiazepino[2,3,4-hi]indole (8aS,12aR)-3-(2,3-Dichlorophenyl)-6,7,8a,9,10,11,12,12a-octahydro-5H-pyrido[4,3-b][1,4]thiazepino[2,3,4-hi]indole was obtained following the procedure listed in example 277, using the appropriate boronic acid to give the title compound (32 mg, 35%). $^1$H NMR ($CDCl_3$, 300 MHz): δ7.44 (d, 1H, J=6.9 Hz); 7.24–7.12 (m, 2H); 6.90–6.86 (m, 1H); 6.49 (dd, 1H, J=2.2, 7.4 Hz); 4.03–3.80 (m, 1H); 3.62–2.61 (m, 9H); 2.18–1.82 (m, 4H) ppm. MS (ApCI): 391 (base, M+H).

Example 279

(8aS,12aR)-3-(2,4-Dichlorophenyl)-6,7,8a,9,10,11,12,12a-octahydro-5H-pyrido[4,3-b][1,4]thiazepino[2,3,4-hi]indole (8aS,12aR)-3-(2,4-Dichlorophenyl)-6,7,8a,9,10,11,12,12a-octahydro-5H-pyrido[4,3-b][1,4]thiazepino[2,3,4-hi]indole was obtained following the procedure listed in example 277, using the appropriate boronic acid to give the title compound (13.5 mg, 15%). $^1$H NMR ($CDCl_3$, 300 MHz): δ7.45 (d, 1H, J=5.5 Hz); 7.40–7.04 (m, 2H); 6.90 (d, 1H, J=7.3 Hz); 6.51 (d, 1H, J=6.2 Hz); 4.16–3.84 (m, 1H); 3.65–2.84 (m, 8H); 2.70 (t, 1H, J=10.5 Hz); 2.17–1.83 (m, 4H) ppm. MS (ApCI): 391 (base, M+H).

Example 280

(8aS,12aR)-3-[2-Chloro-4-(trifluoromethyl)phenyl]-6,7,8a,9,10,11,12,12a-octahydro-5H-pyrido[4,3-b][1,4]thiazepino[2,3,4-hi]indole (8aS,12aR)-3-[2-Chloro-4-(trifluoromethyl)phenyl]-6,7,8a,9,10,11,12,12a-octahydro-5H-pyrido[4,3-b][1,4]thiazepino[2,3,4-hi]indole was obtained following the procedure listed in example 277, using the appropriate boronic acid to give the title compound (13.5 mg, 15%). $^1$H NMR ($CDCl_3$, 300 MHz): δ7.72 (d, 1H, J=5.2 Hz); 7.55 (t, 1H, J=8.25 Hz); 7.39–7.35 (m, 1H); 6.94 (dd, 1H, J=7.3, 2.6 Hz); 6.53 (q, 1H, J=3.8 Hz); 4.11–3.80 (m, 2H); 3.63–3.40 (m, 2H); 3.29–2.85 (m, 5H); 2.73 (t, 1H, J=10.8 Hz); 2.20–1.82 (m, 4H) ppm. MS (ApCI): 425 (base, M+H).

Example 281

(8aS,12aR)-6,7,8a,9,10,11,12,12a-Octahydro-5H-pyrido[4,3-b][1,4]thiazepino[2,3,4-hi]indole-3-carbonitrile dihydrochloride Tert-butyl(8aS,12aR)-3-bromo-6,7,9,10,12,12a-hexahydro-5H-pyrido[4,3-b][1,4]thiazepino[2,3,4-hi]indole-11(8aH)-carboxylate (425 mg, 0.995 mmol) and copper (I) cyanide (107 mg, 1.19 mmol) were dissolved in N,N-dimethyl formamide (8 mL). This solution was degassed under vacuum and nitrogen 5 times and heated at 120° C. for 14 hours. Reaction was cooled to room temperature and quenched with aqueous sodium cyanide (20 mg in 20 mL). The extracted with benzene (3×50 mL). Organics were washed with brine (50 mL) and water (50 mL), then dried over magnesium sulfate. This mixture was filtered and the filtrate was concentrated under reduced pressure to give a brown oil, which was purified by silica gel column chromatography, eluting with (20%) ethyl acetate in hexanes to give an oil. The oil was dissolved in chloroform (5 mL) and ethanol (5 mL) and hydrogen chloride gas was bubbled through for 2 hours. Reaction was concentrated under reduced pressure to give the title compound as a salt. $^1$H NMR ($CD_3OD$, 300 MHz); δ7.08 (s, 2H), 4.01–3.88 (m, 1H), 3.78–3.65 (m, 1H), 3.52–3.33 (m, 3H), 3.24–3.02 (m, 4H), 2.80–2.71 (m, 1H), 2.30–2.00 (m, 4H) ppm. MS (ApCI): 272 (base, M+H).

Example 282

(8aS,12aR)-2-Bromo-6,7,8a,9,10,11,12,12a-octahydro-5H-pyrido[4,3-b][1,4]thiazepino[2,3,4-hi]indole-3-carbonitrile dihydrochloride (8aS,12aR)-6,7,8a,9,10,11,12,12a-octahydro-5H-pyrido[4,3-b][1,4]thiazepino[2,3,4-hi]indole-3-carbonitrile dihydrochloride (95 mg, 0.256 mmol) was dissolved in N,N-dimethyl formamide (1 mL) and cooled to 0° C. in an ice bath. In a separate flask N-bromosuccinimide was dissolved in N,N-dimethyl formamide (1 mL) and added slowly to the first solution over 10 minutes. The reaction was stirred for 10 minutes and followed by thin layer chromatography until no more starting material was present in reaction. Reaction was then quenched with water (10 mL) and extracted with benzene (3×15 mL). The organic layers were collected washed with brine (1×20 mL) and water (1×20 mL) and dried over magnesium sulfate, then filtered and the filtrate concentrated under reduced pressure to give a brown oil. The oil was purified via silica gel column chromatography, eluting with (20, 30, 40%) ethyl acetate in hexanes. Fractions were collected and concentrated under reduced pressure to give a colorless oil. The oil was dissolved in chloroform (10 mL) and cooled to 0° C. in an ice bath and trifluoroacetic acid (2 mL) was added and stirred for 3 hours, during which time reaction warmed to room temperature. This was basified with concentrated ammonium hydroxide to pH 12, then extracted with chloroform (3×50 mL). The organic layers were collected and concentrated under reduced pressure to give an oil. The oil was dissolved in chloroform (2 mL) and then hydrogen chloride 1 molar in diethyl was added until precipitation stopped, this was concentrated under reduced pressure to give the title compound (24 mg, 41%). $^1$H NMR ($CD_3OD$, 300 MHz): δ7.36 (s, 1H); 4.01–3.89 (m, 1H); 3.82–3.70 (m, 1H); 3.58–3.37 (m, 3H); 3.27–3.09 (m, 5H); 2.23–2.00 (m, 4H) ppm. MS (ApCI): 391 (base, M+H).

Example 283

(8aS,12aR)-3-Benzyl-6,7,8a,9,10,11,12,12a-octahydro-5H-pyrido[4,3-b][1,4]thiazepino[2,3,4-hi] indole dihydrochloride Tert-butyl(8aS,12aR)-3-bromo-6,7,9,10,12,12a-hexahydro-5H-pyrido[4,3-b][1,4]thiazepino[2,3,4-hi] indole-11(8aH)-carboxylate (150 mg, 0.353 mol), benzylzinc bromide (250 mg, 1.06 mmol), copper (I) iodide (29 mg, 0.353 mmol), and bis(triphenylphosphine)palladium(II) chloride (29 mg, 0.0353 mmol) were dissolved in tetrahydrofuran (5 mL) under a nitrogen atmosphere and then heated to at reflux for 13 hours. The reaction was concentrated under reduced pressure to give a brown oil. The oil was purified via silica gel column chromatography, eluting with (16%) ethyl acetate in hexanes. Fractions were collected and concentrated under reduced pressure to give a colorless oil. The oil was dissolved in chloroform (10 mL) and cooled to 0° C. in an ice bath and trifluoroacetic acid (2 mL) was added and stirred for 3 hours, during which time reaction warmed to room temperature. This was basified with concentrated ammonium hydroxide to pH 12, then extracted with chloroform (3×50 mL). The organic layers were collected and dried over magnesium sulfate, then concentrated under reduced pressure to give an oil. The oil was dissolved in chloroform (2 mL) and then hydrogen chloride 1 molar in diethyl was added until precipitation stopped, this was concentrated under reduced pressure to give the title compound (25 mg, 21%). $^1$H NMR ($CD_3OD$, 300 MHz): δ7.21–7.09 (m, 5H); 6.94 (d, 1H, J=7.7 Hz); 6.67 (d, 1H, J=7.7 Hz); 3.99 (s, 2H); 3.97–3.89 (m, 1H); 3.62–3.17 (m, 7H); 3.00–2.80 (m, 2H); 2.21–1.86 (m, 4H) ppm. MS (ApCI): 337 (base, M+H).

Example 284

(8aS,12aR)-6,7,8a,9,10,11,12,12a-Octahydro-5H-pyrido[4,3-b][1,4]thiazepino[2,3,4-hi]indole-3-carbaldehyde dihydrochloride (8aS,12aR)-6,7,8a,9,10,11,12,12a-octahydro-5H-pyrido [4,3-b][1,4]thiazepino[2,3,4-hi]indole-3-carbonitrile dihydrochloride (62 mg, 0.167 mol), was dissolved in dichloromethane (1 mL) and cooled to 0° C. in an ice bath and stirred under nitrogen atmosphere for 10 minutes. Then diisobutylaluminum hydride (71 mg, 0.501 mmol) was added dropwise, then stirred for 2 hours. The reaction was quenched with methanol (5 mL), rochell's salts (5 mL) and chloroform (5 mL) and stirred vigorously at room temperature for 12 hours. The reaction mixture was separated and the aqueous layer was back extracted with chloroform (3×10 mL). The organic layers were collected dried over magnesium sulfate and filtered. The filtrate was concentrated under reduced pressure to give an oil. The oil was purified via silica gel column chromatography, eluting with (20%) ethyl acetate in hexanes. Fractions were collected and concentrated under reduced pressure to give a colorless oil. The oil was dissolved in chloroform (2 mL) and then hydrogen chloride 1 molar in diethyl was added until precipitation stopped, this was concentrated under reduced pressure to give the title compound (7 mg, 18%). $^1$H NMR ($CD_3OD$, 300 MHz): δ6.98 (d, 2H, J=1.8 Hz); 5.44 (s, 1H); 4.03–3.98 (m, 1H); 3.58–3.30 (m, 2H); 3.25–3.13 (m, 5H); 2.98–2.87 (m, 1H); 2.79–2.67 (m, 1H); 2.22–1.86 (m, 4H) ppm. MS (ApCI): 275 (base, M+H).

Example 285

(8aS,12aR)-6,7,8a,9,10,11,12,12a-Octahydro-5H-pyrido[4,3-b][1,4]thiazepino[2,3,4-hi]indole-3-carboxylic acid dihydrochloride (8aS,12aR)-6,7,8a,9,10,11,12,12a-Octahydro-5H-pyrido [4,3-b][1,4]thiazepino[2,3,4-hi]indole-3-carbonitrile dihydrochloride (65 mg, 0.175 mol) was dissolved in methanol (0.6 mL), water (0.8 mL) and tetrahydrofuran (0.4 mL) and then potassium hydroxide (190 mg, 3.33 mmol) was added and then heated at reflux for 23 hours. The reaction was acidified to pH=7 with 1 normal hydrochloric acid. The reaction mixture was extracted with chloroform (3×10 mL). The organic layers were collected dried over magnesium sulfate and filtered. The filtrate was concentrated under reduced pressure to give an oil. The oil was purified via silica gel column chromatography, eluting with (16%) ethyl acetate in hexanes, followed by (100%) methanol. Fractions were collected and concentrated under reduced pressure to give a colorless oil. The oil was dissolved in chloroform/methanol (3/2 mL), then hydrogen chloride gas was bubbled through for 20 minutes. The reaction solution was concentrated under reduced pressure to give the title compound (20 mg, 53%). $^1$H NMR ($CD_3OD$, 300 MHz): δ7.26 (d, 1H, J=7.3 Hz); 6.98 (d, 1H, J=7.7 Hz); 4.10–4.01 (m, 1H); 3.62–3.54 (m, 2H); 3.42–3.30 (m, 3H); 3.25–3.09 (m, 2H); 2.92–2.83 (m, 1H); 2.81–2.73 (m, 1H); 2.24–1.83 (m, 4H) ppm.

Example 286

N-[2-((8aS,12aR)-6,7,9,10,12,12a-hexahydro-5H-pyrido[4,3-b][1,4]thiazepino[2,3,4-hi]indol-11(8aH)-yl)ethyl]-2,4-difluorobenzamide Step A To a solution of ethanolamine (1.10 g, 15.8 mmol) in THF at 0° C. under $N_2$ was added 2,4-difluorobenzoyl chloride (500 mg, 2.83 mmol). The reaction mixture was stirred at 0° C. for 4 h, then diluted with ethyl acetate (100 mL) and washed with 1 N HCl (50 mL), saturated $NaHCO_3$ (50 mL), and saturated NaCl (50 mL). The organic solution was dried over $MgSO_4$ and concentrated in vacuo to yield 2,4-difluoro-N-(2-hydroxyethyl)benzamide as a white solid (495 mg, 87%).

Step B

To a solution of 2,4-difluoro-N-(2-hydroxyethyl) benzamide (299 mg, 1.49 mmol) and triethylamine (302 mg, 2.98 mmol) in $CH_2Cl_2$ under nitrogen at 0° C. was added methanesulfonyl chloride (335 mg, 2.98 mmol) The reaction mixture was stirred for 1 h at 0° C. 1 N HCl (5 mL) was added to quench the reaction and the solution was diluted with ethyl acetate (100 mL), washed with saturated $NaHCO_3$ (100 mL) and saturated NaCl (100 mL), dried over $MgSO_4$, filtered and concentrated in vacuo. Purification by column chromatography (hexanes:EtOAc 4:1) yielded 2-[(2,4-difluorobenzoyl)amino]ethyl methanesulfonate (300 mg, 72%) as a clear liquid.

Step C

To a solution of (8aS,12aR)-6,7,8a,9,10,11,12,12a-octahydro-5H-pyrido[4,3-b][1,4]thiazepino[2,3,4-hi]indole (30 mg, 0.12 mmol) and 2-[(2,4-difluorobenzoyl)amino]

ethyl methanesulfonate (102 mg, .0.36 mmol) in 1,4-dioxane (0.6 mL) were added $K_2CO_3$ (24 mg, 0.17 mmol) and KI (catalytic amount) and the reaction mixture was stirred at 100° C. for 48 h. The reaction mixture was diluted with $CHCl_3$ (50 mL) and filtered. The title compound was isolated as a light yellow oil (43 g, 77%) after column purification ($CHCl_3$:MeOH 99:1). $^1H$ NMR ($CDCl_3$) δ1.65 (br-s, 1H), 1.86–2.13 (m, 5H), 2.39 (td, 1H, J=3.3, 11.0 Hz), 2.52–2.66 (m, 3H), 2.72–2.78 (m, 1H), 2.93–3.00 (m, 1H), 3.08–3.18 (m, 2H), 3.28–3.33 (m, 1H), 3.49–3.59 (m, 3H), 3.77–3.85 (m, 1H), 6.59 (t, 1H, J=7.4 Hz), 6.82–7.03 (m, 4H), 8.10–8.18 (m, 1H) ppm.

Example 287

N-[2-((8aS,12aR)-6,7,9,10,12,12a-hexahydro-5H-pyrido[4,3-b][1,4]thiazepino[2,3,4-hi]indol-11(8aH)-yl)ethyl]-N-methylbenzamide 2-(Benzoyl(methyl)amino)ethyl methanesulfonate (987 mg, 49%) was prepared from benzoyl chloride (545 mg, 3.6 mmol) and 2(methylamino)ethanol (1.35 g, 18 mmol) according to the procedure of Example 286, Steps A and B. The title compound was isolated as a yellow oil according to the method of Example 286, Step C (35 mg, 33%) from (8aS,12aR)-6,7,8a,9,10,11,12,12a-octahydro-5H-pyrido[4,3-b][1,4]thiazepino[2,3,4-hi]indole (30 mg, 0.12 mmol) and 2-(benzoyl(methyl)amino)ethyl methanesulfonate (48 mg, 0.24 mmol). $^1H$ NMR ($CDCl_3$): δ1.69–1.95 (m, 3H), 2.01–2.19 (m, 2H), 2.34–2.51 (m, 2H), 2.57–2.81 (m, 2H), 2.93–3.10 (m, 6H), 3.25–3.58 (m, 2H), 2.61–2.85 (m, 3H), 6.61 (t, 1H, J=7.5 Hz), 6.94 (d, 1H, J=7.7 Hz), 7.26–7.50 (m, 4H) ppm. MS (ESI): 408 (base, M+H).

Example 288

N-[2-((8aS,12aR)-6,7,9,10,12,12a-hexahydro-5H-pyrido[4,3-b][1,4]thiazepino[2,3,4-hi]indol-11(8aH)-yl)ethyl]-2-fluoro-N-methylbenzamide 2-[(2-Fluorobenzoyl(methyl)amino)ethyl methanesulfonate (531 mg, 85%) was prepared from 2-fluorobenzoyl chloride (1.12 g, 6.4 mmol) and 2(methylamino)ethanol (2.70 g, 32 mmol) according to the procedure of Example 286, Steps A and B. The title compound was isolated as a yellow oil according to the method of Example 286, Step C (35 mg, 66%) from (8aS,12aR)-6,7,8a,9,10,11,12,12a-octahydro-5H-pyrido[4,3-b][1,4]thiazepino[2,3,4-hi]indole (30 mg, 0.12 mmol) and 2-[(2-fluorobenzoyl)(methyl)amino)ethyl methanesulfonate (48 mg, 0.24 mmol). $^1H$ NMR ($CDCl_3$) δ1.65–1.93 (m, 1H), 2.01–2.17 (m, 3H), 2.25–2.44 (m, 3H), 2.54–2.91 (m, 3H), 2.95–3.05 (m, 3H), 3.10–3.22 (m, 3H), 3.27–3.40 (m, 1H), 3.45–3.90 (m, 4H), 6.58–6.64 (m, 1H), 6.81 (dd, 1H, J=6.6, 38.9 Hz), 6.92–6.96 (m, 1H), 7.06–7.19 (m, 1H), 7.19 (t, 1H, J=6.9 Hz), 7.32–7.40 (m, 2H) ppm. MS (ESI): 426 (base, M+H).

Example 289

N-[2-((8aS,12aR)-6,7,9,10,12,12a-hexahydro-5H-pyrido[4,3-b][1,4]thiazepino[2,3,4-hi]indol-11(8aH)-yl)ethyl]-2,4-difluoro-N-methylbenzamide 2-[(2,4-Difluorobenzyl(methyl)amino)ethyl methanesulfonate (482 mg, 86%) was prepared from 2,4-difluorobenzoyl chloride (1.04 g, 5.9 mmol) and 2(methylamino)ethanol (2.13 g, 28 mmol) according to the procedure of Example 286, Steps A and B. The title compound was isolated as a yellow oil according to the method of Example 286, Step C (17 mg, 31%) from (8aS,12aR)-6,7,8a,9,10,11,12,12a-octahydro-5H-pyrido[4,3-b][1,4]thiazepino[2,3,4-hi]indole (30 mg, 0.12 mmol) and 2-[(2,4-difluorobenzoyl)(methyl)amino)ethyl methanesulfonate (57 mg, 0.24 mmol). $^1H$ NMR ($CDCl_3$) δ1.89–2.01 (m, 2H), 2.05–2.14 (m, 2H), 2.38–2.52 (m, 3H), 3.55–3.78 (m, 2H), 2.81–2.91 (m, 1H), 2.94–3.07 (m, 3H), 3.10–3.19 (m, 2H), 3.24–3.36 (m, 2H), 3.45–3.60 (m, 1H), 3.61–3.85 (m, 3H), 6.61 (t, 1H, J=7.5 Hz), 6.74–6.96 (m, 4H), 7.33–7.38 (m, 1H) ppm.

Example 290

N-[2-((8aS,12aR)-6,7,9,10,12,12a-hexahydro-5H-pyrido[4,3-b][1,4]thiazepino[2,3,4-hi]indol-11(8aH)-yl)ethyl]-4-fluoro-N-methylbenzamide 2-[(4-Fluorobenzoyl(methyl)amino)ethyl methanesulfonate (482 mg, 86%) was prepared from 4-fluorobenzoyl chloride (1.12 g, 3.2 mmol) and 2(methylamino)ethanol (2.70 g, 16 mmol) according to the procedure of Example 286, Steps A and B. The title compound was isolated as a yellow oil according to the method of Example 286, Step C (37 mg, 69%) from (8aS,12aR)-6,7,8a,9,10,11,12,12a-octahydro-5H-pyrido[4,3-b][1,4]thiazepino[2,3,4-hi]indole (30 mg, 0.12 mmol) and 2-[(4-fluorobenzoyl)(methyl)amino)ethyl methanesulfonate (53 mg, 0.24 mmol). $^1H$ NMR ($CDCl_3$) δ1.73–1.95 (m, 3H), 1.98–2.21 (m, 3H), 2.35–2.55 (m, 3H), 3.60–3.78 (m, 1H), 2.86–2.97 (m, 1H), 2.98–3.21 (m, 5H), 3.27–3.45 (m, 1H), 3.52–3.59 (m, 2H), 3.72–3.86 (m, 2H), 6.62 (t, 1H, J=7.5 Hz), 6.71–6.83 (m, 1H), 6.95 (dd, 1H, J=1.1 7.8 Hz), 7.08 (t, 2H, J=8.6 Hz), 7.30–7.50 (m, 2H) ppm.

Example 291

(8aS,12aR)-11-[3-(1H-1,2,3-benzotriazol-1-yl)propyl]-6,7,8a,9,10,11,12,12a-octahydro-5H-pyrido[4,3-b][1,4]thiazepino[2,3,4-hi]indole Step A To a solution of benzotriazole (303 mg, 2.54 mmol) and powdered NaOH (101 mg, 2.52 mmol) in DMSO was added 1-bromo-3-chloro propane (437 mg, 2.77 mmol). The reaction mixture was stirred for 16 h at 20° C. The reaction mixture was then diluted with EtOAc (100 mL) and washed with $H_2O$ (100 mL) and saturated NaCl (100 mL), dried over $MgSO_4$ and concentrated in vacuo. Column purification (hexanes:EtOAc 4:1) yielded 1-(3-chloropropyl)-1H-1,2,3-benzotriazole (167 mg, 34%). The title compound was prepared according to Example 286, Step C as a yellow oil (21 mg, 42%) from (8aS,12aR)-6,7,8a,9,10,11,12,12a-octahydro-5H-pyrido[4,3-b][1,4]thiazepino[2,3,4-hi]indole (30 mg, 0.12 mmol) and 1-(3-chloropropyl)-1H-1,2,3-benzotriazole (48 mg, 0.24 mmol). $^1H$ NMR ($CDCl_3$) δ1.88–1.98 (m, 3H), 1.99–2.18 (m, 2H), 2.20–2.41 (m, 5H), 2.51–2.60 (m, 1H), 2.64–2.71 (m, 1H), 2.89–3.00 (m, 1H), 3.03–3.13 (m, 2H), 3.21–3.27 (m, 1H), 3.47–3.60 (m, 1H), 3.76–3.88 (m, 1H), 4.73 (t, 2H, J=6.6 Hz), 6.61 (t, 1H, J=7.4 Hz), 6.84 (d, 1H, J=6.6 Hz), 6.94 (dd, 1H, J=1.1, 8.1 Hz), 7.37 (td, 1H, J=1.1, 7.4 Hz), 7.49 (td, 1H, J=1.1, 7.8 Hz), 7.57 (d, 1H, J=8.0 Hz), 8.07 (d, 1H, J=8.4 Hz) ppm.

Example 292

(8aS,12aR)-11-[3-(2H-1,2,3-benzotriazol-2-yl)propyl]-6,7,8a,9,10,11,12,12a-octahydro-5H-pyrido[4,3-b][1,4]thiazepino[2,3,4-hi]indole Benzotriazole (303 mg, 2.54 mmol) and 1-bromo-3-chloro propane (437 mg, 2.77 mmol) were used according to the method of Example 291, Step A to yield 2-(3-chloropropyl)-1H-1,2,3-benzotriazole (182 mg, 37%). The title compound was prepared according to Example 286, Step C as a yellow oil (20 mg, 40%) from (8aS,12aR)-6,7,8a,9,10,11,12,12a-octahydro-5H-pyrido[4,3-b][1,4]thiazepino[2,3,4-hi]indole (30 mg, 0.12 mmol) and 2-(3-chloropropyl)-1H-1,2,3-benzotriazole (48 mg, 0.24 mmol). $^1$H NMR ($CDCl_3$) δ1.84–1.94 (m, 3H), 1.99–2.20 (m, 2H), 2.25–2.52 (m, 5H), 2.64–2.72 (m, 1H), 2.74–2.82 (m, 1H), 2.88–3.00 (m, 1H), 3.02–3.18 (m, 2H), 3.22–3.28 (m, 1H), 3.51–3.61 (m, 1H), 3.74–3.85 (m, 1H), 4.80 (t, 2H, J=6.7 Hz), 6.61 (t, 1H, J=7.5 Hz), 6.92 (dd, 2H, J=6.6, 24.9 Hz), 7.35–7.41 (m, 2H), 7.83–7.85 (m, 2H) ppm.

Example 293

(8aS,12aR)-11-{[(2S)-1-benzoylpyrrolidinyl]methyl}-6,7,8a,9,10,11,12,12a-octahydro-5H-pyrido[4,3-b][1,4]thiazepino[2,3,4-hi]indole

[(2S)-1-Benzoylpyrrolidinyl]methyl methanesulfonate (94 mg, 50%) was prepared from (S)-2-pyrrolidine-methanol (150 mg, 1.48 mmol) and benzoyl chloride (208 mg, 1.48 mmol) as in Example 286, Steps A–B. The title compound was isolated as a yellow oil (52 mg, 100%) according to the method of Example 286, Step C from (8aS,12aR)-6,7,8a,9,10,11,12,12a-octahydro-5H-pyrido[4,3-b][1,4]thiazepino[2,3,4-hi]indole (30 mg, 0.12 mmol) and [(2S)-1-benzoylpyrrolidinyl]methyl methanesulfonate (55 mg, 0.24 mmol). $^1$H NMR ($CDCl_3$) δ1.26 (s, 1H), 1.58–2.30 (m, 8H), 2.35–2.86 (m, 3H), 2.90–3.30 (m, 4H), 3.37–3.61 (m, 4H), 3.75–3.86 (m, 2H), 4.38–4.50 (m, 1H), 6.55–6.96 (m, 2H), 7.31–7.96 (m, 6H) ppm. MS (ESI): 434 (base, M+H).

Example 294

(8aS,12aR)-11-{[(2R)-1-benzoylpyrrolidinyl]methyl}-6,7,8a,9,10,11,12,12a-octahydro-5H-pyrido[4,3-b][1,4]thiazepino[2,3,4-hi]indole

[(2R)-1-Benzoylpyrrolidinyl]methyl methanesulfonate (98 mg, 52%) was prepared from (R)-2-pyrrolidine-methanol (150 mg, 1.48 mmol) and benzoyl chloride (208 mg, 1.48 mmol) as in Example 286, Steps A–B. The title compound was isolated as a yellow oil (36 mg, 68%) according to the method of Example 286, Step C from (8aS,12aR)-6,7,8a,9,10,11,12,12a-octahydro-5H-pyrido[4,3-b][1,4]thiazepino[2,3,4-hi]indole (30 mg, 0.12 mmol) and [(2R)-1-benzoylpyrrolidinyl]methyl methanesulfonate (55 mg, 0.24 mmol). $^1$H NMR ($CDCl_3$) δ1.58–2.27 (m, 12H), 2.64–3.30 (m, 4H), 3.49–3.61 (m, 3H), 3.72–3.84 (m, 2H), 6.60 (td, 1H, J=1.9, 7.5 Hz), 6.93 (d, 1H, J=7.5 Hz), 7.31–7.55 (m, 6H) ppm. MS (ESI): 434 (base, M+H).

Example 295

(8aS,12aR)-11-{[(2S)-1-(4-fluorobenzoyl)pyrrolidinyl]methyl}-6,7,8a,9,10,11,12,12a-octahydro-5H-pyrido[4,3-b][1,4]thiazepino[2,3,4-hi]indole

[(2S)-1-(4-Fluorobenzoyl)pyrrolidinyl]methyl methanesulfonate (152 mg, 68%) was prepared from (S)-2-pyrrolidine-methanol (155 mg, 1.53 mmol) and 4-fluorobenzoyl chloride (235 mg, 1.48 mmol) as in Example 286, Steps A–B. The title compound was isolated as a yellow oil (24 mg, 44%) according to the method of Example 286, Step C from (8aS,12aR)-6,7,8a,9,10,11,12,12a-octahydro-5H-pyrido[4,3-b][1,4]thiazepino[2,3,4-hi]indole (30 mg, 0.12 mmol) and [(2S)-1-(4-fluorobenzoyl)pyrrolidinyl]methyl methanesulfonate (59 mg, 0.24 mmol). $^1$H NMR ($CDCl_3$) δ1.63 (s, 2H), 1.70–2.20 (m, 10H), 2.67–3.31 (m, 5H), 3.37–3.55 (m, 4H), 3.71–3.82 (m, 2H), 6.61 (td, 1H, J=2.0, 7.5 Hz), 6.93 (d, 1H, J=7.7 Hz), 7.03–7.18 (m, 3H), 7.45–7.56 (m, 2H) ppm. MS (ESI): 452 (base, M+H).

Example 296

(8aS,12aR)-11-{[(2R)-1(4-fluorobenzoyl)pyrrolidinyl]methyl}-6,7,8a,9,10,11,12,12a-octahydro-5H-pyrido[4,3-b][1,4]thiazepino[2,3,4-hi]indole

[(2R)-1-(4-Fluorobenzoyl)pyrrolidinyl]methyl methanesulfonate (147 mg, 80%) was prepared from (R)-2-pyrrolidine-methanol (155 mg, 1.53 mmol) and 4-fluorobenzoyl chloride (235 mg, 1.48 mmol) as in Example 286, Steps A–B. The title compound was isolated as a yellow oil (27 mg, 49%) according to the method of Example 286, Step C from (8aS,12aR)-6,7,8a,9,10,11,12,12a-octahydro-5H-pyrido[4,3-b][1,4]thiazepino[2,3,4-hi]indole (30 mg, 0.12 mmol) and [(2R)-1-(4-fluorobenzoyl)pyrrolidinyl]methyl methanesulfonate (59 mg, 0.24 mmol). $^1$H NMR ($CDCl_3$) δ1.59–2.21 (m, 11H), 2.94–3.35 (m, 4H), 3.47–3.60 (m, 4H), 3.73–3.84 (m, 2H), 4.39–4.47 (1H, m), 4.77–4.02 (m, 1H), 6.61 (td, 1H, J=1.8, 7.4 Hz), 6.83 (d, 1H, J=9.5 Hz), 7.01–7.14 (m, 3H), 7.47–7.64 (m, 2H) ppm.

Example 297

(8aS,12aR)-11-[2-(1H-1,2,3-benzotriazol-1-yl)ethyl]-6,7,8a,9,10,11,12,12a-octahydro-5H-pyrido[4,3-b][1,4]thiazepino[2,3,4-hi]indole 1-(2-Chloroethyl)-1H-1,2,3-benzotriazole (164 mg, 36%) was prepared from benzotriazole (300 mg, 2.52 mmol) and 1-bromo-2-chloro ethane (397 mg, 2.77 mmol) according to the procedure of Example 291. The title compound was isolated as a yellow oil (48 mg, 98%) according to the method of Example 286, Step C from (8aS,12aR)-6,7,8a,9,10,11,12,12a-octahydro-5H-pyrido[4,3-b][1,4]thiazepino[2,3,4-hi]indole (30 mg, 0.12 mmol) and 1-(2-chloroethyl)-1H-1,2,3-benzotriazole (44 mg, 0.24 mmol). $^1$H NMR ($CDCl_3$) δ1.69–2.20 (m, 4H), 2.39–2.45 (m, 1H), 2.61–2.68 (m, 1H), 2.72–2.81 (m, 1H), 2.84–3.01 (m, 2H), 3.03–3.12 (m, 2H), 3.20–3.27 (m, 1H), 3.49–3.60 (m, 1H), 3.74–3.84 (m, 1H), 4.06 (t, 1H, J=6.7 Hz), 4.76 (t, 1H, J=6.6 Hz), 4.96 (t, 1H, J=6.2 Hz), 6.61 (t, 1H, J=7.5 Hz), 6.82 (d, 1H, J=7 Hz), 6.95 (dd, 1H, J=1.1, 7.7 Hz), 7.34–7.62 (m, 3H), 8.08 (t, 1H, J=7.6 Hz) ppm.

Example 298

(8aS,12aR)-11-[2-(2H-1,2,3-benzotriazol-2-yl)propyl]-6,7,8a,9,10,11,12,12a-octahydro-5H-pyrido[4,3-b][1,4]thiazepino[2,3,4-hi]indole 2-(3-Chloropropyl)-1H-1,2,3-benzotriazole (200 mg, 44%) was prepared from benzotriazole (300 mg, 2.52 mmol) and 1-bromo-3-chloro propane (397 mg, 2.77 mmol) according to the procedure of Example 291. The title compound was isolated as a yellow oil (26 mg, 54%) according to the method of Example 286, Step C from (8aS,12aR)-6,7,8a,9,10,11,12,12a-octahydro-5H-pyrido[4,3-b][1,4]thiazepino[2,3,4-hi]indole (30 mg, 0.12 mmol) and 2-(3-chloropropyl)-1H-1,2,3-benzotriazole (44 mg, 0.24 mmol). $^1$H NMR ($CDCl_3$) δ1.81–1.93 (m, 2H), 1.96–2.14 (m, 3H), 2.41 (td, 1H, J=3.7, 11.7 Hz), 2.64–2.72 (m, 1H), 2.80–2.90 (m, 1H), 2.92–3.00 (m, 1H), 3.02–3.16 (m, 4H), 3.21–3.26 (m, 1H), 3.51–3.62 (m, 1H), 3.78–3.86 (m, 1H), 4.85 (t, 2H, J=7.0 Hz), 6.61 (t, 1H, J=7.5 Hz), 6.83 (d, 1H, J=6.6 Hz), 6.94 (dd, 1H, J=1.2, 8.1 Hz), 7.36–7.41 (m, 2H), 7.84–7.88 (m, 2H) ppm.

Example 299

(8aS,12aR)-11-[3-(3,4-dihydro-1(2H)-quinolinyl) propyl]-6,7,8a,9,10,11,12,12a-octahydro-5H-pyrido [4,3-b][1,4]thiazepino[2,3,4-hi]indole To a solution of 1,2,3,4-tetrahydroquinoline (505 mg, 3.79 mmol) and 1-bromo-3-chloro propane (1.77 g, 11 mmol) in 1,4-dioxane (6 mL) was added $Et_3N$ (1.90 g, 19 mmol). The reaction mixture was stirred at 70° C. for 17 h, and quenched by addition of $H_2O$ (2 mL). Reaction was diluted with $Et_2O$ (100 mL) and washed with brine (100 mL), dried over $MgSO_4$ and concentrated in vacuo. Purification by column chromatography (hexanes:EtOAc 49:1) yielded 1-(3-chloropropyl)-1,2,3,4-tetrahydroquinoline (187 mg, 24%) as a colorless oil. The title compound was isolated as a yellow oil (22 mg, 43%) according to the method of Example 286, Step C from (8aS,12aR)-6,7,8a,9,10,11,12, 12a-octahydro-5H-pyrido[4,3-b][1,4]thiazepino[2,3,4-hi] indole (30 mg, 0.12 mmol) and 1-(3-chloropropyl)-1,2,3,4-tetrahydroquinoline (51 mg, 0.24 mmol). $^1H$ NMR ($CDCl_3$) δ1.77–2.19 (m, 10H), 2.24–2.41 (m, 2H), 2.61–2.69 (m, 1H), 2.75–2.84 (m, 3H), 2.91–3.02 (m, 1H), 3.10–3.21 (m, 2H), 3.26–3.34 (m, 5H), 3.52–3.61 (m, 1H), 3.77–3.96 (m, 1H), 6.49–6.65 (m, 3H), 6.85 (d, 1H, J=7.3 Hz), 6.92–6.96 (m, 2H), 6.99–7.05 (m, 1H) ppm.

Example 300

(8aS,12aR)-11-[(3E)-4-(4-fluorophenyl)3-pentenyl]-6,7,8a,9,10,11,12,12a-octahydro-5H-pyrido[4,3-b][1, 4]thiazepino[2,3,4-hi]indole Step A To a solution of cyclopropyl-4-fluorophenyl ketone (523 mg, 3.19 mmol) in THF (10 mL) at 0° C. under $N_2$ was added 3 M methyl magnesium bromide (1.7 mL, 5.1 mmol) in $Et_2O$. After 90 minutes at 0° C., the reaction was quenched by addition of brine (10 mL) and diluted with $Et_2O$ (100 mL). The organic solution was washed with saturated $NaHCO_3$ (100 mL) and brine (100 mL). Column purification (hexanes:EtOAc 9:1) yielded 1-cyclopropyl-1-(4-fluorophenyl)ethanol (512 mg, 89%) as a colorless oil.

Step B

1-Cyclopropyl-1-(4-fluorophenyl)ethanol (307 mg, 1.70 mmol) in a solution of 1 N HCl in isopropyl alcohol (3.6 mL) was heated at 60° C. for 1 h. The reaction mixture was then concentrated in vacuo, and column chromatography purification yielded 1-[(1E)-4-chloro-1-methyl-1-butenyl]-4-fluorobenzene (282 mg, 84%) as a colorless oil. The title compound was isolated as a yellow oil (36 mg, 70%) according to the method of Example 286, Step C from (8aS,12aR)-6,7,8a,9,10,11,12,12a-octahydro-5H-pyrido[4, 3-b][1,4]thiazepino[2,3,4-hi]indole (30 mg, 0.12 mmol) and 1-[(1E)-4-chloro-1-methyl-1-butenyl]-4-fluorobenzene (48 mg, 0.24 mmol). $^1H$ NMR ($CDCl_3$) δ1.62 (br-s, 1H), 1.90–2.20 (m, 9H), 2.31–2.44 (m, 5H), 2.71–2.80 (m, 1H), 2.81–2.89 (m, 1H), 2.92–3.00 (m, 1H), 3.04–3.13 (m, 1H), 3.17–3.24 (m, 2H), 3.27–3.31 (m, 1H), 3.51–3.63 (m, 1H), 3.80–3.91 (m, 1H), 5.64–5.73 (m, 1H), 6.62 (t, 1H, J=7.5 Hz), 6.87 (d, 1H, J=6.6 Hz), 6.91–7.00 (m, 3H), 7.29–7.34 (m, 2H) ppm)

Example 301

(8aS,12aR)-11-[2-(2,3-dihydro-1H-inden-2-yl)ethyl]-6,7, 8a,9,10,11,12,12a-octahydro-5H-pyrido[4,3-b][1,4] thiazepino[2,3,4-hi]indole Step A To a slurry of NaH (400 mg, 17 mmol) in DME (25 mL) at 20° C. under $N_2$ was added triethylphosphonoacetate (3.30 g, 15 mmol). The reaction mixture was stirred for 45 m. To this white solution was added a solution of 2-indanone (2.00 g, 15 mmol) in DME (5 mL), maintaining the temperature at less than 25° C. The reaction mixture was stirred for 30 m and then quenched with $H_2O$ (5 mL). The reaction mixture was extracted using $Et_2O$ (3×100 mL). The organic solution was then washed with $H_2O$ (200 mL), saturated $NaHCO_3$ (200 mL), and brine (200 mL), dried over $MgSO_4$ and concentrated in vacuo. Ethyl 1,3-dihydro-2H-inden-2-ylideneacetate (2.04 g, 67%) was isolated as a yellow oil.

Step B

To a solution of ethyl 1,3-dihydro-2H-inden-2-ylideneacetate (302 mg, 1.49 mmol) in EtOAc (10 mL) was added 5% Pd/C (76 mg) and $H_2$ was bubbled through the slurry for 20 h. The slurry was then filtered through Celite and the organic solution was concentrated in vacuo. Ethyl 2,3-dihydo-1H-inden-2-ylacetate (285 mg, 94%) was isolated as a colorless oil without purification.

Step C

To a solution of ethyl 2,3-dihydro-1H-inden-2-ylacetate (285 mg, 1.39 mmol) in $Et_2O$ (5 mL) at 0° C. under $N_2$ was added LAH (53 mg, 1.39 mmol). After stirring for 40 minutes at 0° C., 0.4 mL of $H_2O$ was added to quench the reaction. The reaction mixture was diluted with EtOAc (100 mL) and $MgSO_4$ was added with stirring. The reaction mixture was then filtered and concentrated in vacuo to a clear oil. 2-(2,3-dihydro-1H-inden-2-yl)ethanol was isolated without further purification.

2-(2,3-Dihydro-1H-inden-2-yl)ethyl methanesulfonate (128 mg, 98%) was isolated as a clear oil by the method of Example 286, Step B from 2-(2,3-dihydro-1H-inden-2-yl) ethanol (88 mg, 0.54 mmol). The title compound was isolated as a yellow oil (28 mg, 61%) according to the method of Example 286, Step C from (8aS,12aR)-6,7,8a,9, 10,11,12,12a-octahydro-5H-pyrido[4,3-b][1,4]thiazepino[2, 3,4-hi]indole (30 mg, 0.12 mmol) and 2-(2,3-dihydro-1H-inden-2-yl)ethyl methanesulfonate (59 mg, 0.24 mmol). $^1H$ NMR ($CDCl_3$) δ1.65–1.79 (m, 3H), 1.82–1.94 (m, 3H), 2.00–2.21 (m, 2H), 2.24–2.35 (m, 1H), 2.36–2.51 (m, 2H), 2.57–2.78 (m, 3H), 2.77–2.85 (m, 1H), 2.89–2.99 (m, 1H), 3.02–3.14 (m, 3H), 3.17–3.22 (m, 1H), 3.28–3.32 (m, 1H), 3.57–3.63 (m, 1H), 3.80–3.92 (m, 1H), 6.62 (t, 1H, J=7.5 Hz), 6.86 (d, 1H, J=6.6 Hz), 6.95 (dd, 1H, J=1.1, 7.7 Hz), 7.10–7.19 (m, 4H) ppm.

Example 302

4-((8aS,12aR)-6,7,,9,10,,12,12a-hexahydro-5H-pyrido[4,3-b][1,4]thiazepino[2,3,4-hi]indol-11(8aH)-yl)-1-(2-aminophenyl)-1-butanone Step A To a solution of $BCl_3$-$Me_2S$ (2.12 g, 12 mmol) in benzene (10 mL) under $N_2$ and ice cooling was added a solution of aniline (1.00 g, 11 mmol) in benzene (10 mL). This was stirred for 30 minutes and 4-chlorobutyronitrile (1.33 g, 12.8 mmol) was added, followed immediately by the addition of $AlCl_3$ (1.57 g, 12 mmol) was added in one portion. The reaction mixture was then refluxed for 16 h. The reaction mixture was cooled to 0° C. and 2 N HCl (16 ml) was added dropwise, then heated to 80° C. and stirred for 1 h. The reaction mixture was extracted with $CHCl_3$ (3×100 mL), washed with $H_2O$ (100 mL) and brine (100 mL), dried over $MgSO_4$ and concentrated in vacuo. Purification by column chromatography afforded 1-(2-aminophenyl)-4-chloro-1-butanone as a yellow solid (394 mg, 19%).

Step B

The title compound was isolated as a yellow oil (19 mg, 37%) according to the method of Example 286, Step C from (8aS,12aR)-6,7,8a,9,10,11,12,12a-octahydro-5H-pyrido[4,3-b][1,4]thiazepino[2,3,4-hi]indole (30 mg, 0.12 mmol) and 1-(2-aminophenyl)-4-chloro-1-butanone (48 mg, 0.24 mmol). $^1H$ NMR ($CDCl_3$) δ1.85–2.21 (m, 7H), 2.23–2.37 (n, 1H), 2.37–2.44 (m, 2H), 2.63–2.70 (m, 1H), 2.71–2.82 (m, 1H), 2.94–3.16 (m, 5H), 3.24–3.29 (m, 1H), 3.53–3.62 (m, 1H), 3.78–3.86 (m, 1H), 6.26 (br-s, 2H), 6.59–6.67 (m, 3H), 6.85 (d, 1H, J=7.4 Hz), 6.94 (dd, 1H, J=1.1, 8.1 Hz), 7.23–7.29 (m, 1H), 7.77 (dd, 1H, J=1.5, 8.4 Hz) ppm.

Example 303

4-((8aR, 12aS)-6,7,,9,10,,12,12a-hexahydro-5H-pyrido[4,3-b][1,4]thiazepino[2,3,4-hi]indol-11(8aH)-yl)-1-(2-aminophenyl)-1-butanone The title compound was isolated as a yellow oil (45 mg, 18%) according to the method of Example 286, Step C from (8aR, 12aS)-6,7,8a,9,10,11,12,12a-octahydro-5H-pyrido[4,3-b][1,4]thiazepino[2,3,4-hi]indole (150 mg, 0.61 mmol) and 1-(2-aminophenyl)-4-chloro-1-butanone (241 mg, 1.2 mmol). $^1H$ NMR ($CDCl_3$) δ1.85–2.21 (m, 7H), 2.23–2.37 (n, 1H), 2.37–2.44 (m, 2H), 2.63–2.70 (m, 1H), 2.71–2.82 (m, 1H), 2.94–3.16 (m, 5H), 3.24–3.29 (m, 1H), 3.53–3.62 (m, 1H), 3.78–3.86 (m, 1H), 6.26 (br-s, 2H), 6.59–6.67 (m, 3H), 6.85 (d, 1H, J=7.4 Hz), 6.94 (dd, 1H, J=1.1, 8.1 Hz), 7.23–7.29 (m, 1H), 7.77 (dd, 1H, J=1.5, 8.4 Hz) ppm.

Example 304

4-((8aS,12aR)-6,7,,9,10,,12,12a-hexahydro-5H-pyrido[4,3-b][1,4]thiazepino[2,3,4-hi]indol-11(8aH)-yl)-1-(2-amino-5-fluorophenyl)-1-butanone 1-(2-Amino-5-fluorophenyl)-4-chloro-1-butanone (462 mg, 24%) was afforded as a yellow solid according to the procedure of Example 302, Step A from 4-fluoroaniline (1.00g, 9.0 mmol). The title compound was isolated as a yellow oil (13 mg, 25%) according to the method of Example 286, Step C from (8aS,12aR)-6,7,8a,9,10,11,12,12a-octahydro-5H-pyrido[4,3-b][1,4]thiazepino[2,3,4-hi]indole (30 mg, 0.12 mmol) and 1-(2-amino-5-fluorophenyl)-4-chloro-1-butanone (53 mg, 0.24 mmol). $^1H$ NMR ($CDCl_3$) δ1.83–2.20 (m, 7H), 2.24–2.42 (m, 3H), 2.62–2.72 (m, 1H), 2.74–2.83 (m, 1H), 2.87–3.00 (m, 3H), 3.02–3.18 (m, 2H), 3.24–3.30 (m, 1H), 3.51–3.63 (m, 1H), 3.78–3.87 (m, 1H), 6.12 (br-s, 2H), 6.57–6.63 (m, 2H), 6.85 (d, 1H, J=6.6 Hz), 6.94 (dd, 1H, J=1.1, 7.7 Hz), 7.01–7.08 (m, 1H), 7.47 (dd, 1H, J=2.7, 10.1 Hz) ppm.

Example 305

4-((8aS,12aR)-6,7,,9,10,,12,12a-hexahydro-5H-pyrido[4,3-b][1,4]thiazepino[2,3,4-hi]indol-11(8aH)-yl)-1-(2-amino-3-fluorophenyl)-1-butanone 1-(2-Amino-3-fluorophenyl)-4-chloro-1-butanone (238 mg, 12%) was afforded as a yellow solid according to the procedure of Example 302, Step A from 2-fluoroaniline (1.00 g, 9.0 mmol). The title compound was isolated as a yellow oil (12 mg, 23%) according to the method of Example 286, Step C from (8aS,12aR)-6,7,8a,9,10,11,12,12a-octahydro-5H-pyrido[4,3-b][1,4]thiazepino[2,3,4-hi]indole (30 mg, 0.12 mmol) and 1-(2-amino-3-fluorophenyl)-4-chloro-1-butanone (53 mg, 0.24 mmol). $^1H$ NMR ($CDCl_3$) δ1.87–2.19 (m, 7H), 2.24–2.45 (m, 3H), 2.63–2.69 (m, 1H), 2.72–2.81 (m, 1H), 2.93–3.15 (m, 5H), 3.24–3.30 (m, 1H), 3.50–3.61 (m, 1H), 3.78–3.86 (m, 1H), 6.32 (br-s, 2H), 655–6.64 (m, 2H), 6.84 (d, 1H, J=7.4 Hz), 6.94 (dd, 1H, J=1.1, 7.7 Hz), 7.07–7.14 (m, 1H), 7.56 (d, 1H, J=8.4 Hz) ppm.

Example 306

4-((8aS,12aR)-6,7,,9,10,,12,12a-hexahydro-5H-pyrido[4,3-b][1,4]thiazepino[2,3,4-hi]indol-11(8aH)-yl)-1-(2-amino-4-chlorophenyl)-1-butanone 1-(2-Amino-4-chlorophenyl)-4-chloro-1-butanone (586 mg, 32%) was afforded as a yellow solid according to the procedure of Example 302, Step A from 3-chloroaniline (1.00 g, 7.9 mmol). The title compound was isolated as a yellow oil (10 mg, 19%) according to the method of Example 286, Step C from (8aS,12aR)-6,7,8a,9,10,11,12,12a-octahydro-5H-pyrido[4,3-b][1,4]thiazepino[2,3,4-hi]indole (30 mg, 0.12 mmol) and 1-(2-amino-4-chlorophenyl)-4-chloro-1-butanone (53 mg, 0.24 mmol). $^1H$ NMR ($CDCl_3$) δ1.83–2.17 (m, 7H), 2.19–2.41 (m, 3H), 2.57–2.61 (m, 1H), 2.68–2.77 (m, 1H), 2.83–2.92 (m, 3H), 2.96–3.13 (m, 2H), 3.20–3.26 (m, 1H), 3.45–3.58 (m, 1H), 3.71–3.82 (m, 1H), 6.28 (br-s, 2H), 6.51–6.58 (m, 3H), 6.78 (d, 1H, J=6.6 Hz), 6.87 (dd, 1H, J=1.2, 7.9 Hz), 7.62 (d, 1H, J=8.8 Hz)ppm.

Example 307

4-((8aS,12aR)-6,7,,9,10,,12,12a-hexahydro-5H-pyrido[4,3-b][1,4]thiazepino[2,3,4-hi]indol-11(8aH)-yl)-1-(2-amino-4-hydroxyphenyl-1-butanone 1-(2-Amino-4-hydroxyphenyl)-4-chloro-1-butanone (100 mg, 5%) was afforded as a yellow solid according to the procedure of Example 302, Step A from meta-anisidine (1.00 g, 8.2 mmol). The title compound was isolated as a yellow oil (5 mg, 9%) according to the method of Example 286, Step C from (8aS,12aR)-6,7,8a,9,10,11,12,12a-octahydro-5H-pyrido[4,3-b][1,4]thiazepino[2,3,4-hi]indole (30 mg, 0.12 mmol) and 1-(2-amino-4-hydroxyphenyl)-4-chloro-1-butanone (56 mg, 0.24 mmol). $^1H$ NMR ($CDCl_3$) δ1.90–2.19 (m, 6H), 2.31–2.48 (m, 3H), 2.68–2.77 (m, 1H), 2.78–2.84 (m, 1H), 2.89–3.00 (m, 5H), 3.02–3.18 (m, 1H), 3.24–3.31 (m, 1H), 3.54–3.61 (m, 1H), 3.78–3.87 (m, 1H), 4.21 (br-s, 2H), 6.11–6.16 (m, 2H), 6.61 (t, 1H, J=7.5 Hz), 6.85 (d, 1H, J=6.6), 6.94 (dd, 1H, J=1.1, 7.7 Hz), 7.56 (d, 1H, J=8.4 Hz), 12.93 (br-s, 1H) ppm.

Example 308

4-((8aS,12aR)-6,7,,9,10,,12,12a-hexahydro-5H-pyrido[4,3-b][1,4]thiazepino[2,3,4-hi]indol-11(8aH)-yl)-1-(2-amino-4-bromophenyl)-1-butanone 1-(2-Amino-4-bromophenyl)-4-chloro-1-butanone (558 mg, 17%) was afforded as a yellow solid according to the procedure of Example 302, Step A from 3-bromoaniline (2.00 g, 11.7 mmol). The title compound was isolated as a yellow oil (21 mg, 35%) according to the method of Example 286, Step C from (8aS,12aR)-6,7,8a,9,10,11,12,12a-octahydro-5H-pyrido[4,3-b][1,4]thiazepino[2,3,4-hi]indole (30 mg, 0.12 mmol) and 1-(2-amino-4-bromophenyl)-4-chloro-1-butanone (68 mg, 0.24 mmol). $^1$H NMR ($CDCl_3$) δ1.89–2.22 (m, 8H), 2.24–2.45 (m, 3H), 2.61–2.70 (m, 1H), 2.73–2.81 (m, 1H), 2.91–3.01 (m, 2H), 3.04–3.17 (m, 2H), 3.24–3.29 (m, 1H), 3.51–3.62 (m, 1H), 3.78–3.87 (m, 1H), 6.33 (br-s, 2H), 6.61 (t, 1H, J=7.5 Hz), 6.75 (dd, 1H, J=2.0, 8.6 Hz), 6.81–6.87 (m, 2H), 6.94 (dd, 1H, J=1.1, 7.7 Hz), 7.60 (d, 1H, J=8.4 Hz) ppm.

Example 309

(8aS,12aR)-11-[3-(1H-indazol-3-yl)propyl]-6,7,8a,9,10,11,12,12a-octahydro-5H-pyrido[4,3-b][1,4]thiazepino[2,3,4-hi]indole To a suspension of 1-(2-aminophenyl)-4-chloro-1-butanone (508 mg, 2.6 mmol) in concentrated HCl (3.5 mL) at −5° C. was added a solution of $NaNO_2$ (193 mg, 2.8 mmol) in $H_2O$ (0.75 mL), and the reaction mixture was stirred for 1 h. A solution of $SnCl_2$-$2H_2O$ (1.37 g, 6.07 mmol) in concentrated HCl (1.9 mL) was added at −5° C. to the solution, and this stirred for 1 h under ice cooling. The reaction was quenched with $H_2O$ and extracted into $Et_2O$ (100 mL). The organic solution was washed with $H_2O$ (50 mL) and brine (50 mL), dried over $MgSO_4$ and concentrated in vacuo. Purification by column chromatography afforded 3-(3-chloropropyl)-1H-indazole (126 mg, 25%) as a yellow solid. The title compound was isolated as a yellow oil (38 mg, 77%) according to the method of Example 286, Step C from (8aS,12aR)-6,7,8a,9,10,11,12,12a-octahydro-5H-pyrido[4,3-b][1,4]thiazepino[2,3,4-hi]indole (30 mg, 0.12 mmol) and 3-(3-chloropropyl)-1H-indazole (44 mg, 0.24 mmol). $^1$H NMR ($CDCl_3$) δ1.83–2.19 (m, 7H), 2.23–2.35 (m, 1H), 2.43–2.54 (m, 2H), 2.72–2.79 (m, 1H), 2.81–2.88 (m, 1H), 2.92–3.11 (m, 4H), 3.12–3.21 (m, 1H), 3.24–3.29 (m, 1H), 3.51–3.62 (m, 1H), 3.80–3.92 (m, 1H), 6.61 (t, 1H, J=7.5 Hz), 6.84 (d, 1H, J=6.6 Hz), 6.94 (dd, 1H, J=1.1, 7.7 Hz), 7.11–7.16 (m, 1H), 7.34–7.48 (m, 2H), 7.70 (d, 1H, J=8.0 Hz) ppm.

Example 310

(8aS,12aR)-11-[3-(5-fluoro-1H-indazol-3-yl)propyl]-6,7,8a,9,10,11,12,12a-octahydro-5H-pyrido[4,3-b][1,4]thiazepino[2,3,4-hi]indole 3-(3-Chloropropyl)-6-fluoro-1H-indazole (91 mg, 46%) was afforded according to the procedure of Example 309 from 1-(2-amino-5-fluorophenyl)-4-chloro-1-butanone (200 mg, 0.93 mmol). The title compound was isolated as a yellow oil (35 mg, 66%) according to the method of Example 286, Step C from (8aS,12aR)-6,7,8a,9,10,11,12,12a-octahydro-5H-pyrido[4,3-b][1,4]thiazepino[2,3,4-hi]indole (30 mg, 0.12 mmol) and 3-(3-chloropropyl)-6-fluoro-1H-indazole (52 mg, 0.24 mmol). $^1$H NMR ($CDCl_3$) δ1.92–2.15 (m, 7H), 2.34–2.42 (m, 1H), 2.42–2.55 (m, 2H), 2.72–3.10 (m, 6H), 3.20–3.34 (m, 2H), 3.50–3.61 (m, 1H), 3.77–3.86 (m, 1H), 6.61 (t, 1H, J=7.5 Hz), 6.84 (d, 1H, J=7.4 Hz), 6.95 (dd, 1H, J=1.1, 7.7 Hz), 7.13 (td, 1H, J=2.3, 8.8 Hz), 7.29–7.39 (m, 2H) ppm.

Example 311

(8aS,12aR)-11-[3-(7-fluoro-1H-indazol-3-yl)propyl]-6,7,8a,9,10,11,12,12a-octahydro-5H-pyrido[4,3-b][1,4]thiazepino[2,3,4-hi]indole 3-(3-Chloropropyl)-7-fluoro-1H-indazole (14 mg, 10%) was afforded according to the procedure of Example 309 from 1-(2-amino-3-fluorophenyl)-4-chloro-1-butanone (136 mg, 0.63 mmol). The title compound was isolated as a yellow oil (10 mg, 66%) according to the method of Example 286, Step C from (8aS,12aR)-6,7,8a,9,10,11,12,12a-octahydro-5H-pyrido[4,3-b][1,4]thiazepino[2,3,4-hi]indole (17 mg, 0.07 mmol) and 3-(3-chloropropyl)-7-fluoro-1H-indazole (14 mg, 0.07 mmol). $^1$H NMR ($CDCl_3$) δ1.81–2.11 (m, 7H), 2.24–3.33 (m, 1H), 2.42–2.54 (m, 2H), 2.67–3.04 (m, 6H), 3.18–3.26 (m, 2H), 3.42–3.57 (m, 1H), 3.71–3.85 (m, 1H), 6.54 (d, 1H, J=7.5 Hz), 6.77 (dd, 1H, J=1.1, 7.0 Hz), 6.88 (dd, 1H, J=1.3, 7.9 Hz), 6.94–7.01 (m, 2H), 7.37–7.41 (m, 1H) ppm.

Example 312

(8aS,12aR)-11-[3-(6-chloro-1H-indazol-3-yl)propyl]-6,7,8a,9,10,11,12,12a-octahydro-5H-pyrido[4,3-b][1,4]thiazepino[2,3,4-hi]indole 3-(3-Chloropropyl)-6-chloro-1H-indazole (107 mg, 54%) was afforded according to the procedure of Example 309 from 1-(2-amino-4-chlorophenyl)-4-chloro-1-butanone (202 mg, 0.87 mmol). The title compound was isolated as a yellow oil (37 mg, 69%) according to the method of Example 286, Step C from (8aS,12aR)-6,7,8a,9,10,11,12,12a-octahydro-5H-pyrido[4,3-b][1,4]thiazepino[2,3,4-hi]indole (30 mg, 0.12 mmol) and 3-(3-chloropropyl)-6-chloro-1H-indazole (56 mg, 0.24 mmol). $^1$H NMR ($CDCl_3$) δ1.93–2.20 (m, 8H), 2.37–3.38 (m, 1H), 2.41–2.48 (m, 2H), 2.69–2.77 (m, 1H), 2.79–2.86 (m, 1H), 2.91–3.10 (m, 4H), 3.16–3.23 (m, 1H), 3.26–3.31 (m, 1H), 3.50–3.61 (m, 1H), 3.77–3.85 (m, 1H), 6.61 (t, 1H, J=7.5 Hz), 6.89 (d, 1H, J=6.6 Hz), 6.94 (dd, 1H, J=1.1 7.7 Hz), 7.09 (dd, 1H, J=1.7, 7.8 Hz), 7.42 (d, 1H, J=1.1 Hz), 7.61 (d, 1H, J=8.4 Hz)

Example 313

(8aS,12aR)-11-[3-(6-bromo-1H-indazol-3-yl)propyl]-6,7,8a,9,10,11,12,12a-octahydro-5H-pyrido[4,3-b][1,4]thiazepino[2,3,4-hi]indole 3-(3-Chloropropyl)-6-bromo-1H-indazole (228 mg, 74%) was afforded according to the procedure of Example 309 from 1-(2-amino-4-bromophenyl)-4-chloro-1-butanone (311 mg, 1.1 mmol). The title compound was isolated as a yellow oil (40 mg, 69%) according to the method of Example 286, Step C from (8aS,12aR)-6,7,8a,9,10,11,12,12a-octahydro-5H-pyrido[4,3-b][1,4]thiazepino[2,3,4-hi]indole (30 mg, 0.07 mmol) and 3-(3-chloropropyl)-6-bromo-1H-indazole (67 mg, 0.24 mmol). $^1$H NMR ($CDCl_3$) δ1.94–2.17 (m, 7H), 2.34–2.41 (m, 1H), 2.45–2.56 (m, 2H), 2.73–2.81 (m, 1H), 2.83–2.90 (m, 1H), 2.90–3.11 (m, 4H), 3.24–3.35 (m, 2H), 3.49–3.61 (m, 1H), 3.77–3.89 (m, 1H), 6.61 (t, 1H, J=7.5 Hz), 6.84 (d, 1H, J=7.4 Hz), 6.95 (d, 1H, J=7.7 Hz), 7.20–7.26 (m, 1H), 7.53–7.60 (m, 1H) ppm.

Example 314

4-((8aS,12aR)-6,7,,9,10,,12,12a-hexahydro-5H-pyrido[4,3-b][1,4]thiazepino[2,3,4-hi]indol-11(8aH)-yl)-1-(2-(methylamino)phenyl)-1-butanone 1-(2-Methylaminophenyl)-4-chloro-1-butanone (886 mg, 22%) was afforded as a yellow solid according to the procedure of Example 302, Step A from N-methylaniline (2.00 g, 18 mmol). The title compound was isolated as a yellow oil (23 mg, 45%) according to the method of Example 286, Step C from (8aS,12aR)-6,7,8a,9,10,11,12,12a-octahydro-5H-pyrido[4,3-b][1,4]thiazepino[2,3,4-hi]indole (30 mg, 0.12 mmol) and 1-(2-methylaminophenyl)-

4-chloro-1-butanone (52 mg, 0.24 mmol). $^1$H NMR ($CDCl_3$) δ1.91–2.23 (m, 6H), 2.24–3.36 (m, 1H), 2.37–2.44 (m, 2H), 2.63–2.71 (m, 1H), 2.75–2.82 (m, 1H), 2.89–3.17 (m, 9H), 3.24–3.30 (m, 1H), 3.47–3.62 (m, 1H), 3.79–3.87 (m, 1H), 6.56–6.63 (m, 2H), 6.69 (d, 1H, J=8.4 Hz), 6.84 (d, 1H, J=7.0 Hz), 6.94 (dd, 1H , J=1.1, 7.7 Hz), 7.35–7.41 (m, 1H), 7.80 (dd, 1H, J=8.6 Hz), 8.81 (br-s, 1H) ppm.

Example 315

(8aS,12aR)-11-[3-(1-benzothien-3-yl)propyl]-6,7,8a-9,10,11,12,12a-octahydro-5H-pyrido[4,3-b][1,4] thiazepino[2,3,4-hi]indole The title compound was isolated as a yellow oil (49 mg, 52%) according to the method of Example 286, Step C from (8aS,12aR)-6,7,8a,9,10,11,12,12a-octahydro-5H-pyrido[4,3-b][1,4]thiazepino[2,3,4-hi]indole (55 mg, 0.23 mmol) and 3-(1-benzothien-3-yl)propyl methanesulfonate (122 mg, 0.45 mmol). $^1$H NMR ($CDCl_3$) δ1.97–2.20 (m, 7H), 2.31–2.41 (m, 1H), 2.44–2.56 (m, 2H), 2.71–2.79 (m, 1H), 2.81–2.99 (m, 4H), 3.04–3.11 (m, 1H), 3.19–3.35 (m, 2H), 3.50–3.62 (m, 1H), 3.79–3.88 (m, 1H), 6.62 (t, 1H, J=7.5 Hz), 6.85 (d, 1H, J=7.3 Hz), 6.95 (dd, 1H, J=1.3, 7.9 Hz), 7.11 (s, 1H, 7.34–7.41 (m, 2H), 7.74–7.78 (m, 1H), 7.85 (dd, 1H, J=1.5,6.2 Hz) ppm.

Example 316

(8aS,12aR)-2-(2,3-dimethylphenyl)-6,7,8a,9,10,11, 12,12a-octahydro-5H-pyrido[4,3-b][1,4]thiazepino [2,3,4-hi]indole Step A To a solution of 3-bromo-o-xylene (500 mg, 2.7 mmol) in THF (15 mL) at −78° C. under $N_2$ was slowly added 1.7 M tert-butyl lithium in pentane (1.77 mL, 3.0 mmol). This was stirred at −78° C. for 30 m. To the reaction mixture was added $B(OiPr)_3$ (2.05 g, 11 mmol), and the reaction mixture was raised to 20° C. and stirred for 2 h. 3 N HCl (10 mL) was added to the reaction mixture and the acidic solution was stirred for 90 m. The reaction mixture was extracted using EtOAc (4×50 mL), and the organic solution was extracted using a 1 N solution of NaOH (100 mL). The aqueous solution was washed with $Et_2O$ (2×50 mL), acidified to pH 1 using concentrated HCl, and then extracted using EtOAc (4×50 mL). The organic solution was then washed with brine (100 mL), dried over $MgSO_4$ and concentrated in vacuo to afford 2,3-dimethylphenylboronic acid compound (750 mg, 45%) as a white solid.

Step B

The title compound was afforded as a yellow oil (65 mg, 77%) according to the method of Example 436, Steps A, B, from tert-butyl((8aS,12aR)-2-bromo-6,7,8a,9,10,11,12,12a-octahydro-5H-pyrido[4,3-b][1,4]thiazepino[2,3,4-hi]indol-11(8aH)-carboxylate (100 mg, 0.24 mmol) and 2,3-dimethylphenylboronic acid (71 mg, 0.48 mmol). $^1$H NMR ($CDCl_3$) δ1.84–1.97 (m, 2H), 2.04–2.18 (m, 2H), 2.17 (s, 3H), 2.31 (s, 3H), 2.61–2.68 (m, 1H), 2.76 (br-s, 1H), 2.90–3.22 (m, 6H), 3.45–3.51 (m, 1H), 3.54–3.64 (m, 1H), 3.77–3.84 (m, 1H), 6.78 (d, 1H, J=1.5 Hz), 6.91 (d, 1H, J=1.5 Hz), 7.01–7.12 (m, 3H).

Example 317

(8aS,12aR)-2-(5-fluoro-2-methylphenyl)-6,7,8a,9,10, 11,12,12a-octahydro-5H-pyrido[4,3-b][1,4] thiazepino[2,3,4-hi]indole 5-Fluoro-2-methylphenylboronic acid (237 mg, 57%) was afforded as a white solid according to the procedure of Example 316, step A from 2-bromo-4-fluorotoluene (507 mg, 2.7 mmol). The title compound was afforded as a yellow oil (63 mg, 71%) according to the method of Example 436, Steps A, B from tert-butyl(8aS,12aR)-2-bromo-6,7,8a,9,10, 11,12,12a-octahydro-5H-pyrido[4,3-b][1,4]thiazepino[2,3, 4-hi]indol-11(8aH)-carboxylate (100 mg, 0.24 mmol) and 5-fluoro-2-methylphenylboronic acid (71 mg, 0.48 mmol). $^1$H NMR ($CDCl_3$) δ1.93 (br-s, 1H), 2.01–2.22 (m, 2H), 2.33 (s, 3H), 2.62–2.68 (m, 1H), 2.92–3.04 (m, 3H), 3.06–3.45 (m, 6H), 3.47–3.58 (m, 1H), 3.77–3.85 (m, 1H), 6.96–7.10 (m, 3H), 7.13–7.19 (m, 2H) ppm.

Example 318

(8aS,12aR)-2-(2-fluoro-5-methylphenyl)-6,7,8a,9,10, 11,12,12a-octahydro-5H-pyrido[4,3-b][1,4] thiazepino[2,3,4-hi]indole 2-Fluoro-5-methylphenylboronic acid (280 mg, 68%) was afforded as a white solid according to the procedure of Example 316, step A from 3-bromo-4-fluorotoluene (507 mg, 2.7 mmol). The title compound was afforded as a yellow oil (70 mg, 76%) according to the method of Example 436, Steps A, B from tert-butyl(8aS,12aR)-2-bromo-6,7,8a,9,10, 11,12,12a-octahydro-5H-pyrido[4,3-b][1,4]thiazepino[2,3, 4-hi]indol-11(8aH)-carboxylate (100 mg, 0.24 mmol) and 2-fluoro-5-methylphenylboronic acid (71 mg, 0.48 mmol). MS (ESI): 355 (base, M+H).

Example 319

(8aS,12aR)-2-(5-fluoro-2-methoxyphenyl)-6,7,8a,9, 10,11,12,12a-octahydro-5H-pyrido[4,3-b][1,4] thiazepino[2,3,4-hi]indole 5-Fluoro-2-methoxyphenylboronic acid (350 mg, 42%) was afforded as a white solid according to the procedure of Example 316, step A from 2-bromo-4-fluoroanisole (1.00 g, 4.9 mmol). The title compound was afforded as a yellow oil (50 mg, 58%) according to the method of Example 436, Steps A,B from tert-butyl(8aS,12aR)-2-bromo-6,7,8a,9,10, 11,12,12a-octahydro-5H-pyrido[4,3-b][1,4]thiazepino[2,3, 4-hi]indol-11(8aH)-carboxylate (100 mg, 0.24 mmol) and 5-fluoro-2-methoxyphenylboronic acid (80 mg, 0.48 mmol). MS (ESI): 371 (base, M+H).

Example 320

(8aS,12aR)-2-(3-chloro-2-methylphenyl)-6,7,8a,9, 10,11,12,12a-octahydro-5H-pyrido[4,3-b][1,4] thiazepino[2,3,4-hi]indole 3-Chloro-2-methylphenylboronic acid (750 mg, 45%) was afforded as a white solid according to the procedure of Example 316, step A from 2-bromo-6-chlorotoluene (2.00 g, 9.7 mmol). The title compound was afforded as a yellow oil (83 mg, 88%) according to the method of Example 436, Steps A,B from tert-butyl(8aS,12aR)-2-bromo-6,7,8a,9,10, 11,12,12a-octahydro-5H-pyrido[4,3-b][1,4]thiazepino[2,3, 4-hi]indol-11(8aH)-carboxylate (100 mg, 0.24 mmol) and 3-chloro-2-methylphenylboronic acid (84 mg, 0.48 mmol). $^1$H NMR ($CDCl_3$) δ1.92–2.13 (m, 4H), 2.21 (s, 3H), 2.54–2.62 (m, 1H), 2.90–3.24 (m, 6H), 3.34–3.40 (m, 1H), 3.44–3.59 (m, 1H), 3.76–3.84 (m, 1H), 5.08 (br-s, 1H), 6.69 (d, 1H, J=1.6 Hz), 6.83 (d, 1H, J=1.6 Hz), 9.98–7.08 (m, 2H), 7.23 (dd, 1H, J=1.6 Hz) ppm. MS (ESI): 371 (base, M+H).

Example 321

(8aS,12aR)-2-(3-nitrophenyl)-6,7,8a,9,10,11,12,12a-octahydro-5H-pyrido[4,3-b][1,4]thiazepino[2,3,4-hi] indole The title compound was afforded as an orange oil (69 mg, 91%) according to the method of Example 436 from tert-butyl(8aS,12aR)-2-bromo-6,7,8a,9,10,11,12,12a-octahydro-5H-pyrido[4,3-b][1,4]thiazepino[2,3,4-hi]indol-11(8aH)- carboxylate (100 mg, 0.24 mmol) and 3-nitrophenylboronic acid (80 mg, 0.48 mmol). MS (ESI): 368 (base, M+H).

Example 322

(8aS,12aR)-2-(2-nitrophenyl)-6,7,8a,9,10,11,12,12a-octahydro-5H-pyrido[4,3-b][1,4]thiazepino[2,3,4-hi] indole The title compound was afforded as an orange oil (14 mg, 17%) according to the method of Example 436, Steps A, B from tert-butyl(8aS,12aR)-2-bromo-6,7,8a,9,10,11,12,12a-octahydro-5H-pyrido[4,3-b][1,4]thiazepino[2,3,4-hi]indol-11(8aH)-carboxylate (100 mg, 0.24 mmol) and 2-nitrophenylboronic acid (80 mg, 0.48 mmol). MS (ESI): 368 (base, M+H).

Example 323

(8aS,12aR)-2-(2-chloro-4-methylphenyl)-6,7,8a,9,10,11,12,12a-octahydro-5H-pyrido[4,3-b][1,4] thiazepino[2,3,4-hi]indole The title compound was prepared by Example 128, Step F, tert-butyl(8aS,12aR)-2-bromo-6,7,9,10,12,12a-hexahydro-5H-pyrido[4,3-b][1,4]thiazepino[2,3,4-hi] indole-11(8aH)-carboxylate and the corresponding 2-chloro-4-methylbenzeneboronic acid followed by hydrolysis of the resultant BOC protected amine adduct by the procedure of Example 128, Step G. $(M+H)^+$ 371.

Example 324

(8aS,12aR)-2-(2-methoxyphenyl)-6,7,8a,9,10,11,12,12a-octahydro-5H-pyrido[4,3-b][1,4]thiazepino[2,3,4-hi]indole The title compound was prepared by Example 128, Step F, from tert-butyl(8aS,12aR)-2-bromo-6,7,9,10,12,12a-hexahydro-5H-pyrido[4,3-b][1,4]thiazepino[2,3,4-hi] indole-11(8aH)-carboxylate and the corresponding 2-methoxybenzeneboronic acid followed by hydrolysis of the resultant BOC protected amine adduct by the procedure of Example 128, Step G. $^1$H NMR ($CDCl_3$, 300 MHz) δ7.28–7.22 (m, 2H), 7.15 (d, 1H), 7.05 (d, 1H), 7.00–6.92 (m, 2H), 3.81 (s, 3H), 3.55 (dq, 1H), 3.44–3.43 (m, 1H), 3.22 (dt, 1H), 3.09–2.99 (m, 3H), 2.92–2.86 (m, 2H), 2.70–2.66 (m, 1H), 2.09–1.84 (m, 2H), 1.90–1.70 (m, 2H). $(M+H)^+$ 353.

Example 325

(8aS,12aR)-2-(2,3-dichlorophenyl)-6,7,8a,9,10,11,12,12a-octahydro-5H-pyrido[4,3-b][1,4]thiazepino[2,3,4-hi]indole The title compound was prepared by Example 128, Step F, from tert-butyl(8aS,12aR)-2-bromo-6,7,9,10,12,12a-hexahydro-5H-pyrido[4,3-b][1,4]thiazepino[2,3,4-hi] indole-11(8aH)-carboxylate and the corresponding 2,3-dichlorobenzeneboronic acid followed by hydrolysis of the resultant BOC protected amine adduct by the procedure of Example 128, Step G. $^1$H NMR ($CDCl_3$, 300 MHz) δ7.39 (dd, 1H), 7.21–7.17 (m, 2H), 7.00 (d, 1H), 6.92 (d, 1H), 3.83 (dq, 1H), 3.57 (qd, 1H), 3.47–3.45 (m, 1H), 3.22 (dt, 1H), 3.10–2.99 (m, 3H), 2.89–2.86 (m, 2H), 2.65 (td, 1H), 2.20–2.01 (m, 2H), 1.86–1.62 (m, 2H). $(M+H)^+$ 392

Example 326

(8aS,12aR)-2-[2-chloro-4-(trifluoromethyl)phenyl]-6,7,8a,9,10,11,12,12a-octahydro-5H-pyrido[4,3-b][1,4]thiazepino[2,3,4-hi]indole The title compound was prepared by Example 128, Step F, from tert-butyl(8aS,12aR)-2-bromo-6,7,9,10,12,12a-hexahydro-5H-pyrido[4,3-b][1,4]thiazepino[2,3,4-hi] indole-11(8aH)-carboxylate and the corresponding 2-chloro-4-(trifluoromethyl)benzeneboronic acid followed by hydrolysis of the resultant BOC protected amine adduct by the procedure of Example 128, Step G. $^1$H NMR ($CDCl_3$, 300 MHz) δ7.68 (s, 1H), 7.49 (d, 1H), 7.43 (d, 1H), 7.04 (d, 1H), 6.96 (d, 1H), 3.85 (qd, 1H), 3.59 (dq, 1H), 3.57–3.45 (m, 1H), 3.25 (dt, 1H), 3.13–3.00 (m, 3H), 2.98–2.04 (m, 2H), 1.87–1.78 (m, 2H). $(M+H)^+$ 425.

Example 327

(8aS,12aR)-2-(4-ethoxy-2-methylphenyl)-6,7,8a,9,10,11,12,12a-octahydro-5H-pyrido[4,3-b][1,4] thiazepino[2,3,4-hi]indole The title compound was prepared by Example 128, Step F, from tert-butyl(8aS,12aR)-2-bromo-6,7,9,10,12,12a-hexahydro-5H-pyrido[4,3-b][1,4]thiazepino[2,3,4-hi] indole-11(8aH)-carboxylate and the corresponding 4-ethoxy-2-methylbenzeneboronic acid followed by hydrolysis of the resultant BOC protected amine adduct by the procedure of Example 128, Step G. $^1$H NMR ($CDCl_3$, 300 MHz) δ7.09 (d, 1H), 6.89 (s, 1H), 6.80–6.71 (m, 3H), 4.02 (q, 2H), 3.78 (qd, 1H), 3.59 (dq, 1H), 3.50–3.40 (m, 1H), 3.20 (dt, 1H), 3.12–2.82 (m, 5H), 2.64 (td, 1H), 2.25 (s, 3H), 2.20–2.00 (m, 2H), 1.99–1.76 (m, 2H), 1.41 (t, 3H). $(M+H)^+$ 381.

Example 328

(8aS,12aR)-2-(4-fluoro-2-methylphenyl)-6,7,8a,9,10,11,12,12a-octahydro-5H-pyrido[4,3-b][1,4] thiazepino[2,3,4-hi]indole The title compound was prepared by Example 128, Step F, from tert-butyl(8aS,12aR)-2-bromo-6,7,9,10,12,12a-hexahydro-5H-pyrido[4,3-b][1,4]thiazepino[2,3,4-hi] indole-11(8aH)-carboxylate and the corresponding 4-fluoro-2-methylbenzeneboronic acid followed by hydrolysis of the resultant BOC protected amine adduct by the procedure of Example 128, Step G. $^1$H NMR ($CDCl_3$, 300 MHz) δ7.08 (dd, 2H), 6.94 (d, 1H), 6.93–6.83 (m, 1H), 6.78 (d, 1H), 3.97 (qd, 1H), 3.62 (dq, 1H), 3.48–3.42 (m, 1H), 3.36 (dt, 1H), 3.35–2.95 (m, 6H), 2.25–2.08 (m, 4H), 2.22 (s, 3H). $(M+H)^+$ 355.

Example 329

(8aS,12aR)-2-(4-butylphenyl)-6,7,8a,9,10,11,12,12a-octahydro-5H-pyrido[4,3-b][1,4]thiazepino[2,3,4-hi] indole The title compound was prepared by Example 128, Step F, from tert-butyl(8aS,12aR)-2-bromo-6,7,9,10,12,12a-hexahydro-5H-pyrido[4,3-b][1,4]thiazepino[2,3,4-hi] indole-11(8aH)-carboxylate and the corresponding 4-butylbenzeneboronic acid followed by hydrolysis of the resultant BOC protected amine adduct by the procedure of Example 128, Step G. $^1$H NMR ($CDCl_3$, 300 MHz) δ7.39 (d, 2H), 7.19 (d, 2H), 7.16 (d, 1H), 7.06 (d, 1H), 3.78 (qd, 1H), 3.56 (dq, 1H), 3.43–3.39 (m, 1H), 3.22 (dt, 1H), 3.17–3.00 (m, 3H), 2.98–2.80 (m, 2H), 2.71–2.60 (m, 3H, 2.21–2.60 (m, 3H), 2.21–2.01 (m, 2H), 1.96–1.76 (m, 2H), 1.76–1.59 (m, 2H), 1.4201.35 (m, 2H), 0.95 (t, 3H). $(M+H)^+$ 379.

Example 330

(8aS,12aR)-2-[2-(trifluoromethyl)phenyl]-6,7,8a,9,10,11,12,12a-octahydro-5H-pyrido[4,3-b][1,4] thiazepino[2,3,4-hi]indole Step A To a solution of tert-butyl(8aS,12aR)-2-bromo-6,7,9,10,12,12a-hexahydro-5H-pyrido[4,3-b][1,4]thiazepino[2,3,4-hi]indole-11(8aH)-carboxylate (0.500 g, 1.18 mmol) in DME (25 mL) was added 2-(trifluoromethyl) benzeneboronic acid (0.448 g, 2.36 mmol), 1,1'-bis (diphenylphosphino)ferrocene palladium (II) (0.025 g), and triethylamine (1.70 mL). The combined mixture was refluxed for 24 hours and then evaporated to dryness under reduced pressure. The residue was taken up in $H_2O$ (150 mL) and extracted with EtOAc (3×50 mL). The combined extracts were dried over $MgSO_4$ and stripped of the solvent under reduced pressure to yield a mixture of 85% product. Purification of the resinous product on normal phase HPLC (75% hexanes in EtOAc) afforded 0.152 g (30%) of tert-butyl(8aS,12aR)-2-[2-(trifluoromethyl)phenyl]-6,7,9,10,12,12a-hexahydro-5H-pyrido[4,3-b][1,4]thiazepino[2,3,4-hi]indole-11(8aH)-carboxylate as a foam. $^1$H NMR ($CDCl_3$, 300 MHz) δ7.69 (d, 1H), 7.49 (t, 1H), 7.39 (t, 1H), 7.28–7.26 (m, 1H), 6.93 (d, 1H), 6.85 (d, 1H), 3.92–3.80 (m, 2H), 3.69–3.60 (t, 1H), 3.60–3.51 (m, 2H), 3.38–3.17 (m, 3H), 3.03–2.95 (dt, 1H), 2.20–2.04 (m, 2H), 1.57 (s, 9H) ppm. $(M+H)^+$ 491,435, 391.

Step B

A solution of tert-butyl(8aS,12aR)-2-[2-(trifluoromethyl) phenyl]-6,7,9,10,12,12a-hexahydro-5H-pyrido[4,3-b][1,4] thiazepino[2,3,4-hi]indole-11(8aH)-carboxylate (0.066 g, 0.13 mmol) in $CH_2Cl_2$ (5 mL) was treated with TFA (1 mL) and stirred at room temperature for 18 hrs. in a closed vial. The solution was basified with 1N NaOH (10 mL) and extracted with $CH_2Cl$ (3×5 mL). The combined extracts were dried over $Na_2SO4$, and stripped of the solvent under reduced pressure to yield 0.032 g (63%) of (8aS,12aR)-2-[2-(trifluoromethyl)phenyl]-6,7,8a,9,10,11,12,12a-octahydro-5H-pyrido[4,3-b][1,4]thiazepino[2,3,4-hi]indole as a foam. The product was purified on reverse phase HPLC (0–100% gradient of water, acetonitrile with 0.1% TFA) to afford 0.021 g (63%) of pure product. $^1$H NMR ($CDCl_3$, 300 MHz) δ7.70 (d, 1H), 7.49 (dt, 1H), 7.40 (dd, 1H), 7.31 (d, 1H), 6.91 (d, 1H), 6.81 (d, 1H), 3.82 (qd, 1H), 3.58 (dq, 1H), 3.50–3.43 (m, 1H), 3.22 (dt, 1H), 3.18–2.98 (m, 3H), 2.97–2.85 (m, 2H), 2.66 (td, 1H), 2.20–2.10 (m, 2H), 1.89–1.80 (m, 2H). $(M+H)^+$ 391.

Example 331

(8aS,12aR)-2-(2-chloro-6-fluorophenyl)-6,7,8a,9,10,11,12,12a-octahydro-5H-pyrido[4,3-b][1,4]thiazepino[2,3,4-hi]indole The title compound was prepared by Example 330, Step A, from tert-butyl(8aS,12aR)-2-bromo-6,7,9,10,12,12a-hexahydro-5H-pyrido[4,3-b][1,4]thiazepino[2,3,4-hi]indole-11(8aH)-carboxylate and the corresponding 2-chloro-6-fluorobenzeneboronic acid followed by hydrolysis of the resultant BOC protected amine adduct by the procedure of Example 330, Step B. $(M+H)^+$ 375.

Example 332

(8aS,12aR)-2-[2-chloro-4-(difluoromethoxy)phenyl]-6,7,8a,9,10,11,12,12a-octahydro-5H-pyrido[4,3-b][1,4]thiazepino[2,3,4-hi]indole The title compound was prepared by Example 330, Step A, from tert-butyl(8aS,12aR)-2-bromo-6,7,9,10,12,12a-hexahydro-5H-pyrido[4,3-b][1,4]thiazepino[2,3,4-hi]indole-11(8aH)-carboxylate and the corresponding 2-chloro-4-(difluoromethoxy)benzeneboronic acid followed by hydrolysis of the resultant BOC protected amine adduct by the procedure of Example 330, Step B. $^1$H NMR ($CDCl_3$, 300 MHz) δ7.22 (d, 1H), 7.05 (dd, 1H), 7.00 (d, 1H), 6.92 (d, 1H), 6.52 (t, 1H, J=10), 3.82 (qd, 1H), 3.57 (dq, 1H), 3.51–3.43 (m, 1H), 3.25 (dt, 1H) 3.25 (dt, 1H), 3.11–2.98 (m, 3H), 2.96–2.80 (m, 2H), 2.64 (td, 1H), 2.20–2.01 (m, 2H), 1.92–1.70 (m, 3H). $(M+H)^+$ 423.

Example 333

(8aS,12aR)-2-[4-(trifluoromethyl)phenyl]-6,7,8a,9,10,11,12,12a-octahydro-5H-pyrido[4,3-b][1,4]thiazepino[2,3,4-hi]indole The title compound was prepared by Example 330, Step A, from tert-butyl(8aS,12aR)-2-bromo-6,7,9,10,12,12a-hexahydro-5H-pyrido[4,3-b][1,4]thiazepino[2,3,4-hi]indole-11((8aH)-carboxylate and the corresponding 4-(trifluoromethyl)benzeneboronic acid followed by hydrolysis of the resultant BOC protected amine adduct by the procedure of Example 330, Step B. $^1$H NMR ($CDCl_3$, 300 MHz) δ6.96 (d, 1H), 6.93 (d, 1H), 6.86 (d, 1H), 6.83 (d, 1H), 6.62 (t, 2H), 3.75 (qd, 1H), 3.75 (dq, 1H), 3.40–3.38 (m, 1H), 3.21 (dt, 1H), 3.04–2.96 (m, 3H), 2.95–2.82 (m, 2H), 2.61 (td, 1H), 2.20–2.00 (m, 2H), 1.82–1.73 (m, 2H). $(M+H)^+$ 391.

Example 334

(8aS,12aR)-2-(4-methylphenyl)-6,7,8a,9,10,11,12,12a-octahydro-5H-pyrido[4,3-b][1,4]thiazepino[2,3,4-hi]indole The title compound was prepared by Example 330, Step A, from tert-butyl(8aS,12aR)-2-bromo-6,7,9,10,12,12a-hexahydro-5H-pyrido[4,3-b][1,4]thiazepino[2,3,4-hi]indole-11(8aH)-carboxylate and the corresponding 4-methylbenzeneboronic acid followed by hydrolysis of the resultant BOC protected amine adduct by the procedure of Example 330, Step B. $^1$H NMR ($CDCl_3$, 300 MHz) δ7.40 (s, 1H), 7.37 (s, 1H), 7.19 (s, 2H), 7.16 (s, 1H), 7.06 (d, 1H), 3.78 (qd, 1H), 3.58 (dq, 1H), 3.50–3.40 (m, 1H), 3.23 (dt, 1H), 3.18–3.00 (m, 3H), 2.92–2.80 (m, 2H), 2.70 (td, 1H), 2.36 (s, 3H), 2.21–2.07 (m, 2H), 1.85–1.72 (m, 2H). $(M+H)^+$ 337.

Example 335

(8aS,12aR)-2-[4-(trifluoromethoxy)phenyl]-6,7,8a,9,10,11,12,12a-octahydro-5H-pyrido[4,3-b][1,4]thiazepino[2,3,4-hi]indole The title compound was prepared by Example 330, Step A, from tert-butyl(8aS,12aR)-2-bromo-6,7,9,10,12,12a-hexahydro-5H-pyrido[4,3-b][1,4]thiazepino[2,3,4-hi]indole-11(8aH)-carboxylate and the corresponding 4-(trifluoromethoxy)benzeneboronic acid followed by hydrolysis of the resultant BOC protected amine adduct by the procedure of Example 330, Step B. $^1$H NMR ($CDCl_3$, 300 MHz) δ7.49 (d, 2H), 7.21 (dd, 2H), 7.19 (d, 1H), 7.03 (d, 1H), 3.80 (qd, 1H), 3.57 (dq, 1H), 3.44–3.41 (m, 1H), 3.24 (dt, 1H), 3.18–3.00 (m, 3H), 2.98–2.83 (m, 2H), 2.73–2.63 (m, 1H), 2.20–2.04 (m, 2H), 1.96–1.80 (m, 2H). $(M+H)^+$ 407.

Example 336

(8aS,12aR)-2-(2-fluoro-4,6-dimethoxyphenyl)-6,7,8a,9,10,11,12,12a-octahydro-5H-pyrido[4,3-b][1,4]thiazepino[2,3,4-hi]indole The title compound was prepared by Example 330, Step A, from tert-butyl(8aS,12aR)-2-bromo-6,7,9,10,12,12a-hexahydro-5H-pyrido[4,3-b][1,4]thiazepino[2,3,4-hi] indole-11(8aH)-carboxylate and the corresponding 2,4-dimethoxy-6-fluorobenzeneboronic acid followed by hydrolysis of the resultant BOC protected amine adduct by the procedure of Example 330, Step B. $^1$H NMR ($CDCl_3$, 300 MHz) δ7.00 (d, 1H), 6.88 (d, 1H), 6.32–6.29 (m, 2H), 3.82–3.78 (m, 1H), 3.80 (s, 3H), 3.75 (s, 3H), 3.56 (dq, 1H), 3.48–3.40 (m,1H), 3.19 (dt, 1H), 3.10–2.98 (m, 3H), 2.98–2.82 (m, 2H), 2.73 (td, 1H), 2.20–2.00 (m, 2H), 1.96–1.83 (m, 2H). $(M+H)^+$ 401.

Example 337

(8aS,12aR)-2-(2-methylphenyl)-6,7,8a,9,10,11,12, 12a-octahydro-5H-pyrido[4,3-b][1,4]thiazepino[2,3, 4-hi]indole The title compound was prepared by Example 330, Step A, from tert-butyl(8aS,12aR)-2-bromo-6,7,9,10,12,12a-5H-pyrido[4,3-b][1,4]thiazepino[2,3,4-hi]indole-11(8aH)-carboxylate and the corresponding 2-mehtylbenzeneboronic acid followed by hydrolysis of the resultant BOC protected amine adduct by the procedure of Example 330, Step B. $^1$H NMR ($CDCl_3$, 300 MHz) δ7.22–7.18 (m, 4H), 6.91 (d, 1H), 6.80 (d, 1H), 3.80 (qd, 1H), 3.58 (dq, 1H), 3.43–3.40 (m, 1H), 3.23 (dt, 1H), 3.09–2.98 (m, 3H), 2.96–2.80 (m, 2H), 2.65 (td, 1H), 2.28 (s, 3H), 2.21–2.02 (m, 2H), 1.96–1.78 (m, 2H). $(M+H)^+$ 337.

Example 338

(8aS,12aR)-2-[2-fluoro-6-(trifluoromethyl)phenyl]-6,7,8a,9,10,11,12,12a-octahydro-5H-pyrido[4,3-b][1, 4]thiazepino[2,3,4-hi]indole The title compound was prepared by Example 330, Step A, from tert-butyl(8aS,12aR)-2-bromo-6,7,9,10,12,12a-hexahydro-5H-pyrido[4,3-b][1,4]thiazepino[2,3,4-hi] indole-11(8aH)-carboxylate and the corresponding 2-fluoro-6-(trifluoromethyl)benzeneboronic acid followed by hydrolysis of the resultant BOC protected amine adduct by the procedure of Example 330, Step B. $^1$H NMR ($CDCl_3$, 300 MHz) δ7.49–7.35 (m, 3H), 7.19 (t, 1H), 7.06 (t, 1H), 3.85 (qd, 1H), 3.58 (dq, 1H), 3.56–3.47 (m, 1H), 3.28–3.00 (m, 4H), 3.00–2.92 (m, 2H), 2.68 (td, 1H), 2.21–2.00 (m, 2H), 1.98–1.84 (m, 2H). $(M+H)^+$ 409.

Example 339

(8aS,12aR)-2-[2-(thiomethyl)phenyl]-6,7,8a,9,10,11, 12,12a-octahydro-5H-pyrido[4,3-b][1,4]thiazepino [2,3,4-hi]indole The title compound was prepared by Example 330, Step A, from tert-butyl(8aS,12aR)-2-bromo-6,7,9,10,12,12a-hexahydro-5H-pyrido[4,3-b][1,4]thiazepino[2,3,4-hi] indole-11(8aH)-carboxylate and the corresponding 2-(thiomethyl)benzeneboronic acid followed by hydrolysis of the resultant BOC protected amine adduct by the procedure of Example 330, Step B. $^1$H NMR ($CDCl_3$, 300 MHz) δ7.27–7.13 (m, 4H), 7.01 (d, 1H), 6.93 (d, 1H), 3.82 (qd, 1H), 3.58 (dq, 1H), 3.49–3.42 (m, 1H), 3.21 (dt, 1H), 3.12–2.96 (m, 3H), 2.95–2.80 (m, 2H), 2.65 (td, 1H), 2.37 (s, 3H), 2.20–2.01 (m, 2H), 1.96–1.76 (m, 2H). $(M+H)^+$ 369.

Example 340

(8aS,12aR)-2-(2,3,4-trifluorophenyl)-6,7,8a,9,10,11, 12,12a-octahydro-5H-pyrido[4,3-b][1,4]thiazepino [2,3,4-hi]indole The title compound was prepared by Example 330, Step A, from tert-butyl(8aS,12aR)-2-bromo-6,7,9,10,12,12a-hexahydro-5H-pyrido[4,3-b][1,4]thiazepino[2,3,4-hi] indole-11(8aH)-carboxylate and the corresponding 2,4,6-trifluorobenzeneboronic acid followed by hydrolysis of the resultant BOC protected amine adduct by the procedure of Example 330, Step B. $^1$H NMR ($CDCl_3$, 300 MHz) δ7.02 (d, 1H), 6.89 (d, 1H), 6.70 (d, 1H), 3.82 (qd, 1H), 3.59 (dq, 1H), 3.57–3.42 (m, 1H), 3.25(dt, 1H), 3.09–3.01 (m, 3H), 2.88–2.85 (m, 2H), 2.66 (td, 1H), 2.20–2.00 (m, 2H), 1.85–1.79 (m, 2H). $(M+H)^+$ 377.

Example 341

(8aS,12aR)-2-(2,4,6-trichlorophenyl)-6,7,8a,9,10,11, 12,12a-octahydro-5H-pyrido[4,3-b][1,4]thiazepino [2,3,4-hi]indole The title compound was prepared by Example 330, Step A, from tert-butyl(8aS,12aR)-2-bromo-6,7,9,10,12,12a-hexahydro-5H-pyrido[4,3-b][1,4]thiazepino[2,3,4-hi] indole-11(8aH)-carboxylate and the corresponding 2,4, 6trichlorobenzeneboronic acid followed by hydrolysis of the resultant BOC protected amine adduct by the procedure of Example 330, Step B. $^1$H NMR ($CDCl_3$, 300 MHz) δ7.37 (s, 2H), 6.81 (d, 1H), 6.69 (d, 1H), 3.85 (qd, 1H), 3.59 (dq, 1H), 3.49–3.44 (m, 1H), 3.23 (dt, 1H), 3.17–2.94 (m, 3H), 2.92–2.83 (m, 2H), 2.65 (td, 1H), 2.21–2.04 (m, 2H), 1.89–1.73 (m, 2H). $(M+H)^+$ 426.

Example 342

(8aS,12aR)-2-(2,6-dichloro-4-methoxyphenyl)-6,7, 8a,9,10,11,12,12a-octahydro-5H-pyrido[4,3-b][1,4] thiazepino[2,3,4-hi]indole Step A To a solution of tert-butyl(8aS,12aR)-2-bromo-6,7,9,10, 12,12a-hexahydro-5H-pyrido[4,3-b][1,4]thiazepino[2,3,4-hi]indole-11(8aH)-carboxylate (0.200 g, 0.47 mmol) in degassed DMF (15 mL) was added Copper(I)Bromide (0.13 g, 0.094 mmol), triphenylphosphine (0.025 g, 0.094 mmol), and Bis-(triphenylphosphine)palladium(II)chloride (0.033 g, (0.047 mmol) under nitrogen gas. After stirring for 5 minutes at room temperature, (2,6-dichloro-4-methoxyphenyl)(trimethyl)stannane (0.479 g, 1.41 mmol) in DMF (3 mL) was added. The mixture was then heated to 140° C. for 2 hours. Once at room temperature, the solution was diluted in EtOAc (200 mL) and washed with $H_2O$ (4×100 mL), dried over $MgSO_4$, and reduced to dryness under reduced pressure to yield an oil. The impure product was purified by column chromatography using 30% EtOAc/hexanes, and normal phase HPLC (25% EtOAc in hexanes) to afford tert-butyl(8aS,12aR)-2-(2,6-dichloro-4-methoxyphenyl)-6,7,9,10,12,12a-hexahydro-5H-pyrido[4, 3-b][1,4]thiazepino[2,3,4-hi]indole-11(8aH)-carboxylate as a foam.

Step B

A solution of tert-butyl(8aS,12aR)-2-(2,6-dichloro-4-methoxyphenyl)-6,7,9,10,12,12a-hexahydro-5H-pyrido[4, 3-b][1,4]thiazepino[2,3,4-hi]indole-11(8aH)-carboxylate (0.204 g, 0.13 mmol) in $CH_2Cl_2$ (50 mL) was treated with TFA (5 mL) and stirred at room temperature for 18 hrs. in a closed vial. The solution was basified with 1N NaOH (100 mL) and extracted with $CH_2Cl_2$ (3×50 mL). The combined extracts were dried over $Na_2SO_4$, and stripped of the solvent under reduced pressure to yield 0.160 g (63%) of (8aS, 12aR)-2-(2,6-dichloro-4-methoxyphenyl)-6,7,8a,9,10,11, 12,12a-octahydro-5H-pyrido[4,3-b][1,4]thiazepino[2,3,4-hi]indole as a foam. The product was purified on reverse phase HPLC (0–100% gradient of water, acetonitrile with 0.1% TFA) to afford 0.145 g (63%) of pure product. $(M+H)^+$ 422.

Example 343

(8aS,12aR)-2-(2,3,4-trifluorophenyl)-6,7,8a,9,10,11,12,12a-octahydro-5H-pyrido[4,3-b][1,4]thiazepino[2,3,4-hi]indole The title compound was prepared by Example 342, Step A, from tert-butyl(8aS,12aR)-2-bromo-6,7,9,10,12,12a-hexahydro-5H-pyrido[4,3-b][1,4]thiazepino[2,3,4-hi]indole-11(8aH)-carboxylate and the corresponding (2,3,4-trifluorophenyl)(trimethyl)stannane followed by hydrolysis of the resultant BOC protected amine adduct by the procedure of Example 342, Step B. $^1$H NMR ($CDCl_3$, 300 MHz) δ7.10 (t, 1H), 7.08–6.93 (m, 2H), 7.00 (t, 1H), 3.84 (qd, 1H), 3.58 (dq, 1H), 3.48–3.42 (m, 1H), 3.28–2.97 (m, 6H), 2.70 (td, 1H), 2.21–2.02 (m, 2H), 1.99–1.87 (m, 2H). $(M+H)^+$ 377.

Example 344

(8aS,12aR)-2-(4-chloro-2,6-difluorophenyl)-6,7,8a,9,10,11,12,12a-octahydro-5H-pyrido[4,3-b][1,4]thiazepino[2,3,4-hi]indole The title compound was prepared by Example 342, Step A, from tert-butyl(8aS,12aR)-2-bromo-6,7,9,10,12,12a-hexahydro-5H-pyrido[4,3-b][1,4]thiazepino[2,3,4-hi]indole-11(8aH)-carboxylate and the corresponding (4-chloro-2,6-difluorophenyl)(trimethyl)stannane followed by hydrolysis of the resultant BOC protected amine adduct by the procedure of Example 342, Step B. $^1$H NMR ($CDCl_3$, 300 MHz) δ7.33 (dd, 1H), 7.18 (dd, 1H), 6.85 (d, 1H), 6.73 (d, 1H), 3.82 (qd, 1H), 3.59 (dq, 1H), 3.59 (qd, 1H), 3.52–3.45 (m, 1H), 3.24 (dt, 1H), 3.14–2.98 (m, 3H), 2.96–2.82 (m, 2H), 2.64 (td, 1H), 2.21–2.03 (m, 2H), 1.98–1.99 (m, 2H). $(M+H)^+$ 403.

Example 345

(8aS,12aR)-2-(2,3,4,6-tetrafluorophenyl)-6,7,8a,9,10,11,12,12a-octahydro-5H-pyrido[4,3-b][1,4]thiazepino[2,3,4-hi]indole The title compound was prepared by Example 342, Step A, from tert-butyl(8aS,12aR)-2-bromo-6,7,9,10,12,12a-hexahydro-5H-pyrido[4,3-b][1,4]thiazepino[2,3,4-hi]indole-11(8aH)-carboxylate and the corresponding (2,3,4,6-tetrafluorophenyl)(trimethyl)stannane followed by hydrolysis of the resultant BOC protected amine adduct by the procedure of Example 342, Step B. $^1$H NMR ($CDCl_3$, 300 MHz) δ7.02 (d, 1H), 6.83 (d, 1H), 6.85–6.78 (m, 1H), 3.83 (tt, 1H), 3.61–3.39 (m, 2H), 3.24 (dt, 1H), 3.12–2.98 (m, 2H), 2.97–2.80 (m, 2H, 2.68 (dd, 1H), 2.22–2.01 (m, 2H), 1.97–1.72 (m, 2H). $(M+H)^+$ 395.

Example 346

(8aS,12aR)-2-(2,3,4,5,6,-pentafluorophenyl)-6,7,8a,9,10,11,12,12a-octahydro-5H-pyrido[4,3-b][1,4]thiazepino[2,3,4-hi]indole The title compound was prepared by Example 342, Step A, from tert-butyl(8aS,12aR)-2-bromo-6,7,9,10,12,12a-hexahydro-5H-pyrido[4,3-b][1,4]thiazepino[2,3,4-hi]indole-11(8aH)-carboxylate and the corresponding (2,3,4,5,6-pentafluorophenyl)(trimethyl)stannane followed by hydrolysis of the resultant BOC protected amine adduct by the procedure of Example 342, Step B. $^1$H NMR ($CDCl_3$, 300 MHz) δ7.03 (d, 1H), 6.90 (d, 1H), 3.83 (qd, 1H), 3.58 (dq, 1H), 3.27 (dt, 1H), 3.18–2.98 (m, 3H), 2.98–2.90 (m, 2H), 2.65 (dd, 1H), 2.21–2.01 (m, 2H), 1.98–1.78 (m, 2H). $(M+H)^+$ 413.

Example 347

(8aS,12aR)-2-[2,6-di(trifluoromethyl)phenyl]-6,7,8a,9,10,11,12,12a-octahydro-5H-pyrido[4,3-b][1,4]thiazepino[2,3,4-hi]indole The title compound was prepared by Example 342, Step from tert-butyl(8aS,12aR)-2-bromo-6,7,9,10,12,12a-hexahydro-5H-pyrido[[4,3-b][1,4]thiazepino[2,3,4-hi]indole-11(8aH)-carboxylate and the corresponding [2,6-bis(trifluoromethyl)phenyl](trimethyl)stannane followed by hydrolysis of the resultant BOC protected amine adduct by the procedure of Example 342, Step B. $^1$H NMR ($CDCl_3$, 300 MHz) δ7.83 (s, 1H), 7.81 (s, 1H), 7.50 (t, 1H), 6.73 (s, 1H), 6.60 (s, 1H), 3.80–3.63 (m, 1H), 3.58–3.40 (m, 2H), 3.19 (dt, 1H), 3.03–2.78 (m, 5H), 2.56 (dd, 1H), 2.19–1.98 (2 H), 1.98–1.75 (m, 2H). $(M+H)^+$ 459.

Example 348

(8aS,12aR)-2-[2-(trifluoromethoxy)phenyl]-6,7,8a,9,10,11,12,12a-octahydro-5H-pyrido[4,3-b][1,4]thiazepino[2,3,4-hi]indole Step A To a solution of tert-butyl(8aS,12aR)-2-bromo-6,7,9,10,12,12a-hexahydro-5H-pyrido[4,3-b][1,4]thiazepino[2,3,4-hi]indole-11(8aH)-carboxylate (0.200 g, 0.47 mmol) in DME (5 mL) was added 2-(trifluoromethoxy)benzeneboronic acid (0.116 g, 0.56 mmol), Bis(triphenylphosphine)palladium(II)chloride (0.030 g), Barium hydroxide octahydrate (0.224 g, 0.71 mmol), and $H_2O$ (2 mL). The combined mixture was refluxed for 4 hrs. Once at room temperature, the mixture was taken up in $H_2O$ (100 mL) and extracted with EtOAc (3×50 mL). The combined extracts were dried over $MgSO_4$ and stripped of solvent under reduced pressure. Purification by normal phase HPLC using 25% EtOAc in hexanes afforded 0.194 g (82%) of tert-butyl(8aS,12aR)-2-[2-trifluoromethoxy)phenyl]-6,7,9,10,12,12a-hexahydro-5H-pyrido[4,3-b][1,4]thiazepino[2,3,4-hi]indole-11(8aH)-carboxylate.

Step B

A solution of tert-butyl(8aS,12aR)-2-[2-(trifluoromethoxy)phenyl]-6,7,9,10,12,12a-hexahydro-5H-pyrido[4,3-b][1,4]thiazepino[2,3,4-hi]indole-11(8aH)-carboxylate (0.194 g, 0.38 mmol) in $CH_2Cl_2$ (30 mL) was treated with TFA (6 mL) and stirred at room temperature for 18 hrs. in a closed vial. The solution was basified with 1N NaOH (100 mL) and extracted with $CH_2Cl_2$ (3×50 mL). The combined extracts were dried over $Na_2SO_4$, and stripped of the solvent under reduced pressure to yield 0.103 g (67%) of (8aS,12aR)-2-[2-(trifluoromethoxy)phenyl]-6,7,8a,9,10,11,12,12a-octahydro-5H-pyrido[4,3-b][1,4]thiazepino[2,3,4-hi]indole as a foam. $^1$H NMR ($CDCl_3$, 300 MHz) δ7.41–7.37 (m, 1H), 7.36–7.27 (m, 3H), 7.05 (d, 1H), 6.99 (d, 1H), 3.80 (qd, 1H), 3.57 (dq, 1H), 3.52–3.42 (m, 1H), 3.25 (dt, 1H), 3.14–2.98 (m, 3H), 2.98–2.80 (m, 2H), 2.70–2.60 (m, 1H), 2.21–2.01 (m, 2H), 1.96–1.76 (m, 2H). $(M+H)^+$ 407.

Example 349

(8aS,12aR)-2-[4-ethoxy-2-(trifluoromethyl)phenyl]-6,7,8a,9,10,11,12,12a-octahydro-5H-pyrido[4,3-b][1,4]thiazepino[2,3,4-hi]indole The title compound was prepared by Example 348, Step A, from tert-butyl(8aS,12aR)-2-bromo-6,7,9,10,12,12a-hexahydro-5H-pyrido[4,3-b][1,4]thiazepino[2,3,4-hi]indole-11(8aH)-carboxylate and the corresponding 4-ethoxy-2-(trifluoromethyl)benzeneboronic acid followed by hydrolysis of the resultant BOC protected amine adduct by the procedure of Example 348, Step B. $^1$H NMR ($CDCl_3$, 300 MHz) δ7.27–7.18 (m, 2H), 7.06–6.98 (m, 1H), 6.89 (s, 1H), 6.79 (s, 1H), 4.06 (q, 2H), 3.79 (qd, 1H), 3.57 (dq, 1H), 3.44–3.40 (m, 1H), 3.24 (dt, 1H), 3.13–2.97 (m, 3H), 2.96–2.80 (m, 2H), 2.63 (td, 1H), 2.21–2.01 (m, 2H), 1.98–1.78 (m, 2H), 1.44 (t, 3H). $(M+H)^+$ 435.

Example 350

(8aS,12aR)-2-[4-isopropoxy-2-(trifluoromethyl) phenyl]-6,7,8a,9,10,11,12,12a-octahydro-5H-pyrido [4,3-b][1,4]thiazepino[2,3,4-hi]indole The title compound was prepared by Example 348, Step A, from tert-butyl(8aS,12aR)-2-bromo-6,7,9,10,12,12a-hexahydro-5H-pyrido[4,3-b][1,4]thiazepino[2,3,4-hi] indole-11(8aH)-carboxylate and the corresponding 4-isopropoxy-2-(trifluoromethyl)benzeneboronic acid followed by hydrolysis of the resultant BOC protected amine adduct by the procedure of Example 348, Step B. $^1$H NMR ($CDCl_3$, 300 MHz) δ7.21–7.17 (m, 2H), 6.98 (dd, 1H), 6.88 (d, 1H), 6.78 (d, 1H), 4.61–4.56 (m, 1H), 3.78 (qd, 1H), 3.55 (dq, 1H), 3.43–3.40 (m, 1H), 3.21 (dt, 1H), 3.10–2.98 (m, 3H), 1.97–2.80 (m, 2H), 2.62 (td, 1H), 2.20–2.01 (m, 2H), 1.97–1.75 (m, 2H), 1.38 (d, 6H). $(M+H)^+$ 449.

Example 351

(8aS,12aR)-2-(2-naphthyl)-6,7,8a,9,10,11,12,12a-octahydro-5H-pyrido[4,3-b][1,4]thiazepino[2,3,4-hi] indole The title compound was prepared by Example 348, Step A, from tert-butyl(8aS,12aR)-2-bromo-6,7,9,10,12,12a-hexahydro-5H-pyrido[4,3-b][1,4]thiazepino[2,3,4-hi] indole-11(8aH)-carboxylate and the corresponding 2-naphthaleneboronic acid followed by hydrolysis of the resultant BOC protected amine adduct by the procedure of Example 348, Step B. $^1$H NMR ($CDCl_3$, 300 MHz) δ7.93 (s, 1H), 7.83 (t, 3H), 7.65 (dd, 1H), 7.52–7.40 (m, 2H), 7.35 (d, 1H), 7.22 (d, 1H), 3.81 (qd, 1H), 3.58 (dq, 1H), 3.50–3.43 (m, 1H), 3.28 (dt, 1H), 3.20–3.01 (m, 3H), 3.00–2.80 (m, 2H), 2.80–2.74 (m, 1H), 2.23–2.04 (m, 2H), 1.98–1.78 ((m, 2H). $(M+H)^+$ 373.

Example 352

(8aS,12aR)-2-[4-chloro-2-(trifluoromethyl)phenyl]-6,7,8a,9,10,11,12,12a-octahydro-5H-pyrido[4,3-b][1,4]thiazepino[2,3,4-hi]indole The title compound was prepared by Example 348, Step A, from tert-butyl(8aS,12aR)-2-bromo-6,7,9,10,12,12a-hexahydro-5H-pyrido[4,3-b][1,4]thiazepino[2,3,4-hi] indole-11(8aH)-carboxylate and the corresponding 4-chloro-2-(trifluoromethyl)benzeneboronic acid followed by hydrolysis of the resultant BOC protected amine adduct by the procedure of Example 348, Step B. $^1$H NMR ($CDCl_3$, 300 MHz) δ7.67 (d, 1H), 7.46 (dd, 1H), 7.23 (s, 1H), 6.86 (d, 1H), 6.77 (s, 1H), 3.80 (qd, 1H), 3.56 (dq, 1H), 3.48–3.42 (m, 1H), 3.22 (dt, 1H), 3.12–2.97 (m, 3H), 2.97–2.80 (m, 2H), 2.64–2.59 (m, 1H), 2.21–2.00 (m, 2H), 1.97–1.75 (m, 2H). $(M+H)^+$ 425.

Example 353

(8aS,12aR)-2-[4-fluoro-2-(trifluoromethyl)phenyl]-6,7,8a,9,10,11,12,12a-octahydro-5H-pyrido[4,3-b][1,4]thiazepino[2,3,4-hi]indole The title compound was prepared by Example 348, Step A, from tert-butyl(8aS,12aR)-2-bromo-6,7,9,10,12,12a-hexahydro-5H-pyrido[4,3-b][1,4]thiazepino[2,3,4-hi] indole-11(8aH)-carboxylate and the corresponding 4-fluoro-2-(trifluoromethyl)benzeneboronic acid followed by hydrolysis of the resultant BOC protected amine adduct by the procedure of Example 348, Step B. $^1$H NMR ($CDCl_3$, 300 MHz) δ7.68 (dd, 1H), 7.67–7.60 (m, 1H), 7.18 (t, 1H), 7.14 (d, 1H), 7.01 (d, 1H), 3.79 (qd, 1H), 3.55 (dq, 1H), 3.50–3.46 (m, 1H), 3.22 (dt, 1H), 3.17–3.00 (m, 3H), 2.98–2.80 (m, 2H), 2.77–2.60 (m, 1H), 2.21–2.02 (m, 2H), 1.98–1.75 (m, 2H). $(M+H)^+$ 409.

Example 354

(8aS,12aR)-2-(2,6-difluorophenyl)-11-methyl-6,7,8a,9,10,11,12,12a-octahydro-5H-pyrido[4,3-b][1,4] thiazepino[2,3,4-hi]indole The title compound (0.12 g, 83%) was prepared by the method of Example 437 from (8aS,12aR)-2-(2,6-difluorophenyl)-6,7,8a,9,10,11,12,12a-octahydro-5H-pyrido[4,3-b][1,4]thiazepino[2,3,4-hi]indole (0.14, 0.39 mmol), HCHO (0.40 mL, 5.3 mmol) and formic acid (0.24 mL, 6.4 mmol) as a white foam. $^1$H NMR ($CDCl_3$, 300 MHz) δ1.92–2.25 (m, 5H), 2.25–2.50 (m, 4H), 2.68–2.80 (m, 1H), 2.80–2.92 (m, 1H), 2.92–3.05 (m, 1H), 3.05–3.12 (m, 1H), 3.28–3.44 (m, 2H), 3.52–3.68 (m, 1H), 3.88–4.00 (m, 1H), 6.88–7.02 (m, 3H), 7.08–7.20 (m, 1H), 7.15–7.26 (m, 1H) ppm. MS (ESI): 373 (base, M+H).

Example 355

2-[2-((±)-cis-6,7,9,10,12a-hexahydro-5H-pyrido[4,3-b][1,4]thiazepino[2,3,4-hi]indol-11(8aH)-yl)ethyl][1,2,4]trizolo[4,3-a]pyridin-3(2H)-one Step A To a solution of [1,2,4]trizolo[4,3-a]pyridin-3(2H)-one (200 mg, 1.47 mmol) in DMF (7.0 mL) was added NaH (43 mg, 1.76 mmol) at 0° C. under $N_2$. The reaction mixture was stirred for 30 min at 0° C. then 1-bromo-2-chloroethane (424 mg, 2.96 mmol) was added dropwise. The reaction mixture was stirred for 15 h at 20° C. then quenched by addition of $H_2O$ and extracted with $CHCl_3$. The combined organic solution was successively washed with saturated $NaHCO_3$ aqueous solution and brine, dried over $MgSO_4$, filtered and concentrated in vacuo. The residue was chromatographed (silica gel; $CHCl_3$:MeOH 99:1) to give 2-(2-chloroethyl)[1,2,4]trizolo[4,3-a]pyridin-3(2H)-one as a white solid (260 mg, 90%).

Step B

To a solution of (±)-cis-6,7,8a,9,10,11,12,12a-octahydro-5H-pyrido[4,3-b][1,4]thiazepino[2,3,4-hi]indole (30 mg, 0.12 mmol)) in 1,4-dioxane (0.72 mL) were added 2-(2-chloroethyl)[1,2,4]trizolo[4,3-a]pyridin-3(2H)-one (36 mg, 0.18 mmol, KI (catalytic amount) and $K_2CO_3$ (25 mg, 0.18 mmol). The reaction mixture was heated at 100° C. for 48 h. The reaction mixture was cooled to 20° C. then diluted with $CHCl_3$. The solution was filtered to remove excess $K_2CO_3$ and the filtrate was concentrated in vacuo and chromatographed (silica gel, $CHCl_3$:MeOH 98:2) to give the title compound (32 mg, 65%) as a pale yellow oil. $^1$H NMR ($CDCl_3$, 300 MHz) δ1.65–1.77 (br-s, 1H), 1.82–1.95 (m, 2H), 1.97–2.20 (m, 3H), 2.39 (dt, J=11.0, 4.1 Hz, 1H), 2.70–2.90 (m, 3H), 2.92–2.99 (m, 1H), 3.02–3.18 (m, 2H), 3.20–3.24 (m, 1H), 3.49–3.60 (m, 1H), 3.77–3.85 (m, 1H), 4.13 (t, J=16.5 Hz, 2H), 6.48 (qu, J=3.5 Hz, 1H), 6.60 (t, J=7.7 Hz, 1H), 6.85 (d, J=7.0 Hz, 1H), 6.93 (d, J=7.7 Hz, 1H), 7.05–7.09 (m, 2H), 7.75 (d, J=7.0 Hz, 1H) ppm.

Example 356

(±)-cis-11-[3-(6-fluoro-1H-indol-1-yl)propyl]-6,7,8a,9,10,11,12,12a-octahydro-5H-pyrido[4,3-b][1,4] thiazepino[2,3,4-hi]indole Step A To a solution of 1-bromo-3-chloropropane (700 mg, 4.44 mmol) in DMF (2.4 mL) was added 6-fluoroindole (200 mg, 1.48 mmol) and powder KOH (92 mg, 1.63 mmol) at 20° C. The reaction mixture was stirred for 15 h at 20° C. then quenched by addition of $H_2O$ and extracted with $Et_2O$. The combined organic solution was successively washed with brine, dried over $MgSO_4$, filtered and concentrated in vacuo. The residue was chromatographed to give 1-(3-chloropropyl)-6-fluoroindole (190 mg, 66%) as a colorless oil.

Step B

The title compound was prepared by the method of Example 355 Step B as a yellow oil (50 mg, 99%) from (±)-cis-6,7,8a,9,10,11,12,12a-octahydro-5H-pyrido[4,3-b][1,4]thiazepino[2,3,4-hi]indole (30 mg, 0.12 mmol) and 1-(3-chloropropyl)-6-fluoroindole (36 mg, 0.18 mmol). $^1$H NMR ($CDCl_3$, 300 MHz) δ1.85–2.30 (m, 10H), 2.57–2.60 (m, 1H), 2.62–2.70 (m, 1H), 2.92–2.98 (m, 1H), 3.03–3.20 (m, 2H), 3.27–3.32 (m, 1H), 3.49–3.60 (m, 1H), 3.78–3.85 (m, 1H), 4.16 (t, J=16.6 Hz, 2H), 6.46 (d, J=2.9 Hz, 1H), 6.62 (t, J=7.3 Hz, 1H), 6.82–6.90 (m, 2H), 6.95 (dd, J=8.1, 0.8 Hz, 1H), 7.07–7.13 (m, 2H), 7.51 (dd, J=8.8, 5.5 Hz, 1H) ppm.

Example 357

(±)-cis-11-[3-(5-fluoro-1H-indol-1-yl)propyl]-6,7,8a,9,10,11,12,12a-octahydro-5H-pyrido[4,3-b][1,4]thiazepino[2,3,4-hi]indole Step A 1-(3-chloropropyl)-5-fluoroindole (190 mg, 66%) was prepared by the method of Example 355 Step A as a colorless oil from 5-fluoroindole (200 mg, 1.48 mmol).

Step B

The title compound was prepared by the method of Example 355 Step B as a yellow oil (48 mg, 95%) from (±)-cis-6,7,8a,9,10,11,12,12a-octahydro-5H-pyrido[4,3-b][1,4]thiazepino[2,3,4-hi]indole (30 mg, 0.12 mmol) and 1-(3-chloropropyl)-5-fluoroindole (36 mg, 0.18 mmol). $^1$H NMR ($CDCl_3$, 300 MHz) δ1.86–2.30 (m, 10H), 2.55–2.59 (m, 1H), 2.65–2.72 (m, 1H), 2.92–3.00 (m, 1H), 3.05–3.21 (m, 2H), 3.27–3.33 (m, 1H), 3.47–3.59 (m, 1H), 3.75–3.86 (m, 1H), 4.20 (t, J=16.6 Hz, 2H), 6.44 (d, J=3.3 Hz, 1H), 6.62 (t, J=7.3 Hz, 1H), 6.85 (d, J=6.9 Hz, 1H), 6.90–6.98 (m, 2H), 7.14 (d, J=2.9 Hz, 1H), 7.23–7.31 (m, 2H) ppm.

Example 358

(±)-cis-11-[3-(6-fluoro-2,3-dihydro-1H-indol-1-yl)propyl]-6,7,8a,9,10,11,12,12a-octahydro-5H-pyrido[4,3-b][1,4]thiazepino[2,3,4-hi]indole To a solution of (±)-cis-11-[3-(6-fluoro-1H-indol-1-yl)propyl]-6,7,8a,9,10,11,12,12a-octahydro-5H-pyrido[4,3-b][1,4]thiazepino[2,3,4-hi]indol (25 mg, 0.054 mmol) in acetic acid (0.8 mL) was added $NaCNBH_3$ (10.2 mg, 0.16 mmol) slowly at 10° C. The reaction mixture was slowly warmed to 20° C. and stirred for 2 h. The reaction was quenched by addition of ice followed by 1N NaOH. The product was extracted with $CHCl_3$ and the combine organic solution was dried over $MgSO_4$. The title compound was obtained by flash column chromatography as a colorless oil (19 mg, 83%). $^1$H NMR ($CDCl_3$, 300 MHz) δ1.77 (qu, J=7.0 Hz, 2H), 1.80–2.20 (m, 5H), 2.22–2.45 (m, 3H), 2.62–2.72 (m, 1H), 2.73–2.82 (m, 1H), 2.87–2.98 (m, 3H), 3.03–3.22 (m, 4H), 3.25–3.32 (m, 1H), 3.40 (t, J=8.5 Hz, 2H), 3.50–3.61 (m, 1H), 3.78–3.88 (m, 1H), 6.16 (dd, J=10.6, 2.2 Hz, 1H), 6.26 (dt, J=8.0, 2.5 Hz, 1H), 6.62 (t, J=7.3 Hz, 1H), 6.84–6.97 (m, 3H) ppm. MS (CI, $NH_3$): 424.3 (base, M+H).

Example 359

(±)-cis-11-[3-(5-fluoro-2,3-dihydro-1H-indol-1-yl)propyl]-6,7,8a,9,10,11,12,12a-octahydro-5H-pyrido[4,3-b][1,4]thiazepino[2,3,4-hi]indole The title compound was prepared by the method of Example 358 as a colorless oil (19 mg, 69%) from (8aS,12aR)-11-[3-(6-fluoro-1H-indol-1-yl)propyl]-6,7,8a,9,10,11,12,12a-octahydro-5H-pyrido[4,3-b][1,4]thiazepino[2,3,4-hi]indol (30 mg, 0.065 mmol). $^1$H NMR ($CDCl_3$, 300 MHz) δ1.74–1.84 (m, 2H), 1.86–2.20 (m, 5H), 2.22–2.45 (m, 3H), 2.64–2.82 (m, 2H), 2.87–3.22 (m, 7H), 3.25–3.38 (m, 3H), 3.50–3.62 (m, 1H), 3.78–3.85 (m, 1H), 6.35 (dd, J=8.8, 4.4 Hz, 1H), 6.62 (t, J=7.3 Hz, 1H), 6.70–6.90 (m, 3H), 6.95 (dd, J=8.0, 1.0 Hz, 1H) ppm.

Example 360

(±)-cis-11-[3-(6-fluoro-1H-indol-3-yl)propyl]-6,7,8a,9,10,11,12,12a-octahydro-5H-pyrido[4,3-b][1,4]thiazepino[2,3,4-hi]indole Step A The solution of 6-fluoroindol (300 mg, 2.22 mmol), acrylic acid (352 mg, 4.88 mmol) and acetic anhydride (453 mg, 4.44 mmol) in acetic acid (1.1 mL) was heated at 90° C. for 15 h. The reaction mixture was cooled to 20° C. then concentrated in vacuo. The residue was dissolved in 3N NaOH. The solution was filtered to remove insoluble material and the filtrate was acidified with conc. HCl and extracted with $CHCl_3$. The organic solution was dried over $MgSO_4$, filtered and concentrated in vacuo to give 3-(6-fluoroindolyl)propionic acid (240 mg, 52%) as a yellow solid.

Step B

To a solution of 3-(6-fluoroindolyl)propionic acid (235 mg, 1.13 mmol) in THF (5.3 mL) was added $LiAlH_4$ (86 mg, 2.26 mmol) slowly at 0° C. under $N_1$. The reaction mixture was warmed to 20° C. and stirred for 15 h. The reaction was quenched by addition of $H_2O$ (0.5 mL) and diluted with EtOAc. The resulting solution was dried over $MgSO_4$, filtered through Celite and concentrated in vacuo. The residue was chromatographed to give 6-fluoro-3-(3-hydroxypropyl)indole (142 mg, 65%) as a colorless oil.

Step C

To a solution of 6-fluoro-3-(3-hydroxypropyl)indole (140 mg, 0.72 mmol) in $CH_2Cl_2$ (4.5 mL) and $Et_3N$ (147 mg, 1.45 mmol) was added methane sulfonyl chloride (125 mg, 1.09 mmol) at 0° C. under $N_2$. The reaction mixture was stirred for 2 h at 0° C. The reaction was quenched by addition of 1N HCl and diluted with $Et_2O$. The layer was separated and the organic layer was dried over $MgSO_4$, filtered and concentrated in vacuo. The residue was chromatographed to give 3-(6-fluoroindolyl)-propyl methanesulfonate (140 mg, 71%) as a colorless oil.

Step D

The title compound was prepared by the method of Example 355 Step B as a yellow oil (35 mg, 69%) from (±)-cis-6,7,8a,9,10,11,12,12a-octahydro-5H-pyrido[4,3-b][1,4]thiazepino[2,3,4-hi]indole (30 mg, 0.12 mmol) and 3-(6-fluoroindolyl)-propyl methanesulfonate (49 mg, 0.18 mmol). $^1$H NMR ($CDCl_3$, 300 MHz) δ1.86–2.20 (m, 7H), 2.25–2.36 (m, 1H), 2.39–2.46 (m, 2H), 2.67–2.85 (m, 4H), 2.85–2.96 (m, 1H), 3.02–3.15 (m, 1H), 3.17–3.25 (m, 1H), 3.28 (qu, J=3.3 Hz, 1H) 3.50–3.62 (m, 1H), 3.77–3.87 (m, 1H), 6.62 (t, J=7.4 Hz, 1H), 6.83–6.91 (m, 2H), 6.93–6.97 (m, 2H), 7.01 (dd, J=9.9, 2.2 Hz, 1H), 7.48 (dd, J=8.5, 5.2 Hz, 1H), 7.93–7.99 (br-s, 1H) ppm.

Example 361

(8aS,12aR)-11-[3-(6-fluoro-1H-indol-3-yl)propyl]-6,7,8a,9,10,11,12,12a-octahydro-5H-pyrido[4,3-b][1,4]thiazepino[2,3,4-hi]indole To a solution of (8aS,12aR)-6,7,8a,9,10,11,12,12a-octahydro-5H-pyrido[4,3-b][1,4]thiazepino[2,3,4-hi]indole HCl salt (20 mg, 0.063 mmol) in 1,4-dioxane (0.4 mL) and N,N-diisopropylethylamine (82 mg, 0.63 mmol) were added 3-(6-fluoroindolyl)-propyl methanesulfonate (26 mg, 0.89 mmol) and KI (catalytic amount). The reaction mixture was heated at 100° C. for 15 h. The reaction mixture was cooled to 20° C. then concentrated in vacuo and chromatographed (silica gel $CHCl_3$:MeOH 98:2) to give desired the title compound (24 mg, 91%) as a yellow oil. The title compound was spectroscopically identical to Example 360.

Example 362

(±)-cis-11-[3-(5-fluoro-1H-indol-3-yl)propyl]-6,7,8a,9,10,11,12,12a-octahydro-5H-pyrido[4,3-b][1,4]thiazepino[2,3,4-hi]indole Step A 3-(5-Fluoroindolyl)propionic acid (272 mg, 60%) was prepared by the method of Example 360 Step A as a yellow solid from 5-fluoroindole (300 mg, 2.22 mmol)

Step B

5-Fluoro-3-(3-hydroxypropyl)indole (185 mg, 74%) was prepared by the method of Example 360 Step B as a colorless solid from 3-(5-Fluoroindolyl)propionic acid (270 mg, 1.30 mmol).

Step C 3-(5-Fluoroindolyl)-propyl methanesulfonate (185 mg, 74%) was prepared by the method of Example 360 Step C as a colorless solid from 5-fluoro-3-(3-hydroxypropyl) indole (167 mg, 0.86 mmol)

Step D

The title compound was prepared by the method of Example 355 Step B as a yellow oil (35 mg, 69%) from (±)-cis-6,7,8a,9,10,11,12,12a-octahydro-5H-pyrido[4,3-b][1,4]thiazepino[2,3,4-hi]indole (30 mg, 0.12 mmol) and 3-(5-fluoroindolyl)-propyl methanesulfonate (49 mg, 0.18 mmol). $^1$H NMR ($CDCl_3$, 300 MHz) δ1.88–2.19 (m, 7H), 2.24–2.35 (m, 1H), 2.37–2.47 (m, 2H), 2.68–2.85 (m, 4H), 2.88–2.97 (m, 1H), 3.02–3.12 (m, 1H), 3.15–3.30 (m, 2H), 3.48–3.60 (m, 1H), 3.77–3.87 (m, 1H), 6.62 (t, J=7.3 Hz, 1H), 6.85 (d, J=6.6 Hz, 1H), 6.89–6.97 (m, 2H), 7.03 (s, 1H), 7.21–7.30 (m, 2H), 7.93–8.01 (br-s, 1H) ppm.

Example 363

(8aS,12aR)-11-[3-(5-fluoro-1H-indol-3-yl)propyl]-6,7,8a,9,10,11,12,12a-octahydro-5H-pyrido[4,3-b][1,4]thiazepino[2,3,4-hi]indole The title compound was prepared by the method of Example 361 as a yellow oil (19 mg, 72%) from (8aS,12aR)-6,7,8a,9,10,11,12,12a-octahydro-5H-pyrido[4,3-b][1,4]thiazepino[2,3,4-hi]indole HCl salt (20 mg, 0.063 mmol) and 3-(5-fluoroindolyl)-propyl methanesulfonate (26 mg, 0.094 mmol). The title compound was spectroscopically identical to Example 362.

Example 364

(±)-cis-11-[3-(9H-purin-9-yl)propyl]-6,7,8a,9,10,11,12,12a-octahydro-5H-pyrido[4,3-b][1,4]thiazepino[2,3,4-hi]indole Step A To a solution of purine (360 mg, 3.00 mmol) and 1-bromo-3-chloropropane (1.42 g, 9.0 mmol) in DMF (10 mL) was added $K_2CO_3$ (622 mg, 4.5 mmol) at 20° C. The reaction mixture was stirred for 24 h at 20° C. and filtered. The filtrate was concentrated in vacuo and the residue was chromatographed to give 9-(3-chloropropyl)purine (400 mg, 68%) and 7-(3-chloropropyl)purine (136 mg, 23%) as colorless oils.

Step B

The title compound was prepared by the method of Example 355 Step B as a yellow oil (40 mg, 82%) from (±)-cis-6,7,8a,9,10,11,12,12a-octahydro-5H-pyrido[4,3-b][1,4]thiazepino[2,3,4-hi]indole (30 mg, 0.12 mmol) and 9-(3-chloropropyl)purine (36 mg, 0.18 mmol). $^1$H NMR ($CDCl_3$, 300 MHz) δ1.78–2.20 (m, 7H), 2.22–2.33 (m, 3H), 2.47–2.55 (m, 1H), 2.60–2.68 (m, 1H), 2.94 (dt, J=14.3, 4.5 Hz, 1H), 3.03–3.15 (m, 2H), 3.28 (qu, J=3.0 Hz, 1H), 3.47–3.55 (m, 1H), 3.72–3.82 (m, 1H), 4.38 (dt, J=6.6, 1.1 Hz, 2H), 6.62 (t, J=7.3 Hz, 1H), 6.85 (d, J=6.6 Hz, 1H), 6.94 (dd, J=7.7, 0.9 Hz, 1H), 8.12 (s, 1H), 8.98 (s, 1H), 9.14 (s, 1H) ppm.

Example 365

(±)-cis-11-[3-(7H-purin-7-yl)propyl]-6,7,8a,9,10,11,12,12a-octahydro-5H-pyrido[4,3-b][1,4]thiazepino[2,3,4-hi]indole The title compound was prepared by the method of Example 355 Step B as a yellow oil (34 mg, 70%) from (±)-cis-6,7,8a,9,10,11,12,12a-octahydro-5H-pyrido[4,3-b][1,4]thiazepino[2,3,4-hi]indole (30 mg, 0.12 mmol) and 7-(3-chloropropyl)purine (36 mg, 0.18 mmol). $^1$H NMR ($CDCl_3$, 300 MHz) δ1.80–2.30 (m, 10H), 2.45–2.53 (m, 1H), 2.58–2.65 (m, 1H), 2.94 (dt, J=13.9, 4.6 Hz, 1H), 3.05–3.17 (m, 2H), 3.30 (qu, J=3.6 Hz, 1H), 3.45–3.55 (m, 1H), 3.75–3.83 (m, 1H), 4.36–4.45 (m, 2H), 6.63 (t, J=7.6 Hz, 1H), 6.85 (d, J=6.9 Hz, 1H), 6.95 (d, J=7.7 Hz, 1H), 8.25 (s, 1H), 9.00 (s, 1H), 9.16 (s, 1H) ppm.

Example 366

4-[5-((±)-cis 6,7,9,10,12,12a-hexahydro-5H-pyrido[4,3-b][1,4]thiazepino[2,3,4-hi]indol-11(8aH)-ylmethyl)4,5-dihydro-3-isoxazolyl]benzonitrile Step A

[3-(4-Cyanophenyl)-4,5-dihydro-5-isoxazolyl]methyl methanesulfonate (69 mg, 99%) was prepared by the method of Example 360 Step C as a yellow solid from 4-[5-(hydroxymethyl)-4,5-dihydro-3-isoxaolyl]benzonitrile (51 mg, 0.25 mmol)

Step B

The title compound was prepared by the method of Example 355 Step B as a yellow oil (50 mg, 96%) from (±)-cis-6,7,8a,9,10,11,12,12a-octahydro-5H-pyrido[4,3-b][1,4]thiazepino[2,3,4-hi]indole (30 mg, 0.12 mmol) and {3-(4-cyanophenyl)-4,5-dihydro-5-isoxaolyl}methyl methanesulfonate (50 mg, 0.18 mmol). $^1$H NMR ($CDCl_3$, 300 MHz) δ1.89 (qu, J=4.4 Hz, 2H), 2.02–2.20 (m, 3H), 2.40–2.80 (m, 4H), 2.88–2.99 (m, 1H), 3.05–3.35 (m, 5H), 3.43–3.55 (m, 2H), 3.75–3.83 (m, 1H), 4.92–5.01 (m, 1H), 6.58 (td, J=13.9, 7.2 Hz, 1H), 6.84 (dd, J=7.0, 3.0 Hz, 1H), 6.92–6.97 (m, 1H), 7.67–7.60 (m, 4H) ppm.

Example 367

(±)-cis-11-[3-(6-fluoro-1H-indazol-3-yl)propyl]-6,7,8a,9,10,11,12,12a-octahydro-5H-pyrido[4,3-b][1,4]thiazepino[2,3,4-hi]indole Step A To a solution of $BCl_3.Me_2S$ (1.78 g, 9.9 mmol), in anhydrous benzene (9 mL) was added dropwise a solution of 3-fluoroaniline (1.00 g, 9.0 mmol) in benzene (9 mL) under $N_2$ with ice cooling. To this reaction mixture was added 4-chlorobutyronitrile (1.12 g, 10.8 mmol) and $AlCl_3$, successively. The reaction mixture was refluxed for 20 h then cooled to 20° C. Ice cold 2N HCl was added to the reaction mixture to form yellow solid. The resulting mixture was reheated to 80° C. for 1 h. The solution was cooled to 20° C. and extracted with $CHCl_3$. The organic solution was washed with $H_2O$ and brine, dried over $MgSO_4$, filtered and concentrated in vacuo. The residue was chromatographed to give 1-(2-amino-4-fluorophenyl)-4-chloro-1-butanone (1.07 g, 55%) as a white solid.

Step B

To a suspension of 1-(2-amino-4-fluorophenyl)-4-chloro-1-butanone (500 mg, 2.3 mmol) in conc. HCl (3.2 mL) was added a solution of $NaNO_2$ in $H_2O$ (0.7 mL) and stirred for 1 h at −6–0° C. A solution of $SnCl_2.2H_2O$ (1.25 g, 5.51 mmol) in conc. HCl (1.7 mL) was added the reaction mixture and stirred for additional 1 h at 0° C. The reaction was quenched by addition of ice water and extracted with $Et_2O$. The combined organic layer was washed with $H_2O$ and brine, dried over $MgSO_4$, filtered and concentrated in vacuo to give a white solid. It was recrystallized to give pure 3-(3-chloropropyl)-6-fluoroindazole (420 mg, 86%).

Step C

The title compound was prepared by the method of Example 355 Step B as a yellow oil (34 mg, 67%) from (±)-cis-6,7,8a,9,10,11,12,12a-octahydro-5H-pyrido[4,3-b][1,4]thiazepino[2,3,4-hi]indole (30 mg, 0.12 mmol) and 3-(3-chloropropyl)-6-flouroindazole (39 mg; 0.18 mmol). $^1$H NMR ($CDCl_3$, 300 MHz) δ1.86–2.20 (m, 7H), 2.22–2.33 (m, 1H), 2.39–2.47 (m, 2H), 2.65–2.73 (m, 1H), 2.75–2.83 (m, 1H), 2.88–3.08 (m, 4H), 3.12–3.20 (m, 1H), 3.27 (qu, J=3.3 Hz, 1H) 3.50–3.60 (m, 1H), 3.77–3.87 (m, 1H), 6.61 (t, J=7.5 Hz, 1H), 6.83 (d, J=7.9 Hz, 1H), 6.86–6.95 (m, 2H), 7.06 (dd, J=9.1, 2.2 Hz, 1H), 7.62 (dd, J=8.8, 5.1 Hz, 1H), 9.85–10.15 (br-s, 1H) ppm.

Example 368

(8aS,12aR)-11-[3-(6-fluoro-1H-indazol-3-yl)propyl]-6,7,8a,9,10,11,12,12a-octahydro-5H-pyrido[4,3-b][1,4]thiazepino[2,3,4-hi]indole The title compound was prepared by the method of Example 361 as a yellow oil (21 mg, 50%) from (8aS,12aR)-6,7,8a,9,10,11,12,12a-octahydro-5H-pyrido[4,3-b][1,4]thiazepino[2,3,4-hi]indole HCl salt (32 mg, 0.10 mmol) and 3-(3-chloropropyl)-6-fluoroindazole (32 mg, 0.15 mmol). The title compound was spectroscopically identical to Example 367.

Example 369

(8aR, 12aS)-11-[3-(6-fluoro-1H-indazol-3-yl)propyl]-6,7,8a,9,10,11,12,12a-octahydro-5H-pyrido[4,3-b][1,4]thiazepino[2,3,4-hi]indole The title compound was prepared by the method of Example 361 as a yellow oil (31 mg, 73% from (8aR,12aS)-6,7,8a,9,10,11,12,12a-octaydro-5H-pyrido[4,3-b][1,4]thiazepino[2,3,4-hi]indole HCl salt (32 mg, 0.10 mmol) and 3-(3-chloropropyl)-6-fluorindazole (32 mg, 0.15 mmol). The title compound was spectroscopically identical to Example 367.

Example 370

4-((±)-cis-6,7,9,10,12,12a-hexahydro-5H-pyrido[4,3-b][1,4]thiazepino[2,3,4-hi]indol-11(8aH)-yl)-1-(2-amino-4-fluorophenyl)-1-butanone The title compound was prepared by the method of Example 355 Step B as a red oil (330 mg, 64%) from (±)-cis-6,7,8a,9,10,11,12,12a-octahydro-5H-pyrido[4,3-b][1,4]thiazepino[2,3,4-hi]indole (300 mg, 0.121 mmol) and 1-(2-amino-4-fluorophenyl)-4-chloro-1-butanone (400 mg, 1.85 mmol). $^1$H NMR ($CDCl_3$, 300 MHz) δ1.83–2.18 (m, 7H), 2.22–2.40 (m, 3H), 2.60–2.69 (m, 1H), 2.72–2.80 (m, 1H), 2.89–2.99 (m, 3H), 3.03–3.17 (m, 2H), 3.25 (qu, J=2.9 Hz, 1H), 3.49–3.59 (m, 1H), 3.78–3.87 (m, 1H), 6.28–6.38 (m, 2H), 6.40–6.48 (br-s, 2H), 6.61 (t, J=7.4 Hz, 1H), 6.85 (d, J=7.0 Hz, 1H), 6.94 (dd, J=8.1, 1.1 Hz, 1H), 7.77 (dd, J=8.8, 6.4 Hz, 1H) ppm.

Example 371

4-((8aS,12aR)-6,7,9,10,12,12a-hexahydro-5H-pyrido[4,3-b][1,4]thiazepino[2,3,4-hi]indol-11(8aH)-yl)-1-(2-amino-4-fluorophenyl)-1-butanone The title compound was prepared by the method of Example 355 Step B as a yellow oil (130 mg, 24%) from (8aS,12aR)-6,7,8a,9,10,11,12,12a-octahydro-5H-pyrido[4,3-b][1,4]thiazepino[2,3,4-hi]indole (320 mg, 1.3 mmol) and 1-(2-amino-4-fluorophenyl)-4-chloro-1-butanone (564 mg, 2.6 mmol). The title compound was spectroscopically identical to Example 370.

Example 372

N-{2-[4-((±)-cis-6,7,9,10,12,12a-hexahydro-5H-pyrido[4,3-b][1,4]thiazepino[2,3,4-hi]indol-11(8aH)-yl)butanoyl]-5-fluorophenyl}methanesulfonamide To a solution of 4-((±)-cis-6,7,9,10,12,12a-hexahydro-5H-pyrido[4,3-b][1,4]thiazepino[2,3,4-hi]indol-11(8aH)-yl)-1-(2-amino-4-fluorophenyl)-1-butanone (30 mg, 0.070 mmol) in $CH_2Cl_2$ (0.5 mL) was added $Et_3N$ (15 mg, 0.14 mmol) followed by methanesulfonyl chloride (12 mg, 0.11 mmol) at 0° C. under $N_2$. The reaction mixture was stirred for 4 h at 0° C. then quenched by addition of HCl (1.0N, 1.0 mL). The resulting solution was extracted with $CHCl_3$. The combine organic solution was dried over $MgSO_4$. The title compound was obtained by flash column chromatography (silica gel; $CHCl_3$:MeOH 99:1) as a white amorphous solid (35 mg, 99%). $^1$H NMR ($CDCl_3$, 300 MHz) δ1.85–2.18 (m, 7H), 2.24–2.42 (m, 3H), 2.58–2.66 (m, 1H), 2.69–2.77 (m, 1H), 2.89–3.17 (m, 5H), 3.23–3.30 (m, 1H), 3.49–3.59 (m, 4H), 3.74–3.85 (m, 1H), 6.60 (t, J=7.7 Hz, 1H), 6.80–88 (m, 2H), 6.94 (d, J=8.1 Hz, 1H), 7.13 (dd, J=8.5, 2.2 Hz, 1H), 7.20–7.25 (m, 1H), 7.77 (dd, J=8.8, 5.9 Hz, 1H) ppm.

Example 373

N-{2-[4-((±)-cis-6,7,9,10,12,12a-hexahydro-5H-pyrido[4,3-b][1,4]thiazepino[2,3,4-hi]indol-11(8aH)-yl)butanoyl]-5-fluorophenyl}acetamide To a solution of 4-((±)-cis-6,7,9,10,12,12a-hexahydro-5H-pyrido[4,3-b][1,4]thiazepino[2,3,4-hi]indol-11(8aH)-yl)-1-(2-amino-4-fluorophenyl)-1-butanone (28 mg, 0.066 mmol) in $CH_2Cl_2$ (0.5 mL) was added pyridine (16 mg, 0.20 mmol) followed by acetic anhydride (13 mg, 0.13 mmol) at 20° C. under $N_2$. The reaction mixture was stirred for 15 h at 20° C. then quenched by addition of $H_2O$. The resulting solution was extracted with $CHCl_3$. The combine organic solution was dried over $MgSO_4$. The title compound was obtained by flash column chromatography (silica gel; $CHCl_3$:MeOH 99:1) as a white amorphous solid (28 mg, 91%). $^1$H NMR ($CDCl_3$, 300 MHz) δ1.90–2.18 (m, 10H), 2.49–2.69 (m, 3H), 2.88–3.07 (m, 6H), 3.27–3.38 (m, 2H), 3.49–3.59 (m, 1H), 3.79–3.90 (m, 1H), 6.25–6.38 (m, 2H), 6.41–6.50 (br-s, 1H), 6.64 (t, J=7.3 Hz, 1H), 6.87 (d, J=7.0 Hz, 1H), 6.97 (dd, J=7.7, 1.1 Hz, 1H), 7.73 (dd, J=9.2, 6.6 Hz, 1H) ppm.

Example 374

N-{2-[4-((8aS,12aR)-6,7,9,10,12,12a-hexahydro-5H-pyrido[4,3-b][1,4]thiazepino[2,3,4-hi]indol-11(8aH)-yl)butanoyl]-5-fluorophenyl}acetamide The title compound (37 mg, 80%) was prepared by the method of Example 373 from 4-((8aS,12aR)-6,7,9,10,12,12a-hexahydro-5H-pyrido[4,3-b][1,4]thiazepino[2,3,4-hi]indol-11(8aH)-yl)-1-(2-amino-4-fluorophenyl)-1-butanone (43 mg, 0.10 mmol) as a white amorphous solid (28 mg, 91%). The title compound was spectroscopically identical to Example 373.

Example 375

Ethyl 2-[4-((±)-cis-6,7,9,10,12,12a-hexahydro-5H-pyrido[4,3-b][1,4]thiazepino[2,3,4-hi]indol-11(8aH)-yl)butanoyl]-5-fluorophenylcarbamate To a solution of 4-((±)-cis-6,7,9,10,12,12a-hexahydro-5H-pyrido[4,3-b][1,4]thiazepino[2,3,4-hi]indol-11(8aH)-yl)-1-(2-amino-4-fluorophenyl)-1-butanone (35 mg, 0.082 mmol) in pyridine (0.2 mL) was added ethyl chloroformate (16 mg, 0.10 mmol) at 0° C. under $N_2$. The reaction mixture was stirred for 40 min at 0° C. then concentrated in vacuo. The residue was chromatographed (silica gel; $CHCl_3$:MeOH 99:1) to give the title compound as a yellow oil (6.0 mg, 51%). $^1H$ NMR ($CDCl_3$, 300 MHz) δ1.32 (t, J=7.3 Hz, 3H), 1.83–2.18 (m, 7H), 2.25–2.50 (m, 3H), 2.70–2.87 (br-s, 2H), 2.89–3.17 (m, 5H), 3.25–3.32 (m, 1H), 3.50–3.61 (m, 1H), 3.77–3.87 (m, 1H), 4.23 (q, J=7.3 Hz, 2H), 6.61 (t, J=7.4 Hz, 1H), 6.72–6.80 (m, 1H), 6.85 (d, J=7.4 Hz, 1H), 6.94 (dd, J=7.7, 1.1 Hz, 1H), 7.94 (dd, J=9.1, 6.3 Hz, 1H), 8.28 (dd, J=12.1, 2.5 Hz, 1H), 11.39–11.43 (br-s, 1H) ppm.

Example 376

N-{2-[4-((±)-cis-6,7,9,10,12,12a-hexahydro-5H-pyrido[4,3-b][1,4]thiazepino[2,3,4-hi]indol-11(8aH)-yl)butanoyl]-5-fluorophenyl-N'-ethylurea 4-((±)-Cis-6,7,9,10,12,12a-Hexahydro-5H-pyrido[4,3-b][1,4]thiazepino[2,3,4-hi]indol-11(8aH)-yl)-1-(2-amino-4-fluorophenyl)-1-butanone (32 mg, 0.075 mmol) was dissolved in ethyl isocyanate (50 82 ), and the solution was stirred for 20 h at 20° C. under $N_2$. The reaction mixture was concentrated in vacuo then chromatographed (silica gel; $CHCl_3$:MeOH 99:1) to give the title compound as a pale yellow oil (30 mg, 81%). $^1H$ NMR ($CDCl_3$, 300 MHz) δ1.21 (t, J=7.0 Hz, 3H), 1.90–2.18 (m, 7H), 2.25–2.50 (m, 3H), 2.65–2.87 (br-s, 2H), 2.90–3.17 (m, 4H), 3.19–3.35 (m, 4H), 3.50–3.59 (m, 1H), 3.78–3.87 (m, 1H), 4.73–4.79 (br-s, 1H), 6.57–6.77 (m, 2H), 6.84 (d, J=6.2 Hz, 1H), 6.95 (dd, J=7.7, 1.1 Hz, 1H), 7.91 (dd, J=8.7, 6.2 Hz, 1H), 8.41 (dd, J=12.4, 2.6 Hz, 1H), 11.39–11.43 (br-s, 1H) ppm. MS (Cl, $NH_3$): 497.2 (base, M+H).

Example 377

2-[4-((±)-cis-6,7,9,10,12,12a-hexahydro-5H-pyrido[4,3-b][1,4]thiazepino[2,3,4-hi]indol-11(8aH)-yl)butanoyl]-5-fluorophenylformamide 4-((±)-Cis-6,7,9,10,12,12a-Hexahydro-5H-pyrido[4,3-b][1,4]thiazepino[2,3,4-hi]indol-11(8aH)-yl)-1-(2-amino-4-fluorophenyl)-1-butanone (38 mg, 0.090 mmol) was dissolved in acetic formic anhydride (0.2 mL). The reaction mixture was stirred for 2 h at 60° C. under $N_2$. The reaction mixture was concentrated in vacuo, and the residue was chromatographed (silica gel; $CHCl_3$:MeOH 99:1) to give the title compound as a pale yellow oil (31 mg, 76%). $^1H$ NMR ($CDCl_3$, 300 MHz) δ1.89–2.18 (m, 7H), 2.37–2.57 (m, 3H), 2.75–2.97 (m, 3H), 2.99–3.12 (m, 3H), 3.15–3.30 (m, 2H), 3.48–3.58 (m, 1H), 3.77–3.87 (m, 1H), 6.62 (t, J=7.5 Hz, 1H), 6.82–6.90 (m, 2H), 6.95 (dd, J=7.7, 1.1 Hz, 1H), 7.99 (dd, J=9.1, 6.2 Hz, 1H), 8.50 (d, J=1.1 Hz, 1H), 8.55 (dd, J=11.8, 2.5 Hz, 1H), 11.83–11.87 (br-s, 1H) ppm.

Example 378

4-((±)-cis-6,7,9,10,12,12a-hexahydro-5H-pyrido[4,3-b][1,4]thiazepino[2,3,4-hi]indol-11(8aH)-yl)butanoyl]-1-(4-fluoro-2-hydroxyphenyl)-1-butanone The title compound was prepared by the method of Example 355 Step B as a yellow oil (36 mg, 21%) from (±)-cis-6,7,8a,9,10,11,12,12a-octahydro-5H-pyrido[4,3-b][1,4]thiazepino[2,3,4-hi]indole (100 mg, 0.41 mmol) and 4-chloro-1-(4-fluoro-2-hydroxyphenyl)-1-butanone (176 mg, 0.81 mmol). $^1H$ NMR ($CDCl_3$, 300 MHz) δ1.80–2.18 (m, 7H), 2.22–2.45 (m, 3H), 2.57–2.77 (m, 2H), 2.85–3.15 (m, 5H), 3.22–3.27 (m, 1H), 3.47–3.59 (m, 1H), 3.77–3.85 (m, 1H), 6.57–6.70 (m, 3H), 6.83 (d, J=6.7 Hz, 1H), 6.94 (dd, J=7.7, 1.1 Hz, 1H), 7.80 (dd, J=8.7, 6.4 Hz, 1H) ppm.

Example 379

4-((±)-cis-6,7,9,10,12,12a-hexahydro-5H-pyrido[4,3-b][1,4]thiazepino[2,3,4-hi]indol-11(8aH)-yl)-1-[4-fluoro-2-(methylsulfanyl)phenyl]-1-butanone Step A To a solution of 3-fluorothiophenol (4.73 g, 37.0 mmol) in diethyl carbonate (11 mL, 129 mmol) was added $K_2CO_3$ (7.67 g, 55.5 mmol) and 18-crown-6 ether (100 mg, 0.37 mmol). The reaction mixture was refluxed at 100° C. for 12 h. The reaction mixture was cooled to 20° C. then quenched by addition of $H_2O$ and extracted with $Et_2O$. The combine organic solution washed with $H_2O$ and brine, dried over $MgSO_4$ to give 1-fluoro-3-(methylsulfanyl)benzene (5.10 g, 97%) as a colorless oil.

Step B

To a solution of 1-fluoro-3-(methylsulfanyl)benzene (1.98 g, 14.0 mmol) and 4-chlorobutyryl chloride in $CH_2Cl_2$ (15 mL) was added $AlCl_3$ (2.06 g, 15.4 mmol) at 20° C. under $N_2$. The reaction mixture was stirred for 15 h at 20° C. for 12 h then quenched by addition of $H_2O$ and extracted with $Et_2O$. The combine organic solution was washed with $H_2O$ and brine, dried over $MgSO_4$, filtered and concentrated in vacuo. The resulting white solid was recrystallized to give 4-chloro-1-[4-fluoro-2-(methylsulfanyl)phenyl]-1-butanone (2.80 g, 81%) as a white needle shape crystal.

Step C

The title compound was prepared by the method of Example 355 Step B as a yellow oil (45 mg, 45%) from (±)-cis-6,7,8a,9,10,11,12,12a-octahydro-5H-pyrido[4,3-b][1,4]thiazepino[2,3,4-hi]indole (100 mg, 0.41 mmol) and 4-chloro-1-[4-fluoro-2-(methylsulfanyl)phenyl]-1-butanone (50 mg, 0.20 mmol). $^1H$ NMR ($CDCl_3$, 300 MHz) δ1.82–2.18 (m, 7H), 2.24–2.49 (m, 3H), 2.51 (s, 3H), 2.60–2.82 (m, 2H), 2.85–3.15 (m, 5H), 3.21–3.27 (m, 1H), 3.48–3.60 (m, 1H), 3.76–3.87 (m, 1H), 6.61 (t, J=7.3, 1H), 6.83–6.97 (m, 3H), 7.03 (dd, J=8.5, 1.9 Hz, 1H), 7.79 (t, J=8.0 Hz, 1H) ppm.

Example 380

(8aS,12aR)-2-(2-chloro-4-ethoxyphenyl)-6,7,8a,9,10,11,12,12a-octahydro-5H-pyrido[4,3-b][1,4]thiazepino[2,3,4-hi]indole Step A The 4-Bromo-3-chloro-phenol (24 mmol, 5 g) in anhydrous THF (50 mL) was added to a stirred solution of NaH (60%) in mineral oil, 120 mmol, 4.8 g) in THF (100 mL) and DMF (42 mL) under $N_2$ at room temperature. This solution stirred for 30 minutes. The iodethane (240 mmol, 19.2 mL) was then added. The solution was stirred and was refluxed overnight. The reaction was cooled and quenched with 1 N HCl (150 mL), extracted into $CH_2Cl_2$ (2×150 mL), dried over $MgSO_4$, concentrated in vacuo, and distilled under vacuum yielding 1-bromo-2-chloro-4-ethoxybenzene as a brown oil (4.59 g, 81%). $^1$H NMR ($CDCl_3$, 300 MHz): δ7.42 (1H, d, J 8.7 Hz), 6.96 (1H, d, J 2.9 Hz), 6.64 (1H, dd, J 8.8 and 2.5 Hz), 3.95 (2H, q, J 7.0 Hz), 1.39 (3H, t, J 7.0 Hz.)

Step B n-Butyllithium (1.6 M solution in hexanes, 23.5 mmol, 14.7 mL) was added to 1-bromo-2-chloro-4-ethoxybenzene (19.5 mmol, 4.59 g) in THF (120 mL) at −78° C. under an atmosphere of nitrogen. After stirring for thirty minutes the trimethylborate (76.6 mmol, 8.7 mL) was added over twenty minutes. The reaction was allowed to warm to room temperature overnight while stirring. The solution was then acidified with HCl (3 M, 200 mL), and extracted into EtOAc. The EtOAc was then extracted with NaOH (1 N, 4×100 mL), which was subsequently acidified with concentrated HCl forming a white precipitate. The white precipitate (2.25 g, 58%) was filtered and dried to afford (2-Chloro-4-ethoxyphenyl)boronic acid. $^1$H NMR ($CDCl_3$, 300 MHz): 7.87 (1H, d, J8.4 Hz), 6.88 (1H, d, J 2.5 Hz), 6.84 (1H, dd, J 8.4 and 2.5 Hz), 5.53 (2H, br. s), 4.06 (2H, q, J 7.07 Hz), 1.42 (3H, t, J 7.0 Hz.)

Step C

The (2-chloro-4-ethoxyphenyl)boronic acid (0.94 mmol, 188 mg), tert-butyl(8aS,12aR)-2-bromo-6,7,9,10,12,12a-hexahydro-5H-pyrido[4,3-b][1,4]thiazepino[2,3,4-hi]indole-11(8aH)-carboxylate (0.47 mmol, 200 mg), Barium Hydroxide (0.71 mmol, 222 mg), DME (15 mL) and $H_2O$ (5 mL) were combined and degassed with nitrogen for 20 minutes. $Pd(PPh_3)_4$ (0.02 mmol, 27 mg) was then added to the stirred solution. The solution was refluxed and was stirred overnight. The DME was removed in vacuo and the black oil was dissolved in EtOAc (50 mL), washed with $H_2O$ (2×20 mL), dried over $MgSO_4$, and concentrated in vacuo yielding a yellow oil. This oil was purified by column chromatography, eluting with EtOAc/hexanes (1:5) to give the desired adduct (183 mg, 78%) as a yellow oil. $^1$H NMR ($CDCl_3$, 300 MHz): 7.19 (1H, d, J 8.8 Hz), 7.02 (1H, d, J 1.8 Hz), 6.98–6.96 (2H, m), 6.80 (1H, dd, J 8.4 and 2.5 Hz), 4.04 (2H, q, J 6.9 Hz), 3.85 (2H, ddd, J 13.9, 10.2, and 4.7 Hz), 3.66–3.48 (3H, m), 3.27–3.13 (3H, m), 2.97 (2H, dt, J 14.7 and 4.8 Hz), 2.14–2.04 (2H, m), 1.90–1.87 (2H, m), 1.42 (12H, t J 7.0 Hz.)

Step D

TFA (2 mL) was added to a stirred solution of tert-butyl (8aS,12aR)-2-(2-chloro-4-ethoxyphenyl)-6,7,9,10,12,12a-hexahydro-5H-pyrido[4,3-b][1,4]thiazepino[2,3,4-hi]indole-11(8aH)-carboxylate (0.37 mmol, 183 mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO_4$ and concentrated in vacuo to give the titled compound (144 mg, 98%) as a yellow solid. $^1$H NMR ($CDCl_3$, 300 MHz): 7.20 (1H, d, J 8.8 Hz), 7.00 (1H, d, J 1.9 Hz), 6.96 (1H, d, J 2.5 Hz), 6.93 (1H, d, J 1.9 Hz), 6.80 (1H, dd, J 8.4 and 2.6 Hz), 4.03 (2H, q, J 7.0 Hz), 3.80 (1H, ddd, J 13.9, 9.9 and 4.4 Hz), 3.56 (1H, ddd, J 15.0, 9.9 and 5.5 Hz), 3.46–3.41 (1H, m), 3.21 (1H, dt, J 13.6 and 4.1 Hz), 3.11–2.81 (5H, m), 2.68–2.61 (1H, m), 2.15–2.04 (2H, m), 1.90–1.70 (2H, m), 1.43 (3H, t, J 7.0 Hz.)

Example 381

(8aS,12aR)-2-(2-chloro-4-iso-propoxyphenyl)-6,7,8a,9,10,11,12,12a-octahydro-5H-pyrido[4,3-b][1,4]thiazepino[2,3,4-hi]indole Step A A sample of $K_2CO_3$ (52.8 mmol, 7.4 g) was added to the 4-bromo-3-chloro-phenol (24 mmol, 5 g) in anhydrous DMF (100 mL) followed by the addition of 2-iodopropane (100 mmol, 10 mL). This stirred and heated at 60° C. overnight. The reaction was cooled, extracted into EtOAc (150 mL), washed with $H_2$) (2 L), dried over $MgSO_4$, and concentrated in vacuo, yielding 1-bromo-2-chloro-4-isopropoxybenzene as a brown oil (4.85 g, 81%). $^1$H NMR ($CDCl_3$, 300 MHz): 7.35 (1H, d, J 8.7 Hz), 6.89 (1H, d, J 2.9 Hz), 6.57 (1H, dd, J 8.8 and 2.9 Hz), 4.38 (1H, m), 1.22 (6H, d, J 6.2 Hz.)

Step B n-Butyllithium (1.6 M solution in hexanes, 23.5 mmol, 14.7 mL) was added to 1-bromo-2-chloro-4-isopropoxybenzene (19.4 mmol, 4.85 g) in THF (120 mL) at −78° C. under an atmosphere of nitrogen. After stirring for thirty minutes the trimethylborate (76.6 mmol, 8.7 mL) was added over twenty minutes. The reaction was allowed to warm to room temperature overnight while stirring. The solution was then acidified with HCl (3 M, 200 mL), and extracted into EtOAc. The EtOAc was then extracted with NaOH (1 N, 4×100 mL), which was subsequently acidified with concentrated HCl forming (2-Chloro-4-isopropoxyphenyl)boronic acid (1.82 g, 44%) as a white precipitate, which was filtered and dried. $^1$H NMR ($CD_3OD$, 300 MHz): 7.19 (1H, d, J 8.4 Hz), 6.87 (1H, d, J 2.2 Hz), 6.82 (1H, dd, J 8.4 and 2.2 Hz), 4.58 (1H, m), 1.28 (6H, d, J 5.9 Hz.)

Step C

The (2-Chloro-4-iso-propoxyphenyl)boronic acid (0.94 mmol, 201 mg), tert-butyl(8aS,12aR)-2-bromo-6,7,9,10,12,12a-hexahydro-5H-pyrido[4,3-b][1,4]thiazepino[2,3,4-hi]indole-11(8aH)-carboxylate (0.47, 200 mg), Barium Hydroxide (0.71m, 222 mg), DME (15 mL) and $H_2O$ (5 mL) were combined and degassed with nitrogen for 20 minutes. $Pd(PPh_3)_4$ (0.02, 27 mg) was then added to the stirred solution. The solution was refluxed and was stirred overnight. The DME was removed in vacuo and the black oil was dissolved in EtOAc (50 mL), washed with $H_2O$ (2×20 mL), dried over $MgSO_4$, and concentrated in vacuo yielding a yellow oil. This oil was purified by column chromatography, eluting with EtOAc/hexanes (1:9) to give Tert-butyl(8aS,12aR)-2-(2-chloro-4-iso-propoxyphenyl)-6,7,9,10,12,12a-hexahydro-5H-pyrido[4,3-b][1,4]thiazepino[2,3,4-hi]indole-11(8aH)-carboxylate (171 mg, 71%) as a yellow oil. $^1$H NMR ($CDCl_3$, 300 MHz): 7.18 (1H, d, J 8.8 Hz), 7.02 (1H, d, J 1.5 Hz), 6.98–6.95 (2H, m), 6.78 (1H, dd, J 8.4 and 2.5 Hz), 4.58–4.50 (1H, m), 3.85 (2H, ddd, J 14.3, 10.3, and 4.8 Hz), 3.65–3.48 (3H, m), 3.27–3.13 (3H, m), 2.97 (2H, dt, J 14.3 and 4.8 Hz), 2.14–2.05 (2H, m), 1.90–1.87 (2H, m), 1.42 (9H, s), 1.35 (6H, d, J 5.8 Hz.)

Step D

TFA (2 mL) was added to a stirred solution of tert-butyl (8aS,12aR)-2-(2-chloro-4-iso-propoxyphenyl)-6,7,9,10,12,12a-hexahydro-5H-pyrido[4,3-b][1,4]thiazepino[2,3,4-hi]

indole-11(8aH)-carboxylate (0.33 mmol, 171 mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO_4$ and concentrated in vacuo to give the titled compound (107 mg, 78%) as a yellow solid. $^1$H NMR ($CDCl_3$, 300 MHz): 7.19 (1H, d, J 8.5 Hz), 7.00 (1H, d, J 1.4 Hz), 6.96 (1H, d, J 2.6 Hz), 6.94 (1H, d, J 1.5 Hz), 6.80 (1H, dd, J 8.4 and 2.6 Hz), 4.58–4.50 (1H, m), 3.80 (1H, ddd, J 13.9, 9.9 and 4.4 Hz), 3.56 (1H, ddd, J 15.0, 9.9 and 5.5 Hz), 3.45–3.43 (1H, m), 3.21 (1H, dt, J 13.6 and 4.0 Hz), 3.08–2.82 (5H, m), 2.68–2.61 (1H, m), 2.18–2.05 (2H, m), 1.89–1.71 (2H, m), 1.35 (6H, t, J 6.2 Hz.)

Example 382

(8aS,12aR)-2-(2-ethyl-4-methoxyphenyl)-6,7,8a,9,10,11,12,12a-octahydro-5H-pyrido[4,3-b][1,4]thiazepino[2,3,4-hi]indole Step A The (2-formyl-4-methoxyphenyl)boronic acid (0.94, 169 mg), tert-butyl(8aS,12aR)-2-bromo-6,7,9,10,12,12a-hexahydro-5H-pyrido[4,3-b][1,4]thiazepino[2,3,4-hi]indole-11(8aH)-carboxylate (0.47, 200 mg), $Na_2CO_3$ (2M, 2.5 mL), and DME (5 mL) were combined and degassed with nitrogen for 20 minutes. $Pd(PPh_3)_4$ (0.02, 27 mg) was then added to the stirred solution. The solution was refluxed and was stirred overnight. The DME was removed in vacuo and the black oil was dissolved in EtOAc (50 mL), washed with $H_2O$ (2×20 mL), dried over $MgSO_4$, and concentrated in vacuo yielding a yellow oil. This oil was purified by column chromatography, eluting with EtOAc/hexanes (1:5) to give Tert-butyl(8aS,12aR)-2-(2-formyl-4-methoxyphenyl)-6,7,9,10,12,12a-hexahydro-5H-pyrido[4,3-b][1,4]thiazepino[2,3,4-hi]indole-11(8aH)-carboxylate (189 mg, 84%) as a yellow oil. $^1$H NMR ($CDCl_3$, 300 MHz): 9.97 (1H, s), 7.47 (1H, d, J 2.5 Hz), 7.32 (1H, d, J 8.5 Hz), 7.16 (1H, dd, J 8.4 and 2.9 Hz)), 6.95 (1H, m), 6.86 (1H, m), 3.92–3.82 (5H, m), 3.65–3.49 (3H, m), 3.40–3.18 (3H, m), 3.00 (2H, dt, J 14.3 and 4.8 Hz), 2.17–2.05 (2H, m), 1.92–1.86 (2H, m), 1.41 (9H, s.)

Step B

A sample of n-BuLi (1.6 M solution in hexanes, 2.1 mmol, 1.4 mL) was added to a stirred solution of methyltriphenylphosphonium bromide (2.3 mmol, 824 mg) in THF (3 mL) under $N_2$. This stirred for 30 minutes resulting in a red colored solution. To this the Tert-butyl(8aS, 12aR)-2-(2-formyl-4-methoxyphenyl)-6,7,9,10,12,12a-hexahydro-5H-pyrido[4,3-b][1,4]thiazepino[2,3,4-hi]indole-11(8aH)-carboxylate (0.51 mmol, 254 mg) in THF (3 mL) was added. The orange solution stirred overnight. The solid was filtered off and washed with EtOAc (20 mL.) The EtOAc was washed with $H_2O$ (20 mL), dried with $MgSO_4$, and concentrated in vacuo. The oil was purified with column chromatography, eluting with EtOAc/hexanes (1:9) to give Tert-butyl(8aS,12aR)-2-(4-methoxy-2-vinylphenyl)-6,7,9,10,12,12a-hexahydro-5H-pyrido[4,3-b][1,4]thiazepino[2,3,4-hi]indole-11(8aH)-carboxylate (100 mg, 41%) as a yellow oil. $^1$H NMR ($CDCl_3$, 300 MHz): 7.16 (1H, d, J 8.4 Hz), 7.12 (1H, d, J 3.0 Hz), 6.93 (1H, d, J 1.8 Hz), 6.86–6.83 (2H, m), 6.80–6.50 (1H, m), 5.67 (1H, dd, J 17.3 and 1.1 Hz), 5.20 (1H, dd, J 11.0 and 1.5 Hz), 3.87–3.85 (5H, m), 3.84–3.50 (3H, m), 3.40–2.90 (5H, m), 2.17–2.05 (2H, m), 1.92–1.86 (2H, m), 1.41 (9H, s.)

Step C

The tert-butyl(8aS,12aR)-2-(4-methoxy-2-vinylphenyl)-6,7,9,10,12,12a-hexahydro-5H-pyrido[4,3-b][1,4]thiazepino[2,3,4-hi]indole-11(8aH)-carboxylate (0.21 mmol, 100 mg) was dissolve in ethanol (10 mL) with a suspension of palladium (10% on carbon, 10 mg.) This was shaken on a Parr apparatus overnight under $H_2$ (50 psi.) The palladium residues were removed via filtration through silica eluding with EtOAc/hexanes (1:5) yielding Tert-butyl (8aS, 12aR)-2-(2-ethyl-4-methoxyphenyl)-6,7,9,10,12,12a-hexahydro-5H-pyrido[4,3-b][1,4]thiazepino[2,3,4-hi]indole-11(8aH)-carboxylate (44 mg, 44%) as a yellow oil. $^1$H NMR ($CDCl_3$, 300 MHz): 7.08 (1H, d, J 8.4 Hz), 6.89 (1H, d, J 1.5 Hz), 6.82 (1H, d, J 2.6 Hz), 6.80 (1H, s), 6.740 (1H, dd J 8.4 and 2.9 Hz), 3.87–3.77 (5H, m), 3.66 (1H, dt, J 12.8 and 4.0 Hz), 3.59–3.49 (2H, m), 3.34–3.13 (3H, m), 2.96 (2H, dt, J 14.3 and 4.4 Hz), 2.58 (2H, q, J 7.7 Hz), 2.18–2.05 (2H, m), 1.90–1.88 (2H, m), 1.42 (9H, s), 1.12 (3H, t, J 7.3 Hz) ppm.

Step D

TFA (2 mL) was added to a stirred solution of Tert-butyl (8aS,12aR)-2-(2-ethyl-4-methoxyphenyl)-6,7,9,10,12,12a-hexahydro-5H-pyrido[4,3-b][1,4]thiazepino[2,3,4-hi]indole-11(8aH)-carboxylate (0.09 mmol, 44 mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO_4$ and concentrated in vacuo to give the titled compound (34 mg, 100%) as a yellow solid. $^1$H NMR ($CDCl_3$, 300 MHz): 7.09 (1H, d, J 8.5 Hz), 6.87 (1H, d, J 1.5 Hz), 6.81 (1H, d, J 2.6 Hz), 6.75–6.71 (2H, m), 3.82 (3H, s), 3.77 (1H, ddd, J 14.2, 10.2 and 5.5 Hz), 3.56 (1H, ddd, J 14.6, 9.9 and 5.5 Hz), 3.43–3.41 (1H, m), 3.20 (1H, dt, J 13.5 and 3.7 Hz), 3.08–2.81 (5H, m), 2.67–2.54 (3H, m), 2.20–2.02 (2H, m), 1.91–1.71 (2H, m), and 1.12 (3H, t, J 7.7 Hz) ppm; m/z (ES) 381.2 $(M+H)^+$.

Example 383

2-[(8aS,12aR)-6,7,8a,9,10,11,12,12a-octahydro-5H-pyrido[4,3-b][1,4]thiazepino[2,3,4-hi]indole-2-yl]-5-methoxybenzaldehyde TFA (2 mL) was added to a stirred solution of Tert-butyl (8aS,12aR)-2-(2-formyl-4-methoxyphenyl)-6,7,9,10,12,12a-hexahydro-5H-pyrido[4,3-b][1,4]thiazepino[2,3,4-hi]indole-11(8aH)-carboxylate (0.06 mmol, 30 mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO_4$ and concentrated in vacuo to give the desired product (24 mg, 100%) as a yellow oil. $^1$H NMR ($CDCl_3$, 300 MHz): 9.97 (1H, s), 7.46 (1H, d, J 2.6 Hz), 7.33 (1H, d, J 8.4 Hz), 7.15 (1H, dd, J 8.4 and 2.5 Hz), 6.94 (1H, d J 1.5 Hz), 6.80 (1H, d, J 1.4 Hz), 3.88 (3H, s), 3.82 (1H, ddd, J 14.2, 10.2 and 5.5 Hz), 3.57 (1H, ddd, J 14.6, 9.9 and 5.5 Hz), 3.46–3.43 (1H, m), 3.24 (1H, dt, J 13.5 and 3.7 Hz), 3.11–2.81 (5H, m), 2.69–2.60 (1H, m), 2.20–2.05 (2H, m), 1.91–1.73 (2H, m.)

Example 384

1-{2-[(8aS,12aR)-6,7,8a,9,10,11,12,12a-octahydro-5H-pyrido[4,3-b][1,4]thiazepino[2,3,4-hi]indole-2-yl]-5-methoxyphenyl}ethanol Step A To a stirred solution of the Tert-butyl(8aS,12aR)-2-(2-formyl-4-methoxyphenyl)-6,7,9,10,12,12a-hexahydro-5H-pyrido[4,3-b][1,4]thiazepino[2,3,4-hi]indole-11($^8$aH)-carboxylate (0.42 mmol, 200 mg) in THF (10 mL), methylmagnesium bromide (3.0 M solution in ether, 1.26 mmol, 0.42 mL) was added under $N_2$ at 0° C. The solution was stirred at room temperature for two hours and subsequently quenched with saturated $NH_4Cl$ (10 mL.) The reaction was extracted with EtOAc (40 mL), dried with $Na_2SO_4$, and concentrated in vacuo yielding Tert-butyl(8aS,12aR)-2-2-[2-(1-hydroxyethyl)-4-methoxyphenyl]-6,7,9,10,12,12a-hexahydro-5H-pyrido[4,3-b][1,4]thiazepino[2,3,4-hi]indole-11(8aH)-carboxylate as a yellow oil (192.0 mg, 92%.) $^1$H NMR ($CDCl_3$, 300 MHz): 7.17 (1H, d, J 1.8 Hz), 7.09 (1H, d, J 8.5 Hz), 6.87–6.79 (3H, m), 5.02–4.98 (1H, m), 3.88–3.64 (5H, m), 3.59–3.40 (3H, m), 3.36–3.13 (3H, m), 3.02–2.93 (2H, m), 2.12–2.08 (2H, m), 1.88–1.80 (2H, m), 1.73–1.50 (3H, m), 1.43 (9H, s); m/z (ES) 497.1 $(M+H)^+$.

Step B

TFA (8 mL) was added to a stirred solution of tert-butyl (8aS,12aR)-2-2-[2-(1-hydroxyethyl)-4-methoxyphenyl]-6,7,9,10,12,12a-hexahydro-5H-pyrido[4,3-b][1,4]thiazepino[2,3,4-hi]indole-11(8aH)-carboxylate (0.39 mmol, 192 mg) in $CH_2Cl_2$ (40 mL) at room temperature under an atmosphere of nitrogen. The solution was stirred at room temperature for one hour, diluted with $CH_2Cl_2$ (20 mL), washed with NaOH (1N, 2×15 mL), dried over $Na_2SO4$ and concentrated in vacuo to give the titled compound (76 mg, 50%) as a yellow oil. $^1$H NMR ($CDCl_3$, 300 MHz): 7.17 (1H, d, J 2.2 Hz), 7.10 (1H, d, J 8.5 Hz), 6.85 (1H, s), 6.81 (1H, dd, J 8.4 and 2.6 Hz), 6.74 (1H, s), 5.00–4.95 (1H, m), 3.85–3.74 (5H, m), 3.57–3.52 (1H, m), 3.42–3.38 (1H, m), 3.20–2.90 (6H, m), 2.66–2.56 (1H, m), 2.24–2.01 (4H, m), 1.93–1.81 (2H, m); ml/z(ES) 397.1 $(M+H)^+$.

Example 385

(8aS,12aR)-2-[4-methoxy-2-(1-methoxyethyl) phenyl]6,7,8a,9,10,11,12,12a-octahydro-5H-pyrido [4,3-][1,4]thiazepino[2,3,4-hi]indole Step A Under nitrogen NaH (60% in mineral oil, 0.76 mmol, 30 mg) was dissolved in THF (3 mL) at room temperature. To the suspension Tert-butyl(8aS,12aR)-2-2-[2-(1-hydroxyethyl)-4-methoxyphenyl]-6,7,9,10,12,12a-hexahydro-5H-pyrido[4,3-b][1,4]thiazepino[2,3,4-hi] indole-11(8aH)-carboxylate (0.19 mmol, 93 mg) was added via cannula in THF (4 mL.) This stirred at room temperature for thirty minutes. Finally MeI (0.95 mmol, 60 μl) was added to the solution and it was allowed to stir overnight. The reaction was then quenched with saturated $NH_4Cl$ (10 mL), extracted with EtOAc (50 mL), dried with $Na_2SO_4$, and concentrated in vacuo. The oil was subjected to column chromatography eluting with EtOAc/hexanes (1:3) yielding Tert-butyl(8aS,12aR)-2-[4-methoxy-2-(1-methoxyethyl) phenyl]-6,7,9,10,12,12a-hexahydro-5H-pyrido[4,3-b][1,4] thiazepino[2,3,4-hi]indole-11(8aH)-carboxylate as a yellow oil (80 mg, 83%.) $^1$H NMR ($CDCl_3$, 300 MHz): 7.10–7.08 (2H, m), 6.85–6.81 (2H, m), 6.75 (1H, s), 4.46–4.40 (1H, m), 3.88–3.80 (5H, m), 3.70–3.62 (1H, m), 3.60–3.54 (2H, m), 3.36–3.14(6H, m), 3.01–2.96(2H, m), 2.17–2.06 (2H, m), 1.92–1.91 (2H, m), 1.45 (9H, s), and 1.35 (3H, d, J 6.3 Hz.)

Step B

TFA (2 mL) was added to a stirred solution of Tert-butyl (8aS,12aR)-2-[4-methoxy-2-(1-methoxyethyl)phenyl]-6,7,9,10,12,12a-hexahydro-5H-pyrido[4,3-b][1,4]thiazepino[2,3,4-hi]indole-11(8aH)-carboxylate (0.16 mmol, 80 mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO4$ and concentrated in vacuo to give the titled compound (17 mg, 26%) as a yellow oil. $^1$H NMR ($CDCl_3$, 300 MHz): 7.03–6.97 (2H, m), 6.76–6.72 (2H, m), 6.63–6.62 (1H, m), 4.36–4.33 (1H, m), 3.79–3.68 (4H, m), 3.51 (1H, ddd, J 15.0, 9.9 and 5.1 Hz), 3.37–3.35 (1H, m), 3.12 (1H, dt, J 13.6 and 4.0 Hz), 3.06 (3H, d, J 4.4), 2.99–2.80 (4H, m), 2.58–2.51 (1H, m), 2.10–1.97 (2H, m), 1.86–1.80 (3H, m), 1.8 (3H, dd, J 6.6 and 4.8); m/z (ES) 411.1 $(M+H)^+$.

Example 386

1-{2-[(8aS,12aR)-6,7,8a,9,10,11,12,12a-octahydro-5H-pyrido[4,3-b][1,4]thiazepino[2,3,4-hi]indole-2-yl]-5-methoxyphenyl}ethanone Step A To a solution of oxalyl chloride (4.2 mmol, 366.0 μl) in $CH_2Cl_2$ (10 mL) under nitrogen at −78° C., DMSO (8.4 mmol, 596 μl) in $CH_2Cl_2$ (5 mL) was added via cannula. Then the Tert-butyl(8aS,12aR)-2-2-[2-(1-hydroxyethyl)-4-methoxyphenyl]-6,7,9,10,12,12a-hexahydro-5H-pyrido[4,3-b][1,4]thiazepino[2,3,4-hi]indole-11(8aH)-carboxylate (2.10 mmol, 1.04 g) in $CH_2Cl_2$ (10 mL) was added to the solution via cannula and stirred for thirty minutes. Finally, $NEt_3$ (16.8 mmol, 2.25 mL) was added and the solution was allowed to warm to room temperature stirring for two hours. The reaction was diluted with 30 mL $CH_2Cl_2$, quenched with saturated $NH_4Cl$ (15 mL) and washed with $H_2O$ (2×40 mL.) The organic layer was dried with $MgSO_4$ and concentrated in vacuo. The oil was purified with column chromatography, eluting with EtOAc/hexanes (1:4) to give Tert-butyl(8aS,12aR)-2-(2-acetyl-4-methoxyphenyl-6,7,9,10,12,12a-hexahydro-5H-pyrido[4,3-b][1,4]thiazepino[2,3,4-hi]indole-11(8aH)-carboxylate (685 mg, 66%) as a yellow oil. $^1$H NMR ($CDCl_3$, 300 MHz): 7.23 (1H, s), 7.02–6.93 (3H, m), 6.78 (1H, s), 3.89–3.79 (5H, m), 3.66–3.49 (3H, m), 3.34–3.29 (3H, m), 3.20–2.99 (2H, m), 2.13–2.04 (5H, m), 1.89–1.85 (2H, m), 1.42 (9H, s.)

Step B

TFA (8 mL) was added to a stirred solution of tert-butyl (8aS,12aR)-2-(2acetyl-4-methoxyphenyl)-6,7,9,10,12,12a-hexahydro-5H-pyrido[4,3-b][1,4]thiazepino[2,3,4-hi] indole-11(8aH)-carboxylate (1.39 mmol, 685 mg) in $CH_2Cl_2$ (40 mL) at room temperature under an atmosphere of nitrogen. The solution was stirred at room temperature overnight, diluted with $CH_2Cl_2$ (40 mL), washed with NaOH (1N, 2×35 mL), dried over $Na_2SO_4$ and concentrated in vacuo to give the titled compound (54 mg, 100%) as a yellow oil. $^1$H NMR ($CDCl_3$, 300 MHz): 7.18–7.15 (1H, m), 6.92–6.89 (2H, m), 6.85 (1H, d, J 1.9 Hz), 6.62 (1H, d J 1.8 Hz), 6.76–3.66 (4H, m), 3.46 (1H, ddd, J 15.0, 9.9 and 5.5 Hz), 3.35–3.30 (1H, m), 3.10 (1H, dt, J 13.6 and 3.7 Hz), 2.99–2.77 (5H, m), 2.52–2.43 (1H, m), 2.09–1.94 (5H, m), 1.82–1.64 (2H, m); m/z (ES) 395.1 $(M+H)^+$.

Example 387

(8aS,12aR)-2-(2-hydroxymethyl-4-methoxyphenyl)-6,7,8a,9,10,11,12,12a-octahydro-5H-pyrido[4,3-b][1,4]thiazepino[2,3,4-hi]indole Step A Under $N_2$ the tert-butyl(8aS,12aR)-2-(2-formyl-4-methoxyphenyl)-6,7,9,10,12,12a-hexahydro-5H-pyrido[4,3-b]thiazepino[2,3,4-hi]indole-11(8aH)-carboxylate (0.42 mmol, 200 mg) was dissolved in $CH_2Cl_2$ (4 mL) and cooled to 0° C. The solution was treated with DIBAL (1.0 M solution in $CH_2Cl_2$, 0.63 mmol, 0.63 mL) and stirred for one hour. The reaction was quenched with MeOH (1 mL), diluted with $CH_2Cl_2$ (20 mL) and stirred vigorously with Rochelle's salt (15 mL) for one hour. The aqueous layer was extracted twice with $CH_2Cl_2$ (20 mL) and the organic layers were pooled and dried with $Na_2SO_4$. The liquid was concentrated in vacuo to give tert-butyl(8aS,12aR)-2-[2-(hydroxymethyl)-4-methoxyphenyl]-6,7,9,10,12,12a-hexahydro-5H-pyrido[4,3-b][1,4]thiazepino[2,3,4-hi]indole-11(8aH)-carboxylate (204 mg, 100%) as a yellow oil. $^1$H NMR ($CDCl_3$, 300 MHz): 7.17 (1H, d, J 8.5 Hz), 7.07 (1H, s), 6.93–6.91 (2H, m), 6.84 (1H, dd, J 8.5 and 2.5 Hz), 4.60–4.40 (2H, m), 3.84 (3H, s), 3.79–3.04 (9H, m), 2.11–2.05 (2H, m), 1.91–1.48 (3H, m), 1.43 (9H, s.)

Step B

TFA (2 mL) was added to a stirred solution of tert-butyl (8aS,12aR)-2-[2-(hydroxymethyl)-4-methoxyphenyl)-6,7,9,10,12,12a-hexahydro-5H-pyrido[4,3-b][1,4]thiazepino[2,3,4-hi]indole-11(8aH)-carboxylate (0.42 mmol, 204 mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO_4$ and concentrated in vacuo to give the titled compound (108 mg, 67%) as a yellow solid. $^1$H NMR ($CDCl_3$, 300 MHz): 7.16 (1H, d, J 8.4 Hz), 7.11 (1H, d, J 2.5 Hz), 6.91 (1H, d, J 1.1 Hz), 6.86–6.81 (2H, m), 4.60 (2H, s), 3.85–3.74 (4H, m), 3.55 (1H, ddd, J 14.6, 9.9 and 5.5 Hz), 3.40–3.38 (1H, m), 3.19 (1H, dt, J 13.2 and 4.4 Hz), 3.09–2.82 (6H, m), 2.20–2.02 (2H, m), 1.93–1.80 (2H, m); m/z (ES) 383.1 $(M+H)^+$.

Example 388

(8aS,12aR)-2-[4-methoxy-2-(methoxymethyl) phenyl]-6,7,8a,9.10,11,12,12a-octahydro-5H-pyrido [4,3-b][1,4]thiazepino[2,3,4-hi]indole Step A Under nitrogen NaH (60% in mineral oil, 0.76 mmol, 30 mg) was dissolved in THF (3 mL) at room temperature. To the suspension tert-butyl(8aS,12aR)-2-[2-(hydroxymethyl)-4-methoxyphenyl]-6,7,9,10,12,12a-hexahydro-5H-pyrido [4,3-b][1,4]thiazepino[2,3,4-hi]indole-11(8aH)-carboxylate (0.20 mmol, 98 mg) was added via cannula in THF (4 mL.) This stirred at room temperature for thirty minutes. Finally MeI (1.0 mmol, 60 μl) was added to the solution and it was allowed to stir overnight. The reaction was then quenched with $NH_4Cl$ (10 mL), extracted with EtOAc (50 mL), dried with $Na_2SO_4$, and concentrated in vacuo. The oil was subjected to column chromatography eluting with EtOAc/hexanes (1:4) yielding tert-butyl(8aS,12aR)-2-[4-methoxy-2-(methoxymethyl)phenyl]-6,7,9,10,12,12a-hexahydro-5H-pyrido[4,3-b][1,4]thiazepino[2,3,4-hi]indole-11(8aH)-carboxylate as a yellow oil (70 mg, 71%.) $^1$H NMR ($CDCl_3$, 300 MHz): 7.16 (1H, d, J 8.4 Hz), 7.05 (1H, d, J 3.0 Hz), 6.95 (1H, d, J 1.5 Hz), 6.88–6.83 (2H, m), 4.32 (2H, s), 3.89–3.79 (5H, m), 3.71–3.12 (10H, m), 2.96 (1H, dt, J 14.7 and 5.5), 2.14–2.05 (2H, m), 1.90–1.89 (2H, m), and 1.43 (9H, s); m/z (ES) 497.1 $(M+H)^+$.

Step B

TFA (2 mL) was added to a stirred solution of tert-butyl (8aS,12aR)-2-[4-methoxy-2-(methoxymethyl)phenyl]-6,7,9,10,12,12a-hexahydro-5H-pyrido[4,3-b][1,4]thiazepino[2,3,4-hi]indole-11(8aH)-carboxylate (0.14 mmol, 70 mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO_4$ and concentrated in vacuo to give the titled compound (52 mg, 94%) as a yellow solid. $^1$H NMR ($CDCl_3$, 300 MHz): 7.17 (1H, d, J 8.8 Hz), 7.04 (1H, d, J 2.6 Hz), 6.93 (1H, d, J 1.8 Hz), 6.86–6.83 (2H, m), 4.32 (2H, s), 3.84–3.74 (4H, m), 3.57 (1H, ddd, J 14.7, 9.9 and 5.5 Hz), 3.45–3.41 (1H, m), 3.37 (3H, s), 3.21 (1H, dt, J 13.2 and 3.7 Hz), 3.09–2.82 (5H, m), 2.68–2.60 (1H, m), 2.17–2.05 (2H, m), 1.91–1.73 (2H, m); m/z (ES) 397.1 $(M+H)^+$.

Example 389

1-{2-[(8aS,12aR)-6,7,8a,9,10,11,12,12a-octahydro-5H-pyrido[4,3-b][1,4]thiazepino[2,3,4-hi]indol-2-yl]-5-methoxyphenyl}-1-propanol To a stirred solution of the 2-[(8aS,12aR)-6,7,8a,9,10,11,12,12a-octahydro-5H-pyrido[4,3-b][1,4]thiazepino[2,3,4-hi]indole-2-yl]-5-methoxybenzaldehyde (0.42 mmol, 162 mg) in THF (10 mL), the ethylmagnesium bromide (1.0 M solution in THF, 4.2 mmol, 4.2 mL) was added under $N_2$ at 0° C. The solution was stirred at room temperature for two hours and subsequently quenched with saturated $NH_4Cl$ (10 mL.) The reaction was extracted with EtOAc (40 mL), dried with $Na_2SO_4$, and concentrated in vacuo. The product was further purified by reverse phase HPLC yielding the titled compound as a yellow oil (43 mg, 25%.) m/z (ES) 411.1 $(M+H)^+$.

Example 390

1-{2-[(8aS,12aR)-6,7,8a,9,10,11,12,12a-octahydro-5H-pyrido[4,3-b][1,4]thiazepino[2,3,4-hi]indole-2-yl]-5-methoxyphenyl}-1-propanone Step A To a stirred solution of the tert-butyl(8aS,12aR)-2-(2-formyl-4-methoxyphenyl)-6,7,9,10,12,12a-hexahydro-5H-pyrido[4,3-b][1,4]thiazepino[2,3,4-hi]indole-11(8aH)-carboxylate (0.42 mmol, 200 mg) in THF (10 mL), the ethylmagnesium bromide (1.0 M solution in THF, 1.26 mmol, 1.26 mL) was added under $N_2$ at 0° C. The solution was stirred at room temperature for two hours and subsequently quenched with saturated $NH_4Cl$ (10 mL.) The reaction was extracted with EtOAc (40 mL), dried with $Na_2SO_4$, concentrated in vacuo and subjected to column chromatography eluting with EtOAc/hexanes (1:4) yielding tert-butyl(8aS,12aR)-2-2-[2-(1-hydroxypropyl)-4-methoxyphenyl]-6,7,9,10,12,12a-hexahydro-5H-pyrido[4,3-b][1,4]thiazepino[2,3,4-hi]indole-11(8aH)-carboxylate a yellow oil (137.0 mg, 64%.) m/z (ES) 511.2 $(M+H)^+$.

Step B

To a solution of oxalyl chloride (0.43 mmol, 38.0 μl) in $CH_2Cl_2$ (2 mL) under nitrogen at −78° C., DMSO (0.88 mmol, 63 μl) in $CH_2Cl_2$ (2 mL) was added via cannula. Then the tert-butyl(8aS,12aR)-2-2-[2-(1-hydroxypropyl)-4-methoxyphenyl]-6,7,9,10,12,12a-hexahydro-5H-pyrido[4,3-b][1,4]thiazepino[2,3,4-hi]indole-11(8aH)-carboxylate (0.22 mmol, 110 mg) in $CH_2Cl_2$ (2 mL) was added to the solution via cannula and stirred for thirty minutes. Finally, $NEt_3$ (1.76 mmol, 0.251 mL) was added and the solution was allowed to warm to room temperature stirring for two hours. The reaction was diluted with 30 mL $CH_2Cl_2$, quenched with saturated $NH_4Cl$ (15 mL) and washed with $H_2O$ (2×40 mL.) The organic layer was dried with $MgSO_4$ and concentrated in vacuo. The oil was purified with column chromatography, eluting with EtOAc/hexanes (1:4) to give tert-butyl(8aS,12aR)-2-(4-methoxy-2-propionylphenyl)-6,,7,9,10,12,12a-hexahydro-5H-pyrido[4,3-b][1,4]thiazepino[2,3,4-hi]indole-11(8aH)-carboxylate (52 mg, 47%) as a yellow oil. $^1$H NMR ($CDCl_3$, 300 MHz): 7.2–7.24 (1H, m), 6.99 (1H, dd, J 8.4 and 2.6 Hz), 6.91–6.76 (3H, m), 3.88–3.80 (4H, m), 3.79–2.94 (9H, m), 2.31 (2H, q, J 7.3 Hz), 2.17–2.08 (2H, m), 1.89–1.87 (2H, m), 1.42 (9H, s), and 0.96 (3H, t, J 7.4 Hz.)

Step C

TFA (8 mL) was added to a stirred solution of tert-butyl (8aS,12aR)-2-(4-methoxy-2-propionylphenyl)-6,7,9,10,12,12a-hexahydro-5H-pyrido[4,3-b][1,4]thiazepino[2,3,4-hi]indole-11(8aH)-carboxylate (0.1 mmol, 52 mg) in $CH_2Cl_2$ (40 mL) at room temperature under an atmosphere of nitrogen. The solution was stirred at room temperature overnight, diluted with $CH_2Cl_2$ (40 mL), washed with NaOH (1N, 2×35 mL), dried over $Na_2SO_4$ and concentrated in vacuo to give the titled compound (40 mg, 100%) as a yellow oil. $^1$H NMR ($CDCl_3$, 300 MHz): 7.28–7.25 (1H, m), 6.98 (1H, d, J 8.4 and 1.4 Hz), 6.94–6.91 (2H, m), 6.70 (1H, d J 1.8 Hz), 3.84–3.75 (4H, m), 3.56 (1H, ddd, J 14.7, 9.9 and 5.2 Hz), 3.43–3.39 (1H, m), 3.19 (1H, dt, J 13.5 and 3.6 Hz), 3.07–2.51 (6H, m), 2.34–2.27 (2H, m), 2.19–2.03 (2H, m), 1.91–1.69 (2H, m), and 0.95 (3H, t, J 7.0 Hz.)

Example 391

Methyl(2Z)-3-{2-[(8aS,12aR)-6,7,8a,9,10,11,12,12a-octahydro-5H-pyrido[4,3-b][1,4]thiazepino[2,3,4-hi]indol-2-yl]-5-methoxyphenyl}-2-propenoate Step A Under an atmosphere of nitrogen 18-crown-6 (2.1 mmol 555 mg) and bis(2,2,2-trifluoroethyl) methoxycarbonylmethyl)-phosphonate (0.42 mmol, 134 mg) were dissolved in THF (5 mL) and cooled to −78° C. This was treated with $KN(TMS)_2$ (0.5 M solution in toluene, 0.42 mmol, 0.84 mL.) Finally a solution of tert-butyl(8aS,12aR)-2-(2-formyl-4-methoxyphenyl)-6,7,9,10,12,12a-hexahydro-5H-pyrido[4,3-b][1,4]thiazepino[2,3,4-hi]indole-11(8aH)-carboxylate (0.42 mmol, 200 mg) in THF (5 mL) were added via cannula. This stirred for 30 minutes at −78° C. The reaction was warmed to room temperature and quenched with saturated $NH_4Cl$ (10 mL) and extracted into EtOAc (50 mL.) The EtOAc layer was dried with $Na_2SO_4$ and concentrated in vacuo. The product was subjected to column chromatography eluting with EtOAc/hexanes (1:4) yielding tert-butyl(8aS,12aR)-2-[4-methoxy-2-[(1Z)-3-methoxy-3-oxo-1-propenyl]phenyl]-6,7,9,10,12,12a-hexahydro-5H-pyrido[4,3-b][1,4]thiazepino[2,3,4-hi]indole-11(8aH)-carboxylate (152 mg, 99%) as a yellow oil. $^1$H NMR ($CDCl_3$, 300 MHz): 7.22 (1H, d, J 8.4 Hz), 7.14 (1H, s), 6.94–6.81 (4H, m), 5.92 (1H, d, J 12.1 Hz), 3.90–2.93 (15H, m), 2.14–2.05 (2H, m), 1.89–1.88 (2H, m), and 1.42 (9H, s.)

Step B

TFA (2 mL) was added to a stirred solution of tert-butyl (8aS,12aR)-2-[4-methoxy-2-[(1Z)-3-methoxy-3-oxo-1-propenyl]phenyl]-6,7,9,10,12,12a-hexahydro-5H-pyrido[4,3-b][1,4]thiazepino[2,3,4-hi]indole-11(8aH)-carboxylate (0.21 mmol, 75 mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO_4$ and concentrated in vacuo to give the titled compound (70 mg, 100%) as a yellow solid. $^1$H NMR ($CDCl_3$, 300 MHz): 7.23 (1H, d, J 8.8 Hz), 7.14 (1H, d, J 2.2 Hz), 6.92–6.80 (4H, m), 5.91 (1H, d, J 12.4 Hz), 3.88–3.70 (7H, m), 3.56 (1H, ddd, J 14.7, 9.9 and 5.5 Hz), 3.25–3.19 (2H, m), 3.08–2.57 (6H, m), 2.18–2.08 (2H, m), 1.90–1.72 (2H, m.)

Example 392

Methyl-3-{2-[(8aS,12aR)-6,7,8a,9,10,11,12,12a-octahydro-5H-pyrido[4,3-b][1,4]thiazepino[2,3,4-hi]indol-2-yl]-5-methoxyphenyl}

Step A

To a stirred solution of the tert-butyl(8aS,12aR)-2-[4-methoxy-2-[(1Z)-3-methoxy-3-oxo-1-propenyl]phenyl]-6,7,9,10,12,12a-hexahydro-5H-pyrido[4,3-b][1,4]thiazepino[2,3,4-hi]indole-11(8aH)-carboxylate (0.1 mmol, 55 mg) and Wilkinson's catalyst (0.011 mmol, 10 mg) in benzene (3 mL), triethylsilane (0.64 mmol, 0.1 mL) was added under an atmosphere of nitrogen at room temperature. This stirred for 15 hours at room temperature, and was concentrated in vacuo. The product was subjected to column chromatography eluting with EtOAc/hexanes (1:4) yielding tert-butyl (8aS,12aR)-2-[4-methoxy-2-(3-methoxy-3-oxopropyl) phenyl]-6,7,9,10,12,12a-hexahydro-5H-pyrido[4,3-b][1,4]thiazepino[2,3,4-hi]indole-11(8aH)-carboxylate as a yellow oil (25 mg, 46%.) $^1$H NMR ($CDCl_3$, 300 MHz): 7.09 (1H, d, J 8.1 Hz), 6.86 (1H, d, J 1.9 Hz), 6.78–6.74 (3H, m), 3.88–2.88 (18H, m), 2.47 (2H, t, J 7.7 Hz), 2.15–2.05 (2H, m), 1.90–1.88 (2H, m), and 1.43 (9H, s); m/z (ES) 539.1 $(M+H)^+$.

Step B

TFA (2 mL) was added to a stirred solution of tert-butyl (8aS,12aR)-2-[4-methoxy-2-(3-methoxy-3-oxopropyl) phenyl]-6,7,9,10,12,12a-hexahydro-5H-pyrido[4,3-b][1,4]thiazepino[2,3,4-hi]indole-11(8aH)-carboxylate (0.05 mmol, 25 mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO_4$ and concentrated in vacuo to give the titled compound (23 mg, 100%) as a yellow solid. $^1$H NMR ($CDCl_3$, 300 MHz): 7.10 (1H, d, J 8.1 Hz), 6.85 (1H, s), 6.76 (1H, d, J 8.8 Hz), 3.81–3.74 (4H, m), 3.64–3.51 (4H, m), 3.44–3.42 (1H, m), 3.24–3.20 (1H, m), 3.07–2.63 (8H, m), 2.46 (2H, t, J 8.0 Hz), 2.16–2.07 (2H, m), and 1.85–1.78 (2H, m); m/z (ES) 439.4 $(M+H)^+$.

Example 393

(2Z)-3-{2-[(8aS,12aR)-6,7,8a,9,10,11,12,12a-octahydro-5H-pyrido[4,3-b][1,4]thiazepino[2,3,4-hi]indol-2-yl]-5-methoxyphenyl}-2-propen-1-ol Step A DIBAL (1.0 M solution in $CH_2Cl_2$, 0.48 mmol, 0.48 mL) was added to a stirred solution of tert-butyl(8aS,12aR)-2-[4-methoxy-2-[(1Z)-3-methoxy-3-oxo-1-propenyl]phenyl]-6,7,9,10,12,12a-hexahydro-5H-pyrido[4,3-b]1,4]thiazepino[2,3,4-hi]indole-11(8aH)-carboxylate (0.19 mmol, 100 mg) in $CH_2Cl_2$ (4 mL) at 0° C. under an atmosphere of nitrogen. This stirred at room temperature overnight. The reaction was quenched with MeOH (0.5 mL), dilluted with $CH_2Cl_2$ (10 mL), and stirred with Rochelle's salt (10 mL) for 1 hour. The organic layer was dried with $Na_2SO_4$, concentrated in vacuo, and subjected to column chromatography eluting with EtOAc/hexanes (1:1) yielding tert-butyl(8aS,12aR)-2-{2-[(1Z)-3-hydroxy-1-propenyl]-4-methoxyphenyl}-6,7,9,10,12,12a-hexahydro-5H-pyrido[4,3-b][1,4]thiazepino[2,3,4-hi]indole-11(8aH)-carboxylate (50 mg, 52%) as a yellow oil. $^1$H NMR ($CDCl_3$, 300 MHz): 7.21 (1H, d, J 8.4 Hz), 6.94 (1H, d, J 1.9 Hz), 6.86 (1H, d, J 2.9 Hz), 6.84 (1H, d, J 2.5 Hz), 6.76 (1H, d, J 2.6 Hz), 6.46 (1H, d, J 1.7 Hz), 5.82–5.78 (1H, m), 4.31–4.30 (2H, m), 3.85–2.96 (9H, m), 2.12–2.05 (2H, m), 1.87 (2H, br. s), and 1.42 (9H, s.)

Step B

TFA (2 mL) was added to a stirred solution of tert-butyl (8aS,12aR)-2-{2-[(1Z)-3-hydroxy-1-propenyl]-4-methoxyphenyl}-6,7,9,10,12,12a-hexahydro-5H-pyrido[4,3-b][1,4]thiazepino[2,3,4-hi]indole-11(8aH)-carboxylate (0.10 mmol, 50 mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO_4$ and concentrated in vacuo to give the titled compound (26 mg, 65%) as a yellow solid. $^1H$ NMR ($CDCl_3$, 300 MHz): 7.22 (1H, d, J 8.4 Hz), 6.93–6.75 (3H, m), 6.47 (1H, d, J 11.4 Hz), 5.80–5.76 (1H, m), 4.30–4.27 (2H, m), 3.85–3.44 (6H, m), 3.25–2.64 (7H, m), 2.11–2.05 (2H, m), and 1.85–1.76 (2H, m); m/z (ES) 409.4 $(M+H)^+$.

Example 394

Methyl(2E)-3-{2-[(8aS,12aR)-6,7,8a,9,10,11,12,12a-octahydro-5H-pyrido[4,3-b][1,4]thiazepino[2,3,4-hi]indol-2-yl]-5-methoxyphenyl}-2-propenoate Step A Methyl (triphenylphosphoranylidene) acetate (1.26 mmol, 421 mg) was added to a stirred solution of tert-butyl (8aS,12aR)-2-(2-formyl-4-methoxyphenyl)-6,7,9,10,12,12a-hexahydro-5H-pyrido[4,3-b][1,4]thiazepino[2,3,4-hi]indole-11(8aH)-carboxylate (0.42 mmol, 200 mg) in $CH_2Cl_2$ (5 mL.) This stirred overnight at room temperature. The product was concentrated in vacuo, and subjected to column chromatography eluting with EtOAc/hexanes (1:3) yielding tert-buty(8aS,12aR)-2-[4-methoxy-2-[(1E)-3-methoxy-3-oxo-1-propenyl]phenyl]-6,7,9,10,12,12a-hexahydro-5H-pyrido[4,3-b][1,4]thiazepino[2,3,4-hi]indole-11(8aH)-carboxylate as a yellow oil (187 mg, 83%.) $^1H$ NMR ($CDCl_3$, 300 MHz): 7.74 (1H, d, J 16.1 Hz), 7.23 (1H, s), 7.14 (1H, d, J 2.2 Hz), 6.96 (1H, dd, J 8.8 Hz), 6.90 (1H, d, J 1.4 Hz), 6.77 (1H, s), 6.37 (1H, d, J 15.7 Hz), 3.91–3.77 (7H, m), 3.71–2.95 (9H, m), 2.17–2.05 (2H, m), 1.90–1.89 (2H, m), and 1.42 (9H, s.)

Step B

TFA (2 mL) was added to a stirred solution of tert-butyl (8aS,12aR)-2-[4-methoxy-2-[(1E)-3-methoxy-3-oxo-1-propenyl]phenyl]-6,7,9,10,12,12a-hexahydro-5H-pyrido[4,3-b][1,4]thiazepino[2,3,4-hi]indole-11(8aH)-carboxylate (0.04 mmol, 23 mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO_4$ and concentrated in vacuo to give the titled compound (16 mg, 86%) as a yellow solid. $^1H$ NMR ($CDCl_3$, 300 MHz): 7.77 (1H, d, J 15.8 Hz), 7.27–7.25 (1H, m), 7.14 (1H, d, J 2.6 Hz), 6.96 (1H, dd, J 8.5 and 2.6 Hz), 6.90 (1H, d, J 1.5 Hz), 6.72 (1H, d, J 1.5 Hz), 6.36 (1H, d, J 15.7), 3.86–3.71 (7H, m), 3.61–3.45 (2H, m), 3.28–3.23 (1H, m), 3.07–2.65 (6H, m), 2.18–2.00 (2H, m), and 1.90–1.74 (2H, m); m/z (ES) 437.1 $(M+H)^+$.

Example 395

(2E)-3-{2-[(8aS,12aR)-6,7,8a,9,10,11,12,12a-octahydro-5H-pyrido[4,3-b][1,4]thiazepino[2,3,4-hi]indol-2-yl]-5-methoxyphenyl}-2-propen-1-ol Step A DIBAL (1.0 M solution in $CH_2Cl_2$, 0.48 mmol, 0.48 mL) was added to a stirred solution of tert-butyl(8aS,12aR)-2-[4-methoxy-2-[(1Z)-3-methoxy-3-oxo-1-propenyl]phenyl]-6,7,9,10,12,12a-hexahydro-5H-pyrido[4,3-b]1,4]thiazepino[2,3,4-hi]indole-11(8aH)-carboxylate (0.19 mmol, 100 mg) in $CH_2Cl_2$ (4 mL) at 0° C. under an atmosphere of nitrogen. This stirred at room temperature overnight. The reaction was quenched with MeOH (0.5 mL), dilluted with $CH_2Cl_2$ (10 mL), and stirred with Rochelle's salt (10 mL) for 1 hour. The organic layer was dried with $Na_2SO_4$, concentrated in vacuo, and subjected to column chromatography eluting with EtOAc/hexanes (1:1) yielding tert-butyl(8aS,12aR)-2-{2-[(1e)-3-hydroxy-1-propenyl]-4-methoxyphenyl}-6,7,9,10,12,12a-hexahydro-5H-pyrido[4,3-b][1,4]thiazepino[2,3,4-hi]indole-11(8aH)-carboxylate as a yellow oil (74 mg, 77%.) m/z (APc) 509.1 $(M+H)^+$.

Step B

TFA (2 mL) was added to a stirred solution of tert-butyl (8aS,12aR)-2-{2-[(1e)-3-hydroxy-1-propenyl]-4-methoxyphenyl}-6,7,9,10,12,12a-hexahydro-5H-pyrido[4,3-b][1,4]thiazepino[2,3,4-hi]indole-11(8aH)-carboxylate (0.15 mmol, 74 mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO_4$ and concentrated in vacuo. The product was further purified by reverse phase HPLC to give the titled compound (19 mg, 31%) as a yellow solid. m/z (ES) 409.1 $(M+H)^+$.

Example 396

(8aS,12aR)-2-[4-methoxy-2-(methoxyethyl)phenyl]-6,7,8a,9,10,11,12,12a-octahydro-5H-pyrido[4,3-b][1,4]thiazepino[2,3,4-hi]indole Step A Potassium t-butoxide (1.0 M solution in THF, 1.89 mmol, 1.89 mL) was added to a stirred solution of methoxymethyl triphenylphosphonium chloride (2.1 mmol, 720 mg) in THF (3 mL) at 0° C. under an atmosphere of nitrogen. The solution stirred at room temperature for thirty minutes. Tert-butyl(8aS,12aR)-2-(2-formyl-4-methoxyphenyl)-6,7,9,10,12,12a-hexahydro-5H-pyrido[4,3-b][1,4]thiazepino[2,3,4-hi]indole-11(8aH)-carboxylate (0.42 mmol, 200 mg) in THF (3 mL) was then added via cannula and the solution stirred at room temperature overnight. The reaction was diluted with EtOAc (30 mL), and washed with saturated $NH_4Cl$ (2×15 mL.) The product was dried with $Na_2SO_4$, concentrated in vacuo, and subjected to column chromatography eluting with EtOAc/hexanes (1:6) yielding tert-butyl (8aS,12aR)-2-[4-methoxy-2-[(1E)-2-methoxyethenyl]phenyl]-6,7,9,10,12,12a-hexahydro-5H-pyrido[4,3-b][1,4]thiazepino[2,3,4-hi]indole-11(8aH)-carboxylate as a mixture of isomers (140 mg, 66%.) $^1H$ NMR ($CDCl_3$, 300 MHz): 7.69 (0.3H, d, J 2.5 Hz), 7.13 (1H, t, J 8.4 Hz), 6.99–6.73 (3.3H, m), 6.11 (0.3H, d, J 7.3 Hz), 5.83 (0.7H, d, J 12.8 Hz), 5.23 (0.3H, d, J 7.4 Hz), 3.87–3.52 (16H, m), 2.15–2.06 (2H, m), 1.90–1.89 (2H, m), and 1.44 (9H, s.)

Step B

The tert-butyl(8aS,12aR)-2-[4-methoxy-2-[(1E)-2-methoxyethenyl]phenyl]-6,7,9,10,12,12a-hexahydro-5H-pyrido[4,3-b][1,4]thiazepino[2,3,4-hi]indole-11(8aH)-carboxylate (0.23 mmol, 115 mg) was dissolve in ethanol (10 mL) with a suspension of platinum (IV) oxide (10 mg.) This was shaken on a Parr apparatus overnight under $H_2$ (50 psi.) The residues were removed via filtration through silica eluding with EtOAc. The product was further purified by HPLC yielding tert-butyl(8aS,12aR)-2-[4-methoxy-2-(2-methoxyethyl)phenyl]-6,7,9,10,12,12a-hexahydro-5H-pyrido[4,3-b][1,4]thiazepino[2,3,4-hi]indole-11(8aH)-carboxylate (34 mg, 30%) as a yellow oil. $^1H$ NMR ($CDCl_3$, 300 MHz): 7.09 (1H, d, J 8.5 Hz), 6.88 (1H, d, J 1.8 Hz), 6.85 (1H, d, J 2.5 Hz), 6.79–6.74 (2H, m), 3.87–3.77 (4H, m), 3.67 (1H, dt, J 13.2 and 5.2 Hz), 3.58–3.45 (5H, m), 3.35–3.12 (6H, m), 2.95 (2H, dt, J 14.3 and 4.8 Hz), 2.84 (2H, t, J 7.7 Hz), 2.17–2.05 (2H, m), 1.89–1.88 (2H, m), and 1.43 (9H, s.)

Step C

TFA (2 mL) was added to a stirred solution of tert-butyl (8aS,12aR)-2-{4-methoxy-2-(2-methoxyethyl)phenyl]-6,7,9,10,12,12a-hexahydro-5H-pyrido[4,3-b][1,4]thiazepino[2,3,4-hi]indole-11(8aH)-carboxylate (0.06 mmol, 34 mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO_4$ and concentrated in vacuo to give the titled compound (27 mg, 100%) as a yellow solid. $^1$H NMR ($CDCl_3$, 300 MHz): 7.11 (1H, d, J 8.4 Hz), 6.86 (1H, d, J 1.8 Hz), 6.94 (1H, d, J 3.0 Hz), 6.78–6.74 (2H, m), 3.82–3.71 (4H, m), 3.60–3.41 (4H, m), 3.28 (3H, s), 3.20 (1H, dt, J 13.5 and 4.0 Hz), 3.09–2.59 (8H, m), 2.18–2.03 (2H, m), 1.91–1.74 (2H, m.) m/z (ES) 411.1 $(M+H)^+$.

Example 397

(8aS,12aR)-2-(2-fluoro-4-methoxyphenyl)-6,7,8a,9,10,11,12,12a-octahydro-5H-pyrido[4,3-b][1,4]thiazepino[2,3,4-hi]indole Step A n-Butyllithium (1.6 M solution in hexanes, 29.1 mmol, 18.2 mL) was added to 1-bromo-2-fluoro-4-methoxybenzene (24.4 mmol, 5.0 g) in THF (150 mL) at −78° C. under an atmosphere of nitrogen. After stirring for thirty minutes the trimethylborate (95.1 mmol, 10.8 mL) was added over twenty minutes. The reaction was allowed to warm to room temperature overnight while stirring. The solution was then acidified with HCl (3 M, 200 mL), and extracted into EtOAc. The EtOAc was then extracted with NaOH (1 N, 4×100 mL), which was subsequently acidified with concentrated HCl forming (2-fluoro-4-methoxyphenyl) boronic acid as a white precipitate. The white precipitate (2.04 g, 49%) was filtered and dried. $^1$H NMR ($CD_3OD$, 300 MHz): 7.29 (1H, t, J 8.0 Hz), 6.73 (1H, dd, J 8.5 and 2.2 Hz), 6.62 (1H, dd, J 11.4 and 2.2 Hz), 3.78 (3H, s.)

Step B

The (2-fluoro-4-methoxyphenyl)boronic acid (0.94 mmol, 160 mg), tert-butyl(8aS,12aR)-2-bromo-6,7,9,10,12,12a-hexahydro-5H-pyrido[4,3-b][1,4]thiazepino[2,3,4-hi]indole-11(8aH)-carboxylate (0.47, 200 mg), DME (15 mL) and $Na_2CO_3$ (2M, 2.5 mL) were combined and degassed with nitrogen for 20 minutes. $Pd(PPh_3)_4$ (0.02, 27 mg) was then added to the stirred solution. The solution was refluxed and was stirred overnight. The DME was removed in vacuo and the black oil was dissolved in EtOAc (50 mL), washed with $H_2O$ (2×20 mL), dried over $MgSO_4$, and concentrated in vacuo yielding a yellow oil. This oil was purified by HPLC, eluting with EtOAc/hexanes (1:4) to give tert-butyl (8aS,12aR)-2-(2-fluoro-4-methoxyphenyl)-6,7,9,10,12,12a-hexahydro-5H-pyrido[4,3-b][1,4]thiazepino[2,3,4-hi]indole-11(8aH)-carboxylate (105 mg, 48%) as a yellow oil. $^1$H NMR ($CDCl_3$, 300 MHz): 7.29–7.26 (1H, m), 7.12 (1H, d, J 1.5 Hz), 7.05 (1H, d, J 1.95 Hz), 6.74–6.64 (2H, m), 3.88–3.77 (4H, m), 3.63–3.47 (4H, m), 3.35–3.13 (5H, m), 2.97 (2H, dt, J 14.3 and 4.8 Hz), 2.17–2.01 (2H, m), 1.90–1.83 (2H, m), 1.42 (9H, s.)

Step C

TFA (2 mL) was added to a stirred solution of tert-butyl (8aS,12aR)-2-(2-fluoro-4-methoxyphenyl)-6,7,9,10,12,12a-hexahydro-5H-pyrido[4,3-b][1,4]thiazepino[2,3,4-hi]indole-11(8aH)-carboxylate (0.22 mmol, 105 mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO_4$ and concentrated in vacuo to give the titled compound (84 mg, 100%) as a yellow solid. $^1$H NMR ($CDCl_3$, 300 MHz): 7.30–7.25 (1H, m), 7.11–7.10 (1H, m), 7.02–7.01 (1H, m), 6.73–6.64 (2H, m), 3.81–3.78 (4H, m), 3.54–3.52 (1H, m), 3.44–3.39 (1H, m), 3.24–3.10 (1H, m), 3.07–2.85 (5H, m), 2.69–2.65 (1H, m), 2.12–2.10 (2H, m), and 1.85–1.82 (2H, m); m/z (ES) 371.2 $(M+H)^+$.

Example 398

(8aS,12aR)-2-(2,4-dichlorophenyl)-6,7,8a,9,10,11,12,12a-octahydro-5H-pyrido[4,3-b][1,4]thiazepino[2,3,4-hi]indole 4,4-dioxide Step A The tert-butyl(8aS,12aR)-2-bromo-6,7,9,10,12,12a-hexahydro-5H-pyrido[4,3-b][1,4]thiazepino[2,3,4-hi]indole-11(8aH)-carboxylate (2.43 mmol, 1.0 g) was dissolved in MeOH (40 mL), buffered to pH 10, and cooled to 0° C. To this Oxone® (3.65 mmol, 2.24 g) was added and the solution stirred for 2 hours at room temperature. The pH was monitored and maintained at 10 using 1 N NaOH. The product was concentrated in vacuo, dissolved in EtOAc (150 mL), washed with $H_2O$ (70 mL), dried with $Na_2SO_4$, and concentrated in vacuo. The oil was subjected to column chromatography eluting with MeOH/$CH_2Cl_2$ (1:49) yielding tert-butyl(8aS,12aR)-2-bromo-6,7,9,10,12,12a-hexahydro-5H-pyrido[4,3-b][1,4]thiazepino[2,3,4-hi]indole-11(8aH)-carboxylate 4,4-dioxide as a white solid (181 mg, 16%.) $^1$H NMR ($CDCl_3$, 300 MHz): 7.77 (1H, s), 7.29 (1H, s), 3.84 (2H, br.s), 3.55–3.34 (8H, m), 2.29–2.21 (2H, m), 1.98–1.82 (2H, m), and 1.40 (9H, s.)

Step B

The (2,4-dichlorophenyl)boronic acid (0.88 mmol, 168 mg), tert-butyl(8aS,12aR)-2-bromo-6,7,9,10,12,12a-hexahydro-5H-pyrido[4,3-b][1,4]thiazepino[2,3,4-hi]indole-11(8aH)-carboxylate 4,4-dioxide (0.44, 200 mg), Barium Hydroxide (0.66 mmol, 208 mg), DME (15 mL) and $H_2O$ (5 mL) were combined and degassed with nitrogen for 20 minutes. $Pd(PPh_3)_4$ (0.02, 25 mg) was then added to the stirred solution. The solution was refluxed and was stirred overnight. The DME was removed in vacuo and the black oil was dissolved in EtOAc (50 mL), washed with $H_2O$ (2×20 mL), dried over $MgSO_4$, and concentrated in vacuo yielding a yellow oil. This oil was purified by column chromatography, eluting with EtOAc/hexanes (1:3) to give tert-butyl(8aS,12aR)-2-(2,4-dichlorophenyl)-6,7,9,10,12,12a-hexahydro-5H-pyrido[4,3-b][1,4]thiazepino[2,3,4-hi]indole-11(8aH)-carboxylate 4,4-dioxide (90 mg, 40%) as a yellow oil. $^1$H NMR ($CDCl_3$, 300 MHz): 7.72 (1H, d, J 1.9 Hz), 7.47 (1H, d, J 1.9), 7.33 (1H, d, J 1.1 Hz), 7.31–7.22 (2H, m), 3.86–3.80 (1H, m), 3.67–3.34 (9H, m), 2.35–2.26 (2H, m), 2.05–1.91 (2H, m), and 1.39 (9H, s.)

Step C

TFA (2 mL) was added to a stirred solution of tert-butyl (8aS,12aR)-2-(2,4-dichlorophenyl)-6,7,9,10,12,12a-hexahydro-5H-pyrido[4,3-b][1,4]thiazepino[2,3,4-hi]indole-11(8aH)-carboxylate 4,4-dioxide (0.17 mmol, 90 mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO_4$ and concentrated in vacuo to give the titled compound (12 mg, 17%) as a yellow solid. $^1$H NMR ($CDCl_3$, 300 MHz): 7.71 (1H, d, J 1.9 Hz), 7.47 (1H, d, J 1.5 Hz), 7.30–7.27 (3H, m), 3.74–3.69 (1H, m), 3.57–3.43 (4H, m), 3.26 (1H, q, J 6.6

Hz), 3.08 (1H, dd, 12.8 and 6.2 Hz), 2.92–2.87 (2H, m), 2.69 (1H, dd, J 12.8 and 10.0 Hz), 2.38–2.17 (2H, m), 1.96–1.86 (1H, m), and 1.71 (1H, s); m/z (ES) 423.0 $(M+H)^+$.

Example 399

(8aS,12aR)-2-(2,6-difluorophenyl)-6,7,8a,9,10,11,12,12a-octahydro-5H-pyrido[4,3-b][1,4]thiazepino[2,3,4-hi]indole 4,4-dioxide The (2,6-difluorophenyl)boronic acid (0.88 mmol, 139 mg), tert-butyl(8aS,12aR)-2-bromo-6,7,9,10,12,12a-hexahydro-5H-pyrido[4,3-b][1,4]thiazepino[2,3,4-hi]indole-11(8aH)-carboxylate 4,4-dioxide (0.44, 200 mg), Barium Hydroxide (0.66 mmol, 208 mg), DME (15 mL) and $H_2O$ (5 mL) were combined and degassed with nitrogen for 20 minutes. $Pd(PPh_3)_4$ (0.02, 25 mg) was then added to the stirred solution. The solution was refluxed and was stirred overnight. The DME was removed in vacuo and the black oil was dissolved in EtOAc (50 mL), washed with $H_2O$ (2×20 mL), dried over $MgSO_4$, and concentrated in vacuo yielding a yellow oil. This oil was purified by column chromatography, eluting with EtOAc/hexanes (1:3) to give the desired adduct as a yellow oil. The oil was immediately deprotected by dissolving the product in $CH_2Cl_2$ (10 mL) and treating with TFA (2 mL). This stirred for 2 hours and was subsequently diluted with $CH_2Cl_2$ (40 mL), washed with NaOH (1N, 2×20 mL), dried with $Na_2SO_4$, and concentrated in vacuo to give the desired product (4 mg, 2%.) $^1H$ NMR ($CD_3OD$, 300 MHz): 7.63 (1H, s), 7.37–7.32 (2H, m), 7.04 (2H, t, J 8.0 Hz), 3.70–3.67 (1H, m), 3.58–3.25 (5H, m), 3.02 (1H, dd, J 12.8 and 6.6 Hz), 2.88–2.83 (2H, m), 2.52 (1H, dd, J 13.2 and 9.9 Hz), 2.28–2.18 (2H, m), and 2.09–1.89 (2H, m); m/z (ES) 391.2 $(M+H)^+$.

Example 400

(8aS,12aR)-2-(2-chlorophenyl)-6,7,8a,9,10,11,12,12a-octahydro-5H-pyrido[4,3-b][1,4]thiazepino[2,3,4-hi]indole 4,4-dioxide Step A The (2-chlorophenyl)boronic acid (0.88 mmol, 138 mg), tert-butyl(8aS,12aR)-2-bromo-6,7,9,10,12,12a-hexahydro-5H-pyrido[4,3-b][1,4]thiazepino[2,3,4-hi]indole-11-(8aH)-carboxylate 4,4-dioxide (0.44, 200 mg), Barium Hydroxide (0.66 mmol, 208 mg), DME (15 mL) and $H_2O$ (5 mL) were combined and degassed with nitrogen for 20 minutes. $Pd(PPh_3)_4$ (0.02, 25 mg) was then added to the stirred solution. The solution was refluxed and was stirred overnight. The DME was removed in vacuo and the black oil was dissolved in EtOAc (50 mL), washed with $H_2O$ (2×20 mL), dried over $MgSO_4$, and concentrated in vacuo yielding a yellow oil. This oil was purified by column chromatography, eluting with EtOAc/hexanes (1:3) to give tert-butyl(8aS,12aR)-2-(2,4-dichlorophenyl)-6,7,9,10,12,12a-hexahydro-5H-pyrido[4,3-b][1,4]thiazepino[2,3,4-hi]indole-11(8aH)-carboxylate 4,4-dioxide (80 mg, 37%) as a yellow oil. $^1H$ NMR ($CDCl_3$, 300 MHz): 7.75 (1H, d, J 1.5 Hz), 7.46–7.43 (1H, m), 7.38 (1H, d, J 1.1 Hz), 7.33–7.24 (3H, m), 3.86–3.85 (1H, m), 3.59–3.39 (9H, m), 2.33–2.29 (2H, m), 2.01–1.93 (2H, m), and 1.39 (9H, s.)

Step B

TFA (2 mL) was added to a stirred solution of tert-butyl (8aS,12aR)-2-(2-dichlorophenyl)-6,7,9,10,12,12a-hexahydro-5H-pyrido[4,3-b][1,4]thiazepino[2,3,4-hi]indole-11(8aH)-carboxylate 4,4-dioxide (0.16 mmol, 80 mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO_4$ and concentrated in vacuo to give the titled compound (35 mg, 56%) as a yellow solid. $^1H$ NMR ($CDCl_3$, 300 MHz): 7.75 (1H, d, J 1.5 Hz), 7.44 (1H, dd, J 6.9 and 1.4 Hz), 7.41–7.22 (4H, m), 3.73–3.68 (1H, m), 3.59–3.40 (4H, m), 3.25 (1H, q, J 2.9 Hz), 3.08 (1H, dd, 12.8 and 6.2 Hz), 2.96–2.82 (2H, m), 2.69 (1H, dd, J 12.5 and 9.8 Hz), 2.37–2.26 (2H, m), and 1.91–1.86 (2H, m.)

Example 401

(8aS,12aR)-2-(2-fluoro-4-methoxyphenyl)-6,7,8a,9,10,11,12,12a-octahydro-5H-pyrido[4,3-b][1,4]thiazepino[2,3,4-hi]indole 4,4-dioxide Step A The (2-fluoro-4-methoxyphenyl)boronic acid (0.88 mmol, 150 mg), tert-butyl(8aS,12aR)-2-bromo-6,7,9,10,12,12a-hexahydro-5H-pyrido[4,3-b][1,4]thiazepino[2,3,4-hi]indole-11(8aH)-carboxylate 4,4-dioxide (0.44, 200 mg), Barium Hydroxide (0.66 mmol, 208 mg), DME (15 mL) and $H_2O$ (5 mL) were combined and degassed with nitrogen for 20 minutes. $Pd(PPh_3)_4$ (0.02, 25 mg) was then added to the stirred solution. The solution was refluxed and was stirred overnight. The DME was removed in vacuo and the black oil was dissolved in EtOAc (50 mL), washed with $H_2O$ (2×20 mL), dried over $MgSO_4$, and concentrated in vacuo yielding a yellow oil. This oil was purified by column chromatography, eluting with EtOAc/hexanes (1:3) to give tert-butyl(8aS,12aR)-2-(2-fluoro-4-methoxyphenyl)-6,7,9,10,12,12a-hexahydro-5H-pyrido[4,3-b][1,4]thiazepino[2,3,4-hi]indole-11(8aH)-carboxylate 4,4-dioxide (70 mg, 33%) as a yellow oil. $^1H$ NMR ($CDCl_3$, 300 MHz): 7.80 (1H, d, J 1.1 Hz), 7.41 (1H, s), 7.33–7.25 (1H, m), 6.76–6.67 (2H, m), 3.83 (3H, s), 3.59–3.37 (9H, m), 2.34–2.28 (2H, m), 1.94–1.93 (2H, m), 1.67 (1H, s), and 1.39 (9H, br. s.)

Step B

TFA (2 mL) was added to a stirred solution of tert-butyl (8aS,12aR)-2-(2-fluoro-4-methoxyphenyl)-6,7,9,10,12,12a-hexahydro-5H-pyrido[4,3-b][1,4]thiazepino[2,3,4-hi]indole-11(8aH)-carboxylate 4,4-dioxide (0.14 mmol, 70 mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO_4$ and concentrated in vacuo to give the titled compound (5 mg, 8%) as a yellow solid. $^1H$ NMR ($CDCl_3$, 300 MHz): 7.80 (1H, d, J 1.4 Hz), 7.40–7.25 (1H, m), 6.80–6.66 (3H, m), 3.83 (3H, s), 3.70–3.65 (1H, m), 3.56–3.41 (4H, m), 3.29–3.21 (1H, m), 3.08 (1H, dd, 12.8 and 6.2 Hz), 2.92–2.86 (2H, m), 2.76–2.65 (2H, m), 2.33–2.27 (2H, m), and 1.90–1.85 (2H, m.)

Example 402

(8aS,12aR)-2-(2-methyl-4-methoxyphenyl)-6,7,8a,9,10,11,12,12a-octahydro-5H-pyrido[4,3-b][1,4]thiazepino[2,3,4-hi]indole 4,4-dioxide Step A The (2-methyl-4-methoxyphenyl)boronic acid (0.80 mmol, 128 mg), tert-butyl(8aS,12aR)-2-bromo-6,7,9,10,12,12a-hexahydro-5H-pyrido[4,3-b][1,4]thiazepino[2,3,4-hi]indole-11(8aH)-carboxylate 4,4-dioxide (0.40, 181 mg), Barium Hydroxide (0.60 mmol, 189 mg), DME (10 mL) and $H_2O$ (3.5 mL) were combined and degassed with nitrogen for 20 minutes. $Pd(PPh_3)_4$ (0.02, 23 mg) was then added to the stirred solution. The solution was refluxed and was stirred overnight. The DME was removed in vacuo and the black oil was dissolved in EtOAc (50 mL), washed with $H_2O$ (2×20 mL), dried over $MgSO_4$, and concentrated in vacuo yielding a yellow oil. This oil was purified by column chromatography, eluting with EtOAc/hexanes (1:3) to give tert-butyl(8aS,12aR)-2-(2-methyl-4-methoxyphenyl)-6,7,9,10,12,12a-hexahydro-5H-pyrido[4,3-b][1,4]thiazepino[2,3,4-hi]indole-11(8aH)-carboxylate 4,4-dioxide (159 mg, 80%) as a yellow oil. $^1$H NMR ($CDCl_3$, 300 MHz): 7.62 (1H, d, J 1.5 Hz), 7.18 (1H, s), 7.11 (1H, d, J 8.0 Hz), 6.85–6.74 (2H, m), 3.82 (3H, s), 3.76–3.37 (10H, m), 2.32–2.17 (5H, m), 2.05–1.95 (2H, m), and 1.40 (9H, br. s.)

Step B

TFA (2 mL) was added to a stirred solution of tert-butyl (8aS,12aR)-2-(2-methyl-4-methoxyphenyl)-6,7,9,10,12,12a-hexahydro-5H-pyrido[4,3-b][1,4]thiazepino[2,3,4-hi]indole-11(8aH)-carboxylate 4,4-dioxide (0.32 mmol, 159 mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO_4$ and concentrated in vacuo to give the titled compound (139 mg, 100%) as a yellow solid. $^1$H NMR ($CDCl_3$, 300 MHz): 7.62 (1H, d, J 1.8 Hz), 7.13–7.10 (2H, m), 6.79–6.74 (2H, m), 3.82 (3H, s), 3.69–3.38 (5H, m), 3.25–3.18 (1H, m), 3.06 (1H, dd, 12,8 and 6.2 Hz), 2.91–2.84 (2H, m), 2.64 (1H, dd, J 12.8 and 9.5 Hz), 2.34–2.26 (5H, m), and 1.91–1.85 (2H, m); m/z (ES) 399.1 $(M+H)^+$.

Example 403

(8aS,12aR)-2-(2-chloro-4-fluorophenyl)-6,7,8a,9,10,11,12,12a-octahydro-5H-pyrido[4,3-b][1,4]thiazepino[2,3,4-hi]indole Step A n-Butyllithium (1.6 M solution in hexanes, 23.5 mmol, 14.7 mL) was added to 2-chloro-4-fluoro-1-iodobenzene (19.6 mmol, 5.0 g) in THF (120 mL) at −78° C. under an atmosphere of nitrogen. After stirring for thirty minutes the trimethylborate (76.6 mmol, 8.7 mL) was added over twenty minutes. The reaction was allowed to warm to room temperature overnight while stirring. The solution was then acidified with HCl (3 M, 200 mL), and extracted into EtOAc. The EtOAc was then extracted with NaOH (1 N, 4×100 mL), which was subsequently acidified with concentrated HCl forming (2-chloro-4-fluorophenyl)boronic acid as a white precipitate. The white precipitate (1.10 g, 33%) was filtered and dried. $^1$H NMR ($CDCl_3$, 300 MHz): 7.96 (1H, t, J 8.1 Hz), 7.11 (1H, dd, J 8.8 and 2.5 Hz), 7.04 (1H, td, J 8.4 and 2.5 Hz), 5.28 (2H, s.)

Step B

The (2-chloro-4-fluorophenyl)boronic acid (0.94 mmol, 163 mg), tert-butyl(8aS,12aR)-2-bromo-6,7,9,10,12,12a-hexahydro-5H-pyrido[4,3-b][1,4]thiazepino[2,3,4-hi]indole-11(8aH)-carboxylate (0.47 mmol, 200 mg), Barium Hydroxide (0.71 mmol, 222 mg), DME (15 mL) and $H_2O$ (5 mL) were combined and degassed with nitrogen for 20 minutes. $Pd(PPh_3)_4$ (0.02 mmol, 27 mg) was then added to the stirred solution. The solution was refluxed and was stirred overnight. The DME was removed in vacuo and the black oil was dissolved in EtOAc (50 mL), washed with $H_2O$ (2×20 mL), dried over $MgSO_4$, and concentrated in vacuo yielding a yellow oil. This oil was purified by column chromatography, eluting with EtOAc/hexanes (1:9) to give tert-butyl(8aS,12aR)-2-(2-chloro-4-fluorophenyl)-6,7,9,10,12,12a-hexahydro-5H-pyrido[4,3-b][1,4]thiazepino[2,3,4-hi]indole-11(8aH)-carboxylate (150 mg, 67%) as a yellow oil. $^1$H NMR ($CDCl_3$, 300 MHz): 7.33–7.23 (2H, m), 7.17 (1H, dd, J 8.8 and 1.8 Hz), 7.01–6.91 (2H, m), 3.91–2.97 (10H, m), 2.17–2.05 (2H, m), 1.89–1.87 (2H, m), 1.42 (9H, m.)

Step C

TFA (2 mL) was added to a stirred solution of tert-butyl (8aS,12aR)-2-(2-chloro-4-fluorophenyl)-6,7,9,10,12,12a-hexahydro-5H-pyrido[4,3-b][1,4]thiazepino[2,3,4-hi]indole-11(8aH)-carboxylate (0.32 mmol, 150 mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO_4$ and concentrated in vacuo to give the titled compound (121 mg, 100%) as a yellow solid. $^1$H NMR ($CDCl_3$, 300 MHz): 7.29–7.24 (1H, m), 7.17 (1H, dd, J 8.8 and 3.0 Hz), 7.01–6.95 (2H, m), 6.91 (1H, d, J 1.4 Hz), 3.81 (1H, ddd, J 13.9, 9.9 and 4.4 Hz), 3.56 (1H, ddd, J 15.0, 9.9 and 5.5 Hz), 3.47–3.43 (1H, m), 3.22 (1H, dt, J 13.6 and 4.1 Hz), 3.11–2.82 (5H, m), 2.70–2.61 (1H, m), 2.18–2.05 (2H, m), 1.90–1.73 (2H, m.)

Example 404

(8aS,12aR)-2-(2-chloro-4-fluorophenyl)-6,7,8a,9,10,11,12,12a-octahydro-5H-pyrido[4,3-b][1,4]thiazepino[2,3,4-hi]indole 4-oxide Step A To a stirred solution of the tert-butyl(8aS,12aR)-2-(2-chloro-4-fluorophenyl)-6,7,9,10,12,12a-hexahydro-5H-pyrido[4,3-b][1,4]thiazepino[2,3,4-hi]indole-11(8aH)-carboxylate (0.21 mmol, 105 mg) in acetone (5 mL and $H_2O$ (1 mL), $NaIO_4$ (2.1 mmol, 449 mg) was added. This stirred at room temperature overnight. The product was concentrated in vacuo, dissolved in EtOAc (30 mL), washed with $NaHCO_3$ (20 mL), dried with $Na_2SO_4$, and concentrated in vacuo. The product was subjected to column chromatography eluting with EtOAc yielding tert-butyl(8aS,12aR)-2-(2-chloro-4-fluorophenyl)-6,7,9,10,12,12a-hexahydro-5H-pyrido[4,3-b][1,4]thiazepino[2,3,4-hi]indole-11(8aH)-carboxylate 4-oxide as a yellow oil (50 mg, 49%.) $^1$H NMR ($CDCl_3$, 300 MHz): 7.46 (1H, d, J 1.4 Hz), 7.29–7.24 (2H, m), 7.20 (1H, dd, J 8.4 and 2.5 Hz), 7.02 (1H, td, J 11.3 and 2.9 Hz), 3.88–3.18 (9H, m), 3.05–2.85 (1H, m), 2.60–2.32 (2H, m), 2.03–2.01 (1H, m), 1.73 (1H, s), and 1.37 (9H, br. s); m/z (ES) 491.2 $(M+H)^+$.

Step B

TFA (2 mL) was added to a stirred solution of tert-butyl (8aS,12aR)-2-(2-chloro-4-fluorophenyl)-6,7,9,10,12,12a-hexahydro-5H-pyrido[4,3-b][1,4]thiazepino[2,3,4-hi]indole-11(8aH)-carboxylate 4-oxide (0.10 mmol, 50 mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO_4$ and concentrated in vacuo to give the titled compound (39 mg, 100%) as a yellow solid. $^1$H NMR ($CDCl_3$, 300 MHz): 7.47 (1H, d, J 1.9 Hz), 7.30–7.18 (3H, m), 7.01 (1H, td, J 8.4 and 1.4 Hz), 3.61–2.05 (10H, m), 2.01–1.88 (4H, m); m/z (ES) 391.1 $(M+H)^+$.

Example 405

(8aS,12aR)-2-[(E)-2-(2-chlorophenyl)ethenyl]-6,7,8a,9,10,11,12,12a-octahydro-5H-pyrido[4,3-b][1,4]thiazepino[2,3,4-hi]indole Step A A solution of $Pd(OAc)_2$ (0.056 mmol, 10 mg) and tri-o-tolylphosphine (0.056 mmol, 30 mg) in MeCN (2 mL) was added to a stirred solution of tert-butyl(8aS,12aR)-2-vinyl-6,7,9,10,12,12a-hexahydro-5H-pyrido[4,3-b][1,4]thiazepino[2,3,4-hi]indole-11(8aH)-carboxylate (0.49 mmol, 183 mg), 1-bromo-2-chloro-benzene (2.5 mmol, 0.3 mL) and triethylamine (4.9 mmol, 0.56 mL) in MeCN (10 mL) at room temperature under an atmosphere of nitrogen. The mixture was stirred and heated at reflux overnight. The solution was concentrated in vacuo and purified by column chromatography eluting with EtOAc/hexanes (1:9) and normal phase HPLC to give tert-butyl(8aS,12aR)-2-[(E)-2-(2-chlorophenyl)ethenyl]-6,7,9,10,12,12a-hexahydro-5H-pyrido[4,3-b][1,4]thiazepino[2,3,4-hi]indole-11(8aH)-carboxylate (64 mg, 27%.) $^1$H NMR ($CDCl_3$, 300 MHz): 7.62 (1H, dd, J 7.7 and 1.5 Hz), 7.36 (1H, dd, J 7.7 and 1.1 Hz), 7.31–7.12 (5H, m), 6.91 (1H, d, J 16.1 Hz), 3.90–3.70 (2H, m), 3.54–3.15 (6H, m), 2.99 (2H, dt, J 14.3 and 4.8 Hz), 2.15–2.03 (2H, m), 1.88–1.86 (2H, m), 1.44 (9H, s.)

Step B

TFA (2 mL) was added to a stirred solution of tert-butyl (8aS,12aR)-2-[(E)-2-(2-chlorophenyl)ethenyl]-6,7,9,10,12,12a-hexahydro-5H-pyrido[4,3-b][1,4]thiazepino[2,3,4-hi]indole-11(8aH)-carboxylate (0.09 mmol, 42 mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO_4$ and concentrated in vacuo to give the titled compound (33 mg, 100%) as a yellow solid. $^1$H NMR ($CDCl_3$, 300 MHz): 7.62 (1H, dd, J 7.6 and 1.4 Hz), 7.36 (1H, dd, J 7.7 and 1.1 Hz), 7.31–7.09 (5H, m), 6.91 (1H, d, J 16.1 Hz), 3.77 (1H, ddd, J 13.9, 9.9 and 4.4 Hz), 3.56–3.41 (2H, m), 3.24 (1H, dt, J 13.2 and 4.0 Hz), 3.11–2.61 (5H, m), 2.17–2.03 (2H, m), 1.88–1.76 (3H, m); m/z (ES) 383.1 $(M+H)^+$.

Example 406

(8aS,12aR)-2-[(E)-2-(3-chlorophenyl)ethenyl]-6,7,8a,9,10,11,12,12a-octahydro-5H-pyrido[4,3-b][1,4]thiazepino[2,3,4-hi]indole Step A A solution of $Pd(OAc)_2$ (0.056 mmol, 10 mg) and tri-o-tolylphosphine (0.056 mmol, 30 mg) in MeCN (2 mL) was added to a stirred solution of tert-butyl(8aS,12aR)-2-vinyl-6,7,9,10,12,12a-hexahydro-5H-pyrido[4,3-b][1,4]thiazepino[2,3,4-hi]indole-11(8aH)-carboxylate (0.56 mmol, 209 mg), 1-bromo-3-chloro-benzene (2.8 mmol, 0.34 mL) and triethylamine (5.6 mmol, 0.64 mL) in MeCN (10 mL) at room temperature under an atmosphere of nitrogen. The mixture was stirred and heated at reflux overnight. The solution was concentrated in vacuo and purified by column chromatography eluting with EtOAc/hexanes (1:4) and normal phase HPLC to give tert-butyl(8aS,12aR)-2-[(E)-2-(3-chlorophenyl)ethenyl]-6,7,9,10,12,12a-hexahydro-5H-pyrido[4,3-b][1,4]thiazepino[2,3,4-hi]indole-11(8aH)-carboxylate (169 mg, 63%) as a yellow oil. $^1$H NMR ($CDCl_3$, 300 MHz): 7.42 (1H, d, J 1.4 Hz), 7.32–7.15 (3H, m), 7.10 (1H, d, J 1.5 Hz), 7.07 (1H, d, J 1.5 Hz), 6.93–6.78 (2H, m), 3.88–3.78 (2H, m), 3.62–3.13 (6H, m), 2.98 (2H, dt, J 14.2 and 5.1 Hz), 2.14–2.03 (2H, m), 1.87–1.86 (2H, m), 1.44 (9H, s.)

Step B

TFA (2 mL) was added to a stirred solution of tert-butyl (8aS,12aR)-2-[(E)-2-(3-chlorophenyl)ethenyl]-6,7,9,10,12,12a-hexahydro-5H-pyrido[4,3-b][1,4]thiazepino[2,3,4-hi]indole-11(8aH)-carboxylate (0.23 mmol, 111mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO_4$ and concentrated in vacuo to give the titled compound (80 mg, 93%) as a yellow solid. $^1$H NMR ($CDCl_3$, 300 MHz): 7.43 (1H, s), 7.31–7.14 (3H, m), 7.10 (1H, d, J 1.4 Hz), 7.04 (1H, d, J 1.4 Hz), 6.94 (1H, d, J 16.5 Hz), 6.81 (1H, d, J 16.1 Hz), 3.76 (1H, dt, J 13.5 and 4.4 Hz), 3.09–2.61 (5H, m), 2.18–2.00 (2H, m), 1.87–1.70 (3H, m); m/z (ES) 383.1 $(M+H)^+$.

Example 407

(8aS,12aR)-2-[(E)-2-(2,6-difluorophenyl)ethenyl]-6,7,8a,9,10,11,12,12a-octahydro-5H-pyrido[4,3-b][1,4]thiazepino[2,3,4-hi]indole Step A A solution of $Pd(OAc)_2$ (0.046 mmol, 8.5 mg) and tri-o-tolylphosphine (0.046 mmol, 24 mg) in MeCN (2 mL) was added to a stirred solution of tert-butyl(8aS,12aR)-2-vinyl-6,7,9,10,12,12a-hexahydro-5H-pyrido[4,3-b][1,4]thiazepino[2,3,4-hi]indole-11(8aH)-carboxylate (0.46 mmol, 170 mg), 2-bromo-1,3-difluorobenzene (2.3 mmol, 0.29 mL) and triethylamine (4.6 mmol, 0.56 mL) in MeCN (10 mL) at room temperature under an atmosphere of nitrogen. The mixture was stirred and heated at reflux overnight. The solution was concentrated in vacuo and purified by column chromatography eluting with EtOAc/hexanes (1:4) and normal phase HPLC to give tert-butyl (8aS,12aR)-2-[(E)-2-(2,6-difluorophenyl)ethenyl]-6,7,9,10,12,12a-hexahydro-5H-pyrido[4,3-b][1,4]thiazepino[2,3,4-hi]indole-11(8aH)-carboxylate (100 mg, 45%.) $^1$H NMR ($CDCl_3$, 300 MHz): 7.72–6.61 (7H, m), 3.86–3.84 (1H, m), 3.54–2.10 (9H, m), 2.09–1.88 (2H, m), 1.86–1.80 (2H, m), 1.44 (9H, s.)

Step B

TFA (2 mL) was added to a stirred solution of tert-butyl (8aS,12aR)-2-[(E)-2-(2,6-difluorophenyl)ethenyl]-6,7,9,10,12,12a-hexahydro-5H-pyrido[4,3-b][1,4]thiazepino[2,3,4-hi]indole-11(8aH)-carboxylate (0.21 mmol, 100 mg) in $CH_2Cl_2$ (10 mL) at room temperature under an atmosphere of nitrogen. The solution was stirred at room temperature overnight, diluted with $CH_2Cl_2$ (20 mL), washed with NaOH (1N, 2×15 mL), dried over $Na_2SO_4$ and concentrated in vacuo to give the titled compound (3.6 mg, 3%) as a yellow solid. $^1$H NMR ($CDCl_3$, 300 MHz): 7.30–7.20 (2H, m), 7.13–6.85 (5H, m), 3.86–3.78 (1H, m), 3.51–3.42 (2H, m), 3.26–2.65 (6H, m), 2.12–1.79 (4H, m), and 1.62 (1H, s); m/z (ES) 385.2 $(M+H)^+$.

Example 410

(8aS,12aR)-2-cyclohexyl-6,7,8a,9,10,11,12,12a-octahydro-5H-pyrido[4,3-b][1,4]thiazepino[2,3,4-hi]indole Step A Cyclohexylzinc bromide (0.5 M solution in THF, 0.71 mmol, 1.4 mL) was added to a stirred mixture of tert-butyl (8aS,12aR)-2-bromo-6,7,9,10,12,12a-hexahydro-5H-pyrido[4,3-b][1,4]thiazepino[2,3,4-hi]indole-11(8aH)-carboxylate (200 mg, 0.47 mmol), $PdCl_2$(dppf) (19 mg, 0.024 mmol) and CuI (10 mg, 0.052 mmol) in anhydrous THF (5 mL) at room temperature under an atmosphere of nitrogen. The mixture was stirred and heated at 45° C. for 5 min., cooled to room temperature and stirred at room temperature for 2 hr., and then stirred and heated at reflux overnight. The mixture was cooled to room temperature, quenched with 1N HCl (10 mL), extracted into EtOAc (20 mL), dried over $MgSO_4$ and concentrated in vacuo. The residue was purified by column chromatography, eluting with EtOAc/hexanes (1:4) to give tert-butyl(8aS,12aR)-2-cyclohexyl-6,7,9,10,12,12a-hexahydro-5H-pyrido[4,3-b][1,4]thiazepino[2,3,4-hi]indole-11(8aH)-carboxylate (45 mg, 22%) as a colourless oil. $^1$H NMR ($CDCl_3$, 300 MHz): 6.81 (1H, d, J 1.5 Hz), 6.74 (1H, s), 3.80–3.60 (2H, m), 3.55–3.05 (6H, m), 2.96–2.90 (2H, m), 2.38–2.28 (1H, m), 2.16–2.00 (2H, m), 1.86–1.64 (7H, m), 1.45 (9H, s), 1.37–1.24 (5H, m); $^{13}C$ NMR ($CDCl_3$, 75.4 MHz) 154.8, 150.2, 140.0, 132.2, 127.2, 120.3, 119.1, 79.4, 64.5, 48.0, 43.8, 41.0, 34.7, 34.6, 32.0, 30.9, 28.4, 26.9 and 26.2; m/z (ES) 429.1 $(M+H)^+$.

Step B

TFA (2 mL) was added to a stirred solution of tert-butyl (8aS,12aR)-2-cyclohexyl-6,7,9,10,12,12a-hexahydro-5H-pyrido[4,3-b][1,4]thiazepino[2,3,4-hi]indole-11(8aH)-carboxylate (45 mg, 0.105 mmol) in DCM (10 mL) at room temperature under an atmosphere of nitrogen. The solution was stirred at room temperature for 3 hr., washed with NaOH (1N, 2×25 mL), dried over $Na_2SO_4$ and concentrated in vacuo to give the desired product (34 mg, 99%) as a colourless oil. $^1H$ NMR ($CDCl_3$, 300 MHz): 6.80 (1H, d, J 1.8 Hz), 6.70 (1H, d, J 1.5 Hz), 3.70 (1H, ddd, J 14.1, 10.2 and 4.1 Hz), 3.51 (1H, ddd, J 15.0, 10.3 and 5.1 Hz), 3.56–3.31 (1H, m), 3.12 (1H, dt, J 13.6 and 4.3 Hz), 3.05–2.80 (4H, m), 2.63–2.53 (1H, m), 2.40–2.25 (2H, m), 2.14–1.96 (2H, m), 1.89–1.69 (7H, m), 1.41–1.17 (5H, m); $^{13}C$ NMR ($CDCl_3$, 75.4 MHz) 150.1, 139.9, 132.5, 126.8, 119.8, 119.4, 64.4, 48.9, 47.3, 43.8, 41.7, 41.0, 34.7, 34.6, 32.0, 27.0, 26.2 and 26.1; m/z (ES) 329.2 $(M+H)^+$.

Example 411

(8aS,12aR)-2-cyclopentyl-6,7,8a,9,10,11,12,12a-octahydro-5H-pyrido[4,3-b][1,4]thiazepino[2,3,4-hi]indole Step A Cyclopentylzinc bromide (0.5 M solution in THF, 2.0 mmol, 4.0 mL) was added to a stirred mixture of tert-butyl (8aS,12aR)-2-bromo-6,7,9,10,12,12a-hexahydro-5H-pyrido[4,3-b][1,4]thiazepino[2,3,4-hi]indole-11(8aH)-carboxylate (170 mg, 0.40 mmol), $PdCl_2$(dppf) (33 mg, 0.040 mmol) and CuI (17 mg, 0.088 mmol) in anhydrous THF (5 mL) at room temperature under an atmosphere of nitrogen. The mixture was stirred and heated at reflux overnight. The mixture was cooled to room temperature, quenched with 1N HCl (5 mL), extracted into EtOAc (50 mL), dried over $MgSO_4$ and concentrated in vacuo. The residue was purified by column chromatography, eluting with EtOAc/hexanes (1:3) to give tert-butyl(8aS,12aR)-2-cyclopentyl-6,7,9,10,12,12a-hexahydro-5H-pyrido[4,3-b][1,4]thiazepino[2,3,4-hi]indole-11(8aH)-carboxylate (68 mg, 41%.) $^1H$ NMR ($CDCl_3$, 300 MHz): 6.85 (1H, d, J 1.8 Hz), 6.78 (1H, d, J 1.1 Hz), 3.78–3.58 (2H, m), 3.53–3.06 (6H, m), 2.92 (1H, dt, J 14.3 and 4.8 Hz), 2.85–2.79 (1H, m), 2.15–1.90 (4H, m), 1.87–1.49 (9H, m), 1.45 (9H, s); m/z (ES) 415.1 $(M+H)^+$.

Step B

TFA (2 mL) was added to a stirred solution of tert-butyl (8aS,12aR)-2-cyclopentyl-6,7,9,10,12,12a-hexahydro-5H-pyrido[4,3-b][1,4]thiazepino[2,3,4-hi]indole-11(8aH)-carboxylate (68 mg, 0.16 mmol) in DCM (10 mL) at room temperature under an atmosphere of nitrogen. The solution was stirred at room temperature for 2 hr., washed with NaOH (1N, 2×20 mL), dried over $Na_2SO_4$ and concentrated in vacuo to give the desired product (54 mg, 100%). $^1H$ NMR ($CDCl_3$, 300 MHz): 6.83 (1H, d, J 1.5 Hz), 6.74 (1H, d, J 1.4 Hz), 3.70 (1H, ddd, J 14.1, 10.3 and 4.1 Hz), 3.52 (1H, ddd, J 14.8, 10.1 and 5.0 Hz), 3.36–3.32 (1H, m), 3.13 (1H, dt, J 13.6 and 4.2 Hz), 3.05–2.79 (5H, m), 2.58 (1H, dd, J 14.5 and 11.9 Hz), 2.13–1.45 (13H, m.)

Example 412

(8aS,12aR)-2-cyclohexylmethyl-6,7,8a,9,10,11,12,12a-octahydro-5H-pyrido[4,3-b][1,4]thiazepino[2,3,4-hi]indole Step A Cyclohexylmethylzinc bromide (0.5 M solution in THF, 1.84 mmol, 3.7 mL) was added to a stirred mixture of tert-butyl(8aS,12aR)-2-bromo-6,7,9,10,12,12a-hexahydro-5H-pyrido[4,3-b][1,4]thiazepino[2,3,4-hi]indole-11(8aH)-carboxylate (130 mg, 0.31 mmol), $PdCl_2$(dppf) (26 mg, 0.031 mmol) and CuI (13 mg, 0.067 mmol) in anhydrous THF (5 mL) at room temperature under an atmosphere of nitrogen. The mixture was stirred and heated at reflux for 2 hr. The mixture was cooled to room temperature, diluted with EtOAc (20 mL), washed with 1N HCl (10 mL), dried over $MgSO_4$ and concentrated in vacuo. The residue was purified by column chromatography, eluting with EtOAc/hexanes (1:4) to give tert-butyl(8aS,12aR)-2-cyclohexylmethyl-6,7,9,10,12,12a-hexahydro-5H-pyrido[4,3-b][1,4]thiazepino[2,3,4-hi]indole-11(8aH)-carboxylate (24 mg, 18%) as a colourless oil. m/z (ES) 443.2 $(M+H)^+$.

Step B

TFA (1 mL) was added to a stirred solution of tert-butyl (8aS,12aR)-2-cyclohexylmethyl-6,7,9,10,12,12a-hexahydro-5H-pyrido[4,3-b][1,4]thiazepino[2,3,4-hi]indole-11(8aH)-carboxylate (24 mg, 0.054 mmol) in DCM (10 mL) at room temperature under an atmosphere of nitrogen. The solution was stirred at room temperature for 2 hr., diluted with DCM (30 mL), washed with NaOH (1N, 2×20 mL), dried over $Na_2SO_4$ and concentrated in vacuo to give the desired product (18 mg, 97%) as a colourless oil. $^1H$ NMR ($CDCl_3$, 300 MHz): 6.72 (1H, d, J 1.5 Hz), 6.62 (1H, d, J 1.5 Hz), 3.72–3.63 (1H, m), 3.55–3.46 (1H, m), 3.34–3.32 (1H, m), 3.17–3.12 (1H, m), 3.03–2.80 (4H, m), 2.61–2.53 (1H, m), 2.30 (2H, d, J 6.9 Hz), 2.18–2.01 (2H, m), 1.86–1.62 (11H, m), 1.43–1.38 (1H, m), 1.20–1.10 (2H, m); m/z (ES) 343.2 $(M+H)^2$.

Example 413 ethyl 3-[(8aS,12aR)-6,7,8a,9,10,11,12,12a-octahydro-5H-pyrido[4,3-b][1,4]thiazepino[2,3,4-hi]indol-2-yl]propanoate Step A 4-Ethoxy-4-oxypropylzinc bromide (0.5 M solution in THF, 2.4 mmol, 4.8 mL) was added to a stirred mixture of tert-butyl(8aS,12aR)-2-bromo-6,7,9,10,12,12a-hexahydro-5H-pyrido[4,3-b][1,4]thiazepino[2,3,4-hi]indole-11(8aH)-carboxylate (170 mg, 0.40 mmol), $PdCl_2$(dppf) (32 mg, 0.040 mmol) and CuI (16 mg, 0.088 mmol) in anhydrous THF (5 mL) at room temperature under an atmosphere of nitrogen. The mixture was stirred and heated at at reflux overnight. The mixture was cooled to room temperature, quenched with aqueous HCl (1N, 10 mL), extracted into EtOAc (2×30 mL), dried over $MgSO_4$ and concentrated in vacuo. The residue was purified by normal phase HPLC, eluting with EtOAc/hexanes (1:3) to give tert-butyl(8aS,12aR)-2-(3-ethoxy-3-oxopropyl)-6,7,9,10,12,12a-hexahydro-5H-pyrido[4,3-b][1,4]thiazepino[2,3,4-hi]indole-11(8aH)-carboxylate (60 mg, 34%.) $^1H$ NMR ($CDCl_3$, 300 MHz): 6.80 (1H, s), 6.73 (1H, s), 4.13 (2H, q, J 7.1 Hz), 3.78–3.60 (3H, m), 3.52–3.42 (2H, m), 3.33–3.08 (4H, m), 2.92 (1H, dt, J 14.2 and 9.5 Hz), 2.78 (2H, t, J 7.9), 2.53 (2H, t, J 7.7 Hz), 2.11–2.04 (2H, m), 1.86–1.84 (2H, m), 1.45 (9H, s), 1.26 (3H, t, J 7.2 Hz.)

Step B

TFA (1 mL) was added to a stirred solution of tert-butyl (8aS,12aR)-2-(3-ethoxy-3-oxopropyl)-6,7,9,10,12,12a-hexahydro-5H-pyrido[4,3-b][1,4]thiazepino[2,3,4-hi] indole-11(8aH)-carboxylate (40 mg, 0.090 mmol) in DCM (10 mL) at room temperature under an atmosphere of nitrogen. The solution was stirred at room temperature for 2 hr., diluted with DCM (30 mL), washed with NaOH (1N, 2×20 mL), dried over $Na_2SO_4$ and concentrated in vacuo to give the desired product (25 mg, 81%.) $^1H$ NMR ($CDCl_3$, 300 MHz): 6.78 (1H, d, J 1.5 Hz), 6.69 (1H, d, J 1.5 Hz), 4.12 (2H, q, J 7.2 Hz), 3.68 (1H, ddd, J 14.1, 9.7 and 4.5 Hz), 3.50 (1H, ddd, J 14.8, 9.7 and 5.3 Hz), 3.36–3.31 (1H, m), 3.18–3.12 (1H, m), 3.03–2.75 (7H, m), 2.61–2.52 (3H, m), 2.12–2.01 (2H, m), 1.85–1.74 (2H, m), 1.24 (3H, t, J 7.2 Hz.)

Example 414 ethyl 4-[(8aS,12aR)-6,7,8a,9,10,11,12,12a-octahydro-5H-pyrido[4,3-b][1,4]thiazepino[2,3,4-hi] indol-2-yl]butanoate Step A 4-Ethoxy-4-oxybutylzinc bromide (0.5 M solution in THF, 1.64 mmol, 3.3 mL) was added to a stirred mixture of tert-butyl(8aS,12aR)-2-bromo-6,7,9,10,12,12a-hexahydro-5H-pyrido[4,3-b][1,4]thiazepino[2,3,4-hi]indole-11(8aH)-carboxylate (140 mg, 0.33 mmol), $PdCl_2$(dppf) (27 mg, 0.033 mmol) and CuI (14 mg, 0.072 mmol) in anhydrous THF (5 mL) at room temperature under an atmosphere of nitrogen. The mixture was stirred and heated at at reflux overnight. The mixture was cooled to room temperature, quenched with aqueous $NH_4Cl$ (5 mL), extracted into EtOAc (2×50 mL), dried over $MgSO_4$ and concentrated in vacuo. The residue was purified by column chromatography, eluting with EtOAc/hexanes (1:4) to give tert-butyl(8aS, 12aR)-2-(4-ethoxy-4-oxobutyl)-6,7,9,10,12,12a-hexahydro-5H-pyrido[4,3-b][1,4]thiazepino[2,3,4-hi]indole-11(8aH)-carboxylate (125 mg, 82%.) $^1H$ NMR ($CDCl_3$, 300 MHz): 6.78 (1H, d, J 1.5 Hz), 6.71 (1H, d, J 1.5 Hz), 4.13 (2H, q, J 7.2 Hz), 3.78–3.58 (2H, m), 3.54–3.40 (2H, m), 3.35–3.05 (5H, m), 2.97–2.87 (1H, m), 2.48 (2H, t, J 7.7 Hz), 2.30 (2H, t, J 7.5 Hz), 2.17–1.99 (2H, m), 1.95–1.80 (4H, m), 1.45 (9H, s), 1.26 (3H, t, J 7.2 Hz.)

Step B

TFA (1 mL) was added to a stirred solution of tert-butyl (8aS,12aR)-2-(4-ethoxy-4-oxopropyl)-6,7,9,10,12,12a-hexahydro-5H-pyrido[4,3-b][1,4]thiazepino[2,3,4-hi] indole-11(8aH)-carboxylate (25 mg, 0.054 mmol) in DCM (10 mL) at room temperature under an atmosphere of nitrogen. The solution was stirred at room temperature for 2 hr., diluted with DCM (20 mL) washed with NaOH (1N, 2×20 mL), dried over $Na_2SO_4$ and concentrated in vacuo to give the desired product (17 mg, 87%.) $^1H$ NMR ($CDCl_3$, 300 MHz): 6.78 (1H, d, J 1.5 Hz), 6.67 (1H, d, J 1.4 Hz), 4.12 (2H, q, J 7.1 Hz), 3.71 (1H, ddd, J 14.1, 10.5 and 4.0 Hz), 3.51 (1H, ddd, J 14.8, 10.0 and 5.1 Hz), 3.35–3.32 (1H, m), 3.16–2.66 (6H, m), 2.63–2.54 (1H, m), 2.48 (2H, t, J 7.5 Hz), 2.29 (2H, t, J 7.5 Hz), 2.17–2.00 (2H, m), 1.92–1.79 (2H, m), 1.26 (3H, t, J 7.2 Hz); m/z (ES) 361.1 $(M+H)^+$.

Example 415 ethyl 4-[(8aS,12aR)-6,7,8a,9,10,11,12,12a-octahydro-5H-pyrido[4,3-b][1,4]thiazepino[2,3,4-hi] indol-2-yl]pentanoate Step A 4-Ethoxy-4-oxypentylbutylzinc bromide (0.5 M solution in THF, 3.2 mmol, 6.5 mL) was added to a stirred mixture of tert-butyl(8aS,12aR)-2-bromo-6,7,9,10,12,12a-hexahydro-5H-pyrido[4,3-b][1,4]thiazepino[2,3,4-hi] indole-11(8aH)-carboxylate (230 mg, 0.54 mmol), $PdCl_2$ (dppf) (44 mg, 0.054 mmol) and CuI (14 mg, 0.12 mmol) in anhydrous THF (5 mL) at room temperature under an atmosphere of nitrogen. The mixture was stirred and heated at at reflux overnight. The mixture was cooled to room temperature, quenched with aqueous $NH_4Cl$ (5 mL), extracted into EtOAc (2×50 mL), dried over $MgSO_4$ and concentrated in vacuo. The residue was purified by column chromatography, eluting with EtOAc/hexanes (1:4) to give tert-butyl(8aS,12aR)-2-(5-ethoxy-5-oxopentyl)-6,7,9,10,12, 12a-hexahydro-5H-pyrido[4,3-b][1,4]thiazepino[2,3,4-hi] indole-11(8aH)-carboxylate (150 mg, 58%.) $^1H$ NMR ($CDCl_3$, 300 MHz): 6.78 (1H, d, J 1.4 Hz), 6.70 (1H, d, J 1.1 Hz), 4.12 (2H, q, J 7.2 Hz), 3.66–3.58 (2H, m), 3.52–3.38 (2H, m), 3.36–3.05 (5H, m), 2.97–2.85 (1H, m), 2.46 (2H, t, J 7.3 Hz), 2.31 (2H, t, J 7.2 Hz), 2.16–2.00 (2H, m), 1.90–1.80 (2H, m), 1.70–1.60 (4H, m), 1.45 (9H, s), 1.25 (3H, t, J 7.2 Hz); m/z (ES) 475.3 $(M+H)^+$.

Step B

TFA (1 mL) was added to a stirred solution of tert-butyl (8aS,12aR)-2-(5-ethoxy-5-oxopentyl)-6,7,9,10,12,12a-hexahydro-5H-pyrido[4,3-b][1,4]thiazepino[2,3,4-hi] indole-11(8aH)-carboxylate (45 mg, 0.095 mmol) in DCM (6 mL) at room temperature under an atmosphere of nitrogen. The solution was stirred at room temperature for 2 hr., diluted with DCM (20 mL) washed with NaOH (1N, 2×20 mL), dried over $Na_2SO_4$ and concentrated in vacuo to give the desired product (35 mg, 100%.) $^1H$ NMR ($CDCl_3$, 300 MHz): 6.76 (1H, d, J 1.9 Hz), 6.66 (1H, d, J 1.4 Hz), 4.12 (2H, q, J 7.2 Hz), 3.67 (1H, ddd, J 14.1, 10.1 and 4.3 Hz), 3.49 (1H, ddd, J 14.8, 9.9 and 5.2 Hz), 3.38–3.31 (1H, m), 3.15 (1H, dt, J 12.8 and 4.1 Hz), 3.03–2.78 (5H, m), 2.57 (1H, dd, J 14.1 and 11.6 Hz), 2.45 (2H, t, J 7.3 Hz), 2.31 (2H, t, J 7.2 Hz), 2.15–2.00 (2H, m), 1.87–1.54 (6H, m), 1.25 (3H, t, J 7.2 Hz.)

Example 416

(8aS,12aR)-2-Allyl-6,7,8a,9,10,11,12,12a-octahydro-5H-pyrido[4,3-b][1,4]thiazepino[2,3,4-hi] indole Step A A solution of $Pd(PPh_3)_4$ in THF (1 mL+1 mL rinse) was transferred via cannula to a stirred solution of tert-butyl2-bromo-6,7,9,10,12,12a-hexahydro-5H-pyrido[4,3-b][1,4] thiazepino[2,3,4-hi]indole-11(8aH)-carboxylate (58 mg, 0.14 mmol) and allyltributyltin (0.085 mL, 0.27 mmol) in anhydrous THF (3 mL) at room temperature under an atmosphere of nitrogen. The solution was stirred and heated at reflux for 5 days. The mixture was cooled to room temperature, concentrated in vacuo, diluted with $Et_2O$ (10 mL) and stirred with aqueous KF (10 mL) for 1 hr. The mixture was extracted into EtOAc (20 mL), dried over $MgSO_4$, concentrated in vacuo an purified by column chromatography eluting with EtOAc/hexanes (1:9) to give tert-butyl(8aS,12aR)-2-allyl-6,7,9,10,12,12a-hexahydro-5H-pyrido[4,3-b][1,4]thiazepino[2,3,4-hi]indole-11(8aH)-carboxylate (25 mg, 48%) as a colourless $^1H$ NMR ($CDCl_3$, 300 MHz): 6.80 (1H, d, J 1.1 Hz), 6.72 (1H, d, J 1.5 Hz), 5.94–5.85 (1H, m), 5.09–5.01 (2H, m), 3.76–3.57 (3H, m), 3.52–3.09 (8H, m), 2.95–2.89 (1H, m), 2.11–2.03 (2H, m), 1.87–1.83 (2H, m), 1.44 (9H, s); m/z (ES) 387.2 $(M+H)^2$.

Step B

Tert-butyldimethylsilyl trifluoromethanesulphonate (0.030 mL, 0.13 mmol) was added to a stirred solution of tert-butyl(8aS,12aR)-2-allyl-6,7,9,10,12,12a-hexahydro-5H-pyrido[4,3-b][1,4]thiazepino[2,3,4-hi]indole-11(8aH)-carboxylate (25 mg, 0.065 mmol) and 2,6-lutidine (0.019 mmol, 0.163 mmol) in DCM (2 mL) at room temperature under an atmosphere of nitrogen. The solution was stirred at room temperature for 2 hr., washed with 1N HCl, dried over $MgSO_4$ and concentrated in vacuo. The residue was taken up into THF (5 mL), treated with tetrabutylammonium fluoride (1.0 M solution in THF, 3.0 mL, 3.0 mmol) for 5 min., washed with saturated sodium bicarbonate solution, dried over $Na_2SO_4$ and concentrated in vacuo to give a colourless oil (15 mg, 81%.) $^1$H NMR ($CDCl_3$, 300 MHz) 6.78 (1H, d, J 1.5 Hz), 6.68 (1H, J 1.1 Hz), 5.95–5.86 (1H, m), 5.10–5.01 (2H, m), 3.69 (1H, ddd, J 14.1, 9.8 and 4.3 Hz), 3.51 (1H, ddd, J 14.9, 9.9 and 5.3 Hz), 3.36–3.32 (1H, m), 3.22 (2H, d, J 6.9 Hz), 3.19–3.11 (1H, m), 3.03–2.84 (5H, m), 2.58 (1H, dd, J 14.1 and 11.5 Hz), 2.13–2.97 (2H, m), 1.88–1.74 (2H, m.)

Example 417

(8aS,12aR)-2-propyl-6,7,8a,9,10,11,12,12a-octahydro-5H-pyrido[4,3-b][1,4]thiazepino[2,3,4-hi] indole Step A A suspension tert-butyl(8aS,12aR)-2-allyl-6,7,9,10,12,12a-hexahydro-5H-pyrido[4,3-b][1,4]thiazepino[2,3,4-hi] indole-11(8aH)-carboxylate (35 mg, 0.091 mmol) and 10% Palladium on carbon (5 mg) in EtOAc (2 mL) was stirred under an atmosphere of hydrogen for 2 days. The suspension was filtered through Celite and concentrated in vacuo to give tert-butyl(8aS,12aR)-2-propyl-6,7,9,10,12,12a-hexahydro-5-pyrido[4,3-b][1,4]thiazepino]2,3,4-hi]indole-11(8aH)-carboxylate (33 mg, 94%.) $^1$H NMR (300 MHz, $CDCl_3$): 6.78 (1H, d, J 1.5 Hz), 6.71 (1H, d, J 1.1 Hz), 3.75–3.58 (3H, m), 3.51–3.07 (5H, m), 2.92 (2H, dt, J 14.3 and 9.9 Hz), 2.41 (2H, t, J 7.7 Hz), 2.11–2.03 (2H, m), 1.87–1.84 (2H, m), 1.45 (9H, s), 1.42–1.30 (2H, m), 0.95–0.89 (3H, m); m/z (ES) 389.2 $(M+H)^+$.

Step B

Etheral HCl (1M, 5 mL) was added to a stirred solution of tert-butyl(8aS,12aR)-2-propyl-6,7,9,10,12,12a-hexahydro-5H-pyrido[4,3-b][1,4]thiazepino[2,3,4-hi] indole-11(8aH)-carboxylate (33 mg, 0.085 mmol) in $Et_2O$ (2 mL) at room temperature and stirred at room temperature overnight. The mixture was diluted with $Et_2O$ (20 mL) washed with NaOH (1N, 10 mL), dried over $Na_2SO_4$ and concentrated in vacuo to give the desired product (22 mg, 90%.) m/z (ES): 289.2 $(M+H)^+$.

Example 418

(8aS,12aR)-2-benzyl-6,7,8a,9,10,11,12,12a-octahydro-5H-pyrido[4,3-b][1,4]thiazepino[2,3,4-hi] indole Step A Benzylzinc bromide (0.5 M solution in THF, 1.06 mmol, 2.1 mL) was added to a stirred mixture of tert-butyl(8aS,12aR)-2-bromo-6,7,9,10,12,12a-hexahydro-5H-pyrido[4,3-b][1,4]thiazepino[2,3,4-hi]indole-11(8aH)-carboxylate (150 mg, 0.35 mmol), $PdCl_2$(dppf) (29 mg, 0.035 mmol) and CuI (15 mg, 0.078 mmol) in anhydrous THF (15 mL) at room temperature under an atmosphere of nitrogen. The mixture was stirred and heated at reflux overnight after which it quenched with 1N HCl (5 mL), extracted into EtOAc (2×20 mL), dried over $MgSO_4$ and concentrated in vacuo to give a brown oil. This oil was purified by column chromatography, eluting with EtOAc/hexanes (1:3) to give tert-butyl(8aS,12aR)-2-benzyl-6,7,9,10,12,12a-hexahydro-5H-pyrido[4,3-b][1,4]thiazepino[2,3,4-hi]indole-11(8aH)-carboxylate (90 mg, 58%) as a yellow oil. $^1$H NMR ($CDCl_3$, 300 MHz): 7.29–7.25 (2H, m), 7.18 (3H, t, J 6.6 Hz), 6.80 (1H, d, J 1.5 Hz), 6.70 (1H, s), 3.80 (2H, s), 3.72 (1H, ddd, J 14.3, 10.5 and 4.2 Hz), 3.61 (1H, dt, J 12.8 and 4.6 Hz), 3.52–3.07 (6H, m), 2.94–2.89 (2H, m), 2.17–2.00 (2H, m), 1.86–1.83 (2H, m), 1.43 (9H, s.)

Step B

TFA (2 mL) was added to a stirred solution of tert-butyl (8aS,12aR)-2-benzyl-6,7,9,10,12,12a-hexahydro-5H-pyrido[4,3-b][1,4]thiazepino[2,3,4-hi]indole-11(8aH)-carboxylate (90 mg, 0.206 mmol) in DCM (10 mL) at room temperature under an atmosphere of nitrogen. The solution was stirred at room temperature for 2 hr., diluted with DCM (20 mL), washed with NaOH (1N, 2×10 mL), dried over $Na_2SO_4$ and concentrated in vacuo to give the desired product (70 mg, 100%) as a yellow solid. $^1$H NMR ($CDCl_3$, 300 MHz): 7.30–7.20 (2H, m), 7.19–7.16 (3H, m), 6.79 (1H, d, J 1.5 Hz), 6.66 (1H, d, J 1.4 Hz), 3.80 (2H, s), 3.68 (1H, ddd, J 14.1, 10.1 and 4.3 Hz), 3.50 (1H, ddd, J 14.8, 9.7 and 5.3 Hz), 3.35–3.30 (1H, m), 3.14 (1H, dt, J 13.6 and 8.4 Hz), 3.00–2.92 (3H, m), 2.89–2.78 (2H, m), 2.56 (1H, dd, J 14.2 and 11.6 Hz), 2.16–1.97 (2H, m), and 1.89–1.67 (2H, m) ppm; m/z (ES) 337.2 $(M+H)^+$.

Example 419

(8aS,12aR)-2-(2-Fluorobenzyl)-6,7,8a,9,10,11,12,12a-octahydro-5H-pyrido[4,3-b][1,4]thiazepino[2,3,4-hi]indole Step A 2-Fluorobenzylzinc chloride (0.5 M solution in THF, 2.82 mmol, 5.6 mL) was added to a stirred mixture of tert-butyl (8aS,12aR)-2-bromo-6,7,9,10,12,12a-hexahydro-5H-pyrido[4,3-b][1,4]thiazepino[2,3,4-hi]indole-11(8aH)-carboxylate (200 mg, 0.47 mmol), $PdCl_2$(dppf) (39 mg, 0.047 mmol) and CuI (19 mg, 0.10 mmol) in anhydrous THF (5 mL) at room temperature under an atmosphere of nitrogen. The mixture was stirred and heated at reflux overnight after which it quenched with 1N HCl (5 mL), extracted into EtOAc (2×20 mL), dried over $MgSO_4$ and concentrated in vacuo to give an oil. This oil was purified by column chromatography, eluting with EtOAc/hexanes (1:3) to give tert-butyl(8aS,12aR)-2-(2-fluorobenzyl)-6,7,9,10,12,12a-hexahydro-5H-pyrido[4,3-b][1,4]thiazepino[2,3,4-hi]indole-11(8aH)-carboxylate (250 mg, 117%) as a yellow oil. $^1$H NMR ($CDCl_3$, 300 MHz): 7.21–7.11 (2H, m), 7.06–6.98 (2H, m), 6.82 (1H, s), 6.73 (1H, s), 3.82 (2H, s), 3.729 (1H, dd, J 14.3, 10.6 and 4.0 Hz), 3.64–3.57 (1H, m), 3.52–3.06 (7H, m), 2.93–2.87 (1H, m), 2.13–2.0 (2H, m), 1.86–1.83 (2H, m), 1.43 (9H, s)

Step B

TFA (4 mL) was added to a stirred solution of tert-butyl (8aS,12aR)-2-benzyl-6,7,9,10,12,12a-hexahydro-5H-pyrido[4,3-b][1,4]thiazepino[2,3,4-hi]indole-11(8aH)-carboxylate (250 mg, 0.55 mmol) in DCM (20 mL) at room temperature under an atmosphere of nitrogen. The solution was stirred at room temperature for 2 hr., diluted with DCM (30 mL), washed with NaOH (1N, 2×30 mL), dried over $Na_2SO_4$ and concentrated in vacuo to give the desired product (150 mg, 77%) as a white solid. $^1$H NMR ($CDCl_3$, 300 MHz): 7.20–7.12 (2H, m), 7.01–6.98 (2H, m), 6.80 (1H, d, J 1.4 Hz), 6.99 (1H, s), 3.82 (2H, s), 3.68 (1H, ddd, J 14.1, 10.1 and 4.3 Hz), 3.50 (1H, ddd, J 14.8, 9.9 and 5.2 Hz), 3.35–3.31 (1H, m), 3.14 (1H, dt, J 13.6 and 4.2 Hz), 3.00–2.91 (3H, m), 2.88–2.77 (2H, m), 2.56 (1H, dd, J 14.2 and 11.6 Hz), 2.14–1.99 (2H, m) and 1.86–1.68 (2H, m) ppm.

Example 420

(8aS,12aR)-2-(3-Fluorobenzyl)-6,7,8a,9,10,11,12,12a-octahydro-5H-pyrido[4,3-b][1,4]thiazepino[2,3,4-hi]indole Step A 3-Fluorobenzylzinc chloride (0.5 M solution in THF, 2.12 mmol, 4.2 mL) was added to a stirred mixture of tert-butyl (8aS,12aR)-2-bromo-6,7,9,10,12,12a-hexahydro-5H-pyrido[4,3-b][1,4]thiazepino[2,3,4-hi]indole-11(8aH)-carboxylate (150 mg, 0.35 mmol), $PdCl_2$(dppf) (30 mg, 0.035 mmol) and CuI (15 mg, 0.078 mmol) in anhydrous THF (5 mL) at room temperature under an atmosphere of nitrogen. The mixture was stirred and heated at reflux overnight after which it quenched with 1N HCl (10 mL), extracted into EtOAc (2×20 mL), dried over $MgSO_4$ and concentrated in vacuo to give an oil. This oil was purified by column chromatography, eluting with EtOAc/hexanes (1:3) to give tert-butyl(8aS,12aR)-2-(3-fluorobenzyl)-6,7,9,10,12,12a-hexahydro-5H-pyrido[4,3-b][1,4]thiazepino[2,3,4-hi]indole-11(8aH)-carboxylate (150 mg, 94%) as a yellow oil. $^1$H NMR ($CDCl_3$, 300 MHz): 7.24–7.19 (1H, m), 6.95 (1H, d, J 7.7 Hz), 6.87 (1H, J 8.8 Hz), 6.78 (1H, d, J 1.8 Hz), 6.68 (1H, d, J 1.4 Hz), 3.78 (2H, s), 3.78–3.69 (1H, m), 3.64–3.57 (1H, m), 3.52–3.08 (7H, m), 2.96–2.88 (1H, m), 2.14–2.01 (2H, m), 1.86–1.83 (2H, m), 1.43 (9H, s)

Step B

TFA (4 mL) was added to a stirred solution of tert-butyl (8aS,12aR)-2-benzyl-6,7,9,10,12,12a-hexahydro-5H-pyrido[4,3-b][1,4]thiazepino[2,3,4-hi]indole-11(8aH)-carboxylate (150 mg, 0.33 mmol) in DCM (20 mL) at room temperature under an atmosphere of nitrogen. The solution was stirred at room temperature for 2 hr., diluted with DCM (50 mL), washed with NaOH (1N, 2×30 mL), dried over $Na_2SO_4$ and concentrated in vacuo to give the desired product (110 mg, 94%) as a white solid. $^1$H NMR ($CDCl_3$, 300 MHz): 7.24–7.19 (1H, m), 6.96 (1H, d, J 7.7 Hz), 6.90–6.84 (2H, m), 6.77 (1H, d, J 1.9 Hz), 6.64 (1H, d, J 1.5 Hz), 3.79 (2H, s), 3.69 (1H, ddd, J 14.1, 10.3 and 4.2 Hz), 3.50 (1H, ddd, J 14.9, 9.9 and 5.2 Hz), 3.36–3.32 (1H, m), 3.15 (1H, dt, J 13.6 and 4.4 Hz), 3.01–2.89 (3H, m), 2.88–2.77 (2H, m), 2.56 (1H, dd, J 14.3 and 11.4 Hz), 2.16–2.00 (2H, m) and 1.86–1.69 (2H, m) ppm.

Example 421

(8aS,12aR)-2-(4-Fluorobenzyl)-6,7,8a,9,10,11,12,12a-octahydro-5H-pyrido[4,3-b][1,4]thiazepino[2,3,4-hi]indole Step A 4-Fluorobenzylzinc chloride (0.5 M solution in THF, 2.12 mmol, 4.2 mL) was added to a stirred mixture of tert-butyl (8aS,12aR)-2-bromo-6,7,9,10,12,12a-hexahydro-5H-pyrido[4,3-b][1,4]thiazepino[2,3,4-hi]indole-11(8aH)-carboxylate (150 mg, 0.35 mmol), $PdCl_2$(dppf) (30 mg, 0.035 mmol) and CuI (15 mg, 0.0780 mmol) in anhydrous THF (5 mL) at room temperature under an atmosphere of nitrogen. The mixture was stirred and heated at reflux overnight after which it quenched with 1N HCl (10 mL), extracted into EtOAc (2×20 mL), dried over $MgSO_4$ and concentrated in vacuo to give an oil. This oil was purified by column chromatography, eluting with EtOAc/hexanes (3:7) to give tert-butyl(8aS,12aR)-2-(4-fluorobenzyl)-6,7,9,10,12,12a-hexahydro-5H-pyrido[4,3-b][1,4]thiazepino[2,3,4-hi]indole-11(8aH)-carboxylate (150 mg, 94%) as a yellow oil. $^1$H NMR ($CDCl_3$, 300 MHz): 7.24–7.19 (1H, m), 6.95 (1H, d, J 7.7 Hz), 6.87 (1H, J 8.8 Hz), 6.78 (1H, d, J 1.8 Hz), 6.68 (1H, d, J 1.4 Hz), 3.78 (2H, s), 3.78–3.69 (1H, m), 3.64–3.57 (1H, m), 3.52–3.08 (7H, m), 2.96–2.88 (1H, m), 2.14–2.01 (2H, m), 1.86–1.83 (2H, m), 1.43 (9H, s)

Step B

TFA (4 mL) was added to a stirred solution of tert-butyl (8aS,12aR)-2-(4-fluorobenzyl)-6,7,9,10,12,12a-hexahydro-5H-pyrido[4,3-b][1,4]thiazepino[2,3,4-hi]indole-11(8aH)-carboxylate (150 mg, 0.33 mmol) in DCM (20 mL) at room temperature under an atmosphere of nitrogen. The solution was stirred at room temperature for 2 hr., diluted with DCM (50 mL), washed with NaOH (1N, 2×30 mL), dried over $Na_2SO_4$ and concentrated in vacuo to give the desired product (110 mg, 94%) as a white solid. $^1$H NMR ($CDCl_3$, 300 MHz): 7.24–7.19 (1H, m), 6.96 (1H, d, J 7.7 Hz), 6.90–6.84 (2H, m), 6.77 (1H, d, J 1.9 Hz), 6.64 (1H, d, J 1.5 Hz), 3.79 (2H, s), 3.69 (1H, ddd, J 14.1, 10.3 and 4.2 Hz), 3.50 (1H, ddd, J 14.9, 9.9 and 5.2 Hz), 3.36–3.32 (1H, m), 3.15 (1H, dt, J 13.6 and 4.4 Hz), 3.01–2.89 (3H, m), 2.88–2.77 (2H, m), 2.56 (1H, dd, J 14.3 and 11.4 Hz), 2.16–2.00 (2H, m) and 1.86–1.69 (2H, m) ppm.

Example 422

(8aS,12aR)-2-(3-Methoxybenzyl)-6,7,8a,9,10,11,12,12a-octahydro-5H-pyrido[4,3-b][1,4]thiazepino[2,3,4-hi]indole Step A 3-Methoxybenzylzinc chloride (0.5 M solution in THF, 2.97 mmol, 5.9 mL) was added to a stirred mixture of tert-butyl(8aS,12aR)-2-bromo-6,7,9,10,12,12a-hexahydro-5H-pyrido[4,3-b][1,4]thiazepino[2,3,4-hi]indole-11(8aH)-carboxylate (210 mg, 0.49 mmol), $PdCl_2$(dppf) (42 mg, 0.049 mmol) and CuI (21 mg, 0.11 mmol) in anhydrous THF (5 mL) at room temperature under an atmosphere of nitrogen. The mixture was stirred and heated at reflux overnight. The mixture was cooled to room temperature, quenched with 1N HCl (30 mL), extracted into EtOAc (50 mL), dried over $MgSO_4$ and concentrated in vacuo. The residue was purified by column chromatography, eluting with EtOAc/hexanes (1:4) to give tert-butyl(8aS,12aR)-2-(3-methoxybenzyl)-6,7,9,10,12,12a-hexahydro-5H-pyrido[4,3-b][1,4]thiazepino[2,3,4-hi]indole-11(8aH)-carboxylate (215 mg, 94%) as a yellow oil. $^1$H NMR ($CDCl_3$, 300 MHz): 7.19 (1H, t, J 7.7 Hz), 6.81–6.70 (5H, m), 3.78 (3H, s), 3.77 (2H, s), 3.77–3.58 (3H, m), 3.52–3.07 (8H, m), 2.93–2.89 (2H, m), 2.10–2.01 (2H, m), 1.85–1.83 (2H, m), 1.43 (9H, s.)

Step B

TFA (4 mL) was added to a stirred solution of tert-butyl (8aS,12aR)-2-benzyl-6,7,9,10,12,12a-hexahydro-5H-pyrido[4,3-b][1,4]thiazepino[2,3,4-hi]indole-11(8aH)-carboxylate (215 mg, 0.46 mmol) in DCM (10 mL) at room temperature under an atmosphere of nitrogen. The solution was stirred at room temperature for 1 hr., diluted with DCM (50 mL) washed with NaOH (1N, 2×20 mL), dried over $Na_2SO_4$ and concentrated in vacuo to give the desired product (168 mg, 100%.) $^1$H NMR ($CDCl_3$, 300 MHz): 7.19 (1H, t, J 8.3 Hz), 6.79 (1H, s), 6.75 (1D, d, J 7.0 Hz), 6.72 (1H, s), 6.66 (1H, d, J 1.4 Hz), 3.78 (5H, s), 3.68 (1H, ddd, J 14.1, 10.3 and 4.1 Hz), 3.50 (1H, ddd, J 14.9, 9.7 and 5.3 Hz), 3.47–3.30 (1H, m), 3.14 (1H, dt, J 13.5 and 4.4 Hz), 3.00–2.78 (5H, m), 2.56 (1H, dd, J 14.2 and 11.5 Hz), 2.14–2.00 (2H, m), 1.86–1.68 (2H, m); m/z (ES) 367.1 $(M+H)^+$.

Example 423

3-[(8aS,12aR)-6,7,8a,9,10,11,12,12a-octahydro-5H-pyrido[4,3-b][1,4]thiazepino[2,3,4-hi]indol-2-ylmethyl]phenol Boron tribromide (0.4 M solution in DCM, 0.68 mmol, 1.7 mL) was added to a stirred solution of (8aS,12aR)-2-

(3-methoxybenzyl)-6,7,8a,9,10,12,12a-octahydro-5H-pyrido[4,3-b][1,4]thiazepino[2,3,4-hi]indole (50 mg, 0.14 mmol) in DCM at room temperature under an atmosphere of nitrogen. The resultant suspension was stirred at room temperature for 1 hr., diluted with EtOAc (30 mL), washed with $NaHCO_3$ (2×10 mL), dried over $Na_2SO_4$ and concentrated in vacuo to give the desired product (30 mg, 63%) as an orange foam. m/z (ES) 353.2 $(M+H)^+$.

Example 424

(8aS,12aR)-2-(2-Methoxybenzyl)-6,7,8a,9,10,11,12,12a-octahydro-5H-pyrido[4,3-b][1,4]thiazepino[2,3,4-hi]indole Step A 2-Methoxybenzylzinc chloride (0.5 M solution in THF, 2.68 mmol, 5.4 mL) was added to a stirred mixture of tert-butyl(8aS,12aR)-2-bromo-6,7,9,10,12,12a-hexahydro-5H-pyrido[4,3-b][1,4]thiazepino[2,3,4-hi]indole-11(8aH)-carboxylate (190 mg, 0.45 mmol), $PdCl_2$(dppf) (38 mg, 0.045 mmol) and CuI (19 mg, 0.098 mmol) in anhydrous THF (5 mL) at room temperature under an atmosphere of nitrogen. The mixture was stirred and heated at at reflux overnight. The mixture was cooled to room temperature, quenched with 1N HCl (30 mL), extracted into EtOAc (50 mL), dried over $MgSO_4$ and concentrated in vacuo. The residue was purified by column chromatography, eluting with EtOAc/hexanes (1:4) to give tert-butyl(8aS,12aR)-2-(2-methoxybenzyl)-6,7,9,10,12,12a-hexahydro-5H-pyrido[4,3-b][1,4]thiazepino[2,3,4-hi]indole-11(8aH)-carboxylate (215 mg, 94%) as a yellow oil. $^1$H NMR ($CDCl_3$, 300 MHz): 7.18 (1H, td, J 7.9 and 1.6 Hz), 7.05 (1H, d, J 6.2 Hz), 6.89–6.84 (2H, m), 6.74 (1H, s), 3.82 (3H, s), 3.80 (2H, s), 3.77–3.61 (3H, m), 3.52–3.05 (6H, m), 2.92–2.87 (1H, m), 2.18–2.03 (2H, m), 1.85–1.83 (2H, m), 1.44 (9H, s.)

Step B

TFA (2 mL) was added to a stirred solution of tert-butyl (8aS,12aR)-2-(2-methoxybenzyl-6,7;9,10,12,12a-hexahydro-5H-pyrido[4,3-b][1,4]thiazepino[2,3,4-hi]indole-11(8aH)-carboxylate (65 mg, 0.14 mmol) in DCM (15 mL) at room temperature under an atmosphere of nitrogen. The solution was stirred at room temperature for 2 hr., diluted with DCM (20 mL) washed with NaOH (1N, 2×10 mL), dried over $Na_2SO_4$ and concentrated in vacuo to give the desired product (50 mg, 98%.) m/z (ES) 367.0 $(M+H)^+$.

Example 425

2-[(8aS,12aR)-6,7,8a,9,10,11,12,12a-octahydro-5H-pyrido[4,3-b][1,4]thiazepino[2,3,4-hi]indol-2-ylmethyl]phenol Boron tribromide (0.4 M solution in DCM, 1.3 mmol, 3.2 mL) was added to a stirred solution of tert-butyl(8aS,12aR)-2-(2-methoxybenzyl)-6,7,9,10,12,12a-hexahydro-5H-pyrido[4,3-b][1,4]thiazepino[2,3,4-hi]indole-11(8aH)-carboxylate (60 mg, 0.13 mmol) in DCM (5 mL) at room temperature under an atmosphere of nitrogen. The resultant suspension was stirred at room temperature for 30 min., quenched with $NaHCO_3$ (10 mL), extracted into EtOAc (100 mL), dried over $NaSO_4$ and concentrated in vacuo to give the desired product (40 mg, 87%) as a white solid. $^1$H NMR ($CD_3OD$, 300 MHz) 7.02–6.91 (2H, m), 6.81 (1H, d, J 3.6 Hz), 6.77–6.68 (3H, m), 3.75 (2H, s), 3.73–3.32 (3H, m), 3.25–3.06 (4H, m), 2.95–2.87 (2H, m), 2.60 (1H, dd, J 14.5 and 12.7 Hz), 2.19–1.90 (4H, m); m/z (ES) 353.2 $(M+H)^+$.

Example 426

Methyl-2-[(8aS,12aR)-6,7,8a,9,10,11,12,12a-octahydro-5H-pyrido[4,3-b][1,4]thiazepino[2,3,4-hi]indol-2-yl]-5-methoxybenzoate Step A Tert-butyllithium (1.7 M in hexanes, 2.2 mmol, 1.3 mL) was added to a stirred solution of tert-butyl(8aS,12aR)-2-bromo-6,7,9,10,12,12a-hexahydro-5H-pyrido[4,3-b][1,4]thiazepino[2,3,4-hi]indole-11(8aH)-carboxylate (420 mg, 0.99 mmol) in anhydrous THF (15 mL) at −78C. under an atmosphere of nitrogen. The solution was stirred at −78C. for 1 hr. and then tri-n-butyltin chloride (1.2 mmol, 0.32 mL) was added in a single portion. The solution was allowed to warm to room temperature, stirred at room temperature for 3 hr., and then quenched with water (10 mL.) The mixture was extracted into EtOAc (2×20 mL), dried over $Na_2SO_4$ and concentrated in vacuo to give a colourless oil. This oil was purified by column chromatography ($NEt_3$ washed silica) eluting EtOAc/hexanes (1:9) to give tert-butyl(8aS,12aR)-2-(tributylstannyl)-6,7,9,10,12,12a-hexahydro-5H-pyrido[4,3-b][1,4]thiazepino[2,3,4-hi]indole-11(8aH)-carboxylate (120 mg, 19%) as a colourless oil. $^1$H NMR (300 MHz, $CDCl_3$): 7.01 (1H, s), 6.94 (1H, s), 3.87–3.77 (1H, m), 3.66–3.60 (1H, m), 3.54–3.46 (2H, m), 3.35–3.18 (2H, m), 3.10–3.06 (2H, m), 2.93 (2H, dt, J 14.3 and 9.5 Hz), 2.15–2.00 (2H, m), 1.92–1.82 (2H, m), 1.56–1.45 (15H, m), 1.38–1.26 (6H, sextet, J 7.3 Hz), 1.01–0.96 (6H, m), 0.89 (9H, t, J 7.4 Hz.)

Step B

A solution of $Pd_2dba_3$ (17 mg, 0.019 mmol) and triphenylarsine (25 mg, 0.076 mmol) in anhydrous THF (1 mL) was transferred (via cannula) to a stirred solution of tert-butyl(8aS,12aR)-2-(tributylstannyl)-6,7,9,10,12,12a-hexahydro-5H-pyrido[4,3-b][1,4]thiazepino[2,3,4-hi]indole-11(8aH)-carboxylate (120 mg, 0.19 mmol) and methyl 2-bromo-5-methoxybenzoate (70 mg, 0.29 mmol) in anhydrous THF (3 mL) at room temperature under an atmosphere of nitrogen. The resulting solution was stirred and heated at reflux overnight. The resultant mixture was cooled to room temperature, concentrated in vacuo and purified by flash column chromatography eluting with EtOAc/hexanes (1:4) to give tert-butyl(8aS,12aR)-2-[4-methoxy-2-(methoxycarbonyl)phenyl]-6,7,9,10,12,12a-hexahydro-5H-pyrido[4,3-b][1,4]thiazepino[2,3,4-hi]indole-11(8aH)-carboxylate as a yellow oil (32 mg, 33%.) $^1$H NMR (300 MHz, $CDCl_3$) 7.31–7.23 (2H, m), 7.02 (1H, dd, J 8.6 and 2.7 Hz), 6.93 (1H, d, J 1.5 Hz), 6.79 (1H, d, J 1.3 Hz), 3.88–3.78 (4H, m), 3.71–3.63 (4H, m), 3.57–3.47 (2H, m), 3.31–3.11 (4H, m), 2.97–2.93 (2H, m), 2.20–2.05 (2H, m), 1.93–1.83 (2H, m), 1.43 (9H, s.)

Step C

TFA (2 mL) was added to a stirred solution of tert-butyl (8aS,12aR)-2-[4-methoxy-2-(methoxycarbonyl)phenyl]-6,7,9,10,12,12a-hexahydro-5H-pyrido[4,3-b][1,4]thiazepino[2,3,4-hi]indole-11(8aH)-carboxylate (32 mg, 0.063 mmol) in dichloromethane (10 mL) at room temperature under an atmosphere of nitrogen. The solution was stirred at room temperature for 2 hr., diluted with DCM (20 mL) washed with 1N NaOH (2×10 mL), dried over $Na_2SO_4$ and concentrated in vacuo to give the desired product (25 mg, 100%) as a colourless oil. $^1$H NMR (300 MHz, $CDCl_3$): 7.27–7.23 (2H, m), 7.01 (1H, dd, J 8.6 and 2.7 Hz), 6.92 (1H, d, J 1.8 Hz), 6.75 (1H, d, J 1.8 Hz), 3.85 (3H, s), 3.83–3.73 (1H, m), 3.69 (3H, s), 3.55 (1H, ddd, J 14.9, 9.9 and 5.3 Hz), 3.44–3.40 (1H, m), 3.21–3.15 (1H, m), 3.09–2.87 (4H, m), 2.66–2.58 (2H, m), 2.15–2.05 (2H, m), 1.91–1.74 (2H, m); m/z (ES) 411.1 $(M+H)^+$ Example 427

(8aS,12aR)-2-(2,6-difluorophenyl)-6,7,8a,9,10,11,12,12a-octahydro-5H-pyrido[4,3-b][1,4]thiazepino[2,3,4-hi]indole Step A Degassed DMF (25 $cm^3$) was added to a mixture of tert-butyl(8aS,12aR)-2-bromo-6,7,9,10,12,12a-hexahydro-5H-pyrido[4,3-b][1,4]thiazepino[2,3,4-hi]indole-11(8aH)-carboxylate (650 mg, 1.53 mmol), $PPh_3$ (80 mg, 0.31 mmol), CuBr (44 mg, 0.31 mmol) and $PdCl_2(PPh_3)_2$ (110 mg, 0.15 mmol) via cannula, at room temperature under an atmosphere of nitrogen. Stirred at room temperature for 5 min and then (2,6-difluoro)(trimethyl)stannane (640 mg, 2.3 mmol) in degassed DMF (5 $cm^3$) was added via cannula. The mixture was stirred and heated at 60° C. for 30 min after which a further quantity of (2,6-difluoro)(trimethyl)stannane (320 mg, 1.1 mmol) in degassed DMF (2.5 $cm^3$) was added via cannula and the reaction stirred and heated at 140° C. After 10 min. the solution began to turn black, and a final quantity of the stannane (320 mg, 1.1 mmol) in DMF (2.5 $cm^3$) was added. The mixture was stirred and heated at 140° C. for 1 hr., cooled to room temperature, diluted with EtOAc (100 mL), washed with water (4×100 mL), dried over $MgSO_4$ and concentrated in vacuo to give a yellow oil. Purified by column chromatography (10% EtOAc/hexanes) to give tert-butyl(8aS,12aR)-2-(2,6-difluorophenyl)-6,7,9,10,12,12a-hexahydro-5H-pyrido[4,3-b][1,4]thiazepino[2,3,4-hi]indole-11(8aH)-carboxylate (510 mg, 71%) as a white foam. $^1H$ NMR (300 MHz, $CDCl_3$): 7.25–7.15 (1H, m), 7.10–7.08 (1H, m), 6.99 (1H, d, J 1.5 Hz), 6.93 (2H, t, J 8.1 Hz), 3.91 (1H, ddd, J 14.3, 10.5 and 4.1 Hz), 3.63–3.13 (8H, m), 2.99 (1H, dt, J 14.2 and 4.9 Hz), 2.15–2.05 (2H, m), 1.90–1.88 (2H, m), 1.42 (9H, s.)

Step B

TFA (15 mL) was added to a stirred solution of tert-butyl (8aS,12aR)-2-(2,6-difluorophenyl)-6,7,9,10,12,12a-hexahydro-5H-pyrido[4,3-b][1,4]thiazepino[2,3,4-hi]indole-11(8aH)-carboxylate (680 mg, 1.48 mmol) in DCM (100 mL) and stirred at room temperature overnight. The solution was washed with 1N NaOH (3×50 mL), extracted into EtOAc (100 mL), dried over $Na_2SO_4$ and concentrated in vacuo to give the title compound (550 mg, 103%) as a foam. m/z (ES) 359.3 $(M+H)^+$.

Example 428

(8aS,12aR)-2-[(E)-2-phenylethenyl]-6,7,8a,9,10,11,12,12a-octahydro-5H-pyrido[4,3-b][1,4]thiazepino[2,3,4-hi]indole Step A A solution of palladium (II) acetate (34 mg, 0.15 mmol) and triphenylphosphine (80 mg, 0.31 mmol) in THF (5 mL) was added to a stirred solution of tert-butyl(8aS,12aR)-2-cyclopentyl-6,7,9,10,12,12a-hexahydro-5H-pyrido[4,3-b][1,4]thiazepino[2,3,4-hi]indole-11(8aH)-carboxylate (650 mg, 1.53 mmol) and vinyltributylstannane (0.67 mL, 2.3 mmol) in toluene (10 mL) at room temperature under an atmosphere of nitrogen via cannula. The solution was stirred and heated at reflux overnight, cooled to room temperature and concentrated in vacuo to give a black oil. The oil was purified by column chromatography eluting with EtOAc/hexanes (1:4) to give tert-butyl(8aS,12aR)-2-vinyl-6,7,9,10,12,12a-hexahydro-5H-pyrido[4,3-b][1,4]thiazepino[2,3,4-hi]indole-11(8aH)-carboxylate as a colourless oil (500 mg, 88%.) $^1H$ NMR ($CDCl_3$, 300 MHz): 7.00 (2H, dd, J 6.6 and 1.5 Hz), 6.53 (1H, dd, J 17.4 and 10.9 Hz), 5.55 (1H, d, J 17.5 Hz), 5.04 (1H, d, J 10.9 and 1.0 Hz), 3.79 (1H, ddd, J 14.1, 10.1 and 4.3 Hz), 3.61–3.12 (8H, m), 2.96 (1H, dt, J 14.3 and 9.5 Hz), 2.16–2.02 (2H, m), 2.02–1.83 (2H, m), 1.43 (9H, s.)

Step B

Sodium carbonate (2M, 2.5 mL, 5.0 mmol) was added to a stirred solution of tert-butyl(8aS,12aR)-2-cyclopentyl-6,7,9,10,12,12a-hexahydro-5H-pyrido[4,3-b][1,4]thiazepino[2,3,4-hi]indole-11(8aH)-carboxylate (200 mg, 0.47 mmol), trans-phenylethenylboronic acid (135 mg, 0.94 mmol) and tetrakis(triphenylphosphine)palladium(0) (27 mg, 0.024 mmol) is degassed DME (5 mL) at room temperature under an atmosphere of nitrogen. The mixture was stirred and heated at reflux overnight, cooled to room temperature, extracted into EtOAc (2×20 mL), dried over $Na_2SO_4$ and concentrated in vacuo. The resulting oil was purified by column chromatography, eluting with EtOAc/hexanes (1:4) to give tert-butyl(8aS,12aR)-2-[(E)-2-phenylethenyl]-6,7,9,10,12,12a-hexahydro-5H-pyrido[4,3-b][1,4]thiazepino[2,3,4-hi]indole-11(8aH)-carboxylate (150 mg, 71%.) $^1H$ NMR ($CDCl_3$, 300 MHz): 7.46 (1H, d, J 8.4 Hz), 7.36–7.19 (4H, m), 7.11 (1H, d, J 7.7 Hz), 6.92 (1H, d, J 3.3 Hz), 3.87–3.77 (2H, m), 3.61–3.15 (7H, m), 3.01–2.95 (1H, m), 2.18–2.07 (2H, m), 1.88–1.86 (2H, m), 1.44 (9H, s.)

Step C

TFA (1 mL) was added to a stirred solution of tert-butyl (8aS,12aR)-2-[(E)-2-phenylethenyl]-6,7,9,10,12,12a-hexahydro-5H-pyrido[4,3-b][1,4]thiazepino[2,3,4-hi]indole-11(8aH)-carboxylate (30 mg, 0.067 mmol) in DCM (5 mL) and stirred at room temperature for 1 hr. The solution was quenched with 1N NaOH (10 mL), extracted into DCM (10 mL), dried over $Na_2SO_4$ and concentrated in vacuo to give the desired product (17 mg, 73%.) $^1H$ NMR ($CDCl_3$, 300 MHz): 7.47 (1H, d, J 1.1 Hz), 7.44–7.21 (4H, m), 7.09 (1H, dd, J 16.9 and 1.5 Hz), 3.82–3.70 (1H, m), 3.57–2.84 (8H, m), 2.70–2.60 (1H, m), 2.20–2.05 (2H, m), 1.90–1.87 (2H, m.)

Example 429

(8aS,12aR)-2-[(E)-2-(4-methoxy-2-methylphenyl)ethenyl]-6,7,8a,9,10,11,12,12a-octahydro-5H-pyrido[4,3-b][1,4]thiazepino[2,3,4-hi]indole Step A A solution of $Pd(OAc)_2$ (7 mg, 0.038 mmol) and tri-o-tolylphosphine (20 mg, 0.076 mmol) in MeCN (2 mL) was added to a stirred solution of tert-butyl(8aS,12aR)-2-vinyl-6,7,9,10,12,12a-hexahydro-5H-pyrido[4,3-b][1,4]thiazepino[2,3,4-hi]indole-11(8aH)-carboxylate (140 mg, 0.38 mmol), 4-bromo-3-methylanisole (0.23 mL, 1.9 mmol) and triethylamine (0.46 mmol, 3.8 mmol) in MeCN (5 mL) at room temperature under an atmosphere of nitrogen. The mixture was stirred and heated at reflux overnight. The solution was concentrated in vacuo and purified by column chromatography eluting with EtOAc/hexanes (1:4) and normal phase HPLC to give tert-butyl(8aS,12aR)-2-[(E)-2-(4-methoxy-2-methylphenyl)ethenyl]-6,7,9,10,12,12a-hexahydro-5H-pyrido[4,3-b][1,4]thiazepino[2,3,4-hi]indole-11(8aH)-carboxylate (14 mg, 8%.) $^1H$ NMR ($CDCl_3$, 300 MHz): 7.47 (1H, d, J 8.4 Hz), 7.11–7.02 (3H, m), 6.75–6.70 (3H, m), 3.87–3.76 (4H, m), 3.65–3.10 (8H, m), 3.02–2.90 (1H, m), 2.39 (3H, s), 2.12–2.02 (2H, m), 1.92–1.82 (2H, m), 1.44 (9H, s.)

Step B

TFA (1 mL) was added to a stirred solution of tert-butyl (8aS,12aR)-2-[(E)-2-(4-methoxy-2-methylphenyl)ethenyl]-6,7,9,10,12,12a-hexahydro-5H-pyrido[4,3-b][1,4]thiazepino[2,3,4-hi]indole-11(8aH)-carboxylate (14 mg, 0.028 mmol) in dichloromethane (5 mL) at room temperature under an atmosphere of nitrogen. The solution was stirred at room temperature overnight, diluted with DCM (20 mL), washed with 1N NaOH (2×10 mL), dried over $Na_2SO_4$ and concentrated in vacuo to give the desired product (10 mg, 90%.) m/z (ES) 393.2 $(M+H)^+$.

Example 430

N,N-dimethyl-6,7,8a,9,10,11,12,12a-octahydro-5H-pyrido[4,3-b][1,4]thiazepino[2,3,4-hi]indol-2-amine Step A $Pd_2dba_3$ (13 mg, 0.014 mmol) was added to a stirred solution of tert-butyl 2-bromo-6,7,9,10,12,12a-hexahydro-5H-pyrido[4,3-b][1,4]thiazepino[2,3,4-hi]indole-11(8aH)-carboxylate (120 mg, 0.28 mmol), BINAP (13 mg, 0.014 mmol), benzophenone imine (61 mg, 0.057 mL, 0.34 mmol) and sodium tert-butoxide (38 mg, 0.40 mmol) in anhydrous, degassed toluene (5 mL) at room temperature under an atmosphere of nitrogen. The mixture was stirred and heated at reflux for 3 days, cooled to room temperature, concentrated in vacuo and purified by column chromatography eluting with EtOAc/hexane (3:17) to give tert-butyl 2-[(diphenylmethylene)amino]-6,7,9,10,12,12a-hexahydro-5H-pyrido[4,3-b][1,4]thiazepino[2,3,4-hi]indole-11(8aH)-carboxylate (136 mg, 92%) as a yellow oil. m/z (ES) 526.1 $(M+H)^+$.

Step B

Hydroxylamine hydrochloride (2.4 mg, 0.034 mmol) was added to a stirred solution of tert-butyl 2-[(diphenylmethylene)amino]-6,7,9,10,12,12a-hexahydro-5H-pyrido[4,3-b][1,4]thiazepino[2,3,4-hi]indole-11(8aH)-carboxylate (10 mg, 0.019 mmol) and sodium acetate (3.7 mg, 0.046 mmol) in methanol (1 mL) at room temperature. The mixture was stirred at room temperature for 15 min, quenched by the addition of NaOH (0.2 M, 3 mL) and extracted into DCM (2×15 mL.) The organic extracts were dried over $Na_2SO_4$, concentrated in vacuo and purified by column chromatography eluting with EtOAc/hexanes (3:7) to give tert-butyl 2-amino-6,7,9,10,12,12a-hexahydro-5H-pyrido[4,3-b][1,4]thiazepino[2,3,4-hi]indole-11(8aH)-carboxylate (5 mg, 73%.) $^1H$ NMR ($CDCl_3$, 300 MHz): 6.42 (1H, d, J 1.8 Hz), 6.37 (1H, s), 4.00–2.82 (10H, m), 2.10–2.05 (2H, m), 1.90–1.88 (2H, m), 1.45 (9H, s); m/z (ES) 362.2 $(M+H)^+$.

Step C

A slurry of tert-butyl 2-amino-6,7,9,10,12,12a-hexahydro-5H-pyrido[4,3-b][1,4]thiazepino[2,3,4-hi]indole-11(8aH)-carboxylate (84 mg, 0.23 mmol) and sodium borohydride (63 mg, 1.6 mmol) in THF (2 mL) was added to a stirred solution of sulphuric acid (3 M, 0.019 mL, 0.058 mmol) and formaldehyde at OC dropwise over 5 min. The mixture was quenched with NaOH (100 mg), extracted into EtOAc (20 mL), dried over $Na_2SO_4$, concentrated in vacuo and purified by column chromatography eluting with EtOAc/hexanes (1:4) to tert-butyl 2-(dimethylamino)-6,7,9,10,12,12a-hexahydro-5H-pyrido[4,3-b][1,4]thiazepino[2,3,4-hi]indole-11(8aH)-carboxylate (40 mg, 44%.) $^1H$ NMR (300 MHz, $CDCl_3$): 6.47 (1H, d, J 1.8 Hz), 6.43 (1H, d, J 1.8 Hz), 3.71–3.02 (9H, m), 2.94–2.82 (7H, m and s), 2.12–2.00 (2H, m), 1.87–1.79 (2H, m), 1.46 (9H, s.)

Step D

TFA (1 mL) was added to a stirred solution of tert-butyl 2-(dimethylamino)-6,7,9,10,12,12a-hexahydro-5H-pyrido[4,3-b][1,4]thiazepino[2,3,4-hi]indole-11(8aH)-carboxylate (40 mg, 0.10 mmol) in DCM (10 mL) and stirred at room temperature overnight. The solution was diluted with EtOAc (20 mL), washed with NaOH (1 N, 10 mL), dried over $Na_2SO_4$ and concentrated in vacuo to give the desired product (30 mg, 100%.) $^1H$ NMR (300 MHz, $CD_3OD$): 7.32 (1H, d, J 2.6 Hz), 7.25 (1H, d, J 2.5 Hz), 3.93–3.83 (1H, m), 3.61 (1H, ddd, J 15.2, 10.7 and 4.9 Hz), 3.50–3.38 (4H, m), 3.32–3.13 (8H, m and s), 3.07–2.99 (1H, m), 2.76 (1H, dd, J 9.0 and 12.3 Hz), 2.28–2.03 (4H, m.)

Example 431

2-(1-pyrrolidinyl)-6,7,8a,9,10,11,12,12a-octahydro-5H-pyrido[4,3-b][1,4]thiazepino[2,3,4-hi]indol-2-amine Step A A mixture of tert-butyl 2-amino-6,7,9,10,12,12a-hexahydro-5H-pyrido[4,3-b][1,4]thiazepino[2,3,4-hi]indole-11(8aH)-carboxylate (114 mg, 0.32 mmol) and 1,4-dibromombutane was heated at 100C. for 2 hr., cooled to room temperature, washed with 1N HCl (10 mL), dried over Na2$SO_4$ and concentrated in vacuo. The reaction mixture was purified by column chromatography, eluting with EtOAc/hexanes (1:4) to give tert-butyl 2-(1-pyrrolidinyl)-6,7,9,10,12,12a-hexahydro-5H-pyrido[4,3-b][1,4]thiazepino[2,3,4-hi]indole-11(8aH)-carboxylate (39 mg, 30%.) m/z (ES) 415.4 $(M+H)^+$.

Step B

Etheral HCl (1.0 M, 2.0 mL, 2.0 mmol) was added to a stirred solution of tert-butyl 2-(1-pyrrolidinyl)-6,7,9,10,12,12a-hexahydro-5H-pyrido[4,3-b][1,4]thiazepino[2,3,4-hi]indole-11(8aH)-carboxylate (15 mg, 0.036 mmol) in $Et_2O$ (2 mL) at room temperature. The mixture was stirred at room temperature for 1 hr., filtered, the residue basified with 1N NaOH, extracted into EtOAc, dried over $Na_2SO_4$ and concentrated in vacuo to give the product as a colourless oil (10 mg, 88%.) $^1H$ NMR ($CDCl_3$, 300 MHz): 6.23 (2H, s), 3.49–3.41 (2H, m), 3.27–2.80 (11H, m), 2.65–2.56 (1H, m), 2.09–2.05 (2H, m), 1.97–1.92 (4H, m), 1.83–1.78 (4H, m); m/z (ES) 316.2 $(M+H)^+$.

Example 432

N-6,7,8a,9,10,11,12,12a-octahydro-5H-pyrido[4,3-b][1,4]thiazepino[2,3,4-hi]indol-2-yl]-4-methyl-N-[(4-methylphenyl)sulfonyl]benzenesulfonamide Step A N,N-Dimethylaminopyridine (2 mg, 0.018 mmol) was added to a stirred solution of tert-butyl 2-amino-6,7,9,10,12,12a-hexahydro-5H-pyrido[4,3-b][1,4]thiazepino[2,3,4-hi]indole-11(8aH)-carboxylate (65 mg, 0.18 mmol), para-toluenesulfonyl chloride (114 mg, 0.60 mmol) and triethylamine (0.075 mL, 0.54 mmol) in DCM (3 mL) at room temperature. The mixture was stirred at room temperature for 6 hr., diluted with EtOAc (20 mL), washed with 1N HCl (5 mL), extracted into EtOAc (30 mL), dried over $Na_2SO_4$ and concentrated in vacuo. The crude reaction mixture was purified by column chromatography eluting with EtOAc/hexanes (1:4) to tert-butyl 2-{bis[(4-methylphenyl)sulphonyl]amino}-6,7,9,10,12,12a-hexahydro-5H-pyrido[4,3-b][1,4]thiazepino[2,3,4-hi]indole-11(8aH)-carboxylate (30 mg, 25%.) m/z (AP) 669.2 $(M+H)^+$.

Step B

Etheral HCl (1.0 M, 3 mL, 3 mmol) was added to a stirred solution of tert-butyl 2-{bis[(4-methylphenyl)sulphonyl]amino}-6,7,9,10,12,12a-hexahydro-5H-pyrido[4,3-b][1,4]thiazepino[2,3,4-hi]indole-11(8aH)-carboxylate (30 mg, 0.049 mmol) in diethyl ether (2 mL) at room temperature. The solution was stirred at room temperature overnight, diluted with $Et_2O$ (10 mL), washed with NaOH (1 M, 2×5 mL), dried over $Na_2SO_4$ and concentrated in vacuo to give the desired product (20 mg, 72%); m/z (ES) 570.1 $(M+H)^+$.

Example 433

(8aS,12aR)-2-Methoxy-6,7,8a,9,10,11,12,12a-octahydro-5H-pyrido[4,3-b][1,4]thiazepino[2,3,4-hi] indole Step A Sodium methoxide (700 mg, 13.5 mmol) was added to a mixture of tert-butyl(8aS,12aR)-2-bromo-6,7,9,10,12,12a-hexahydro-5H-pyrido[4,3-b][1,4]thiazepino[2,3,4-hi] indole-11(8aH)-carboxylate (300 mg, 0.71 mmol) and CuI (70 mg, 0.37 mmol) in anhydrous MeOH (2 mL) and anhydrous DMF (2 mL) at room temperature under an atmosphere of nitrogen. The mixture was stirred and heated at reflux for 24 hr., cooled to room temperature and quenched by the addition of water (30 mL). The mixture was extracted into EtOAc (2×20 mL), dried over $MgSO_4$, concentrated in vacuo and purified by HPLC eluting with EtOAc/hexanes (3:7) to tert-butyl(8aS,12aR)-2-methoxy-6,7,9,10,12,12a-hexahydro-5H-pyrido[4,3-b][1,4]thiazepino[2,3,4-hi]indole-11(8aH)-carboxylate (37 mg, 14%) as a colorless oil. $^1$H NMR ($CDCl_3$, 300 MHz): 6.54–6.52 (2H, m), 3.71 (3H, s), 3.68–3.07 (9H, m), 2.94–2.87 (1H, m), 2.13–2.02 (2H, m), 1.85–1.82 (2H, m), 1.45 (9H, s); m/z (ES) 377.2 $(M+H)^+$.

Step B

TFA (1 mL) was added to a stirred solution of tert-butyl (8aS,12aR)-2-methoxy-6,7,9,10,12,12a-hexahydro-5H-pyrido[4,3-b][1,4]thiazepino[2,3,4-hi]indole-11(8aH)-carboxylate (37 mg, 0.098 mmol) in DCM (5 mL) at room temperature. The solution was stirred at room temperature for 18 hr., quenched with NaOH (1N, 10 mL), extracted into DCM (2×10 mL), dried over $Na_2SO_4$ and concentrated in vacuo to give the desired product (20 mg, 74%.) $^1$H NMR ($CDCl_3$, 300 MHz): 6.52 (1H, d, J 2.6 Hz), 6.48 (1H, d, J 2.6 Hz), 3.71 (3H, s), 3.62–3.46 (2H, m), 3.32–3.30 (1H, m), 3.18–3.12 (1H, m), 3.01–3.82 (5H, m), 2.63–2.55 (1H, m), 2.12–2.03 (2H, m), 1.81–1.71 (2H, m); m/z (ES) 277.2 $(M+H)^+$.

Example 434

(8aS,12aR)-2-(2,4-Dichlorophenyl)-6,7,8a,9,10,11,12,12a-octahydro-5H-pyrido[4,3-b][1,4]thiazepino[2,3,4-hi]indole oxide Step A $NaIO_4$ (88 mg, 0.41 mmol) was added to a stirred solution of tert-butyl(8aS,12aR)-2-(2,4-dichlorophenyl)-6,7,9,10,12,12a-hexahydro-5H-pyrido[4,3-b][1,4]thiazepino[2,3,4-hi] indole-11(8aH)-carboxylate (100 mg, 0.21 mmol) in THF/$H_2O$ (5 mL:5 mL) at room temperature and stirred at room temperature for 3 hr. The mixture was quenched with $NaHCO_3$ (20 mL), extracted into EtOAc (100 mL), dried over $Na_2SO_4$ and filtered through a plug of silica to give tert-butyl(8aS,12aR)-2-(2,4-dichlorophenyl)-6,7,9,10,12,12a-hexahydro-5H-pyrido[4,3-b][1,4]thiazepino[2,3,4-hi] indole-11(8aH)-carboxylate 4-oxide (50 mg, 48%) as a mixture of diastereomers. $^1$H NMR (300 MHz, $CDCl_3$): 7.48–7.46 (2H, m), 7.30–7.21 (3H, m), 3.86–3.35 (7H, m), 3.27–3.18 (2H, m), 3.05–2.84 (1H, m), 2.60–2.44 (1H, m), 2.40–2.24 (1H, m), 2.05–1.96 (1H, m), 1.95–1.67 (1H, m), 1.37 (9H, s.)

Step B

TFA (5 mL) was added to a stirred solution of tert-butyl (8aS,12aR)-2-(2,4-dichlorophenyl)-6,7,9,10,12,12a-hexahydro-5H-pyrido[4,3-b][1,4]thiazepino[2,3,4-hi] indole-11(8aH)-carboxylate 4-oxide (50 mg, 0.099 mmol) in DCM (20 mL) at room temperature. The solution was stirred at room temperature overnight, quenched with NaOH (1N, 50 mL), extracted into DCM (2×50 mL), dried over $Na_2SO_4$ and concentrated in vacuo to give the desired product (38 mg, 94%.) m/z (ES) 407.1 $(M+H)^+$.

Example 435

(8aS,12aR)-2-(4-Methoxy-2-methylphenyl)-6,7,8a,9,10,11,12,12a-octahydro-5H-pyrido[4,3-b][1,4] thiazepino[2,3,4-hi]indole 4-oxide Step A $NaIO_4$ (660 mg, 3.1 mmol) was added to a stirred solution of of tert-butyl(8aS,12aR)-2-bromo-6,7,9,10,12,12a-hexahydro-5H-pyrido[4,3-b][1,4]thiazepino[2,3,4-hi] indole-11(8aH)-carboxylate (1.3 g, 3.1 mmol) in MeOH/$H_2O$ (50 mL:15 mL) at 0C. under nitrogen, stirred at 0C. for 1 hr. and then at room temperature overnight. The mixture was quenched with $NaHCO_3$ (200 mL), extracted into EtOAc (2×200 mL), dried over $Na_2SO_4$ and concentrated in vacuo. The solid was purified by column chromatography eluting with EtOAc to give tert-butyl(8aS,12aR)-2-bromo-6,7,9,10,12,12a-hexahydro-5H-pyrido[4,3-b][1,4] thiazepino[2,3,4-hi]indole-11(8aH)-carboxylate 4-oxide (1.1 g, 82%) as a mixture of diastereomers. $^1$H NMR (300 MHz, $CDCl_3$): 7.55 (1H, d, J 1.8 Hz), 7.23 (1H, d, J 1.8 Hz), 3.9–3.31 (8H, m), 3.20–3.14 (1H, m), 2.99–2.78 (1H, m), 2.56–2.17 (2H, m), 1.97–1.85 (2H, m), 1.44 (9H, s); m/z (ES) 441.1 and 443.1 $(M+H)^+$.

Step B $Pd(PPh_3)_4$ (25 mg, 0.020 mmol) was added to a stirred solution of tert-butyl(8aS,12aR)-2-bromo-6,7,9,10,12,12a-hexahydro-5H-pyrido[4,3-b][1,4]thiazepino[2,3,4-hi] indole-11(8aH)-carboxylate 4-oxide (180 mg, 0.41 mmol), 4-methoxy-2-methylphenylboronic acid (130 mg, 0.82 mmol) and barium hydroxide octahydrate (105 mg, 0.61 mmol) in DME/$H_2O$ (13 mL:2 mL) at room temperature under an atmosphere of nitrogen. The mixture was then stirred and heated at reflux overnight, cooled to room temperature, concentrated in vacuo, extracted into EtOAc (2×20 mL), dried over $Na_2SO_4$ and concentrated in vacuo. The mixture was purified by column chromatography eluting with MeOH/DCM (1:49) to give tert-butyl(8aS,12aR)-2-(4-methoxy-2-methylphenyl)-6,7,9,10,12,12a-hexahydro-5H-pyrido[4,3-b][1,4]thiazepino[2,3,4-hi]indole-11(8aH)-carboxylate 4-oxide (160 mg, 81%) as a mixture of diastereomers. $^1$H NMR (300 MHz, $CDCl_3$): 7.36 (1H, d, J 1.8 Hz), 7.15–7.09 (2H, m), 6.80–6.73 (2H, m), 3.82 (3H, s), 3.80–3.17 (9H, m), 2.99–2.84 (1H, m), 2.62–2.20 (5H, m and s), 2.20–1.80 (2H, m), 1.39 (9H, S); m/z (AP) 438.1 $(M+H)^+$.

Step C

TFA (2 mL) was added to a stirred solution of tert-butyl (8aS,12aR)-2-(4-methoxy-2-methylphenyl)-6,7,9,10,12,12a-hexahydro-5H-pyrido[4,3-b][1,4]thiazepino[2,3,4-hi] indole-11(8aH)-carboxylate 4-oxide (160 mg, 0.33 mmol) in DCM (10 mL) at room temperature under an atmosphere of nitrogen, and stirred at room temperature overnight. The solution was quenched with NaOH (1N, 10 mL), extracted into DCM (2×20 mL), dried over $Na_2SO_4$ and concentrated in vacuo to give the product (110 mg, 86%) as a yellow solid. $^1$H NMR ($CDCl_3$, 300 MHz) 7.37 (1H, d, J 1.8 Hz), 7.14–7.08 (2H, m), 6.79–6.74 (2H, m), 3.82 (3H, s), 3.75–3.50 (3H, m), 3.42–3.37 (1H, m), 3.26–2.86 (5H, m), 2.27–2.25 (3H, m), 2.17–2.14 (1H, m), 2.04–1.82 (2H, m); m/z (ES) 383.2 $(M+H)^+$.

Example 436

(6R,10aS)-5-(2-chlorophenyl)-1,2,6b,9,10,10a-hexahydro[1,4]oxazino[2,3,4-hi]pyrido[4,3-b]indole Step A To a solution of tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 2-chlorophenylboronic acid (156 mg, 2.0 mmol) in DME (30 mL) was added 2 M $Na_2CO_3$ (10 mL). The solution was degassed for 10 m at 40° C. $Pd(PPh_3)_4$ (22 mg, 0.02 mmol) was added in one portion to the solution, and the reaction mixture was degassed again for 10 m at the same temperature. The reaction mixture was stirred at 75° C. under $N_2$ for 20 h, then diluted with $Et_2O$ (100 mL), washed with brine (100 mL), dried over $MgSO_4$ and concentrated in vacuo. Column chromatography afforded tert-butyl(6bR,10aS)-5-(2-chlorophenyl)-1,2,6b,9,10,10a-hexahydro[1,4]oxazino[2,3,4-hi]pyrido[4,3-b]indole-8(7H)-carboxylate (179 mg, 84%) as a colorless oil.

Step B

To a solution of tert-butyl(6bR,10aS)-5-(2-chlorophenyl)-1,2,6b,9,10,10a-hexahydro[1,4]oxazino[2,3,4-hi]pyrido[4,3-b]indole-8(7H)-carboxylate in $CH_2Cl_2$ (2.4 mL) was added TFA (0.6 mL) and the reaction mixture was stirred for 3 h. The reaction mixture was concentrated in vacuo, diluted with $CH_2Cl_2$ (100 mL), washed with $NaHCO_3$ (100 mL) and brine (100 mL), dried over $MgSO_4$ and concentrated in vacuo to afford the title compound (130 mg, 95%) as a light yellow oil. $^1$H NMR ($CDCl_3$) δ1.78–1.99 (m, 2H), 2.11 (br-s, 1H), 2.76–2.95 (m, 4H), 3.09–3.20 (m, 2H), 2.32–2.39 (m, 1H), 2.41–2.46 (m, 1H), 4.44–4.52 (m, 2H), 6.76 (dd, 1H, J=1.5, 13.2 Hz), 7.19–7.36 (m, 4H), 7.42 (dd, 1H, J=1.4, 7.7 Hz) ppm.

Example 437

(7aS,11aR)-2-(2,6-difluorophenyl)-10-methyl-5,6,7a,8,9,10,11,11a-octahydro-4H-pyrido[3',4':4,5]pyrrolo[3,2,1-ij]quinoline A mixture of (7aS,11aR)-2-(2,6-difluorophenyl)-5,6,7a,8,9,10,11,11a-octahydro-4H-pyrido[3',4':4,5]pyrrolo[3,2,1-ij]quinoline (0.050, 0.15 mmol), HCHO (0.20 mL, 2.9 mmol) and formic acid (1.0 mL, 2.9 mmol) was heated at 80° C. for 4 hrs and cooled to room temperature. Water (5.0 mL) was added and the solution was basified with saturated $Na_2CO_3$ until pH>8. The mixture was extracted with $CH_2Cl_2$ (3×10 mL), dried ($Na_2SO_4$) and flash column chromatography (1–5% MeOH in $CHCl_3$) gave the title compound (0.032 g, 62%) as a white foam. $^1$H NMR ($CDCl_3$, 300 MHz) δ2.00–2.20 (m, 5H), 2.20–2.50 (m, 4H), 2.55–2.68 (m, 1H), 2.68–2.82 (m, 3H), 2.86–2.98 (m, 1H), 3.28–3.42 (m, 3H), 6.90–7.08 (m, 4H), 7.14–7.25 (m, 1H) ppm. MS (ESI): 341 (base, M+H).

Example 438

1-(2-aminophenyl)-4-((6bR,10aS)-1,2,6b,9,10,10a-hexahydropyrido[4,3-b][1,4]thiazino[2,3,4-hi]indol-8(7H)-yl)-1-butanone The title compound was isolated as a yellow oil (95 mg, 37%) according to the method of Example 286, Step C from (6bR,10aS)-1,2,6b,7,8,9,10,10a-octahydropyrido[4,3-b][1,4]thiazino[2,3,4-hi]indole (150 mg, 0.65 mmol) and 1-(2-aminophenyl)-4-chloro-1-butanone (255 mg, 1.29 mmol). $^1$H NMR ($CDCl_3$) δ1.94–2.03 (M, 5H), 2.21–2.33 (m, 1H), 2.37–2.44 (m, 2H), 2.63–2.71 (m, 1H), 2.82–2.89 (m, 1H), 2.90–3.21 (m, 5H), 3.33–3.40 (m, 1H), 3.45–3.64 (m, 2H), 6.60–6.67 (m, 3H), 6.80–6.85 (m, 2H), 7.22–7.28 (m, 1H), 7.76 (dd, 1H, J=1.5, 8.5 Hz) ppm.

Example 439

1-(2-aminophenyl)-4-((6bS,10aR)-1,2,6b,9,10,10a-hexahydropyrido[4,3-b][1,4]thiazino[2,3,4-hi]indol-8(7H)-yl)-1-butanone The title compound was isolated as a yellow oil (98 mg, 38%) according to the method of Example 286, Step C from (6bS,10aR)-1,2,6b,7,8,9,10,10a-octahydropyrido[4,3-b][1,4]thiazino[2,3,4-hi]indole (150 mg, 0.65 mmol) and 1-(2-aminophenyl)-4-chloro-1-butanone (255 mg, 1.29 mmol). $^1$H NMR ($CDCl_3$) δ1.94–2.03 (M, 5H), 2.21–2.33 (m, 1H), 2.37–2.44 (m, 2H), 2.63–2.71 (m, 1H), 2.82–2.89 (m, 1H), 2.90–3.21 (m, 5H), 3.33–3.40 (m, 1H), 3.45–3.64 (m, 2H), 6.60–6.67 (m, 3H), 6.80–6.85 (m, 2H), 7.22–7.28 (m, 1H), 7.76 (dd, 1H, J=1.5, 8.5 Hz) ppm.

Example 440

1-(2-amino-4-fluorophenyl)-4-((6bR,10aS)-1,2,6b,9,10,10a-hexahydro[4,3-b][1,4]thiazino[2,3,4-hi]indol-8(7H)-yl)-1-butanone The title compound was prepared by the method of Example 355 Step B as a yellow oil (103 mg, 59%) from (6bR,10aS)-1,2,6b,7,8,9,10,10a-octahydro[4,3-b][1,4]thiazino-[2,3,4-hi]indole (100 mg, 0.43 mmol) and 1-(2-amino-4-fluorophenyl)-4-chloro-1-butanone (186 mg, 0.85 mmol). $^1$H NMR ($CDCl_3$, 300 MHz) δ1.90–2.05 (m, 5H), 2.23–2.33 (m, 1H), 2.39–2.47 (m, 2H), 2.63–2.75 (m, 1H), 2.82–2.89 (m, 1H), 2.82–2.98 (m, 4H), 3.02–3.10 (m, 1H), 3.12–3.20 (m, 1H), 3.35–3.40 (m, 1H), 3.43–3.60 (m, 2H), 6.27–6.39 (m, 2H), 6.40–6.50 (br-s, 2H) 6.64 (t, J=7.3 Hz, 1H), 6.80–6.89 (m, 2H), 7.76 (dd, J=9.1, 6.6 Hz, 1H) ppm.

Example 441

1-(2-amino-4-fluorophenyl)-4-((6bS,10aR)-1,2,6b,9,10,10a-hexahydro[4,3-b][1,4]thiazino[2,3,4-hi]indol-8(7H)-yl)-1-butanone The title compound was prepared by the method of Example 355 Step B as a yellow oil (101 mg, 58%) from (6bS,10aR)-1,2,6b,7,8,9,10,10a-octahydro[4,3-b][1,4]thiazino[2,3,4-hi]indole (100 mg, 0.43 mmol) and 1-(2-amino-4-fluorophenyl)-4-chloro-1-butanone (186 mg, 0.85 mmol). The title compound was spectroscopically identical, to Example 440.

Example 442

N-{2-[4-((±)-cis-6,7,9,10,12,12a-hexahydro-5H-pyrido[4,3-b][1,4]thiazepino[2,3,4-hi]indole-11(8aH)-yl)butanoyl]-5-fluorophenyl}methanesulfonamide To a solution of 4-((±)-cis-6,7,9,10,12,12a-hexahydro-5H-pyrido[4,3-b][1,4]thiazepino[2,3,4-hi]indol-11(8aH)-yl)-1-(2-amino-4-fluorophenyl)-1-butanone (30 mg, 0.070 mmol) in $CH_2Cl_2$ (0.5 mL) was added $Et_3N$ (15 mg, 0.14 mmol) followed by methanesulfonyl chloride (12 mg, 0.11 mmol) at 0° C. under $N_2$. The reaction mixture was stirred for 4 hr at 0° C. then quenched by addition of HCl (1.0N, 1.0 mL). The resulting solution was extracted with $CHCl_3$. The combine organic solution was dried over $MgSO_4$. The title compound was obtained by flash column chromatography (silica gel; $CHCl_3$:MeOH 99:1) as a white amorphous solid (35 mg, 99%). $^1H$ NMR ($CDCl_3$, 300 MHz) δ1.85–2.18 (m, 7H), 2.24–2.42 (m, 3H), 2.58–2.66 (m, 1H), 2.69–2.77 (m, 1H), 2.89–3.17 (m, 5H), 3.23–3.30 (m, 1H), 3.49–3.59 (m, 4H), 3.74–3.85 (m, 1H), 6.60 (t, J=7.7 Hz, 1H), 6.80–88 (m, 2H), 6.94 (d, J=8.1 Hz, 1H), 7.13 (dd, J=8.5, 2.2 Hz, 1H), 7.20–7.25 (m, 1H), 7.77 (dd, J=8.8, 5.9 Hz, 1H) ppm.

Example 443

(6bR,10aS)-5-(2,3-dichlorophenyl)-1,2,6b,7,8,9,10,10a-octahydropyrido[4,3-b][1,4]thiazino[2,3,4-hi]indole Step A A solution of tert-butyl(6bR,10aS)-5-bromo-1,2,6b,9,10,10a-hexahydropyrido[4,3-b][1,4]thiazino[2,3,4-hi]indole-8(7H)-carboxylate (150 mg, 0.37 mmol) and 2,3-dichlorophenylboronic acid (143 mg, 0.75 mmol) in benzene (10 mL) and 2M $Na_2CO_3$ aqueous solution (0.74 mL, 1.48 mmol) was degassed at 20° C. $Pd(PPh_3)_2Cl_2$ (7.8 mg, 0.01 mmol) was added, and the reaction mixture was degassed one more time. The reaction mixture was refluxed for 15 h then cooled to 20° C. The reaction mixture was diluted with EtOAc and washed with saturated $NaHCO_3$ and brine. The combined organic layer was dried over $MgSO_4$, filtered and concentrated in vacuo. The residue was chromatographed (silica gel; Hexane:EtOAc 3:1) to give tert-butyl(6bR,10aS)-5-(2,3-dichlorophenyl)-1,2,6b,9,10,10a-hexahydropyrido[4,3-b][1,4]thiazino[2,3,4-hi]indole carboxylate as a light yellow solid (140 mg, 81%).

Step B

A solution of tert-butyl(6bR,10aS)-5-(2,3-dichlorophenyl)-1,2,6b,9,10,10a-hexahydropyrido[4,3-b][1,4]thiazino[2,3,4-hi]indole carboxylate (10 mg, 0.21 mmol) in $CH_2Cl_2$ (4.0 mL) was added TFA (1.0 mL). The reaction mixture was stirred at 20° C. for 1 h then concentrated in vacuo. The residue was dissolved in $H_2O$ and the solution was adjusted to pH 2 by addition of 1N HCl. The aqueous layer was washed with $Et_2O$ then basified to pH 12 by addition of 50% NaOH. The solution was extracted with $CHCl_3$, and the organic layer was washed with brine, dried over $MgSO_4$, filtered and concentrated in vacuo to give the title compound as a pale yellow oil (79 mg, 99%). $^1H$ NMR ($CDCl_3$, 300 MHz) δ1.93–2.05 (br-s, 2H), 2.65–2.99 (m, 4H), 3.01–3.25 (m, 4H), 3.44–3.68 (m, 3H), 6.88 (s, 1H), 6.90 (s, 1H), 7.18 (d, J=4.6 Hz, 2H), 7.40 (t, J=4.6 Hz, 1H) ppm.

Example 444

(6bR,10aS)-5-(2,3-difluorophenyl)-1,2,6b,7,8,9,10,10a-octahydropyrido[4,3-b][1,4]thiazino[2,3,4-hi]indole Tert-butyl(6bR,10aS)-5-(2,3-difluorophenyl)-1,2,6b,9,10,10a-hexahydropyrido[4,3-b][1,4]thiazino[2,3,4-hi]indole carboxylate (50 mg, 45%) was prepared by the method of Example 443 Step A as a yellow oil from tert-butyl(6bR,10aS)-5-bromo-1,2,6b,9,10,10a-hexahydropyrido[4,3-b][1,4]thiazino[2,3,4-hi]indole-8(7H)-carboxylate (100 mg, 0.25 mmol) and 2,3-difluorophenylboronic acid (80 mg, 0.50 mmol). The title compound (22 mg, 96%) was prepared by the method of Example 443 Step B as a yellow oil from tert-butyl(6bR,10aS)-5-(2,3-difluorophenyl)-1,2,6b,9,10,10a-hexahydropyrido[4,3-b][1,4]thiazino[2,3,4-hi]indole carboxylate (30 mg, 0.067 mmol). $^1H$ NMR ($CDCl_3$, 300 MHz) δ1.91–2.05 (m, 2H), 2.60–2.80 (m, 1H), 2.81–3.02 (m, 2H), 3.03–3.18 (m, 2H), 3.20–3.38 (m, 2H), 3.39–3.63 (m, 4H), 6.97 (dd, J=22.4, 2.2 Hz, 1H), 7.02–7.14 (m, 4H) ppm.

Example 445

2-(4-methoxy-2-methylphenyl)-1-methyl-6,7,8a,9,10,12,12a-octahydro-5H-pyrido[4,3-b][1,4]thiazepino[2,3,4-hi]indole Step A Tert-butyl 2-(4-methoxy-2-methylphenyl)-1-methyl-6,7,9,10,12,12a-hexahydro-5H-pyrido[4,3-b][1,4]thiazepino[2,3,4-hi]indole-11(8aH)-carboxylate was prepared by the method of Example 89 step C from tert-butyl 2-bromo-1-methyl-6,7,9,10,12,12a-hexahydro-5H-pyrido[4,3-b][1,4]thiazepino[2,3,4-hi]indole-11(8aH)-carboxylate (220 mg, 0.50 mmol) and corresponding 4-methoxy-2-methylphenylboronic acid (166 mg, 1.0 mmol) to afford after chromatographic purification the desired compound (186 mg, 78%). MS-ApCI: 481 [M+H$^+$].

Step B

The title compound was prepared by the method of Example 98 from tert-butyl 2-(4-methoxy-2-methylphenyl)-1-methyl-6,7,9,10,12,12a-hexahydro-5H-pyrido[4,3-b][1,4]thiazepino[2,3,4-hi]indole-11(8aH)-carboxylate to afford the title compound (18 mg, 87%). $^1H$ NMR ($CDCl_3$, 300 MHz) δ6.93–7.04 (m, 1H), 6.69–6.77 (m, 3H), 3.85–3.94 (m, 1H), 3.81 (s, 3H), 3.57–3.73 (m, 1H), 3.31–3.33 (m, 1H), 2.86–3.15 (m, 6H), 2.40–2.49 (m, 1H), 1.76–2.14 (m, 11H) ppm. MS-ApCI: 381 [M+H$^+$].

Example 446

2-[4-Methoxy-2-(trifluoromethyl)phenyl]-1-methyl-6,7,8a,9,10,12,12a-octahydro-5H-pyrido[4,3-b][1,4]thiazepino[2,3,4-hi]indole Step A Tert-butyl 2-[4-methoxy-2-(trifluoromethyl)phenyl]-1-methyl-6,7,9,10,12,12a-hexahydro-5H-pyrido[4,3-b][1,4]thiazepino[2,3,4-hi]indole-11(8aH)-carboxylate was prepared by the method of Example 89 step C from tert-butyl 2-bromo-1-methyl-6,7,9,10,12,12a-hexahydro-5H-pyrido[4,3-b][1,4]thiazepino[2,3,4-hi]indole-11(8aH)-carboxylate (220 mg, 0.5 mmol) and corresponding 4-methoxy-2-(trifluoromethyl)phenylboronic acid (220 mg, 0.5 mmol) and corresponding 4-methoxy-2-(trifluoromethyl)phenylboronic acid (220 mg, 1.0 mmol) to afford after chromatographic purification the desired compound (196 mg, 73%). MS-APCI: 535 [M+H$^+$].

Step B

The title compound was prepared by the method of Example 98 from tert-butyl 2-[4-methoxy-2-(trifluoromethyl)phenyl]-1-methyl-6,7,9,10,12,12a-hexahydro-5H-pyrido[4,3-b][1,4]thiazepino[2,3,4-hi]indole-11(8aH)-carboxylate to afford the title compound (21 mg, 89%). $^1H$ NMR ($CDCl_3$, 300 MHz) δ6.99–7.21 (m, 3H), 6.72 (d, 1H, 7.6 Hz), 3.81–3.99 (m, 1H), 3.87 (s, 3H), 3.56–3.68 (m, 1H), 3.31–3.35 (m, 1H), 2.86–3.16 (m, 6H), 2.38–2.49 (m, 1H), 1.74–2.15 (m, 5H), 1.81 (s, 3H) ppm. MS-ESI: 435 [MH]$^+$.

Example 447

(6bR,10aS)-5-(2,6-dichlorophenyl)-1,2,6b,7,8,9,10,10a-octahydropyrido[4,3-b][1,4]thiazino[2,3,4-hi]indole hydrochloride Step A A 5-L 3 neck round-bottom flask, equipped with a mechanical stirrer, a dropping funnel and a condenser was charged with the commercially available 2H-1,4-benzothiazin-3(4H)-one (190 g, 1.15 moles) followed by anhydrous benzene (950 mL) at room temperature under a nitrogen atmosphere. The mixture was cooled in an ice/acetone bath and Vitride (640 mL, 2.30 moles) was added dropwise over the course of 2.5 hours. After the addition was completed the reaction mixture was brought to reflux for 1.5 hours. After the starting material completely disappeared (TLC, 70:30 Hexanes, ethyl acetate), the mixture was cooled to 0° C. and a solution of 1 N NaOH (1.7 L) was carefully added dropwise while maintaining the inner-temperature below 20° C. After the addition the mixture was extracted with benzene (3×1.0 L). The combined organic extracts were washed with water and brine, dried over anhydrous sodium sulfate, and concentrated to dryness under reduced pressure to give the desired product 3,4-dihydro-2H-1,4-benzothiazine as a brown oil (171.2 g, 98%), which was used in the next step without further purification. $^1$H NMR (300 MHz, $CDCl_3$) δ2.92–3.03 (m, 2H), 3.49–3.57 (m, 2H), 3.79–4.09 (br-s, 1H), 6.40 (d, 2H, J=9.90 Hz), 6.59 (t, 1H, J=7.70 Hz, $J_2$=9.90 Hz), 6.88 (t, 2H, $J_1$=7.70 Hz, $J_2$=9.90 Hz), 6.96 (d, 1H, J=9.90 Hz) ppm.

Step B

To a solution of 3,4-dihydro-2H-1,4-benzothiazine (50.0 g, 330.8 mmol) in acetic acid (170 mL.), cooled at −10° C. in an ice/acetone bath, was added sodium nitrite (27.4 g, 397.1 mmol) in 75 mL of water over 35 min. After the addition, the mixture was warmed to room temperature and stirred for additional 1.5 hours. Cold water (150 mL) was added and the resulting mixture was extracted with dichloromethane (4×250 mL). The combined organic extracts were washed with water and brine, dried over anhydrous sodium sulfate, and concentrated to dryness under reduced pressure to give 4-nitroso-3,4-dihydro-2H-1,4-benzothiazine as a semi-solid (60.26 g, 101%), which was used in the next step without further purification. $^1$H NMR (300 MHz, DMSO-$d_6$) δ2.99–3.05 (m, 2H), 4.16–4.24 (m, 2H), 7.15–7.31 (m, 3H), 7.88–7.97 (m, 1H) ppm.

Step C

To a solution of lithium aluminum hydride in THF (1 M) (331 mL, 331 mmol) was added 4-nitroso-3,4-dihydro-2H-1,4-benzothiazine (59.6 g, 330.8 mmol) in 150 mL of THF at −15° C. over 2 hours under nitrogen atmosphere. After the addition, the mixture was slowly warmed to room temperature. After 4 hours, the reaction was complete (TLC, 70:30 hexanes, ethyl acetate) and hydrated sodium sulfate (approximately 150 g) was added carefully until bubbling ceased. The resulting slurry mixture was filtered and washed with THF (5×50 mL). The organic filtrate was concentrated under reduced pressure to give a red oil. This residue was taken in EtOAc (300 mL), cooled to 0° C., and treated with 1 M solution of ethereal hydrochloric acid (230 mL). The precipitate obtained was collected by filtration, washed with EtOAc (50 mL) and dried under vacuum to give 2,3-dihydro-4H-1,4-benzothiazin-4-amine hydrochloride as a white solid (48.8 g, 73%). $^1$H NMR (300 MHz, $CDCl_3$) δ3.21–3.32 (m, 2H), 3.69–3.78 (m, 2H), 4.70–5.11 (br-s, 2H), 6.98–7.36 (m, 4H) ppm.

Step D

The 2,3-dihydro-4H-1,4-benzothiazin-4-amine hydrochloride (30.6 g, 0.15 moles) and 4-piperidinone hydrochloride hydrate (23.3 g, 0.15 moles) were mixed with isopropanol (300 mL) and heated at reflux for 30 min. Then, the mixture was cooled to room temperature and concentrated hydrochloric acid (37.7 mL, 0.45 moles) was added in one portion and the reflux resumed overnight. Upon cooling, the resulting solid was filtered, washed with cold isopropanol (10 mL) and air dried to 1,2,7,8,9,10-hexahydropyrido[4,3-b][1,4]thiazino[2,3,4-hi]indole hydrochloride as an off-white solid (39.58 g, 98%). $^1$H NMR (DMSO, 500 MHz) δ3.01–3.11 (m, 2H), 3.29 (s, 2H), 3.40–3.50 (m, 2H), 4.21–4.32 (m, 4H), 6.91–6.98 (m, 2H), 7.24–7.31 (m, 1H), 9.62–9.71 (brs, 1H) ppm. MS (CI, Methane) m/z=231 $[C_{13}H_{14}N_2S+H]^+$.

Step E

To a solution of 1,2,7,8,9,10-hexahydropyrido[4,3-b][1,4]thiazino[2,3,4-hi]indole hydrochloride (35.8 g crude, 134.2 mmol) in 450 mL of trifluoroacetic acid was added sodium cyanoborohydride (32.0 g, 507.9 mmol) portionwise over 2 hours at −15° C. After the addition, the slurry was vigorously stirred for 2 hours at room temperature and then carefully quenched with 6 N HCl (900 mL). The resulting mixture was then heated at reflux for 1 hour. The solvent was removed under reduced pressure and the residue was neutralized with 50% wt/wt NaOH. The aqueous layer was extracted repeatedly with dichloromethane (3×500 mL). The organic extracts were mixed with 1 N NaOH (250 mL) and $Boc_2O$ (32.0 g, 146.6 mmol). The biphasic mixture was stirred overnight, and the organic layer separated, washed with brine (250 mL), and dried over anhydrous sodium sulfate. After removing the solvent under reduced pressure, the desired indoline product was obtained as a semi-solid. This residue was triturated with hexane to tert-butyl 1,2,6b,9,10,10a-hexahydropyrido[4,3-b][1,4]thiazino[2,3,4-hi]indole-8(7H)-carboxylate as a white solid (31.4 g, 70%). $^1$H NMR ($CDCl_3$, 300 MHz) δ1.47 (s, 9H), 1.86–1.94 (m, 2H), 2.78–3.29 (m, 5H), 3.34–4.10 (m, 5H), 6.64 (t, 1H, J=7.92), 6.82–6.88 (m, 2H) ppm. MS (CI, Methane) m/z=333 $[C_{18}H_{24}N_2O_2S+H]^+$.

Step F

The tert-butyl 1,2,6b,9,10,10a-hexahydropyrido[4,3-b][1,4]thiazino[2,3,4-hi]indole-8(7H)-carboxylate (2.00 g, 6.02 mmol) was dissolved in anhydrous DMF (50 mL) and then cooled in an ice/acetone bath at −10° C. for 20 min. Next, N-bromosuccinimide (1.18 g, 6.62 mmol) was added in one portion. The reaction mixture was stirred for 40 min at −10° C., then poured over an ice/water mixture (300 mL). The resulting suspension was stirred at room temperature for 30 min, and extracted with diethyl ether (4×100 mL). The organic extracts were pooled together, washed with brine and dried over anhydrous sodium sulfate. After removing the solvent under reduced pressure, tert-butyl 5-bromo-1,2,6b,9,10,10a-hexahydropyrido[4,3-b][1,4]thiazino[2,3,4-hi]indole-8(7H)-carboxylate was obtained as a yellow foam (2.24 g, 91%). $^1$H NMR (300 MHz, $CDCl_3$) δ1.47 (s, 9H), 1.77 (m, 2H), 3.46–3.48 (m, 4H), 2.87–3.48 (m, 6H), 6.93 (s, 1H), 6.97 (s, 1H) ppm.

Step G

General procedure for stannane coupling with aryl bromide: Degassed DMF (25 mL) was added to a mixture of tert-butyl(6bR,10aS)-5-bromo-1,2,6b,9,10,10a-hexahydropyrido[4,3-b][1,4]thiazino[2,3,4-hi]indole-8(7H)-carboxylate (316 mg, 0.768 mmol), $PPh_3$ (40.4 mg, 0.154 mmol), CuBr (22 mg, 0.20 mmol) and $Pd(PPh_3)_2Cl_2$ (55 mg, 0.0768 mmol) via cannula, at room temperature under $N_2$ blanket. The reaction mixture was stirred at room temperature for 5 min and then 2,6-dichlorophenyl trimethylstannane (357 mg, 1.15 mmol) was added as a solution in degassed DMF (2.5 mL) and the reaction mixture was heated at 140° C. After 10 min, the solution began to turn black, and a second portion (178 mg, 0.575 mmol) was added after 1 hour, followed by a final portion (178 mg, 0.575 mmol) an hour later. Heating resumed for another 30 min, then the reaction mixture was cooled to room temperature and diluted with ethylacetate/water (20 mL/20 mL). Organic layer was separated, dried over sodium sulfate an concentrated to dryness under reduced pressure to a dark oil. This residue was purified by flash chromatography eluting with 10% EtOAc/Hexanes to give tert-butyl(6bR,10aS)-5-(2,4-dichlorophenyl)-1,2,6b,9,10,10a-hexahydropyrido[4,3-b][1,4]thiazino[2,3,4-hi]indole-8(7H)-carboxylate (185 mg, 50%). $^1$H NMR ($CDCl_3$, 300 MHz) δ1.46 (s, 9H), 1.82–2.00 (m, 2H), 2.93–3.33 (m, 5H), 3.40–3.51 (m, 4H), 3.52–3.75 (m, 1H), 6.71 (s, 1H), 6.75 (s, 1H), 7.12 (t, 1H, J=7.9 Hz), 7.33 (d, 2H, J=7.9 Hz) ppm.

Step H

The title compound (71 mg, 43%) was prepared from tert-butyl(6bR,10aS)-5-(2,4-dichlorophenyl-1,2,6b,9,10,10a-hexahydropyrido[4,3-b][1,4]thiazino[2,3,4-hi]indole-8(7H)-carboxylate (197 mg) using the procedure described in EXAMPLE 448 Step B. $^1$H NMR ($CD_3OD$, 300 MHz) δ2.09–2.21 (m, 1H), 2.32–2.45 (dm, 1H, J=13.0 Hz), 2.78 (t, 1H, J=13.0 Hz), 2.99 (dt, 1H, J=1.8, 11.2 Hz), 3.12–3.65 (m, 8H), 3.70–3.80 (m, 1H), 6.72 (s, 1H), 6.81 (s, 1H), 7.25–7.30 (m, 1H), 7.43 (s, 1H), 7.47 (s, 1H) ppm. CIMS (Methane) m/z=378 $[C_{19}H_{18}Cl_2N_2S+H]^+$.

Example 448

(6bR,10aS)-1,2,6b,7,8,9,10,10a-octahydropyrido[4,3-b][1,4]thiazino[2,3,4-hi]indole 3,3-dioxide hydrochloride Step A Typical procedure for sulfur to sulfone oxidations: Solid tert-butyl(6bR,10aS)-1,2,6b,9,10,10a-hexahydropyrido[4,3-b][1,4]thiazino[2,3,4-hi]indole-8(7H)-carboxylate (150 mg, 0.451 mmol) was dissolved in MeOH (6 mL) at rt. An aqueous $NaHCO_3$/NaOH buffer solution; prepared by diluting a satd. solution of $NaHCO_3$ with an equal volume of water and adjusting the pH to 11–12 with 6N NaOH, (4 mL) was added to form a single heterogeneous layer. The suspension was cooled to ~0° C. in an ice/water bath, and solid Oxone® (416 mg, 0.677 mmol) was added in a single portion. The suspension was stirred at ~0° C. for 15 min before warming to rt. The reaction was followed by the disappearance of starting material (2–14 h) by TLC chromatography ($SiO_2$, 60% EtOAc:40% hexanes). The suspension was evaporated under reduced pressure to a paste. The paste was taken up into ethyl acetate (50 mL) and water (25 mL), and the aqueous layer was extracted with ethyl acetate (10 mL). The organic layers were combined and washed with sat. NaCl (30 mL), dried ($Na_2SO_4$), and evaporated under reduced pressure to afford 130 mg of crude sulfone a clear and colorless foam. Purification of an 80 mg portion of crude sulfone by flash column chromatography ($SiO_2$:14 mm×38 cm) gave 63 mg (79%) of purified tert-butyl(6bR,10aS)-1,2,6b,9,10,10a-hexahydropyrido[4,3-b][1,4]thiazono[2,3,4-hi]indole-8(7H)-carboxylate 3,3-dioxide as a colorless solid.

Step B

The tert-butyl(6bR,10aS)-1,2,6b,9,10,10a-hexahydropyrido[4,3-b][1,4]thiazino[2,3,4-hi]indole-8(7H)-carboxylate 3,3-dioxide (130 mg) was mixed with cold ethanol hydrochloride (4M) (5 mL), and the solution was stirred for 10 min at 0° C. The solvent was removed under reduced pressure and the residue was dissolved in hot acetonitrile with a small amount of methanol. Upon cooling to room temperature, the title compound (78 mg, 73%) was obtained as white crystalline material. $^1$H NMR ($CD_3OD$, 500 MHz) δ2.13–2.22 (m, 1H), 2.23–2.32 (m, 1H), 2.88 (t, 1H, J=11.3 Hz), 3.19–3.35 (m, 4H), 3.45–3.66 (m, 4H), 3.78–3.88 (m, 2H), 6.92 (t, 1H, J=7.8 Hz), 7.39 (d, 1H, J=7.8 Hz), 7.49 (d, 1H, J=8.5 Hz) ppm. CIMS (Methane) m/z=265 $[C_{13}H_{16}N_2O_2S+H]^+$.

Example 449

(6bS,10aR)-1,2,6b,7,8,9,10,10a-octahydropyrido[4,3-b][1,4]thiazino[2,3,4-hi]indole 3-oxide Step A Typical procedure for sulfide to sulfoxide oxidations: tert-butyl(6bS,10aR)-1,2,6b,9,10,10a-hexahydropyrido[4,3-b][1,4]thiazino[2,3,4-hi]indole-8(7H)-carboxylate (110 mg, 0.331 mmol) was dissolved in 2.5:1 methanol, $H_2O$ (7 mL) and cooled to 0° C. Sodium periodate (71.0 mg, 0.331 mmol) was then added and the reaction mixture was stirred at 0° C. Stirring was continued until complete reaction (3–6 h), as monitored by TLC (silica gel; 60:40 hexane, ethyl acetate). The suspension was then filtered through a sintered glass funnel, followed by washing of the precipitate with methanol (50 mL). The combined filtrates were concentrated to an aqueous slurry under reduced pressure and the resulting residue was diluted with brine. The aqueous solution was then extracted with $CH_2Cl_2$ (4×75 mL). The combined organic layers were dried over $Na_2SO_4$ and concentrated in vacuo to give a mixture of diastereomers of tert-butyl(5bS,10aR)-1,2,6b,9,10,10a-hexahydropyrido[4,3-b][1,4]thiazino[2,3,4-hi]indole-8(7H)-carboxylate 3-oxide (110 mg, 96%) as a colorless oil. $^1$H NMR (300 MHz, $CDCl_3$) δ1.37 (s, 9H), 1.82–2.18 (m, 2H), 2.63–3.62 (m, 7H), 3.63–4.25 (m, 3H), 6.58–6.88 (m, 1H), 7.11–7.29 (m, 1H), 7.29–7.49 (m, 1H) ppm.

Step B

The title compound (28 mg, 17%) was prepared by treatment of tert-butyl(6bS,10aR)-1,2,6b,9,10,10a-hexahydropyrido[4,3-b][1,4]thiazino[2,3,4-hi]indole-8(7H)-carboxylate 3-oxide (110 mg) with excess TFA in $CH_2Cl_2$ at 0 C. followed by treatment with 1 N aq. NaOH. $^1$H NMR (300 MHz, $CDCl_3$) 1.79–1.99 (m, 1H), 2.10 (d, 1H, J=12.2 Hz), 2.39–2.57 (m, 1H), 2.72–3.01 (m, 3H), 3.01–3.22 (m, 2H), 3.22–3.51 (m, 3H), 3.61–3.72 (m, 1H), 6.69–6.89 (m, 1H), 7.17 (d, 1H, J=7.0 Hz), 7.42 (d, 1H, J=9.6 Hz) ppm. CI MS m/z=249 $[C_{13}H_{16}N_2OS+H]^+$.

Example 450

(6bR,10aS)-5-[4-methoxy-2-(trifluoromethyl)phenyl]-1,2,6b,7,8,9,10,10a-octahydropyrido[4,3-b][1,4]thiazino[2,3,4-hi]indole 3,3-dioxide hydrochloride Step A Tert-butyl(6bR,10aS)-5-bromo-1,2,6b,9,10,10a-hexahydropyrido[4,3-b][1,4]thiazino[2,3,4-hi]indole-8(7H)-carboxylate 3,3-dioxide was prepared from tert-butyl(6bR,10aS)-5-bromo-1,2,6b,9,10,10a-hexahydropyrido[4,3-b][1,4]thiazino[2,3,4-hi]indole-8(7H)-carboxylate following the procedure of Example 398, Part A.

Step B: Typical Procedure for Suzuki Coupling

The bromo-indoline (0.6 mmol), boronic acid (0.8 mmol) and barium hydroxide (1 mmol) were stirred into a solution of water (4 mL) and DME (8 mL), then heated at 60° C. while bubbling through a stream of Argon gas for 20 min. The reaction mixture was then cooled to room temperature and $Pd(PPh_3)_2Cl_2$ (0.03 mmol) and $PPh_3$ (0.09 mmol) were quickly added and refluxing resumed for 4 hours. When the reaction was completed as shown by TLC, ethyl acetate (10 mL) was added and the mixture was filtered through a Celite bed. Organic layer was separated, dried over sodium sulfate and concentrated under reduced pressure. This residue was purified on a flash column eluting with 10% EtOAc/Hexanes to give the desired product in 60–95% yield. tert-butyl(6bR,10aS)-5-[4-methoxy-2-(trifluoromethyl)phenyl]-1,2,6b,9,10,10a-hexahydropyrido[4,3-b][1,4]thiazino[2,3,4-hi]indole-8(7H)-carboxylate 3,3-dioxide (135 mg, 74%) was prepared via coupling of the tert-butyl(6bR,10aS)-5-bromo-1,2,6b,9,10,10a-hexahydropyrido[4,3-b][1,4]thiazino[2,3,4-hi]indole-8(7H)-carboxylate 3,3-dioxide (150 mg, 0.338 mmol) with 2-trifluoromethyl-4-methoxyphenyl boronic acid (112 mg, 0.507 mmol) using the general procedure described above.

Step C

The title compound (75 mg, 63%) was prepared from tert-butyl(6bR,10aS)-5-[4-methoxy-2-(trifluoromethyl)phenyl]-1,2,6b,9,10,10a-hexahydropyrido[4,3-b][1,4]thiazino[2,3,4-hi]indole-8(7H)-carboxylate 3,3-dioxide (135 mg) using the procedure described in EXAMPLE 448 Step B. $^1$H NMR ($CD_3OD$, 500 MHz) δ2.15–2.24 (m, 1H), 2.31–2.39 (m, 1H), 2.91 (t, 1H, J=12.1 Hz), 3.22–3.32 (m, 2H), 3.48–3.70 (m, 6H), 3.90 (s, 5H), 7.21 (d, 1H, J=3.0 Hz), 7.27 (m, 2H), 7.36 (s, 1H), 7.38 (s, 1H) ppm. CI-MS (Methane) m/z=439 $[C_{21}H_{21}F_3N_2O_3S+H]^+$.

Example 451

(6bR,10aS)-5-(2,4-dichlorophenyl)-1,2,6b,7,8,9,10,10a-octahydropyrido[4,3-b][1,4]thiazino[2,3,4-hi]indole 3,3-dioxide hydrochloride Step A Tert-butyl(6bR,10aS)-5-(2,4-dichlorophenyl)-1,2,6b,9,10,10a-hexahydropyrido[4,3-b][1,4]thiazino[2,3,4-hi]indole-8(7H)-carboxylate 3,3-dioxide (94 mg, 88%) was prepared via coupling of tert-butyl(6bR,10aS)-5-bromo-1,2,6b,9,10,10a-hexahydropyrido[4,3-b][1,4]thiazino[2,3,4-hi]indole-8(7H)-carboxylate 3,3-dioxide (93 mg, 0.210 mmol) with 2,4-dichlorophenyl boronic acid (60 mg, 0.315 mmol) using the procedure described in Example 450 Step A. $^1$H NMR ($CDCl_3$, 300 MHz) δ1.42 (s, 9H), 1.82–2.05 (m, 2H), 3.30–3.60 (m, 6H), 3.60–4.00 (m, 4H), 7.20–7.32 (m, 3H), 7.45 (s, 1H), 7.51 (s, 1H) ppm.

Step B

The title compound (37 mg, 80%) was prepared from tert-butyl(6bR,10aS)-5-(2,4-dichlorophenyl)-1,2,6b,9,10,10a-hexahydropyrido[4,3-b][1,4]thiazino[2,3,4hi]indole-8(7H)-carboxylate 3,3-dioxide (52 mg) using the procedure described in Example 448 Step B. $^1$H NMR ($CD_3OD$, 500 MHz) δ2.20–2.25 (m, 1H), 2.25–2.35 (m, 1H), 3.00 (t, 1H, 12.5 Hz), 3.18–3.38 (m, 3H), 3.45–3.75 (m, 5H), 3.83–3.95 (m, 2H), 7.35 (d, 1H, J=6.8 Hz), 7.40 (m, 1H), 7.49 (m, 1H), 7.51 (m, 1H), 7.59 (m, 1H) ppm. CIMS (Methane) m/z=410 $[C_{19}H_{18}Cl_2N_2O_2S+H]^+$.

Example 452

(6bR,10aS)-5-(4-methoxy-2-methylphenyl)-1,2,6b,7,8,9,10,10a-octahydropyrido[4,3-b][1,4]thiazino[2,3,4-hi]indole hydrochloride Step A The tert-butyl(6bR,10aS)-5-(4-methoxy-2-methylphenyl)-1,2,6b,9,10,10a-hexahydropyrido[4,3b][1,4]thiazino[2,3,4-hi]indole-8(7H)-carboxylate (420 mg, 55%) was prepared via coupling of tert-butyl(6bR,10aS)-5bromo-1,2,6b,9,10,10a-hexahydropyrido[4,3-b][1,4]thiazino[2,3,4-hi]indole-8(7H)-carboxylate (700 mg, 1.70 mmol) with 2-methyl-4-methoxyphenyl boronic acid (424 mg, 2.55 mmol) using the procedure described in Example 450 Step A.

Step B

The title compound (338 mg, 94%) was prepared from tert-butyl(6bR,10aS)-5-(4-methoxy-2-methylphenyl)-1,2,6b,9,10,10a-hexahydropyrido[4,3-b][1,4]thiazino[2,3,4-hi]indole-8(7H)-carboxylate by the procedure described in EXAMPLE 448 Step B. $^1$H NMR ($CD_3OD$, 500 MHz) δ2.12–2.23 (m, 1H), 2.21 (s, 3H), 2.36 (d, 1H, 13.0 Hz), 2.80 (t, 1H, J=12.4 Hz), 2.96 (t, 1H, J=11.4 Hz), 3.20–3.35 (m, 2H), 3.37–3.60 (m, 6H), 3.72 (td, 1H, J=2.0, 8.5 Hz), 3.79 (s, 3H), 6.75 (m, 2H), 6.78 (s, 1H), 6.83 (s, 1H), 7.03 (d, 1H, J=9.0 Hz) ppm. CI-MS (Methane) m/z=353 $[C_{21}H_{24}N_2OS+H]^+$.

Example 453

(6bR,10aS)-5-(2-chloro-6-fluorophenyl)-1,2,6-b,7,8,9,10,10a-octahydropyrido[4,3-b][1,4]thiazino[2,3,4-hi]indole hydrochloride Step A The tert-butyl(6bR,10aS)-5-(2-chloro-6-fluorophenyl)-1,2,6b,9,10,10a-hexahydropyrido[4,3-b][1,4]thiazino[2,3,4-hi]indole-8(7H)-carboxylate (276 mg, 57%) was prepared via coupling tert-butyl(6bR,10aS)-5-bromo-1,2,6b,9,10,10a-hexahydropyrido[4,3-b][1,4]thiazino[2,3,4-hi]indole-8(7H)-carboxylate (1.0 g, 1.043 mmol) with 2-chloro-6-fluorophenyltrimethyl stannane (3.0 g, 3.129 mmol) as illustrated by the general procedure described in Example 447 Step G. $^1$H NMR ($CDCl_3$, 300 MHz) δ1.44 (s, 9H), 1.83–1.99 (m, 2H), 2.80–3.32 (m, 5H), 3.33–3.50 (m, 2H), 3.55–3.71 (m, 3H), 6.82 (d, 1H, J=8.1 Hz), 7.01 (t, 1H, J=8.1 Hz), 7.12–7.35 (m, 3H) ppm.

Step B

The title compound (101 mg, 43%) was formed from tert-butyl(6bR,10aS)-5-(2-chloro-6-fluorophenyl)-1,2,6b,9,10,10a-hexahydropyrido[4,3b][1,4]thiazino[2,3,4-hi]indole-8(7H)-carboxylate (270 mg) using the procedure described in EXAMPLE 448 Step B. $^1$H NMR ($CD_3OD$, 300 MHz) δ2.16 (m, 1H), 2.31 (d, 1H, J=12.8 Hz), 2.85 (t, 1H, J=13.0 Hz), 3.00 (t, 1H, J=12.4 Hz), 3.15–3.20 (m, 3H), 3.20–3.30 (m, 1H), 3.33–3.39 (m, 2H), 3.40–3.51 (m, 2H), 3.79 (m, 1H), 6.83 (s, 1H), 6.90 (s, 1H), 7.15 (m, 1H), 7.31 (m, 2H) ppm. CIMS (Methane) m/z=362 $[C_{19}H_{18}ClFN_2S+H^+]$ Example 454

(6bR,10aS)-5-(2,6-difluorophenyl)-1,2,6b,7,8,9,10,10a-octahydropyrido[4,3-b][1,4]thiazino[2,3,4-hi]indole hydrochloride Step A The tert-butyl(6bR,10aS)-5-(2,6-difluorophenyl)-1,2,6b,9,10,10a-hexahydropyrido[4,3-b][1,4]thiazino[2,3,4-hi]indole-8(7H)-carboxylate (288 mg, 76%) was prepared via coupling of tert-butyl(6bR,10aS)-5-bromo-1,2,6b,9,10,10a-hexahydropyrido[4,3-b][1,4]thiazino[2,3,4-hi]indole-8(7H)-carboxylate (0.350 g, 0.851 mmol) with 2,6-difluorophenyltrimethyl stannane (0.707 g, 2.553 mmol) using the procedure described in Example 447 Step G.

Step B

The title compound (200 mg, 80%) was prepared from tert-butyl(6bR,10aS)-5-(2,6-difluorophenyl)-1,2,6b,9,10,10a-hexahydropyrido[4,3-b][1,4]thiazino[2,3,4-hi]indole-8(7H)-carboxylate (288 mg) using the procedure described in EXAMPLE 448 Step B. $^1$H NMR ($CD_3OD$, 300 MHz) δ2.09–2.25 (m, 1H), 2.30–2.42 (m, 1H), 2.80 (t, 1H, J=14 Hz), 3.00 (t, 1H, J=9.4 Hz), 3.12–3.29 (m, 3H), 3.38–3.65 (m, 5H), 3.75 (td, 1H, J=1.1, 10.2 Hz), 6.92 (s, 1H), 6.98–7.10 (m, 3H), 7.25–7.49 (m, 1H) ppm. CI-MS (Methane) m/z=345 $[C_{19}H_{18}F_2N_2S+H]^+$.

Example 455

(6bR,10aS)-5-(2,4-dichlorophenyl)-1,2,6b,7,8,9,10,10a-octahydropyrido[4,3-b][1,4]thiazino[2,3,4-hi]indole hydrochloride Step A The tert-butyl(6bR,10aS)-5-(2,4-dichlorophenyl)-1,2,6b,9,10,10a-hexahydropyrido[4,3-b][1,4]thiazino[2,3,4-hi]indole-8(7H)-carboxylate (136 mg, 47%) was prepared via coupling of the appropriate tert-butyl(6bR,10aS)-5-bromo-1,2,6b,9,10,10a-hexahydropyrido[4,3-b][1,4]thiazino[2,3,4-hi]indole-8(7H)-carboxylate (250 mg, 0.608 mmol) with 2,4-dichlorophenyl boronic acid (116 mg, 0.608 mmol) using the procedure described in Example 450 Step A.

Step B

The title compound (80 mg, 68%) was prepared from tert-butyl(6bR,10aS)-5-(2,4-dichlorophenyl)-1,2,6b,9,10,10a-hexahydropyrido[4,3-b][1,4]thiazino[2,3,4-hi]indole-8(7H)-carboxylate (116 mg) using the procedure described in EXAMPLE 448 Step B. $^1$H NMR ($CD_3OD$, 300 MHz) δ2.05–2.12 (m, 1H), 2.30–2.41 (m, 1H), 2.74–2.88 (m, 1H), 2.95 (t, 1H, J=11.2 Hz), 3.12–3.25 (m, 3H), 3.35–3.60 (m, 5H), 3.69–3.79 (m, 1H), 6.92 (s, 1H), 6.99 (s, 1H), 7.25–7.40 (m, 2H), 7.51 (d, 1H, J=0.8 Hz) ppm. ESIMS m/z=378 $[C_{19}H_{18}Cl_2N_2S+H]^+$.

Example 456

4-((6bS,10aR)-1,2,6b,9,10,10a-hexahydropyrido[4,3-b][1,4]thiazino[2,3,4-hi]indol-8(7H)-yl)-1-(4-fluorophenyl)-1-butanone hydrochloride Step A Typical procedure for alkylation of amines: A mixture of indoline hydrochloride (approx 200 mg) in dioxane (4 mL) was treated with Hunig's base (10 equivs) and heated to reflux for 15 min. To the cooled reaction mixture was added 4-chloro-1-(4-fluorophenyl)-1-butanone (5 equivs), KI (0.9 equivs), then the whole mixture was refluxed for 48 h. The reaction was then diluted with chloroform (20 mL) and extracted once with saturated solution of ammonium chloride (10 mL) and twice with ice-cold water (100 mL). The organic layer was dried over sodium sulfate and concentrated to dryness under reduced pressure. The residue was purified by flash chromatography eluting with a gradient of hexane/ethylacetate (e.g. 96:4 to 50:50), following with a gradient methanol/dichloromethane (e.g.1:99 to 3:97) to give the desired product.

The 4-((6bS,10aR)-1,2,6b,9,10,10a-hexahydropyrido[4,3-b][1,4]thiazino[2,3,4-hi]indol-8(7H)-yl)-1-(4-fluorophenyl)-1-butanone(478 mg, 52%) was obtained from (6bS,10aR)-1,2,6b,7,8,9,10,10a-octahydropyrido[4,3-b][1,4]thiazino[2,3,4-hi]indole hydrochloride (750 mg, 2.79 mmol) and 4-chloro-1-(4-fluorophenyl)-1-butanone (3.0 mL, 15.24 mmol) using the procedure described above.

Step B

The title compound (483 mg, 81%) was prepared from 4-((6bS,10aR)-1,2,6b,9,10,10a-hexahydropyrido[4,3-b][1,4]thiazino[2,3,4-hi]indol-8(7H)-yl)-1-(4-fluorophenyl)-1-butanone (578 mg) using the procedure described in EXAMPLE 448 Step B. $^1$H NMR (DMSO, 300 MHz) δ1.92–2.13 (m, 2H), 2.28 (br-s, 2H), 2.80 (t, 1H, J=9.9 Hz), 2.92–3.63 (m, 12H), 3.63–3.75 (m, 1H), 6.67 (t, 1H, J=7.9), 6.87 (d, 1H, J=8.9), 6.96 (d, 1H, J=6.9), 7.30–7.48 (m, 2H), 7.48–8.12 (m, 2H), 10.43 (br-s, 1H) ppm. m/z=397 $[C_{23}H_{25}FN_2OS+H]^+$.

Example 457

4-((6bR,10aS)-1,2,6b,9,10,10a-hexahydropyrido[4,3-b][1,4]thiazino[2,3,4-hi]indol-8(7H)-yl)-1-(4-fluorophenyl)-1-butanone hydrochloride Step A The 4-((6bR,10aS)-1,2,6b,9,10,10a-hexahydropyrido[4,3-b][1,4]thiazino[2,3,4-hi]indol-8(7H)-yl)-1-(4-fluorophenyl)-1-butanone (349 mg, 25%) was prepared from (6bR,10aS)-1,2,6b,7,8,9,10,10a-octahydropyrido[4,3-b][1,4]thiazino[2,3,4-hi]indolehydrochloride (750 mg, 2.79 mmol) with 4-chloro-1-(4-fluorophenyl)-1-butanone (3.0 mL, 15.24 mmol) using the procedure described in Example 456 Step A.

Step B

The title compound (72 mg, 25%) was prepared from 4-((6bR,10aS)-1,2,6b,9,10,10a-hexahydropyrido[4,3-b][1,4]thiazino[2,3,4-hi]indol-8(7H)-yl)-1-(4-fluorophenyl)-1-butanone (340 mg) using the procedure described in EXAMPLE 448 Step B. $^1$H NMR (DMSO, 300 MHz) δ1.92–2.13 (m, 2H), 2.28 (br-s, 2H), 2.80 (t, 1H, J=9.9 Hz), 2.92–3.63 (m, 12H), 3.63–3.75 (m, 1H), 6.67 (t, 1H, J=7.9), 6.87 (d, 1H, J=8.9), 6.96 (d, 1H, J=6.9), 7.30–7.48 (m, 2H), 7.48–8.12 (m, 2H), 10.43 (br-s, 1H) ppm. m/z=397 $[C_{23}H_{25}FN_2OS+H]^+$.

Example 458

(8aS,12aR)-2-[4-methoxy-2-(trifluoromethyl)phenyl]-3-methyl-6,7,8a9,10,11,12,12a-octahydro-5H-pyrido[4,3-b][1,4]thiazepino[2,3,4-hi]indole hydrochloride Step A The tert-butyl(8aS,12aR)-2-[4-methoxy-2-(trifluoromethyl)phenyl]-3-methyl-6,7,9,10,12,12a-hexahydro-5H-pyrido[4,3-b][1,4]thiazepino[2,3,4-hi]indole-11(8aH)-carboxylate (49 mg, 28%) was prepared via coupling of the tert-butyl(8aS,12aR)-2-bromo-3-methyl-6,7,9,10,12,12a-hexahydro-5H-pyrido[4,3-b][1,4]thiazepino[2,3,4-hi]indole-11(8aH)-carboxylate (145 mg, 0.33 mmol) with 2-trifluoromethyl-4-methoxyphenyl boronic acid (109 mg, 0.49 mmol) using the procedure described in EXAMPLE 450 Step A. This material was used in the subsequent step without further purification.

Step B

The title compound (25 mg, 58%) was prepared from tert-butyl(8aS,12aR)-2-[4-methoxy-2-(trifluoromethyl)phenyl]-3-methyl-6,7,9,10,12,12a-hexahydro-5H-pyrido[4,3-b][1,4]thiazepino[2,3,4-hi]indole-11(8aH)-carboxylate (49 mg) using the procedure described in EXAMPLE 448 Step B. $^1$H NMR ($CD_3OD$, 300 MHz) δ1.89 (d, 3 H, J=3.2 Hz), 1.93–2.12 (m, 3H), 2.19–2.35 (m, 3H), 2.66–2.79 (m, 1H), 2.95–3.39 (m, 3H), 3.21–3.49 (m, 1H), 3.62–3.90 (m, 5H), 4.05–4.14 (m, 1H), 6.70 (s, 1H), 7.03–7.11 (m, 1H), 7.12–7.18 (m, 1H), 7.22–7.25 (s, 1H). m/z=435 $[C_{23}H_{25}F_3N_2OS+H]^+$.

Example 459

(8aS,12aR)-2-(2,4-dichlorophenyl)-3-methyl-6,7,8a,9,10,11,12,12a-octahydro-5H-pyrido[4,3-b][1,4]thiazepino[2,3,4-hi]indole hydrochloride Step A The tert-butyl(8aS,12aR)-2-(2,4-dichlorophenyl)-3-methyl-6,7,9,10,12,12a-hexahydro-5H-pyrido[4,3-b][1,4]thiazepino[2,3,4-hi]indole-11(8aH)-carboxylate (45 mg, 37%) was prepared via coupling of tert-butyl(8aS,12aR)-2-bromo-3-methyl-6,7,9,10,12,12a-hexahydro-5H-pyrido[4, 3-b][1,4]thiazepino[2,3,4-hi]indole-11(8aH)-carboxylate (105 mg, 0.239 mmol) with 2,4-dichlorophenyl boronic acid (69 mg, 0.350 mmol) using the procedure described in Example 450 Step A. $^1$H NMR ($CDCl_3$, 300 NMR) δ1.45 (s, 9H), 1.81–1.89 (m, 2H), 1.98–2.19 (m, 5H), 2.98–3.42 (m, 5H), 3.43–3.95 (m, 3H), 4.03–4.18 (m, 2H), 6.58–6.63 (m, 1H), 7.07–7.14 (m, 1H), 7.19–7.28 (m, 1H), 7.45 (s, 1H).

Step B

The title compound (11 mg, 27%) was prepared from tert-butyl(8aS,12aR)-2-(2,4-dichlorophenyl)-3-methyl-6,7,9,10,12,12a-hexahydro-5H-pyrido[4,3-b][1,4]thiazepino[2,3,4-hi]indole-11(8aH)-carboxylate (45 mg) using the procedure described in EXAMPLE 448 Step B. $^1$H NMR (500 MHz, $CD_3OD$) δ1.97–2.11 (m, 6H), 2.18–2.32 (m, 3H), 2.72–2.82 (m, 1H), 3.00–3.09 (m, 1H), 3.12–3.19 (m, 1H), 3.20–3.45 (m, 3H), 3.69–3.71 (m, 1H), 4.03–4.14 (m, 1H), 6.71 (s, 1H), 7.01–7.09 (m, 1H), 7.31–7.38 (m, 1H), 7.51 (s, 1H. m/z=406 $[C_{21}H_{22}Cl_2N_2+H]^+$.

Example 460

3-[((8aS,12aR)-6,7,8,a,9,10,11,12,12a-octahydro-5H-pyrido[4,3-b][1,4]thiazepino[2,3,4-hi]indol-2-yl] benzonitrile, trifluoroacetic acid salt Step A To a solution of tert-butyl(8aS,12aR)-2-bromo-6,7,9,10,12,12a-hexahydro-5H-pyrido[4,3-b][1,4]thiazepino[2,3,4-hi]indole-11(8aH)-carboxylate (0.32 g, 0.74 mmol) in 75 mL of 1,2-dimethoxyethane and 25 mL of water was added 3-cyanophenyl boronic acid (0.22 g, 1.48 mmol) and barium hydroxide octahydrate (0.70 g, 2.22 mmol). The mixture was degassed with a stream of nitrogen for 20 min and then there was added tetrakis(triphenylphosphine)palladium (26 mg, 0.02 mmol) and the mixture was stirred at 100° C. for 3 h. The reaction was allowed to cool to ambient temperature and was diluted with ethyl acetate, washed with sat'd aqueous sodium bicarbonate and brine, dried ($MgSO_4$), filtered through Celite and concentrated in vacuo. The residue was purified by flash chromatography (elution with hexanes/ethyl acetate) to afford 0.22 g (52%) of tert-butyl (8aS,12aR)-2-(3-cyanophenyl)-6,7,9,10,12,12a-hexahydro-5H-pyrido[4,3-b][1,4]thiazepino[2,3,4-hi]indole-11(8aH)-carboxylate. $^1$H NMR ($CDCl_3$): δ7.76 (s, 1H), 7.70 (app d, 1H, J=7.6 Hz), 7.52 (app dt, 1H, J=7.7, 1.5 Hz), 7.47 (t, 1H, J=7.7 Hz), 7.18 (d, 1H, J=1.9 Hz), 7.09 (d, 1H, J=1.9 Hz), 3.90–3.80 (m, 2H), 3.63–3.52 (m, 2H), 3.51–3.45 (m, 1H), 3.42–3.28 (m, 3H), 3.21 (dt, 1H, J=13.1, 4.2 Hz), 3.02, (dt, 1H, J=13.6, 4.9 Hz), 2.15–2.10 (m, 2H), 1.91–1.87 (m, 2H), 1.41 (s, 9H).

Step B

To a solution of tert-butyl(8aS,12aR)-2-(3-cyanophenyl)-6,7,9,10,12,12a-hexahydro-5H-pyrido[4,3-b][1,4]thiazepino[2,3,4-hi]indole-11(8aH)-carboxylate from Part A (0.20 g, 0.45 mmol) in 80 mL of methylene chloride was added 20 mL of trifluoroacetic acid and the mixture was allowed to stir at ambient temperature for 3 h. The volatiles were removed in vacuo and the residue was purified by prep HPLC (C18 reverse phase column, elution with a $H_2O$/$CH_3CN$ gradient with 0.5% TFA) and lyophilized to afford 45 mg (22%) of the title compound. $^1$H NMR ($CDCl_3$): δ9.62 (broad s, 1H), 9.39 (broad s, 1H), 7.74 (s, 1H), 7.69 (app d, 1H, J=7.7 Hz), 7.57 (app d, 1H, J=7.7 Hz), 7.49 (t, 1H, J=7.7 Hz), 7.24 (d, 1H, J=1.5 Hz), 7.09 (d, 1H, J=1.9 Hz), 4.02–3.92 (m, 1H), 3.65–3.55 (m, 1H), 3.50–3.45 (m, 2H), 3.41–3.30 (m, 2H), 3.26–3.19 (m, 1H), 3.10–2.96 (m, 2H), 2.78–2.70 (m, 1H), 2.26–2.10 (m, 4H). LRMS ($ES^+$): 348.2 $(M+H)^+$.

Example 461

4-[((8aS,12aR)-6,7,8a,9,10,11,12,12a-octahydro-5H-pyrido[4,3-b][1,4]thiazepino[2,3,4-hi]indol-2-yl]-3-methylbenzonitrile, trifluoroacetic acid salt Using 2-methyl-4-cyanophenyl boronic acid and following the procedures described in Example 460, the title compound was prepared. $^1$H NMR ($CDCl_3$): δ9.61 (broad s, 1H), 9.26 (broad s, 1H), 7.45 (s, 1H), 7.41 (d, 1H, J=8.0 Hz), 7.17 (d, 1H, J=8.0 Hz), 6.89 (s, 1H), 6.74 (s, 1H), 3.97–3.85 (m, 1H), 3.60–3.50 (m, 1H), 3.42–3.35 (m, 2H), 3.30–3.20 (m, 2H), 3.18–3.10 (m, 1H), 3.00–2.87 (m, 2H), 2.70–2.60 (m, 1H), 2.22 (s, 3H), 2.15–2.02 (m, 4H). LRMS (ES+): 362.2 $(M+H)^+$.

Example 462

3-[(8aS,12aR)-6,7,8a,9,10,11,12,12a-octahydro-5H-pyrido[4,3-b][1,4]thiazepino[2,3,4-hi]indol-2-yl]-2-methylbenzonitrile, trifluoroacetic acid salt Using 2-methyl-3-cyanophenyl boronic acid and following the procedures described in Example 460, the title compound was prepared. $^1$H NMR ($CDCl_3$): δ9.21 (broad s, 1H), 8.95 (broad s, 1H), 7.57 (dd, 1H, J=7.5, 1.3 Hz), 7.36 (dd, 1H, J=7.4, 1.4 Hz), 7.27 (t, 1H, J=7.7 Hz), 6.93 (d, 1H, J=1.1 Hz), 6.78 (d, 1H, J=1.1 Hz), 4.02–3.95 (m, 1H), 3.65–56 (m, 1H), 3.50–3.42 (m, 2H), 3.41–3.32 (m, 2H), 3.22–3.15 (m, 1H), 3.10–2.96 (m, 2H), 2.78–2.72 (m, 1H), 2.44 (s, 3H), 2.25–2.10 (m, 4H). LRMS ($ES^+$): 362.4 $(M+H)^+$.

Example 463

2-[(8aS,12aR)-6,7,8,a,9,10,11,12,12a-octahydro-5H-pyrido[4,3-b][1,4]thiazepino[2,3,4-hi]indol-2-yl] benzonitrile, trifluoroacetic acid salt Step A To a solution of tert-butyl(8aS,12aR)-6,7,9,10,12,12a-hexahydro-5H-pyrido[4,3-b][1,4]thiazepino[2,3,4-hi]indole-11(8aH)-carboxylate (5.0 g, 14.4 mmol) in 50 mL of DMF at 0° C. was added N-iodosuccinimide (3.6 g, 15.9 mmol). The reaction was stirred with slow warming to ambient temperature for 4 h. The mixture was diluted with ethyl acetate, washed with water and brine, dried ($MgSO_4$), filtered and concentrated in vacuo. The residue was purified by flash chromatography (elution with hexane/ethyl acetate) to afford 1.6 g (23%) of tert-butyl(8aS,12aR)-2-iodo-6,7,9,10,12,12a-hexahydro-5H-pyrido[4,3-b][1,4]thiazepino[2,3,4-hi]indole-11(8aH)-carboxylate. $^1$H NMR ($CDCl_3$): δ7.23 (d, 1H, J=1.9Hz), 7.12 (d, 1H, J=1.4 Hz), 3.80–3.65 (m, 2H), 3.52–3.38 (m, 5H) 3.18 (app q, 2H, J=6.2 Hz), 3.00–2.90 (m, 1H), 2.08–2.00 (m, 2H), 1.85–1.78 (m, 2H), 1.43 (s, 9H).

Step B

To a solution of tert-butyl(8aS,12aR)-2-iodo-6,7,9,10,12,12a-hexahydro-5H-pyrido[4,3-b][1,4]thiazepino[2,3,4-hi]indole-11(8aH)-carboxylate (1.60 g, 3.39 mmol) in 100 mL of DMSO was added diboron pinacol ester (1.29 g, 5.09 mmol) and potassium acetate (1.0 g, 10.2 mmol). The mixture was degassed with a stream of nitrogen for 20 min and then there was added tetrakis(triphenylphosphine) palladium (200, 0.17 mmol) and the mixture was stirred at 80° C. for 16 h. The reaction was allowed to cool to ambient temperature and was diluted with ethyl acetate, washed with brine, dried ($MgSO_4$), filtered through Celite and concentrated in vacuo. The residue was purified by flash chromatography (elution with hexanes/ethyl acetate) to afford 0.76 g (48%) of tert-butyl(8aS,12aR)-2(4,4,5,5-tetramethyl-1,3,2-dioxaborolan-2-yl)-6,7,9,10,12,12a-hexahydro-5H-pyrido[4,3-b][1,4]thiazepino[2,3,4-hi]indole-11(8aH)-carboxylate. $^1$H NMR ($CDCl_3$): δ7.45 (d, 1H, J=0.8 Hz), 7.32 (app s, 1H), 3.89–3.80 (m, 2H), 3.65–3.60 (m, 1H), 3.59–3.39 (m, 4H), 3.26–3.18 (m, 2H), 3.05–2.95 (m, 1H), 2.12–2.02 (m, 2H), 1.88–1.80 (m, 2H), 1.43 (s, 9H), 1.30 (s, 12H).

Step C

To a solution of tert-butyl(8aS,12aR)-2-(4,4,5,5-tetramethyl-1,3,2-dioxaborolan-2-yl)-6,7,9,10,12,12a-hexahydro-5H-pyrido[4,3-b][1,4]thiazepino[2,3,4-hi]indole-11(8aH)-carboxylate (0.10 g, 0.21 mmol) in 15 mL of 1,2-dimethoxyethane and 5 mL of water was added 2-bromobenzonitrile (0.08 g, 0.42 mmol) and barium hydroxide octahydroate (0.20 g, 0.63 mmol). The mixture was degassed with a stream of nitrogen for 20 min and then there was added tetrakis(triphenylphosphine)palladium (10 mg, 0.009 mmol) and the mixture was stirred at 80° C. for 3 h. The reaction was allowed to cool to ambient temperature and was diluted with ethyl acetate, washed with sat'd aqueous sodium bicarbonate and brine, dried ($MgSO_4$), filtered through Celite and concentrated in vacuo. The residue was purified by flash chromatography (elution with hexanes/ethyl acetate) to afford 55 mg (61%) of tert-butyl (8aS,12aR)-2(2-cyanophenyl)-6,7,9,10,12,12a-hexahydro-5H-pyrido[4,3-b][1,4]thiazepino[2,3,4-hi]indole-11(8aH)-carboxylate. $^1$H NMR ($CDCl_3$): δ7.69 (dd, 1H, J=7.3, 0.8 Hz), 7.56 (td, 1H, J=7.7, 1.5 Hz), 7.42 (app d, 1H, J=7.7 Hz), 7.33 (td, 1H, J=7.7, 1.1 Hz), 7.14 (s, 1H), 7.11 (s, 1H), 3.94–3.82 (m, 2H), 3.3.63–3.43 (m, 4H), 3.41–3.28 (m, 2H), 3.21–3.10 (m, 1H), 3.04–2.96, (m, 1H), 2.18–2.02 (m, 2H), 1.94–1.85 (m, 2H), 1.39 (s, 9H). LRMS ($ES^+$): 448.1 $(M+H)^+$.

Step D

To a solution of tert-butyl(8aS,12aR)-2-(2-cyanophenyl)-6,7,9,10,12,12a-hexahydro-5H-pyrido[4,3-b][1,4]thiazepino[2,3,4-hi]indole-11(8aH)-carboxylate from Part A (0.10 g, 0.22 mmol) in 20 mL of methylene chloride was added 5 mL of trifluoroacetic acid and the mixture was allowed to stir at ambient temperature for 4 h. The volatiles were removed in vacuo and the residue was purified by prep HPLC (C18 reverse phase column, elution with a $H_2O$/$CH_3CN$ gradient with 0.5% TFA) and lyophilized to afford 65 mg (64%) of the title compound. $^1$H NMR ($CDCl_3$): δ9.40 (broad s, 1H), 9.23 (broad s, 1H), 7.69 (d, 1H, J=7.7 Hz), 7.59 (app t, 1H, J=7.7 Hz), 7.43 (d, 1H, J=7.7 Hz), 7.38 (t, 1H, J=7.7 Hz), 7.18 (d, 1H, J=1.8 Hz), 7.16 (s, 1H), 4.06–3.96 (m, 1H), 3.67–3.58 (m, 1H), 3.52–3.48 (m, 2H), 3.43–3.33 (m, 2H), 3.26–3.19 (m, 1H), 3.10–2.96 (m, 2H), 2.80–2.70 (m, 1H), 2.25–2.05 (m, 4H). LRMS ($ES^+$): 348.3 $(M+H)^+$.

Example 464

4-[(8aS,12aR)-6,7,8a,9,10,11,12,12a-octahydro-5H-pyrido[4,3-b][1,4]thiazepino[2,3,4-hi]indol-2-yl]-3-(trifluoromethyl)benzonitrile, trifluoroacetic acid salt.

Using 4-bromo-3-(trifluoromethyl)benzonitrile and following the procedures described in Example 463, Parts C and D, the title compound was prepared. $^1$H NMR ($CDCl_3$): δ9.38 (broad s, 1H), 9.02 (broad s, 1H), 7.99 (s, 1H), 7.81 (d, 1H, J=7.6 Hz), 7.43 (d, 1H, J=7.7 Hz), 6.97 (s, 1H), 6.83 (s, 1H), 4.06–3.96 (m, 1H), 3.68–3.58 (m, 1H), 3.52–3.45 (m, 2H), 3.44–3.30 (m, 2H), 3.27–3.18 (m, 1H), 3.10–2.95 (m, 2H), 2.78–2.64 (m, 1H), 2.25–2.05 (m, 4H). LRMS ($ES^+$): 416.3 $(M+H)^+$.

Example 465

3-[(8aS,12aR)-6,7,8a,9,10,11,12,12a-octahydro-5H-pyrido[4,3-b][1,4]thiazepino[2,3,4-hi]indol-2-yl] benzaldehyde, trifluoroacetic acid salt Step A To a solution of tert-butyl(8aS,12aR)-2-bromo-6,7,9,10,12,12a-hexahydro-5H-pyrido [4,3-b][1,4]thiazepino[2,3,4-hi]indole-11(8aH)-carboxylate (0.50 g, 1.17 mmol) in 75 mL of 1,2-dimethoxyethane and 25 mL of water was added 3-formylphenyl boronic acid (0.52 g, 3.52 mmol) and barium hydroxide octahydrate (1.11 g, 3.52 mmol). The mixture was degassed with a stream of nitrogen for 20 min and then there was added tetrakis(triphenylphosphine) palladium (0.04 g, 0.035 mmol) and the mixture was stirred at 100° C. for 3 h. The reaction was allowed to cool to ambient temperature and was diluted with ethyl acetate, washed with sat'd aqueous sodium bicarbonate and brine, dried ($MgSO_4$), filtered through Celite and concentrated in vacuo. The residue was purified by flash chromatography (elution with hexanes/ethyl acetate) to afford 0.51 g (96%) of tert-butyl(8aS,12aR)-2(3-formylphenyl)-6,7,9,10,12,12a-hexahydro-5H-pyrido[4,3-b][1,4]thiazepino[2,3,4-hi]indole-11(8aH)-carboxylate. $^1$H NMR ($CDCl_3$): δ10.05 (s, 1H), 8.00 (s, 1H), 7.78–7.74 (m, 2H), 7.54 (t, J=7.7 Hz, 1H), 7.16 (d, J=1.9 Hz, 2H), 7.16 & 7.07 (two d due to rotomers, J=1.8 Hz, 1H), 4.85–2.97 (broad m, 8H), 2.18–2.04 (m, 2H), 1.89–1.18 (m, 2H), 1.63–1.49 (m, 2H), 1.42, (s, 9H). LRMS (ApcI): 451.0 $(M+H)^+$.

Step B

To a solution of tert-butyl(8aS,12aR)-2-(3-formylphenyl)-6,7,9,10,12,12a-hexahydro-5H-pyrido[4,3-b][1,4]thiazepino[2,3,4-hi]indole-11(8aH)-carboxylate (0.051 g, 0.113 mmol) in 20 mL of methylene chloride was added 5 mL of trifluoroacetic acid and the mixture was allowed to stir at ambient temperature for 3 h. The volatiles were removed in vacuo and the residue was purified by prep HPLC (C18 reverse phase column, elution with a $H_2O$/$CH_3CN$ gradient with 0.5% TFA) and lyophilized to afford 25 mg (45%) of the title compound. $^1$H NMR (DMSO-$d_6$) δ10.04 (s, 1H), 8.68 (broad s, 4H), 8.08 (s, 1H), 7.91 (d, J=8 Hz, 1H), 7.80 (d, J=7.6 Hz, 1H), 7.62 (t, J=7.6 Hz, 1H), 7.42 (d, 1.8 Hz), 7.37 (d, 1.9 Hz, 1H), 7.17 & 7.05 (two d due to rotomers, J=1.8 Hz, 1H), 4.50 &4.38 (two m, due to rotomers, 1H), 3.70–2.95 (broad m, 7H), 2.17–1.90 (broad m, 6H). LRMS ($ES^+$): 351.2 $(M+H)^+$.

Example 466

{3-[(8aS,12aR)-6,7,8a,9,10,11,12,12a-octahydro-5H-pyrido[4,3-b][1,4]thiazepino[2,3,4-hi]indol-2-yl] phenyl}methanol, trifluoroacetic acid salt Step A To a solution of tert-butyl(8aS,12aR)-2-(3-formylphenyl)-6,7,9,10,12,12a-hexahydro-5H-pyrido[4,3-b][1,4]thiazepino[2,3,4-hi]indole-11(8aH)-carboxylate (0.28 g, 0.62 mmol) in 50 mL of methanol was added $NaBH_4$ (0.045 g, 1.24 mmol) and the mixture was stirred at room temperature for 2 h. The volatiles were removed under vacuum and the residue was purified by column chromatography (elution with 1:1 EtOAc:hex) yielding 120 mg (43%) of tert-butyl(8aS,12aR)-2-[3-(hydroxymethyl) phenyl]-6,7,9,10,12,12a-hexahydro-5H-pyrido[4,3-b][1,4] thiazepino[2,3,4-hi]indole-11(8aH)-carboxylate. $^1$H NMR (300 MHz, $CDCl_3$): δ7.79–7.14 (m, 6H), 4.74 (s, 2H), 3.90–2.95 (broad m, 10H), 2.20–1.85 (broad m, 4H), 1.43 (s, 9H). LRMS (ApcI): 453.1 $(M+H)^+$.

Part B

Following the procedure described in Example 465, Part B, tert-butyl(8aS,12aR)-2-[3-(hydroxymethyl)phenyl]-6,7,9,10,12,12a-hexahydro-5H-pyrido[4,3-b][1,4]thiazepino[2,3,4-hi]indole-11(8aH)-carboxylate was converted into the title compound. $^1$H NMR (DMSO-$d_6$) δ8.72–8.68 (m, 4H), 7.58–7.18 (broad m, 6H), 4.52 (s, 2H), 3.70–2.95 (broad m, 7H), 2.78–2.65 (m, 1H), 2.19–1.89 (broad m, 4H). LRMS (ES$^+$): 353.2 (M+H)$^+$.

Example 467

3-[(8aS,12aR)-6,7,8a,9,10,11,12,12a-octahydro-5H-pyrido[4,3-b][1,4]thiazepino[2,3,4-hi]indol-2-yl] benzyl methyl ether, trifluoroacetic acid salt Step A To a solution of tert-butyl(8aS,12aR)-2-[3-(hydroxymethyl)phenyl]-6,7,9,10,12,12a-hexahydro-5H-pyrido [4,3-b][1,4]thiazepino[2,3,4-hi]indole-11(8aH)-carboxylate (0.12 g, 0.27 mmol) in 100 mL of THF was added NaH (0.03 g, 1.27 mmol) and iodomethane (0.165 mL, 2.65 mmol) and the solution was stirred at room temperature overnight. The solution was quenched with methanol and the solution was diluted with ethyl acetate and washed with brine. The organics were dried over magnesium sulfate, filtered through a pad of silica gel and the volatiles were removed under reduced pressure to afford 100 mg (81%) of tert-butyl(8aS,12aR)-2-[3-(methoxymethyl) phenyl]-6,7,9,10,12,12a-hexahydro-5H-pyrido[4,3-b][1,4] thiazepino[2,3,4-hi]indole-11(8aH)-carboxylate, which was used without purification. $^1$H NMR ($CDCl_3$): δ7.48–7.06 (broad m, 6H), 4.51 (s, 2H), 3.85–1.85 (broad m, 11H), 1.65–1.25 (13H). LRMS (ApcI): 467.1 (M+H)$^+$.

Step B

Following the procedure described in Example 465, Part B, tert-butyl(8aS,12aR)-2-[3-(methoxymethyl)phenyl]-6,7,9,10,12,12a-hexahydro-5H-pyrido[4,3-b][1,4]thiazepino[2,3,4-hi]indole-11(8aH)-carboxylate was converted into the title compound. $^1$H NMR (DMSO-$d_6$) δ8.71 (m, 4H), 7.45–7.17 (m, 6H), 4.40 (s, 2H), 3.63–2.97 (broad m, 10H), 2.68 (m 1H), 2.08–1.93 (broad m, 4H). LRMS (ES$^+$): 367.2 (M+H)$^+$.

Example 468

N-{3-[(8aS,12aR)-6,7,8a,9,10,11,12,12a-octahydro-5H-pyrido[4,3-b][1,4]thiazepino[2,3,4-hi]indol-2-yl] benzyl}-N,N-dimethylamine, bis trifluoroacetic acid salt Step A To a solution of tert-butyl(8aS,12aR)-2-(3-formylphenyl)-6,7,9,10,12,12a-hexahydro-5H-pyrido[4,3-b][1,4]thiazepino[2,3,4-hi]indole-11(8aH)-carboxylate (0.15 g, 0.33 mmol) in 150 mL of THF was added dimethylamine (0.66 mL of a 2M solution in methanol, 1.33 mmol), $NaBH(OAc)_3$ (0.14 g, 0.60 mmol) and an excess of HOAc (1 mL). The residue was allowed to stir at room temperature overnight. The solution was filtered through a pad of silica gel and the volatiles were removed. The reaction was passed through a short column of silica gel (elution with 4:1 EtOH:EtOAc) to afford tert-butyl(8aS,12aR)-2-[3-(dimethylaminomethyl)phenyl]-6,7,9,10,12,12a-hexahydro-5H-pyrido[4,3-b][1,4]thiazepino[2,3,4-hi]indole-11(8aH)-carboxylate. $^1$H NMR ($CDCl_3$) δ7.52–7.13 (broad m, 6H), 3.95 (s, 2H), 3.88–2.96 (broad m, 10H), 2.57 (s, 6H), 2.20–2.07 (broad m, 2H), 1.90 (broad s, 2H), 1.42 (broad s, 9H). LRMS (ApcI): 480.1 (M+H)$^+$.

Step B

Following the procedure described in Example 465, Part B, tert-butyl(8aS,12aR)-2-[3-(dimethylaminomethyl) phenyl]-6,7,9,10,12,12a-hexahydro-5H-pyrido[4,3-b][1,4] thiazepino[2,3,4-hi]indole-11(8aH)-carboxylate was converted into the title compound. $^1$H NMR (DMSO-$d_6$) δ8.85–8.79 (m, 3H), 7.68 (s, 1H), 7.62 (d, J=6.6 Hz, 1H), 7.45 (t, J=7.3 Hz, 1H), 7.35–7.32 (m, 2H), 7.24 (s, 1H), 4.28 (s, 2H), 3.66–2.97 (broad m, 9H), 2.74 (s, 6H), 2.70 (s, 1H), 2.20–1.94 (m, 4H). LRMS (ES$^+$): 380.1 (M+H)$^+$.

Example 469 and Example 470

5-[(8aS,12aR)-6,7,8a,9,10,11,12,12a-octahydro-5H-pyrido[4,3-b][1,4]thiazepino[2,3,4-hi]indol-2-yl]-2-fluorobenzonitrile, trifluoroacetic acid salt (Example 469) and 5-[(8aS,12aR)-6,7,8a,9,10,11,12,12a-octahydro-5-H-pyrido[4,3-b][1,4]thiazepino[2,3,4-hi]indol-2-yl]-2-fluorobenzamide, trifluoroacetic acid salt (Example 470)

Using 3-cyano-4-fluorophenyl boronic acid and following the procedures described in Example 460, 5-[(8aS,12aR)-6,7,8a,9,10,11,12,12a-octahydro-5H-pyrido[4,3-b][1,4] thiazepino[2,3,4-hi]indol-2-yl]-2-fluorobenzonitrile, trifluoroacetic acid salt was prepared and there was also isolated 5-[(8aS,12aR)-6,7,8a,9,10,11,12,12a-octahydro-5H-pyrido [4,3-b][1,4]thiazepino[2,3,4-hi]indol-2-yl]-2-fluorobenzamide, trifluoroacetic acid salt as a by-product. Example 469: $^1$H NMR ($CDCl_3$): δ9.55 (broad s, 1H), 9.26 (broad s, 1H), 7.68–7.63 (m, 2H), 7.26–7.22 (m, 1H), 7.17 (d, 1H, J=1.5 Hz), 7.03 (s, 1H), 4.00–3.90 (m, 1H), 3.63–3.52 (m, 1H), 3.50–3.43 (m, 2H), 3.41–3.30 (m, 2H), 3.24–3.18 (m, 1H), 3.10–2.95 (m, 2H), 2.55–2.45 (m, 1H), 2.25–2.10 (m 4H). LRMS (ES$^+$): 366.6 (M+H)$^+$. Example 470:LRMS (ES$^+$): 384.1 (M+H)$^+$.

Example 471

6,7,9,10,11,12,13,13a-octahydro-5H,8aH-azepino[4,5-b][1,4]thiazepino[2,3,4-hi]indole Step A 3,4-Dihydro-1,5-benzothiazepin-5(2H)-amine hydrochloride (3.96 g, 22 mmol) and hexahydro-4H-azepin-4-one hydrochloride (3.3 g, 22 mmol) were suspended in EtOH (40 mL). 12M HCl was added (3.7 mL, 44 mmol). The reaction was degassed and refluxed for 48 hrs under a nitrogen atmosphere. The reaction was cooled to room temperature and stirred 18 hrs. The precipitate was filtered, washed with cold EtOH, and air-dried for 18 hrs. 6,7,10,11,12,13-hexahydro-5H,9H-azepino[4,5b][1,4]thiazepino[2,3,4-hi] indole hydrochloride (4.42 g, 15 mmol, 68%) was isolated as a white powder. $^1$H NMR ($CDCl_3$, 300 MHz) δ7.22 (1H, dd, 1.1 Hz, 7.7 Hz), 6.99 (1H, dd, 1.1 Hz, 7.4 Hz), 6.89 (1H, t, 7.6 Hz), 4.60 (2H, t, 5.9 Hz), 3.38 (2H, t, 6.6 Hz), 3.07–3.14 (4H, m), 2.82–2.96 (4H, m), 2.03–2.31 (2H, m).

Step B 6,7,10,11,12,13-Hexahydro-5H,9H-azepino[4,5-b][1,4] thiazepino[2,3,4-hi]indole hydrochloride (4.42 g, 15 mmol) was dissolved in TFA (40 mL). The solution was cooled to 0° C., and then $NaCNBH_3$ (2.8 g, 45 mmol) was added in small portions keeping the temperature less than 15° C. After the addition was complete, the reaction was stirred at 0C. for 1 hr. Ice chips (~3 g) were added to the reaction flask and 50% NaOH was added until the pH=14. This aqueous mixture was extracted with $CHCl_3$ (3×30 mL). The combined organic layers were washed with brine, dried, and concentrated. The organic residue was dissolved in dioxane and 1M NaOH. The solution was cooled to 0° C. and $BOC_2O$ was added. The reaction was stirred for 3 hr at room temperature and subsequently concentrated. EtOAc and brine were added to the residue and stirred for 10 min. The layers were separated, and the aqueous mixture was re-extracted with EtOAc. The combined organic layers were washed with brine, dried, and concentrated to yield 4 g of a brown viscous oil. This crude material was purified by column chromatography (10–50% EtOAc/hexane), to afford tert-butyl 6,7,8a,9,10,12,13,13a-octahydro-5H,11H-azepino[4,5-b][1,4]thiazepino[2,3,4-hi]indole-11-carboxylate (3.47 g, 9.6 mmol, 64%) as a transparent pale-brown amorphous solid. $^1$H NMR ($CDCl_3$, 300 MHz) δ6.95 (1H, d, 7.7 Hz), 6.82 (1H, d, 7.4 Hz), 6.16 (1H, t, 7.7 Hz), 3.7–3.9 (1H, m), 3.2–3.9 (8H, m), 2.9–3.05 (1H, m), 2.75–2.9 (1H, m), 1.8–2.2 (5H, m), 1.45 (9H, s).

Step C

Tert-butyl 6,7,8a,9,10,12,13,13a-octahydro-5H,11H-azepino[4,5-b][1,4]thiazepino[2,3,4-hi]indole-11-carboxylate (1.7 g, 4.7 mmol) was dissolved in TFA (20 mL) The solution was allowed to stir for 2 hrs. Ice was added to the reaction vessel and 50% NaOH was added until the pH=14. This aqueous solution was extracted with $CHCl_3$ (2×15 mL). The combined organic layers were washed with brine, dried, and concentrated to afford the title compound (1.2 g, 4.6 mmol, 98%) as a light-brown amorphous solid. $^1$H NMR ($CDCl_3$, 300 MHz) δ6.95 (1H, d, 7.7 Hz), 6.82 (1H, d, 7.3 Hz), 6.16 (1H, t, 7.6 Hz), 3.75–3.9 (1H, m), 3.3–3.7 (3H, m), 2.6–3.2 (6H, m), 1.7–2.2 (6H, m).

Example 472

4-[6,7,8a,9,10,12,13,13a-octahydro-5H,11H-azepino[4,5-b][1,4]thiazepino[2,3,4-hi]indol-11-yl]-1-(4-fluorophenyl)-1-butanone 6,7,9,10,11,12,13,13a-Octahydro-5H,8aH-azepino[4,5-b][1,4]thiazepino[2,3,4-hi]indole (200 mg, 0.78 mmol), 4-chloro-4'-fluorobutyrophenone (213 mg, 1.6 mmol), KI (129 mg, 0.78 mmol), $K_2CO_3$ (322 mg, 2.3 mmol), and 2 drops of TEA were suspended in MEK (4 mL). The mixture was heated for 60 hrs. The reaction was cooled to room temperature and concentrated. The residue was purified by column chromatography (5, 7, 10% MeOH/$CH_2Cl_2$) to afford the title compound (234 mg, 0.55 mmol, 71%) as a pale-brown viscous oil. $^1$H NMR ($CDCl_3$, 300 MHz) δ6.95 (2 H, ddd, 2.9 Hz, 5.1 Hz, 12.1 Hz), 7.06 (2H, m), 6.91 (1H, 7.7 Hz), 6.74 (1H, d, 7.3 Hz), 6.55 (1H, t, 7.7 Hz), 3.65–3.75 (1H, m), 3.45–3.61 (2H, m), 3.29–3.38 (1H, m), 2.85–3.0 (4H, m), 2.2–2.8 (6H, m), 1.7–2.2 (8H, m). MS (ESI): 425.3 (base, M+H)

Example 473

(8aS,13aS)-11-[3-(4-fluorophenoxy)propyl]-[6,7,9,10,11,12,13,13a-octahydro-5H,8aH-azepino[4,5-b][1,4]thiazepino[2,3,4-hi]indole 6,7,9,10,11,12,13,13a-Octahydro-5H,8aH-azepino[4,5-b][1,4]thiazepino[2,3,4-hi]indole (43.3 mg, 0.17 mmol), 1-(3-chloropropoxy)-4-fluorobenzene (40.8 mg, 0.22 mmol), KI (27.6 mg, 0.17 mmol), and $K_2CO_3$ (69 mg, 0.50 mmol) were suspended in 4 mL of MEK. The suspension was heated at 80° C. for 18 hrs. The reaction was cooled to rt and concentrated. The residue was purified by column chromatography (5, 7, 10% MeOH/$CH_2Cl_2$) to afford the racemic title compound (24.5 mg, 0.06 mmol, 35%) as a pale-brown viscous oil. The enantiomers were separated on a Chiracel OD column using hexane/IPA/TFA (75/25/0.1) as the eluent to give the title compound. $^1$H NMR ($CDCl_3$, 300 MHz) δ6.85–6.95 (2 H, m), 7.06 (2H, m), 6.68–6.80 (2H, m), 6.53 (1H, t, 7.6 Hz), 3.90 (2H, t, 6.2 Hz), 3.70–3.80 (1H, m), 3.32–3.59 (3H, m), 2.71–2.94 (3H, m), 2.45–2.58 (5H, m), 1.7–2.1 (8H, m). MS (ESI): 413.3 (base, M+H)

Example 474

11-[2-(6-fluoro-1,2-benzisoxazol-3-yl)propyl]-6,7,9,10,11,12,13,13a-octahydro-5H,8aH-azepino[4,5-b][1,4]thiazepino[2,3,4-hi]indole The title compound was prepared by the same general method as example 473 from 6,7,9,10,11,12,13,13a-octahydro-5H,8aH-azepino[4,5-b][1,4]thiazepino[2,3,4-hi]indole (45 mg, 0.17 mmol) and 3-(3-chloropropyl)-1,2-benzisoxazole (61.3 mmol, 0.35 mmol) to afford the desired product (46.1 mg, 11 mmol, 62%) after chromatographic purification. $^1$H NMR ($CDCl_3$, 300 MHz) δ7.71 (1 H, dd, 5.1 Hz, 8.8 Hz), 7.23 (1H, dd, 1.8 Hz, 8.4 Hz), 7.06 (1H, dt, 2.2 Hz, 8.4 Hz), 6.94 (1H, br-d, 7.6 Hz), 6.80 (1h, 7.4 Hz), 6.59 (1H, t, 7.3 Hz), 3.81 (1H, ddd, 5.1 Hz, 9.9 Hz, 13.6 Hz), 3.38–3.65 (3H, m), 2.92–3.00 (3H, m), 2.68–2.88 (2H, m), 2.44–2.61 (5H, m), 1.87–2.12 (8H, m). MS (ESI): 438.2 (base, M+H)

Example 475

4-[6,7,8a,9,10,12,13,13a-octahydro-5H,11H-azepino[4,5-b][1,4]thiazepino[2,3,4-hi]indol-11-yl]-1-(4-pyridinyl)-1-butanone The title compound was prepared by the same general method as example 473 from 6,7,9,10,11,12,13,13a-octahydro-5H,8aH-azepino[4,5-b][1,4]thiazepino[2,3,4-hi]indole (275 mg, 1.1 mmol) and 4-chloro-1-(4-pyridinyl)-1-butanone (387 mmol, 2.1 mmol) to afford the desired product (60.2 mg, 0.15 mmol, 14%) after chromatographic purification. $^1$H NMR ($CDCl_3$, 300 MHz) δ8.81 (2H, dd, 1.4 Hz, 4.4 Hz), 7.73 (2H, dd, 1.4 Hz, 4.4 Hz), 6.99 (1H, d, 7.7 Hz), 6.81 (1H, d, 7.3 Hz), 6.61–6.60 (1H, m), 3.5–3.8 (3H, m), 3.3–3.5 (1H, m), 2.5–3.1 (9H, m), 1.8–2.4 (10H, m). MS (ESI): 408.4 (base, M+H)

Example 476

6,7,9,10,11,12,13,13a-octahydro-5H,8aH-azepino[3,4-b][1,4]thiazepino[2,3,4-hi]indole Step A 6,7,8a,11,12,12a-Hexahydro-5H-[1,4]thiazepino-2,3,4-jk]carbazol-10(9H)-one (455 mg, 1.75 mmol) was dissolved in 4 mL of $MeSO_3H$. The solution was cooled to 0° C. NaN3 (171 mg, 2.63 mmol) was added in one portion. Ice chips were added (~2 g) and the reaction was basified with 50% NaOH until pH=14. The reaction was extracted with $CH_2Cl_2$ (3×10 mL). The combined organic layers were washed with brine, dried, and concentrated to afford 551 mg of a brown powder. This crude product was purified by column chromatography to afford an inseparable 1:1 mixture of 6,7,8a,9,11,12,13,13a-octahydro-5H,10H-azepino[4,5-b][1,4]thiazepino[2,3,4-hi]indol-10-one and 6,7,8a,9,10,12,13,13a-octahydro-5H,11H-azepino[3,4-b][1,4]thiazepino[2,3,4-hi]indol-11-one (504 mg, 105%) as a white powder. $^1$H NMR ($CDCl_3$, 300 MHz) δ6.94–6.99 (1H, m), 6.82–6.86 (1H, m), 6.61–6.69 (1H, m), 3.65–3.85 (1H, m), 3.1–3.8 (6H, m), 2.8–3.05 (2H, m), 2.5–2.7 (1H), 1.7–2.3 (4H, m).

Step B

A mixture of 6,7,8a,9,11,12,13,13a-octahydro-5H,10H-azepino[4,5-b][1,4]thiazepino[2,3,4-hi]indol-10-one and 6,7,8a,9,10,12,13,13a-octahydro-5H,11H-azepino[3,4-b][1,4]thiazepino[2,3,4-hi]indol-11-one (483 mg, 1.76 mmol) was dissolved in toluene (10 mL). The solution was cooled to 0° C. and 65RED-Al in toluene (1.59 mL, 5.29 mmol) was added drop-wise. The reaction was warmed to room temperature and stirred for 1 hr, and it was subsequently heated to reflux for 2 hrs. The reaction was cooled to room temperature and quenched with 1M NaOH (2 mL). The layers were separated and the aqueous was re-extracted with toluene (2×15 mL). The combined organic layers were washed with brine, dried, and concentrated to afford a mixture of 6,7,9,10,11,12,13,13a-octahydro-5H,8aH-azepino[4,5-b][1,4]thiazepino[2,3,4-hi]indole and (8aR,13aS)-6,7,9,10,11,12,13,13a-octahydro-5H,8aH-azepino[3,4-b][1,4]thiazepino[2,3,4-hi]indole (343 mg, 1.32 mmol, 75%) as a brown oil. The regioisomers were separated on a chiracel OD column using 10% IPA/hexane as the eluent to give the title compound. $^1$H NMR ($CDCl_3$, 300 MHz) δ6.94–6.99 (1H, m), 6.81–6.86 (1H, m), 6.57–6.66 (1H, m), 3.3–3.8 (4H, m), 2.6–3.3 (6H, m), 1.6–2.2 (6H, m). MS (ESI): 261.2 (base, M+H)

Example 477

4-[6,7,8a,9,11,12,13,13a-octahydro-5H,10H-azepino[3,4-b][1,4]thiazepino[2,3,4-hi]indol-10-yl]-1-(4-fluorophenyl)-1-butanone 6,7,9,10,11,12,13,13a-Octahydro-5H,8aH-azepino[3,4-b][1,4]thiazepino[2,3,4-hi]indole (14.7 mg, 0.056 mmol), 4-chloro-4'-fluorobutyrophenone (14.7 mg, 0.073 mmol), KI (9.4 mg, 0.056 mmol), $K_2CO_3$ (23.4 mg, 0.17 mmol were suspended in MEK (4 mL). The mixture was heated for 18 hrs. The reaction was cooled to room temperature and concentrated. The residue was purified by column chromatography (5, 7, 10% MeOH/$CH_2Cl_2$) to afford the title compound (9.9 mg, 0.024 mmol, 42%) as a pale-brown viscous oil. $^1$H NMR ($CDCl_3$, 300 MHz) δ7.93 (2H, ddd, 2.6 Hz, 4.8 Hz, 12.2 Hz), 7.04 (2H, t, 8.6 Hz), 6.90 (1H, 7.7 Hz), 6.75 (1H, 7.3 Hz), 6.54 (1H, dd, 7.3 Hz, 7.7 Hz), 3.5–3.7 (2H, m), 3.2–3.7 (2H, m), 2.75–3.0 (5H, m), 2.3–2.74 (4H, m), 2.3–2.4 (1H, m), 1.5–2.1 (10 H, m). MS (ESI): 425.3 (base, M+H)

Example 478

10-[2-(6-fluoro-1,2-benzisoxazol-3-yl)ethyl]-6,7,9,10,11,12,13,13a-octahydro-5H,8aH-azepino[3,4-b][1,4]thiazepino[2,3,4-hi]indole 10-[2-(6-Fluoro-1,2benzisoxazol-3-yl)ethyl]-6,7,9,10,11,12,13,13a-octahydro-5H,8aH-azepino[3,4-b][1,4]thiazepino[2,3,4-hi]indole was prepared by the same general method as example 477 from 6,7,9,10,11,12,13,13a-octahydro-5H,8aH-azepino[3,4-b][1,4]thiazepino[2,3,4-hi]indole (56.5 mg, 0.22 mmol) and 3-(3-chloropropyl)-1,2-benzisoxazole (77 mg, 0.43 mmol) to afford the title compound (59.6 mg, 14 mmol, 62%) after chromatographic purification. $^1$H NMR ($CDCl_3$, 300 MHz) δ7.60 (1H, dd, 5.1 Hz, 8.4 Hz), 7.23 (1H, m), 7.06 (1H, dt, 2.1 Hz, 8.8 Hz), 6.95 (1H, d, 7.7 Hz), 6.83 (1H, 6.9 Hz), 6.58–6.63 (1H, m), 3.3–3.8 (4H, m), 2.8–3.1 (5H, m), 2.6–2.8 (4H, m), 2.3–2.4 (1H, m), 1.9–2.21 (3 H, m), 1.6–1.8 (4H, m). MS (ESI): 424.2 (base, M+H)

Example 479

2-(2,4-dichlorophenyl)-6,7,9,10,11,12,13,13a-octahydro-5H,8aH-azepino[4,5-b][1,4]thiazepino[2,3,4-hi]indole Step A To a solution of tert-butyl 6,7,8a,9,10,12,13,13a-octahydro-5H,11H-azepino[4,5-b][1,4]thiazepino[2,3,4-hi]indole-11-carboxylate (3.17 g, 8.8 mmol) dissolved in 15 mL of DMF, a solution of NBS (1.72 g, 1.1 mmol, in 10 mL DMF) was added at 0° C. The reaction was warmed to room temperature and stirred for 2 hrs. Brine (20 mL) and EtOAc (20 mL) were added to the reaction flask; the bi-phasic mixture was stirred for 10 min. The layers were separated, and the aqueous was re-extracted with EtOAc (2×20 mL). The combined organic layers were washed with brine, dried, and concentrated to afford 3.8 g of a brown oil. This crude material was purified by column chromatography to yield tert-butyl 2-bromo-6,7,8a,9,10,12,13,13a-octahydro-5H,11H-azepino[4,5-b][1,4]thiazepino[2,3,4-hi]indole-11-carboxylate (2.57 g, 80%) as an amorphous solid. $^1$H NMR ($CDCl_3$, 300 MHz) 7.07 (1H, d, 1.8 Hz), 6.89 (1H, br-s), 3.39–3.78 (8H, m), 2.940–2.99 (1H, m), 2.80–2.85 (1H, m), 1.8–2.2 (6H, m), 1.46 (9H, m).

Step B

Tert-butyl 2-bromo-6,7,8a,9,10,12,13,13a-octahydro-5H,11H-azepino[4,5-b][1,4]thiazepino[2,3,4-hi]indole-11-carboxylate (231 mg, 0.53 mmol) was dissolved in 3:1 DME:H2O (4 mL) 2,4-dichlorophenyl boronic acid (110 mg, 0.59 mmol), $Pd(PPh_3)_4$ (12 mg, 0.01 mmol), and $Ba(OH)_2$ (149 mg, 0.79 mmol) were then added. The reaction vessel was degassed 4 times and kept under an atmosphere of nitrogen. The reaction was refluxed for 18 hours and then cooled to rt. The reaction was concentrated in vacuo. Brine (10 mL) and EtOAc (10 mL) were added to the reaction flask; the mixture was stirred for 10 min. The layers were separated, and the aqueous was re-extracted with EtOAc (2×20 mL). The combined organic layers were washed with brine, dried, and concentrated to afford a crude brown oil. The crude product was purified by column chromatography (20–40% EtOAc/Hexane) to afford tert-butyl 2-(2,4-dichlorophenyl)-6,7,8a,9,10,12,13,13a-octahydro-5H,11H-azepino[4,5-b][1,4]thiazepino[2,3,4-hi]indole-11-carboxylate (195 mg, 0.39 mmol, 73%) as an amorphous solid.

Step C

Tert-butyl(8aS,13aS)-2-(2,4-dichlorophenyl)-6,7,8a,9,10,12,13,13a-octahydro-5H,11H-azepino[4,5-b][1,4]thiazepino[2,3,4-hi]indole-11-carboxylate was dissolved in 20% TFA in methylene chloride (3.5 mL) and was stirred at room temperature for 1 hr. The reaction was cooled to 0° C. and two ice chips were added to the reaction. The mixture was basified with 50% NaOH until pH 14.5 mL of brine and 5 mL of chloroform were added. The layers were separated, and the aqueous layer was re-extracted with $CHCl_3$ (2×15 mL). The combined organic layers were washed with brine (2×30 mL), dried, and concentrated to afford the title compound (148.6 mg, 95%) as an amorphous solid. $^1$H NMR ($CDCl_3$, 300 MHz) δ7.43–7.44 (1H, m), 7.23 (2H, d, 1.1 Hz), 6.91–7.0 (1H, m), 6.90–6.91 (1H, m), 3.92 (1H, ddd, 4.8, 10.6, 13.5 Hz), 3.69–3.76 (1H, m), 3.45–3.64 (2H, m), 3.15 (1H, dd, 8.4, 13.2 Hz), 2.70–3.05 (5H, m), 1.80–2.20 (6H, m). MS (ESI): 405 (base, M+H)

Example 480

2-(2-chloro-4-methoxyphenyl)-6,7,9,10,11,12,13,13a-octahydro-5H,8aH-azepino[4,5-b][1,4]thiazepino[2,3,4-hi]indole Step A Tert-butyl 2-(2-chloro-4-methoxyphenyl-6,7,8a,9,10,12,13,13a-octahydro-5H,11H-azepino[4,5-b][1,4]thiazepino[2,3,4-hi]indole-11-carboxylate was prepared by the same method as example 479, step B from tert-butyl 2-bromo-6,7,8a,9,10,12,13,13a-octahydro-5H,11H-azepino[4,5-b][1,4]thiazepino[2,3,4-hi]indole-11-carboxylate (250.7 mg, 0.57 mmol), 2-chloro-4-methoxyphenylboronic acid (107 mg, 0.63 mmol), to afford after chromatographic purification tert-butyl 2-(2-chloro-4-methoxyphenyl)-6,7,8a,9,10,12,13,13a-octahydro-5H,11H-azepino[4,5-b][1,4]thiazepino[2,3,4-hi]indole-11-carboxylate (250 mg, 0.49 mmol, 88%) as a white amorphous solid. $^1$H NMR ($CDCl_3$, 500 MHz) δ7.24 (1H, d, 8.8 Hz), 7.01 (1H, br-d, 1.5 Hz), 6.97 (1 H, d, 2.6 Hz), 6.92 (1H, br-s), 6.81 (1H, dd, 2.9, 8.8 Hz), 3.3–4.0 (11H, m), 2.97–3.04 (1H, m), 2.82–2.90 (1H, m), 1.8–2.2 (6H, m), 1.46 (9H, s).

Step B

The title compound was prepared by the same general method as example 479, step C from tert-butyl 2-(2-chloro-4-methoxyphenyl)-6,7,8a,9,10,12,13,13a-octahydro-5H,11H-azepino[4,5-b][1,4]thiazepino[2,3,4-hi]indole-11-carboxylate (238.9 mg, 0.48 mmol) to afford the desired product (173.8 mg, 0.44 mmol, 91%) as a pale yellow amorphous solid. $^1$H NMR ($CDCl_3$, 300 MHz) δ7.21 (1H, d, 8.4 Hz), 7.01 (1H, d, 1.5 Hz), 6.97 (1H, d, 2.6 Hz), 6.91 (1H, m), 6.81 (1H, dd, 2.5, 8.8 Hz), 3.4–4.0 (7H, m), 2.6–3.2 (6H, m), 1.80–2.20 (6H, m). MS (ESI): 401 (base, M+H)

Example 481

2-(4-methoxy-2-methylphenyl)-6,7,9,10,11,12,13,13a-octahydro-5H,8aH-azepino[4,5-b][1,4]thiazepino[2,3,4-hi]indole Step A Tert-butyl 2-(4-methoxy-2-methylphenyl)-6,7,8a,9,10,12,13,13a-octahydro-5H,11H-azepino[4,5-b][1,4]thiazepino[2,3,4-hi]indole-11-carboxylate was prepared by the same method as example 479, step B from tert-butyl 2-bromo-6,7,8a,9,10,12,13,13a-octahydro-5H,11H-azepino[4,5-b][1,4]thiazepino[2,3,4-hi]indole-11-carboxylate (261.9 mg, 0.60 mmol), 2-methyl-4-methoxyphenylboronic acid (109 mg, 0.66 mmol), to afford after chromatographic purification tert-butyl 2-(4-methoxy-2-methylphenyl)-6,7,8a,9,10,12,13,13a-octahydro-5H,11H-azepino[4,5-b][1,4]thiazepino[2,3,4-hi]indole-11-carboxylate (274 mg, 0.57 mmol, 100%) as a white amorphous solid. $^1$H NMR ($CDCl_3$, 500 MHz) δ7.43–7.44 (1H, m), 7.23 (2H, d, 1.5 Hz), 7.0 (1 H, d, 1.5 Hz), 6.91 (1H, br-s), 3.8–4.0 (1H, m), 3.3–3.8 (7 H, m), 2.91–3.04 (1H, m), 2.84–2.90 (1H, m),), 1.8–2.2 (6H, m), 1.46 (9H, s).

Step B

The title compound was prepared by the same general method as example 479, step C from tert-butyl 2-(4-methoxy-2-methylphenyl)-6,7,8a,9,10,12,13,13a-octahydro-5H,11H-azepino[4,5-b][1,4]thiazepino[2,3,4-hi]indole-11-carboxylate (269.4 mg, 0.56 mmol) to afford the desired product (216.5 mg, 0.56 mmol, 100%) as a pale yellow amorphous solid. $^1$H NMR ($CDCl_3$, 300 MHz) δ7.11 (1H, d, 8.5 Hz), 6.90 (1H, m), 6.72–6.77(3H, m), 3.3–4.0 (7H, m), 2.6–3.25 (6H, m), 1.80–2.30 (9H, m). MS (ESI): 381 (base, M+H)

Example 482

2-bromo-6,7,9,10,11,12,13,13a-octahydro-5H,8aH-azepino[4,5-b][1,4]thiazepino[2,3,4-hi]indole Tert-butyl 2-bromo-6,7,8a,9,10,12,13,13a-octahydro-5H,11H-azepino[4,5-b][1,4]thiazepino[2,3,4-hi]indole-11-carboxylate (157 mg, 0.36 mmol) was dissolved in 20% TFA (3 mL) in $CH_2Cl_2$. The reaction was stirred for 2 hr at rt. Ice chips were added, and then the reaction was basified with 50% NaOH until pH=14. Brine (5 mL) was added to the reaction mixture. The resulting solution was extracted with $CHCl_3$ (3×15 mL). The combined organic layers were washed with brine, dried, and concentrated to afford the title compound (130 mg, 100%) as a light brown oil. $^1$H NMR ($CDCl_3$, 300 MHz) δ7.06–7.08 (1H, m), 6.87–6.88 (1H, m), 3.78 (1H, ddd, 4.8 Hz, 10.6 Hz, 13.5 Hz), 3.65 (1H, ddd, 3.7 Hz, 8.8 Hz, 10.6 Hz), 3.39–3.56 (2H, m), 3.11 (1H, dd, 8.8 Hz, 13.5 Hz), 2.68–2.99 (5H, m), 1.75–2.2 (6H, m).

Example 483

4-[2-bromo-6,7,8a,9,10,12,13,13a-octahydro-5H,11H-azepino[4,5-b][1,4]thiazepino[2,3,4-hi]indol-11-yl]-1-(4-fluorophenyl)-1-butanone 2-Bromo-6,7,9,10,11,12,13,13a-octahydro-5H,8aH-azepino[4,5-b][1,4]thiazepino[2,3,4-hi]indole (121 mg, 0.36 mg), 4-chloro-4'-fluorobutyrophenone (107 mg, 0.53 mmol), KI (59.2 mg, 0.36 mmol), and K2CO3 (148 mg, 1.1 mmol) were added to 4 mL of MEK. The reaction was refluxed for 18 hr. The reaction was then cooled to rt and concentrated. The resulting residue was immediately purified by column chromatography (2, 5, 7% MeOH/CH2Cl) to afford the title compound (115.6 mg, 64%) as a light-brown oil. $^1$H NMR ($CDCl_3$, 300 MHz) δ7.96–8.02 (2H, m), 7.10–7.16 (2H, m), 7.05–7.06 (1h, m), 6.86–6.87 (1H, m), 3.73–3.83 (1H, m), 3.59 (1H, dt, 4 Hz, 10.3 Hz), 3.36–3.51 (2H, m), 2.91–3.00 (3H, m), 2.76–2.84 (2H, m), 2.59–2.65 (1H, m), 2.42–2.53 (4H, m), 1.81–2.10 (9H, m). MS (ESI): 505.3(base, M+H)

Example 484

3-[2-bromo-6,7,8a,9,10,12,13,13a-octahydro-5H,11H-azepino[4,5-b][1,4]thiazepino[2,3,4-hi]indol-11-yl]propyl 4-fluorophenyl ether 3-[2-Bromo-6,7,8a,9,10,12,13,13a-octahydro-5H,11H-azepino[4,5-b][1,4]thiazepino[2,3,4-hi]indol-11-yl]propyl 4-fluorophenyl ether was prepared by the same general method as example 483 from 2-bromo-6,7,9,10,11,12,13,13a-octahydro-5H,8aH-azepino[4,5-b][1,4]thiazepino[2,3,4-hi]indole (141 mg, 0.42 mmol) and 1-(3-chloropropoxy)-4-fluorobenzene (118 mg, 0.62 mmol) to afford the title compound (158 mg, 77%) after chromatographic purification. $^1$H NMR ($CDCl_3$, 300 MHz) δ7.08 (1H, 1.8 Hz), 6.93–6.99 (2H, m), 6.88–0.689 (1H, m), 6.78–6.85 (2H, m), 3.97 (2H, t, 6.2 Hz), 3.72–3.82 (1H, m), 3.64 (1H, dt, 3.6 Hz, 10.2 Hz), 3.36–3.56 (2H, m), 2.78–2.99 (3H, m), 2.59–2.76 (5H, m), 1.89–2.11 (8H, m). MS (ESI): 491.2+(base, M+H)

Example 485

Methyl 4-(6,7,9,10,12,12a-hexahydro-5H-pyrido[4,3b][1,4]thiazepino[2,3,4-hi]indol-11(8aH)-yl)-2-methylbutanoate Step A 3-Methyldihydro-2(3H)-furanone (2.13 g, 21,3 mmol) was dissolved in $CH_2Cl_2$ (15 mL). $BBr_3$ was added dropwise as a solution in 1M $CH_2Cl_2$. The reaction was stirred at rt for 18 hrs. MeOH (2 mL) was added at room temperature. Saturated aqueous $Na_2CO_3$ (20 mL) and $CH_2Cl_2$ (10 mL) were added. The layers were separated, and the aqueous was re-extracted with $CH_2Cl_2$ (2×20 mL). The combined organic layers were washed with brine, dried, and concentrated to afford 3.77 g of a brown liquid. This crude product was purified by column chromatography to afford methyl 4-bromo-2-methylbutanoate (3.39 g, 82%) as a clear liquid. $^1$H NMR ($CDCl_3$, 300 MHz) δ3.69 (3H, s), 3.42 (2H, t, 6.6 Hz), 2.68–2.75 (1H, m), 2.20–2.32 (1H, m), 1.86–1.97 (1H, m), 1.19 (3H, d, 7.0 Hz).

Step B 6,7,8a,9,10,11,12,12a-Octahydro-5H-pyrido[4,3-b][1,4]thiazepino[2,3,4-hi]indole (302 mg, 1.24 mmol), methyl 4-bromo-2-methylbutanoate (315 mg, 1.62 mmol), KI (206 mg, 1.24 mmol), and $K_2CO_3$ (514 mg, 3.72 mmol) were suspended in MEK. The mixture was refluxed for 18 hrs. The reaction was cooled and concentrated. The residue was purified by column chromatography (3, 5, 7% MeOH/$CH_2Cl_2$) to afford the title compound (477 mg, 99%) as a clear, amorphous solid. $^1$H NMR ($CDCl_3$, 300 MHz) δ6.93 (1H, d, 7.7 Hz), 6.84 (1H, d, 7.3 Hz), 6.61 (1H, m), 3.71–3.86 (1H, m), 3.67 (3H, d, 5.1 Hz), 2.5–3.3 (10H, m), 1.4–2.4 (10H, m), 1.12 (3H, d, 6.9 Hz). CI MS (NH3): 390 (base, M+H)

Example 486

4-(6,7,9,10,12,12a-hexahydro-5H-pyrido[4,3-b][1,4]thiazepino[2,3,4-hi]indol-11(8aH)-yl)-1,1-bis(4-fluorophenyl)-2-methyl-1-butanol Methyl 4-(6,7,9,10,12,12a-hexahydro-5H-pyrido[4,3-b][1,4]thiazepino[2,3,4-hi]indol-11(8aH)-yl)-2-methylbutanoate (110.5 mg, 0.28 mmol) was dissolved in THF (0.5 mL). 4-Fluorophenylmagnesium bromide (1.4 mL, 1.4 mmol) was added as a 1M solution in THF. The reaction was stirred at room temperature for 20 hrs. The reaction was quenched with 1M HCl (5 mL). The reaction was extracted with $CH_2Cl_2$ (3×15 mL). The combined organic layers were washed with brine, dried, and concentrated to afford 125 mg of a viscous oil. This crude material was purified by column chromatography to afford the title compound (72.9 mg, 50%) as a light-yellow oil. $^1$H NMR ($CDCl_3$, 300 MHz) δ7.61–7.68 (2H, m), 7.46–7.51 (2H, m), 6.8–7.1 (6H, m), 6.5–6.7 (2H, m), 3.7–4.0 (1H, m), 3.4–3.7 (1H, m), 3.1–3.4 (2H, m), 2.5–3.1 (5H, m), 2.3–2.45 (1H, m), 1.7–2.2 (8H, m), 1.2–1.4 (1H, m), 0.88 (3H, d, 7.0 Hz). CI MS (NH3): 521 (base, M+H)

Example 487

4-(6,7,9,10,12,12a-hexahydro-5H-pyrido[4,3-b][1,4]thiazepino[2,3,4-hi]indol-11(8aH)-yl)-1,1,-bis(4-chlorophenyl)-2-methyl-1-butanol 4-(6,7,9,10,12,12a-Hexahydro-5H-pyrido[4,3-b][1,4]thiazepino[2,3,4-hi]indol-11(8aH)-yl)-1,1,-bis(4-chlorophenyl)-2-methyl-1-butanol was prepared by the same general method as example 486 from methyl 4-((8aS,12aR)-6,7,9,10,12,12a-hexahydro-5H-pyrido[4,3b][1,4]thiazepino[2,3,4-hi]indol-11(8aH)-yl)-2-methylbutanoate (108 mg, 0.36 mmol) and 4-chlorophenylmagnesium bromide (1.8 mL, 1.8 mmol) to afford the title compound (106.9 mg, 54%) as a pale yellow amorphous solid. $^1$H NMR ($CDCl_3$, 300 MHz) δ7.5–7.7 (2H, m), 7.2–7.5 (4H, m), 7.15–7.25 (2H, m), 6.8–7.0 (2H, m), 6.5–6.7 (2H, m), 3.7–3.9 (1H, m), 3.4–3.65 (1H, m), 3.2–3.4 (2H, m), 2.5–3.1 (5H, m), 2.3–2.5 (1H, m), 1.7–2.2 (7H, m), 1.2–1.5 (2H, m), 0.88 (3H, d, 7.0 Hz). ESI MS: 553.2 (base, M+H)

Example 488 tert-butyl 1,2,6b,7,8,10,11,11a-octahydro-9H-azepino[4,5-b][1,4]thiazino[2,3,4-hi]indole-9-carboxylate Step A 1,2,8,9,10,11-Hexahydro-7H-azepino[4,5-b][1,4]thiazino[2,3,4-hi]indole hydrochloride was prepared from 2,3-dihydro-4H-1,4-benzothiazin-4-amine and hexahydro-4H-azepin-4-one hydrochloride following the procedure of example 471, step A to give the 1,2,8,9,10,11-hexahydro-7H-azepino[4,5-b][1,4]thiazino[2,3,4-hi]indole hydrochloride.

Step B—Typical Procedure for $NaBH_3CN$ Reduction

A solution the indole (40 mmol) in trifluoroacetic acid (135 mL) was stirred at room temperature for 1.5 h, cooled in an ice bath, and treated portionwise every 15 min over the course of three hours with sodium cyanoborohydride (200 mmol). Stirring was continued at room temperature for 4 h, then 6N hydrochloric acid (350 mL) was added and the resulting mixture was refluxed for 30 min and evaporated to dryness under reduced pressure. The residue was rendered strongly alkaline with 1 N NaOH to pH=10 and the mixture was extracted with dichloromethane (3×400 mL). The combined extracts were dried with sodium sulfate and concentrated to a solid. This solid was carried on without further purification and redissolved in dichloromethane (1.2 L). A solution of 1 N NaOH (200 mL) was added, followed with $Boc_2O$ (1 eq). The reaction mixture was stirred overnight, the organic layer separated, dried over $Na_2SO_4$ and concentrated to a residue which upon trituration with Ether/Hexanes (1:1) affords the desired product.

The title compound (1.15 g, 62%) was prepared from 1,2,8,9,10,11-hexahydro-7H-azepino[4,5-b][1,4]thiazino[2,3,4-hi]indole hydrochloride (1.85 g, 5.37 mmol) using the general procedure described above. $^1$H NMR ($CDCl_3$, 300 MHz) δ1.49 (br-s, 9H), 1.83–2.15 (m, 4H), 2.98–3.13 (m, 2H), 3.34–3.61 (m, 7H), 3.70–3.81 (m, 1H), 6.59–6.65 (m, 1H), 6.76–6.85 (m,2H) ppm.

Example 489

4-(6,7,9,10,12,12a-hexahydro-5H-pyrido[4,3-b][1,4]thiazino[2,3,4-hi]indol-11(8aH)-yl)-1-(4-fluorophenyl)-2-methyl-1-butanone Step A N-O-Dimethylhydroxylamine hydrochloride (1.11 g, 11.4 mmol) was dissolved in toluene (30 mL). This solution was cooled to 0° C., and a 2M solution of $AlMe_3$ (8.5 mL, 17 mmol) in toluene was added. The reaction was warmed to room temperature and stirred for 1 h. The reaction was then re-cooled to 0° C., and then methyl 4-(6,7,9,10,12,12a-hexahydro-5H-pyrido[4,3-b][1,4]thiazepino[2,3,4-hi]indol-11(8aH)-yl)-2-methylbutanoate (2.05 g, 5.71 mmol was added as a solution in toluene (20 mL). The reaction was stirred at room temperature for 1 hr, and then at 4° C. for 18 hrs. The reaction was warmed to room temperature and stirred for 2 hrs. More N-O-dimethylhydroxylamine hydrochloride (277 mg, 2.83 mmol) and $AlMe_3$ (1.4 mL, 2.8 mmol) were added. The reaction was stirred 2 more hrs at rt. It was cooled back to 0° C. and quenched with 1M aqueous tartaric acid (25 mL). The layers were separated, and the aqueous was extracted with $CHCl_3$ (3×15 mL). The combined organic layers were washed with brine, dried, and concentrated to afford 3.0 g of an amorphous solid. The crude product was purified by column chromatography (5, 7% MeOH/$CH_2Cl_2$) to afford 4-(6,7,9,10,12,12a-hexahydro-5H-pyrido[4,3-b][1,4]thiazepino[2,3,4-hi]indol- 11(8aH)-yl)-N-methoxy-N,2-dimethylbutanamide (1.81 g, 81%) as a light-yellow amorphous solid.

Step B 4-(6,7,9,10,12,12a-Hexahydro-5H-pyrido[4,3-b][1,4]thiazepino[2,3,4-hi]indol-11(8aH)-yl)-N-methoxy-N,2-dimethylbutanamide (109.9 mg, 0.28 mmol) was dissolved in THF (0.5 mL). 4-fluorophenylmagnesium bromide (1.41 mL, 1.41 mmol) was added as a 1M solution in THF. The reaction was stirred at room temperature for 18 hrs. More THF (1 mL) and 4-fluorophenylmagnesium bromide (1.41 mL, 1.41 mmol) were added. The reaction was stirred for 2 more hrs and then it was quenched with 1M HCl (3 mL). The layers were separated, and then the aqueous was basified with 1M NaOH (aq) until pH=14. The aqueous phase was extracted with $CH_2Cl_2$ (3×10 mL). The combined organic layers were washed with brine, dried, and concentrated to afford 167.7 mg of a brown oil. This material was purified by column chromatography (5, 7, 10% MeOH/CH2Cl2) to afford the title compound (36.4 mg, 31%) as a light-yellow amorphous solid. $^1$H NMR ($CDCl_3$, 300 MHz) δ7.9–8.1 (2H, m), 7.0–7.2 (2H, m), 6.93 (1H, d, 7.7 Hz), 6.7–6.9 (1H, m), 6.5–6.6 (1H, m), 3.6–3.9 (1H, m), 3.4–3.6 (2H, m), 2.7–3.2 (4H, m), 2.3–2.7 (2H, m), 1.7–2.3 (7H, m), 1.18 (3H, d, 7.0 Hz). ESI MS: 425.3 (base, M+H).

Example 490

4-(6,7,9,10,12,12a-hexahydro-5H-pyrido[4,3-b][1,4]thiazino[2,3,4-hi]indol-11(8aH)-yl)-1-(4-fluoro-2-methoxyphenyl)-2-methyl-1-butanone 4-(6,7,9,10,12,12a-Hexahydro-5H-pyrido[4,3b][1,4]thiazepino[2,3,4-hi]indol-11(8aH)-yl)-N-methoxy-N,2-dimethylbutanamide (48 mg, 0.12 mmol) was dissolved in THF (0.5 mL). 4-Fluoro-2-methoxyphenylmagnesium bromide (0.62 mL, 0.62 mmol) was added as a 1M solution in THF. The reaction was stirred at room temperature for 8 hrs, and then more 4-fluoro-2-methoxyphenylmagnesium bromide (0.62 mL, 0.62 mmol) was added. The reaction was stirred for 18 hrs, and then quenched with 1M HCl (3 mL). The layers were separated, and the aqueous was basified with 1M NaOH until pH=14. The aqueous was extracted with $CH_2Cl_2$ (3×10 mL). The combined organic layers were washed with brine, dried and concentrated to afford 65 mg of a brown material. This crude product was purified by column chromatography (5, 7, 10% MeOH/$CH_2Cl_2$) to afford the title compound (45 mg, 82%) as light-yellow amorphous solid. $^1$H NMR (CDCl3, 300 MHz) δ7.27–7.32 (1H, m), 7.09–7.15 (1 H, m), 6.80–6.95 (3H, m), 6.57–6.62 (1H, m), 3.7–2.9 (4H, m),3.3–3.6 (3H, m), 3.1–3.3 (1H, m), 2.8–3.1 (3H, m), 2.5–2.7 (2H, m), 1.7–2.4 (10H, m), 1.4–1.7 (1H, m), 1.13 (3H, d, 6.9 Hz). CI MS: (NH3): 455 (base, M+H).

Example 491

4-(6,7,9,10,12,12a-hexahydro-5H-pyrido[4,3-b][1,4]thiazino[2,3,4-hi]indol-11(8aH)-yl)-1-(4-fluoro-3-methylphenyl)-2-methyl-1-butanone 4-(6,7,9,10,12,12a-Hexahydro-5H-pyrido[4,3-b][1,4]thiazino[2,3,4-hi]indol-11(8aH)-yl)-1-(4-fluoro-3-methylphenyl)-2-methyl-1-butanone was prepared by the same general method as example 489, step B from 4-(6,7,9,10,12,12a-hexahydro-5H-pyrido[4,3-b][1,4]thiazepino[2,3,4-hi]indol-11(8aH)-yl)-N-methoxy-N,2-dimethylbutanamide (108.2 mg, 0.28 mmol) and 4-fluoro-3-methylphenylmagnesium bromide (1.39 mL, 1.39 mmol) to afford the title compound (45.6 mg, 37%) after chromatographic purification. $^1$H NMR (CDCl3, 300 MHz) δ7.82–7.84 (2H, m), 7.05–7.080 (1 H, m), 6.91–6.94 (1H, m), 6.82–6.85 (1H, m), 6.59–6.60 (1H, m), 3.4–3.9 (4H, m), 2.8–3.2 (4H, m), 2.4–2.7 (2H, m), 1.7–2.4 (13H, m), 1.17 (3H, d, 7.0 Hz). ESI MS: 439.3 (M+H).

Example 492

4-(6,7,9,10,12,12a-hexahydro-5H-pyrido[4,3-b][1,4]thiazepino[2,3,4-hi]indol-11(8aH)-yl)-2-methyl-1-(2-methylphenyl)-1-butanone 4-(6,7,9,10,12,12a-Hexahydro-5H-pyrido[4,3-b][1,4]thiazepino[2,3,4-hi]indol-11(8aH)-yl)-N-methoxy-N,2-dimethylbutanamide (92.2 mg, 0.31 mmol) was dissolved in THF (0.5 mL). 2-Methylphenylmagnesium bromide (0.77 mL, 0.77 mmol) was added as a 1M solution in THF. The reaction was stirred for 18 hrs, and then more 2-methylphenylmagnesium bromide (0.39 mL, 0.39 mmol) was added. The reaction was stirred for another 24 hrs, and then quenched with 1M HCl (3 mL). The layers were separated, and the aqueous was basified with 1M NaOH until pH=14. The aqueous was extracted with $CH_2Cl_2$ (3×10 mL). The combined organic layers were washed with brine, dried and concentrated to afford 105 mg of a brown material. This crude product was purified by column chromatography (5, 7, 10% MeOH/$CH_2Cl_2$) to afford the title compound (73.2 mg, 56%) as light-yellow amorphous solid. $^1$H NMR (CDCl3, 300 MHz) δ7.59–7.64 (1H, m), 7.32–7.38 (1 H, m), 7.20–7.26 (1H, m), 7.20–7.22 (1H, m), 6.9–7.0 (1H, m), 6.8–6.9 (1H, m), 6.5–6.7 (1H, m), 3.3–3.9 (3H, m), 3.1–3.3 (1H, m), 2.8–3.1 (3H, m), 1.4–2.8 (15H, m), 1.14 (3H, d, 7.0 Hz). ESI MS: 421.3 (base, M+H).

Example 493

4-(6,7,9,10,12,12a-hexahydro-5H-pyrido[4,3-b][1,4]thiazepino[2,3,4-hi]indol-11(8aH)-yl)-2-methyl-1-phenyl-1-butanone 4-(6,7,9,10,12,12a-Hexahydro-5H-pyrido[4,3-b][1,4]thiazepino[2,3,4-hi]indol-11(8aH)-yl)-N-methoxy-N,2-dimethylbutanamide (52.5 mg, 0.13 mmol) was dissolved in THF (0.5 mL). Phenylmagnesium bromide (0.22 mL, 0.66 mmol) was added as a 1M solution in THF. The reaction was stirred at room temperature for 18 hrs, and then quenched with 1M HCl (3 mL). The layers were separated, and the aqueous was basified with 1M NaOH until pH=14. The aqueous was extracted with $CH_2Cl_2$ (3×10 mL). The combined organic layers were washed with brine, dried and concentrated to afford 75 mg of a brown material. This crude product was purified by column chromatography (5, 7, 10% MeOH/$CH_2Cl_2$) to afford the title compound (14.1 mg, 27%) as light-yellow amorphous solid. $^1$H NMR (CDCl3, 300 MHz) δ7.95–7.99 (2H, m), 7.42–7.55 (3 H, m), 6.92 (1H, d, 8.1 Hz), 6.84 (1H, d, 6.6 Hz), 6.77 (1H, d, 6.6 Hz), 6.56–6.63 (1H, m), 3.4–3.7 (3H, m), 2.4–3.2 (5H, m), 1.5–2.4 (11H, m), 1.19 (3H, d, 7.0 Hz). ESI MS: 421.3 (base, M+H). CI MS (NH3): 407 (base, M+H).

Example 494

1-(2-aminophenyl)-4-((6bR,10aS)-1,2,6b,9,10,10a-hexahydro[1,4]oxazino[2,3,4-hi]pyrido[4,3-b]indol-8(7H)-yl)-1-butanone The title compound was isolated as a yellow oil (105 mg, 41%) according to the method of Example 286, Step C from (6bR,10aS)-1,2,6b,7,8,9,10,10a-octahydro[1,4]oxazino[2,3, 4-hi]pyrido[4,3-b]indole (150 mg, 0.68 mmol) and 1-(2-aminophenyl)-4-chloro-1-butanone (274 mg, 1.38 mmol). $^1$H NMR ($CDCl_3$) δ1.90–2.00 (m, 3H), 2.03–2.11 (m, 1H), 2.29–2.38 (m, 1H), 2.39–2.47 (m, 2H), 2.67–2.80 (m, 2H), 2.91–3.04 (m, 4H), 3.12–3.21 (m, 1H), 3.24–3.35 (m, 2H), 4.40–4.46 (m, 2H), 6.26 (br-s, 2H), 6.61–6.73 (m, 4H), 7.23–7.29 (m, 2H), 7.77 (dd, 1H, J=1.3, 8.3 Hz) ppm.

Example 495

1-(2-aminophenyl)-4-((6bS,10aR)-1,2,6b,9,10,10a-hexahydro[1,4]oxazino[2,3,4-hi]pyrido[4,3-b]indol-8(7H)-yl)-1-butanone The title compound was isolated as a yellow oil (115 mg, 44%) according to the method of Example 286, Step C from (6bS,10aR)-1,2,6b,7,8,9,10,10a-octahydro[1,4]oxazino[2,3,4-hi]pyrido[4,3-b]indole (150 mg, 0.68 mmol) and 1-(2-aminophenyl)-4-chloro-1-butanone (274 mg, 1.38 mmol). $^1$H NMR ($CDCl_3$) δ1.90–2.00 (m, 3H), 2.03–2.11 (m, 1H), 2.29–2.38 (m, 1H), 2.39–2.47 (m, 2H), 2.67–2.80 (m, 2H), 2.91–3.04 (m, 4H), 3.12–3.21 (m, 1H), 3.24–3.35 (m, 2H), 4.40–4.46 (m, 2H), 6.26 (br-s, 2H), 6.61–6.73 (m, 4H), 7.23–7.29 (m, 2H), 7.77 (dd, 1H, J=1.3, 8.3 Hz) ppm.

Example 496

(6bR,10aS)-8-[3-(1H-indazol-3-yl)propyl]-1,2,6b,7,8,9,10,10a-octahydro[1,4]oxazino[2,3,4-hi]pyrido[4,3-b]indole The title compound was isolated as a yellow oil (54 mg, 100%) according to the method of Example 286, Step C from (6bR,10aS)-1,2,6b,7,8,9,10,10a-octahydro[1,4]oxazino[2,3,4-hi]pyrido[4,3-b]indole (31 mg, 0.14 mmol) and 3-(3-chloropropyl)-1H-indazole (56 mg, 0.28). $^1$H NMR ($CDCl_3$) δ1.92–2.17 (m, 5H), 2.29–2.40 (m, 1H), 2.47–2.59 (m, 2H), 2.73–2.81 (m, 2H), 2.91–3.07 (m, 3H), 3.21–3.34 (m, 3H), 4.42–4.47 (m, 2H), 6.59–6.69 (m, 3H), 7.13 (t, 1H, J=7.0 Hz), 7.33–7.45 (m, 2H), 7.70 (d, 1H, J=8.1 Hz) ppm.

Example 497

(6bR,10aS)-5-(2-chlorophenyl)-1,2,6b,9,10,10a-hexahydro[1,4]oxazino[2,3,4-hi]pyrido[4,3-b]indole Step A To a solution of tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 2-chlorophenylboronic acid (156 mg, 2.0 mmol) in DME (30 mL) was added 2 M $Na_2CO_3$ (10 mL). The solution was degassed for 10 m at 40° C. $Pd(PPh_3)_4$ (22 mg, 0.02 mmol) was added in one portion to the solution, and the reaction mixture was degassed again for 10 m at the same temperature. The reaction mixture was stirred at 75° C. under $N_2$ for 20 h, then diluted with $Et_2O$ (100 mL), washed with brine (100 mL), dried over $MgSO_4$ and concentrated in vacuo. Column chromatography afforded tert-butyl(6bR,10aS)-5-(2-chlorophenyl)-1,2,6b,9,10,10a-hexahydro[1,4]oxazino[2,3,4-hi]pyrido[4,3-b]indole-8(7H)-carboxylate (179 mg, 84%) as a colorless oil.

Step B

To a solution of tert-butyl(6bR,10aS)-5-(2-chlorophenyl)-1,2,6b,9,10,10a-hexahydro[1,4]oxazino[2,3,4-hi]pyrido[4,3-b]indole-8(7H)-carboxylate in $CH_2Cl_2$ (2.4 mL) was added TFA (0.6 mL) and the reaction mixture was stirred for 3 h. The reaction mixture was concentrated in vacuo, diluted with $CH_2Cl_2$ (100 mL), washed with $NaHCO_3$ (100 mL) and brine (100 mL), dried over $MgSO_4$ and concentrated in vacuo to afford the title compound (130 mg, 95%) as a light yellow oil. $^1$H NMR ($CDCl_3$) δ1.78–1.99 (m, 2H), 2.11 (br-s, 1H), 2.76–2.95 (m, 4H), 3.09–3.20 (m, 2H), 2.32–2.39 (m, 1H), 2.41–2.46 (m, 1H), 4.44–4.52 (m, 2H), 6.76 (dd, 1H, J=1.5, 13.2 Hz), 7.19–7.36 (m, 4H), 7.42 (dd, 1H, J=1.4, 7.7 Hz) ppm.

Example 498

(6bR,10aS)-5-(3-chlorophenyl)-1,2,6b,7,8,9,10,10a-octahydro[1,4]oxazino[2,3,4-hi]pyrido[4,3-b]indole The title compound was afforded as a yellow oil (102 mg, 71%) according to the method of Example 497, Steps A, B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 3-chlorophenylboronic acid (156 mg, 1.0 mmol). $^1$H NMR ($CDCl_3$) δ1.84–1.99 (m, 2H), 2.73–2.86 (m, 2H), 2.91–3.00 (m, 2H), 3.10–3.31 (m, 3H), 3.32–3.42 (m, 2H), 4.43–4.49 (m, 2H), 6.88 (dd, 2H, J=1.3, 8.1 Hz), 7.20–7.48 (m, 4H) ppm.

Example 499

(6bR,10aS)-5-(3-fluorophenyl)-1,2,6b,7,8,9,10,10a-octahydro[1,4]oxazino[2,3,4-hi]pyrido[4,3-b]indole The title compound was afforded as a yellow oil (110 mg, 69%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 3-fluorophenylboronic acid (140 mg, 1.0 mmol). $^1$H NMR ($CDCl_3$) δ1.89–2.00 (m, 2H), 2.74–2.87 (m, 3H), 2.92–2.99 (m, 2H), 3.16–3.27 (m, 2H), 3.31–3.42 (m, 2H), 4.48 (dd, 2H, J=2.2, 6.2 Hz), 6.87 (d, 1H, J=1.4 Hz), 6.91–6.99 (m, 2H), 7.16–7.37 (m, 3H) ppm.

Example 500

(6bR,10aS)-5-(4-chlorophenyl)-1,2,6b,7,8,9,10,10a-octahydro[1,4]oxazino[2,3,4-hi]pyrido[4,3-b]indole The title compound was afforded as a yellow oil (126 mg, 77%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 4-chlorophenylboronic acid (156 mg, 1.0 mmol). $^1$H NMR ($CDCl_3$) δ1.87–2.07 (m, 3H), 2.73–2.83 (m, 2H), 2.86–2.90 (m, 2H), 3.07–3.19 (m, 2H), 3.31–3.40 (m, 2H), 4.45–4.52 (m, 2H), 6.83 (s, 2H), 6.90 (s, 1H), 7.33 (d, 2H, J=8.5 Hz), 7.42 (d, 2H, J=8.4 Hz) ppm.

Example 501

(6bR,10aS)-5-(4-fluorophenyl)-1,2,6b,7,8,9,10,10a-octahydro[1,4]oxazino[2,3,4-hi]pyrido[4,3-b]indole The title compound was afforded as a yellow oil (109 mg, 70%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 4-fluorophenylboronic acid (140 mg, 1.0 mmol). $^1$H NMR ($CDCl_3$) δ1.78–2.14 (m, 3H), 2.70–2.82 (m, 2H), 2.87–2.95 (m, 2H), 3.06–3.20 (m, 2H), 3.32–3.43 (m, 2H), 4.44–4.50 (m, 2H), 6.82 (d, 1H, J=1.5 Hz), 6.88 (d, 1H, J=1.5 Hz) 7.01–7.10 (m, 2H), 7.40–7.47 (m, 2H) ppm.

Example 502

(6bR,10aS)-5-(2,3-dichlorophenyl)-1,2,6b,7,8,9,10,10a-octahydro[1,4]oxazino[2,3,4-hi]pyrido[4,3-b]indole The title compound was afforded as a yellow oil (148 mg, 52%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 2,3-dichlorophenylboronic acid (191 mg, 1.0 mmol). $^1$H NMR ($CDCl_3$) δ1.77–1.92 (m, 2H), 2.69–2.84 (m, 3), 2.86–2.91 (m, 2H), 3.04–3.13 (m, 2H), 3.24–3.30 (m, 1H), 3.32–3.40 (m, 1H), 4.38–4.44 (m, 2H), 6.65 (dd, 2H, J=1.4, 12.4 Hz), 7.06–7.19 (m, 2H), 7.29–7.34 (m, 1H) ppm.

Example 503

(6bR,10aS)-5-(2,3-difluorophenyl)-1,2,6b,7,8,9,10,10a-octahydro[1,4]oxazino[2,3,4-hi]pyrido[4,3-b]indole The title compound was afforded as a yellow oil (58 mg, 36%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 2,3-difluorophenylboronic acid (158 mg, 1.0 mmol). $^1$H NMR ($CDCl_3$) δ1.82–2.07 (m, 3H), 2.75–2.96 (m, 4H), 3.09–3.21 (m, 2H), 3.35–3.46 (m, 2H), 4.43–4.49 (m, 2H), 6.83 (t, 1H, J=1.5 Hz), 6.89 (t, 1H, J=1.5 Hz), 7.03–7.16 (m, 3H) ppm.

Example 504

(6bR,10aS)-5-(3,5-dichlorophenyl)-1,2,6b,7,8,9,10,10a-octahydro[1,4]oxazino[2,3,4-hi]pyrido[4,3-b]indole The title compound was afforded as a yellow oil (152 mg, 84%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 3,5-dichlorophenylboronic acid (190 mg, 1.0 mmol). $^1$H NMR ($CDCl_3$) δ1.85–1.98 (m, 2H), 2.04 (br-s, 1H), 2.69–2.91 (m, 4H), 3.04–3.17 (m, 2H), 3.30–3.41 (m, 2H), 4.43–4.48 (m, 2H), 6.85 (dd, 2H, J=1.5, 10.9 Hz), 7.22 (t, 1H, J=1.8 Hz), 7.36 (d, 2H, J=1.7 Hz) ppm.

Example 505

(6bR,10aS)-5-(3,5-difluorophenyl)-1,2,6b,7,8,9,10,10a-octahydro[1,4]oxazino[2,3,4-hi]pyrido[4,3-b]indole The title compound was afforded as a yellow oil (129 mg, 78%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 3,5-difluorophenylboronic acid (158 mg, 1.0 mmol). MS (ESI): 329 (base, M +H).

Example 506

(6bR,10aS)-5-(3,4-dichlorophenyl)-1,2,6b,7,8,9,10,10a-octahydro[1,4]oxazino[2,3,4-hi]pyrido[4,3-b]indole The title compound was afforded as a yellow oil (126 mg, 70%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 3,4-dichlorophenylboronic acid (191 mg, 1.0 mmol). $^1$H NMR ($CDCl_3$) δ1.81–2.09 (m, 3H), 2.69–2.88 (m, 4H), 3.04–3.18 (m, 2H), 3.29–3.41 (m, 2H), 4.43–4.49 (m, 2H), 6.85 (dd, 2H, J=1.4, 10.5 Hz), 7.31 (dd, 1H, J=2.2, 8.5 Hz), 7.41 (d, 1H, J=8.5 Hz), 7.57 (d, 1H, J=1.8 Hz) ppm.

Example 507

(6bR,10aS)-5-(3,4-difluorophenyl)-1,2,6b,7,8,9,10,10a-octahydro[1,4]oxazino[2,3,4-hi]pyrido[4,3-b]indole The title compound was afforded as a yellow oil (115 mg, 70%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 3,4-difluorophenylboronic acid (156 mg, 1.0 mmol). $^1$H NMR ($CDCl_3$) δ1.80–1.99 (m, 2H), 2.28 (br-s, 1H), 2.70–2.83 (m, 2H), 2.84–2.91 (m, 2H), 3.04–3.19 (m, 2H), 3.31–3.43 (m, 2H), 4.45–4.50 (m, 2H), 6.79 (d, 1H, J=1.3 Hz), 6.86 (d, 1H, J=1.3 Hz), 7.09–7.31 (m, 3H) ppm.

Example 508

(6bR,10aS)-5-(3-chloro-4-fluorophenyl)-1,2,6b,7,8,9,10,10a-octahydro[1,4]oxazino[2,3,4-hi]pyrido[4,3-b]indole The title compound was afforded as a yellow oil (160 mg, 93%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 3-chloro-4-fluorophenylboronic acid (174 mg, 1.0 mmol). $^1$H NMR ($CDCl_3$) δ1.87–1.96 (m, 2H), 2.70–2.84 (m, 2H), 2.91–3.01 (m, 2H), 3.09–3.24 (m, 3H), 3.29–3.42 (m, 2H), 4.46–4.51 (m, 2H), 6.78 (s, 1H), 6.85 (d, 1H, J=1.1 Hz), 7.11 (t, 1H, J=8.6 Hz), 7.29–7.33 (m, 1H), 7.49 (dd, 1H, J=2.2, 7.0 Hz) ppm.

Example 509

(6bR,10aS)-5-(4-chloro-2-fluorophenyl)-1,2,6b,7,8,9,10,10a-octahydro[1,4]oxazino[2,3,4-hi]pyrido[4,3-b]indole The title compound was afforded as a yellow oil (149 mg, 85%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 4-chloro-2-fluorophenylboronic acid (174 mg, 1.0 mmol). $^1$H NMR ($CDCl_3$) δ1.82–1.99 (m, 2H), 2.69–2.86 (m, 3H), 2.92–2.99 (m, 2H), 3.13–3.23 (m, 2H), 3.35–3.46 (m, 2H), 4.44–4.49 (m, 2H), 6.80 (t, 1H, J=1.5 Hz), 6.85 (d, 1H, J=1.4 Hz), 7.10–7.19 (m, 2H), 7.26–7.33 (m, 1H) ppm.

Example 510

(6bR,10aS)-5-(2-chloro-4-fluorophenyl)-1,2,6b,7,8,9,10,10a-octahydro[1,4]oxazino[2,3,4-hi]pyrido[4,3-b]indole The title compound was afforded as a yellow oil (57 mg, 33%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 2-chloro-4-fluorophenylboronic acid (174 mg, 1.0 mmol). $^1$H NMR ($CDCl_3$) δ1.77–1.91 (m, 2H), 2.59–2.79 (m, 3H), 2.91–2.96 (m, 2H), 3.03–3.13 (m, 2H), 3.24–3.39 (m, 2H), 4.38–4.45 (m, 2H), 6.63 (d, 2H, J=14.3 Hz), 6.89–6.97 (m, 1H), 7.08–7.12 (m, 1H), 7.16–7.22 (m, 1H) ppm. MS (ESI): 345 (base, M+H).

Example 511

(6bR,10aS)-5-(2,5-dichlorophenyl)-1,2,6b,7,8,9,10,10a-octahydro[1,4]oxazino[2,3,4-hi]pyrido[4,3-b]indole The title compound was afforded as a yellow oil (58 mg, 32%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 2,5-dichlorophenylboronic acid (156 mg, 1.0 mmol). $^1$H NMR ($CDCl_3$) δ1.81–1.99 (m, 2H), 2.39 (br-s, 1H), 2.70–2.92 (m, 4H), 3.08–3.19 (m, 2H), 3.35–3.39 (m, 1H), 3.43–3.48 (m, 1H), 4.43–4.48 (m, 2H), 6.71 (d, 1H, J=1.3 Hz), 6.75 (d, 1H, J=1.3 Hz), 7.15–7.20 (m, 1H), 7.29–7.39 (m, 2H) ppm.

Example 512

(6bR,10aS)-5-(2,6-dichlorophenyl)-1,2,6b,7,8,9,10,10a-octahydro[1,4]oxazino[2,3,4-hi]pyrido[4,3-b]indole To a solution of tert-butyl(6bR,10aS)-5-bromo-1,2,6b,7,8,9,10,10a-octahydro[1,4]oxazino[2,3,4-hi]pyrido[4,3-b]indole (200 mg, 0.50 mmol) in DMF (10 mL) under $N_2$ was added $PdCl_2(PPh_3)_2$ (35 mg, 0.05 mmol), CuBr (14 mg, 0.1 mmol), and $PPh_3$ (26 mg, 0.1 mmol). This was degassed for 10 m at 60° C., and to this was added a solution of (2,6-chlorolphenyl)(trimethyl)stannane (230 mg, 0.75 mmol) in DMF (2 mL). This was stirred for 30 m. To the reaction mixture was added a solution of (2,6-dichlorophenyl(trimethyl)stannane (116 mg, 0.37 mmol) in DMF (1 mL), and this was heated at 140° C. for 10 m. To this was then added another portion of (2,6-dichlorophenyl)(trimethyl)stannane (116 mg, 0.37 mmol) in DMF (1 mL), and the reaction mixture was stirred at 140° C. for 1 h. The reaction mixture was cooled to 20° C., diluted with $Et_2O$ (100 mL) and washed with $H_2O$. The aqueous solution was extracted with $Et_2O$ (3×50 mL), and the combined organic solution was washed with brine (50 mL), dried over $MgSO_4$ and concentrated in vacuo. Column purification (hexanes:EtOAc 4:1) afforded tert-butyl(6bR,10aS)-5-(2,6-dichlorophenyl)-1,2,6b,9,10,10a-hexahydro[1,4]oxazino[2,3,4-hi]pyrido[4,3-b]indole-8(7H)-carboxylate (155 mg, 67%) as a colorless oil. The title compound was afforded as a yellow oil (125 mg, 100%) according to the method of Example 497 Step B from tert-butyl(6bR,10aS)-5(2,6-dichlorophenyl)-1,2,6b,9,10,10a-hexahydro[1,4]oxazino[2,3,4-hi]pyrido[4,3-b]indole-8(7H)-carboxylate (155 mg, 0.43 mmol). MS (ESI): 361 (base, M+H).

Example 513

(6bR,10aS)-5-[2-trifluoromethyl)phenyl]-1,2,6b,7,8,9,10,10a-octahydro[1,4]oxazino[2,3,4-hi]pyrido[4,3-b]indole The title compound was afforded as a yellow oil (127 mg, 71%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 2-(trifluoromethyl) phenylboronic acid (190 mg, 1.0 mmol). $^1$H NMR ($CDCl_3$) δ1.86–2.02 (m, 2H), 2.72–2.87 (m, 2H), 2.92–2.98 (m, 2H), 3.10–3.21 (m, 2H), 3.27–3.46 (m, 3H), 4.41–4.47 (m, 2H), 6.63 (d, 2H, J=11.1 Hz), 7.31 (d, 1H, J=7.7 Hz), 7.39 (t, 1H, J=7.5 Hz), 7.49 (t, 1H, J=7.2 Hz), 7.69 (d, 1H, J=8.0 Hz) ppm.

Example 514

(6bR,10aS)-5-(4-(trifluoromethyl)phenyl)-1,2,6b,7,8,9,10,10a-octahydro[1,4]oxazino[2,3,4-hi]pyrido[4,3-b]indole The title compound was afforded as a yellow oil (130 mg, 73%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 4-(trifluoromethyl) phenyl boronic acid (190 mg, 1.0 mmol). $^1$H NMR ($CDCl_3$) δ1.91–2.02 (m, 2H), 2.66 (br-s, 1H), 2.71–2.89 (m, 2H), 2.94–3.01 (m, 2H), 3.18–3.28 (m, 2H), 3.35–3.44 (m, 2H), 4.51 (dd, 2H, J=2.6, 6.3 Hz), 6.91 (d, 1H, J=1.3 Hz), 6.98 (d, 1H, J=1.3 Hz), 7.58–7.65 (m, 4H) ppm.

Example 515

(6bR,10aS)-5-(2,4-bis(trifluoromethyl)phenyl)-1,2,6b,7,8,9,10,10a-octahydro[1,4]oxazino[2,3,4-hi]pyrido[4,3-b]indole The title compound was afforded as a yellow oil (86 mg, 40%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 2,4-bis (trifluoromethyl)phenylboronic acid (258 mg, 1.0 mmol). MS (ESI): 429 (base, M+H).

Example 516

(6bR,10aS)-5-(2-chloro-4-(trifluoromethyl)phenyl)-1,2,6b,7,8,9,10,10a-octahydro[1,4]oxazino[2,3,4-hi]pyrido[4,3-b]indole The title compound was afforded as a yellow oil (130 mg, 63%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 2-chloro-4-(trifluoromethyl)phenylboronic acid (224 mg, 1.0 mmol). $^1$H NMR ($CDCl_3$) δ1.89–2.05 (m, 2H), 2.74–2.90 (m, 3H), 2.95–3.01 (m, 2H), 3.16–3.25 (m, 2H), 3.36–3.42 (m, 1H), 3.49–3.54 (m, 1H), 4.50–4.57 (m, 2H), 6.75 (d, 1H, J=1.4 Hz), 6.80 (d, 1H, J=1.4 Hz), 7.44 (d, 1H, J=8.0 Hz), 7.52 (dd, 1H, J=1.1, 8.0 Hz), 7.71 (s, 1H) ppm. MS (ESI): 395 (base, M+H).

Example 517

(6bR,10aS)-5-(2-methoxyphenyl)-1,2,6b,7,8,9,10,10a-octahydro[1,4]oxazino[2,3,4-hi]pyrido[4,3-b]indole The title compound was afforded as a yellow oil (58 mg, 71%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)- carboxylate (100 mg, 0.25 mmol) and 2-methoxyphenylboronic acid (76 mg, 0.5 mmol). MS (ESI): 323 (base, M+H).

Example 518

(6bR,10aS)-5-(2,4-dimethoxyphenyl)-1,2,6b,7,8,9,10,10a-octahydro[1,4]oxazino[2,3,4-hi]pyrido[4,3-b]indole The title compound was afforded as a yellow oil (163 mg, 91%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 2,4-dimethoxyphenylboronic acid (182 mg, 1.0 mmol). MS (ESI): 353 (base, M+H).

Example 519

(6bR,10aS)-5-(5-isopropyl-2-methoxyphenyl)-1,2,6b,7,8,9,10,10a-octahydro[1,4]oxazino[2,3,4-hi]pyrido[4,3-b]indole The title compound was afforded as a yellow oil (140 mg, 77%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 2-methoxy-5-isopropylphenyl boronic acid (194 mg, 1.0 mmol). $^1$H NMR ($CDCl_3$) δ1.23–1.29 (m, 7H), 1.94–1.99 (m, 2H), 2.79–2.97 (m, 3H), 2.97–3.02 (m, 2H), 3.17–3.25 (m, 2H), 3.30–3.35 (m, 1H), 3.39–3.44 (m, 1H), 3.79 (s, 3H), 4.45–4.50 (m, 2H), 6.86–6.91 (m, 3H), 7.10–7.17 (m, 2H) ppm.

Example 520

(6bR,10aS)-5-(3-nitrophenyl)-1,2,6b,7,8,9,10,10a-octahydro[1,4]oxazino[2,3,4-hi]pyrido[4,3-b]indole The title compound was afforded as an orange oil (162 mg, 96%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 3-nitrophenylboronic acid (167 mg, 1.0 mmol). $^1$H NMR (DMSO-$D_6$) δ1.70–1.84 (m, 1H), 1.86–1.93 (m, 1H), 2.68–2.58 (m, 3H), 3.06–3.19 (m, 2H), 3.24–3.45 (m, 4H), 4.29–4.40 (m, 1H), 4.43–4.50 (m, 1H), 6.95 (d, 1H, J=1.4 Hz), 7.12 (d, 1H, 1.1 Hz), 7.63 (t, 1H, J=8.0 Hz), 7.98 (d, 1H, J=8.4 Hz), 8.06 (dd, 1H, J=1.8, 7.5 Hz), 8.26 (t, 1H, J=2.0 Hz) ppm.

Example 521

2-[(6bR,10aS)-1,2,6b,7,8,9,10,10a-octahydro[1,4]oxazino[2,3,4-hi]pyrido[4,3-b]indol-5-yl]benzaldehyde The title compound was afforded as a yellow oil (19 mg, 48%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (500 mg, 0.50 mmol) and 2-formylphenylboronic acid (380 mg, 1.0 mmol). MS (ESI): 321 (base, M+H).

Example 522

1-{2-[(6bR,10aS)-1,2,6b,7,8,9,10,10a-octahydro[1,4]oxazino[2,3,4-hi]pyrido[4,3-b]indole-5-yl]phenyl}ethanol Tert-butyl(6bR,10aS)-5-(2-formylphenyl)-1,2,6b,7,8,9,10,10a-octahydro[1,4]oxazino[2,3,4-hi]pyrido[4,3-b]indole-8(7H)-carboxylate was prepared as in Example 521. To a solution of this (30 mg, 0.07 mmol) in THF (1.5 mL) at −10° C. under $N_2$ was added 3 M $CH_3MgBr$ in $Et_2O$ (0.21 mL). This was stirred for 1 h and quenched with saturated $NH_4Cl$ (0.5 mL), diluted with $Et_2O$ (50 mL) and washed with brine (30 mL). The organic solution was dried over $MgSO_4$ and concentrated in vacuo to a colorless oil. To this were added $CH_2Cl_2$ (2.9 mL) and TFA (0.1 mL) successively, and the solution stirred for 30 m. The work-up was performed as in Example 497 to afford the title compound as a yellow oil (28 mg, 91%). MS (ESI): 337 (base, M+H).

Example 523

{2-[(6bR,10aS)-1,2,6b,7,8,9,10,10a-octahydro[1,4]oxazino[2,3,4-hi]pyrido[4,3-b]indole-5-yl]phenyl}methanol To a solution of tert-butyl(6bR,10aS)-5-(2-formylphenyl)-1,2,6b,7,8,9,10,10a-octahydro[1,4]oxazino[2,3,4-hi]pyrido[4,3-b]indole-8(7H)-carboxylate (30 mg, 0.07 mmol) in $CH_2Cl_2$ (1.5 mL) was added dropwise 1 M DIBAL in $CH_2Cl_2$ (0.11 mL, 0.11 mmol) at −78° C. under $N_2$. The reaction mixture was raised to 20° C. and 0.05 mL of MeOH was added to quench the reaction. The reaction mixture was filtered and concentrated in vacuo to a colorless oil. This was treated with $CH_2Cl_2$ and TFA according to the procedure of EXAMPLE 522 to afford the title compound (24 mg, 93%) as a yellow oil. $^1$H NMR ($CDCl_3$) δ1.84–1.97 (m, 2H), 2.57–2.82 (m, 4H), 2.89–2.99 (m, 2H), 3.05–3.21 (m, 2H), 3.23–3.56 (m, 2H), 3.38–3.45 (m, 2H), 4.56 (s, 1H), 6.57 (d, 1H, J=1.5 Hz), 6.62 (d, 1H, J=1.1 Hz), 7.20–7.31 (m, 3H), 7.41–7.45 (m, 1H) ppm. MS (ESI): 323 (base, M+H).

Example 524

2-[(6bR,10aS)-1,2,6b,7,8,9,10,10a-octahydro[1,4]oxazino[2,3,4-hi]pyrido[4,3-b]indole-5-yl]-5-methoxybenzaldehyde The title compound was afforded as a yellow oil (124 mg, 45%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (300 mg, 0.75 mmol) and 2-formyl-4-methoxyphenyl boronic acid (270 mg, 1.5 mmol), except that the de-protection procedure was performed as in Example 522. $^1$H NMR ($CDCl_3$) δ2.07–2.24 (m, 2H), 2.84–2.91 (m, 2H), 3.04–3.17 (m, 2H), 3.18–3.47 (m, 5H), 3.88 (s, 3H), 3.47–3.53 (m, 2H), 6.66 (dd, 2H, J=1.4, 6.2 Hz), 7.15 (dd, 1H, J=2.9, 8.4 Hz), 7.29–7.33 (m, 1H), 7.45 (d, 1H, J=2.6 Hz) ppm. MS (ESI): 351 (base, M+H).

Example 525

2-[(6bR,10aS)-1,2,6b,7,8,9,10,10a-octahydro[1,4]oxazino[2,3,4-hi]pyrido[4,3-b]indole-5-yl]phenol To a solution of (6bR,10aS)-5-(2-methoxyphenyl)-1,2,6b,7,8,9,10,10a-octahydro[1,4]oxazino[2,3,4-hi]pyrido[4,3-b]indole (20 mg, 0.06 mmol) in $CH_2Cl_2$ (4 mL) under $N_2$ was added a 0.91 M solution of $BBr_3$ in $CH_2Cl_2$ (0.41 mL, 0.37 mmol). The reaction mixture was stirred at 20° C. for 16 h, and then quenched with water (1 mL). The aqueous layer was basified with 1 N NaOH to pH 7, and the reaction mixture was extracted with $CH_2Cl_2$ (3×30 mL). The organic solution was then dried over $MgSO_4$ and concentrated in vacuo to afford the title compound as a yellow oil (10 mg, 50%). $^1$H NMR ($CDCl_3$) δ1.88–2.01 (m, 2H), 2.10–2.22 (m, 1H), 2.60–2.79 (m, 2H), 2.90–2.99 (m, 1H), 3.18–3.37 (m, 3H), 3.36–3.43 (m, 2H), 3.61–3.66 (m, 1H), 4.39–4.44 (m, 2H), 6.70–6.79 (m, 1H), 6.80–6.99 (m, 2H), 7.08–7.18 (m, 2H) ppm.

Example 526

(6bR,10aS)-5-(4-ethoxy-2-(trifluoromethyl)phenyl)-1,2,6b,7,8,9,10,10a-octahydro[1,4]oxazino[2,3,4-hi]pyrido[4,3-b]indole The title compound was afforded as a yellow oil (67 mg, 62%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (200 mg, 0.50 mmol) and 4-ethoxy-2-(trifluoromethyl)phenylboronic acid (117 mg, 1.0 mmol). $^1$H NMR ($CDCl_3$) δ1.35 (t, 3H, J=7.0 Hz), 1.80–1.91 (m, 2H), 2.46 (br-s, 1H), 2.61–2.78 (m, 2H), 2.83–2.90 (m, 2H), 3.01–3.13 (m, 2H), 3.22–3.30 (m, 1H), 3.31–3.36 (m, 1H), 3.99 (q, 2H, J=7.0 Hz), 3.35–4.41 (m, 2H), 6.48 (s, 1H), 6.52 (s, 1H), 6.91 (dd, 1H, J=2.7, 8.3 Hz), 7.10–7.14 (m, 2H) ppm. MS (ESI): 405 (base, M+H).

Example 527

(6bR,10aS)-5-(4-isopropoxy-2-(trifluoromethyl)phenyl)-1,2,6b,7,8,9,10,10a-octahydro[1,4]oxazino[2,3,4-hi]pyrido[4,3-b]indole The title compound was afforded as a yellow oil (110 mg, 96%) according to the method of Example 497, Steps A,B from tert-butyl(6bR,10aS)-5-bromo-1,2,6b,7,8,9,10,10a-octahydro[1,4]oxazino[2,3,4-hi]pyrido[4,3-b]indole-8(7H)-carboxylate (100 mg, 0.25 mmol) and 4-isopropoxy-2-(trifluoromethyl)phenylboronic acid (124 mg, 0.5 mmol). $^1$H NMR ($CDCl_3$) δ1.37 (d, 6H, J=6.3 Hz), 1.88–1.98 (m, 2H), 2.77–91 (m, 3H), 2.96–3.01 (m, 2H), 3.09–3.23 (m, 2H), 3.31–3.38 (m, 1H), 3.39–3.43 (m, 1H), 4.43–4.48 (m, 2H), 4.52–4.65 (m, 1H), 6.58 (s, 1H), 6.62 (s, 1H), 6.99 (dd, 1H, J=2.6, 8.4 Hz), 7.17–7.21 (m, 2H) ppm. MS (ESI): 419 (base, M+H).

Example 528

(6bR,10aS)-8-[3-(6-fluoro-1H-indazol-3yl)propyl]1,2,6b,7,8,9,10,10a-octahydro[1,4]oxazino[2,3,4-hi]pyrido[4,3-b]indole The title compound was prepared by the method of Example 355 Step B as a yellow oil (60 mg, 63%) from (6bR,10aS)-1,2,6b,7,8,9,10,10a-octahydro[1,4]oxazino-[2,3,4-hi]pyrido[4,3-b]indole (63 mg, 0.29 mmol) and 3-(3-chloropropyl)-6-fluoroindazole (93 mg, 0.43 mmol). $^1$H NMR ($CDCl_3$, 300 MHz) δ1.89–2.15 (m, 5H), 2.27–2.38 (m, 1H), 2.43–2.55 (m, 2H), 2.71–2.80 (m, 2H), 2.88–3.02 (m, 3H), 3.18–3.32 (m, 3H), 4.43 (dd, J=6.2, 1.8 Hz, 2H), 6.60–6.72 (m, 3H), 6.90 (dt, J=9.1, 2.2 Hz, 1H), 7.07 (dd, J=9.2, 1.9 Hz, 1H), 7.63 (dd, J=8.8, 5.1 Hz, 1H), 9.85–10.15 (br-s, 1H) ppm.

Example 529

1-(2-amino-4-fluorophenyl)-4-((±)-cis-1,2,6b,9,10,10a-hexahydro[1,4]oxazino[2,3,4-hi]pyrido[4,3-b]indol-8(7H)-yl)-1-butanone The title compound was prepared by the method of Example 361 as a red oil (11 mg, 24%) from (±)-cis-1,2,6b,7,8,9,10,10a-octahydro[1,4]oxazino-[2,3,4-hi]pyrido[4,3-b]indole (30 mg, 0.12 mmol) and 1-(2-amino-4-fluorophenyl)-4-chloro-1-butanone (51 mg, 0.24 mmol). $^1$H NMR ($CDCl_3$, 300 MHz) δ1.87–2.15 (m, 5H), 2.25–2.45 (m, 3H), 2.65–2.79 (m, 2H), 2.86–2.95 (m, 3H), 3.15–3.30 (m, 3H), 4.44 (dd, J=6.9, 2.2 Hz, 2H), 6.26–6.38 (m, 2H), 6.41–6.50 (br-s, 2H), 6.60–6.72 (m, 3H), 7.78 (dd, J=9.1, 6.6 Hz, 1H) ppm.

Example 530

1-(2-amino-4-fluorophenyl)-4-((6bR,10aS)-1,2,6b,9,10,10a-hexahydro[1,4]oxazino-[2,3,4-hi]pyrido[4,3-b]indol-8(7H)-yl)-1-butanone The title compound was prepared by the method of Example 355 Step B as a yellow oil (172 mg, 57%) from (6bR,10aS)-1,2,6b,7,8,9,10,10a-octahydro[1,4]oxazino[2,3,4-hi]pyrido[4,3-b]indole (165 mg, 0.76 mmol) and 1-(2-amino-4-fluorophenyl)-4-chloro-1-butanone (329 mg, 1.5 mmol). The title compound was spectroscopically identical to Example 529.

Example 531

4((±)-cis-1,2,6b,9,10,10a-hexahydro[1,4]oxazino[2,3,4-hi]pyrido[4,3-b]indol-8(7H)-yl)-1-(4-fluoro-2-hydroxyphenyl)-1-butanone The title compound was prepared by the method of Example 361 as a yellow oil (8 mg, 17%) from (±)-cis-1,2,6b,7,8,9,10,10a-octahydro[1,4]oxazino[2,3,4-hi]pyrido[4,3-b]indole (30 mg, 0.12 mmol) and 4-chloro-1-(4-fluoro-2-hydroxyphenyl)-1-butanone (52 mg, 0.24 mmol). $^1$H NMR ($CDCl_3$, 300 MHz) δ1.85–2.13 (m, 5H), 2.25–2.47 (m, 3H), 2.63–2.95 (m, 3H), 2.99 (t, J=7.0 Hz, 2H), 3.17–3.35 (m, 3H), 4.43 (dd, J=6.9, 2.2 Hz, 2H), 6.59–6.75 (m, 5H), 7.81 (dd, J=8.7, 6.6 Hz, 1H) ppm.

Example 532

(6bR,10aS)-5-(4-methoxy-2-methylphenyl)-1,2,6b,7,8,9,10,10a-octahydro[1,4]oxazino[2,3,4-hi]pyrido[4,3-b]indole Step A Tert-butyl(6bR,10aS)-5-(4-methoxy-2-methylphenyl)-1,2,6b,9,10,10a-hexahydro[1,4]oxazino[2,3,4-hi]pyrido[4,3-b]indole-8(7H)-carboxylate (0.16 g, 73%) was prepared by the general method of Example 89, step C from tert-butyl (6bR,10aS)-5-bromo-1,2,6b,9,10,10a-hexahydro[1,4]oxazino[2,3,4-hi]pyrido[4,3-b]indole-8(7H)-carboxylate (0.20 g, 0.50 mmol), 4-methoxy-2-methylphenyl boronic acid (0.17 g, 1.0 mmol), $Pd(PPh_3)_2Cl_2$ (17 mg, 0.025 mmol), $Na_2CO_3$ (2.0 M, 1.0 mL, 2.0 mmol) as a white foam. MS (ESI): 437 (base, M+H).

Step B

The title compound (0.12 g, 97%) was prepared by the general method of Example 98 from tert-butyl(6bR,10aS)-5-(4-methoxy-2-methylphenyl)-1,2,6b,9,10,10a-hexahydro[1,4]oxazino[2,3,4-hi]pyrido[4,3-b]indole-8(7H)-carboxylate (0.16 g, 0.37 mmol) as a white foam. $^1$H NMR ($CDCl_3$, 300 MHz) δ1.80–2.00 (m, 2H), 2.07 (s, 1H), 2.29 (s, 3H), 2.70–2.88 (m, 2H), 2.88–2.96 (m, 2H), 3.15–3.20 (m, 2H), 3.30–3.44 (m, 2H), 3.83 (s, 3H), 4.45–4.58 (m, 2H), 6.59 (d, J=1.3 Hz, 1H), 6.64 (d, J=1.3 Hz, 1H), 6.72–6.82 (m, 2H), 7.12 (d, J=8.4 Hz, 1H) ppm. MS (ESI): 337 (base, M+H).

Example 533

(6bR,10aS)-5-[4-methoxy-2-(trifluoromethyl) phenyl]-1,2,6b,7,8,9,10,10a-octahydro[1,4]oxazino [2,3,4-hi]pyrido[4,3-b]indole Step A Tert-butyl(6bR,10aS)-5-[4-methoxy-2-(trifluoromethyl) phenyl]-1,2,6b,9,10,10a-hexahydro[1,4]oxazino[2,3,4-hi] pyrido[4,3-b]indole-10(7aH)-carboxylate (0.21 g, 87%) was prepared by the general method of Example 89, step C from tert-butyl(6bR,10aS)-5-bromo-1,2,6b,7,8,9,10,10a-hexahydro[1,4]oxazino[2,3,4-hi]pyrido[4,3-b]indole-8(7H)-carboxylate (0.20 g, 0.50 mmol), 4-methoxy-2-(trifluoromethyl)phenyl boronic acid (0.22 g, 1.0 mmol), $Pd(PPh_3)_2Cl_2$ (17 mg, 0.025 mmol), $Na_2CO_3$ (2.0 M, 1.0 mL, 2.0 mmol) as a white foam. MS (ESI): 491 (base, M+H).

Step B

The title compound (0.16 g, 96%) was prepared by the general method of Example 98 from tert-butyl(6bR,10aS)-5-[4-methoxy-2-(trifluoromethyl)phenyl]-1,2,6b,9,10,10a-hexahydro[1,4]oxazino[2,3,4-hi]pyrido[4,3-b]indole-8(7H)-carboxylate (0.21 g, 0.43 mmol) as a white foam. $^1$H NMR ($CDCl_3$, 300 MHz) δ1.80–2.00 (m, 2H), 2.32 (br-s, 1H), 2.68–2.78 (m, 2H), 2.78–2.98 (m, 2H), 3.15–3.20 (m, 2H), 3.35 (td, J=2.4, 10.6 Hz, 1H), 3.40–3.48 (m, 1H), 3.87 (s, 3H), 4.45–4.58 (m, 2H), 6.59 (s, 1H), 6.63 (s, 1H), 7.04 (dd, J=2.6, 8.4 Hz, 1H), 7.20–7.26 (m, 2H) ppm. MS (ESI): 391 (base, M+H).

Example 534

5(3,4,5-trimethoxyphenyl)-1,2,7,8,9,10,11,11a-octahydro-6bH-azepino[4,5-b][1,4]oxazino[2,3,4-hi] indole Step A-Typical Procedure for $NaBH_2CN$ Reduction A solution fo 1,2,7,8,9,10-hexahydro[1,4]oxazino[2,3,4-hi]pyrido [4,3-b]indole (10.0 g, 39.88 mmol) in trifluoroacetic acid (135 mL) was stirred at room temperature for 1.5 h, cooled in an ice bath, and treated portionwise every 15 min over the course of three hours with sodium cyanoborohydride (12.5 g, 199.4 mmol). Stirring continued at room temperature for 4 h, then 6N hydrochloric acid (338 mL) was added and the resulting mixture was refluxed for 30 min and evaporated to dryness under reduced pressure. The residue was rendered strongly alkaline with 1 N NaOH to pH=10 and the mixture was extracted with dichloromethane (3×400 mL). The combined extracts were dried with sodium sulfate and concentrated to a solid foam. This solid (8.63 g) was carried on without further purification and redissolved in dichloromethane (1.2 L). A solution of 1 N NaOH (200 mL) was added, followed with $Boc_2O$ (9.57 g, 1 eq). The reaction mixture was stirred overnight, the organic layer separated, dried over $Na_2SO_4$ and concentrated to an oily residue which upon trituration with Ether/Hexanes (1:1), the desired product (8.87 g, 80%) was obtained as a white solid. $^1$NMR ($CDCl_3$, 300 MHz) δ1.49 (s, 9H), 1.80–1.95 (m, 2H), 2.72–2.85 (m, 1H), 2.75–3.00 (bs, 1H), 3.05–3.20 (m, 2H), 3.30–3.45 (m, 2H), 3.70–3.80 (m, 1H), 3.90–4.20 (bs, 1H), 4.48–4.51 (m, 2H), 6.60–6.80 (m, 3H) ppm. CIMS (Methane) m/z=317 $[MH]^+$.

Step B

Tert-butyl 5-bromo-1,2,6b,7,8,10,11,11a-octahydro-9H-azepino[4,5-b][1,4]oxazino[2,3,4-hi]indole-9-carboxylate (0.90 g, 73%) was prepared by method Example 89 step B from tert-butyl 1,2,6b,7,8,10,11,11a-octahydro-9H-azepino [4,5-b][1,4]oxazino[2,3,4-hi]indole-9-carboxylate(0.993 g, 3.01 mmol). $^1$H NMR ($CDCl_3$, 300 MHz) δ1.48 (s, 9H), 1.88 (br.s, 1H), 1.91–2.16 (m, 3H), 2.70–2.85 (m, 1H), 3.21 (d, 1H, J=12.6 Hz), 3.29–3.64 (m, 6H), 4.38 (s, 1H), 4.41 (s, 1H), 6.74 (s, 1H), 6.78 (s, 1H) ppm. MS (CI, Methane) m/z=408 $[MH]^+$.

STEP C-Typical Procedure for Suzuki Coupling

Tert-butyl 5-bromo-1,2,6b,7,8,10,11,11a-octahydro-9H-azepino[4,5-b][1,4]oxazino[2,3,4-hi]indole-9-carboxylate (1.0 equiv), the corresponding boronic acid (1.5–2 equivs) and barium hydroxide (1.5 equivs) were stirred into a solution of water and DME, then heated at 60° C. while bubbling through a stream of Argon gas for 20 min. The reaction mixture was then cooled to room temperature and $Pd(PPh_3)_2Cl_2$ (2.5–5 mol %) and $PPh_3$ (3 equivs based on Pd source) were quickly added and refluxing resumed for 4 hours. When the reaction was completed as shown by TLC, ethyl acetate was added and the mixture was filtered through a Celite bed. Organic layer was separated, dried over sodium sulfate and concentrated under reduced pressure to an oil. This residue was purified on a flash column eluting with 10% EtOAc/Hexanes to give the desired product.

Tert-butyl 5-(3,4,5-trimethoxyphenyl)-1,2,6b,7,8,10,11,11a-octahydro-9H-azepino[4,5-b][1,4]oxazino[2,3,4-hi] indole-9-carboxylate (609 mg, 75%) was prepared via coupling of the tert-butyl 5-bromo-1,2,6b,7,8,10,11,11a-octahydro-9H-azepino[4,5-b][1,4]oxazino[2,3,4-hi]indole-9-carboxylate (671 mg, 1.64 mmol) with 3,4,5-trimethoxyphenyl boronic acid (522 mg, 2.46 mmol) as illustrated above using the typical procedure for Suzuki coupling. $^1$H NMR ($CDCl_3$, 300 MHz) δ1.49 (s, 9H), 1.80–2.20 (m, 4H), 2.80–2.91 (m, 1H), 3.25 (d, 1H, J=10.8 Hz), 3.42–3.70 (m, 1H), 3.83 (s, 3H), 3.88 (s, 6H), 4.40–4.51 (m, 2H), 6.69 (s, 2H), 6.82 (s, 1H), 6.86 (s, 1H) ppm. CIMS (Methane) m/z=497 $[MH]^+$.

STEP D-Typical Procedure for Removal of Boc Protecting Group

The corresponding indoline from step A (100–150 mg) is mixed with cold ethanolic hydrochloric acid (4M) (5 mL), and the solution is stirred for 10 min at 0° C. The solvent is removed under reduced pressure and the residue is disolved in hot acetonitrile with a small amount of methanol. Upon cooling to room temperature, the desired salt is obtained as a crystalline material.

The corresponding hydrochloride salt of the title compound was formed from tert-butyl 5-(3,4,5-trimethoxyphenyl)-1,2,6b,7,8,10,11,11a-octahydro-9H-azepino[4,5-b][1,4]oxazino[2,3,4-hi]indole-9-carboxylate (608 mg) using the general procedure described above. Then, this salt was free-based using 6 N NaOH, to afford the title compound (479 mg, 63%). $^1$H NMR ($CDCl_3$, 300 MHz) δ1.81–2.08 (m, 3H), 2.09–2.26 (m, 2H), 2.70–2.96 (m, 3H), 3.01–3.30 (m, 3H), 3.45–3.60 (m, 1H), 3.65–3.80 (m, 1H), 3.89 (s, 3H), 3.90 (s, 6H), 4.45 (s, 2H), 6.69 (s, 2H), 6.82 (s, 1H), 6.86 (s, 1H) ppm. CIMS (Methane) m/z=397 $[MH]^+$.

Example 535

5-(1-naphthyl)-1,2,7,8,9,10,11,11a-octahydro-6bH-azepino[4,5-b][1,4]oxazino[2,3,4-hi]indole Tert-butyl 5-(1-naphthyl)-1,2,6b,7,8,10,11,11a-octahydro-9H-azepino[4,5-b][1,4]oxazino[2,3,4-hi]indole-9-carboxylate (671 mg, 90%) was prepared via coupling of tert-butyl 5-bromo-1,2,6b,7,8,10,11,11a-octahydro-9H-azepino[4,5-b][1,4]oxazino[2,3,4-hi]indole-9-carboxylate (671 mg, 1.64 mmol) with 1-naphthyl boronic acid (423 mg, 2.46 mmol) as illustrated by the general procedure described in Example 534 Step C. CIMS (Methane) m/z=457 $[MH]^+$ The corresponding hydrochloride salt of the title compound was formed from tert-butyl 5-(1-naphthyl)-1,2,6b,7,8,10,11,11a-octahydro-9H-azepino[4,5-b][1,4]oxazino[2,3,4-hi]indole-9-carboxylate (670 mg) using the procedure described in Example 534 Step C. Then, this salt was free-based using 6 N NaOH, to give the title compound (527 mg,99%). $^1$H NMR ($CDCl_3$, 300 MHz) δ1.80–2.40 (m, 5H), 2.80–3.00 (m, 3H), 3.00–3.15 (m, 1H), 3.40–3.60 (m, 1H), 3.62–3.86 (m, 1H), 4.28–4.62 (m, 4H), 6.77 (s, 2H), 7.30–7.60 (m, 4H), 7.75 (d, 1H, J=8.1 Hz), 7.85 (d, 1H, J=8.0 Hz), 8.04 (d, 1H, J=8.1 Hz) ppm. CIMS (Methane) m/z=357 $[MH]^+$.

Example 536

5-(3-methoxyphenyl)-1,2,7,8,9,10,11,11a-octahydro-6bH-azepino[4,5-b][1,4]oxazino[2,3,4-hi]indole Tert-butyl 5-(3-methoxyphenyl)-1,2,6b,7,8,10,11,11a-octahydro-9H-azepino[4,5-b][1,4]oxazino[2,3,4-hi]indole-9-carboxylate (502 mg, 70%) was prepared via coupling of tert-butyl 5-bromo-1,2,6b,7,8,10,11,11a-octahydro-9H-azepino[4,5-b][1,4]oxazino[2,3,4-hi]indole-9-carboxylate (671 mg, 1.64 mmol) with 3-methoxyphenyl boronic acid (374 mg, 2.46 mmol) as illustrated by the general procedure described in Example 534 Step C. CIMS (Methane) m/z=437 $[MH]^+$. The corresponding hydrochloride salt of the title compound was formed from tert-butyl 5-(3-methoxyphenyl)-1,2,6b,7,8,10,11,11a-octahydro-9H-azepino[4,5-b][1,4]oxazino[2,3,4-hi]indole-9-carboxylate (500 mg) using the procedure described in Example 534 Step D. Then, this salt was free-based using 6 N NaOH, to give the title compound (395 mg, 99%). $^1$H NMR ($CDCl_3$, 500 MHz) δ1.80–2.30 (m, 4H), 2.75–2.98 (m, 3H), 3.00–3.12 (m, 1H), 3.13–3.29 (m, 2H), 3.43–3.53 (m, 1H), 3.63–3.78 (m, 1H), 3.85 (s, 3H), 4.11 (brs, 1H), 4.41 (brs, 2H), 6.82 (dd, 1H, J=0.8, 8.3 Hz), 6.88 (s, 1H), 6.90 (s, 1H), 7.02 (s, 1H), 7.10 (d, 1H, J=8.3 Hz), 7.30 (t, 1H, J=8.3 Hz) ppm. CIMS (Methane) m/z=337 $[MH]^+$.

Example 537

5-(2,4-dichlorophenyl)-1,2,7,8,9,10,11,11a-octahydro-6bH-azepino[4,5-b][1,4]oxazino[2,3,4-hi]indole Tert-butyl 5-(2,4-dichlorophenyl)-1,2,6b,7,8,10,11,11a-octahydro-9H-azepino[4,5-b][1,4]oxazino[2,3,4-hi]indole-9-carboxylate (510 mg, 65%) was prepared via coupling of tert-butyl 5-bromo-1,2,6b,7,8,10,11,11a-octahydro-9H-azepino[4,5-b][1,4]oxazino[2,3,4-hi]indole-9-carboxylate (671 mg, 1.64 mmol) with 2,4-dichlorophenyl boronic acid (470 mg, 2.46 mmol) as illustrated by the general procedure described in Example 534 Step C. $^1$H NMR ($CDCl_3$, 300 MHz) δ1.48 (s, 9H), 1.81–2.22 (m, 4H), 2.80–3.00 (m, 1H), 3.25 (d, 1H, J=11.5 Hz), 3.31–3.75 (m, 6H), 4.49–4.50 (m, 2H), 6.66 (s, 1H), 6.72 (s, 1H), 7.23 (s, 2H), 7.43 (s, 1H) ppm. CIMS (Methane) m/z=476 $[MH]^+$. The corresponding hydrochloride salt of the title compound was formed from tert-butyl 5-(2,4-dichlorophenyl)-1,2,6b,7,8,10,11,11a-octahydro-9H-azepino[4,5-b][1,4]oxazino[2,3,4-hi]indole-9-carboxylate (505 mg) using the procedure described in Example 534 Step D. Then, this salt was free-based using 6 N NaOH, to give the title compound (398 mg, 99%). $^1$H NMR ($CDCl_3$, 300 MHz) δ1.60–2.30 (m, 5H), 2.70–3.30 (m, 6H), 3.40–3.60 (m, 1H), 3.70–3.80 (m, 1H), 4.30–4.60 (m, 2H), 6.70 (s, 1H), 6.73 (s, 1H), 7.28 (s, 1H), 7.29 (s, 1H), 7.43 (s, 1H) ppm. CIMS (Methane) m/z=376 $[MH]^+$.

Example 538

1,2,7,8,9,10,11,11a-octahydro-6bH-azepino[4,3-b][1,4]oxazino[2,3,4-hi]indole

The hydrochloride salt of the title compound (130 mg, 51%) was prepared from the reduction of the 1,2,8,9,10,11-hexahydro-7H-azepino[4,3-b][1,4]oxazino[2,3,4-hi]indole (250 mg, 0.76 mmol) from Example 545 step A using $NaBH_3CN$ (267 mg, 4.26 mmol) following the procedure described in Example 534. $^1$H NMR (300 MHz, $CDCl_3$) δ1.77–1.94 (m, 1H), 2.08–2.45 (m, 2H), 2.86–3.00 (m, 1H), 3.34–3.59 (m, 6H), 3.68–3.91 (m,2H), 4.36–4.58 (m, 2H), 6.65 (m, 1H), 6.83 (m, 2H) ppm. CIMS m/z=231 $[MH]^+$ Example 539

3-(1,2,6b,7,8,10,11,11a-octahydro-9H-azepino[4,5-b][1,4]oxazino[2,3,4-hi]indol-9-yl)propyl 4-fluorophenyl ether hydrochloride Typical Procedure for Alkylation of Amines A mixture of indoline hydrochloride (approx 200 mg) in dioxane (4 mL) was treated with Hunig's base (10 equivs) and heated to reflux for 15 min. To the cooled reaction mixture was added appropriate side chain (5 equivs), KI (0.9 equivs), then the whole mixture was refluxed for 48 hr. The reaction was then diluted with chloroform (20 mL) and extracted once with saturated solution of ammonium chloride (10 mL) and twice with ice-cold water (100 mL). The organic layer was dried over sodium sulfate and concentrated to dryness under reduced pressure. The residue was purified by flash chromatography eluting with a gradient of hexane/ethylacetate (e.g. 96:4 to 50:50), following with a gradient methanol/dichloromethane (e.g.1:99 to 3:97) to give the desired product.

3-(1,2,6b,7,8,10,11,11a-octahydro-9H-azepino[4,5-b][1,4]oxazino[2,3,4-hi]indol-9-yl)propyl 4-fluorophenyl ether (400 mg, 62%) was obtained from the alkylation of 1,2,7,8,9,10,11,11a-octahydro-6bH-azepino[4,5-b][1,4]oxazino[2,3,4-hi]indole (560 mg, 1.69 mmol) with 1-(3-chloropropoxy)-4-fluorobenzene (1.32 mL, 8.47 mmol) using the procedures described above. $^1$H NMR (300 MHz, $CDCl_3$) δ1.79–1.99 (m, 1H), 2.10 (d, 1H, J=12.2 Hz), 2.39–2.57 (m, 1H), 2.72–3.01 (m, 3H), 3.01–3.22 (m, 2H), 3.22–3.51 (m, 3H), 3.61–3.72 (m, 1H), 6.69–6.89 (m, 1H), 7.17 (d, 1H, J=7.0 Hz), 7.42 (d, 1H, J=9.6 Hz) ppm. CI MS m/z=249 $[MH]^+$. The title compound (380 mg, 89%) was obtained by the procedure described in Example 535 Step B. $^1$H NMR (300 MHz, $CD_3OD$) δ2.19–2.60 (m, 5H), 2.59–2.96 (m, 1H), 3.01–3.19 (m, 1H), 3.25–3.91 (m, 9H), 3.92–4.21 (m, 2H), 4.32–4.61 (m, 2H), 6.53–6.89 (m, 2H), 6.88–7.22 (m, 5H); CI MS m/z=383 $[MH]^+$.

Example 540

9-[3-(6-fluoro-1,2-benzisoxazol-3-yl)propyl]-1,2,7,8,9,10,11,11a-octahydro-6bH-azepino[4,5-b][1,4]oxazino[2,3,4-hi]indole hydrochloride 9-[3-(6-Fluoro-1,2-benzisoxazol-3-yl)propyl]-1,2,7,8,9,10,11,11a-octahydro-6bH-azepino[4,5-b][1,4]oxazino[2,3,4-hi]indole hydrochloride (351 mg, 48%) was obtained from the alkylation of 1,2,7,8,9,10,11,11a-octahydro-6bH-azepino[4,5-b][1,4]oxazino[2,3,4-hi]indole (595 mg, 1.80 mmol) with 3-(3-chloropropyl)-6-fluoro-1,2-benzisoxazole (1.54 g, 7.20 mmol) using the procedure described in Example 539. $^1$H NMR ($CD_3OD$, 300 MHz) δ2.10–2.51 (m, 4H), 2.53–2.80 (m, 2H), 2.80–3.00 (m, 1H), 3.10–3.25 (m, 3H), 3.23–3.65 (m, 4H), 3.70–3.90 (m, 3H), 4.12 (q, 1H, J=9.0 Hz), 4.40–4.60 (m, 2H), 6.58–6.80 (m, 1H), 6.92 (d, 1H, J=8.1 Hz), 7.06 (t, 1H, J=8.1 Hz), 7.12–7.25 (m, 1H), 7.35–7.45 (m, 1H), 7.80–7.90 (m, 1H) ppm. CIMS (Methane) m/z=408 $[MH]^+$.

Example 541

6,7,9,10,11,12-hexahydro-5H-[1,4]oxazepino[2,3,4-hi]pyrido[4,3-b]indole hydrochloride A mixture of 3,4-dihydro-1,5-benzoxazepin-5(2H)-ylamine (2.85 g, 14.23 mol) and 4-piperidinone hydrochloride (2.21 g, 14.37 mol) in ethanol (50 mL) was heated to reflux overnight. The resulting suspension was then cooled, filtered, washed successively with ethanol (10 mL) and diethyl ether (10 mL), and air dried to afford the title compound (2.28 g, 61%) $^1$H NMR ($CD_3OD$, 300 NMR) δ2.33–2.40 (m, 2H), 3.15 (t, 2H, J=6.2), 3.65 (t, 2H, J=6.2), 4.06 (t, 2H, J=5.7), 4.26–4.29 (m, 2H), 4.41 (s, 2H), 6.74 (d, 2H, J=7.1), 6.96 (t, 1H, J=8.0), 7.06 (d, 1H, J=7.1) ppm. CIMS (Methane) m/z=435 $[MH]^+$.

Example 542

6,7,8a,9,10,11,12,12a-octahydro-5H-[1,4]oxazepino [2,3,4-hi]pyrrido[4,3-b]indole Tert-butyl 6,7,9,10,12,12a-hexahydro-5H-[1,4]oxazepino [2,3,4-hi]pyrido[4,3-b]indole-11(8aH)-carboxylate was prepared from the reduction of 6,7,9,10,11,12hexahydro-5H-[1,4]oxazepino[2,3,4-hi]pyrido[4,3-b]indole using $NaBH_3CN$ as described in Example 534 step A. $^1$H NMR ($CDCl_3$, 500 MHz) δ1.41 (s, 9H), 1.85–1.91 (m, 2H), 2.01–2.12 (m, 2H), 2.6–3.00 (m, 2 H), 3.48–3.42 (m, 4H), 3.60–3.69 (m, 4H), 3.70–4.2 (m, 2H), 4.35–4.40 (m, 1H), 6.62–6.70 (m, 1 H), 6.76–6.82 (m, 2H) ppm. CIMS (Methane) m/z=331 $[MH]^+$.

The title compound (82 mg, 86%) was formed from tert-butyl 6,7,9,10,12,12a-hexahydro-5H-[1,4]oxazepino[2,3,4-hi]pyrido[4,3-b]indole-11(8aH)-carboxylate (117 mg) using the procedure described in Example 534 Step D. $^1$H NMR (DMSO-$d_6$, 300 NMR) δ1.85–2.26 (m, 4H), 2.26–2.53 (m, 2H), 2.85–3.01 (m, 1H), 3.12–3.51 (m, 5H), 3.62–3.74 (m, 1H), 4.31–4.41 (m, 1H), 6.65–6.80 (m, 2H), 6.86–6.91 (m, 1H) ppm. CIMS (Methane) m/z=231 $[MH]^+$.

Example 543

2-(2,6-difluorophenyl)-6,7,8a,9,10,11,12,12a-octahydro-5H-[1,4]oxazepino[2,3,4-hi]pyrido[4,3-b] indole hydrochloride Typical Procedure for Stannane Coupling Degassed DMF (25 mL) was added to a mixture the aryl bromide (316 mg, 0.768 mmoles), $PPh_3$ (40.4 mg, 0.154 mmol), CuBr (22 mg, 0.20 mmol) and $Pd(PPh_3)_2Cl_2$ (55 mg, 0.0768 mmol) via cannula, at room temperature under $N_2$ atmosphere. The reaction mixture was stirred at room temperature for 5 min and then aryl trimethylstannane (1.5 equiv. to aryl bromide) was added as a solution in degassed DMF (2.5 mL) and the reaction mixture was heated at 140° C. After 10 min, the solution began to turn black, and a second portion (0.75 equiv. to aryl bromide) was added after 1 hour, followed by a final portion (0.75 equiv. to aryl bromide) an hour later. Heating resumed for another 30 min, then the reaction mixture was cooled to room temperature and diluted with ethylacetate/water (20 mL/20 mL). Organic layer was separated, dried over sodium sulfate an concentrated to dryness under reduced pressure to a dark oil. This residue was purified by flash chromatography eluting with 10% EtOAc/Hexanes to afford desired product.

Tert-butyl 2-(2,6-difluorophenyl)-6,7,9,10,12,12a-hexahydro-5H-[1,4]oxazepino[2,3,4-hi]pyrido[4,3-b] indole-11(8aH)-carboxylate (179 mg, 77%) was prepared via coupling of tert-butyl 2-bromo-6,7,9,10,12,12a-hexahydro-5H-[1,4]oxazepino[2,3,4-hi]pyrido[4,3-b] indole-11(8aH)-carboxylate (217 mg, 0.53 mmol) with 2,6-difluorophenyltrimethyl stannane (440 mg, 1.6 mmol) as illustrated by the general procedure described above. The title compound (50 mg, 58%) was formed by the deprotection procedure described in Example 534 Step C. $^1$H NMR ($CD_3OD$, 300 MHz) δ2.03–2.20 (m, 4H), 2.31–2.42 (m, 1H), 2.04–2.21 (m, 2H), 3.15–3.58 (m, 5H), 3.64–3.84 (m, 1H), 4.39–4.50 (m, 1H), 6.81–7.05 (m, 4H), 7.27–7.39 (m, 1H) ppm. CIMS (Methane) m/z=343 $[MH]^+$.

Example 544

4-(6,7,9,10,12,12a-hexahydro-5H-[1,4]oxazepino[2,3,4-hi]pyrido[4,3-b]indol-11(8aH)-yl)-1-(4-fluorophenyl)-1-butanone hydrochloride 4-(6,7,9,10,12,12a-hexahydro-5H-[1,4]oxazepino[2,3,4-hi]pyrido[4,3-b]indol-11(8aH)-yl)-1-(4-fluorophenyl)-1-butanone(100 mg, 55%) was obtained from the alkylation of 6,7,8a,9,10,11,12,12a-octahydro-5H-[1,4]oxazepino[2,3,4-hi]pyrido[4,3-b]indole (188 mg, 0.7 mmol) with 4-chloro-4'-fluoro-butyrophenone (608, 3.5 mmoles) using the procedure described in EXAMPLE 539. The title compound was obtained using the procedure described in EXAMPLE 534 Step C. $^1$H NMR ($CD_3OD$, 300 MHz) δ2.01–2.29 (m, 4H), 2.43–2.61 (m, 2H), 3.11–3.80 (m, 13H), 4.39–4.59 (m, 1H), 6.71–6.83 (m, 2H), 6.82–6.91 (m, 1H), 7.18–7.20 (m, 2H), 8.03–8.13 (m, 2H) ppm. CIMS (Methane) m/z=395 $[MH]^+$.

Example 545

1,2,7,8,9,10,11,11a-octahydro-6bH-azepino[4,5-b][1,4]oxazino[2,3,4-hi]indole

Step A 2,3-dihydro-4H-1,4-benzoxazin-4-amine (494 mg, 2.64 mmol) and hexahydro-4H-azepin-4-one (396 mg, 2.64 mmol) were dissolved in EtOH (5 mL). This solution was refluxed for 10 min, and then re-cooled to rt. HCl gas was bubbled into the solvent for 10 s. The reaction was then refluxed for another 2 hrs, and cooled to rt. 1M NaOH (15 mL) and dioxane (10 mL) were added to the reaction flask. The flask was cooled to 0° C., and $BOC_2O$ (578 mg, 2.90 mmol) was added. The reaction was warmed to rt and stirred for 18 hrs. The reaction was concentrated. Brine (20 mL) and $CHCl_3$ (20 mL) were added to the residue; the mixture was stirred for 10 min. The layers were separated, and the aqueous was re-extracted with $CHCl_3$ (2×20 mL). The combined organic layers were washed with brine, dried, and concentrated to afford 805 mg of an orange oil. Purification by column chromatography (0, 1, 2% $MeOH/CH_2Cl_2$) afforded the title compound (666 mg, 77%) as an amorphous solid $^1$H NMR ($CDCl_3$, 300 MHz) δ7.03–7.06 (1H, m), 6.60 (1H, m), 6.60 (1H, d, J=7.7Hz), 4.52 (2H, t, J=4.8 Hz), 4.11 (2H, t, J=5.2 Hz), 3.64–3.75 (4H, m), 2.92–2.99 (4H, m), 1.49 (9H, s), in addition to the regioisomeric 1,2,8,9,10,11-hexahydro-7H-azepino[4,3-b][1,4]oxazino[2,3,4-hi]indole compound in ca. 10% yield.

Step B

Tert-butyl 1,7,8,10,11,11b-hexahydropyrano[4',3',2':3,4] indeno[1,2-d]azepine-9(2H)-carboxylate (407 mg, 1.24 mmol) was dissolved in TFA (10 mL). This solution was cooled to 0° C., and $NaCNBH_3$ (234 mg, 3.72 mmol) was added in small portions. The reaction was stirred at 0° C. for 1 hr. Conc. HCl (5 mL) was added to the reaction flask, and then the mixture was refluxed at 50° C. for 30 min. The reaction was re-cooled to 0° C., and ice chips were added. The solution was basified with 50% NaOH until a pH=14. The reaction was extracted with $CHCl_3$ (3×20 mL). The combined organic layers were washed with brine, dried, and concentrated to afford the title compound (321 mg, 100%) as an amorphous solid. $^1$H NMR ($CDCl_3$, 300 MHz) δ6.57–6.67 (3H, m), 4.39–4.43 (2H, m), 3.61–3.69 (1H, m), 3.45 (1H, dt, J=3.3 Hz, 9.2 Hz), 3.00–3.24 (3H, m), 2.69–2.89 (3H, m), 2.02–2.16 (2H, m), 1.83–1.97 (2H, m).

Example 546

4-(1,2,6b,7,8,10,11,11a-octahydro-9H-azepino[4,5-b][1,4]oxazino[2,3,4-hi]indol-9-yl)-1-(4-fluorophenyl)-1-butanone 1,2,7,8,9,10,11,11a-octahydro-6bH-azepino[4,5-b][1,4]oxazino[2,3,4-hi]indole (97.8 mg, 0.42 mmol), 4-chloro-1-(4-fluorophenyl)-1-butanone (172 mg, 0.86 mmol), KI (71.2 mg, 0.43 mmol), and DIEA (550 mg, 4.3 mmol) were suspended in dioxane (2 mL). The reaction mixture was refluxed for 18 hrs. After cooling to rt, the solution was concentrated. The residue was immediately purified by column chromatography to afford the title compound. MS-ESI: 395[MH]$^+$.

Example 547

(8aS,12aR)-2-[4-methoxy-2-(trifluoromethyl) phenyl]-6,7,8a,9,10,11,12,12a-octahydro-5H-[1,4] oxazepino[2,3,4-hi]pyrido[4,3-b]indole Step A Tert-butyl(8aS,12aR)-6,7,9,10,12,12a-hexahydro-5H-[1,4]oxazepino[2,3,4-hi]pyrido[4,3-b]indole-11(8aH)-carboxylate were obtained from chiral separation of tert-butyl 6,7,9,10,12,12a-hexahydro-5H-[1,4]oxazepino[2,3,4-hi]pyrido[4,3-b]indol-11(8aH)-carboxylate using a chiralcel OJ preparative high performance liquid chromatographic column.

Step B

Tert-butyl(8aS,12aR)-2-bromo-6,7,9,10,12,12a-hexahydro-5H-[1,4]oxazepino[2,3,4-hi]pyrido[4,3-b] indole-11(8aH)-carboxylate was prepared by method Example 89 Step B from tert-butyl(8aS,12aR)-6,7,9,10,12,12a-hexahydro-5H-[1,4]oxazepino[2,3,4-hi]pyrido[4,3-b] indole-11(8aH)-carboxylate (4.4 g, 13.3 mmol) to afford the desired product (4.9 g, 12.1 mmol). MS-ApCI: 409 [M+H$^+$].

Step C

Tert-butyl(8aS,12aR)-2-[4-methoxy-2-(trifluoromethyl) phenyl]-6,7,9,10,12,12a-hexahydro-5H-[1,4]oxazepino[2,3,4-hi]pyrido[4,3-b]indole-11(8aH)-carboxylate was prepared by the method of Example 89 step C from tert-butyl(8aS,12aR)-2-bromo-6,7,9,10,12,12a-hexahydro-5H-[1,4] oxazepino[2,3,4-hi]pyrido[4,3-b]indole-11(8aH)-carboxylate (409 mg, 1.0 mmol) and corresponding 4-methoxy-2-(trifluoromethyl)phenylboronic acid (440 mg, 2.0 mmol) to afford after chromatographic purification the desired product (360 mg, 71%). $^1$H NMR ($CDCl_3$, 300 MHz) δ7.20–7.23 (m, 2H), 7.02 (dd, 1H, J=8.4 Hz, 2.6 Hz), 6.75 (s,1H), 6.74 (s, 1H), 4.41–4.45 (m, 1H), 3.85 (s, 3H), 3.24–3.80 (, 7H), 2.56–3.00 (m, 2H), 1.94–2.08 (m, 4H), 1.44 (s, 9H) ppm. MS-ApCI: 505 [M+H$^+$].

Step D

The title compound was prepared by the method of Example 98 from tert-butyl(8aS,12aR)-2-[4-methoxy-2-(trifluoromethyl)phenyl]6,7,9,10,12,12a-hexahydro-5H-[1,4]oxazepino[2,3,4-hi]pyrido[4,3-b]indole-11(8aH)-carboxylate to afford the title compound (260 mg, 90%). $^1$H NMR ($CDCl_3$, 300 MHz) δ7.20–7.24 (m, 2H), 7.02 (dd, 1H, J=8.5 Hz, 2.6 Hz), 6.75 (s, 1H), 6.70 (s, 1H), 4.39–4.46 (m, 1H), 3.86 (s, 3H), 3.75–3.83 (m, 1H), 3.39–3.44 (m, 2H), 3.16–3.24 (m, 1H), 3.01–3.08 (m, 1H), 2.89–2.93 (m, 2H), 2.52–2.62 (m, 2H), 2.48 (bs, 1H), 1.83–2.13 (m, 4H) ppm. MS-ApCI: 405 [M+H$^+$].

Example 548

(8aS,12aR)-2-(4-methoxy-2-methylphenyl)-6,7,8a,9,10,11,12,12a-octahydro-5H-[1,4]oxazepino[2,3,4-hi] pyrido[4,3-b]indole Step A Tert-butyl(8aS,12aR)-2-(4-methoxy-2-methylphenyl)-6,7,9,10,12,12a-hexahydro-5H-[1,4]oxazepino[2,3,4-hi] pyrido[4,3-b]indole-11(8aH)-carboxylate was prepared by the method of Example 89 step C from tert-butyl(8aS,12aR)-2-bromo-6,7,9,10,12,12a-hexahydro-5H-[1,4] oxazepino[2,3,4-hi]pyrido[4,3-b]indole-11(8aH)-carboxylate (409 mg, 1.0 mmol) and corresponding 4-methoxy-2-methylphenylboronic acid (332 mg, 2.0 mmol) to afford after chromatographic purification the desired product (265 mg, 59%). $^1$H NMR ($CDCl_3$, 300 MHz) δ7.12–7.14 (m, 1H), 6.74–6.79 (m, 4H), 4.41–4.47 (m, 1H), 4.11–4.13 (m, 1H), 3.81 (s, 3H), 3.66–3.78 (m, 2H), 3.24–3.48 (m, 4H), 2.58–3.04 (m, 2H), 2.28 (s, 3H), 1.96–2.12 (m, 4H), 1.45 (s, 9H) ppm. MS-ApCI: 451 [M+H$^+$].

Step B

The title compound was prepared by the method of Example 98 from tert-butyl(8aS,12aR)-2-(4-methoxy-2-methylphenyl)-6,7,9,10,12,12a-hexahydro-5H-[1,4] oxazepino[2,3,4-hi]pyrido[4,3-b]indole-11(8aH)-carboxylate to afford the title compound (150 mg, 73%). $^1$H NMR ($CDCl_3$, 300 MHz) δ7.11–7.14 (m, 1H), 6.70–6.78 (m, 4H), 4.40–4.46 (m, 1H), 3.81 (s, 3H), 3.37–3.44 (m, 2H), 3.19–3.26 (m, 1H), 3.03–3.10 (m, 1H), 2.92–2.95 (m, 2H), 2.51–2.61 (m, 2H), 2.27 (s, 3H), 1.85–2.17 (m, 6H) ppm. MS-ESI: 351 [MH]$^+$.

Example 549

(8aS,12aR)-2-[2-chloro-4-(trifluoromethyl)phenyl]-6,7,8a,9,10,11,12,12a-octahydro-5H-[1,4]oxazepino [2,3,4-hi]pyrido[4,3-b]indole Step A Tert-butyl(8aS,12aR)-2-[2-chloro-4-(trifluoromethyl) phenyl]-6,7,9,10,12,12a-hexahydro-5H-[1,4]oxazepino[2,3,4-hi]pyrido[4,3-b]indole-11(8aH)-carboxylate was prepared by the method of Example 78 step C from tert-butyl(8aS,12aR)-2-bromo-6,7,9,10,12,12a-hexahydro-5H-[1,4] oxazepino[2,3,4-hi]pyrido[4,3-b]indole-11(8aH)-carboxylate (205 mg, 0.5 mmol) and corresponding 2-chloro-4-(trifluoromethyl)phenylboronic acid (212 mg, 1.0 mmol) to afford after chromatographic purification the desired product (130 mg, 51%). $^1$H NMR ($CDCl_3$, 300 MHz) δ7.63 (s, 1H), 7.44 (d, 1H, J=8.1 Hz), 7.34 (d, 1H, J=8.1H), 6.85 (s, 2H), 4.34–4.39 (m, 1H), 3.64–4.02 (m, 2H), 3.44–3.64 (m, 2H), 3.20–3.42 (m, 3H), 2.58–3.02 (m, 2H), 1.86–2.10 (m, 4H), 1.36 (s, 9H) ppm. MS-ApCI: 509 [M+H$^+$].

Step B

The title compound was prepared by the method of Example 98 from tert-butyl(8aS,12aR)-2-[2-chloro-4-(trifluoromethyl)phenyl]-6,7,9,10,12,12a-hexahydro-5H-[1,4]oxazepino[2,3,4-hi]pyrido[4,3-b]indole-11(8aH)-carboxylate to afford the title compound (79 mg, 76%). $^1$H NMR ($CDCl_3$, 300 MHz) δ7.62 (s, 1H), 7.44 (d, 1H, J=8.0 Hz), 7.35 (d, 1H, J=8.0 Hz), 6.80–6.85 (m, 2H), 4.33–4.39 (m, 1H), 3.72–3.80 (m, 1H), 3.31–3.39 (m, 1H), 3.14–3.22 (m, 2H), 2.98–3.02 (m, 1H), 2.80–2.87 (m, 2H), 2.45–2.59 (m, 2H), 1.75–2.07 (m, 5H) ppm. MS-ESI: 409 [MH]$^+$.

Example 550

(8aS,12aR)-2-(2,3-dichlorophenyl)-6,7,8a,9,10,11,12,12a-octahydro-5H-[1,4]oxazepino[2,3,4-hi]pyrido[4,3-b]indole Step A Tert-butyl(8aS,12aR)-2-(2,3-dichlorophenyl)-6,7,9,10,12,12a-hexahydro-5H-[1,4]oxazepino[2,3,4-hi]pyrido[4,3-b]indole-11(8aH)-carboxylate was prepared by the method of Example 89 step C from tert-butyl(8aS,12aR)-2-bromo-6,7,9,10,12,12a-hexahydro-5H-[1,4]oxazepino[2,3,4-hi]pyrido[4,3-b]indole-11(8aH)-carboxylate (205 mg, 0.5 mmol) and corresponding 2,3-dichlorophenylboronic acid (191 mg, 1.0 mmol) to afford after chromatographic purification the desired product (124 mg, 52%). $^1$H NMR ($CDCl_3$, 300 MHz) δ7.28–7.32 (m, 2H), 7.07–7.18 (m, 2H), 6.81 (s, 2H), 4.33–4.39 (m, 1H), 3.17–4.01 (m, 7H), 2.55–3.02 (m, 2H), 1.87–2.05 (m, 4H), 1.36 (s, 9H) ppm. MS-ApCI: 475 [M+H$^+$].

Step B

The title compound was prepared by the method of Example 98 from tert-butyl(8aS,12aR)-2-(2,3-dichlorophenyl)-6,7,9,10,12,12a-hexahydro-5H-[1,4]oxazepino[2,3,4-hi]pyrido[4,3-b]indole-11(8aH)-carboxylate to afford the title compound (79 mg, 79%). $^1$H NMR ($CDCl_3$, 300 MHz) δ7.32–7.42 (m, 1H), 7.15–7.23 (m, 2H), 6.84–6.92 (m, 2H), 4.39–4.46 (m, 1H), 3.78–3.86 (m, 1H), 3.38–3.45 (m, 2H), 3.16–3.27 (m, 1H), 3.00–3.07 (m, 1H), 2.87–2.95 (m, 2H), 2.51–2.65 (m, 2H), 1.77–2.17 (m, 5H) ppm. MS-ApCI: 375 [M+H$^+$].

Example 551

(8aS,12aR)-2-(2,4-dimethoxyphenyl)-6,7,8a,9,10,11,12,12a-octahydro-5H-[1,4]oxazepino[2,3,4-hi]pyrido[4,3-b]indole Step A Tert-butyl(8aS,12aR)-2-(2,4-dimethoxyphenyl)-6,7,9,10,12,12a-hexahydro-5H-[1,4]oxazepino[2,3,4-hi]pyrido[4,3-b]indole-11(8aH)-carboxylate was prepared by the method of Example 89 step C from tert-butyl(8aS,12aR)-2-bromo-6,7,9,10,12,12a-hexahydro-5H-[1,4]oxazepino[2,3,4-hi]pyrido[4,3-b]indole-11(8aH)-carboxylate (205 mg, 0.5 mmol) and corresponding 2,4-dichlorophenylboronic acid (182 mg, 1.0 mmol) to afford after chromatographic purification the desired product (180 mg, 77%). MS-ApCI: 467 [M+H$^+$].

Step B

The title compound was prepared by the method of Example 98 from tert-butyl(8aS,12aR)-2-(2,4-dimethoxyphenyl)-6,7,9,10,12,12a-hexahydro-5H-[1,4]oxazepino[2,3,4-hi]pyrido[4,3-b]indole-11(8aH)-carboxylate to afford the title compound (130 mg, 92%). MS-ApCI: 367 [M+H$^+$].

Example 552

(8aS,12aR)-2-(3,4-dimethoxyphenyl)-6,7,8a,9,10,11,12,12a-octahydro-5H-[1,4]oxazepino[2,3,4-hi]pyrido[4,3-b]indole Step A Tert-butyl(8aS,12aR)-2-(3,4-dimethoxyphenyl)-6,7,9,10,12,12a-hexahydro-5H-[1,4]oxazepino[2,3,4-hi]pyrido[4,3-b]indole-11(8aH)-carboxylate was prepared by the method of Example 89 step C from tert-butyl(8aS,12aR)-2-bromo-6,7,9,10,12,12a-hexahydro-5H-[1,4]oxazepino[2,3,4-hi]pyrido[4,3-b]indole-11(8aH)-carboxylate (205 mg, 0.5 mmol) and corresponding 3,4-dimethoxyphenylboronic acid (182 mg, 1.0 mmol) to afford after chromatographic purification the desired product (124 mg, 52%). $^1$H NMR ($CDCl_3$, 300 MHz) δ6.95–7.01 (m, 4H), 6.82 (d, 1H, J=8.4 Hz), 4.35–4.39 (m, 1H), 3.85 (s, 3H), 3.82 (s, 3H), 3.22–3.80 (m, 7H), 2.54–3.02 (m, 2H), 1.88–2.02 (m, 4H), 1.38 (s, 9H) ppm. MS-ApCI: 467 [M+H$^+$].

Step B

The title compound was prepared by the method of Example 98 from tert-butyl(8aS,12aR)-2-(3,4-dimethoxyphenyl)-6,7,9,10,12,12a-hexahydro-5H-[1,4]oxazepino[2,3,4-hi]pyrido[4,3-b]indole-11(8aH)-carboxylate to afford the title compound (70 mg, 71%). $^1$H NMR ($CDCl_3$, 300 MHz) δ6.87–6.99 (m, 4H), 6.79 (d, 1H, J=8.0 Hz), 4.30–4.37 (m, 1H), 3.83 (s, 3H), 3.80 (s, 3H), 3.68–3.76 (m, 1H), 3.26–3.34 (m, 2H), 3.06–3.14 (m, 1H), 2.93–2.99 (m, 1H), 2.77–2.81 (m, 2H), 2.41–2.51 (m, 2H), 1.71–2.05 (m, 5H) ppm. MS-ApCI: 367 [M+H$^+$].

Example 553

(8aS,12aR)-2-(2,4-dichlorophenyl)-6,7,8a,9,10,11,12,12a-octahydro-5H-[1,4]oxazepino[2,3,4-hi]pyrido[4,3-b]indole Step A Tert-butyl(8aS,12aR)-2-(2,4-dichlorophenyl)-6,7,9,10,12,12a-hexahydro-5H-[1,4]oxazepino[2,3,4-hi]pyrido[4,3-b]indole-11(8aH)-carboxylate was prepared by the method of Example 89 step C from tert-butyl(8aS,12aR)-2-bromo-6,7,9,10,12,12a-hexahydro-5H-[1,4]oxazepino[2,3,4-hi]pyrido[4,3-b]indole-11(8aH)-carboxylate (205 mg, 0.5 mmol) and corresponding 2,4-dichlorphenylboronic acid (191 mg, 1.0 mmol) to afford after chromatographic purification the desired product (98 mg, 41%). $^1$H NMR ($CDCl_3$, 300 MHz) δ7.37 (s, 1H), 7.16 (s, 2H), 6.81 (s, 2H), 4.32–4.38 (m, 1H), 3.18–4.05 (m, 7H), 2.55–2.97 (m, 2H), 1.81–2.05 (m, 2H), 1.37 (s, 9H) ppm. MS-ApCI: 475 [M+H$^+$].

Step B

The title compound was prepared by the method of Example 98 from tert-butyl(8aS,12aR)-2-(2,4-dichlorophenyl)-6,7,9,10,12,12a-hexahydro-5H-[1,4]oxazepino[2,3,4-hi]pyrido[4,3-b]indole-11(8aH)-carboxylate to afford the title compound (63 mg, 81%). $^1$H NMR ($CDCl_3$, 300 MHz) δ7.43–7.44 (m, 1H), 7.24 (s, 2H), 6.84–6.88 (m, 2H), 4.40–4.45 (m, 1H), 3.78–3.85 (m, 1H), 3.40–3.44 (m, 2H), 2.83–3.23 (m, 4H), 2.44–2.64 (m, 2H), 1.76–2.13 (m, 5H) ppm. MS-ApCI: 375 [M+H$^+$].

Example 554

(8aS,12aR)-2-(3,4-dichlorophenyl)-6,7,8a,9,10,11,12,12a-octahydro-5H-[1,4]oxazepino[2,3,4-hi]pyrido[4,3-b]indole Step A Tert-butyl(8aS,12aR)-2-(3,4-dichlorophenyl)-6,7,9,10,12,12a-hexahydro-5H-[1,4]oxazepino[2,3,4-hi]pyrido[4,3-b]indole-11(8aH)-carboxylate was prepared by the method of Example 89 step C from tert-butyl(8aS,12aR)-2-bromo-6,7,9,10,12,12a-hexahydro-5H-[1,4]oxazepino[2,3,4-hi]pyrido[4,3-b]indole-11(8aH)-carboxylate (205 mg, 0.5 mmol) and corresponding 3,4-dichlorphenylboronic acid (191 mg, 1.0 mmol) to afford after chromatographic purification the desired product (90 mg, 38%). MS-ApCI: 475 [M+H$^+$].

Step B

The title compound was prepared by the method of Example 98 from tert-butyl(8aS,12aR)-2-(3,4-dichlorophenyl)-6,7,9,10,12,12a-hexahydro-5H-[1,4]

oxazepino[2,3,4-hi]pyrido[4,3-b]indole-11(8aH)-carboxylate to afford the title compound (41 mg, 58%). MS-ApCI: 375 [M+H$^+$].

Example 555

(8aS,12aR)-2-(2,5-dichlorophenyl)-6,7,8a,9,10,11,12,12a-octahydro-5H-[1,4]oxazepino[2,3,4-hi]pyrido[4,3-b]indole Step A Tert-butyl(8aS,12aR)-2-(2,5-dichlorophenyl)-6,7,9,10,12,12a-hexahydro-5H-[1,4]oxazepino[2,3,4-hi]pyrido[4,3-b]indole-11(8aH)-carboxylate was prepared by the method of Example 89 step C from tert-butyl(8aS,12aR)-2-bromo-6,7,9,10,12,12a-hexahydro-5H-[1,4]oxazepino[2,3,4-hi]pyrido[4,3-b]indole-11(8aH)-carboxylate (205 mg, 0.5 mmol) and corresponding 2,5-dichlorphenylboronic acid (191 mg, 1.0 mmol) to afford after chromatographic purification the desired product (119 mg, 50%). $^1$H NMR ($CDCl_3$, 300 MHz) δ7.18–7.24 (m, 2H), 7.08 (dd, 1H, J=8.8 Hz, 2.6 Hz), 6.82 (s, 2H), 4.31–4.36 (m, 1H), 3.08–4.02 (m, 7H), 2.54–3.02 (m, 2H), 1.84–2.02 (m, 4H), 1.36 (s, 9H) ppm. MS-ApCI: 475 [M+H$^+$].

Step B

The title compound was prepared by the method of Example 98 from tert-butyl(8aS,12aR)-2-(2,5-dichlorophenyl)-6,7,9,10,12,12a-hexahydro-5H-[1,4]oxazepino[2,3,4-hi]pyrido[4,3-b]indole-11(8aH)-carboxylate to afford the title compound (61 mg, 65%). $^1$H NMR ($CDCl_3$, 300 MHz) δ7.29–7.37 (m, 2H), 7.15–7.19 (m, 1H), 6.85–6.97 (m, 2H), 4.39–4.59 (m, 1H), 3.78–3.86 (m, 1H), 3.34–3.44 (m, 2H), 3.17–3.25 (m, 1H), 3.02–3.09 (m, 1H), 2.83–2.96 (m, 2H), 2.51–2.64 (m, 2H), 1.78–2.20 (m, 5H) ppm. MS-ApCI: 375 [M+H$^+$].

Example 556

(8aS,12aR)-2-[2-(trifluoromethyl)phenyl]-6,7,8a,9,10,11,12,12a-octahydro-5H-[1,4]oxazepino[2,3,4-hi]pyrido[4,3-b]indole Step A Tert-butyl(8aS,12aR)-2-[2-trifluoromethyl)phenyl]-6,7,9,10,12,12a-hexahydro-5H-[1,4]oxazepino[2,3,4-hi]pyrido[4,3-b]indole-11(8aH)-carboxylate was prepared by the method of Example 89 step C from tert-butyl(8aS,12aR)-2-bromo-6,7,9,10,12,12a-hexahydro-5H-[1,4]oxazepino[2,3,4-hi]pyrido[4,3-b]indole-11(8aH)-carboxylate (205 mg, 0.5 mmol) and corresponding 2-(trifluoromethyl)phenylboronic acid (190 mg, 1.0 mmol) to afford after chromatographic purification the desired product (124 mg, 52%). $^1$H NMR ($CDCl_3$, 300 MHz) δ7.69 (d, 1H, J=7.6 Hz), 7.48–7.53 (m, 1H), 7.37–7.42 (m, 1H), 7.31 (d, 1H, J=7.7 Hz), 6.79 (s, 1H), 6.77 (s, 1H), 4.41–4.46 (m, 1H), 3.23–4.02 (m, 7H), 2.60–2.91 (m, 2H), 1.95–2.12 (m, 4H), 1.44 (s, 9H) ppm. MS-ApCI: 475 [M+H$^+$].

Step B

The title compound was prepared by the method of Example 98 from tert-butyl(8aS,12aR)-2-[2-(trifluoromethyl)phenyl]-6,7,9,10,12,12a-hexahydro-5H-[1,4]oxazepino[2,3,4-hi]pyrido[4,3-b]indole-11(8aH)-carboxylate to afford the title compound (85 mg, 87%). $^1$H NMR ($CDCl_3$, 300 MHz) δ7.69 (d, 1H, J=7.7 Hz), 7.52–7.61 (m, 1H), 7.41–7.50 (m, 1H), 7.31 (d, 1H, J=7.3 Hz), 6.78 (s, 1H), 6.73 (s, 1H), 4.39–4.46 (m, 1H), 3.76–3.84 (m, 1H), 3.39–3.45 (m, 2H), 3.13–3.21 (m, 1H), 2.94–3.05 (m, 1H), 2.86–2.91 (m, 2H), 2.48–2.62 (m, 2H), 1.76–2.18 (m, 5H) ppm. MS-ApCI: 375 [M+H$^+$].

Example 557

(8aS,12aR)-2-(2-methylphenyl)-6,7,8a,9,10,11,12,12a-octahydro-5H-[1,4]oxazepino[2,3,4-hi]pyrido[4,3-b]indole Step A Tert-butyl(8aS,12aR)-2-(2-methylphenyl)-6,7,9,10,12,12a-hexahydro-5H-[1,4]oxazepino[2,3,4-hi]pyrido[4,3-b]indole-11(8aH)-carboxylate was prepared by the method of Example 89 step C from tert-butyl(8aS,12aR)-2-bromo-6,7,9,10,12,12a-hexahydro-5H-[1,4]oxazepino[2,3,4-hi]pyrido[4,3-b]indole-11(8aH)-carboxylate (205 mg, 0.5 mmol) and corresponding 2-methylphenylboronic acid (136 mg, 1.0 mmol) to afford after chromatographic purification the desired product (134 mg, 64%). $^1$H NMR ($CDCl_3$, 300 MHz) δ7.10–7.18 (m, 4H), 6.72 (s, 1H), 6.70 (s, 1H), 4.35–4.40 (m, 1H), 3.59–4.05 (m, 3H), 3.16–3.42 (m, 4H), 2.52–3.02 (m, 2H), 2.22 (s, 3H), 1.88–2.05 (m, 4H), 1.37 (s, 9H) ppm. MS-ApCI: 421 [M+H$^+$].

Step B

The title compound was prepared by the method of Example 98 from tert-butyl(8aS,12aR)-2-(2-methylphenyl)-6,7,9,10,12,12a-hexahydro-5H-[1,4]oxazepino[2,3,4-hi]pyrido[4,3-b]indole-11(8aH)-carboxylate to afford the title compound (81 mg, 79%). $^1$H NMR ($CDCl_3$, 300 MHz) δ7.07–7.17 (m, 4H), 6.70 (s, 1H), 6.68 (s, 1H), 4.31–4.36 (m, 1H), 3.67–3.75 (m, 1H), 3.24–3.40 (m, 2H), 2.91–3.11 (m, 2H), 2.78–2.85 (m, 2H), 2.40–2.49 (m, 2H), 2.20 (s, 3H), 1.77–2.02 (m, 5H) ppm. MS-ApCI: 321 [M+H$^+$].

Example 558

(8aS,12aR)-2-(2-chlorophenyl)-6,7,8a,9,10,11,12,12a-octahydro-5H-[1,4]oxazepino[2,3,4-hi]pyrido[4,3-b]indole Step A Tert-butyl(8aS,12aR)-2-(2-chlorophenyl)-6,7,9,10,12,12a-hexahydro-5H-[1,4]oxazepino[2,3,4-hi]pyrido[4,3-b]indole-11(8aH)-carboxylate was prepared by the method of Example 89 step C from tert-butyl(8aS,12aR)-2-bromo-6,7,9,10;12,12a-hexahydro-5H-[1,4]oxazepino[2,3,4-hi]pyrido[4,3-b]indole-11(8aH)-carboxylate (205 mg, 0.5 mmol) and corresponding 2-chlorophenylboronic acid (156 mg, 1.0 mmol) to afford after chromatographic purification the desired product (145 mg, 66%). $^1$H NMR ($CDCl_3$, 300 MHz) δ7.41–7.44 (m, 1H), 7.18–7.33 (m, 3H), 6.93 (s, 2H), 4.42–4.47 (m, 1H), 3.24–4.02 (m, 7H), 2.62–3.02 (m, 2H), 1.95–2.12 (m, 4H), 1.44 (s, 9H) ppm. MS-ApCI: 441 [M+H$^+$].

Step B

The title compound was prepared by the method of Example 98 from tert-butyl(8aS,12aR)-2-(2-chlorophenyl)-6,7,9,10,12,12a-hexahydro-5H-[1,4]oxazepino[2,3,4-hi]pyrido[4,3-b]indole-11(8aH)-carboxylate to afford the title compound (81 mg, 72%). $^1$H NMR ($CDCl_3$, 300 MHz) δ7.40–7.43 (m, 1H), 7.17–7.36 (m, 3H), 6.89–6.92 (m, 2H), 4.39–4.46 (m, 1H), 3.78–3.86 (m, 1H), 3.38–3.44 (m, 2H), 3.15–3.24 (m, 1H), 3.00–3.06 (m, 1H), 2.86–2.95 (m, 2H), 2.51–2.64 (m, 2H), 1.76–2.17 (m, 5H) ppm. MS-ApCI: 341 [M+H$^+$].

Example 559

(8aS,12aR)-2-(3-fluorophenyl)-6,7,8a,9,10,11,12,12a-octahydro-5H-[1,4]oxazepino[2,3,4-hi]pyrido[4,3-b]indole Step A Tert-butyl(8aS,12aR)-2-(3-fluorophenyl)-6,7,9,10,12,12a-hexahydro-5H-[1,4]oxazepino[2,3,4-hi]pyrido[4,3-b]

indole-11(8aH)-carboxylate was prepared by the method of Example 89 step C from tert-butyl(8aS,12aR)-2-bromo-6,7,9,10,12,12a-hexahydro-5H-[1,4]oxazepino[2,3,4-hi]pyrido[4,3-b]indole-11(8aH)-carboxylate (205 mg, 0.5 mmol) and corresponding 3-fluorophenylboronic acid (140 mg, 1.0 mmol) to afford after chromatographic purification the desired product (108 mg, 51%). MS-ApCI: 425 [M+H$^+$].

Step B

The title compound was prepared by the method of Example 98 from tert-butyl(8aS,12aR)-2-(3-fluorophenyl)-6,7,9,10,12,12a-hexahydro-5H-[1,4]oxazepino[2,3,4-hi]pyrido[4,3-b]indole-11(8aH)-carboxylate to afford the title compound (38 mg, 46%). $^1$H NMR ($CDCl_3$, 300 MHz) δ7.69 (d, 1H, J=7.7 Hz), 7.49–7.61 (m, 1H), 7.39–7.47 (m, 1H), 7.38 (d, 1H, J=7.7 Hz), 6.78 (s, 1H), 6.73 (s, 1H), 4.39–4.46 (m, 1H), 3.76–3.84 (m, 1H), 3.39–3.45 (m, 2H), 3.13–3.21 (m, 1H), 2.98–3.05 (m, 1H), 2.86–2.91 (m, 2H), 2.48–2.62 (m, 2H), 1.76–2.18 (m, 5H) ppm. MS-ApCI: 325 [M+H$^+$].

Example 560

(8aS,12aR)-2-phenyl-6,7,8a,9,10,11,12,12a-octahydro-5H-[1,4]oxazepino[2,3,4-hi]pyrido[4,3-b]indole Step A Tert-butyl(8aS,12aR)-2-phenyl-6,7,9,10,12,12a-hexahydro-5H-[1,4]oxazepino[2,3,4-hi]pyrido[4,3-b]indole11(8aH)-carboxylate was prepared by the method of Example 89 step C from tert-butyl(8aS,12aR)-2-bromo-6,7,9,10,12,12a-hexahydro-5H-[1,4]oxazepino[2,3,4-hi]pyrido[4,3-b]indole-11(8aH)-carboxylate (205 mg, 0.5 mmol) and corresponding phenylboronic acid (122 mg, 1.0 mmol) to afford after chromatographic purification the desired product (80 mg, 40%). MS-ApCI: 407 [M+H$^+$].

Step B

The title compound was prepared by the method of Example 98 from tert-butyl(8aS,12aR)-2-phenyl-6,7,9,10,12,12a-hexahydro-5H-[1,4]oxazepino[2,3,4-hi]pyrido[4,3-b]indole-11(8aH)-carboxylate to afford the title compound (54 mg, 90%). $^1$H NMR ($CDCl_3$, 300 MHz) δ7.42–7.45 (m, 2H), 7.26–7.30 (m, 2H), 7.13–7.19 (m, 1H), 6.98 (d, 1H, J=1.8 Hz), 6.92 (d, 1H, J=1.5 Hz), 4.30–4.40 (m, 1H), 3.69–3.77 (m, 1H), 3.28–3.35 (m, 2H), 3.06–3.14 (m, 1H), 2.92–2.99 (m, 1H), 2.77–2.82 (m, 2H), 2.42–2.53 (m, 2H), 1.66–2.05 (m, 4H), 1.51 (bs, 1H) ppm. MS-ApCI: 307 [M+H$^+$].

Example 561

(8aS,12aR)-2-[4-ethoxy-2-(trifluoromethyl)phenyl]-6,7,8a,9,10,11,12,12a-octahydro-5H-[1,4]oxazepino[2,3,4-hi]pyrido[4,3-b]indole Step A Tert-butyl(8aS,12aR)-2-[4-ethoxy-2-(trifluoromethyl)phenyl]-6,7,9,10,12,12a-hexahydro-5H-[1,4]oxazepino[2,3,4-hi]pyrido[4,3-b]indole-11(8aH)-carboxylate was prepared by the method of Example 89 step C from tert-butyl(8aS,12aR)-2-bromo-6,7,9,10,12,12a-hexahydro-5H-[1,4]oxazepino[2,3,4-hi]pyrido[4,3-b]indole-11(8aH)-carboxylate (205 mg, 0.5 mmol) and corresponding 4-ethoxy-2-(trifluoromethyl)phenylboronic acid (234 mg, 1.0 mmol) to afford after chromatographic purification the desired product (155 mg, 74%). MS-ApCI: 519[M+H$^+$].

Step B

The title compound was prepared by the method of Example 98 from tert-butyl(8aS,12aR)-2-[4-ethoxy-2-(trifluoromethyl)phenyl]-6,7,9,10,12,12a-hexahydro-5H-[1,4]oxazepino[2,3,4-hi]pyrido[4,3-b]indole-11(8aH)-carboxylate to afford the title compound (106 mg, 85%). $^1$H NMR ($CDCl_3$, 300 MHz) δ7.10–7.16 (m, 2H), 6.93 (dd, 1H, J=8.1 Hz, 5.5 Hz), 6.64 (s, 1H), 6.60 (s, 1H), 4.29–4.35 (m, 1H), 3.98 (q, 2H, J=2.3 Hz), 3.65–3.74 (m, 1H), 3.28–3.34 (m, 2H), 3.02–3.12 (m, 1H), 2.88–2.95 (m, 1H), 2.76–2.84 (m, 2H), 2.38–2.51 (m, 2H), 1.65–2.04 (m, 4H), 1.55 (bs, 1H), 1.34 (t, 3H, J=2.3 Hz) ppm. MS-ApCI: 419 [M+H$^+$].

Example 562

(8aS,12aR)-2-[4-isopropoxy-2-(trifluoromethyl)phenyl]-6,7,8a,9,10,11,12,12a-octahydro-5H-[1,4]oxazepino[2,3,4-hi]pyrido[4,3-b]indole Step A Tert-butyl(8aS,12aR)-2-[4-isopropoxy-2-(trifluoromethyl)phenyl]-6,7,9,10,12,12a-hexahydro-5H-[1,4]oxazepino[2,3,4-hi]pyrido[4,3-b]indole-11(8aH)-carboxylate was prepared by the method of Example 89 step C from tert-butyl(8aS,12aR)-2-bromo-6,7,9,10,12,12a-hexahydro-5H-[1,4]oxazepino[2,3,4-hi]pyrido[4,3-b]indole-11(8aH)-carboxylate (205 mg, 0.5 mmol) and corresponding 4-isopropoxy-2-(trifluoromethyl)phenylboronic acid (248 mg, 1.0 mmol) to afford after chromatographic purification the desired product (153 mg, 58%). MS-ApCI: 533[M+H$^+$].

Step B

The title compound was prepared by the method of Example 98 from tert-butyl(8aS,12aR)-2-[4-isopropoxy-2-(trifluoromethyl)phenyl]-6,7,9,10,12,12a-hexahydro-5H-[1,4]oxazepino[2,3,4-hi]pyrido[4,3-b]indole-11(8aH)-carboxylate to afford the title compound (90 mg, 72%). $^1$H NMR ($CDCl_3$, 300 MHz) δ7.18–7.22 (m, 2H), 7.00 (dd, 1H, J=8.4 Hz, 2.5 Hz), 6.74 (s, 1H), 6.70 (s, 1H), 4.55–4.63 (m, 1H), 4.38–4.45 (m, 1H), 3.75–3.83 (m, 1H), 3.38–3.43 (m, 2H), 3.12–3.20 (m, 1H), 2.98–3.04 (m, 1H), 2.86–2.90 (m, 2H), 2.48–2.62 (m, 2H), 1.65–2.13 (m, 5H), 1.36 (d, 6H, J=5.9 Hz) ppm. MS-ESI: 433 [MH]$^+$.

EXAMPLE 563

(8aS,12aR)-2-(5-isopropyl-2-methoxyphenyl)-6,7,8a,9,10,11,12,12a-octahydro-5H-[1,4]oxazepino[2,3,4-hi]pyrido[4,3-b]indole Step A Tert-butyl(8aS,12aR)-2-(5-isopropyl-2-methoxyphenyl)-6,7,9,10,12,12a-hexahydro-5H-[1,4]oxazepino[2,3,4-hi]pyrido[4,3-b]indole-11(8aH)-carboxylate was prepared by the method of Example 89 step C from tert-butyl(8aS,12aR)-2-bromo-6,7,9,10,12,12a-hexahydro-5H-[1,4]oxazepino[2,3,4-hi]pyrido[4,3-b]indole-11(8aH)-carboxylate (205 mg, 0.5 mmol) and corresponding 5-isopropyl-2-methoxyphenylboronic acid (194 mg, 1.0 mmol) to afford after chromatographic purification the desired product (180 mg, 75%). MS-ApCI: 479[M+H$^+$].

Step B

The title compound was prepared by the method of Example 98 from tert-butyl(8aS,12aR)-2-(5-isopropyl-2-methoxyphenyl)-6,7,9,10,12,12a-hexahydro-5H-[1,4]oxazepino[2,3,4-hi]pyrido[4,3-b]indole-11(8aH)-carboxylate to afford the title compound (128 mg, 90%). $^1$H NMR ($CDCl_3$, 300 MHz) δ7.08 (d, 1H, J=2.2 Hz), 7.02 (dd, 1H, J=8.5 Hz, 2.6 Hz), 6.95 (d, 1H, J=1.5 Hz), 6.91 (m, 1H, J=1.1 Hz), 6.79 (d, 1H, J=8.4 Hz), 4.31–4.38 (m, 1H), 3.71–3.79 (m, 1H), 3.70 (s, 3H), 3.28–3.33 (m, 2H), 3.06–3.14 (m, 1H), 2.92–2.98 (m, 1H), 2.75–2.84 (m, 2H), 2.45–2.55 (m, 2H), 1.56–2.04 (m, 4H), 1.48 (bs, 1H), 1.16 (d, 6H, J=7.0 Hz) ppm. MS-ESI: 379 [MH]$^+$.

Example 564

(8aS,12aR)-2-(4-chloro-2-fluorophenyl)-6,7,8a,9,10,11,12,12a-octahydro-5H-[1,4]oxazepino[2,3,4-hi]pyrido[4,3-b]indole Step A Tert-butyl(8aS,12aR)-2-(4-chloro-2-fluorophenyl)-6,7,9,10,12,12a-hexahydro-5H-[1,4]oxazepino[2,3,4-hi]pyrido[4,3-b]indole-11(8aH)-carboxylate was prepared by the method of Example 89 step C from tert-butyl(8aS, 12aR)-2-bromo-6,7,9,10,12,12a-hexahydro-5H-[1,4]oxazepino[2,3,4-hi]pyrido[4,3-b]indole-11(8aH)-carboxylate (205 mg, 0.5 mmol) and corresponding 4-chloro-2-fluorophenylboronic acid (175 mg, 1.0 mmol) to afford after chromatographic purification the desired product (152 mg, 66%). MS-ApCI: 459[M+H$^+$].

Step B

The title compound was prepared by the method of Example 98 from tert-butyl(8aS,12aR)-2-(4-chloro-2-fluorophenyl)-6,7,9,10,12,12a-hexahydro-5H-[1,4]oxazepino[2,3,4-hi]pyrido[4,3-b]indole-11(8aH)-carboxylate to afford the title compound (98 mg, 82%). $^1$H NMR ($CDCl_3$, 300 MHz) δ7.30–7.48 (m, 1H), 7.08–7.15 (m, 2H), 6.98 (s, 1H), 6.95 (s, 1H), 4.38–4.46 (m, 1H), 3.79–3.87 (m, 1H), 3.37–3.43 (m, 2H), 3.16–3.23 (m, 1H), 3.01–3.07 (m, 1H), 2.86–2.95 (m, 2H), 2.52–2.64 (m, 2H), 1.76–2.12 (m, 5H) ppm. MS-ApCI: 359[M+H$^+$].

Example 565

(8aS,12aR)-2-(2-chloro-4-methoxyphenyl)-6,7,8a,9,10,11,12,12a-octahydro-5H-[1,4]oxazepino[2,3,4-hi]pyrido[4,3-b]indole Step A Tert-butyl(8aS,12aR)-2-(2-chloro-4-methoxyphenyl)-6,7,9,10,12,12a-hexahydro-5H-[1,4]oxazepino[2,3,4-hi]pyrido[4,3-b]indole-11(8aH)-carboxylate was prepared by the method of Example 89 step C from tert-butyl(8aS,12aR)-2-bromo-6,7,9,10,12,12a-hexahydro-5H-[1,4]oxazepino[2,3,4-hi]pyrido[4,3-b]indole-11(8aH)-carboxylate (205 mg, 0.5 mmol) and corresponding 2-chloro-4-methoxyphenylboronic acid (170 mg, 1.0 mmol) to afford after chromatographic purification the desired product (140 mg, 60%). MS-ApCI: 471[M+H$^+$].

Step B

The title compound was prepared by the method of Example 98 from tert-butyl(8aS,12aR)-2-(2-chloro-4-methoxyphenyl)-6,7,9,10,12,12a-hexahydro-5H-[1,4]oxazepino[2,3,4-hi]pyrido[4,3-b]indole-11(8aH)-carboxylate to afford the title compound (81 mg, 73%). $^1$H NMR ($CDCl_3$, 300 MHz) δ7.23 (d, 1H, J=8.5 Hz), 6.98 (d, 1H, J=2.6 Hz), 6.80–6.88 (m, 3H), 4.39–4.46 (m, 1H), 3.78–3.86 (m, 1H), 3.81 (s, 3H), 3.37–3.42 (m, 2H), 3.14–3.22 (m, 1H), 3.00–3.06 (m, 1H), 2.86–2.90 (m, 2H), 2.51–2.63 (m, 2H), 2.06–2.13 (m, 2H), 1.96–2.02 (m, 1H), 1.76–1.87 (m, 1H), 1.66 (bs, 1H) ppm. MS-ApCI: 371[M+H$^+$].

Example 566

2-[(8aS,12aR)-6,7,8a-9,10,11,12,12a-octahydro-5H-[1,4]oxazepino[2,3,4-hi]pyrido[4,3-b]indol-2-yl]benzaldehyde Step A Tert-butyl(8aS,12aR)-2-(2-formylphenyl)-6,7,9,10,12,12a-hexahydro-5H-[1,4]oxazepino[2,3,4-hi]pyrido[4,3-b]indole-11(8aH)-carboxylate was prepared by the method of Example 89 step C from tert-butyl(8aS,12aR)-2-bromo-6,7,9,10,12,12a-hexahydro-5H-[1,4]oxazepino[2,3,4-hi]pyrido[4,3-b]indole-11(8aH)-carboxylate (205 mg, 0.5 mmol) and corresponding 2-formylphenylboronic acid (150 mg, 1.0 mmol) to afford after chromatographic purification the desired product (130 mg, 60%). MS-ApCI: 435[M+H$^+$].

Step B

The title compound was prepared by the method of Example 98 from tert-butyl(8aS,12aR)-2-(2-formylphenyl)-6,7,9,10,12,12a-hexahydro-5H-[1,4]oxazepino[2,3,4-hi]pyrido[4,3-b]indole-11(8aH)-carboxylate to afford the title compound (75 mg, 75%). $^1$H NMR ($CDCl_3$, 300 MHz) δ10.01 (s, 1H), 7.97 (d, 1H, J=8.1 Hz), 7.55–7.61 (m, 1H), 7.39–7.44 (m, 2H), 6.84 (d, 1H, J=1.8 Hz), 6.76 (d, 1H, J=1.5 Hz), 4.40–4.47 (m, 1H), 3.79–3.87 (m, 1H), 3.40–3.46 (m, 2H), 3.16–3.24 (m, 1H), 3.01–3.07 (m, 1H), 2.87–2.95 (m, 2H), 2.51–2.66 (m, 2H), 1.78–2.17 (m, 5H) ppm. MS-ApCI: 335[M+H$^+$].

Example 567

2-[(8aS,12aR)-6,7,8a,9,10,11,12,12a-octahydro-5H-[1,4]oxazepino[2,3,4-hi]pyrido[4,3-b]indol-2-yl]-5-methoxybenzaldehyde Step A Tert-butyl(8aS,12aR)-2-(2-formyl-4-methoxyphenyl)-6,7,9,10,12,12a-hexahydro-5H-[1,4]oxazepino[2,3,4-hi]pyrido[4,3-b]indole-11(8aH)-carboxylate was prepared by the method of Example 89 step C from tert-butyl(8aS,12aR)-2-bromo-6,7,9,10,12,12a-hexahydro-5H-[1,4]oxazepino[2,3,4-hi]pyrido[4,3-b]indole-11(8aH)-carboxylate (205 mg, 0.5 mmol) and corresponding to afford after chromatographic purification the desired product (120 mg, 52%). MS-ApCI: 465[M+H$^+$].

Step B

The title compound was prepared by the method of Example 98 from tert-butyl(8aS,12aR)-2-(2-formyl-4-methoxyphenyl)-6,7,9,10,12,12a-hexahydro-5H-[1,4]oxazepino[2,3,4-hi]pyrido[4,3-b]indole-11(8aH)-carboxylate to afford the title compound (75 mg, 75%). $^1$H NMR ($CDCl_3$, 300 MHz) δ9.97 (s, 1H), 7.45 (d, 1H, J=2.9 Hz), 7.34 (d, 1H, J=8.4 Hz), 7.15 (dd, 1H, J=8.4 Hz, 2.5 Hz), 6.80 (d, 1H, J=1.4 Hz), 6.72 (d, 1H, J=1.8 Hz), 4.39–4.46 (m, 1H), 3.88 (s, 3H), 3.78–3.86 (m, 1H), 3.40–3.45 (m, 2H), 3.16–3.24 (m, 1H), 3.01–3.07 (m, 1H), 2.88–2.91 (m, 2H), 2.50–2.65 (m, 2H), 2.41 (bs, 1H), 1.82–2.17 (m, 4H) ppm. MS-ApCI: 365[M+H$^+$].

Example 568

{2-[(8aS,12aR)-6,7,8a,9,10,11,12,12a-octahydro-5H-[1,4]oxazepino[2,3,4-hi]pyrido[4,3-b]indol-2-yl]-5-methoxyphenyl}methanol Tert-butyl(8aS,12aR)-2-(2-formyl-4-methoxyphenyl)-6,7,9,10,12,12a-hexahydro-5H-[1,4]oxazepino[2,3,4-hi]pyrido[4,3-b]indole-11(8aH)-carboxylate (20 mg, 0.04 mmol) was dissolved in $CH_2Cl_2$. The mixture was cooled down to −78° C. under an inert atmosphere. DIBAL in $CH_2Cl_2$ (0.07 mL, 0.07 mmol) (1 mL) was added dropwise at −78° C. The reaction mixture was warmed up to r.t. in 2 hours. The reaction mixture was concentrated in vacuo. $CH_2Cl_2$(2 mL) and sat. Rochelle salt solution (2 mL) were added, the layers were separated. The organic layer is dried over $MgSO_4$ and concentrated in vacuo to afford tert-butyl (8aS,12aR)-2-[2-hydroxymethyl)-4-methoxyphenyl]-6,7,9,10,12,12a-hexahydro-5H-[1,4]oxazepino[2,3,4-hi]pyrido[4,3-b]indole-11(8aH)-carboxylate. The title compound was prepared by the method of Example 98 from tert-butyl(8aS, 12aR)-2-[2-(hydroxymethyl)-4-methoxyphenyl]-6,7,9,10,12,12a-hexahydro-5H-[1,4]oxazepino[2,3,4-hi]pyrido[4,3-b]indole-11(8aH)-carboxylate to afford the title compound (10 mg, 68%). $^1$H NMR ($CDCl_3$, 300 MHz) δ7.17 (d, 1H, J=8.4 Hz), 7.09 (d, 1H, J=2.5 Hz), 6.84 (dd, 1H, J=8.4 Hz, 2.6 Hz), 6.76 (d, 1H, J=1.5 Hz), 6.72 (d, 1H, J=1.5 Hz), 4.63 (s, 2H), 4.38–4.46 (m, 1H), 3.77–3.88 (m, 1H), 3.84 (s, 3H), 3.35–3.44 (m, 2H), 3.14–3.20 (m, 1H), 2.97–3.04 (m, 1H), 2.85–2.88 (m, 2H), 2.48–2.62 (m, 2H), 1.75–2.12 (m, 5H), 1.25 (s, 1H) ppm. MS-ESI: 367[MH]$^+$.

Example 569

{2-[(8aS,12aR)-6,7,8a,9,10,11,12,12a-octahydro-5H-[1,4]oxazepino[2,3,4-hi]pyrido[4,3-b]indol-2-yl] phenyl}methanol The title compound was prepared by the method of Example 568 from tert-butyl(8aS,12aR)-2-(2-formylphenyl)-6,7,9,10,12,12a-hexahydro-5H-[1,4]oxazepino[2,3,4-hi]pyrido[4,3-b]indole-11(8aH)-carboxylate (20 mg, 0.05 mmol) to afford the title compound (12 mg, 71%). $^1$H NMR ($CDCl_3$, 300 MHz) δ7.49–7.53 (m, 1H), 7.24–7.36 (m, 3H), 6.82 (d, 1H, J=1.8 Hz), 6.77 (d, 1H, J=1.5 Hz), 4.65 (s, 2H), 4.39–4.46 (m, 1H), 3.77–3.85 (m, 1H), 3.39–3.45 (m, 2H), 3.14–3.21 (m, 1H), 2.98–3.05 (m, 1H), 2.86–2.91 (m, 2H), 2.49–2.63 (m, 2H), 1.76–2.17 (m, 5H), 1.25 (s, 1H) ppm. MS-ESI: 337[MH]$^+$.

Example 570

N-[4-[(8aS,12aR)-6,7,8a,9,10,11,12,12a-octahydro-5H-[1,4]oxazepino[2,3,4-hi]pyrido[4,3-b]indol-2-yl]-3-(trifluoromethyl)phenyl]-N-methylamine Step A Tert-butyl(8aS,12aR)-2-[4-[(tert-butoxycarbonyl)(methyl)amino]-2-(trifluoromethyl)phenyl]-6,7,9,10,12,12a-hexahydro-5H-[1,4]oxazepino[2,3,4-hi]pyrido[4,3-b]indole-11(8aH)-carboxylate was prepared by the method of Example 89 step C from tert-butyl(8aS,12aR)-2-bromo-6,7,9,10,12,12a-hexahydro-5H-[1,4]oxazepino[2,3,4-hi]pyrido[4,3-b]indole-11(8aH)-carboxylate (205 mg, 0.5 mmol) and corresponding 4-[(tert-butoxycarbonyl)(methyl)amino]-2-(trifluoromethyl)phenylboronic acid (319 mg, 1.0 mmol) to afford after chromatographic purification the desired product (226mg, 75%). MS-ApCI: 604[M+H$^+$].

Step B

The title compound was prepared by the method of Example 98 from tert-butyl(8aS,12aR)-2-[4-[(tert-butoxycarbonyl)(methyl)amino]-2-(trifluoromethyl)phenyl]-6,7,9,10,12,12a-hexahydro-5H-[1,4]oxazepino[2,3,4-hi]pyrido[4,3-b]indole-11(8aH)-carboxylate to afford the title compound (130 mg, 86%). $^1$H NMR ($CDCl_3$, 300 MHz) δ7.12 (d, 1H, J=8.5 Hz), 6.93 (d, 1H, J=1.8 Hz), 6.69–6.88 (m, 3H), 4.38–4.45 (m, 1H), 3.77–3.89 (m, 2H), 3.34–3.45 (m, 2H), 3.09–3.19 (m, 1H), 2.90–3.04 (m, 1H), 2.89 (s, 3H), 2.87 (s, 3H), 2.47–2.79 (m, 2H), 1.70–2.17 (m, 5H) ppm. MS-ApCI: 404[M+H$^+$].

Example 571

4-[(8aS,12aR)-6,7,8a,9,10,11,12,12a-octahydro-5H-[1,4]oxazepino[2,3,4-hi]pyrido[4,3-b]indol-2-yl]-3-(trifluoromethyl)phenylamine Step A Tert-butyl(8aS,12aR)-2-[4-[(tert-butoxycarbonyl)amino]-2-(trifluoromethyl)phenyl]-6,7,9,10,12,12a-hexahydro-5H-[1,4]oxazepino[2,3,4-hi]pyrido[4,3-b]indole-11(8aH)-carboxylate was prepared by the method of Example 89 step C from tert-butyl(8aS,12aR)-2-bromo-6,7,9,10,12,12a-hexahydro-5H-[1,4]oxazepino[2,3,4-hi]pyrido[4,3-b]indole-11(8aH)-carboxylate (205 mg, 0.5 mmol) and corresponding 4-[(tert-butoxycarbonyl)amino]-2-(trifluoromethyl)phenylboronic acid (305 mg, 1.0 mmol) to afford after chromatographic purification the desired product (145 mg, 50%).

Step B

The title compound was prepared by the method of Example 98 from tert-butyl(8aS,12aR)-2-[4-[(tert-butoxycarbonyl)amino]-2-(trifluoromethyl)phenyl]-6,7,9,10,12,12a-hexahydro-5H-[1,4]oxazepino[2,3,4-hi]pyrido[4,3-b]indole-11(8aH)-carboxylate to afford the title compound (8 mg, 84%). $^1$H NMR ($CDCl_3$, 300 MHz) δ7.10 (d, 1H, J=8.1 Hz), 6.98 (d, 1H, J=2.2 Hz), 6.78 (dd, 1H, J=8.1 Hz, 1.9 Hz), 6.71 (d, 2H, J=10.6 Hz), 4.38–4.45 (m, 1H), 3.75–3.81 (m, 3H), 3.38–3.42 (m, 2H), 3.11–3.19 (m, 1H), 2.97–3.04 (m, 1H), 2.85–2.89 (m, 2H), 2.47–2.60 (m, 2H), 1.76–2.12 (m, 4H), 1.62 (bs, 1H) ppm. MS-ESI: 390[MH]$^+$.

Example 572

1-{2-[(8aS,12aR)-6,7,8a,9,10,11,12,12a-octahydro-5H-[1,4]oxazepino[2,3,4-hi]pyrido[4,3-b]indol-2-yl] phenyl}ethanone Step A To tert-butyl(8aS,12aR)-2-(2-formylphenyl)-6,7,9,10,12,12a-hexahydro-5H-[1,4]oxazepino[2,3,4-hi]pyrido[4,3-b]indole-11(8aH)-carboxylate (114 mg, 0.26 mmol) in freshly distilled THF (4 mL) at r.t. was added MeMgBr (0.44 mL, 1.3 mmol) dropwise. The reaction mixture was stirred at r.t. for for 18 hours. The $CH_3OH$ (0.5 mL) was added dropwise to the reation mixture and concentrated in vacuo. EtOAc (5 mL) was added, washed with brine(5 mL), the organic layer was dried over $MgSO_4$, concentrated to afford tert-butyl (8aS,12aR)-2-[2-(1-hydroxyethyl)phenyl]-6,7,9,10,12,12a-hexahydro-5H-[1,4]oxazepino[2,3,4-hi]pyrido[4,3-b]indole-11(8aH)-carboxylate. The crude product was used in next step.

Step B

Oxalyl Chloride (0.038 mL, 0.432 mmol) was dissolved in $CH_2Cl_2$ (3 mL), cooled down to −60° C. DMSO in $CH_2Cl_2$ (1 mL) was added dropwise to above solution. After the reaction mixture was stirred at −60° C. for 10 min., tert-butyl(8aS,12aR)-2-[2-(1-hydroxyethyl)phenyl]-6,7,9,10,12,12a-hexahydro-5H-[1,4]oxazepino[2,3,4-hi]pyrido[4,3-b]indole-11(8aH)-carboxylate (97 mg, crude from step 1) in $CH_2Cl_2$ (2 mL) was added dropwise. The reaction mixture was stirred at −60° C. for 15 min.. Triethylamine (0.24 mL, 1.73 mmol) was added at −60° C. The cooling bath was removed and $H_2O$ (6 mL) was added at r.t., the stir was continued for ca. 10 min. and organic layer was separated. The aqueous phase was extracted with $CH_2Cl_2$ (2×6 mL). The combined organic layer was dried over $MgSO_4$ to afford after chromatographic purification tert-butyl(8aS,12aR)-2-(2-acetylphenyl)-6,7,9,10,12,12a-hexahydro-5H-[1,4]oxazepina[2,3,4-hi]pyrido[4,3-b]indole-11(8aH)-carboxylate (48 mg, 41%) in two steps. MS-ApCI: 449[M+H$^+$].

Step C

The title compound was prepared by the method of Example 98 from tert-butyl(8aS,12aR)-2-(2-acetylphenyl)-6,7,9,10,12,12a-hexahydro-5H-[1,4]oxazepina[2,3,4-hi]pyrido[4,3-b]indole-11(8aH)-carboxylate to afford the title compound (32 mg, 86%). $^1$H NMR ($CDCl_3$, 300 MHz) δ7.42–7.48 (m, 2H), 7.30–7.37 (m, 2H), 6.83 (d, 1H, J=1.5 Hz), 6.69 (d, 1H, J=1.5 Hz), 4.40–4.47 (m, 1H), 3.75–3.83

(m, 1H), 3.37–3.46 (m, 2H), 3.11–3.19 (m, 1H), 2.98–3.05 (m, 1H), 2.85–2.89 (m, 2H), 2.44–2.61 (m, 2H), 1.96–2.12 (m, 3H), 2.00 (s, 3H), 1.75–1.86 (m, 1H), 1.64 (bs, 1H) ppm. MS-ESI: 349[MH]$^+$.

Example 573

1-{2-[(8aS,12aR)-6,7,8a,9,10,11,12,12a-octahydro-5H-[1,4]oxazepino[2,3,4-hi]pyrido[4,3-b]indol-2-yl]-5-methoxyphenyl}ethanone Step A Tert-butyl(8aS,12aR)-2-(2-acetyl-4-methoxphenyl)-6,7,9,10,12,12a-hexahydro-5H-[1,4]oxazepina[2,3,4-hi]pyrido[4,3-b]indole-11(8aH)-carboxylate was prepared by the method of Example 600 from tert-butyl(8aS,12aR)-2-(2-formyl-4-methoxyphenyl)-6,7,9,10,12,12a-hexahydro-5H-[1,4]oxazepino[2,3,4-hi]pyrido[4,3-b]indole-11(8aH)-carboxylate (72 mg, 0.16 mmol) and MeMgBr(0.26 mL, 0.78 mmol) to afford after two steps the desired product (24 mg, 33%). MS-ApCI: 479[M+H$^+$].

Step B

The title compound was prepared by the method of Example 98 from tert-butyl(8aS,12aR)-2-(2-acetyl-4-methoxyphenyl)-6,7,9,10,12,12a-hexahydro-5H-[1,4]oxazepinao[2,3,4-hi]pyrido[4,3-b]indole-11(8aH)-carboxylate to afford the title compound (11 mg, 63%). $^1$H NMR ($CDCl_3$, 300 MHz) δ7.27–7.29 (m, 1H), 6.99–7.01 (m, 2H), 6.79 (d, 1H, J=1.8 Hz), 6.65 (d, 1H, J=1.5 Hz), 4.39–4.46 (m, 1H), 3.74–3.88 (m, 1H), 3.84 (s, 3H), 3.38–3.44 (m, 2H), 3.11–3.19 (m, 1H), 2.98–3.05 (m, 1H), 2.73–2.89 (m, 2H), 2.43–2.59 (m, 2H), 1.70–2.17 (m, 5H), 1.99 (s, 3H) ppm. MS-ESI: 379[MH]$^+$.

Example 574

1-{2-[(8aS,12aR)-6,7,8a,9,10,11,12,12a-octahydro-5H-[1,4]oxazepino[2,3,4-hi]pyrido[4,3-b]indol-2-yl] phenyl}ethanol To 1-{2-[(8aS,12aR)-6,7,8a,9,10,11,12,12a-octahydro-5H-[1,4]oxazepino[2,3,4-hi]pyrido[4,3-hi]indol-2-yl] phenyl}ethanone (10 mg, 0.03 mmol) in $CH_3OH$ (1 mL) at r.t. was added $NaBH_4$ (5.4 mg, 0.15 mmol) in three portions. The reaction mixture was stirred at r.t. for for 2 hours. 2 drops of 1N HCl were added to the reaction mixture, concentrated in vacuo. $NH_4OH$ (1 mL) and water (2 mL) were added, extracted with $CH_2Cl_2$ (3×3 mL). The combined organic layer was dried over $MgSO_4$, concentrated to afford the title compound (7 mg, 70%) $^1$H NMR ($CDCl_3$, 300 MHz) δ7.62 (d, 1H, J=3.7 Hz), 7.17–7.38 (m, 3H), 6.69–6.77 (m, 2H), 5.01–5.08 (m, 1H), 4.40–4.45 (m, 1H), 3.78–3.84 (m, 1H), 3.38–3.44 (m, 2H), 3.11–3.17 (m, 1H), 2.97–3.06 (m, 1H), 2.86–2.89 (m, 2H), 2.48–2.61 (m, 2H), 1.68–2.10 (m, 6H), 1.32–1.47 (m, 3H) ppm. MS-ESI: 351 [MH]$^+$.

Example 575

1-{2-[(8aS,12aR)-6,7,8a,9,10,11,12,12a-octahydro-5H-[1,4]oxazepino[2,3,4-hi]pyrido[4,3-b]indol-2-yl]-5-methoxyphenyl}ethanol The title compound was prepared by the method of Example 574 from 1-{2-[(8aS,12aR)-6,7,8a,9,10,11,12,12a-octahydro-5H-[1,4]oxazepino[2,3,4-hi]pyrido[4,3-b]indol-2-yl]-5-methoxyphenyl}ethanone (9 mg, 0.02 mmol) to afford the title compound (8 mg, 80%). $^1$H NMR ($CDCl_3$, 300 MHz) δ7.17 (d, 1H, J=2.6 Hz), 7.11 (d, 1H, J=8.4 Hz), 6.81(dd, 1H, J=8.4 Hz, 2.6 Hz), 6.70 (d, 1H, J=2.6 Hz), 6.65 (s, 1H), 4.99–5.05 (m, 1H), 4.40–4.44 (m, 1H), 3.85 (s, 3H), 3.75–3.81 (m, 1H), 3.38–3.43. (m, 2H), 3.10–3.17 (m, 1H), 2.95–3.01(m, 1H), 2.84–2.88 (m, 2H), 2.46–2.60 (m, 2H), 1.67–2.11 (m, 6H), 1.25–1.44 (m, 3H) ppm. MS-ESI: 381 [MH]$^+$.

Example 576

4-[(8aS,12aR)-6,7,8a,9,10,11,12,12a-octahydro-5H-[1,4]oxazepino[2,3,4-hi]pyrido[4,3-b]indol-2-yl]-3-(trifluoromethyl)phenol Step A Tert-butyl(8aS,12aR)-2-[4-hydroxy-2-(trifluoromethyl) phenyl]-6,7,9,10,12,12a-hexahydro-5H-[1,4]oxazepino[2,3,4-hi]pyrido[4,3-b]indole-11(8aH)-carboxylate was prepared by the method of Example 89 step C from tert-butyl(8aS,12aR)-2-bromo-6,7,9,10,12,12a-hexahydro-5H-[1,4]oxazepino[2,3,4-hi]pyrido[4,3-b]indole-11(8aH)-carboxylate (205 mg, 0.5 mmol) and corresponding 2-(trifluoromethyl)-4-[(triisopropylsily)oxy]phenylboronic acid (363 mg, 1.0 mmol) to afford after chromatographic purification tert-butyl(8aS,12aR)-2-[4-hydroxy-2-(trifluoromethyl)phenyl]-6,7,9,10,12,12a-hexahydro-5H-[1,4]oxazepino[2,3,4-hi]pyrido[4,3-b]indole-11(8aH)-carboxylate (47 mg, 19%) MS-ApCI: 491[M+H$^+$] and tert-butyl(8aS,12aR)-2-{2-(trifluoromethyl)-4-[(triisopropylsilyl)oxy]phenyl}-6,7,9,10,12,12a-hexahydro-5H-[1,4]oxazepino[2,3,4-hi]pyrido[4,3-b]indole-11(8aH)-carboxylate (167 mg, 52%) MS-ApCI: 647[M+H$^+$].

Step B

Tert-butyl(8aS,12aR)-2-{2-(trifluoromethyl)-4-[(triisopropylsily)oxy]phenyl}-6,7,9,10,12,12a-hexahydro-5H-[1,4]oxazepino[2,3,4-hi]pyrido[4,3-b]indole-11(8aH)-carboxylate (167 mg, 0.26 mmol) was dissolved in $CH_3CN$(5 mL), added KF $2H_2O$, the reaction mixture was stirred at r.t. under an inert atmosphere for 20 hr. EtOAc (20 mL) and brine (15 mL) were added, the organic layer was dried over $MgSO_4$ and concentrated in vacuo to afford tert-butyl(8aS,12aR)-2-[4-hydroxy-2-(trifluoromethyl) phenyl]-6,7,9,10,12,12a-hexahydro-5H-[1,4]oxazepino[2,3,4-hi]pyrido[4,3-b]indole-11(8aH)-carboxylate (100 mg, 79%).

Step C

The title compound was prepared by the method of Example 98 from tert-butyl(8aS,12aR)-2-[4-hydroxy-2-(trifluoromethyl)phenyl]-6,7,9,10,12,12a-hexahydro-5H-[1,4]oxazepino[2,3,4-hi]pyrido[4,3-b]indole-11(8aH)-carboxylate (47 mg, 0.1 mmol) to afford the title compound (20 mg, 51%). $^1$H NMR ($CDCl_3$, 300 MHz) δ7.02–7.06 (m, 2H), 6.81(dd, 1H, J=8.4 Hz, 2.5 Hz), 6.68 (s, 1H), 6.60 (s, 1H), 4.31–4.38 (m, 1H), 4.14 (bs, 1H), 3.68–3.76 (m, 1H), 3.31–3.36 (m, 2H), 3.10–3.17 (m, 1H), 2.88–3.02 (m, 3H), 2.46–2.56 (m, 2H), 1.81–2.10 (m, 5H) ppm. MS-ESI: 391 [MH]$^+$.

Example 577

4-[(8aS,12aR)-6,7,8a,9,10,11,12,12a-octahydro-5H-[1,4]oxazepino[2,3,4-hi]pyrido[4,3-b]indol-2-yl]-3-(trifluoromethyl)phenyl acetate Step A To tert-butyl(8aS,12aR)-2-[4-hydroxy-2-(trifluoromethyl)phenyl[-6,7,9,10,12,12a-hexahydro-5H-[1,4]oxazepino[2,3,4-hi]pyrido[4,3-b]indole-11(8aH)-carboxylate (50 mg, 0.13 mmol), $Et_3N$ (0.091 mL, 1.3 mmol) in DMF (2 mL), added acetyl chloride (0.45 mL, 3.2 mmol) at r.t., the reaction mixture was stirred at r.t. for 2 hr. EtOAc (4 mL) and water (2 mL) were added. The organic layer was dried over $MgSO_4$, concentrated in vacuo to afford after chromatographic purification the desired product (30 mg, 44%). MS-ApCI: 533[M+H$^+$].

Step B

The title compound was prepared by the method of Example 98 from tert-butyl(8aS,12aR)-2-[4-(acetyloxy)-2-(trifluoromethyl)phenyl]-6,7,9,10,12,12a-hexahydro-5H-[1,4]oxazepino[2,3,4-hi]pyrido[4,3-b]indole-11(8aH)-carboxylate (30 mg, 0.06 mmol) to afford the title compound (5 mg, 21%) after High Pressure Liquid Chromatography purification. MS-ESI: 433[MH]$^+$.

Example 578

(8aS,12aR)-N-(diphenylmethylene)-6,7,8a,9,10,11,12,12a-octahydro-5H-pyrido[4,3-b][1,4]thiazepino[2,3,4-hi]indol-2-amine Step A Tert-butyl(8aS,12aR)-2-bromo-6,7,9,10,12,12a-hexahydro-5H-pyrido[4,3-b][1,4,]thiazepino[2,3,4-hi]indole-11(8aH)-carboxylate (0.25 g, 0.58 mmol) was stirred with benzophenone imine (0.125 g, 0.69 mmol), sodium tertbutoxide (0.078 g, 0.82 mmol), and (R) BINAP (0.026 g, 0.042 mmol) in dry toluene (10.4 mL) under $N_2$ for 15 minutes. $Pd_2dba_3$ (0.026 g, 0.029 mmol) was added in one portion and the reaction brought to 80° C. for fifteen hours. The reaction was concentrated and purified by silica gel column chromatography (10% EtOAc/Hexanes). tert-butyl (8aS,12aR)-2-[(diphenylmethylene)amino]-6,7,9,10,12,12a-hexahydro-5H-pyrido[4,3-b][1,4,]thiazepino[2,3,4-hi]indole-11(8aH)-carboxylate (0.261 g, 86%) was collected as a bright orange semi-solid. $^1$H NMR ($CDCl_3$, 300 MHz) 7.71 (d, 2H, J=6.6 Hz), 7.35–7.48 (m, 3H), 7.30–7.35 (m, 3H), 7.10–7.18 (m, 2H), 6.55 (br s, 1H), 6.19 (br s, 1H), 3.60–3.74 (m, 3H), 3.30–3.47 (m, 2H), 3.12–3.24 (m, 1H), 2.92–3.07 (m, 2H), 2.81–2.90 (m, 1H), 1.98–2.10 (m, 3H), 1.80–1.88 (m, 2H), 1.47 (s, 9H) ppm.

Step B

Tert-butyl(8aS,12aR)-2-[(diphenylmethylene)amino]-6,7,9,10,12,12a-hexahydro-5H-pyrido[4,3-b][1,4,]thiazepino[2,3,4-hi]indole-11(8aH)-carboxylate (0.025 g, 0.047 mmol) was dissolved in $CH_2Cl_2$ (1 mL) with TFA (0.3 mL) and stirred at room temperature for one hour. The reaction was basified to a pH of 10 with $NH_4OH$ (sat.) and the aqueous layer extracted with $CHCl_3$ (3×10 mL). The combined extracts were washed with brine (5 mL) and dried ($MgSO_4$) and evaporated to give the title compound as a light yellow residue (0.016 g, 78% yield). $^1$H NMR ($CDCl_3$, 300 MHz) 7.81 (dd, 4H, J=1.1, 6.9 Hz), 7.57–7.64 (m, 2H), 7.48 (t, 4H, J=7.7 Hz), 6.36 (d, 1H, J=2.6 Hz), 6.30 (d, 1H, J=2.2 Hz), 3.41–3.59 (m, 3H), 3.25–3.36 (m, 2H), 3.08–3.18 (m, 1H), 2.79–2.98 (m, 3H), 2.57–2.63 (m 1H), 2.01–2.14 (m, 2H), 1.67–1.82 (m, 2H) ppm.

Example 579

(8aS,12aR)-N-(diphenylmethylene)-6,7,8a,9,10,11,12,12a-octahydro-5H-pyrido[4,3-b][1,4]thiazepino[2,3,4-hi]indol-3-amine Step A Tert-butyl(8aS,12aR)-3-[(diphenylmethylene)amino]-6,7,9,10,12,12a-hexahydro-5H-pyrido[4,3-b][1,4,]thiazepino[2,3,4-hi]indole-11(8aH)-carboxylate was prepared (0.304 g, 99%) according to the procedure given for Example 578, Step A substituting tert-butyl(8aS,12aR)-3-bromo-6,7,9,10,12,12a-hexahydro-5H-pyrido[4,3-b][1,4,]thiazepino[2,3,4-hi]indole-11(8aH)-carboxylate for tert-butyl(8aS,12aR)-2-bromo-6,7,9,10,12,12a-hexahydro-5H-pyrido[4,3-b][1,4,]thiazepino[2,3,4-hi]indole-11(8aH)-carboxylate. $^1$H NMR ($CDCl_3$, 300 MHz) 7.89 (d, 2H, J=6.9 Hz), 7.39–7.48 (m, 3H), 7.19–7.25 (m, 5H), 6.57 (d, 1H, J=7.7 Hz), 5.81 (d, 1H, J=7.7 Hz). 3.83–4.01 (m, 2H), 3.78–3.90 (m, 2H), 3.21–3.39 (m, 2H), 2.90–3.11 (m, 4H), 1.93–2.18 (m, 2H), 1.75–1.85 (m, 2H), 1.45 (s, 9H) ppm.

Step B

The title compound was prepared according to the procedure of Example 578, Step B (0.014 g, 68%). $^1$H NMR ($CDCl_3$, 300 MHz) 7.81 (dd, 4H, J=1.5, 6.9 Hz), 7.57–7.64 (m, 2H), 7.48 (t, 4H, J=7.7 Hz), 6.67 (t, 1H, J=4.0 Hz), 6.11 (d, 1H, J=7.7 Hz), 3.82–3.93 (m, 2H), 3.51–3.60 (m, 1H), 3.34–3.40 (m, 1H), 3.18–3.22 (m, 1H), 2.80–3.07 (m, 4H), 2.58–2.62 (m, 1H), 2.01–2.18 (m, 2H), 1.70–1.81 (m, 2H) ppm.

Example 580

(8aS,12aR)-6,7,8a,9,10,11,12,12a-octahydro-5H-pyrido[4,3-b][1,4]thiazepino[2,3,4-hi]indol-3-amine Step A Tert-butyl(8aS,12aR)-3-amino-6,7,9,10,12,12a-hexahydro-5H-pyrido[4,3-b][1,4,]thiazepino[2,3,4-hi]indole-11(8aH)-carboxylate was prepared according to the procedure in Example 430, Step B using tert-butyl(8aS,12aR)-3-[(diphenylmethylene)amino]-6,7,9,10,12,12a-hexahydro-5H-pyrido[4,3-b][1,4,]thiazepino[2,3,4-hi]indole-11(8aH)-carboxylate as starting material in 75% yield (0.051 g). $^1$H NMR ($CDCl_3$, 300 MHz) 6.71 (d, 1H, J=7.6 Hz), 6.12 (d, 1H, J=7.7 Hz), 3.97–4.01 (m, 1H), 3.42–3.65 (m, 4H), 3.21–3.39 (m, 1H), 2.98–3.19 (m, 4H), 2.01–2.19 (m, 2H), 1.81–1.92 (m, 2H), 1.45 (s, 9H) ppm.

Step B

The title compound was prepared according to the procedure in Example 578, Step B (0.012 g, 86%) using tert-butyl(8aS,12aR)-3-amino-6,7,9,10,12,12a-hexahydro-5H-pyrido[4,3-b][1,4,]thiazepino[2,3,4-hi]indole-11(8aH)-carboxylate as starting material. $^1$H NMR ($CDCl_3$, 300 MHz) 6.66 (t, 1H, J32 1.1 Hz), 6.11 (d, 1H, J=7.7 Hz), 3.81–3.97 (m, 2H), 3.52–3.61 (m, 1H), 3.35–3.41 (m, 1H), 3.10–3.22 (m, 1H), 2.81–3.05 (m, 5H), 2.58–2.62 (m, 1H), 2.01–2.21 (m, 2H), 1.78–1.83 (m, 2H) ppm.

Example 581

(8aS,12aR)-N-phenyl-6,7,8a,9,10,11,12,12a-octahydro-5H-pyrido[4,3-b][1,4]thiazepino[2,3,4-hi]indol-2-amine Step A Triphenylbismuth (0.220 g, 0.50 mmol) was stirred with iodobenzene diacetate (0.177 g, 0.55 mmol) in $CH_2Cl_2$ (5 mL) for 15 hours at room temperature. The solvent was evaporated and $Et_2O$ (2 mL) with heptane (2 mL) was added and heated. The resulting solid was filtered hot affording bis(acetato)triphenylbismuth (0.192 g, 70%) as a white flaky solid. $^1$H NMR ($CDCl_3$, 300 MHz) 8.15 (dd, 6H, J=1.1, 8.4 Hz), 7.62 (t, 6H, J=7.3 Hz), 7.50 (t, 3H, J=8.4 Hz), 1.81 (s, 6H) ppm.

Step B

Tert-butyl(8aS,12aR)-2-amino-6,7,9,10,12,12a-hexahydro-5H-pyrido[4,3-b][1,4,]thiazepino[2,3,4-hi]indole-11(8aH)-carboxylate (0.260 g, 0.72 mmol) was combined with bis(acetato)trisphenylbismuth (0.422 g, 0.756 mmol) and copper (II) acetate (0.013 g, 0.072 mmol) in $CH_2Cl_2$ (7.2 mL) and stirred for 30 minutes. The solvent was evaporated and the black residue purified by silica gel column chromatography (10% EtOAc/Hex) affording a blue foam. The compound was then dissolved in MeOH (2 mL)

and HCl gas was bubbled through for 10 minutes. The solvent was evaporated and the residue basified by sat $NH_4OH$. The aqueous layer was extracted with $CHCl_3$ (3×5 mL), washed with brine (10 mL) and dried ($MgSO_4$) and evaporated to give the title compound in 70% yield (0.169 g). $^1H$ NMR ($CDCl_3$, 300 MHz) 7.20 (t, 2H, J=8.4 Hz), 6.87 (dd, 2H, J=1.1, 8.5 Hz), 6.83 (t, 1H, J=7.4 Hz), 6.76 (d, 1H, J=2.2 Hz), 6.71 (d, 1H, J=2.2 Hz), 5.37 (s, 1H), 3.60–3.72 (m, 1H), 3.47–3.59 (m, 1H), 3.36–3.42 (m, 1H), 3.12–3.22 (m, 1H), 2.91–3.12 (m, 5H), 2.58–3.65 (m, 1H), 2.01–2.20 (m, 2H), 1.78–1.93 (m, 3H) ppm.

Example 582

(8aS,12aR)-N-phenyl-6,7,8a,9,10,11,12,12a-octahydro-5H-pyrido[4,3-b][1,4]thiazepino[2,3,4-hi]indol-3-amine The title compound was synthesized (0.029 g, 78%) according to procedure for Example 581, Step B using tert-butyl(8aS,12aR)-3-amino-6,7,9,10,12,12a-hexahydro-5H-pyrido[4,3-b][1,4,]thiazepino[2,3,4-hi]indole-11(8aH)-carboxylate as the starting material. $^1H$ NMR ($CDCl_3$, 300 MHz) 7.21–7.26 (m, 2H), 7.05 (dd, 2H, J=1.1, 8.8 Hz), 6.91 (t, 1H, J=7.3 Hz), 6.74 (d, 1H, J=7.7 Hz), 6.70 (d, 1H, J=8.1 Hz), 5.91 (s, 1H), 3.94–4.01 (m, 1H), 3.57–3.62 (m, 1H), 3.36–3.42 (m, 1H), 3.12–3.22 (m, 2H), 2.91–3.12 (m, 5H), 2.58–3.65 (m, 1H), 2.01–2.20 (m, 2H), 1.81–1.93 (m, 2H) ppm.

Example 583

(8aS,12aR)-N-(4-fluorophenyl)-6,7,8a,9,10,11,12,12a-octahydro-5H-pyrido[4,3-b][1,4]thiazepino[2,3,4-hi]indol-2-amine Step A To a solution of 4-flurorphenylmagnesium bromide (48.8 mL, 1.0 M THF) in dry diethyl ether (20 mL) was added bismuth(III)chloride (5.0 g, 15.8 mmol). The reaction was allowed to proceed at room temperature for two hours. Ice was added and the aqueous layer extracted with ether (3×25 mL). The combined extracts were washed with brine (25 mL) and dried ($MgSO_4$) and evaporated. The residue was combined iodobenzene diacetate (3.4 g, 10.5 mmol) in $CH_2Cl_2$ (20 mL) for 15 hours at room temperature. The solvent was evaporated affording Bis(acetato)tris(4-fluorophenyl)bismuth in overall 34% (3.28 g).%). $^1H$ NMR ($CDCl_3$, 300 MHz) 8.15–8.21 (m, 6H), 7.20–7.28 (m, 6H), 1.81 (s, 6H) ppm.

Step B

The title compound was prepared according to Example 581, Step B (0.118 g, 39%) using bis(acetato)tris(4-fluorophenyl)bismuth. $^1$HNMR ($CDCl_3$, 300 MHz) 6.81–6.99 (m, 4H), 6.71 (d, 1H, J=2.2 Hz), 6.63 (d, 1H, J=2.2 Hz), 5.27 (s, 1H), 3.60–3.72 (m, 1H), 3.47–3.59 (m, 1H), 3.36–3.42 (m, 1H), 3.12–3.22 (m, 1H), 2.91–3.12 (m, 5H), 2.58–3.65 (m, 1H), 2.01–2.20 (m, 2H), 1.78–1.93 (m, 3H) ppm.

Example 584

(8aS,12aR)-N-(2,4-dichlorophenyl)-6,7,8a,9,10,11,12,12a-octahydro-5H-pyrido[4,3-b][1,4]thiazepino[2,3,4-hi]indol-2-amine Tert-butyl(8aS,12aR)-2-amino-6,7,9,10,12,12a-hexahydro-5H-pyrido[4,3-b][1,4,]thiazepino[2,3,4-hi]indole-11(8aH)-carboxylate (0.100 g, 0.27 mmol) was combined with 2,4-dichlorobenzeneboronic acid (0.104 g, 0.55 mmol), triethylamine (0.055 g, 0.55 mmol), copper(II) acetate (0.049 g, 0.27 mmol) and $CH_2Cl_2$ (3 mL) and stirred for 24 hours. The solvent was evaporated and the residue purified by silica gel chromatography (15% EtOAc/Hex). The resulting oil was dissolved in MeOH (2 mL) and HCl (g) was bubbled through for 10 minutes. The solvent was stripped and the residues partitioned between $NH_4OH$ (sat.) and $CHCl_3$. The aqueous layer was extracted with $CHCl_3$ (3×10 mL). The combined organics were washed with brine (5 mL) and dried ($MgSO_4$) and evaporated affording the title compounds in 14% yield (15 mg). $^1H$ NMR ($CDCl_3$, 300 MHz) 7.28 (d, 1H, J=2.5 Hz), 7.02 (dd, 1H, J=2.6, 8.8 Hz), 6.84 (d, 1H, J=9.2 Hz), 6.79 (d, 1H, J=2.2 Hz), 6.68 (d, 1H, J=1.8 Hz), 5.79 (s, 1H), 3.62–3.72 (m, 1H), 3.47–3.59 (m, 1H), 3.36–3.42 (m, 1H), 3.12–3.22 (m, 1H), 2.91–3.12 (m, 5H), 2.58–3.65 (m, 1H), 2.01–2.20 (m, 2H), 1.78–1.93 (m, 3H) ppm.

Example 585

N-[(8aS,12aR)-6,7,8a,9,10,11,12,12a-octahydro-5H-pyrido[4,3-b][1,4]thiazepino[2,3,4-hi]indol-2-ylbenzamide Step A Tert-butyl(8aS,12aR)-2-amino-6,7,9,10,12,12a-hexahydro-5H-pyrido[4,3-b][1,4,]thiazepino[2,3,4-hi]indole-11(8aH)-carboxylate (0.070 g, 0.194 mmol) was combined with benzoyl chloride (0.033 g, 0.23 mmol), triethylamine (0.022 g, 0.213 mmol) and $CH_2Cl_2$ (1.0 mL) and stirred for one hour at room temperature. The solvent was evaporated and the residue purified by silica gel column chromatography (25%EtOAc/Hex). Collection afforded tert-butyl(8aS,12aR)-2-(benzoylamino)-6,7,9,10,12,12a-hexahydro-5H-pyrido[4,3-b][1,4,]thiazepino[2,3,4-hi]indole-11(8aH)-carboxylate as a white foam (0.057 g, 63%). $^1H$ NMR ($CDCl_3$, 300 MHz) 7.83 (d, 2H, J=6.6 Hz), 7.62–7.71 (m, 1H), 7.25–7.39 (m, 2H), 3.61–3.83 (m, 2H), 3.41–3.58 (m, 2H), 3.07–3.31 (m, 4H), 2.85–3.02 (m, 2H), 2.01–2.18 (m, 2H), 1.81–1.91 (m, 2H), 1.44 (s, 9H) ppm.

Step B

The title compound was prepared according to the procedure in Example 578, Step B to give a light yellow oil (89%). $^1H$ NMR ($CDCl_3$, 300 MHz) 7.83 (dd, 2H, J=1.5, 6.9 Hz), 7.70 (s, 1H), 7.42–7.58 (m, 3H), 7.35 (s, 1H), 7.05 (d, 1H, J=1.9 Hz), 3.60–3.72 (m, 1H), 3.47–3.59 (m, 1H), 3.36–3.42 (m, 1H), 3.17–3.22 (m, 1H), 2.82–3.12 (m, 5H), 2.58–2.65 (m, 1H), 2.01–2.20 (m, 2H), 1.78–1.93 (m, 3H) ppm.

Example 586

(8aS,12aR)-N-benzyl-6,7,8a,9,10,11,12,12a-octahydro-5H-pyrido[4,3-b][1,4]thiazepino[2,3,4-hi]indol-2-amine N-[(8aS,12aR)-6,7,8a,9,10,11,12,12a-octahydro-5H-pyrido[4,3-b][1,4]thiazepnio[2,3,4-hi]indol-2-ylbenzamide (0.055 g, 0.149 mmol) was dissolved in THF (0.57 mL) and $LiAlH_4$ (0.299 mL, 1M THF), was added dropwise. The reaction was refluxed for 2 hours. The reaction was quenched and the mixture filtered. The filtrate was evaporated and the product purified by HPLC (Chiralcel OD/20% EtOH/Hexanes w/0.05% diethylamine at 7 ml/min). Compound collected as a light orange oil affording the title compound in 59% yield (0.031 g). $^1H$ NMR ($CDCl_3$, 300 MHz) 7.26–7.41 (m, 5H), 6.33 (d, 1H, J=2.2 Hz), 6.28 (d, 1H, J=2.2 Hz), 4.21 (s, 2H), 3.41–3.57 (m, 2H), 3.25–3.31 (m, 1H), 3.02–3.18 (m, 1H), 2.80–3.02 (m, 5H), 3.57–3.64 (m, 1H), 2.01–2.17 (m, 2H), 2.70–2.91 (m, 2H) ppm.

Example 587

(8aS,12aR)-2-(phenylsulfanyl)-6,7,8a,9,10,11,12,12a-octahydro-5H-pyrido[4,3-b][1,4]thiazepino[2,3,4-hi]indole Step A Tert-butyl(8aS,12aR)-2-bromo-6,7,9,10,12,12a-hexahydro-5H-pyrido[4,3-b][1,4,]thiazepino[2,3,4-hi]indole-11(8aH)-carboxylate (0.100 g, 0.235 mmol), was stirred in anhydrous diethyl ether (0.5 mL) with N,N,N',N'-tetramethylethylenediamine (0.054 g, 0.47 mmol) at −78° C. for 10 minutes under $N_2$. Tert-butyllithium (0.276 mL, 1.7M in Hexanes) was added dropwise and the reaction stirred at −78° C. for 20 minutes. The S-phenyl benzethiosulfonate (0.117 g, 0.47 mmol) was added and the reaction brought to room temperature for 1 hour. The reaction was poured onto 1M $H_3PO_4$ and the aqueous layer extracted with $CHCl_3$ (3×10 mL). The combined extracts were washed with sat. $NaHCO_3$ (aq.) (10 mL), brine (10 mL) and dried ($MgSO_4$) and evaporated. The resulting yellow oil was purified by silica gel column chromatography (10% EtOAc/Hex) and collected to afford tert-butyl(8aS,12aR)-2-(phenylsulfanyl)6,7,9,10,12,12a-hexahydro-5H-pyrido[4,3-b][1,4,]thiazepino[2,3,4-hi]indole-11(8aH)-carboxylate in 50% yield. $^1$H NMR ($CDCl_3$, 300 MHz) 7.12–7.26 (m, 6H), 7.00 (s, 1H), 3.81–3.92 (m, 1H), 3.42–3.63 (m, 3H), 3.31–3.41 (m, 1H), 3.07–3.25 (m, 3H), 2.87–3.04 (m, 2H), 2.01–2.19 (m, 2H), 1.82–1.91 (m, 2H), 1.43 (s, 9H) ppm.

Step B

Tert-butyl(8aS,12aR)-2-(phenylsulfanyl)6,7,9,10,12,12a-hexahydro-5H-pyrido[4,3-b][1,4,]thiazepino[2,3,4-hi]indole-11(8aH)-carboxylate was dissolved in ethanol (1 mL) and 1N HCl/Ether (2 mL) was added and the reaction stirred for 1 hour. $NH_4OH$ (sat.) was added and the aqueous layer partitioned over $CHCl_3$. The aqueous layer is extracted with $CHCl_3$ (3×5 mL). The combined extracts are washed with brine (5 mL) and dried ($MgSO_4$) and evaporated. The yellow residue was purified by HPLC (Chiralcel OD column/10% EtOH/Hexanes with 0.05 diethylamine/flow rate-7 ml/min) affording the title compound (0.033 g, 80%) as a clear, colorless oil. $^1$HNMR ($CDCl_3$, 300 MHz) 7.12–7.26 (m, 6H), 6.96 (d, 1H, J=1.8 Hz), 3.81–3.89 (m, 1H), 3.51–3.62 (m, 1H), 3.40–3.49 (m, 1H), 3.19–3.27 (m, 1H), 3.01–3.07 (m, 3H), 2.82–2.93 (m, 2H), 2.01–2.21 (m, 2H), 1.78–1.83 (m, 3H) ppm.

Example 588

(8aS,12aR)-3-methoxy-6,7,8a,9,10,11,12,12a-octahydro-5H-pyrido[4,3-b][1,4]thiazepino[2,3,4-hi]indole Step A Tert-butyl(8aS,12aR)-3-bromo-6,7,9,10,12,12a-hexahydro-5H-pyrido[4,3-b][1,4]thiazepino[2,3,4-hi]indole-11(8H)-carboxylate (0.100 g, 0.235 mmol) was combined with copper (I) iodide (0.023 g, 0.121 mmol), sodium methoxide (0.233 g, 4.23 mmol), methanol (0.66 mL) and dimethylformamide (0.66 mL) and stirred for 15 hours. The reaction was partitioned between water and $CHCl_3$. The aqueous layer was extracted with $CHCl_3$ (3×10 mL). The combined organics were dried ($MgSO_4$) and evaporated. The resulting residue was purified by silica gel column chromatography (10% EtOAc/Hexanes) affording tert-butyl (8aS,12aR)-3-methoxy-6,7,9,10,12,12a-hexahydro-5H-pyrido[4,3-b][1,4,]thiazepino[2,3,4-hi]indole-11(8aH)-carboxylate in 29% yield. $^1$H NMR ($CDCl_3$, 300 MHz) 6.81 (d, 1H, J=8.0 Hz), 6.24 (d, 1H, J=8.1 Hz), 3.98–4.11 (m, 1H), 3.82 (s, 3H), 3.61–3.74 (m, 3H), 3.42–3.51 (m, 1H), 3.22–3.37 (m, 1H), 2.95–3.19 (m, 4H), 1.95–2.21 (m, 2H), 1.81–1.87 (m, 2H), 1.45 (s, 9H) ppm.

Step B

The title compound was prepared according to the procedure of Example 578, Step B in 78% yield. $^1$H NMR ($CDCl_3$, 300 MHz) 6.79 (d, 1H, J=8.1 Hz), 6.24 (d, 1H, J=7.6 Hz), 3.98–4.11 (m, 1H), 3.82 (s, 3H), 3.59–3.71 (m, 1H), 3.30–3.41 (m, 1H), 2.93–3.17 (m, 6H), 2.59–2.65 (1H), 1.95–2.21 (m, 2H), 1.87–1.99 (m, 2H) ppm.

Example 589

{2-[(8aS,12aR)-6,7,8a,9,10,11,12,12a-octahydro-5H-prydiro[4,3-b][1,4]thiazepino[2,3,4-hi]indol-2-yl]-5-methoxyphenyl}methanamine Step A Tert-butyl(8aS,12aR)-2-(2-formyl-4-methoxyphenyl)-6,7,9,10,12,12a-hexhydro-5H-pyrido[4,3-b][1,4]thiazepino[2,3,4-hi]indole-11(8aH)-carboxylate (0.340 g, 0.70 mmol) was stirred with allyl amine (0.040 g, 0.70 mmol), dichloroethane (3.5 mL) and acetic acid (1.5 mL) for 0.5 hours under $N_2$. Sat. sodium bicarbonate is added slowly and the mixtured basified to a pH of 10 with $NH_4OH$ (sat.). The layers were separated and the aqueous layer extracted with $CHCl_3$ (3×25 mL). The combined organics were washed with brine (20 mL), and dried ($MgSO_4$) and evaporated. The resulting yellow foam was purified by silica gel column chromatography (30% EtOAc/Hex) affording tert-butyl (8aS,12aR)-2-{2-[(allylamino)methyl]-4-methoxyphenyl)-6,7,9,10,12,12a-hexahydro-5H-pyrido[4,3-b][1,4]thiazepino[2,3,4-hi]indole-11(8H)-carboxylate as a light yellow foam (0.150 g, 41%). $^1$H NMR ($CDCl_3$, 300 MHz) 7.13 (d, 1H, J=8.5 Hz), 7.00 (d, 1H, J=2.6 Hz), 6.96 (d, 1H, J=1.5 Hz), 6.88 (s, 1H), 6.82 (dd, 1H, J=2.5, 8.4 Hz) 5.75–5.92 (m, 1H), 5.02–5.37 (m, 2H), 3.85 (s, 3H), 3.72–3.80 (m, 2H), 3.72 (s, 2H), 3.52–3.61 (m, 2H), 3.20–3.39 (m, 2H), 3.11–3.21 (m, 2H), 2.91–3.03 (m, 2H), 2.01–2.21 (m, 2H), 1.83–1.93 (m, 2H), 1.44 (s, 9H) ppm.

Step B

Tert-butyl(8aS,12aR)-2-{2-[(allylamino)methyl]-4-methoxyphenyl)-6,7,9,10,12,12a-hexahydro-5H-pyrido[4,3-b][1,4]thiazepino[2,3,4-hi]indole-11(8H)-carboxylate (0.080 g, 0.154 mmol), was stirred with N,N dimethylbarbituric acid (0.072 g, 0.462 mmol), $Pd(PPh_3)_4$ (0.0017 g, 1.54 μmol), and $CH_2Cl_2$ (0.5 mL) under $N_2$ for 3 hours at 35° C. The solvent was evaporated and the residue partitioned between EtOAc and sodium carbonate (sat. aq.). The organic layer was washed with sodium carbonate (sat. aq., 2×10 mL) and dried ($MgSO_4$) and evaporated. The resulting residue was purified by silica gel column chromatography (3% MeOH/$CH_2Cl_2$). The collected solid was dissolved in MeOH (2 mL) and HCl gas was bubbled through for 15 minutes. The solvent was evaporated and the solid recrystallized in EtOH to afford the title compound (0.020 g, 38%) as a light tan solid. $^1$H NMR ($CD_3OD$, 300 MHz) 7.17 (d, 1H, J=8.4 Hz), 7.07 (d, 1H, J=2.6 Hz), 6.91–7.97 (m, 1H), 6.91 (s, 2H), 4.04 (s, 2H), 3.82 (s, 3H), 3.81–3.94 (m, 1H), 3.52–3.63 (m, 1H), 3.30–3.24 (m, 4H), 3.12–3.23 (m, 2H), 2.93–3.02 (m, 1H), 2.71–2.81 (m, 1H), 2.01–2.31 (m, 4H) ppm.

Example 590

4-[(8aS,12aR)-3-chloro-6,7,8a,9,10,11,12,12a-octahydro-5H-pyrido[4,3-b][1,4]thiazepino[2,3,4-hi]indol-2-yl]-3-methylphenylmethylether Tert-butyl(8aS,12aR)-2-bromo-6,7,9,10,12,12a-hexahydro-5H-pyrido[4,3-b][1,4,]thiazepino[2,3,4-hi]indole-11(8aH)-carboxylate (0.050 g, 0.108 mmol) was combined with 2-methyl, 4-methoxyphenylboronic acid (0.021 g, 0.130 mmol), barium hydroxide octahydrate (0.030 g, 0.15 mmol) in ethyleneglycol dimethylether (1.5 mL) and water (0.7 mL) and degassed for 15 minutes. $Pd(Ph_3)_4$ (0.0047 g, 4 μmol) was added in one portion and the reaction brought to reflux for 15 hours. The solvent was evaporated and the residue partitioned over water and $CHCl_3$. The aqueous layer was extracted with $CHCl_3$ (3×10 mL). The combined extracts were washed with brine (10 mL) and dried ($MgSO_4$) and evaporated. The residue was purified by silica gel column chromatography (10% EtOAc/Hex). The collected residue was dissolved in MeOH (2 mL) and HCl gas was bubbled through for 15 minutes. The solvent was evaporated and the residue basified with $NH_4OH$ (sat.) to a pH of 12. The aqueous layer was extracted with $CHCl_3$ (3×5 mL). The combined organics were washed with brine (5 mL) and dried ($MgSO_4$) and evaporated affording the title compound (0.028 g, 65%) as a white solid. $^1H$ NMR ($CDCl_3$, 300 MHz) 6.91–7.01 (m, 1H), 6.62–6.75 (m, 3H), 6.58 (d, 1H, J=2.9 Hz), 3.86–4.01 (m, 1H), 3.70 (m, 3H), 3.68–3.78 (m, 1H), 3.31–3.39 (m, 1H), 2.85–3.17 (m, 4H), 3.81–3.87 (m, 2H), 2.51–2.60 (m, 1H), 2.03 (d, 3H, J=8.4 Hz), 1.62–1.95 (m, 5H) ppm.

The residue was chiral separated by HPLC (Chiralcel OD column/8% EtOH/Hex with 0.05% diethylamine/7 ml/min) affording both enantiomers of the title compound.

Example 591

4-((8aS,12aR)-3-chloro-6,7,9,10,12,12a-hexahydro-5H-pyrido[4,3-b][1,4]thiazepino[2,3,4-hi]indol-11(8aH)-yl)-1-(2-amino-4-fluorophenyl)-1-butanone (8aS,12aR)-3-Chloro-6,7,8a,9,10,11,12,12a-octahydro-5H-pyrido[4,3-b][1,4]thiazepino[2,3,4-hi]indole (0.090 g, 0.38 mmol) was stirred with 1-(2-amino-4-fluorophenyl)-5-1-pentanone (0.164 g, 0.76 mmol), potassium carbonate (0.210 g, 1.52 mmol) and potassium iodide (0.020 g, 0.120 mmol) in 1,4 dioxane (2 mL) and refluxed for 72 hours. $H_2O$ (5 mL) was added and the aqueous layer was extracted with $CHCl_3$ (3×10 mL). The combined extracts were washed with brine (10 mL) and dried ($MgSO_4$) and evaporated. The resulting residue was purified by silica gel column chromatography (2.5% MeOH/$CH_2Cl_2$) affording the title compound in 27% yield (0.046 g). $^1H$ NMR ($CDCl_3$, 300 MHz) 7.78–7.81 (m, 2H), 3.73 (s, 1H), 6.24–6.42 (m, 4H), 3.98–4.07 (m, 1H), 3.63–3.78 (m, 2H), 3.23–3.31 (m, 2H), 2.81–3.07 (m, 4H), 2.61–2.80 (m, 3H), 2.11–2.31 (m, 2H), 1.82–2.01 (m, 6H) ppm.

Example 592

(8aS,12aR)-N-(2-methyl-4-methoxyphenyl)-6,7,8a,9,10,11,12,12a-octahydro-5H-pyrido[4,3-b][1,4]thiazepino[2,3,4-hi]indol-2-amine Step A 3-Bromo-4-methylanisole (0.576 g, 3.0 mmol) was dissolved in dry THF (15 mL). Mg (1.46 g, 60 mmol) turnings were then added. The reaction was heated to 60° C., one crystal of $I_2$ was added and the magnesium turnings were gently crushed with a glass rod. Upon emergence of bubbling, the remainder of the 3-bromo-4-methylanisole (5.18 g, 27 mmol) was added in 25 mL of THF. The reaction continued at room temperature for 15 minutes. The solution was transferred slowly to a flask containing $BiCl_3$ (2.84 g, 9.0 mmol) white cooling at 0° C. A heterogeneous solution formed and was stirred for 4 hours at room temperature. The mixture was then filtered through a celite bed and the filtrate poured onto ice/$H_2O$ and EtOAc. The aqueous layer was extracted with EtOAc (2×50 mL). The combined organic layers were evaporated leaving a off-white solid. The solid was washed with cold EtOAc to give tris(2-methyl-4-methoxyphenyl)bismuth as a white solid (2.29 g, 47%). $^1H$ NMR ($CDCl_3$, 300 MHz) 7.40 (d, 3H, J=8.4 Hz), 6.88 (d, 3H, J=2.5 Hz), 6.62 (dd, 3H, J=2.5, 8.4 Hz), 3.37 (s, 9H), 2.40 (s, 3H) ppm.

Step B

Tris(2-methyl-4-methoxyphenyl)bismuth (0.933 g, 1.7 mmol) was combined with iodobenzenediacetate (0.544 g, 1.7 mmol) in 19 mL of $CH_2Cl_2$ and stirred for 16 hours. The solvent was evaporated yielding bis(acetato)tris(2-methyl-4-methoxyphenyl)bismuth as an off white solid (0.805 g, 74%). $^1H$ NMR ($CDCl_3$, 300 MHz) 8.22 (d, 3H, J=8.5 Hz), 6.95–7.00 (m, 6H), 3.85 (s, 9H), 2.57 (m, 9H), 1.73 (m, 6H) ppm.

Step C

The title compound was prepared according to Example 581, Step B (0.032 g, 49%) using bis(acetato)tris(2-methyl-4-methoxyphenyl)bismuth. $^1$HNMR ($CDCl_3$, 300 MHz) 7.01 (d, 1H, J=8.8 Hz), 6.63–6.77 (m, 2H), 6.45 (dd, 2H, J=2.2, 13.6 Hz), 4.88 (s, 1h), 3.77 (s, 3H), 3.40–3.61 (m, 2H), 3.24–3.37 (m, 1H), 3.07–3.17 (m, 1H), 2.78–3.01 (m, 4H), 2.56–2.63 (m, 1H), 2.19 (s, 3H), 2.00–2.20 (m, 2H), 1.65–1.83 (m, 3H) ppm.

Example 593

(8aS,12aR)-N-(2-fluoro-4-methoxyphenyl)-6,7,8a,9,10,11,12,12a-octahydro-5H-pyrido[4,3-b][1,4]thiazepino[2,3,4-hi]indol-2-amine Step A An oven-dried three neck round bottom flask was charged with tert-butyl(8aS,12aR)-2-amino-6,7,9,10,12,12a-hexahydro-5H-pyrido[4,3-b][1,4]thiazepino[2,3,4-hi]indole-11(8aH)-carboxylate (200 mg, 0.55 mmol), anhydrous toluene (4 mL), and NaOtBu (70.9 mg, 0.737 mmol), and 4-bromo-3-fluoroanisole (94.5 mg, 0.461 mmol) under argon. The solvent was degassed with argon at room temperature for 10 min and at 80° C. for 25 min then cooled to room temperature. To the reaction flask was added $Pd_2(dba)_3$ (1.0 mg, 0.00115 mmol) and BINAP (2.1 mg, 0.00347 mmol). The mixture was heated to 80° C. for 16 hours under an Ar atmosphere until the starting material was consumed as shown by TLC analysis (1:1, Hexanes:Ethyl Acetate). The mixture was cooled to room temperature, diluted with diethyl ether, filtered through a celite bed, and the filtrate was concentrated to give a dark oil. The latter residue was purified by chromatography on silica gel (CombiFlash) (gradient eluent 97:3 to 75:25, Hexanes:Ethyl Acetate) to afford tert-butyl(8aS,12aR)-2-(2-fluoro-4-methoxyanilino)-6,7,9,10,12,12a-hexahydro-5H-pyrido[4,3-b][1,4]thiazepino[2,3,4-hi]indole-11(8aH)-carboxylate as a clear oil (118 mg, 53%). $^1H$ NMR ($CDCl_3$, 300 MHz) δ1.43 (s, 9H), 1.83–1.86 (m, 3 H), 2.04–2.10 (m, 3 H), 2.88–3.69 (m, 8 H), 3.78 (s, 3 H), 5.18 –5.19 (m, 1 H), 6.58–6.70 (m,4 H), 7.02–7.09 (m,1H). ESI:MS m/z=486 $[C_{26}H_{32}FN_3O_3S+H]^+$.

Step B

Tert-butyl(8aS,12aR)-2-(2-fluoro-4-methoxyanilino)-6,7,9,10,12,12a-hexahydro-5H-pyrido[4,3-b][1,4]thiazepino[2,3,4-hi]indole-11(8aH)-carboxylate was deprotected using trifluroacetic acid to give the title compound. MS/ESI m/z=386 $[C_{21}H_{24}FN_3OS+H]^+$.

Example 594

(8aS,12aR)-N-(4-methoxy-2-methylphenyl)-6,7,8a,9,10,11,12,12a-octahydro-5H-pyrido[4,3-b][1,4]thiazepino[2,3,4-hi]indol-2-amine Step A Tert-butyl(8aS,12aR)-2-(4-methoxy-2-methylanilino)-6,7,9,10,12,12a-hexahydro-5H-pyrido[4,3-b][1,4]thiazepino[2,3,4-hi]indole-11(8aH)-carboxylate (219 mg, 93%) was prepared from the reaction of 1-bromo-4-methoxy-2-methylbenzene (107.9 mg, 0.488 mmol) and tert-butyl(8aS, 12aR)-2-amino-6,7,9,10,12,12a-hexahydro-5H-pyrido[4,3-b][1,4]thiazepino[2,3,4-hi]indole-11(8aH)-carboxylate (212 mg, 0.586 mmol) following the procedure described in example 593, Step A. $^1$H NMR ($CDCl_3$, 500 MHz) δ1.43 (s, 9 H), 1.81–1.83 (m, 3 H), 2.03–2.11 (m, 3 H), 2.21 (s, 3 H), 2.89–3.65 (m, 8 H), 3.79 (s, 3 H), 4.87–4.88 (m, 1 H), 6.44–6.48 (m, 2 H), 6.67–6.68 (m, 1 H), 6.73 (s, 1 H), 6.99–7.01 (m, 1 H). MS-ESI m/z=382 $[C_{27}H_{35}N_3O_3S-C_5H_9O_2+H]^+$.

Step B

Tert-butyl(8aS,12aR)-2-(4-methoxy-2-methylanilino)-6,7,9,10,12,12a-hexahydro-5H-pyrido[4,3-b][1,4]thiazepino[2,3,4-hi]indole-11(8aH)-carboxylate was deprotected with Ethanol/HCl to give the title compound. $^1$H NMR ($CDCl_3$, 500 MHz) δ1.70–187 (m, 3 H), 2.02–2.12 (m,3 H), 2.19 (s, 3 H), 2.54–3.59 (m, 8 H), 3.77 (s, 3 H), 4.86 (s, 1 H), 6.41 (s, 1 H), 6.46 (s, 1 H), 6.67 (dd, 1 H, J=8.6 Hz, J=2.7 Hz), 6.74 (d, 1 H, J=2.7 Hz), 6.99 (d, 1 H, J=8.6). MS-ESI m/z 382 $[C_{22}H_{27}N_3OS+H]^+$.

Example 595

(8aS,12aR)-N-(4-fluoro-2-methylphenyl)-6,7,8a,9,10,11,12,12a-octahydro-5H-pyrido[4,3-b][1,4]thiazepino[2,3,4-hi]indol-2-amine Step A Tert-butyl(8aS,12aR)-2-(4-fluoro-2-methylanilino)-6,7,9,10,12,12a-hexahydro-5H-pyrido[4,3-b][1,4]thiazepino[2,3,4-hi]indole-11(8aH)-carboxylate (176 mg, 85%) was prepared from the reaction of 1-bromo-4-fluoro-2-methylbenzene (88.0 mg, 0.465 mmol) and tert-butyl(8aS,12aR)-2-amino-6,7,9,10,12,12a-hexahydro-5H-pyrido[4,3-b][1,4]thiazepino[2,3,4-hi]indole-11(8aH)-carboxylate (202 mg, 0.56 mmol) following the procedure described in example 593, Step A. $^1$H NMR ($CDCl_3$, 500 MHz) δ1.43 (s, 9 H), 1.82–1.83 (m, 3 H), 2.04–2.11 (m, 3 H), 2.22 (s, 3 H), 2.89–3.88 (m, 8H), 4.92 (s, 1 H), 6.52–6.58 (m, 2 H), 6.75–6.82 (m, 1 H), 6.83–6.89 (m, 1 H), 6.92–6.97 (m, 1 H). MS-ESI m/z=470 $[C_{26}H_{32}FN_3O_2S+H]^+$.

Step B

Tert-butyl(8aS,12aR)-2-(4-fluoro-2-methylanilino)-6,7,9,10,12,12a-hexahydro-5H-pyrido[4,3-b][1,4]thiazepino[2,3,4-hi]indole-11(8aH)-carboxylate was deprotected using trifluroacetic acid to give the title compound. $^1$H NMR ($CDCl_3$, 500 MHz) δ1.72–1.87 (m, 2 H), 2.05–2.19 (m, 5 H), 2.55–2.63 (m, 1 H), 2.79–2.99 (m, 5 H), 3.13–3.19 (m, 1 H), 3.33–3.35 (m, 1 H), 3.45–3.65 (m, 2 H), 4.93 (s, 1 H), 6.51 (d, 1 H, J=2.1 Hz), 6.56 (d, 1 H, J=2.2 Hz), 6.73–6.98 (m, 3 H). MS-ESI m/z=370 $[C_{21}H_{24}FN_3S+H]^+$.

Example 596

1-{2-[(8aS,12aR)-6,7,8a,9,10,11,12,12a-octahydro-5H-pyrido[4,3-b][1,4]thiazepino[2,3,4-hi]indole-2-yl]-5-fluorophenyl}ethanol Step A 2-Bromo-5-fluorobenzoic acid (4.60 g, 0.02 mol), N,O-Dimethylhydroxylamine hydrochloride (2.05 g, 0.02 mol), carbon tertabromide (6.9 g, 0.02 mol) was added to mixture of methylene chloride (100 mL) and triethylamine (2.9 mL, 0.02 mol). Triphenylphospine (5.53 g, 0.02 mol) was added to the solution over 1 hour and stirred for another 1 hour. The solution was concentrated to an oil. Hexanes (100 mL) and Ethyl Acetate (100 mL) were added to the oil and stirred for 1 hour then filtered. The filtrate was concentrated and the residue was purified by chromatography (Hexanes/Ethyl Acetate) on silica gel to afford 2-bromo-5-fluoro-N-methoxy-N-methylbenzamide as a foamy white solid in 73% yield. $^1$H NMR ($CDCl_3$, 500 MHz) δ3.00–3.98 (m, 6 H), 6.97–7.08 (m, 2H), 7.51–7.54 (m, 1H).

Step B

2-Bromo-5-fluoro-N-methoxy-N-methylbenzamide (4.0 g, 0.015 mol) was dissolved in THF (30 mL) and the solution was cooled to 0° C. under $N_2$blanket. Methyl magnesium bromide (15.26 mL, 0.046 mol) was added dropwise over 30 min. The solution was warmed to room temperature and stirred for 1 hour. The solution was cooled to 0° C. and quenched with HCl/EtOH (9 mL, 4 M solution). The reaction mixture was transferred to a separatory funnel, diluted with $H_2O$ (30 mL), and extracted with Ethyl Acetate (2×40 mL). The combined organic extracts were washed with $H_2O$, brine, and dried over $Na_2SO_4$. The solution was concentrated to afford 1-(2-bromo-5-fluorophenyl)ethanone as a yellow oil in 93% yield. This material was used in the subsequent step without further purification. $^1$H NMR ($CDCl_3$, 500 MHz) δ2.61 (s, 3H), 7.00–7.04 (m, 1H) 7.15–7.18 (m, 1H), 7.53–7.59 (m, 1H).

Step C

Ethylene glycol (25.6 mL, 458 mmol) and p-toluenesulfonic acid (4.36 g, 22.9 g) were added to a solution of 1-(2-bromo-5-fluorophenyl)ethanone (10.5 g, 45.8 mmol) stirring in benzene (250 mL). The reaction mixture was equipped with a Dean Stark trap containing 4.0 angstrom molecular sieves and refluxed for 16 h. The reaction was transferred to a separatory funnel containing a 1:1 mixture of $H_2O$ and sat. $NaHCO_3$ (aq) and extracted with EtOAc (3×100 mL). The combined organics were washed with $H_2O$, brine, dried over $Na_2SO_4$ and concentrated. The resulting oil was purified by column chromatography to give 2-(2-bromo-5-fluorophenyl)-2-methyl-1,3-dioxolane (7.20 g) in 58% yield. $^1$H NMR ($CDCl_3$, 300 MHz) δ2.60 (s, 3 H) 4.02–4.20 (m, 4H), 6.85–6.90 (m, 1H), 7.29–7.33 (m, 1H), 7.48–7.56 (m, 1H).

Step D

A solution of t-butyl lithium (19.0 mL) was added dropwise to a solution of 2-(2-bromo-5-fluorophenyl)-2-methyl-1,3-dioxolane (4.02 g, 15.40 mmols) and triisopropyl borate (4.6 mL, 19.93 mmols in anhydrous THF (40 mL), stirring under an inert atmosphere at −78° C. The resulting yellow solution was stirred at −78° C. for ½ h and then allowed to warm to −15° C. The resulting boronic ester was hydrolyzed in situ with sat'd $NH_3Cl$ (aq) at room temperature. The reaction mixture was transferred to a separatory funnel, diluted with $H_2O$ (50 mL), and extracted with EtOAc (3×50 mL). The combined organics were washed with $H_2O$, brine, dried over $Na_2SO_4$, and concentrated. The resulting residue was recrystallized from EtOAc and hexanes to give 4-fluoro-2-(2-methyl-1,3-dioxolan-2-yl)phenylboronic acid at an orange solid (2.62 g, 75%). $^1$H NMR (DMSO, 300 MHz) δ1.60 (s, 3H), 3.61–3.67 (m, 2H), 3.87–3.93 (m, 2H), 7.02–7.08 (m, 2H), 7.24–7.30 (m, 1H), 7.59 (s, 1H) ppm; $^1$H NMR (DMSO+$D_2O$, 300 MHz) δ1.61 (s, 3H), 3.61–3.67 (m, 2H), 3.78 (brs, 2H) 3.89–3.94 (m, 2H), 7.04–7.10 (m, 2H), 7.26–7.31 (m, 1H) ppm.

Step E

The 4-fluoro-2-(2-methyl-1,3-dioxolan-2-yl) phenylboronic acid (0.94, 212 mg), tert-butyl(8aS,12aR)-2-bromo-6,7,9,10,12,12a-hexahydro-5H-pyrido[4,3-b][1,4]thiazepino[2,3,4-hi]indole-11(8aH)-carboxylate (0.47, 200 mg), $Na_2CO_3$ (2M, 8 mL), and DME (15 mL) were combined and degassed with nitrogen for 20 minutes. $Pd(OAc)_2$ (0.047 mmol, 11 mg) and $PPh_3$ (0.94 mmol, 26 mg) were combined under nitrogen in THF (5 mL) and added to the stirred solution via cannula. The solution was refluxed and was stirred overnight. The DME was removed in vacuo and the black oil was dissolved in EtOAc (50 mL), washed with $H_2O$ (2×20 mL), dried over $MgSO_4$, and concentrated in vacuo yielding a yellow oil. This oil was purified by column chromatography, eluting with EtOAc/hexanes (1:5) to give tert-butyl(8aS,12aR)-2-[4-fluoro-2-(2-methyl-1,3-dioxolan-2-yl)phenyl]-6,7,9,10,12,12a-hexahydro-5H-pyrido[4,3-b][1,4]thiazepino[2,3,4-hi]indole-11(8aH)-carboxylate (190 mg, 77%) as a yellow oil; m/z (APcI) 527.1 $(M+H)^+$.

Step F

TFA (2 mL) was added to a stirred solution of tert-butyl (8aS,12aR)-2-[4-fluoro-2-(2-methyl-1,3-dioxolan-2-yl) phenyl]-6,7,9,10,12,12a-hexahydro-5H-pyrido[4,3-b][1,4] thiazepino[2,3,4-hi]indole-11(8aH)-carboxylate (0.10 mmol, 50 mg) in $CH_2Cl_2$ (10 mL) at room temperature under an atmosphere of nitrogen. The solution was stirred at room temperature for one hour, diluted with $CH_2Cl_2$ (20 mL), washed with NaOH (1N, 2×15 mL), dried over $Na_2SO_4$ and concentrated in vacuo to give (8aS,12aR)-2-[4-fluoro-2-(2-methyl-1,3-dioxolan-2-yl)phenyl]-6,7,8a,9,10,11,12,12a-octahydro-5H-pyrido[4,3-b][1,4]thiazepino[2,3,4-hi]indole (41 mg, 100%) as a yellow oil; m/z (ES) 427.3 $(M+H)^+$.

Step G

The (8aS,12aR)-2-[4-fluoro-2-(2-methyl-1,3-dioxolan-2-yl)phenyl]-6,7,8a,9,10,11,12,12a-octahydro-5H-pyrido[4,3-b][1,4]thiazepino[2,3,4-hi]indole was dissolve in acetone (10 mL) and $H_2O$ (10 mL), and treated with TsOH (10 mg) under $N_2$ at 40° C. overnight. The reaction was cooled and diluted with EtOAc (50 mL) and washed with 1N NaOH (2×25 mL.) The EtOAc was dried with $Na_2SO_4$ and concentrated in vacuo to yield 1-{2-[(8aS,12aR)-6,7,8a-9,10,11,12,12a-octahydro-5H-pyrido[4,3-b][1,4]thiazepino[2,3,4-hi]indol-2-yl]-5-fluorophenyl}ethanone (28, 73%) as a yellow oil; m/z (ES) 383.3 $(M+H)^+$.

Step H

1-{2-[(8aS,12aR)-6,7,8a,9,10,11,12,12a-octahydro-5H-pyrido[4,3-b][1,4]thiazepino[2,3,4-hi]indol-2-yl]-5-fluorophenyl}ethanone was dissolved in MeOH (2 mL) and treated with $NaBH_4$ for 2 hrs. at room temperature. The reaction was quenched with 1 drop 1 N HCl. The reaction was diluted with 30 mL DCM and was washed with 50% $NH_4OH$ (2×10 mL.) The DCM was dried with $Na_2SO_4$ and concentrated. The product was purified by reverse phase HPLC yielding the titled compound as a yellow oil (18 mg, 67%); m/z (ES) 385.3 $(M+H)^+$.

UTILITY

The compounds of the present invention have therapeutic utility for illnesses or disorders involving the neurotransmitter serotonin (5-hydroxy tryptamine or 5-HT) and either agonism or antagonism of 5-HT2 receptors, as demonstrated by the assays described below. Therapeutic utility for these illnesses or disorders could involve numerous biological processes affected by serotonin including, but not limited to, appetite, mood, sleep, sexual activity, and arterial constriction. These biological processes may also be important to numerous central nervous system (CNS) disorders including those related to the affective disorders of depression, anxiety, psychosis, and schizophrenia, as well as, disorders of food intake such as anorexia, bulemia, and obesity. The compounds of the present invention potentially have therapeutic utility in other conditions in which serotonin has been implicated, such as migraine, attention deficit disorder or attention deficit hyperactivity disorder, addictive behavior, and obsessive-compulsive disorder, as well as, conditions associated with cephalic pain, social phobias, and gastrointestinal disorders such as dysfunction of the gastrointestinal tract motility. Lastly, compounds of the present invention potentially have therapeutic utility in neurodegenerative diseases and traumatic conditions represented by the examples of Alzheimer's disease and brain/spinal cord trauma.

The pharmacological analysis of each compound fro either antagonism or agonism of at 5-HT2A and 5-HT2C receptors consisted of in vitro and in vivo studies. In vitro analyses included $K_i$ determinations at 5-HT2A and 5-HT2C receptors and an assessment of functional (i.e., agonism or antagonism) activity at each receptor class by IP3 hydrolysis assays. Additional receptor assays were conducted to evaluate receptor specificity of 5-HT2A and 5-HT2C receptors over monoamine and nuisance receptors (e.g. histamine, dopamine, and muscarinic). A compound is considered active as a 5-HP2A antagonist or a 5-HT2C agonist if it has an $IC_{50}$ value or a $K_i$ value of less than about 1 micromolar; preferably less than about 0.1 micromolar; more preferably less than about 0.01 micromolar. Compounds of the invention have been shown to have an $IC_{50}$ value of less than about 1 micromolar for 5-HP2A antagonism or a 5-HT2C agonism.

In vivo assays assessed compound activity in a variety of behavioral paradigms including quipazine head twitch, acute and chronic feeding models, anxiety and depression models (learned-helplessness, elevated plus maze, Geller-Siefter, conditioned taste aversion, taste reactivity, satiety sequence). In aggregate, these models reflect activity as a 5-HT2A antagonist (quipazine head twitch, depressing models) or 5-HT2C agonist (feeding models, anxiety models, depression models) and provide some indication as to bioavailability, metabolism and pharmacokinetics.

Radioligand binding experiments were conducted on recombinant human 5-HT2A and 5-HT2C receptors expressed in HEK293E cells. The affinities of compounds of the present invention to bind at these receptors is determined by their capacity to complete for [$^{125}$I]-1-(2,5-dimethoxy-4-iodophenyl)-2-amino-propane (DOI) binding at the 5-HT2A or 5-HT2C. General references for binding assays include 1) Lucaites V L, Nelson D L, Wainscott D B, Baez M (1996) Receptor subtype and density determine the coupling repertoire of the 5-HT2 receptor subfamily. Life Sci., 59(13) :1081–95. J Med Chem January 1988; 31(1) :5–7; 2) Glennon R A, Seggel M.R, Soine W H, Herrick-Davis K, Lyon R A, Titeler M (1988) [125I]-1-(2,5-dimethoxy-4-iodophenyl)-2-aminopropane: an iodinated radioligand that specifically labels the agonist high-affinity state of 5-HT2 serotonin receptors. J Med. Chem. 31(1):5–7 and 3) Leonhardt S, Gorospe E, Hoffman B J, Teitler M (1992) Molecular pharmacological differences in the interaction of serotonin with 5-hydroxytryptamine1C and 5-hydroxytryptamine2 receptors. Mol Pharmacol., 42(2) :328–35.

The functional properties of compounds (efficacy and potency) were determined in whole cells expressing 5-HT2A or 5-HT2C receptors by assessing their ability to stimulate or inhibit receptor-mediated phosphoinositol hydrolysis. The procedures used are described below.

In Vitro Binding Assays

Stable Expression of 5-HT2A and 5-HT2C Receptors in HEK293E Cells.

Stable cell lines were generated by transfecting 293EBNA cells with plasmids containing human 5-HT2A, 5-HT2B, or 5-HT2C (VNV edited isoform) cDNA using calcium phosphate. These plasmids also contained the cytomegalovirus (CMV) immediate early promoter to drive receptor expression and EBV orip for their maintenance as an extrachromosomal element, and the hph gene from E. Coli to yield hygromycin B resistance (Horlick et al., 1997). Transfected cells were maintained in Dulbecco's Modified Eagle medium (DMEM) containing dialyzed 10% fetal bovine serum at 37° C. in a humid environment (5% $CO_2$) for 10 days. The 5-HT2A cells were adapted to spinner culture for bulk processing whereas it was necessary to maintain the other lines as adherent cultures. On the day of harvest, cells were washed in phosphate-buffered saline (PBS), counted, and stored at −80° C.

Membrane Preparation

On the day of assay, pellets of whole cells (containing approximately 1×108 cells) expressing the 5-HT2A or 5-HT2C receptor were thawed on ice and homogenized in 50 mM Tris HCl (pH 7.7) containing 1.0 mM EDTA using a Brinkman Polytron (PT-10, setting 6 for 10 sec). The homogenate was centrifuged at 48,000×g for 10 min and the resulting pellet washed twice by repeated homogenization and centrifugation steps. The final pellet was resuspended in tissue buffer and protein determinations were made by the bichichoninic acid (BCA) assay (Pierce Co., IL) using bovine serum albumin as the standard.

Radioligand Binding Assays for the 5-HT2A, and 5-HT2C Receptors

Radioligand binding studies were conducted to determine the binding affinities (KI values) of compounds for the human recombinant 5-HT2A, 5-HT2B, and 5-HT2C receptors (Fitzgerald et al., 1999). Assays were conducted in disposable polypropylene 96-well plates (Costar Corp., Cambridge, Mass.) and were initiated by the addition of 5-HT2A, 5-HT2B, or 5-HT2C membrane homogenate in tissue buffer (10–30 (g/well) to assay buffer (50 mM Tris HCl, 0.5 mM EDTA, 10 mM pargyline, 10 MM $MgSO_4$, 0.05% ascorbic acid, pH 7.5) containing [$^{125}$I]DOI for the 5-HT2A and 5-HT2C receptors (0.3–0.5 nM, final) or [$^3$H] LSD (2–2.5 nM, final) for the 5-HT2B receptor, with or without competing drug (i.e, newly synthesized chemical entity). For a typical competition experiment, a fixed concentration of radioligand was competed with duplicate concentrations of ligand (12 concentrations ranging from 10 picomolar to 10 micromolar). The reaction mixtures were incubated to equilibrium for 45 min at 37° C. and terminated by rapid filtration (cell harvestor; Inotech Biosystems Inc., Lansing, Mich.) over GFF glass-fiber filters that had been pre-soaked in 0.3% polyethyleneimine. Filters were washed in ice-cold 50 mM Tris HCl buffer (pH 7.5) and then counted in a gamma counter for the 5-HT2A and 5-HT2C assays, or by liquid scintillation spectroscopy for the 5-HT2B assay.

Phosphoinositide Hydrolysis Studies

The ability of newly synthesized compounds to stimulate phosphoinositide (PI) hydrolysis was monitored in whole cells using a variant (Egan et al., 1998) of a protocol described previously (Berridge et al., 1982). HEK293E cells expressing the human 5-HT2A, 5-HT2B, or 5-HT2C receptor were lifted with 0.5 mM EDTA and plated at a density of 100,000/well onto poly-D-lysine-coated 24-well plates (Biocoat; Becton Dickinson, Bedford, Mass.) in Dulbecco's modified Eagle's serum (DMEM; Gibco BRL) containing high glucose, 2mM glutamine, 10% dialyzed fetal calf serum, 250 (g/ml hygromycin B, and 250(g/ml G418. Following a 24–48 hr period, the growth media was removed and replaced with DMEM without fetal calf serum and inositol (Gibco BRL). The cells were then incubated with DMEM (without serum and inositol) containing a final concentration of 0.5 uCi/well myo-[$^3$H]inositol for 16–18 hr. Following this incubation, the cells were washed with DMEM (without serum or inositol) containing 10 mM LiCl and 10 (M pargyline and then incubated for 30 min with the same media but now containing one of several test compounds. Reactons were terminated by aspirating the media and lysing the cells by freeze-thaw. [$^3$H]phosphoinositides were extracted with chloroform/methanol (1:2 v/v), separated by anion exchange chromatography (Bio-Rad AGI-X8 resin), and counted by liquid scintillation spectroscopy as described previously (Egan et al., 1998).

Data Analyses

The equilibrium apparent dissociation constants (Ki's) from the competition experiments were calculated using an iterative nonlinear regression curve-fitting program (GraphPad Prism; San Diego, Calif.). For the PI hydrolysis experiments, EC50's were calculated using a one-site 'pseudo' Hill model: y=((Rmax−Rmin)/(1+R/EC50)nH))+Rmax where R=response (DeltaGraph, Monterey, Calif.). Emax (maximal response) was derived from the fitted curve maxima (net IP stimulation) for each compound. Intrinsic activity (IA) was determined by expressing the Emax of a compound as a percentage of the Emax of 5-HT (IA=1.0).

In Vivo Experiments for Serotonergic Ligands

Preclinical Efficacy, Potency, and Side Effect Liability.

a) Anti-Serotonin Efficacy

Antagonism of Quipazine-Induced Head Twitch in Rat. Quipazine, an agonist at 5-HT receptors, produces a characteristic head twitch response in rats. 5-HT receptor antagonists effectively antagonize this 5-HT agonist-induced behavioral effect (Lucki et al., 1984). Accordingly, the quipazine-induced head twitch model in rat can function as an in vivo behavioral correlate to 5-HT receptor binding. Compounds are administered 30 minutes before behavioral testing (and 25 minutes before quipazine), and a dose-related antagonism of the quipazine response is determined.

b) Antipsychotic Efficacy

Inhibition of the Conditioned Avoidance Response (CAR) in Rat. Rats are trained to consistently avoid (by climbing onto a pole suspended from the ceiling of the test chamber) an electric foot shock (0.75 mA) delivered to the grid floor of the testing chamber. All antipsychotic drugs effectively inhibit this conditioned avoidance response (Arnt, 1982). The ability of a compound to inhibit this response is used to determine the antipsychotic efficacy of potential drug candidates.

c) Extrapyramidal Side Effect Liability.

Induction of Catalepsy in Rat. Typical antipsychotic drugs produce extrapyramidal side effects (EPS) at clinically effective doses. The most widely accepted preclinical indicator of EPS liability in humans is a drug-induce catalepsy syndrome in rat (Costall and Naylor, 1975), a condition whereby the animal will remain immobile in an externally imposed posture (analogous to a catatonic stupor in humans). Rats are tested for induction of catalepsy in a dose-response test after oral administration of compounds.

d) CNS penetration; In Vivo Brain Receptor Occupancy

In Vivo Binding. To determine the level of in vivo receptor occupancy, an in vivo receptor binding protocol is used. This procedure uses an appropriate radioligand to label the receptor of interest. For example, to measure both Dopamine D2 and 5-HT2A receptors in vivo, one can use $^3$H-N-methyl spiperone ($^3$H -NMSP), (Frost, et. al. 1987) The procedure uses rats (or mice) fasted overnight. To measure the effects of compounds on the receptors of interest, compounds are dosed, usually p.o. for example in 2 microliters/gram body weight in 0.25% Methocel suspension. The radiolabeled compound (in this example, $^3$H-NMSP) is administered by i.v. tail vein injection (10 microcuries label/200 gram rat). Time course experiments are used to determine the optimal time of binding for both the radiolabeled and unlabeled compound. These optimal time frames are used for all subsequent dose-response experiments. After the appropriate time frame of compound/radioligand exposure, the animals are sacrificed and the relevant brain regions dissected (frontal cortex for 5-HT2A and striatum for D2 receptors) and examined for their content of radioactivity. The level of non-specific binding is determined by examining a brain region known not to contain the receptor of interest (in this case the cerebellum) or by administering an excess of compound known pharmacologically to interact with the receptor.

REFERENCES

Arnt, J. Acta Pharmacol. et Toxicol. 1982: 51, 321–329.

Berridge M. J., Downes P. C., Hanley M. R. (1982) Lithium amplifies agonist-dependent phosphotidyinositol response in brain and salivary glands. Biochem. J., 206, 587–595.

Costall, B and Naylor, R J. Psychopharmacology. 1975: 43, 69–74.

Egan C. T., Herrick-Davis K., Miller K., Glennon R. A., and Teitler M. (1998) Agonist activity of LSD and lisuride at cloned 5-HT2A and 5-HT2C receptors. Psychopharmacology, 136, 409–414.

Fitzgerald L W, Conklin D S, Krause C M, Marshall A P, Patterson J P, Tran D P, Iyer G, Kostich W A, Largent B L, Hartig P R (1999) High-affinity agonist binding correlates with efficacy (intrinsic activity) at the human serotonin 5-HT2A and 5-HT2C receptors: evidence favoring the ternary complex and two-state models of agonist action. J. Neurochem., 72, 2127–2134.

Frost, J. J., Smith, A. C., Kuhar, M. J., Dannals, R. F., Wagner, H. N., 1987, In Vivo Binding of 3H-N-Methylspiperone to Dopamine and Serotonin Receptors. Life Sciences, 40:987–995.

Horlick, R. A., Sperle, K., Breth, L. A., Reid, C. C., Shen, E. S., Robbinds, A. K., Cooke, G. M., Largent, B. L. (1997) Rapid Generation of stable cell lines expressing corticotrophin-releasing hormone receptor for drug discovery. Protein Expr. Purif. 9, 301–308.

Lucki, I, Nobler, M. S., Frazer, A., 1984, Differential actions of serotonin antagonists on two behavioral models of serotonin receptor activation in the rat. J. Pharmacol. Exp. Ther. 228(1):133–139.

Dosage and Formulation

The serotonin agonist and serotonin antagonist compounds of this invention can be administered as treatment for the control or prevention of central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility by any means that produces contact of the active agent with the agent's site of action, i.e., 5-HT2 receptors, in the body of a mammal. It can be administered by any conventional means available for use in conjunction with pharmaceuticals, either as an individual therapeutic agent or in a combination of therapeutic agents. It can be administered alone, but preferably is administered with a pharmaceutical carrier selected on the basis of the chosen route of administration and standard pharmaceutical practice.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. By way of general guidance, a daily dosage of active ingredient can be expected to be about 0.001 to about 1000 milligrams per kilogram of body weight, with the preferred dose being about 0.01 to about 100 mg/kg; with the more preferred dose being about 0.1 to about 30 mg/kg. Advantageously, compounds of the present invention may be administered in a single daily dose, or the total daily dosage may be administered in divided doses of two, three, or four times daily.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in Remington's Pharmaceutical Sciences, supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

The Tables below provide representative Examples, the synthesis of which are described above, of the compounds of Formula (I) of the present invention.

TABLE 1

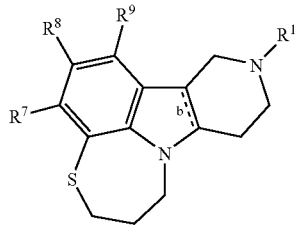

| Ex # | R7 | R8 | R9 | b | R1 |
|---|---|---|---|---|---|
| 4 | H | H | F | dbl | —$CO_2$Et |
| 5 | H | H | F | dbl | H |
| 6 | H | H | Me | dbl | H |
| 7 | H | H | Me | dbl | —$CO_2$-tBu |
| 8 | H | H | Me | sgl | H |
| 9 | H | H | H | sgl | H |
| 10 | H | H | $NO_2$ | dbl | H |
| 11 | H | H | $NO_2$ | sgl | H |
| 12 | Cl | H | H | dbl | H |
| 13 | Cl | H | H | sgl | H |
| 14 | Me | H | H | dbl | H |
| 15 | Me | H | H | sgl | H |
| 18 | H | H | Br | dbl | H |
| 19 | H | H | Br | sgl | H |
| 25 | H | H | H | sgl | —C(═O)(3,4-diMeO-phenyl) |
| 26 | H | H | H | sgl | —C(═O)(2,5-diMeO-phenyl) |
| 27 | H | H | H | sgl | —C(═O)(3,5-diMeO-phenyl) |
| 28 | H | H | H | sgl | 2,6-diMeO-benzyl |
| 29 | H | H | H | sgl | 2,4-diMeO-benzyl |
| 30 | H | H | H | sgl | 2,4,6-triMeO-benzyl |
| 31 | H | H | H | sgl | 2,3-diMeO-benzyl |
| 32 | H | H | H | sgl | 2,4,5-triMeO-benzyl |
| 33 | H | H | H | sgl | cyclohexylmethyl |
| 34 | H | H | H | sgl | 2,3,4-triMeO-benzyl |
| 35 | H | H | H | sgl | 3,4-diMeO-benzyl |
| 36 | H | H | H | sgl | 3,4,5-triMeO-benzyl |
| 39 | H | H | H | sgl | —$CO_2$Et |
| 40 | H | —C(═O)$CH_3$ | H | sgl | —$CO_2$Et |
| 41 | H | —NHC(═O)$CH_3$ | H | sgl | —$CO_2$Et |
| 42 | H | H | H | sgl | —$CH_1CH_2$(4-F-phenyl) |
| 43 | H | H | H | sgl | Et |
| 44 | H | H | H | sgl | Pr |
| 45 | H | H | H | sgl | butyl |
| 46 | H | H | H | sgl | pentyl |
| 47 | H | H | H | sgl | hexyl |
| 48 | H | H | H | sgl | 2-propyl |
| 49 | H | H | H | sgl | 2-butyl |
| 50 | H | H | H | sgl | 2-pentyl |
| 51 | H | H | H | sgl | 2-hexyl |
| 52 | H | H | H | sgl | 2-Me-propyl |
| 53 | H | H | H | sgl | 2-Me-butyl |
| 54 | H | H | H | sgl | 2-Me-pentyl |
| 55 | H | H | H | sgl | 2-Et-butyl |
| 56 | H | H | H | sgl | 3-Me-pentyl |
| 57 | H | H | H | sgl | 3-Me-butyl |

TABLE 1-continued

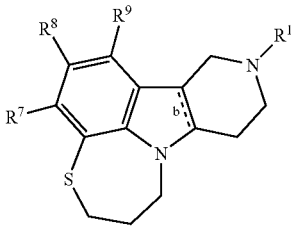

| Ex # | R7 | R8 | R9 | b | R1 |
|---|---|---|---|---|---|
| 58 | H | H | H | sgl | 4-Me-pentyl |
| 59 | H | H | H | sgl | cyclopropylmethyl |
| 60 | H | H | H | sgl | cyclobutylmethyl |
| 61 | H | H | H | sgl | cyclohexylmethyl |
| 62 | H | H | H | sgl | 2-propenyl |
| 63 | H | H | H | sgl | 2-Me-2-propenyl |
| 64 | H | H | H | sgl | trans-2-butenyl |
| 65 | H | H | H | sgl | 3-Me-butenyl |
| 66 | H | H | H | sgl | 3-butenyl |
| 67 | H | H | H | sgl | trans-2-pentenyl |
| 68 | H | H | H | sgl | cis-2-pentenyl |
| 69 | H | H | H | sgl | 4-pentenyl |
| 70 | H | H | H | sgl | 4-Me-3-pentenyl |
| 71 | H | H | H | sgl | 3,3-diCl-2-propenyl |
| 72 | H | H | H | sgl | benzyl |
| 73 | H | H | H | sgl | 2-Me-benzyl |
| 74 | H | H | H | sgl | 3-Me-benzyl |
| 75 | H | H | H | sgl | 4-Me-benzyl |
| 76 | H | H | H | sgl | 2,5-diMe-benzyl |
| 77 | H | H | H | sgl | 2,4-diMe-benzyl |
| 78 | H | H | H | sgl | 3,5-diMe-benzyl |
| 79 | H | H | H | sgl | 2,4,6-triMe-benzyl |
| 80 | H | H | H | sgl | 3-MeO-benzyl |
| 81 | H | H | H | sgl | 3,5-diMeO-benzyl |
| 82 | H | H | H | sgl | pentafluorobenzyl |
| 83 | H | H | H | sgl | 2-phenylethyl |
| 84 | H | H | H | sgl | 1-phenyl-2-propyl |
| 85 | H | H | H | sgl | trans-3-phenyl-2-propenyl |
| 86 | H | H | H | sgl | 4-phenylbutyl |
| 87 | H | H | H | sgl | 4-phenylbenzyl |
| 88 | H | H | H | sgl | 2-phenylbenzyl |
| 169 | H | Me | H | sgl | H |
| 170 | H | CN | H | sgl | H |
| 171 | H | Et | H | sgl | H |
| 175 | H | H | H | dbl | Me |
| 176 | H | H | H | sgl | Me |
| 177 | H | H | H | sgl | H |
| 178 | Cl | H | H | sgl | —$(CH_2)_3C(=O)$(4-F-phenyl) |
| 179 | Me | H | H | sgl | —$(CH_2)_3C(=O)$(4-F-phenyl) |
| 180 | H | H | H | sgl | —$(CH_2)_3S$(3-F-phenyl) |
| 181 | H | H | H | sgl | —$(CH_2)_3CH(OH)$(4-F-phenyl) |
| 186 | H | H | H | sgl | —$(CH_2)_3C(=O)$(4-F-phenyl) |
| 187 | H | MeO | H | sgl | —$(CH_2)_3C(=O)$(4-F-phenyl) |
| 192 | H | H | H | sgl | —$(CH_2)_3C(=O)$(4-Br-phenyl) |
| 193 | H | H | H | sgl | —$(CH_2)_3SO_2$(3-F-phenyl) |
| 194 | H | H | H | sgl | —$(CH_2)_3C(=O)$(4-(3,4-diCl-phenyl)phenyl) |
| 197 | H | H | H | sgl | —$(CH_2)_3C(=O)$(4-Me-phenyl) |
| 198 | H | H | H | sgl | —$(CH_2)_3C(=O)$(4-F-phenyl) |
| 199 | H | H | H | sgl | —$(CH_2)_3C(=O)$(4-MeO-phenyl) |
| 200 | H | H | H | sgl | —$(CH_2)_3C(=O)$(4-F-phenyl) |
| 201 | H | H | H | sgl | —$(CH_2)_3SO_2$(4-F-phenyl) |
| 202 | H | H | H | sgl | —$(CH_2)_3S(=O)$(4-F-phenyl) |
| 203 | H | H | H | sgl | —$(CH_2)_3O$(4-F-phenyl) |
| 204 | H | H | H | sgl | —$(CH_2)_3O$(phenyl) |
| 205 | H | H | H | sgl | —$(CH_2)_3S$(4-F-phenyl) |
| 206 | H | H | H | sgl | —$(CH_2)_3NH$(4-F-phenyl) |
| 207 | H | H | H | sgl | —$(CH_2)_3N(CH_3)$(4-F-phenyl) |
| 208 | H | H | H | sgl | —$(CH_2)_3C(=O)$(4-pyridyl) |
| 209 | H | H | H | sgl | —$(CH_2)_3C(=O)$(3-pyridyl) |

TABLE 1-continued

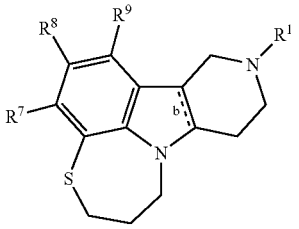

| Ex # | R7 | R8 | R9 | b | R1 |
|---|---|---|---|---|---|
| 214 | H | H | H | sgl | 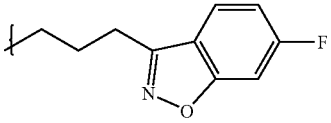 |
| 215 | H | H | H | sgl | 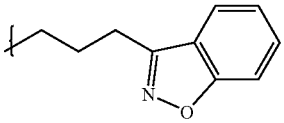 |
| 219 | H | H | H | sgl | —$(CH_2)_3CO_2Et$ |
| 220 | H | H | H | sgl | —$(CH_2)_4CO_2Et$ |
| 221 | H | H | H | sgl | —$(CH_2)_3C(=O)N(CH_3)(OCH_3)$ |
| 222 | H | H | H | sgl | —$(CH_2)_4C(=O)N(CH_3)(OCH_3)$ |
| 223 | H | H | H | sgl | —$(CH_2)_3C(=O)$(3-Me-4-F-phenyl) |
| 224 | H | H | H | sgl | —$(CH_2)_3C(=O)$(phenyl) |
| 225 | H | H | H | sgl | —$(CH_2)_3C(=O)$(4-Cl-phenyl) |
| 226 | H | H | H | sgl | —$(CH_2)_3C(=O)$(3-Me-phenyl) |
| 227 | H | H | H | sgl | —$(CH_2)_3C(=O)$(4-tBu-phenyl) |
| 228 | H | H | H | sgl | —$(CH_2)_3C(=O)$(3,4-diF-phenyl) |
| 229 | H | H | H | sgl | —$(CH_2)_3C(=O)$(2-MeO-5-F-phenyl) |
| 230 | H | H | H | sgl | —$(CH_2)_4C(=O)$(phenyl) |
| 231 | H | H | H | sgl | —$(CH_2)_3C(=O)$(4-F-1-naphthyl) |
| 232 | H | H | H | sgl | —$(CH_2)_3C(=O)$(benzyl) |
| 233 | H | H | H | sgl | —$(CH_2)_2C(=O)NH$(4-F-phenyl) |
| 234 | H | H | H | sgl | —$(CH_2)_3C(=O)NH$(4-F-phenyl) |
| 235 | H | H | H | sgl | —$(CH_2)_3CH(OH)$(4-F-phenyl) |
| 236 | H | H | H | sgl | —$(CH_2)_3CH(OH)$(4-pyridyl) |
| 237 | H | H | H | sgl | —$(CH_2)_3CH(OH)$(2,3-diMeO-phenyl) |
| 238 | H | H | H | sgl | —$(CH_2)_3C(=O)$(2,3-diMeO-phenyl) |
| 239 | H | H | H | sgl | —$(CH_2)_4$(cyclohexyl) |
| 240 | H | H | H | sgl | —$(CH_2)_3CH(phenyl)_2$ |
| 241 | H | H | H | sgl | —$CH_2CH_2CH{=}C(phenyl)_2$ |
| 242 | H | H | H | sgl | —$(CH_2)_3CH(4\text{-}F\text{-}phenyl)_2$ |
| 243 | H | H | H | sgl | —$CH_2CH_2CH{=}C(4\text{-}F\text{-}phenyl)_2$ |
| 244 | H | H | H | sgl | —$(CH_2)_2NHC(=O)$(phenyl) |
| 245 | H | H | H | sgl | —$(CH_2)_2NHC(=O)$(2-F-phenyl) |
| 246 | H | H | H | sgl | —$(CH_2)_2NHC(=O)$(4-F-phenyl) |
| 247 | H | H | H | sgl | —$(CH_2)_3$(3-indolyl) |
| 248 | H | H | H | sgl | —$(CH_2)_3$(1-Me-3-indolyl) |
| 249 | H | H | H | sgl | —$CH_2CH_2$(3-indolyl) |
| 250 | H | H | H | sgl | —$(CH_2)_3$(1-indolyl) |
| 251 | H | H | H | sgl | —$(CH_2)_3$(1-indolinyl) |
| 252 | H | H | H | sgl | —$(CH_2)_3$(1-benzimidazolyl) |
| 253 | H | H | H | sgl | 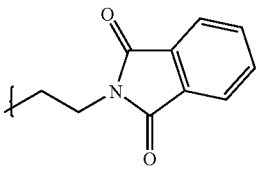 |
| 254 | H | H | H | sgl | 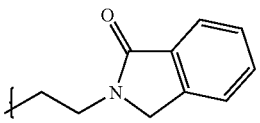 |
| 268 | H | F | H | sgl | —$(CH_2)_3C(=O)$(4-F-phenyl) |

TABLE 1-continued

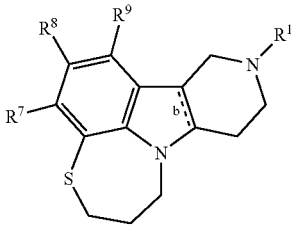

| Ex # | R7 | R8 | R9 | b | R1 |
|---|---|---|---|---|---|
| 271 | H | H | H | sgl | H |
| 273 | H | F | H | sgl | H |
| S274 | Br | H | H | sgl | H |
| S275 | 2,6-diF-phenyl | H | H | sgl | H |
| S276 | 2-Me-4-MeO-phenyl | H | H | sgl | H |
| S277 | 4-$CF_3$-phenyl | H | H | sgl | H |
| S278 | 2,3-diCl-phenyl | H | H | sgl | H |
| S279 | 2,4-diCl-phenyl | H | H | sgl | H |
| S280 | 2-Cl-4-$CF_3$-phenyl | H | H | sgl | H |
| S281 | CN | H | H | sgl | H |
| S282 | CN | Br | H | sgl | H |
| S283 | benzyl | H | H | sgl | H |
| 284 | CHO | H | H | sgl | H |
| 285 | $CO_2H$ | H | H | sgl | H |
| 286 | H | H | H | sgl | —$(CH_2)_2$NHC(═O)(2,4-diF-phenyl) |
| 287 | H | H | H | sgl | —$(CH_2)_2$NMeC(═O)-phenyl |
| 288 | H | H | H | sgl | —$(CH_2)_2$NMeC(═O)(2-F-phenyl) |
| 289 | H | H | H | sgl | —$(CH_2)_2$NMeC(═O)(2,4-diF-phenyl) |
| 290 | H | H | H | sgl | —$(CH_2)_2$NMeC(═O)(4-F-phenyl) |
| 291 | H | H | H | sgl | —$(CH_2)_3$(1H-1,2,3-benzotriazol-1-yl) |
| 292 | H | H | H | sgl | —$(CH_2)_3$(1H-1,2,3-benzotriazol-2-yl) |
| 293 | H | H | H | sgl | 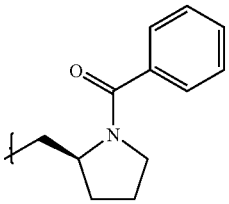 |
| 294 | H | H | H | sgl | 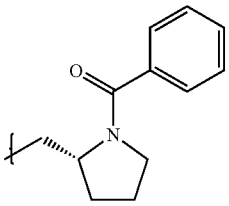 |
| 295 | H | H | H | sgl | 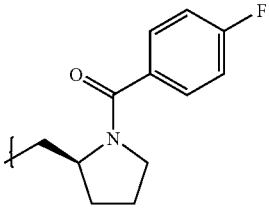 |
| 296 | H | H | H | sgl | 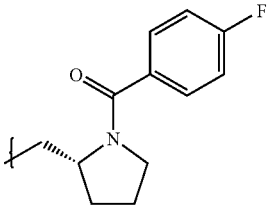 |

TABLE 1-continued

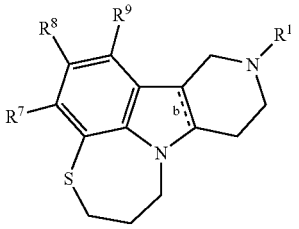

| Ex # | R7 | R8 | R9 | b | R1 |
|---|---|---|---|---|---|
| 297 | H | H | H | sgl | —$(CH_2)_2$(1H-1,2,3-benzotriazol-1-yl) |
| 298 | H | H | H | sgl | —$(CH_2)_2$(1H-1,2,3-benzotriazol-1-yl) |
| 299 | H | H | H | sgl | —$(CH_2)_3$(3,4-dihydro-1(2H)-quinolinyl) |
| 300 | H | H | H | sgl | —$CH_2CH_2CH{=}CMe$-(4-F-phenyl) |
| 301 | H | H | H | sgl | —$(CH_2)_2$(2,3-dihydro-1H-inden-2-yl) |
| 302 | H | H | H | sgl | —$(CH_2)_3C(=O)$(2-$NH_2$-phenyl) |
| 303 | H | H | H | sgl | —$(CH_2)_3C(=O)$(2-$NH_2$-phenyl) |
| 304 | H | H | H | sgl | —$(CH_2)_3C(=O)$(2-$NH_2$-5-F-phenyl) |
| 305 | H | H | H | sgl | —$(CH_2)_3C(=O)$(2-$NH_2$-3-F-phenyl) |
| 306 | H | H | H | sgl | —$(CH_2)_3C(=O)$(2-$NH_2$-4-Cl-phenyl) |
| 307 | H | H | H | sgl | —$(CH_2)_3C(=O)$(2-$NH_2$-4-OH-phenyl) |
| 308 | H | H | H | sgl | —$(CH_2)_3C(=O)$(2-$NH_2$-4-Br-phenyl) |
| 309 | H | H | H | sgl | —$(CH_2)_3$(1H-indazol-3-yl) |
| 310 | H | H | H | sgl | —$(CH_2)_3$(5-F-1H-indazol-3-yl) |
| 311 | H | H | H | sgl | —$(CH_2)_3$(7-F-1H-indazol-3-yl) |
| 312 | H | H | H | sgl | —$(CH_2)_3$(6-Cl-1H-indazol-3-yl) |
| 313 | H | H | H | sgl | —$(CH_2)_3$(6-Br-1H-indazol-3-yl) |
| 314 | H | H | H | sgl | —$(CH_2)_3C(=O)$(2-NHMe-phenyl) |
| 315 | H | H | H | sgl | —$(CH_2)_3$(1-benzothien-3-yl) |
| 355 | H | H | H | sgl | 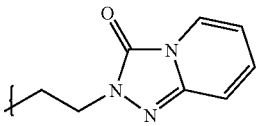 |
| 356 | H | H | H | sgl | —$(CH_2)_3$(6-F-1H-indol-1-yl) |
| 357 | H | H | H | sgl | —$(CH_2)_3$(5-F-1H-indol-1-yl) |
| 358 | H | H | H | sgl | —$(CH_2)_3$(6-F-2,3-dihydro-1H-indol-1-yl) |
| 359 | H | H | H | sgl | —$(CH_2)_3$(5-F-2,3-dihydro-1H-indol-1-yl) |
| 360 | H | H | H | sgl | —$(CH_2)_3$(6-F-1H-indol-3-yl) |
| 361 | H | H | H | sgl | —$(CH_2)_3$(6-F-1H-indol-3-yl) |
| 362 | H | H | H | sgl | —$(CH_2)_3$(5-F-1H-indol-3-yl) |
| 363 | H | H | H | sgl | —$(CH_2)_3$(5-F-1H-indol-3-yl) |
| 364 | H | H | H | sgl | —$(CH_2)_3$(9H-purin-9-yl) |
| 365 | H | H | H | sgl | —$(CH_2)_3$(7H-purin-7-yl) |
| 366 | H | H | H | sgl | 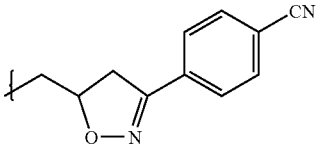 |
| 367 | H | H | H | sgl | —$(CH_2)_3$(6-F-1H-indazol-3-yl) |
| 368 | H | H | H | sgl | —$(CH_2)_3$(6-F-1H-indazol-3-yl) |
| 369 | H | H | H | sgl | —$(CH_2)_3$(6-F-1H-indazol-3-yl) |
| 370 | H | H | H | sgl | —$(CH_2)_3C(=O)$(2-$NH_2$-4-F-phenyl) |
| 371 | H | H | H | sgl | —$(CH_2)_3C(=O)$(2-$NH_2$-4-F-phenyl) |
| 372 | H | H | H | sgl | —$(CH_2)_3C(=O)$(2-$NHSO_2Me$-4-F-phenyl) |
| 373 | H | H | H | sgl | —$(CH_2)_3C(=O)$(2-NHC(=O)Me-4-F-phenyl) |
| 374 | H | H | H | sgl | —$(CH_2)_3C(=O)$(2-NHC(=O)Me-4-F-phenyl) |
| 375 | H | H | H | sgl | —$(CH_2)_3C(=O)$(2-$NHCO_2Et$-4-F-phenyl) |
| 376 | H | H | H | sgl | —$(CH_2)_3C(=O)$(2-NHC(=O)NHEt-4-F-phenyl) |
| 377 | H | H | H | sgl | —$(CH_2)_3C(=O)$(2-NHCHO)-4-F-phenyl) |
| 378 | H | H | H | sgl | —$(CH_2)_3C(=O)$(2-OH-4-F-phenyl) |
| 379 | H | H | H | sgl | —$(CH_2)_3C(=O)$(2-MeS-4-F-phenyl) |
| 442 | H | H | H | sgl | —$(CH_2)_3C(=O)$(2-$NHSO_2Me$-4-F-phenyl) |
| 485 | H | H | H | sgl | —$(CH_2)_2C(Me)CO_2Me$ |
| 486 | H | H | H | sgl | —$(CH_2)_2C(Me)C(=O)(4\text{-F-phenyl})_2$ |
| 487 | H | H | H | sgl | —$(CH_2)_2C(Me)C(OH)(4\text{-Cl-phenyl})_2$ |
| 489 | H | H | H | sgl | —$(CH_2)_2C(Me)C(=O)$(4-F-phenyl) |

TABLE 1-continued

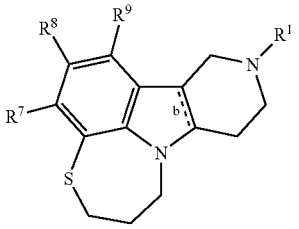

| Ex # | R7 | R8 | R9 | b | R1 |
|---|---|---|---|---|---|
| 490 | H | H | H | sgl | —$(CH_2)_2C(Me)C(=O)$(2-MeO-4-F-phenyl) |
| 491 | H | H | H | sgl | —$(CH_2)_2C(Me)C(=O)$(3-MeO-4-F-phenyl) |
| 492 | H | H | H | sgl | —$(CH_2)_2C(Me)C(=O)$(2-Me-phenyl) |
| 493 | H | H | H | sgl | —$(CH_2)_2C(Me)C(=O)$phenyl |
| 591 | Cl | H | H | sgl | —$(CH_2)_3C(=O)$(2-$NH_2$-4-F-phenyl |

TABLE 1A

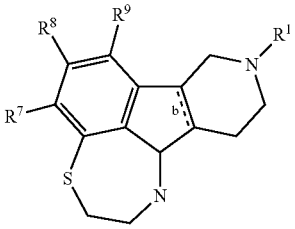

| Ex # | R7 | R8 | R9 | b | R1 |
|---|---|---|---|---|---|
| 115 | H | H | Br | dbl | —$CO_2$-tBu |
| 116 | H | H | 2,3-diCl-phenyl | dbl | —$CO_2$-tBu |
| 117 | H | H | 3,4-diCl-phenyl | dbl | —$CO_2$-tBu |
| 118 | H | H | 2-Cl-4-$CF_3$-phenyl | dbl | —$CO_2$-tBu |
| 119 | H | H | 2,3-diCl-phenyl | dbl | H |
| 120 | H | H | 3,4-diCl-phenyl | dbl | H |
| 121 | H | H | 2-Cl-4-$CF_3$-phenyl | dbl | H |
| 122 | H | H | 2,3-diCl-phenyl | sgl | H |
| 123 | H | H | 3,4-diCl-phenyl | sgl | H |
| 124 | H | H | 2-Cl-4-$CF_3$-phenyl | sgl | H |
| 125 | H | H | Br | sgl | —$CO_2$-tBu |
| 126 | H | H | 2,3-diF-phenyl | sgl | —$CO_2$-tBu |
| 127 | H | H | 2,3-diF-phenyl | sgl | H |
| 128 | H | 2,4-diCl-phenyl | H | sgl | H |
| 129 | H | phenyl | H | sgl | H |
| 130 | H | 4-F-phenyl | H | sgl | H |
| 131 | H | 4-Cl-phenyl | H | sgl | H |
| 132 | H | 2-Cl-phenyl | H | sgl | H |
| 133 | H | 2-MeO-phenyl | H | sgl | H |
| 134 | H | 2-Cl-4-$CF_3$-phenyl | H | sgl | H |
| 135 | H | 2,4-diMe-phenyl | H | sgl | H |
| 136 | H | 2-Cl-4-MeO-phenyl | H | sgl | H |
| 137 | H | 4-iPr-phenyl | H | sgl | H |
| 138 | H | 4-Bu-phenyl | H | sgl | H |
| 139 | H | 2-Me-4-MeO-5-F-phenyl | H | sgl | H |
| 140 | H | 2-Me-4-MeO-phenyl | H | sgl | H |
| 141 | H | 2-Cl-4-$CF_3O$-phenyl | H | sgl | H |
| 142 | H | 2,4,5-triMe-phenyl | H | sgl | H |
| 143 | H | 3-Cl-phenyl | H | sgl | H |
| 144 | H | 4-Me-phenyl | H | sgl | H |
| 145 | H | 2-Me-4-Cl-phenyl | H | sgl | H |
| 146 | H | 2,5-diCl-phenyl | H | sgl | H |
| 147 | H | 2-MeO-4-iPr-phenyl | H | sgl | H |
| 148 | H | 2,6-diCl-phenyl | H | sgl | H |
| 149 | H | 2,6-diF-phenyl | H | sgl | H |
| 150 | H | 2-$CF_3$-4-MeO-phenyl | H | sgl | H |
| 151 | H | 2-$CF_3$-phenyl | H | sgl | H |
| 152 | H | 4-pyridyl | H | sgl | H |
| 153 | H | 2-furanyl | H | sgl | H |
| 154 | H | 2-thiophenyl | H | sgl | H |

TABLE 1A-continued

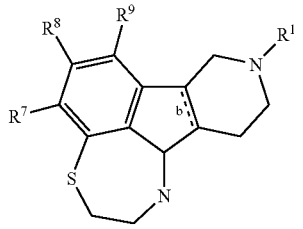

| Ex # | R7 | R8 | R9 | b | R1 |
|---|---|---|---|---|---|
| 155 | H | 4-F-phenyl | H | sgl | H |
| 156 | H | 2,3-diCl-phenyl | H | sgl | H |
| 157 | H | 4-Et-phenyl | H | sgl | H |
| 158 | H | 2,4-diMeO-phenyl | H | sgl | H |
| 159 | H | 2-F-3-Cl-phenyl | H | sgl | H |
| 160 | H | 4-MeO-phenyl | H | sgl | H |
| 161 | H | 4-MeS-phenyl | H | sgl | H |
| 162 | H | 4-CN-phenyl | H | sgl | H |
| 163 | H | 3-$CF_3$-phenyl | H | sgl | H |
| 164 | H | 2-MeO-phenyl | H | sgl | H |
| 165 | H | 2-naphthyl | H | sgl | H |
| 166 | H | 4-acetylphenyl | H | sgl | H |
| 167 | H | 3-acetamidophenyl | H | sgl | H |
| 168 | H | 2,4-diCl-phenyl | H | sgl | Me |
| 316 | H | 2,3-diMe-phenyl | H | sgl | H |
| 317 | H | 2-Me-5-F-phenyl | H | sgl | H |
| 318 | H | 2-F-5-Me-phenyl | H | sgl | H |
| 319 | H | 2-MeO-5-F-phenyl | H | sgl | H |
| 320 | H | 2-Me-3-Cl-phenyl | H | sgl | H |
| 321 | H | 3-$NO_2$-phenyl | H | sgl | H |
| 322 | H | 2-$NO_2$-phenyl | H | sgl | H |
| 323 | H | 2-Cl-3-Me-phenyl | H | sgl | H |
| 324 | H | 2-MeO-phenyl | H | sgl | H |
| 325 | H | 2,3-diCl-phenyl | H | sgl | H |
| 326 | H | 2-Cl-4-$CF_3$-phenyl | H | sgl | H |
| 327 | H | 2-Me-4-EtO-phenyl | H | sgl | H |
| 328 | H | 2-Me-4-F-phenyl | H | sgl | H |
| 329 | H | 4-Bu-phenyl | H | sgl | H |
| 330 | H | 2-$CF_3$-phenyl | H | sgl | H |
| 331 | H | 2-Cl-6-F-phenyl | H | sgl | H |
| 332 | H | 2-Cl-4-($CHF_2$)O-phenyl | H | sgl | H |
| 333 | H | 4-$CF_3$-phenyl | H | sgl | H |
| 334 | H | 4-Me-phenyl | H | sgl | H |
| 335 | H | 4-$CF_3O$-phenyl | H | sgl | H |
| 336 | H | 2,4-diMeO-6-F-phenyl | H | sgl | H |
| 337 | H | 2-Me-phenyl | H | sgl | H |
| 338 | H | 2-$CF_3$-6-F-phenyl | H | sgl | H |
| 339 | H | 2-MeS-phenyl | H | sgl | H |
| 340 | H | 2,4,6-triF-phenyl | H | sgl | H |
| 341 | H | 2,4,6-triCl-phenyl | H | sgl | H |
| 342 | H | 2,6-diCl-4-MeO-phenyl | H | sgl | H |
| 343 | H | 2,3,4-triF-phenyl | H | sgl | H |
| 344 | H | 2,6-diF-4-Cl-phenyl | H | sgl | H |
| 345 | H | 2,3,4,6-tetraF-phenyl | H | sgl | H |
| 346 | H | 2,3,4,5,6-pentaF-phenyl | H | sgl | H |
| 347 | H | 2,6-di$CF_3$-phenyl | H | sgl | H |
| 348 | H | 2-$CF_3O$-phenyl | H | sgl | H |
| 349 | H | 2-$CF_3$-4-EtO-phenyl | H | sgl | H |
| 350 | H | 2-$CF_3$-4-iPrO-phenyl | H | sgl | H |
| 351 | H | 2-naphtyl | H | sgl | H |
| 352 | H | 2-$CF_3$-4-Cl-phenyl | H | sgl | H |
| 353 | H | 2-$CF_3$-4-F-phenyl | H | sgl | H |
| 354 | H | 2,4-diF-phenyl | H | sgl | Me |
| 380 | H | 2-Cl-4-EtO-phenyl | H | sgl | H |
| 381 | H | 2-Cl-4-iPrO-phenyl | H | sgl | H |
| 382 | H | 2-Et-4-MeO-phenyl | H | sgl | H |
| 383 | H | 2-CHO-4-MeO-phenyl | H | sgl | H |
| 384 | H | 2-CH(OH)Me-4-MeO-phenyl | H | sgl | H |
| 385 | H | 2-CH(OMe)Me-4-MeO-phenyl | H | sgl | H |
| 386 | H | 2-C(=O)Me-4-MeO-phenyl | H | sgl | H |
| 387 | H | 2-$CH_2$(OH)-4-MeO-phenyl | H | sgl | H |

TABLE 1A-continued

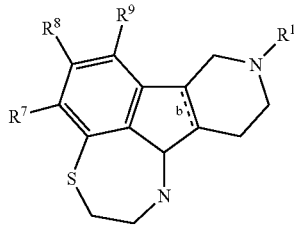

| Ex # | R7 | R8 | R9 | b | R1 |
|---|---|---|---|---|---|
| 388 | H | 2-$CH_2$(OMe)-4-MeO-phenyl | H | sgl | H |
| 389 | H | 2-CH(OH)Et-4-MeO-phenyl | H | sgl | H |
| 390 | H | 2-C(═O)Et-4-MeO-phenyl | H | sgl | H |
| 391 | H | (Z)-2-CH═CH$CO_2$Me-4-MeO-phenyl | H | sgl | H |
| 392 | H | 2-$CH_2CH_2CO_2$Me-4-MeO-phenyl | H | sgl | H |
| 393 | H | (Z)-2-CH═CH$CH_2$(OH)-4-MeO-phenyl | H | sgl | H |
| 394 | H | (E)-2-CH═CH$CO_2$Me-4-MeO-phenyl | H | sgl | H |
| 395 | H | (E)-2-CH═CH$CH_2$(OH)-4-MeO-phenyl | H | sgl | H |
| 396 | H | 2-$CH_2CH_2$OMe-4-MeO-phenyl | H | sgl | H |
| 397 | H | 2-F-4-MeO-phenyl | H | sgl | H |
| 403 | H | 2-Cl-4-F-phenyl | H | sgl | H |
| 405 | H | (2-Cl-phenyl)-CH═CH— | H | sgl | H |
| 406 | H | (3-Cl-phenyl)-CH═CH— | H | sgl | H |
| 407 | H | (2,6-diF-phenyl)-CH═CH— | H | sgl | H |
| 410 | H | cyclohexyl | H | sgl | H |
| 411 | H | cyclopentyl | H | sgl | H |
| 412 | H | cyclohexylmethyl | H | sgl | H |
| 413 | H | —$CH_2CH_2CO_2$Et | H | sgl | H |
| 414 | H | —$(CH_2)_3CO_2$Et | H | sgl | H |
| 415 | H | —$(CH_2)_4CO_2$Et | H | sgl | H |
| 416 | H | —$CH_2$CH═$CH_3$ | H | sgl | H |
| 417 | H | Pr | H | sgl | H |
| 418 | H | benzyl | H | sgl | H |
| 419 | H | 2-F-benzyl | H | sgl | H |
| 420 | H | 3-F-benzyl | H | sgl | H |
| 421 | H | 4-F-benzyl | H | sgl | H |
| 422 | H | 3-MeO-benzyl | H | sgl | H |
| 423 | H | 3-OH-benzyl | H | sgl | H |
| 424 | H | 2-MeO-benzyl | H | sgl | H |
| 425 | H | 2-OH-benzyl | H | sgl | H |
| 426 | H | 2-$CO_2$Me-3-MeO-phenyl | H | sgl | H |
| 427 | H | 2,6-diF-phenyl | H | sgl | H |
| 428 | H | phenyl-CH═CH— | H | sgl | H |
| 429 | H | (2-Me-4-MeO-phenyl)—CH═CH═ | H | sgl | H |
| 430 | H | —$NMe_2$ | H | sgl | H |
| 431 | H | 1-pyrrolidinyl | H | sgl | H |
| 432 | H | —$NTs_2$ | H | sgl | H |
| 433 | H | MeO | H | sgl | H |
| 445 | H | 2-Me-4-MeO-phenyl | Me | sgl | H |
| 446 | H | 2-$CF_3$-4-MeO-phenyl | Me | sgl | H |
| 458 | Me | 2-$CF_3$-4-MeO-phenyl | H | sgl | H |
| 459 | Me | 2,4-diCl-phenyl | H | sgl | H |
| 460 | H | 3-CN-phenyl | H | sgl | H |
| 461 | H | 2-Me-4-CN-phenyl | H | sgl | H |
| 462 | H | 2-Me-3-CN-phenyl | H | sgl | H |
| 463 | H | 2-CN-phenyl | H | sgl | H |
| 464 | H | 2-$CF_3$-4-CN-phenyl | Me | sgl | H |
| 465 | H | 3-CHO-phenyl | Me | sgl | H |
| 466 | H | 3-$CH_2$(OH)-phenyl | Me | sgl | H |
| 467 | H | 3-$CH_2$(OMe)-phenyl | Me | sgl | H |
| 468 | H | 3-$CH_2$(O$NMe_2$)-phenyl | Me | sgl | H |

TABLE 1A-continued

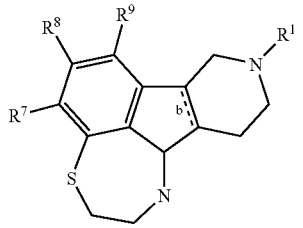

| Ex # | R7 | R8 | R9 | b | R1 |
|---|---|---|---|---|---|
| 469 | H | 3-CN-4-F-phenyl | Me | sgl | H |
| 470 | H | 3-$CONH_2$-4-F-phenyl | Me | sgl | H |
| 580 | $NH_2$ | H | H | sgl | H |
| 581 | H | phenyl-NH— | H | sgl | H |
| 582 | phenyl-NH— | H | H | sgl | H |
| 583 | H | (4-F-phenyl)-NH— | H | sgl | H |
| 584 | H | (2,4-diCl-phenyl)-NH— | H | sgl | H |
| 585 | H | phenyl-C(═O)NH— | H | sgl | H |
| 586 | H | benzyl-NH— | H | sgl | H |
| 587 | H | phenyl-S— | H | sgl | H |
| 588 | MeO | H | H | sgl | H |
| 589 | H | 2-$CH_2(NH_2)$-4-MeO-phenyl- | H | sgl | H |
| 590 | H | 2-Me-4-MeO-phenyl- | H | sgl | H |
| 592 | H | (2-Me-4-MeO-phenyl)-NH— | H | sgl | H |
| 593 | H | (2-F-4-MeO-phenyl)-NH— | H | sgl | H |
| 595 | H | (2-Me-4-F-phenyl)-NH— | H | sgl | H |
| 596 | H | 2-CH(OH)Me-4-F-phenyl | H | sgl | H |

TABLE 2

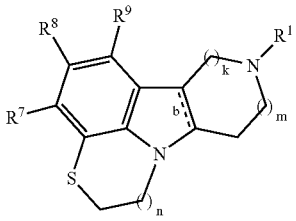

| Ex # | n | k | m | R7 | R8 | R9 | b | R1 |
|---|---|---|---|---|---|---|---|---|
| 471 | 2 | 2 | 1 | H | H | H | sgl | H |
| 472 | 2 | 2 | 1 | H | H | H | sgl | —$(CH_2)_3C(═O)$(4-F-phenyl) |
| 473 | 2 | 2 | 1 | H | H | H | sgl | —$(CH_2)_3O$(4-F-phenyl) |
| 474 | 2 | 2 | 1 | H | H | H | sgl | —$(CH_2)_3$(6-F-benzisoxazol-3-yl) |
| 475 | 2 | 2 | 1 | H | H | H | sgl | —$(CH_2)_3C(═O)$(4-pyridyl) |
| 476 | 2 | 3 | 0 | H | H | H | sgl | H |
| 477 | 2 | 3 | 0 | H | H | H | sgl | —$(CH_2)_3C(═O)$(4-F-phenyl) |
| 478 | 2 | 3 | 0 | H | H | H | sgl | —$(CH_2)_3$(6-F-benzisoxazol-3-yl) |
| 483 | 2 | 2 | 1 | H | Br | H | sgl | —$(CH_2)_3C(═O)$(4-F-phenyl) |
| 484 | 2 | 2 | 1 | H | Br | H | sgl | —$(CH_2)_3O$(4-F-phenyl) |
| 488 | 1 | 2 | 1 | H | Br | H | sgl | —$CO_2$-tBu |

TABLE 2A

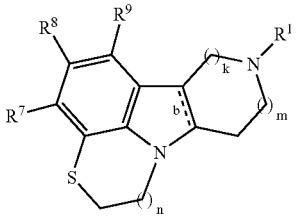

| Ex # | n | k | m | R7 | R8 | R9 | b | R1 |
|---|---|---|---|---|---|---|---|---|
| 479 | 2 | 2 | 1 | H | 2,4-diCl-phenyl | H | sgl | H |
| 480 | 2 | 2 | 1 | H | 2-Cl-4-MeO-phenyl | H | sgl | H |
| 481 | 2 | 2 | 1 | H | 2-Me-4-MeO-phenyl | H | sgl | H |
| 482 | 2 | 2 | 1 | H | Br | H | sgl | H |
| 497 | 1 | 1 | 1 | H | 2-Cl-phenyl | H | sgl | H |
| 498 | 1 | 1 | 1 | H | 3-Cl-phenyl | H | sgl | H |
| 499 | 1 | 1 | 1 | H | 3-F-phenyl | H | sgl | H |
| 500 | 1 | 1 | 1 | H | 4-Cl-phenyl | H | sgl | H |
| 501 | 1 | 1 | 1 | H | 4-F-phenyl | H | sgl | H |
| 502 | 1 | 1 | 1 | H | 2,3-diCl-phenyl | H | sgl | H |
| 503 | 1 | 1 | 1 | H | 2,4-diF-phenyl | H | sgl | H |
| 504 | 1 | 1 | 1 | H | 3,5-diCl-phenyl | H | sgl | H |
| 505 | 1 | 1 | 1 | H | 3,5-diF-phenyl | H | sgl | H |
| 506 | 1 | 1 | 1 | H | 3,4-diCl-phenyl | H | sgl | H |
| 507 | 1 | 1 | 1 | H | 3,4-diF-phenyl | H | sgl | H |
| 508 | 1 | 1 | 1 | H | 3-Cl-4-F-phenyl | H | sgl | H |
| 509 | 1 | 1 | 1 | H | 2-F-4-Cl-phenyl | H | sgl | H |

TABLE 3

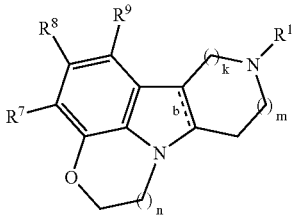

| Ex # | n | k | m | R7 | R8 | R9 | b | R1 |
|---|---|---|---|---|---|---|---|---|
| 182 | 1 | 1 | 1 | H | H | H | sgl | —$(CH_2)_3C(=O)$(4-F-phenyl) |
| 266 | 1 | 1 | 1 | H | H | Me | sgl | —$(CH_2)_3C(=O)$(4-F-phenyl) |
| 270 | 1 | 1 | 1 | H | H | H | sgl | —$(CH_2)_3O$(4-F-phenyl) |
| 272 | 1 | 1 | 1 | H | H | H | sgl | H |
| 494 | 1 | 1 | 1 | H | H | H | sgl | —$(CH_2)_3C(=O)$(2-$NH_2$-phenyl) |
| 495 | 1 | 1 | 1 | H | H | H | sgl | —$(CH_2)_3C(=O)$(2-$NH_2$-phenyl) |
| 496 | 1 | 1 | 1 | H | H | H | sgl | —$(CH_2)_3$(1H-indazol-3-yl) |
| 528 | 1 | 1 | 1 | H | H | H | sgl | —$(CH_2)_3$(6-F-1H-indazol-3-yl) |
| 529 | 1 | 1 | 1 | H | H | H | sgl | —$(CH_2)_3C(=O)$(2-$NH_2$-4-F-phenyl) |
| 530 | 1 | 1 | 1 | H | H | H | sgl | —$(CH_2)_3C(=O)$(2-$NH_2$-4-F-phenyl) |
| 531 | 1 | 1 | 1 | H | H | H | sgl | —$(CH_2)_3C(=O)$(2-OH-4-F-phenyl) |
| 539 | 1 | 2 | 1 | H | H | H | sgl | —$(CH_2)_3O$(4-F-phenyl) |
| 540 | 1 | 2 | 1 | H | H | H | sgl | —$(CH_2)_3$(6-F-1,2-benzisoxazol-3-yl) |
| 544 | 2 | 1 | 1 | H | H | H | sgl | —$(CH_2)_3C(=O)$(4-F-phenyl) |
| 546 | 1 | 2 | 1 | H | H | H | sgl | —$(CH_2)_3C(=O)$(4-F-phenyl |

TABLE 3A

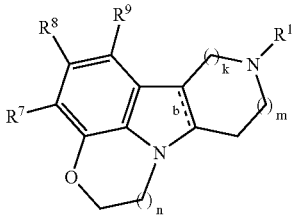

| Ex # | n | k | m | R7 | R8 | R9 | b | R1 |
|---|---|---|---|---|---|---|---|---|
| 172 | 2 | 1 | 1 | H | H | H | sgl | H |
| 173 | 1 | 1 | 1 | H | 2,4-diCl-phenyl | H | sgl | H |
| 174 | 1 | 1 | 1 | H | 2-Cl-4-MeO-phenyl | H | sgl | H |
| 436 | 1 | 1 | 1 | H | 2-Cl-phenyl | H | sgl | H |
| 497 | 1 | 1 | 1 | H | 2-Cl-phenyl | H | sgl | H |
| 498 | 1 | 1 | 1 | H | 3-Cl-phenyl | H | sgl | H |
| 499 | 1 | 1 | 1 | H | 3-F-phenyl | H | sgl | H |
| 500 | 1 | 1 | 1 | H | 4-Cl-phenyl | H | sgl | H |
| 501 | 1 | 1 | 1 | H | 4-F-phenyl | H | sgl | H |
| 502 | 1 | 1 | 1 | H | 2,3-diCl-phenyl | H | sgl | H |
| 503 | 1 | 1 | 1 | H | 2,3-diF-phenyl | H | sgl | H |
| 504 | 1 | 1 | 1 | H | 3,5-diCl-phenyl | H | sgl | H |
| 505 | 1 | 1 | 1 | H | 3,5-diF-phenyl | H | sgl | H |
| 506 | 1 | 1 | 1 | H | 3,4-diCl-phenyl | H | sgl | H |
| 507 | 1 | 1 | 1 | H | 3,4-diF-phenyl | H | sgl | H |
| 508 | 1 | 1 | 1 | H | 3-Cl-4-F-phenyl | H | sgl | H |
| 509 | 1 | 1 | 1 | H | 2-F-4-Cl-phenyl | H | sgl | H |
| 510 | 1 | 1 | 1 | H | 2-Cl-4-F-phenyl | H | sgl | H |
| 511 | 1 | 1 | 1 | H | 2,5-diCl-phenyl | H | sgl | H |

TABLE 3A-continued

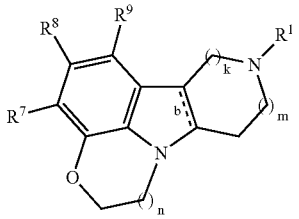

| Ex # | n | k | m | R7 | R8 | R9 | b | R1 |
|---|---|---|---|---|---|---|---|---|
| 512 | 1 | 1 | 1 | H | 2,6-diCl-phenyl | H | sgl | H |
| 513 | 1 | 1 | 1 | H | 2-$CF_3$-phenyl | H | sgl | H |
| 514 | 1 | 1 | 1 | H | 4-$CF_3$-phenyl | H | sgl | H |
| 515 | 1 | 1 | 1 | H | 2,4-di$CF_3$-phenyl | H | sgl | H |
| 516 | 1 | 1 | 1 | H | 2-Cl-4-$CF_3$-phenyl | H | sgl | H |
| 517 | 1 | 1 | 1 | H | 2-MeO-phenyl | H | sgl | H |
| 518 | 1 | 1 | 1 | H | 2,4-diMeO-phenyl | H | sgl | H |
| 519 | 1 | 1 | 1 | H | 2-MeO-5-iPr-phenyl | H | sgl | H |
| 520 | 1 | 1 | 1 | H | 3-$NO_2$-phenyl | H | sgl | H |
| 521 | 1 | 1 | 1 | H | 2-CHO-phenyl | H | sgl | H |
| 522 | 1 | 1 | 1 | H | 2-CH(Me)(OH)-phenyl | H | sgl | H |
| 523 | 1 | 1 | 1 | H | 2-$CH_2$(OH)-phenyl | H | sgl | H |
| 524 | 1 | 1 | 1 | H | 2-CHO-4-MeO-phenyl | H | sgl | H |
| 525 | 1 | 1 | 1 | H | 2-OH-phenyl | H | sgl | H |
| 526 | 1 | 1 | 1 | H | 2-$CF_3$-4-EtO-phenyl | H | sgl | H |
| 527 | 1 | 1 | 1 | H | 2-$CF_3$-4-iPrO-phenyl | H | sgl | H |
| 532 | 1 | 1 | 1 | H | 2-Me-4-MeO-phenyl | H | sgl | H |
| 533 | 1 | 1 | 1 | H | 2-$CF_3$-4-MeO-phenyl | H | sgl | H |
| 534 | 1 | 2 | 1 | H | 3,4,5-triMeO-phenyl | H | sgl | H |
| 535 | 1 | 2 | 1 | H | 1-naphthyl | H | sgl | H |
| 536 | 1 | 2 | 1 | H | 3-MeO-phenyl | H | sgl | H |
| 537 | 1 | 2 | 1 | H | 2,4-diCl-phenyl | H | sgl | H |
| 538 | 1 | 1 | 2 | H | H | H | sgl | H |
| 541 | 2 | 1 | 1 | H | H | H | sgl | H |
| 542 | 2 | 1 | 1 | H | H | H | sgl | H |
| 543 | 2 | 1 | 1 | H | 2,6-diF-phenyl | H | sgl | H |
| 545 | 1 | 2 | 1 | H | H | H | sgl | H |
| 547 | 2 | 1 | 1 | H | 2-$CF_3$-4-MeO-phenyl | H | sgl | H |
| 548 | 2 | 1 | 1 | H | 2-Me-4-MeO-phenyl | H | sgl | H |
| 549 | 2 | 1 | 1 | H | 2-Cl-4-$CF_3$-phenyl | H | sgl | H |
| 550 | 2 | 1 | 1 | H | 2,3-diCl-phenyl | H | sgl | H |
| 551 | 2 | 1 | 1 | H | 2,4-diMeO-phenyl | H | sgl | H |
| 552 | 2 | 1 | 1 | H | 3,4-diMeO-phenyl | H | sgl | H |
| 553 | 2 | 1 | 1 | H | 2,4-diCl-phenyl | H | sgl | H |
| 554 | 2 | 1 | 1 | H | 3,4-diCl-phenyl | H | sgl | H |
| 555 | 2 | 1 | 1 | H | 2,5-diCl-phenyl | H | sgl | H |
| 556 | 2 | 1 | 1 | H | 2-$CF_3$-phenyl | H | sgl | H |
| 557 | 2 | 1 | 1 | H | 2-Me-phenyl | H | sgl | H |
| 558 | 2 | 1 | 1 | H | 2-Cl-phenyl | H | sgl | H |
| 559 | 2 | 1 | 1 | H | 3-F-phenyl | H | sgl | H |
| 560 | 2 | 1 | 1 | H | phenyl | H | sgl | H |
| 561 | 2 | 1 | 1 | H | 2-$CF_3$-4-EtO-phenyl | H | sgl | H |
| 562 | 2 | 1 | 1 | H | 2-$CF_3$-4-iPrO-phenyl | H | sgl | H |
| 563 | 2 | 1 | 1 | H | 2-MeO-4-iPr-phenyl | H | sgl | H |
| 564 | 2 | 1 | 1 | H | 2-F-4-Cl-phenyl | H | sgl | H |
| 565 | 2 | 1 | 1 | H | 2-Cl-4-MeO-phenyl | H | sgl | H |
| 566 | 2 | 1 | 1 | H | 2-CHO-phenyl | H | sgl | H |
| 567 | 2 | 1 | 1 | H | 2-CHO-4-MeO-phenyl | H | sgl | H |
| 568 | 2 | 1 | 1 | H | 2-$CH_2$(OH)-4-MeO-phenyl | H | sgl | H |
| 569 | 2 | 1 | 1 | H | 2-$CH_2$(OH)-phenyl | H | sgl | H |
| 570 | 2 | 1 | 1 | H | 2-$CF_3$-4-NHMe-phenyl | H | sgl | H |
| 571 | 2 | 1 | 1 | H | 2-$CF_3$-4-$NH_2$-phenyl | H | sgl | H |
| 572 | 2 | 1 | 1 | H | 2-C(=O)Me-phenyl | H | sgl | H |
| 573 | 2 | 1 | 1 | H | 2-C(=O)Me-4-MeO-phenyl | H | sgl | H |
| 574 | 2 | 1 | 1 | H | 2-CH(Me)(OH)-phenyl | H | sgl | H |
| 575 | 2 | 1 | 1 | H | 2-CH(Me)(OH)-4-MeO-phenyl | H | sgl | H |
| 576 | 2 | 1 | 1 | H | 2-$CF_3$-4-OH-phenyl | H | sgl | H |
| 577 | 2 | 1 | 1 | H | 2-$CF_3$-4-O(C=O)Me-phenyl | H | sgl | H |

TABLE 4

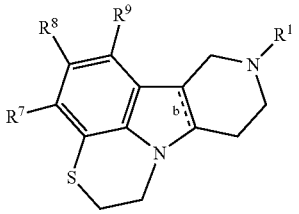

| Ex # | R7 | R8 | R9 | b | R1 |
|---|---|---|---|---|---|
| 183 | H | H | $CF_3$ | dbl | —$(CH_2)_3CH(OH)$(4-F-phenyl) |
| 184 | H | H | $CF_3$ | dbl | —$(CH_2)_3C(OCH_2CH_2O)$(4-F-phenyl) |
| 185 | H | H | $CF_3$ | sgl | —$(CH_2)_4$(4-F-phenyl) |
| 188 | H | H | H | sgl | —$(CH_2)_3C(=O)$(4-F-phenyl) |
| 195 | H | H | $CF_3$ | dbl | —$(CH_2)_3C(=O)$(4-F-phenyl) |
| 213 | H | $CH_3$ | H | sgl | —$(CH_2)_3C(=O)$(4-F-phenyl) |
| 438 | H | H | H | sgl | —$(CH_2)_3C(=O)$(2-$NH_2$-phenyl) |
| 439 | H | H | H | sgl | —$(CH_2)_3C(=O)$(2-$NH_2$-phenyl) |
| 440 | H | H | H | sgl | —$(CH_2)_3C(=O)$(2-$NH_2$-4-F-phenyl) |
| 441 | H | H | H | sgl | —$(CH_2)_3C(=O)$(2-$NH_2$-4-F-phenyl) |
| 456 | H | H | H | sgl | —$(CH_2)_3C(=O)$(4-F-phenyl) |
| 457 | H | H | H | sgl | —$(CH_2)_3C(=O)$(4-F-phenyl) |

TABLE 4A

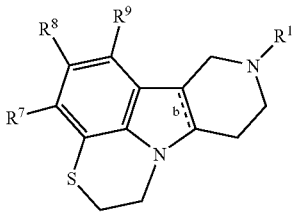

| Ex # | R7 | R8 | R9 | b | R1 |
|---|---|---|---|---|---|
| 443 | 2,3-diCl-phenyl | H | H | sgl | H |
| 444 | 2,3-diF-phenyl | H | H | sgl | H |
| 447 | 2,6-diCl-phenyl | H | H | sgl | H |
| 452 | 2-Me-4-MeO-phenyl | H | H | sgl | H |
| 453 | 2-Cl-6-F-phenyl | H | H | sgl | H |
| 454 | 2,6-diF-phenyl | H | H | sgl | H |
| 455 | 2,4-diCl-phenyl | H | H | sgl | H |

TABLE 6

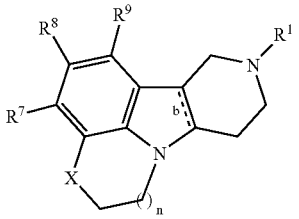

| Ex # | X | n | R7 | R8 | R9 | b | R1 |
|---|---|---|---|---|---|---|---|
| 398 | $SO_2$ | 2 | H | 2,4-diCl-phenyl | H | sgl | H |
| 399 | $SO_2$ | 2 | H | 2,6-diF-phenyl | H | sgl | H |
| 400 | $SO_2$ | 2 | H | 2-Cl-phenyl | H | sgl | H |
| 401 | $SO_2$ | 2 | H | 2-F-4-MeO-phenyl | H | sgl | H |
| 402 | $SO_2$ | 2 | H | 2-Me-4-MeO-phenyl | H | sgl | H |
| 404 | SO | 2 | H | 2-Cl-4-F-phenyl | H | sgl | H |
| 434 | SO | 2 | H | 2,4-diCl-phenyl | H | sgl | H |
| 435 | SO | 2 | H | 2-Me-4-MeO-phenyl | H | sgl | H |
| 448 | $SO_2$ | 1 | H | H | H | sgl | H |

TABLE 6-continued

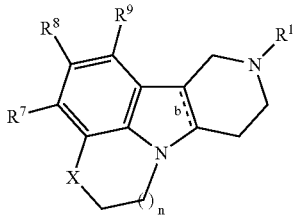

| Ex # | X | n | R7 | R8 | R9 | b | R1 |
|---|---|---|---|---|---|---|---|
| 449 | SO | 1 | H | H | H | sgl | H |
| 450 | $SO_2$ | 1 | H | 2-$CF_3$-4-MeO-phenyl | H | sgl | H |
| 451 | $SO_2$ | 1 | H | 2,4-diCl-phenyl | H | sgl | H |

What is claimed is:

1. A compound of formula (I):

(I)

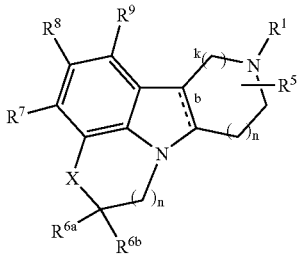

or stereoisomers or pharmaceutically acceptable salt forms thereof, wherein:

b is a single bond;

X is —O—, —S—, —S(=O)—, or —$S(=O)_2$—;

$R^1$ is selected from

H, $C(=O)R^2$, $C(=O)OR^2$, $C_{1-8}$ alkyl, $C_{2-8}$ alkenyl, $C_{2-8}$ alkynyl, $C_{3-7}$ cycloalkyl, $C_{1-6}$ alkyl substituted with 0–2 $R^2$, $C_{2-6}$ alkenyl substituted with 0–2 $R^2$, aryl substituted with 0–2 $R^2$, and 5–6 membered heterocyclic ring system containing at least one heteroatom selected from the group consisting of N, O, and S, said heterocyclic ring system substituted with 0–2 $R^2$;

$R^2$, at each occurrence, is independently selected from

F, Cl, $CH_2F$, $CHF_2$, $CF_3$, $C_{1-4}$ alkyl, $C_{2-4}$ alkenyl, $C_{2-4}$ alkynyl, $C_{3-6}$ cycloakyl, phenyl substituted with 0–5 $R^{42}$;

$C_{3-10}$ carbocyclic group substituted with 0–3 $R^{41}$, and

5–10 membered heterocyclic ring system containing from 1–4 heteroatoms selected from the group consisting of N, O, and S substituted with 0–3 $R^{42}$;

$R^5$ is H, methyl, ethyl, propyl, or butyl;

$R^{6a}$ is selected from H;

H, —OH, —$NR^{46}R^{47}$, —$CF_3$, $C_{1-4}$ alkyl, $C_{1-4}$ alkoxy, $C_{3-4}$ haloalkyl, and aryl substituted with O–3 $R^{44}$;

$R^{6b}$ is H;

$R^7$ and $R^9$, at each occurrence, are independently selected from

H, halo, —$CF_3$, —$OCF_3$, —OH, —CN, —$NO_2$, —$NR^{46}R^{47}$, $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{3-10}$ carbocyclic group substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, C(O)H, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^8$ is selected from

—OH, —CN, —$NO_2$, $C_{2-8}$ alkenyl, $C_{2-8}$ alkynyl, ($C_{1-4}$ haloalkyl)oxy, $C_{3-10}$ cycloalkyl substituted with 0–2 $R^{33}$, $C_{1-4}$ alkyl substituted with 1–2 $R^{33}$, $C_{2-4}$ alkenyl substituted with 0–2 $R^{13}$, $C_{2-4}$ alkynyl substituted with 0–1 $R^{11}$, $C_{3-10}$ carbocyclic group substituted wit 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, C(O)H, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from

—CN, —$NO_2$, $C_{2-8}$ alkenyl, $C_{2-8}$ alkynyl, $C_{1-8}$ alkoxy, $C_{3-10}$ cycloalkyl, $C_{3-10}$ carbocyclic group substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, C(O)H, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)NR^{12}R^{13}$, $SO(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{12}$, at each occurrence, is independently selected from $C_{1-4}$ alkyl substituted with 0–1 $R^{12a}$, $C_{2-4}$ alkenyl substituted with 0–1 $R^{12a}$, $C_{2-4}$ alkynyl substituted with 0–1 $R^{12a}$, $C_{3-6}$ cycloalkyl substituted with 0–3 $R^{33}$, phenyl substituted with 0–5 $R^{33}$;

$C_{3-10}$ carbocyclic group substituted with 0–3 $R^{33}$, and

5–10 membered heterocyclic ring system containing from 1–4 heteroatoms selected from the group consisting of N, O, and S substituted with 0–3 $R^{31}$;

$R^{12a}$, at each occurrence, is independently selected from phenyl substituted with 0–5 $R^{33}$;

$C_{3-10}$ carbocyclic group substituted with 0–3 $R^{33}$, and

5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, R12 and R13 join to form a 5- or 6-membered ring optionally substituted with —O— or —N(R14)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H and $C_{1-4}$ alkyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from H, OH, halo, CN, $NO_2$, $CF_3$, $SO_2R^{45}$, $NR^{46}R^{47}$, —C(=O)H, $C_{1-4}$ alkyl, $C_{2-4}$ alkenyl, $C_{2-4}$ alkynyl, $C_{1-4}$ haloalkyl, $C_{1-3}$ haloalkyl-oxy-, and $C_{1-3}$ alkyloxy;

$R^{32}$, at each occurrence, is independently selected from H, OH, halo, $CF_3$, $SO_2R^{45}$, $NR^{46}R^{47}$, and $C_{1-4}$ alkyl;

$R^{33}$, at each occurrence, is independently selected from H, OH, halo, CN, $NO_2$, $CF_3$, $SO_2R^{45}$, $NR^{46}R^{47}$, —C(=O)H, $C_{1-6}$ alkyl, $C_{2-4}$ alkenyl, $C_{2-6}$ alkynyl, $C_{2-6}$ cycloalkyl, $C_{1-4}$ haloalkyl, $C_{1-4}$ haloalkyl-oxy-, $C_{1-4}$ alkyloxy, $C_{1-4}$ alkylthio-, $C_{1-4}$ alkyl-C(=)—, $C_{1-4}$ alkyl-C(=O)NH—, $C_{1-4}$ alkyl-OC(=)—, $C_{1-4}$ alkyl-C(=O)O—, $C_{3-6}$ cycloalkyl-oxy-, $C_{3-6}$ cycloalkylmethyl-oxy-;

$C_{1-4}$ alkyl substituted with OH, methoxy, ethoxy, propoxy, or butoxy; and $C_{2-6}$ alkenyl substituted with OH, methoxy, ethoxy, propoxy, or butoxy;

$R^{41}$, at each occurrence, is independently selected from H, $CF_3$, halo, OH, $CO_2H$, $SO_2R^{45}$, $NR^{46}R^{47}$ , $NO_2$, CN; $C_{2-8}$ alkenyl, $C_{2-8}$ alkynyl, $C_{1-4}$ alkoxy, $C_{1-4}$ haloalkyl $C_{1-4}$ alkyl substituted with 0–1 $R^{43}$;

aryl substituted with 0–3 $R^{42}$, and

5–10 membered heterocyclic ring system containing from 1–4 heteroatoms selected from the group consisting of N, O, and S substituted with 0–3 $R^{44}$;

$R^{42}$, at each occurrence, is independently selected from H, $CF_3$, halo, OH, $CO_2H$, $SO_2R^{45}$, $NR^{46}R^{47}$, $NO_2$, CN, $CH(=NH)NH_2$, $NHC(=NH)NH_2$, $C_{2-6}$ alkenyl, $C_{2-6}$ alkynyl, $C_{1-4}$ alkoxy, $C_{1-4}$ haloalkyl, $C_{3-6}$ cycloalkyl, $C_{1-4}$ alkyl substituted with 0–1 $R^{43}$;

aryl substituted with 0–3 $R^{44}$, and

5–10 membered heterocyclic ring system containing from 1–4 heteroatoms selected from the group consisting of N, O, and S substituted with 0–3 $R^{44}$;

$R^{43}$ is $C_{2-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H and $C_{1-4}$ alkyl;

k is 1 or 2;

m is 0, 1, or 2; and n is 1, 2, or 3;

provided when m is 0 or 1 then k is 1 or 2;

provided when m is 2 then k is 1.

2. A compound of claim 1 wherein:

X is —O— or —S—;

$R^1$ is selected from H,
$C(=O)R^2$,
$C(=O)OR^2$,
$C_{1-6}$ alkyl,
$C_{2-6}$ alkenyl,
$C_{2-6}$ alkynyl,
$C_{3-6}$ cycloalkyl,
$C_{1-4}$ alkyl substituted with 0–2 $R^2$,
$C_{2-4}$ alkenyl substituted with 0–2 $R^2$, and
$C_{2-4}$ alkynyl substituted with 0–2 $R^2$;

$R^2$, at each occurrence, is independently selected from
$C_{1-4}$ alkyl,
$C_{2-4}$ alkenyl,
$C_{2-4}$ alkynyl,
$C_{3-6}$ cycloakyl,
phenyl substituted with 0–5 $R^{42}$;
$C_{3-10}$ carbocyclic group substituted with 0–3 $R^{41}$, and
5–10 membered heterocyclic ring system containing from 1–4 heteroatoms selected from the group consisting of N, O, and S substituted with 0–3 $R^{41}$;

$R^5$ is H, methyl, ethyl, propyl, or butyl;

$R^{6a}$ is selected independently from
H, —OH, —$NR^{46}R^{47}$, —$CF_3$, $C_{1-3}$ alkyl, and $C_{1-3}$ alkoxy;

$R^{6b}$ is H;

$R^7$ and $R^9$, at each occurrence, are independently selected from
H, halo, —$CF_3$, —$OCF_3$, —OH, —CN, —$NO_2$, —$NR^{46}R^{47}$,
$C_{1-6}$ alkyl, $C_{2-6}$ alkenyl, $C_{2-6}$ alkynyl, $C_{1-6}$ haloalkyl, $C_{1-6}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$;

$R^8$ is selected from
—OH, —CN, —$NO_2$,
$C_{2-6}$ alkenyl, $C_{2-6}$ alkynyl, ($C_{1-4}$ haloalkyl)oxy,
$C_{3-10}$ cycloalkyl substituted with 0–2 $R^{33}$,
$C_{1-4}$ alkyl substituted with 1–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic group substituted wit 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
—CN, —$NO_2$,
$C_{2-6}$ alkenyl, $C_{2-6}$ alkynyl, $C_{1-6}$ alkoxy, $C_{3-10}$ cycloalkyl,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $SO(O)NR^{12}R^{13}$, $S(O)_2NR^{12}R^{13}$, $NR^{14}S(O)R^{12}$, and $NR^{14}S(O)_2R^{12}$;

$R^{12}$, at each occurrence, is independently selected from
$C_{1-4}$ alkyl substituted with 0–1 $R^{12a}$,
$C_{1-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —$N(R^{14})$—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H, methyl, ethyl, propyl, and butyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from H, OH, F, Cl, CN, $NO_2$, $CF_3$, $SO_2R^{45}$, $NR^{46}R^{47}$, —C(=O)H, methyl, ethyl, methoxy, ethoxy, trifluoromethyl, and trifluoromethoxy;

$R^{31}$, at each occurrence, is independently selected from H, OH, halo, $CF_3$, $SO_2R^{45}$, $NR^{46}R^{47}$, and $C_{1-4}$ alkyl;

$R^{33}$, at each occurrence, is independently selected from H, OH, halo, CN, $NO_2$, $CF_3$, $SO_2R^{45}$, $NR^{46}R^{47}$, —C(=O)H, $C_{1-6}$ alkyl, $C_{2-6}$ alkenyl, $C_{2-6}$ alkynyl,
$C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(═)—, $C_{1-4}$ alkyl-C(═O)NH—, $C_{1-4}$ alkyl-OC(═)—, $C_{1-4}$ alkyl-C(═O)O—, $C_{3-6}$ cycloalkyl-oxy-, $C_{3-6}$ cycloalkylmethyl-oxy-;

$C_{1-6}$ alkyl substituted with OH, methoxy, ethoxy, propoxy, or butoxy; and $C_{2-6}$ alkenyl substituted with OH, methoxy, ethoxy, propoxy, or butoxy;

$R^{41}$, at each occurrence, is independently selected from H, $CF_3$, halo, OH, $CO_2H$, $SO_2R^{45}$, $NR^{46}R^{47}$, $NO_2$, CN, $C_{2-8}$ alkenyl, $C_{2-8}$ alkynyl, $C_{1-4}$ alkoxy, $C_{1-4}$ haloalkyl
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from H, $CF_3$, halo, OH, $CO_2H$, $SO_2R^{45}$, $NR^{46}R^{47}$, $NO_2$, CN, CH(═NH)$NH_2$, NHC(═NH)$NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$;
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H and $C_{1-4}$ alkyl;

k is 1 or 2;

m is 0 or 1; and n is 1 or 2.

3. A compound of claim 1 wherein:

X is —S—;

$R^1$ is selected from
H,
$C_{1-4}$ alkyl,
$C_{2-4}$ alkenyl,
$C_{2-4}$ alkynyl,
$C_{3-4}$ cycloalkyl,
$C_{1-3}$ alkyl substituted with 0–1 $R^2$,
$C_{2-3}$ alkenyl substituted with 0–1 $R^2$, and
$C_{2-3}$ alkynyl substituted with 0–1 $R^2$;

$R^2$, at each occurrence, is independently selected from
$C_{1-4}$ alkyl,
$C_{2-4}$ alkenyl,
$C_{2-4}$ alkynyl,
$C_{3-6}$ cycloakyl,
phenyl substituted with 0–5 $R^{42}$;
$C_{3-6}$ carbocyclic group substituted with 0–3 $R^{41}$, and
5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;

$R^{6a}$ is H, methyl, ethyl, methoxy, —OH, or —$CF_3$;

$R^{6b}$ is H;

$R^7$ and $R^9$, at each occurrence, are independently selected from
H, halo, —$CF_3$, —$OCF_3$, —OH, —CN, —$NO_2$, —$NR^{46}R^{47}$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic group substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^8$ is selected from
—OH, —CN, —$NO_2$,
$C_{2-4}$ alkenyl, $C_{2-4}$ alkynyl, ($C_{1-4}$ haloalkyl)oxy,
$C_{3-10}$ cycloalkyl substituted with 0–2 $R^{33}$,
$C_{1-4}$ alkyl substituted with 1–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic group substituted wit 0–3 $R^{33}$,
aryl substituted with 0–5 $R^{33}$,
5–6 membered heterocyclic ring system containing 1, 2, or 3 heteroatoms selected from the group consisting of N, O, and S substituted with 0–3 $R^{31}$;
$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
—CN, —$NO_2$,
$C_{2-4}$ alkenyl, $C_{2-4}$ alkynyl, $C_{1-4}$ alkoxy, ($C_{1-4}$ haloalkyl) oxy,
$C_{3-10}$ cycloalkyl substituted with 0–2 $R^{33}$,
$C_{3-10}$ carbocyclic group substituted with 0–3 $R^{33}$,
aryl substituted with 0–5 $R^{33}$, and
5–6 membered heterocyclic ring system containing 1, 2, or 3, heteroatoms selected from the group consisting of N, O, and S substituted with 0–3 $R^{31}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of one N, two N, three N, one N one O, and one N one S; wherein said bicyclic heterocyclic ring system is unsaturated or partially saturated, wherein said bicyclic heterocyclic ring system is substituted with 0–2 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{31}$, at each occurrence, is independently selected from H, OH, halo, $CF_3$, methyl, ethyl, and propyl;

$R^{33}$, at each occurrence, is independently selected from
H, OH, halo, CN, $NO_2$, $CF_3$, $SO_2R^{45}$, $NR^{46}R^{47}$, —C(═O)H,
$C_{1-6}$ alkyl, $C_{2-6}$ alkenyl, $C_{2-6}$ alkynyl,
$C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(═)—,
$C_{1-4}$ alkyl-C(═O)NH—, $C_{1-4}$ alkyl-OC(═)—,
$C_{1-4}$ alkyl-C(═O)O—, $C_{3-6}$ cycloalkyl-oxy-,
$C_{3-6}$ cycloalkylmethyl-oxy-;
$C_{1-6}$ alkyl substituted with OH, methoxy, ethoxy, propoxy, or butoxy; and
$C_{2-6}$ alkenyl substituted with OH, methoxy, ethoxy, propoxy, or butoxy;

$R^{41}$, at each occurrence, is independently selected from H, $CF_3$, halo, OH, $CO_2H$, $SO_2R^{45}$, $NR^{46}R^{47}$ , $NO_2$, CN, $C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from H, $CF_3$, halo, OH, $CO_2H$, $SO_2R^{45}$, $NR^{46}R^{47}$, $NO_2$, CN, CH(═NH)$NH_2$, NHC(═NH)$NH_2$,
$C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cycloalkyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

k is 1;

m is 1; and n is 1 or 2.

4. A compound of claim 1 wherein:

X is —S—;

$R^1$ is selected from
H,
$C_{1-4}$ alkyl,
$C_{2-4}$ alkenyl,
$C_{2-4}$ alkynyl,
$C_{3-4}$ cycloalkyl,
$C_{1-3}$ alkyl substituted with 0–1 $R^2$,
$C_{2-3}$ alkenyl substituted with 0–1 $R^2$, and
$C_{2-3}$ alkynyl substituted with 0–1 $R^2$;

$R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-6}$ carbocyclic group substituted with 0–3 $R^{41}$, and
5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;

$R^{6a}$ is H, methyl, ethyl, methoxy, —OH, or —$CF_3$;

$R^{6b}$ is H;

$R^7$ and $R^9$, at each occurrence, are independently selected from
H, F, Cl, —$CH_3$, —$OCH_3$, —$CF_3$, —$OCF_3$, —CN, and —$NO_2$, $R^8$ is selected from
—OH, —CN, —$NO_2$,
$C_{2-4}$ alkenyl, $C_{2-4}$ alkynyl, ($C_{1-4}$ haloalkyl)oxy,
$C_{3-10}$ cycloalkyl substituted with 0–2 $R^{33}$,
$C_{1-4}$ alkyl substituted with 1–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic group substituted with 0–3 $R^{33}$,
aryl substituted with 0–5 $R^{33}$,
5–6 membered heterocyclic ring system comprising 1, 2, or 3 heteroatoms selected from the group consisting of N, O, and S substituted with 0–3 $R^{31}$;
$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
—CN, —$NO_2$,
$C_{2-4}$ alkenyl, $C_{2-4}$ alkynyl, $C_{1-4}$ alkoxy, ($C_{1-4}$ haloalkyl) oxy,
$C_{3-10}$ cycloalkyl substituted with 0–2 $R^{33}$,
$C_{3-10}$ carbocyclic group substituted with 0–3 $R^{33}$,
aryl substituted with 0–5 $R^{33}$, and
5–6 membered heterocyclic ring system containing 1, 2, or 3 heteroatoms selected from the group consisting of N, O , and S substituted with 0–3 $R^{31}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{33}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, and benztriazolyl; wherein said bicyclic heterocyclic ring system is substituted with 0–1 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$, at each occurrence, is independently selected from

H, OH, F, Cl, CN, $NO_2$, methyl, ethyl, methoxy, ethoxy, trifluoromethyl, and trifluoromethoxy;

$R^{31}$, at each occurrence, is independently selected from H, OH, halo, $CF_3$, methyl, ethyl, and propyl;

$R^{33}$, at each occurrence, is independently selected from H, OH, halo, CN, $NO_2$, $CF_3$, $SO_2R^{45}$, $NR^{46}R^{47}$, —C(═O)H,
$C_{1-6}$ alkyl, $C_{2-6}$ alkenyl, $C_{2-6}$ alkynyl,
$C_{3-6}$ cycloalkyl, $C_{1-4}$ haloalkyl, $C_{1-4}$ haloalkyl-oxy-, $C_{1-4}$ alkyloxy;
$C_{1-4}$ alkylthio-, $C_{1-4}$ alkyl-C(═O)—, $C_{1-4}$ alkyl-C(═O)NH—, $C_{1-4}$ alkyl-OC(═O)—,
$C_{1-4}$ alkyl-C(═O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, or butoxy; and
$C_{2-6}$ alkenyl substituted with OH, methoxy, ethoxy, propoxy, or butoxy;

$R^{41}$, at each occurrence, is independently selected from H, $CF_3$, halo, OH, $CO_2H$, $SO_2R^{45}$, $NR^{46}R^{47}$, $NO_2$, CN, $C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from H, $CF_3$, halo, OH, $CO_2H$, $SO_2R^{45}$, $NR^{46}R^{47}$, $NO_2$, CN, $CH(═NH)NH_2$, $NHC(═NH)NH_2$, $C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

k is 1;

m is 1; and n is 1 or 2.

5. A compound of claim 1 wherein:

X is —S—;

$R^1$ is selected from H,
$C_{1-5}$ alkyl substituted with 0–1 $R^2$,
$C_{2-5}$ alkenyl substituted with 0–1 $R^2$, and
$C_{2-3}$ alkynyl substituted with 0–1 $R^2$;

$R^2$ is $C_{3-6}$ cycloalkyl;

$R^5$ is H, methyl, ethyl, or propyl;

$R^{6a}$ is H, methyl, or ethyl;

$R^{6b}$ is H;

$R^7$ and $R^9$, at each occurrence, are independently selected from
H, F, Cl, —$CH_3$, —$OCH_3$, —$CF_3$, —$OCF_3$, —CN, and —$NO_2$, $R^8$ is selected from
methyl substituted with $R^{11}$;
ethenyl substituted with $R^{11}$;
$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
phenyl-substituted with 0–5 fluoro;
2-($H_3CCH_2C$(═O))-phenyl substituted with $R^{33}$;
2-($H_3CC$(═O))-phenyl-substituted with $R^{33}$;
2-(HC(═O))-phenyl-substituted with $R^{32}$;
2-($H_3CCH$(OH))-phenyl-substituted with $R^{32}$;
2-($H_3CCH_2CH$(OH))-phenyl-substituted with $R^{33}$;
2-($HOCH_2$)-phenyl-substituted with $R^{33}$;
2-($HOCH_2CH_2$)-phenyl-substituted with $R^{33}$;
2-($H_3COCH_2$)-phenyl-substituted with $R^{33}$;
2-($H_3COCH_2CH_2$)-phenyl-substituted with $R^{33}$;
2-($H_3CCH$(OMe))-phenyl-substituted with $R^{33}$;
2-($H_3COC$(═O))-phenyl-substituted with $R^{33}$;
2-(HOCH-CH═CH)-phenyl-substituted with $R^{33}$;
2-((MeOC═O)CH═CH)-phenyl-substituted with $R^{33}$;
2-(methyl)-phenyl-substituted with $R^{33}$;
2-(ethyl)-phenyl-substituted with $R^{33}$;
2-(i-propyl)-phenyl-substituted with $R^{33}$;
2-($F_3C$)-phenyl-substituted with $R^{33}$;
2-(NC)-phenyl-substituted with $R^{33}$;
2-($H_3CO$)-phenyl-substituted with $R^{33}$;
2-(fluoro)-phenyl-substituted with $R^{33}$;
2-(chloro)-phenyl-substituted with $R^{33}$;
3-(NC)-phenyl-substituted with $R^{33}$;
3-($H_3CO$)-phenyl-substituted with $R^{33}$;
3-(fluoro)-phenyl-substituted with $R^{33}$;
3-(chloro)-phenyl-substituted with $R^{33}$;
4-(NC)-phenyl-substituted with $R^{33}$;
4-(fluoro)-phenyl-substituted with $R^{33}$;
4-(chloro)-phenyl-substituted with $R^{32}$;
4-($H_3CS$)-phenyl-substituted with $R^{33}$;
4-($H_3CO$)-phenyl-substituted with $R^{33}$;
4-(ethoxy)-phenyl-substituted with $R^{33}$;
4-(i-propoxy)-phenyl-substituted with $R^{33}$;
4-(i-butoxy)-phenyl-substituted with $R^{33}$;
4-($H_3CCH_2CH_2C$(═O))-phenyl-substituted with $R^{33}$;
4-($(H_3)_2CHC$(═O))-phenyl-substituted with $R^{33}$;
4-($H_3CCH_2C$(═O))-phenyl-substituted with $R^{33}$;
4-($H_3CC$(═O)-phenyl-substituted with $R^{33}$;
4-($H_3CCH_2CH_2CH$(OH))-phenyl-substituted with $R^{33}$;
4-($(H_3C)_2CHCH$(OH)-phenyl-substituted with $R^{32}$;
4-($H_3CCH_2CH$(OH))-phenyl-substituted with $R^{33}$;
4-($H_3CCH$(OH))-phenyl-substituted with $R^{33}$;
4-(cyclopropyloxy)-phenyl-substituted with $R^{33}$;
4-(cyclobutyloxy)-phenyl-substituted with $R^{33}$; and
4-(cyclopentyloxy)-phenyl-substituted with $R^{33}$;

$R^{12}$ is selected from
phenyl-substituted with 0–5 fluoro;
2-($H_3CCH_2C$(═O))-phenyl-substituted with $R^{33}$;
2-($H_3CC$(═O))-phenyl-substituted with $R^{33}$;
2-(HC(═O))-phenyl-substituted with $R^{33}$;
2-($H_3CCH$(OH))-phenyl substituted with $R^{33}$;
2-($H_3CCH_2CH$(OH))-phenyl-substituted with $R^{33}$;
2-($HOCH_2$)-phenyl-substituted with $R^{33}$;
2-($HOCH_2CH_2$)-phenyl-substituted with $R^{33}$;
2-($H_3COCH_2$)-phenyl-substituted with $R^{33}$;
2-($H_3COCH_2CH_2$)-phenyl-substituted with $R^{33}$;
2-($H_3CCH$(OMe))-phenyl-substituted with $R^{33}$;
2-($H_3COC$(═O))-phenyl-substituted with $R^{33}$;
2-($HOCH_2CH$═CH)-phenyl-substituted with $R^{33}$;
2-((MeOC═O)CH═CH)-phenyl-substituted with $R^{33}$;
2-(methyl)-phenyl-substituted with $R^{33}$;
2-(ethyl)-phenyl-substituted with $R^{33}$;
2-(i-propyl)-phenyl-substituted with $R^{33}$;
2-($F_3C$)-phenyl-substituted with $R^{33}$;
2-(NC)-phenyl-substituted with $R^{33}$;
2-($H_3CO$)-phenyl-substituted with $R^{33}$;
2-(fluoro)-phenyl-substituted with $R^{33}$;

2-(chloro)-phenyl-substituted with $R^{33}$;
3-(NC)-phenyl-substituted with $R^{33}$;
3-($H_3CO$)-phenyl-substituted with $R^{33}$;
3-(fluoro)-phenyl-substituted with $R^{33}$;
3-(chloro)-phenyl-substituted with $R^{33}$;
4-(NC)-phenyl-substituted with $R^{33}$;
4-(fluoro)-phenyl-substituted with $R^{33}$;
4-(chloro)-phenyl-substituted with $R^{33}$;
4-($H_3CS$)-phenyl-substituted with $R^{33}$;
4-($H_3CO$)-phenyl-substituted with $R^{33}$;
4-(ethoxy)-phenyl-substituted with $R^{33}$;
4-(i-propoxy)-phenyl-substituted with $R^{33}$;
4-(i-butoxy)-phenyl-substituted with $R^{33}$;
4-($H_3CCH_2CH_2C(=O)$)-phenyl-substituted with $R^{33}$;
4-($(H_2C)_2CHC(=O)$ )-phenyl-substituted with $R^{33}$;
4-($H_3CCH_2C(=O)$)-phenyl-substituted with $R^{33}$;
4-($H_3CC(=)$)-phenyl-substituted with $R^{33}$;
4-($H_3CCH_2CH_2CH(OH)$)-phenyl-substituted with $R^{33}$;
4-($(H_3C)_2CHCH(OH)$)-phenyl-substituted with $R^{33}$;
4-($H_3CCH_2CH(OH)$)-phenyl-substituted with $R^{33}$;
4-($H_3CCH(OH)$)-phenyl-substituted with $R^{33}$;
4-(cyclopropyloxy)-phenyl-substituted with $R^{33}$;
4-(cyclobutyloxy)-phenyl-substituted with $R^{33}$; and
4-(cyclopentyloxy)-phenyl-substituted with $R^{33}$;

$R^{13}$ is H, methyl, or ethyl;

alternatively, $R^{12}$ and $R^{13}$ join to form a 5- or 6-membered ring selected from pyrrolyl, pyrrolidinyl, imidazolyl, piperidinyl, piperizinyl, methylpiperizinyl, and morpholinyl;

alternatively, $R^{12}$ and $R^{13}$ when attached to N may be combined to form a 9- or 10-membered bicyclic heterocyclic ring system containing form 1–3 heteroatoms selected from the group consisting of N, O, and S; wherein said bicyclic heterocyclic ring system is selected from indolyl, indolinyl, indazolyl, benzimidazolyl, benzimidazolinyl, and benztriazolyl; wherein said bicyclic heterocyclic ring system is substituted with 0–1 $R^{16}$;

$R^{15}$ is H, methyl, ethyl, propyl, or butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{33}$, at each occurrence, is independently selected from H, F, Cl, —$CH_3$, —$OCH_3$, —$CF_3$, —$OCF_3$, —CN, and —$NO_2$;

k is 1;

m is 1; and n is 1 or 2.

6. A compound of claim 1 wherein:

X is —O—;

$R^1$ is selected from
H,
$C_{1-4}$ alkyl,
$C_{2-4}$ alkenyl,
$C_{2-4}$ alkynyl,
$C_{3-4}$ cycloalkyl,
$C_{1-3}$ alkyl substituted with 0–1 $R^2$,
$C_{2-3}$ alkenyl substituted with 0–1 $R^2$, and
$C_{2-3}$ alkynyl substituted with 0–1 $R^2$, $R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-6}$ carbocyclic group substituted with 0–3 $R^{42}$, and
5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;

$R^{6a}$ is H, methyl, ethyl, methoxy, —OH, or —$CF_3$;

$R^{6b}$ is H;

$R^7$ and $R^9$, at each occurrence, are independently selected from
H, halo, —$CF_3$, —$OCF_3$, —OH, —CN, —$NO_2$, —$NR^{46}R^{47}$,
$C_{1-4}$ alkyl, $C_{2-4}$ alkenyl, $C_{2-4}$ alkynyl, $C_{1-4}$ haloalkyl, $C_{1-4}$ alkoxy ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic group substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^8$ is selected from
—OH, —CN, —$NO_2$,
$C_{2-4}$ alkenyl, $C_{2-4}$ alkynyl, ($C_{1-4}$ haloalkyl)oxy,
$C_{3-10}$ cycloalkyl substituted with 0–2 $R^{33}$,
$C_{1-4}$ alkyl substituted with 1–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic group substituted with 0–3 $R^{33}$,
aryl substituted with 0–5 $R^{33}$,
5–6 membered heterocyclic ring system containing 1, 2, or 3 heteroatoms selected from the group consisting of N, O, and S substituted with 0–3 $R^{31}$;
$OR^{12}$, $SR^{12}$, $NR^{12}R^{15}$, $C(O)R^{15}$, $NR^{12}C(O)OR^{15}$, $NR^{12}S(O)_2R^{15}$, and $NR^{12}C(O)NHR^{15}$;

$R^{11}$ is selected from
—CN, —$NO_2$,
$C_{2-4}$ alkenyl, $C_{2-4}$ alkynyl, $C_{1-4}$ alkoxy, ($C_{1-4}$ haloalkyl) oxy,
$C_{3-10}$ cycloalkyl substituted with 0–2 $R^{33}$,
$C_{3-10}$ carbocyclic group substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{13}$,
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, each occurrence, is independently selected from
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9-membered bicyclic heterocyclic ring system containing from 1–3 heteroatoms selected from the group consisting of one N, two N, three N, one N one O, and one N one S, wherein said bicyclic heterocyclic ring system is unsaturated or partially saturated, wherein said bicyclic heterocyclic ring system is substituted with 0–2 $R^{16}$;

$R^{14}$, at each occurrence, is independently selected from H, methyl, ethyl, propyl, and butyl;

$R^{15}$, at each occurrence, is independently selected from H, methyl, ethyl propyl, and butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{31}$, at each occurrence, is independently selected from H, OH, halo, $CF_3$, methyl, ethyl, and propyl;

$R^{33}$, at each occurrence, is independently selected from
H, OH, halo, CN, $NO_2$, $CF_3$, $SO_2R^{45}$, $NR^{46}R^{47}$, —C(═O)H,
$C_{1-6}$ alkyl, $C_{2-6}$ alkenyl, $C_{2-6}$ alkynyl,
$C_{3-6}$ cycloalkyl, $C_{3-4}$ haloalkyl, $C_{1-4}$ haloalkyl-oxy-, $C_{1-4}$ alkyloxy-,
$C_{1-4}$ alkylthio-, $C_{1-4}$ alkyl-C(═O)—, $C_{1-4}$ alkyl-C(═O)NH—, $C_{1-4}$ alkyl-OC(═O)—,
$C_{1-4}$ alkyl-C(═O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, or butyoxy; and
$C_{2-6}$ alkenyl substituted with OH, methoxy, ethoxy, propoxy, or butoxy;

$R^{41}$, at each occurrence, is independently selected from H, $CF_3$, halo, OH, $CO_2H$, $SO_2R^{45}$, $NR^{46}R^{47}$, $NO_2$, CN, $C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from H, $CF_3$, halo, OH, $CO_2H$, $SO_2R^{45}$, $NR^{46}R^{47}$, $NO_2$, CN, CH(═NH)$NH_2$, NHC(═NH)$NH_2$, $C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ al $R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

k is 1;

m is 1; and n is 1 or 2.

7. A compound of claim 1 wherein

X is —O—;

$R^1$ is selected from
H,
$C_{1-4}$ alkyl,
$C_{2-4}$ alkenyl,
$C_{2-4}$ alkynyl,
$C_{3-4}$ cycloalkyl,
$C_{1-3}$ alkyl substituted with 0–1 $R^2$,
$C_{2-3}$ alkenyl substituted with 0–1 $R^2$, and
$C_{2-3}$ alkynyl substituted with 0–1 $R^2$, $R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-6}$ carbocyclic group substituted with 0–3 $R^{41}$, and
5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;

$R^{6a}$ is H, methyl, ethyl, methoxy, —OH, or —$CF_3$;

$R^{6b}$ is H;

$R^7$ and $R^9$, at each occurrence, are independently selected from
H, F, Cl, —$CH_3$, —$OCH_3$, —$CF_3$, —$OCF_3$, —CN, and —$NO_2$, $R^8$ is selected from
—OH, —CN, —$NO_2$,
$C_{2-4}$ alkenyl, $C_{2-4}$ alkynyl, ($C_{1-4}$ haloalkyl)oxy,
$C_{3-10}$ cycloalkyl substituted with 0–2 $R^{33}$,
$C_{1-4}$ alkyl substituted with 1–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic group substituted with 0–3 $R^{33}$,
aryl substituted with 0–5 $R^{33}$,
5–6 membered heterocyclic ring system containing 1, 2, or 3 heteroatoms selected from the group consisting of N, O, and S substituted with 0–3 $R^{31}$;
$OR^{12}$, $SR^{12}$, $NR^{12}R^{13}$, $C(O)R^{15}$, $NR^{12}C(O)OR^{15}$, $NR^{12}S(O)_2R^{15}$, and $NR^{12}C(O)NHR^{15}$;

$R^{11}$ is selected from
—CN, —$NO_2$,
$C_{2-4}$ alkenyl, $C_{2-4}$ alkynyl, $C_{1-4}$ alkoxy, ($C_{1-4}$ haloalkyl) oxy,
$C_{3-10}$ cycloalkyl substituted with 0–2 $R^{33}$,
$C_{3-10}$ carbocyclic group substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, each occurrence, is independently selected from
phenyl substituted with 0–5 $R^{33}$;
$C_{3-10}$ carbocyclic group substituted with 0–3 $R^{33}$, and
b 5–10membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is benzimidazolyl, benzimidazolinyl, benztriazolyl, benzoxazolyl, benzoxazolinyl, benzthiazolyl, and dioxobenzthiazolyl; wherein said bicyclic heterocyclic ring system is substituted with 0–1 $R^{16}$;

$R^{14}$, at each occurrence, is independently selected from H, methyl, ethyl, propyl, and butyl;

$R^{15}$, at each occurrence, is independently selected from H, methyl, ethyl propyl, and butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{31}$, at each occurrence, is independently selected from H, OH, halo, $CF_3$, methyl, ethyl, and propyl;

$R^{33}$, at each occurrence, is independently selected from H, OH, halo, CN, $NO_2$, $CF_3$, $SO_2R^{45}$, $NR^{46}R^{47}$, —C(═O)H,
$C_{1-6}$ alkyl, $C_{2-6}$ alkenyl, $C_{2-6}$ alkynyl,
$C_{3-6}$ cycloalkyl, $C_{3-4}$ haloalkyl, $C_{1-4}$ haloalkyl-oxy-, $C_{1-4}$ alkyloxy-,
$C_{1-4}$ alkylthio-, $C_{1-4}$ alkyl-C(═O)—, $C_{1-4}$ alkyl-C(═O)NH—, $C_{1-4}$ alkyl-OC(═O)—,
$C_{1-4}$ alkyl-C(═O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, or butyoxy; and
$C_{2-6}$ alkenyl substituted with OH, methoxy, ethoxy, propoxy, or butoxy;

$R^{41}$, at each occurrence, is independently selected from H, $CF_3$, halo, OH, $CO_2H$, $SO_2R^{45}$, $NR^{46}R^{47}$, $NO_2$, CN, $C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from H, $CF_3$, halo, OH, $CO_2H$, $SO_2R^{45}$, $NR^{46}R^{47}$, $NO_2$, CN, $CH(═NH)NH_2$, $NHC(═NH)NH_2$,
$C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

k is 1;

m is 1; and n is 1 or 2.

8. A compound of claim 1 wherein:

X is —O—;

$R^1$ is selected from H,
$C_{1-5}$ alkyl substituted with 0–1 $R^2$,
$C_{2-5}$ alkenyl substituted with 0–1 $R^2$, and
$C_{2-3}$ alkynyl substituted with 0–1 $R^2$;

$R^2$ is $C_{3-6}$ cycloalkyl;

$R^5$ is H, methyl, ethyl, or propyl;

$R^{6a}$ is H, methyl, or ethyl;

$R^{6b}$ is H;

$R^7$ and $R^9$, at each occurrence, are independently selected from
H, F, Cl, —$CH_3$, —$OCH_3$, —$CF_3$, —$OCF_3$, —CN, and —$NO_2$, $R^8$ is selected from
methyl substituted with $R^{11}$;
ethenyl substituted with $R^{11}$;
$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
phenyl-substituted with 0–5 fluoro;
2-($H_3CCH_2C$(═O))-phenyl-substituted with $R^{33}$;
2-($H_3CC$(═O))-phenyl-substituted with $R^{33}$;
2-(HC(═O))-phenyl-substituted with $R^{33}$;
2-($H_3CCH$(OH))-phenyl-substituted with $R^{33}$;
2-($H_3CCH_2CH$(OH))-phenyl substituted with $R^{33}$;
2-($HOCH_2$)-phenyl-substituted with $R^{33}$;
2-($HOCH_2$)-phenyl-substituted with $R^{33}$;
2-($HOCH_3CH_2$)-phenyl-substituted with $R^{33}$;
2-($H_3COCH_2$)-phenyl-substituted with $R^{33}$;
2-($H_3COCH_2CH_2$)-phenyl-substituted with $R^{33}$;
2-($H_3CCH$(OMe))-phenyl-substituted with $R^{33}$;
2-($H_3COC$(═O))-phenyl-substituted with $R^{33}$;
2-($HOCH_2CH$═CH)-phenyl-substituted with $R^{33}$;
2-((MeOC═O)CH═CH)-phenyl-substituted with $R^{33}$;
2-(methyl)-phenyl-substituted with $R^{33}$;
2-(ethyl)-phenyl-substituted with $R^{33}$;
2-(i-propyl)-phenyl-substituted with $R^{33}$;
2-($F_3C$)-phenyl-substituted with $R^{33}$;
2-(NC)-phenyl-substituted with $R^{33}$;
2-($H_3CO$)-phenyl-substituted with $R^{33}$;
2-(fluoro)-phenyl-substituted with $R^{33}$;
2-(chloro)-phenyl-substituted with $R^{33}$;
3-(NC)-phenyl-substituted with $R^{33}$;
3-($H_3CO$)-phenyl-substituted with $R^{33}$;
3-(fluoro)-phenyl-substituted with $R^{33}$;
3-(chloro)-phenyl-substituted with $R^{33}$;
4-(NC)-phenyl-substituted with $R^{33}$;
4-(fluoro)-phenyl-substituted with $R^{33}$;
4-(chloro)-phenyl-substituted with $R^{33}$;
4-($H_3CS$)-phenyl-substituted with $R^{33}$;
4-($H_3CO$)-phenyl-substituted with $R^{33}$;
4-(ethoxy)-phenyl-substituted with $R^{33}$;
4-(i-propoxy)-phenyl-substituted with $R^{33}$;
4-(i-butoxy)-phenyl-substituted with $R^{33}$;
4-($H_3CCH_2CH_2C$(═O))-phenyl-substituted with $R^{33}$;
4-($(H_3C)_2CHC$(═O))-phenyl-substituted with $R^{33}$;
4-($H_3CCH_2C$(═O))-phenyl-substituted with $R^{33}$;
4-($H_3CC$(═O)-phenyl-substituted with $R^{33}$;
4-($H_3CCH_2CH_2CH$(OH))-phenyl-substituted with $R^{33}$;
4-($(H_3C)_2CHCH$(OH)-phenyl-substituted with $R^{33}$;
4-($H_3CCH_2CH$(OH))-phenyl-substituted with $R^{33}$;
4-($H_3CCH$(OH))-phenyl-substituted with $R^{33}$;
4-(cyclopropyloxy)-phenyl-substituted with $R^{33}$;
4-(cyclobutyloxy)-phenyl-substituted with $R^{33}$; and
4-(cyclopentyloxy)-phenyl-substituted with $R^{33}$;

$R^{12}$ is selected from
phenyl-substituted with 0–5 fluoro;
2-($H_3CCH_2C$(═O))-phenyl-substituted with $R^{33}$;
2-($H_3CC$(═O))-phenyl-substituted with $R^{33}$;
2-(HC(═O))-phenyl-substituted with $R^{33}$;
2-($H_3CCH$(OH))-phenyl substituted with $R^{33}$;
2-($H_3CCH_2CH$(OH))-phenyl-substituted with $R^{33}$;
2-($HOCH_2$)-phenyl-substituted with $R^{33}$;
2-($HOCH_2CH_2$)-phenyl-substituted with $R^{33}$;
2-($H_3COCH_2$)-phenyl-substituted with $R^{33}$;
2-($H_3COCH_2CH_2$)-phenyl-substituted with $R^{33}$;
2-($H_3CCH$(OMe))-phenyl-substituted with $R^{33}$;
2-($H_3COC$(═O))-phenyl-substituted with $R^{33}$;
2-($HOCH_2CH$═CH)-phenyl-substituted with $R^{33}$;

2-((MeOC═O)CH═CH)-phenyl-substituted with $R^{33}$;

2-(methyl)-phenyl-substituted with $R^{33}$;

2-(ethyl)-phenyl-substituted with $R^{33}$;

2-(i-propyl)-phenyl-substituted with $R^{33}$;

2-($F_3C$)-phenyl-substituted with $R^{33}$;

2-(NC)-phenyl-substituted with $R^{33}$;

2-($H_3CO$)-phenyl-substituted with $R^{33}$;

2-(fluoro)-phenyl-substituted with $R^{33}$;

2-(chloro)-phenyl-substituted with $R^{33}$;

3-(NC)-phenyl-substituted with $R^{33}$;

3-($H_3CO$)-phenyl-substituted with $R^{33}$;

3-(fluoro)-phenyl-substituted with $R^{33}$;

3-(chloro)-phenyl-substituted with $R^{33}$;

4-(NC)-phenyl-substituted with $R^{33}$;

4-(fluoro)-phenyl-substituted with $R^{33}$;

4-(chloro)-phenyl-substituted with $R^{33}$;

4-($H_3CS$)-phenyl-substituted with $R^{33}$;

4-($H_3CO$)-phenyl-substituted with $R^{33}$;

4-(ethoxy)-phenyl-substituted with $R^{33}$;

4-(i-propoxy)-phenyl-substituted with $R^{33}$;

4-(i-butoxy)-phenyl-substituted with $R^{33}$;

4-($H_3CCH_2CH_2C$(═O))-phenyl-substituted with $R^{33}$;

4-(($(H_3C)_2CHC$(═O) )-phenyl-substituted with $R^{33}$;

4-($H_3CCH_2C$(═O))-phenyl-substituted with $R^{33}$;

4-($H_3CC$(═))-phenyl-substituted with $R^{33}$;

4-($H_3CCH_2CH_2CH$(OH))-phenyl-substituted with $R^{33}$;

4-(($(H_3C)_2CHCH$(OH))-phenyl-substituted with $R^{33}$;

4-($H_3CCH_2CH$(OH))-phenyl-substituted with $R^{33}$;

4-($H_3CCH$(OH))-phenyl-substituted with $R^{33}$;

4-(cyclopropyloxy)-phenyl-substituted with $R^{33}$;

4-(cyclobutyloxy)-phenyl-substituted with $R^{33}$; and 4-(cyclopentyloxy)-phenyl-substituted with $R^{33}$;

$R^{13}$ is H, methyl, or ethyl;

alternatively, $R^{12}$ and $R^{13}$ join to form a 5- or 6-membered ring selected from pyrrolyl, pyrrolidinyl, imidazolyl, piperidinyl, piperizinyl, methylpiperizinyl, and morpholinyl;

alternatively, $R^{12}$ and $R^{13}$ when attached to N may be combined to form a 9- or 10-membered bicyclic heterocyclic ring system containing form 1–3 heteroatoms selected from the group consisting of N, O, and S; wherein said bicyclic heterocyclic ring system is selected from indolyl, indolinyl, indazolyl, benzimidazolyl, benzimidazolinyl, and benztriazolyl, benzoxazolyl, benzoxazolinyl, benzthiazolyl, and dioxobenzthiazolyl; wherein said bicyclic heterocyclic ring system is substituted with 0–1 $R^{16}$;

$R^{15}$ is H, methyl, ethyl, propyl, or butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{33}$, at each occurrence, is independently selected from H, F, Cl, —$CH_3$, —$OCH_3$, —$CF_3$, —$OCF_3$, —CN, and —$NO_2$;

k is 1;

m is 1; and n is 1 or 2.

9. A compound of claim 2 of Formula (I-a)

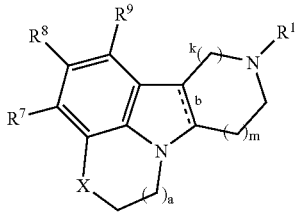

wherein:

b is a single bond;

X is —S— or —O—;

$R^1$ is selected from hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 2-methylpentyl, 3-methylbutyl, 4-methylpentyl, 2-fluoroethyl, 2,2-difluoroethyl, 2,2,2-trifluoroethyl, 2-propenyl, 2-methyl-2-propenyl, trans-2-butenyl, 3-methyl-butenyl, 3-butenyl, trans-2-pentenyl, cis-2-pentenyl, 4-pentenyl, 4-methyl-3-pentenyl, 3,3-dichloro-2-propenyl, trans-3-phenyl-2-propenyl, cyclopropyl, cyclobutyl, cyclopentyl, cyclohexyl, cyclopropylmethyl, cyclobutylmethyl, cyclopentylmethyl, cyclohexylmethyl, benzyl, 2-methylbenzyl, 3-methylbenzyl, 4-methylbenzyl, 2,5-dimethylbenzyl, 2,4-dimethylbenzyl, 3,5-dimethylbenzyl, 2,4,6-trimethyl-benzyl, 3-methoxy-benzyl, 3,5-dimethoxy-benzyl, pentafluorobenzyl, 2-phenylethyl, 1-phenyl-2-propyl, 4-phenylbutyl, 4-phenylbenzyl, 2-phenylbenzyl, (2,3-dimethoxy-phenyl)C(═O)—, (2,5-dimethoxy-phenyl)C(═O)—, (3,5-dimethoxy-phenyl)C(═O)—, cyclopropyl-C(═O)—, isopropyl-C(═O)—, ethyl-$CO_2$—, propyl-$CO_2$—, t-butyl-$CO_2$—, 2,6-dimethoxy-benzyl, 2,4-dimethoxy-benzyl, 2,4,6-trimethoxy-benzyl, 2,3-dimethoxy-benzyl, 2,4,5-trimethoxy-benzyl, 2,3,4-trimethoxy-benzyl, 3,4-dimethoxy-benzyl, 3,4,5-trimethoxy-benzyl, (4-fluoro-phenyl)ethyl, —CH═$CH_2$, —$CH_2$—CH═$CH_2$, —CH═CH—$CH_3$, —C═CH, —C═CH—$CH_3$, and —$CH_2$C═—CH;

$R^8$ is selected from cyano, nitro, trifluoromethoxy, phenyl, methylC(═)—, ethylC(═)—, propylC(═O)—, isopropylC(═O)—, butylC(═O)—, phenylC(═O)—, methyl$CO_2$—, ethyl$CO_2$—, propyl$CO_2$—, isopropyl$CO_2$—, butyl$CO_2$—, phenyl$CO_2$—, dimethylamino-S(═O)—, diethylamino-S(═O)—, dipropylamino-S(═O)—, di-isopropylamino-S(═O)—, dibutylamino-S(═O)—, diphenylamino-S(═O)—, dimethylamino-$SO_2$—, diethylamino-$SO_2$—, dipropylamino-$SO_2$—, di-isopropylamino-$SO_2$—, dibutylamino-$SO_2$—, diphenylamino-$SO_2$—, dimethylamino-C(═O)—, diethylamino-C(═O)—, dipropylamino-C(═O)—, di-isopropylamino-C(═O)—, dibutylamino-C(═O)—, diphenylamino-C(═O)—,
2-chlorophenyl, 2-fluorophenyl, 2-bromophenyl, 2-cyanophenyl, 2-methylphenyl, 2-trifluoromethylphenyl,
2-methoxyphenyl, 2-trifluoromethoxyphenyl,
3-chlorophenyl, 3-fluorophenyl, 3-bromophenyl,
3-cyanophenyl, 3-methylphenyl, 3-ethylpropyl,
3-propylphenyl, 3-isopropylphenyl, 3-butylphenyl,
3-trifluoromethylphenyl, 3-methoxyphenyl,
3-isopropoxyphenyl, 3-trifluoromethoxyphenyl,
3-thiomethoxyphenyl,
4-chlorophenyl, 4-fluorophenyl, 4-bromophenyl,
4-cyanophenyl, 4-methylphenyl, 4-ethylphenyl,
4-propylphenyl, 4-isopropylphenyl, 4-butylphenyl,
4-trifluoromethylphenyl, 4-methoxyphenyl,
4-isopropoxyphenyl, 4-trifluoromethoxyphenyl,
4-thiomethoxyphenyl,
2,3-dichlorophenyl, 2,3-difluorophenyl, 2,3-dimethylphenyl,
2,3-ditrifluoromethylphenyl-2,3-dimethoxyphenyl,
2,3-ditrifluoromethoxyphenyl,
2,4-dichlorophenyl, 2,4-difluorophenyl, 2,4-dimethylphenyl,
2,4-ditrifluoromethylphenyl, 2,4-dimethoxyphenyl,
2,4-ditrifluoromethoxyphenyl,
2,5-dichlorophenyl, 2,5-difluorophenyl, 2,5-dimethylphenyl,
2,5-trifluoromethylphenyl, 2,5-dimethoxyphenyl,
2,5-ditrifluoromethoxyphenyl,
2,6-dichlorophenyl, 2,6-difluorophenyl, 2,6-dimethylphenyl,
2,6-ditrifluoromethylphenyl, 2,6-dimethoxyphenyl,
2,6-ditrifluoromethoxyphenyl,
3,4-dichlorophenyl, 3,4-difluorophenyl, 3,4-dimethylphenyl,
3,4-ditrifluoromethylphenyl, 3,4-dimethoxyphenyl,
3,4-ditrifluoromethoxyphenyl,
2,4,6-trichlorohenyl, 2,4,6-trifluorophenyl,
2,4,6-trimethylphenyl, 2,4,6-trifluoromethylphenyl,
2,4,6-trimethoxyphenyl, 2,4,6-trifluoromethoxyphenyl,
2-chloro-4-$CF_3$-phenyl, 2-fluoro-3-chloro-phenyl,
2-chloro-4-$CF_3$-phenyl, 2-chloro-4-methoxy-phenyl,
2-methoxy-4-isopropyl-butyl, 2-$CF_3$-4-methoxy-phenyl,
2-methyl-4-methoxy-5-fluoro-phenyl,
2-methyl-4-methoxy-phenyl, 2-chloro-4-$CF_3O$-phenyl,
2,4,5-trimethyl-phenyl, 2-methyl-4-chloro-phenyl,
methyl-C(═O)NH—, ethyl-C(═O)NH—, propyl-C(═O)NH—,
isopropyl-C(═O)NH—, butyl-C(═O)NH—, phenyl-C(═O)NH—,
4-acetylphenyl, 3-acetamidophenyl, 4-pyridyl, 2-furanyl,
2-thiophenyl, 2-naphthyl;
2-Me-4-F-phenyl, 2-F-5-Me-phenyl, 2-MeO-5-F-phenyl,
2-Me-3-Cl-phenyl, 3-$NO_2$-phenyl, 2-$NO_2$-phenyl,
2-Cl-3-Me-phenyl, 2-Me-4-EtO-phenyl, 2-Me-4-F-phenyl,
2-Cl-6-F-phenyl, 2-Cl-4-($CHF_2$)O-phenyl,
2,4-diMeO-6-F-phenyl, 2-$CF_3$-6-F-phenyl,
2-MeS-phenyl, 2,6-diCl-4-MeO-phenyl,
2,3,4-triF-phenyl, 2,6-diF-4-Cl-phenyl,
2,3,4,6-tert-F-phenyl, 2,3,4,5,6-pentaF-phenyl,
2-$CF_3$-4-EtO-phenyl, 2-$CF_3$-4-iPrO-phenyl,
2-$CF_3$-4-Cl-phenyl, 2-$CF_3$-4-F-phenyl, 2-Cl-4-EtO-phenyl,
2-Cl-4-iPrO-phenyl, 2-Et-4-MeO-phenyl,
2-CHO-4-MeO-phenyl, 2-CH(OH)Me-4-MeO-phenyl,
2-CHO(OMe)Me-4-MeO-phenyl, 2-C(═O)Me-4-MeO-phenyl,
2-$CH_2$(OH)-4-MeO-phenyl, 2-$CH_2$(OMe)-4-MeO-phenyl,
2-CH(OH)Et-4-MeO-phenyl, 2-C(═O)Et-4-MeO-phenyl,
(Z)-2-CH═CH$CO_2$Me-4-MeO-phenyl,
2-$CH_2CH_2CO_2$Me-4-MeO-phenyl,
(Z)-2-CH═CH$CH_2$(OH)-4-MeO-phenyl,
(E)-2-CH═CH$CO_2$Me-4-MeO-phenyl,
(E)-2-CH═CH$CH_2$(OH)-4-MeO-phenyl,
2-$CH_2CH_2$OMe-4-MeO-phenyl,
2-F-4-MeO-phenyl, 2-Cl-4-F-phenyl,
(2-Cl-phenyl)-CH═CH—, (3-Cl-phenyl)-CH═CH—,
(2,6-diF-phenyl)-CH═CH—, —$CH_2$CH═$CH_2$,
phenyl-CH═CH—, (2-Me-4-MeO-phenyl)-CH═CH—,
cyclohexyl, cyclopentyl, cyclohexylmethyl,
—$CH_2CH_2CO_2$Et, —$(CH_2)_3CO_2$Et, —$(CH_2)_4CO_2$Et,
benzyl, 2-F-benzyl, 3-F-benzyl, 4-F-benzyl,
3-MeO-benzyl, 3-OH-benzyl, 2-MeO-benzyl,
2-OH-benzyl, 2-$CO_2$Me-3-MeO-phenyl,
2-Me-4-CN-phenyl, 2-Me-3-CN-phenyl, 2-$CF_3$-4-CN-phenyl,
3-CHO-phenyl, 3-$CH_2$(OH)-phenyl, 3-$CH_2$(OMe)-phenyl,
3-$CH_2$($NMe_2$)-phenyl, 3-CN-4-F-phenyl,
3-$CONH_2$-4-F-phenyl, 2-$CH_2$($NH_2$)-4-MeO-phenyl-,
phenyl-NH—, (4-F-phenyl)-NH—, (2,4-diCl-phenyl)-NH—,
phenyl-C(═O)NH—, benzyl-NH—, (2,4-Me-4-MeO-phenyl)-NH—,
(2-F-4-MeO-phenyl)-NH—, (2-Me-4-F-phenyl)-NH—,
phenyl-S—, —$NMe_2$, 1-pyrrolidinyl, and
-N(tosylate)$_2$, $R^7$ and $R^9$, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy;

m is 1; and n is 1 or 2.

10. A compound of claim 9 of Formula (II)

(II)

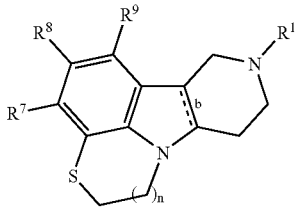

wherein:

b is a single bond, wherein the bridge hydrogens are in a cis position;

$R^1$ is selected from hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl, 4-methylphenyl, 2-fluoroethyl, 2,2-difluoroethyl, 2,2,2-trifluoroethyl, 2-propyl, 2-methyl-2-propenyl, trans-2-butenyl, 3-methyl-butenyl, 3-butenyl, trans-2-pentenyl, cis-2-pentenyl, 4-pentenyl, 4-methyl-3-pentenyl, 3,3-dichloro-2-propenyl, trans-3-phenyl-2-propenyl, cyclopropyl, cyclobutyl, cyclopentyl, cyclohexyl, cyclopropylmethyl, cyclobutylmethyl, cyclopentylmethyl, cyclohexylmethyl,

—CH═$CH_2$, —$CH_2$—CH═$CH_2$, —CH═CH—$CH_3$, —C≡CH, —C≡C—$CH_3$,

—CH═$CH_2$, —$CH_2$—CH═$CH_2$, —CH═CH—$CH_3$, —C≡—CH, —C≡—C—$CH_3$, and —$CH_2$—CH≡CH;

$R^7$ and $R^9$, at each occurrence, are independently selected from hydrogen, fluoro, methyl, trifluoromethyl, and methoxy;

$R^8$ is selected from cyano, nitro, trifluoromethoxy, phenyl, methylC(═O)—, ethylC(═O)—, propylC(═O)—, isopropylC(═O)—, butylC(═O)—, phenylC(═)—, methylCo$_2$—, ethylCO$_2$—, propylCO$_2$—, isopropylCO$_2$—, butylCO$_2$—, phenylCO$_2$—, dimethylamino-S(═O)—, diethylamino-S(═O)—, dipropylamino-S(═O)—, di-isopropylamino-S(═O)—, dibutylamino-S(═O)—, diphenylamino-S(═O)—, dimethylamino-SO$_2$—, diethylamino-SO$_2$—, dipropylamino-SO$_2$—, di-isopropylamino-SO$_2$—, dibutylamino-SO$_2$—, diphenylamino-SO$_2$—, dimethylamino-C(═O)—, diethylamino-C(═O)—, dipropylamino-C(═O)—, di-isopropylamino-C(═O)—, dibutylamino-C(═O)—, diphenylamino-C(═O)—, 2-chlorophenyl, 2-fluorophenyl, 2-bromophenyl, 2-cyanophenyl, 2-methylphenyl, 2-trifluromethylphenyl, 2-methoxyphenyl, 2-trifluoromethoxyphenyl, 3-chlorophenyl, 3-fluorophenyl, 3-bromophenyl, 3-cyanophenyl, 3-methylphenyl, 3-ethylphenyl, 3-propylphenyl, 3-isopropylphenyl, 3-butylphenyl, 3-trifluoromethyl, 3-methoxyphenyl, 3-isopropoxyphenyl, 3-trifluoromethoxyphenyl, 3-thiomethoxyphenyl, 4-chlorophenyl, 4-fluorophenyl, 4-bromophenyl, 4-cyanophenyl, 4-methylphenyl, 4-ethylphenyl, 4-propylphenyl, 4-isopropylphenyl, 4-butylphenyl, 4-trifluoromethylphenyl, 4-methoxyphenyl, 4-isopropoxyphenyl, 4-trifluoromethoxyphenyl, 4-thiomethoxyphenyl, 2,3-dichlorophenyl, 2,3-difluorophenyl, 2,3-dimethylphenyl, 2,3-ditrifluoromethylphenyl, 2,3-dimethoxyphenyl, 2,3-ditrifluoromethoxyphenyl, 2,4-dichlorophenyl, 2,4-difluorophenyl, 2,4-dimethylphenyl, 2,4-ditrifluoromethylphenyl, 2,4-dimethoxyphenyl, 2,4-ditrifluoromethoxyphenyl, 2,5-dichlorophenyl, 2,5-difluorophenyl, 2,5-dimethylphenyl, 2,5-trifluoromethylphenyl, 2,5-dimethoxyphenyl, 2,5-ditrifluoromethoxyphenyl, 2,6-dichlorophenyl, 2,6-difluorophenyl, 2,6-dimethylphenyl, 2,6-ditrifluoromethylphenyl, 2,6-dimethoxyphenyl, 2,6-ditrifluoromethoxyphenyl, 3,4-dichlorophenyl, 3,4-difluorophenyl, 3,4-dimethylphenyl, 3,4-ditrifluoromethylphenyl, 3,4-dimethoxyphenyl, 3,4-ditrifluoromethoxyphenyl, 2,4,6-trichlorohenyl, 2,4,6-trifluorophenyl, 2,4,6-trimethylphenyl, 2,4,6-trifluoromethylphenyl, 2,4,6-trimethoxyphenyl, 2,4,6-trifluoromethoxyphenyl, 2-chloro-4-$CF_3$-phenyl, 2-fluoro-3-chloro-phenyl, 2-chloro-4-$CF_3$-phenyl, 2-chloro-4-methoxy-phenyl, 2-methoxy-4-isopropyl-butyl, 2-$CF_3$-4-methoxy-phenyl, 2-methyl-4-methoxy-5-fluoro-phenyl, 2-methyl-4-methoxy-phenyl, 2-chloro-4-$CF_3$O-phenyl, 2,4,5-trimethyl-phenyl, 2-methyl-4-chloro-phenyl, methyl-C(═O)NH—, ethyl-C(═O)NH—, propyl-C(═O)NH—, isopropyl-C(═O)NH—, butyl-C(═O)NH—, phenyl-C(═O)NH—; 4-acetylphenyl, 3-acetamidophenyl, 4-pyridyl, 2-furanyl, 2-thiophenyl, 2-naphthyl; 2-Me-4-F-phenyl, 2-F-5-Me-phenyl, 2-MeO-5-F-phenyl, 2-Me-3-Cl-phenyl, 3-$NO_2$-phenyl, 2-$NO_2$-phenyl, 2-Cl-3-Me-phenyl, 2-Me-4-EtO-phenyl, 2-Me-4-F-phenyl, 2-Cl-6-F-phenyl, 2-Cl-4-($CHF_2$)O-phenyl, 2,4-diMeO-6-F-phenyl, 2-$CF_3$-6-F-phenyl, 2-MeS-phenyl, 2,6-diCl-4-MeO-phenyl, 2,3,4-triF-phenyl, 2,6-diF-4-Cl-phenyl, 2,3,4,6-tert-F-phenyl, 2,3,4,5,6-pentaF-phenyl, 2-$CF_3$-4-EtO-phenyl, 2-$CF_3$-4-iPrO-phenyl, 2-$CF_3$-4-Cl-phenyl, 2-$CF_3$-4-F-phenyl, 2-Cl-4-EtO-phenyl, 2-Cl-4-iPrO-phenyl, 2-Et-4-MeO-phenyl, 2-CHO-4-MeO-phenyl, 2-CH(OH)Me-4-MeO-phenyl, 2-CHO(OMe)Me-4-MeO-phenyl, 2-C(═O)Me-4-MeO-phenyl, 2-$CH_2$(OH)-4-MeO-phenyl, 2-$CH_2$(OMe)-4-MeO-phenyl, 2-CH(OH)Et-4-MeO-phenyl, 2-C(═O)Et-4-MeO-phenyl, (Z)-2-CH═CH$CO_2$Me-4-MeO-phenyl, 2-$CH_2CH_2CO_2$Me-4-MeO-phenyl, (Z)-2-CH═CH$CH_2$(OH)-4-MeO-phenyl, (E)-2-CH═CH$CO_2$Me-4-MeO-phenyl, (E)-2-CH═CH$CH_2$(OH)-4-MeO-phenyl, 2-$CH_2CH_2$OMe-4-MeO-phenyl, 2-F-4-MeO-phenyl, 2-Cl-4-F-phenyl, (2-Cl-phenyl)-CH═CH—, (3-Cl-phenyl)-CH═CH—, (2,6-diF-phenyl)-CH═CH—, —$CH_2$CH═$CH_2$, phenyl-CH═CH—, (2-Me-4-MeO-phenyl)-CH═CH—, cyclohexyl, cyclopentyl, cyclohexylmethyl, —$CH_2CH_2CO_2$Et, —$(CH_2)_3CO_2$Et, —$(CH_2)_4CO_2$Et, benzyl, 2-F-benzyl, 3-F-benzyl, 4-F-benzyl, 3-MeO-benzyl, 3-OH-benzyl, 2-MeO-benzyl, 2-OH-benzyl, 2-$CO_2$Me-3-MeO-phenyl, 2-Me-4-CN-phenyl, 2-Me-3-CN-phenyl, 2-$CF_3$-4-CN-phenyl, 3-CHO-phenyl, 3-$CH_2$(OH)-phenyl, 3-$CH_2$(OMe)-phenyl, 3-$CH_2$($NMe_2$)-phenyl, 3-CN-4-F-phenyl, 3-$CONH_2$-4-F-phenyl, 2-$CH_2$($NH_2$)-4-MeO-phenyl, phenyl-NH—, (4-F-phenyl)-NH—, (2,4-diCl-phenyl)-NH—, phenyl-C(═O)NH—, benzyl-NH—, (2,4-Me-4-MeO-phenyl)-NH—,
(2-F-4-MeO-phenyl)-NH—, (2-Me-4-F-phenyl)-NH—,
phenyl-S—, —$NMe_2$, 1-pyrrolidinyl, and
-N(tosylate)$_2$; and n is 1 or 2.

11. A compound of claim 9 of Formula (III)

(III)

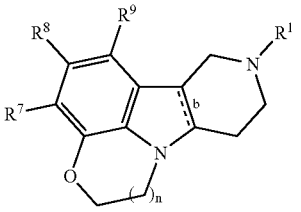

wherein:

b is a single bond, wherein the bridge hydrogens are in a cis position;

$R^1$ is selected from hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl,
4-methylphenyl, 2-fluoroethyl, 2,2-difluoroethyl,
2,2,2-trifluoroethyl, 2-propyl, 2-methyl-2-propenyl, trans-2-butenyl, 3-methyl-butenyl, 3-butenyl,
trans-2-pentenyl, cis-2-pentenyl, 4-pentenyl,
4-methyl-3-pentenyl, 3,3-dichloro-2-propenyl,
trans-3-phenyl-2-propenyl, cyclopropyl, cyclobutyl, cyclopentyl, cyclohexyl, cyclopropylmethyl, cyclobutylmethyl, cyclopentylmethyl, cyclohexylmethyl,
—CH═$CH_2$, —$CH_2$—CH═$CH_2$, —CH═CH—$CH_3$, —C≡CH, —C≡C—$CH_3$,
and —$CH_2$—CH≡CH;

$R^7$ and $R^9$, at each occurrence, are independently selected from hydrogen, fluoro, methyl, trifluoromethyl, and methoxy; and $R^8$ is selected from cyano, nitro, trifluoromethoxy, phenyl,
methylC(═O)—, ethylC(═O)—, propylC(═O)—, isopropylC(═O)—, butylC(═O)—, phenylC(═)—,
methyl$CO_2$—, ethyl$CO_2$—, propyl$CO_2$—, isopropyl$CO_2$—, butyl$CO_2$—, phenyl$CO_2$—,
dimethylamino-S(═O)—, diethylamino-S(═O)—,
dipropylamino-S(═O)—, di-isopropylamino-S(═O)—, dibutylamino-S(═O)—, diphenylamino-S(═O)—,
dimethylamino-$SO_2$—, diethylamino-$SO_2$—,
dipropylamino-$SO_2$—, di-isopropylamino-$SO_2$—,
dibutylamino-$SO_2$—, diphenylamino-$SO_2$—,
dimethylamino-C(═O)—, diethylamino-C(═O)—,
dipropylamino-C(═O)—, di-isopropylamino-C(═O)—, dibutylamino-C(═O)—, diphenylamino-C(═O)—,
2-chlorophenyl, 2-fluorophenyl, 2-bromophenyl,
2-cyanophenyl, 2-methylphenyl, 2-trifluoromethylphenyl,
2-methoxyphenyl, 2-trifluoromethoxyphenyl,
3-chlorophenyl, 3-fluorophenyl, 3-bromophenyl,
3-cyanophenyl, 3-methylphenyl, 3-ethylphenyl,
3-propylphenyl, 3-isopropylphenyl, 3-butylphenyl,
3-trifluoromethylphenyl, 3-methoxyphenyl,
3-isopropoxyphenyl, 3-trifluoromethoxyphenyl,
3-thiomethoxyphenyl,
4-chlorophenyl, 4-fluorophenyl, 4-bromophenyl,
4-cyanophenyl, 4-methylphenyl, 4-ethylphenyl,
4-propylphenyl, 4-isopropylphenyl, 4-butylphenyl,
4-trifluoromethylphenyl, 4-methoxyphenyl,
4-isopropoxyphenyl, 4-trifluoromethoxyphenyl,
4-thiomethoxyphenyl,
2,3-dichlorophenyl, 2,3-difluorophenyl,
2,3-dimethylphenyl, 2,3-ditrifluoromethylphenyl,
2,3-dimethoxyphenyl, 2,3-ditrifluoromethoxyphenyl,
2,4-dichlorophenyl, 2,4-difluorophenyl,
2,4-dimethylphenyl, 2,4-ditrifluoromethylphenyl,
2,4-dimethoxyphenyl, 2,4-ditrifluoromethoxyphenyl,
2,5-dichlorophenyl, 2,5-difluorophenyl,
2,5-dimethylphenyl, 2,5-ditrifluoromethylphenyl,
2,5-dimethoxyphenyl, 2,5-ditrifluoromethoxyphenyl,
2,6-dichlorophenyl, 2,6-difluorophenyl,
2,6-dimethylphenyl, 2,6-ditrifluoromethylphenyl,
2,6-dimethoxyphenyl, 2,6-trifluoromethoxyphenyl,
3,4-dichlorophenyl, 3,4-difluorophenyl,
3,4-dimethylphenyl, 3,4-ditrifluoromethylphenyl,
3,4-dimethoxyphenyl, 3,4-ditrifluoromethoxyphenyl,
2,4,6-trichlorophenyl, 2,4,6-trifluorophenyl,
2,4,6-trimethylphenyl, 2,4,6-trifluoromethylphenyl,
2,4,6-trimethoxyphenyl, 2,4,6-trifluoromethoxyphenyl,
2-chloro-4-$CF_3$-phenyl, 2-fluoro-3-chloro-phenyl,
2-chloro-4-$CF_3$-phenyl, 2-chloro-4-methoxy-phenyl,
2-methoxy-4-isopropyl-phenyl, 2-$CF_3$-4-methoxy-phenyl,
2-methyl-4-methoxy-5-fluoro-phenyl,
2-methyl-4-methoxy-phenyl, 2-chloro-4-$CF_3$O-phenyl,
2,4,5-trimethyl-phenyl, 2-methyl-4-chloro-phenyl,
methyl-C(═O)NH—, ethyl-C(═O)NH—, propyl-C(═O)NH—,
isopropyl-C(═O)NH—, butyl-C(═O)NH—, phenyl-C(═O)NH—,
4-acetylphenyl, 3-acetamidophenyl, 4-pyridyl, 2-furanyl,
2-thiophenyl, 2-naphthyl;
2-Me-5F-phenyl, 2-F-5-Me-phenyl, 2-MeO-5-F-phenyl,
2-Me-3-Cl-phenyl, 3-$NO_2$-phenyl, 2-$NO_2$-phenyl,
2-Cl-3-Me-phenyl, 2-Me-phenyl, 2-Me-4-EtO-phenyl, 2-Me-4-F-phenyl,
2-Cl-6-F-phenyl, 2-Cl-4-($CHF_2$)O-phenyl,
2,4-diMeO-6-F-phenyl, 2-$CF_3$-6-F-phenyl,
2-MeS-phenyl, 2,6-diCl-4-MeO-phenyl,
2,3,4-triF-phenyl, 2,6-diF-5-Cl-phenyl,
2,3,4-tetraF-phenyl, 2,3,4,5,6-pentaF-phenyl,
2-$CF_3$-4-EtO-phenyl, 2-$CF_3$-iPrO-phenyl,
2-$CF_3$-4-Cl-phenyl, 2-$CF_3$-4-F-phenyl, 2-Cl-4-EtO-phenyl,
2-Cl-4-iPrO-phenyl, 2-Et-4-MeO-phenyl,
2-CHO-4-MeO-phenyl, 2-CH(OH)Me-4-MeO-phenyl,
2-CH(OMe)Me-4-MeO-phenyl, 2C(═O)Me-4-MeO-phenyl,
2-$CH_2$(OH)-4-O-phenyl, 2-$CH_3$(OMe)-phenyl,
2-CH(OH)Et-4-MeO-phenyl, 2-C(═O)Et-4-MeO-phenyl,
(Z)-2-CH═$CHCO_2$Me-4-MeO-phenyl,
2-$CH_2CH_2CO_2$Me-4-MeO-phenyl,
(Z)-2-CH═$CHCH_2$(OH)-4-MeO-phenyl,
(E)-2-CH═$CHCO_2$Me-4-MeO-phenyl, (E)-2-CH═CHCH$_2$(OH)-4-MeO-phenyl,
2-CH$_2$C$_2$OMe-4-MeO-phenyl,
2-F-4-MeO-phenyl, 2-Cl-4-F-phenyl,
(2-Cl-phenyl)-CH═CH—, (3-Cl-phenyl)-CH═CH—,
(2,6-diF-phenyl)-CH═CH—, —CH$_2$CH═CH$_2$,
phenyl-CH═CH—, (2-Me-4-MeO-phenyl)CH═C—,
cyclohexyl, cyclopentyl, cyclohexylmethyl,
13 CH$_2$CH$_2$CO$_2$Et, —(CH$_2$)$_3$CO$_2$Et, —(CH$_2$)$_4$CO$_2$Et,
benzyl, 2-F-benzyl, 3-F-benzyl, 4-F-benzyl,
3-MeO-benyzl, 3-OH-benzyl, 2-MeO-benzyl,
2-OH-benzyl, 2-CO$_2$Me-3-MeO-phenyl,
2-Me-4-CN-phenyl, 2-Me-3-CN-phenyl, 2-CF$_3$-4-CN-phenyl,
3-CHO-phenyl, 3-CH$_2$(OH)-phenyl, 3-CH$_2$(OMe)-phenyl,
3-CH$_2$(NMe$_2$)-phenyl, 3-CN-4-F-phenyl,
3-CONH$_2$-4-F-phenyl, 2-CH$_2$(NH$_2$)-4-MeO-phenyl-,
phenyl-NH—, (4-F-phenyl)-NH—, (2,4-diCl-phenyl)-NH—,
phenyl-C(═O)NH—, benzyl-NH—, (2-Me-4-MeO-phenyl)-NH—,
(2-F-4-MeO-phenyl)-NH—, (2-Me-4-F-phenyl)-NH—,
phenyl-S—, —NM$_2$, 1-pyrrolidinyl, and —N(tosylate)2; and
n is 1 or 2.

12. A compound of formula (I):

(I)

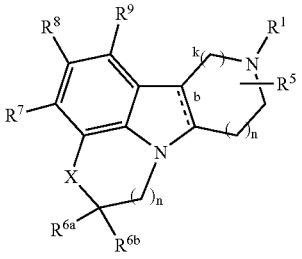

or steroisomers or pharmaceutically acceptable salt forms thereof, wherein:

b is a single bond;

X is —O—, —S—, —S(═O)—, or —S(═O)$_2$—,

R$^1$ is selected from
C$_{1-6}$ alkyl substituted with Z,
C$_{2-6}$ alkenyl substituted with Z,
C$_{2-6}$ alkynyl substituted with Z,
C$_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z,
C$_{1-6}$ alkyl substituted with 1–2 R$^2$, but R$^2$ cannot be alkyl;
C$_{2-6}$ alkenyl substituted with 0–2 R$^2$,
C$_{2-6}$ alkynyl substituted with 0–2 R$^2$,
aryl substituted with 0–2 R$^2$, and
5–6 membered heterocyclic ring system containing at least one heteroatom selected from the group consisting of N, O, and S, said heterocyclic ring system substituted with 0–2 R$^2$, Z is selected from
—CH(OH)$^2$,
—C(ethylenedioxy)R$^2$,
—OR$^2$,
—SR$^2$,
—NR$^2$R$^3$,
—C(O)R$^2$,
—C(O)N$^2$R$^3$,
—NR$^3$C(O)R$^2$,
—C(O)OR$^2$,
—OC(O)R$^2$,
—CH(═NR$^4$)NR$^2$R$^3$,
—NHC(═NR$^4$)NR$^2$R$^3$,
—S(O)R$^2$,
—S(O)$_2$R$^2$,
—S(O)$_2$NR$^2$R$^3$, and —NR$^3$S(O)$_2$R$^2$, R$^2$, at each occurrence, is independently selected from
C$_{1-4}$ alkyl,
C$_{2-4}$ alkenyl,
C$_{2-4}$ alkynyl,
C$_{3-6}$ cycloalkyl,
aryl substituted with 0–5 R$^{42}$;
C$_{3-10}$ carbocyclic group substituted with 0–3 R$^{41}$, and
5–10 membered heterocyclic ring system containing from 1–4 heteroatoms selected from the group consisting of N, O, and S substituted with 0–3 R$^{41}$;

R$^3$, at each occurrence, is independently selected from H, C$_{1-4}$ alkyl, C$_{2-4}$ alkenyl, C$_{2-4}$ alkynyl, and C$_{3-4}$ alkoxy;
alternatively, R$^2$ and R$^3$ join to form a 5- or 6-membered ring optionally substituted with —O— or —N(R$^4$)—;

R$^4$, at each occurrence, is independently selected from H, methyl, ethyl, propyl, and butyl;

R$^5$ is H, methyl, ethyl, propyl, or butyl;

R$^{6a}$ is selected from
H, —OH, —NR$^{46}$R$^{47}$, —CF$_3$,
C$_{1-4}$ alkyl, C$_{2-4}$ alkenyl, C$_{1-4}$ alkynyl, C$_{1-4}$ alkoxy, C$_{1-4}$ haloalkyl, C$_{3-6}$ cycloalkyl, and
aryl substituted with 0–3 R$^{44}$;

R$^{6b}$ is H;

R$^7$, R$^8$, and R$^9$, at each occurrence, are independently selected from
H, halo, —CF$_3$, —OCF$_3$, —OH, —CN, —NO$_2$, —NR$^{46}$R$^{47}$,
C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
C$_{1-4}$ alkyl substituted with 0–2 R$^{11}$,
C$_{3-10}$ carbocyclic group substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(═NR$^{14}$)NR$^{12}$R$^{13}$, NHC(═NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

R$^{11}$ is selected from
H, halo, —CF$_3$, —CN, —NO$_2$,
C$_{1-8}$ alkyl, C$_{2-8}$ alkenyl, C$_{2-8}$ alkynyl, C$_{1-4}$ haloalkyl, C$_{1-8}$ alkoxy, C$_{3-10}$ cycloalkyl,
C$_{3-10}$ carbocyclic group substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, (O)OR$^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, and $NR^{14}S(O)_2R^{12}$, $R^{12}$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$; p1 $R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —$N(R^{14})$—;

$R^{14}$, at each occurrence, is independently selected from H and $C_{1-4}$ alkyl;

$R^{31}$, at each occurrence, is independently selected from H, OH, halo, $CF_3SO_2R^{45}$, $NR^{46}R^{47}$, methyl, ethyl, and propyl;

$R^{33}$, at each occurrence, is independently selected from H, OH, halo, CN, $NO_2$, $CF_3$, $SO_2R^{45}$, $NR^{46}R^{47}$,
$C_{1-3}$ alkyl, $C_{2-3}$ alkenyl, $C_{2-3}$ alkynyl, $C_{3-5}$ cycloalkyl, $C_{1-3}$ haloalkyl, $C_{1-3}$ haloalkyl-oxy-, $C_{1-3}$ alkyloxy-, $C_{1-3}$ alkylthio, $C_{1-3}$ alkyl-C(=O)—, and $C_{1-3}$ alkyl-C(=O)NH—;

$R^{41}$, at each occurrence, is independently selected from H, $CF_3$, halo, OH, $CO_2H$, $SO_2R^{45}$, $NR^{46}R^{47}$, $NO_2$, CN, =O,
$C_{2-8}$ alkenyl, $C_{2-8}$ alkynyl, $C_{1-4}$ alkoxy, $C_{1-4}$ haloalkyl $C_{1-4}$ alkyl substituted with 0–1 $R^{43}$,
aryl substituted with 0–3 $R^{42}$, and
5–10 membered heterocycle ring system containing from 1–4 heteroatoms selected from the group consisting of N, O, and S substituted with 0–3 $R^{44}$;

$R^{42}$, at each occurrence, is independently selected from H, $CF_3$, halo, OH, $CO_2H$, $SO_2R^{45}$, $SR^{45}$, $NR^{46}R^{47}$, $OR^{48}$, $NO_2$, CN, $CH(=NH)NH_2$, $NHC(=NH)NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{45}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H, $C_{1-4}$ alkyl, —C(=O)NHC($C_{1-4}$ alkyl), —$SO_2$($C_{1-4}$ alkyl), —$SO_2$(phenyl), —C(=O)O($C_{1-4}$ alkyl), —C(=O)($C_{1-4}$ alkyl), and —C(=O)H;

$R^{48}$, at each occurrence, is independently selected from H, $C_{1-4}$ alkyl, —C(=O)NH($C_{1-4}$ alkyl), —C(=O)O($C_{1-4}$ alkyl), —C(=O)($C_{1-4}$alkyl), and —C(=O)H;

k is 1 or 2;

m is 0, 1, or 2; and n is 1 or 2;

provided when m is 0 or 1 then k is 1 or 2;

provided when m is 2 then l is 1;

provided that when b is a single bond; n is 1 or 2; m is 1; k is 1; X is O or S; and $R^1$ is $C_{1-4}$ alkyl or cyclopropyl, then $R^8$ is a substituent other than H.

13. A compound of claim 12 wherein:

X is —O— or —S—;

$R^1$ is selected from
$C_{2-5}$ alkyl substituted with Z,
$C_{2-5}$ alkenyl substituted with Z,
$C_{2-5}$ alkynyl substituted with Z,
$C_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z;
$C_{1-5}$ alkyl substituted with 1–2 $R^2$, but $R^2$ cannot be alkyl;
$C_{2-5}$ alkenyl substituted with 0–2 $R^2$, and
$C_{2-5}$ alkynyl substituted with 0–2 $R^2$;

Z is selected from
—$CH(OH)R^2$,
—C(ethylenedioxy)$R^2$,
—$OR^2$,
—$SR^2$,
—$NR^2R^3$,
—$C(O)R^2$,
—$C(O)NR^2R^3$,
—$NR^3C(O)R^2$,
—$C(O)OR^2$,
—$OC(O)R^2$,
$CH(=NR^4)NR^2R^3$,
—$NHC(=NR^4)NR^2R^3$,
—$S(O)R^2$,
—$S(O)R_2R^2$,
—$S(O)_2NR^2R^3$, and —$NR^3S(O)_2R^2$;

$R^3$, at each occurrence, is independently selected from
$C_{1-4}$ alkyl,
$C_{2-4}$ alkenyl,
$C_{2-4}$ alkynyl,
$C_{3-6}$ cycloalkyl,
aryl substituted with 0–5 $R^{42}$;
$C_{3-10}$ carbocyclic group substituted with 0–3 $R^{43}$, and
5–10 membered heterocyclic ring system containing from 1–4 heteroatoms selected from the group consisting of N, O, and S substituted with 0–3 $R^{41}$;

$R^3$, at each occurrence, is independently selected from H, $C_{1-4}$ alkyl, $C_{2-4}$ alkenyl, $C_{2-4}$ alkynyl, and $C_{1-4}$ alkoxy;

alternatively, $R^2$ and $R^3$ join to form a 5- or 6-membered ring optionally substituted with —O— or —$N(R^6)$—;

$R^4$, at each occurrence, is independently selected from H, methyl, ethyl, propyl, and butyl;

$R^5$ is H, methyl, or ethyl;

$R^{6a}$ is selected from
H, —OH, —$NR^{46}R^{47}$, —$CF_3$,
$C_{1-4}$ alkyl, $C_{2-4}$ alkenyl, $C_{2-4}$ alkynyl, $C_{1-4}$ alkoxy, $C_{1-4}$ haloalkyl, and $C_{3-6}$ cycloalkyl;

$R^{6b}$ is H;

$R^7$, $R^8$, and $R^9$, at each occurrence, are independently selected from
H, halo, —$CF_3$, —$OCF_3$, —OH, —$OCH_3$, —CN, —$NO_2$, —$NR^{46}R^{47}$,
$C_{1-4}$ alkyl, $C_{2-6}$ alkenyl, $C_{2-6}$ alkynyl, $C_{1-4}$ haloalkyl, $C_{1-6}$ alkoxy, ($C_{1-4}$ haloalkyl)oxy, $C_{1-4}$ alkyl substituted with 0–2 $R^{11}$,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, $C(O)R^{12}$, $C(O)NR^{12}R^{13}$, $NR^{14}C(O)R^{12}$, $C(O)OR^{12}OC(O)R^{12}$, $CH(=NR^{14})NR^{12}R^{13}$, $NHC(=NR^{14})NR^{12}R^{13}$, $S(O)R^{12}$, $S(O)_2R^{12}$, $S(O)_2NR^{12}R^{13}$, $NR^{14}S(O)_2R^{12}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
H, halo, —$CF_3$, —$OCF_3$, —OH, —$OCH_3$, —CN, —$NO_2$, —$NR^{46}R^{47}$,
$C_{1-6}$ alkyl, $C_{2-6}$ alkenyl, $C_{2-6}$ alkynyl, $C_{1-4}$ haloalkyl, $C_{1-6}$ alkoxy, ($C_{1-4}$ haloalkyl)oxy,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the groups consisting of N, O, and S substituted with 0–3 $R^{31}$,
$OR^{12}$, $SR^{12}NR^{12}R^{13}$, C(O)H, $C(O)R^{12}$, $C(O)NR^{12}R^{13}$, $NR^{14}C(O)R^{12}$, $C(O)R^{12}$, $OC(O)R^{12}$, $CH(=NR^{14})NR^{12}R^{13}$, $NHC(=NR^{14})NR^{12}R^{13}$, $S(O)R^{12}$, $S(O)_2R^{12}$, $S(O)_2NR^{12}R^{13}$, and $NR^{14}S(O)_2R^{12}$;

$R^{12}$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —$N(R^{14})$—;

$R^{14}$, at each occurrence, is independently selected from H and $C_{1-4}$ alkyl;

$R^{33}$, at each occurrence, is independently selected from H, OH, halo, $CF_3$, methyl, and ethyl;

$R^{13}$, at each occurrence, is independently selected from H, OH, halo, CN, $NO_2$, $CF_3$, methyl, and ethyl;

$R^{41}$, at each occurrence, is independently selected from H, $CF_3$, halo, OH, $CO_2H$, $SO_{22}R^{45}$, $NR^{46}R^{47}$, $NO_2$, CN, =O,
$C_{2-8}$ alkenyl, $C_{2-8}$ alkynyl, $C_{1-4}$ alkoxy, $C_{1-4}$ haloalkyl,
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from H, $CF_3$, halo, OH, $CO_2H$, $SO_2R^{45}$, $SR^{45}$, $NR^{46}R^{47}$, $OR^{48}$, $NO_2$, CN, $CH(=NH)NH_2$, $NHC(=NH)NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H, and $C_{1-3}$ alkyl;

$R^{47}$, at each occurrence, is independently selected from H, $C_{1-4}$ alkyl, —C(=O)NH($C_{1-4}$ alkyl),
—$SO_2$($C_{1-4}$ alkyl),
—$SO_2$(phenyl), —C(=O)O($C_{1-4}$ alkyl), —C(=O)($C_{1-4}$ alkyl), and —C(=O)H;

$R^{48}$, at each occurrence, is independently selected from H, $C_{1-4}$ alkyl, —C(=O)NH($C_{1-4}$ alkyl),
—C(=O)O($C_{1-4}$ alkyl),
—C(=O)($C_{1-4}$ alkyl), and —C(=O)H;
k is 1 or 2;

m is 0, 1, 2; and n is 1 or 2.

14. A compound of claim 12 wherein:

X —O—;

$R^1$ is selected from
$C_{2-4}$ alkyl substituted with Z,
$C_{2-4}$ alkenyl substituted with Z,
$C_{2-4}$ alkynyl substituted with Z,
$C_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z;

$C_{2-4}$ alkyl substituted with 1–2 $R^2$, but $R^2$ is other than alkyl; and
$C_{2-4}$ alkenyl substituted with 0–2 $R^2$;

Z is selected from
—CH(OH)$R^2$, —C(ethylenedioxy)$R^2$,
—$OR^2$,
—$SR^2$,
—$NR^2R^3$,
—$C(O)R^2$,
—$C(O)NR^2R^3$,
—$NR^3C(O)R^2$, ——$C(O)OR^2$,
—$S(O)R^2$,
—$S(O)_2R^2$,
—$S(O)_2NR^2R^3$, and —$NR^3S(O)_2R^2$;

$R^2$, at each occurrence, is independently selected from phenyl substituted with 0–5 $R^{42}$;
$C_{3-10}$ carbocyclic group substituted with 0–3 $R^{41}$, and
5–10 membered heterocyclic ring system containing from 1–4 heteroatoms selected from the group consisting of N, O, and S substituted with 0–3 $R^{41}$;

$R^3$, at each occurrence, is independently selected from H, $C_{1-4}$ alkyl, $C_{2-4}$ alkenyl, $C_{2-4}$ alkynyl, and $C_{1-4}$ alkoxy;

alternatively, $R^2$ and $R^3$ join to form a 5- or 6-membered ring optionally substituted with —O— or —$N(R^4)$—;

$R^4$, at each occurrence, is independently selected from H, methyl, ethyl, propyl, and butyl, $R^5$ is H;

$R^{6a}$ is selected from H, —OH, —$CF_3$, methyl, ethyl, propyl, butyl, methoxy, and ethoxy;

$R^{6b}$ is H;

$R^7$, $R^8$, and $R^9$, at each occurrence, are independently selected from

H, halo, —$CF_3$, —$OCF_3$, —OH, —$OCH_3$, —CN, —$NO_2$,
$C_{1-4}$ alkyl, $C_{1-4}$ haloalkyl, $C_{1-4}$ alkoxy, ($C_{1-3}$ haloalkyl) oxy, and
$C_{1-4}$ alkyl substituted with 0–2 $R^{11}$;

$R^{11}$ is selected from
H, halo, —$CF_3$, —$OCF_3$, —OH, —$OCH_3$, —CN, —$NO_2$,
$C_{1-4}$ alkyl, $C_{1-4}$ haloalkyl, $C_{1-4}$ alkoxy, and ($C_{1-3}$ haloalkyl)oxy;

$R^{33}$, at each occurrence, is independently selected from H, OH, halo, $CF_3$, and methyl;

$R^{41}$, at each occurrence, is independently selected from H, $CF_3$, halo, OH, $CO_2H$, $SO_2R^{45}$, $NR^{46}R^{47}$, $NO_2$, CN, =O,
$C_{2-8}$ alkenyl, $C_{2-8}$ alkynyl, $C_{1-4}$ alkoxy, $C_{1-4}$ haloalkyl, $C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from H, $CF_3$, halo, OH, $CO_2H$, $SO_2R^{45}$, $SR^{45}$, $NR^{46}R^{47}$, $OR^{48}$, $NO_2$, CN, CH(=NH)$NH_2$, NHC(=NH)$NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{43}$ is methyl, ethyl, propyl, or butyl;

$R^{46}$, at each occurrence, is independently selected from H, methyl, ethyl, propyl, and butyl;

$R^{47}$, at each occurrence, is independently selected from H, methyl, ethyl, n-propyl, i-propyl, n-butyl, i-butyl, —C(=O)NH(methyl), —C(=O)NH(ethyl), —$SO_2$(methyl), —$SO_2$(ethyl), —$SO_2$(phenyl), —C(=O)O(methyl), —C(=O)O(ethyl), —C(=O)(methyl), —C(=O)(ethyl), and —C(=O)H;

$R^{48}$, at each occurrence, is independently selected from H, methyl, ethyl, n-propyl, i-propyl, —C(=O)NH(methyl), —C(=O)NH(ethyl), —C(=O)O(methyl), —C(=O)O(ethyl), —C(=O)(methyl), —C(=O)(ethyl), and —C(=O)H;

k is 1;

m is 0, 1, or 2; and n is 1 or 2.

15. A compound of claim 12 wherein:

X is —O—;

$R^1$ is selected from
ethyl substituted with Z,
propyl substituted with Z,
butyl substituted with Z,
propenyl substituted with Z,
butenyl substituted with Z,
ethyl substituted with $R^2$,
propyl substituted with $R^2$,
butyl substituted with $R^2$,
propenyl substituted with $R^2$, and
butenyl substituted with $R^2$; provided that with respect to ethyl, propyl and butyl, $R^2$ is other than alkyl;

Z is selected from
—CH(OH)$R^2$,
—$OR^2$,
—$SR^2$,
—$NR^2R^3$,
—C(O)$R^2$,
—C(O)$NR^2R^3$,
—$NR^3$C(O)$R^2$,
C(O)$OR^2$,
—S(O)$R^2$,
—$S(O)_2R^2$,
—$S(O)_2NR^2R^3$, and —$NR^3S(O)_2R^2$;

$R^2$, at each occurrence, is independently selected from
phenyl substituted with 0–3 $R^{42}$;
naphthyl substituted with 0–3 $R^{42}$;
cyclopropyl substituted with 0–3 $R^{41}$;
cyclobutyl substituted with 0–3 $R^{41}$;
cyclopentyl substituted with 0–3 $R^{41}$;
cyclohexyl substituted with 0–3 $R^{41}$;
pyridyl substituted with 0–3 $R^{41}$;
indolyl substituted with 0–3 $R^{41}$;
indolinyl substituted with 0–3 $R^{41}$;
benzimidazolyl substituted with 0–3 $R^{41}$;
benzotriazolyl substituted with 0–3 $R^{41}$;
benzothienyl substituted with 0–3 $R^{41}$;
benzofuranyl substituted with 0–3 $R^{41}$;
phthalimid-1-yl substituted with 0–3 $R^{41}$;
inden-2-yl substituted with 0–3 $R^{41}$;
2,3-dihydro-1H-inden-2-yl substituted 0–3 $R^{41}$;
indazolyl substituted with 0–3 $R^{41}$;
tetrahydroquinolinyl substituted with 0–3 $R^{41}$; and
tetrahydro-isoquinolinyl substituted with 0–3 $R^{41}$;

$R^3$, at each occurrence, is independently selected from H, methyl, and ethyl;

$R^3$ is H;

$R^{6a}$ is selected from H, —OH, methyl, and methoxy;

$R^{6b}$ is H;

$R^7$, $R^8$, and $R^9$, at each occurrence, are independently selected from H, F, Cl, methyl, ethyl, methoxy, —$CF_3$, and —$OCF_3$;

$R^{41}$, at each occurrence, is independently selected from H, F, Cl, Br, OH, $CF_3$, $NO_2$, CN, =O, methyl, ethyl, propyl, butyl, methoxy, and ethoxy;

$R^{42}$, at each occurrence, is independently selected from H, F, Cl, Br, OH, $CF_3$, $SO_2R^{45}$, $SR^{45}$, $NR^{46}R^{47}$, $OR^{48}$, $NO_2$, CN, =O, methyl, ethyl, propyl, butyl, methoxy, and ethoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from H, methyl, ethyl, n-propyl, i-propyl, n-butyl, i-butyl, —C(=O)NH(methyl), —C(=O)NH(ethyl), —$SO_2$(methyl), —$SO_2$(ethyl), —$SO_2$(phenyl), —C(=O)O(methyl), —C(=O)O(ethyl), —C(=O)(methyl), —C(=O)(ethyl), and —C(=O)H;

$R^{48}$, at each occurrence, is independently selected from H, methyl, ethyl, n-propyl, i-propyl, —C(=O)NH(methyl), —C(=O)NH(ethyl), —C(=O)O(methyl), —C(=O)O(ethyl), —C(=O)(methyl), —C(=O)(ethyl), and —C(=O)H;

k is 1;

m is 0, 1, or 2; and n is 1 or 2.

16. A compound of claim 12 wherein:

X is —S—;

$R^1$ is selected from $C_{2-4}$ alkyl substituted with Z, $C_{2-4}$ alkenyl substituted with Z, $C_{2-4}$ alkynyl substituted with Z, $C_{3-6}$ cycloalkyl substituted with Z, aryl substituted with Z, 5–6 membered heterocyclic ring system containing at least one heteroatom selected from the group consisting of N, O, and S, said heterocyclic ring system substituted with Z;

$C_{2-4}$ alkyl substituted with 1–2 $R^2$, where $R^2$ is other than alkyl; and $C_{2-4}$ alkenyl substituted with 0–2 $R^2$;

Z is selected from

—CH(OH)$R^2$,

—C(ethylenedioxy)$R^2$,

—$OR^2$,

—$SR^2$,

—$NR^2R^3$,

—C(O)$R^2$,

—S(O)$R^2$,

—S(O)$R^2$,

—$S(O)_2NR^2R^3$, and —$NR^3S(O)_2R^2$;

$R^2$, at each occurrence, is independently selected from phenyl substituted with 0–5 $R^{42}$;

$C_{3-10}$ carbocyclic group substituted with 0–3 $R^{41}$, and

5–10 membered heterocyclic ring system containing from 1–4 heteroatoms selected from the group consisting of N, O, and S substituted with 0–3 $R^{41}$;

$R^3$, at each occurrence, is independently selected from H, $C_{1-4}$ alkyl, $C_{2-4}$ alkenyl, $C_{2-4}$ alkynyl, and $C_{1-4}$ alkoxy;

alternatively, $R^2$ and $R^3$ join to form a 5- or 6-membered ring optionally substituted with —O— or $N(R^{4)}$—;

$R^4$, at each occurrence, is independently selected from H, methyl, ethyl, propyl, and butyl;

$R^5$ is H;

$R^{6a}$ is selected from H, —OH, —$CF_3$, methyl, ethyl, propyl, butyl, methoxy, and ethoxy;

$R^{6b}$ is H;

$R^7$, $R^8$, and $R^9$, at each occurrence, are independently selected from

H, halo, —$CF_3$, —$OCF_3$, —OH, —$OCH_3$, —CN, —$NO_2$, $C_{1-4}$ alkyl, $C_{3-4}$ haloalkyl, $C_{1-4}$ alkoxy, ($C_{1-3}$ haloalkyl)oxy, and $C_{1-4}$ alkyl substituted with 0–2 $R^{11}$;

$R^{11}$ is selected from

H, halo, —$CF_3$, —$OCF_3$, —OH, —$OCH_3$, —CN: —$NO_2$, $C_{1-4}$ alkyl, $C_{1-4}$ haloalkyl, $C_{1-4}$ alkoxy, and ($C_{1-3}$ haloalkyl)oxy;

$R^{33}$, at each occurrence, is independently selected from H, OH, halo, $CF_3$, and methyl;

$R^{42}$, at each occurrence, is independently selected from H, $CF_3$, halo, OH, $CO_2H$, $SO_2R^{45}$, $NR^{46}R^{47}$, $NO_2$, CN, =O, $C_{2-8}$ alkenyl, $C_{2-8}$ alkynyl, $C_{1-4}$ alkoxy, $C_{1-4}$ haloalkyl, $C_{1-4}$ alkyl substituted with 0–1 $R^{43}$, aryl substituted with 0–3 $R^{42}$, and 5–10 membered heterocyclic ring system containing from 1–4 heteroatoms selected from the group consisting of N, O, and S substituted with 0–3 $R^{44}$;

$R^{42}$, at each occurrence, is independently selected from H, $CF_3$, halo, OH, $CO_2H$, $SO_2R^{45}$, $SR^{45}$, $NR^{46}R^{47}$, $OR^{48}$, $NO_2$, CN, CH(=NH)$NH_2$, NHC(=NH)$NH_2$, $C_{2-6}$ alkenyl, $C_{2-6}$ alkynyl, $C_{1-4}$ alkoxy, $C_{1-4}$ haloalkyl, $C_{3-6}$ cycloalkyl, $C_{1-4}$ alkyl substituted with 0–1 $R^{43}$, aryl substituted with 0–3 $R^{44}$, and 5–10 membered heterocyclic ring system containing from 1–4 heteroatoms selected from the group consisting of N, O, and S substituted with 0–3 $R^{44}$;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl, $R^{47}$, at each occurrence, is independently selected from H, methyl, ethyl, n-propyl, i-propyl, n-butyl, i-butyl, —C(=O)NH(methyl), —C(=O)NH(ethyl), —$SO_2$(methyl), —$SO_2$(ethyl), —$SO_2$(phenyl), —C(=O)O(methyl), —C(=O)O(ethyl), —C(=O)(methyl), —C(=O)(ethyl), and —C(=O)H;

$R^{49}$, at each occurrence, is independently selected from H, methyl, ethyl, n-propyl, —C(=O)NH(methyl), —C(=O)NH(ethyl), —C(=O)O(methyl),—C(=O)O(ethyl), —C(=O)O(methyl), —C(=O)(ethyl), and —C(=)H;

k is 1;

m is 0, 1 or 2; and n is 1 or 2.

17. A compound of claim 12 wherein:

X is —O—;

$R^1$ is selected from ethyl substituted with Z;

propyl substituted with Z;

butyl substituted with Z;

propenyl substituted with Z;

butenyl substituted with Z;

ethyl substituted with $R^2$;

propyl substituted with $R^2$;

butyl substituted with $R^2$; provided that with respect to ethyl, propyl and butyl, $R^2$ is other than alkyl;

propenyl substituted with $R^2$; and butenyl substituted with $R^2$;

Z is selected from

—CH(OH)$R^2$,

—$OR^2$,

—$SR^2$,

—$NR^2R^3$,

—C(O)$R^2$,

—(O)$NR^2R^3$,

—$NR^3C(O)R^2$,

—C(O)$OR^2$,

—S(O)$R^2$,

—$S(O)_2R^2$,

—$S(O)_2NR^2R^3$, and —$NR^3S(O)_2R^2$;

$R^2$, at each occurrence, is independently selected from phenyl substituted with 0–3 $R^{42}$, naphthyl substituted with 0–3 $R^{42}$; cyclopropyl substituted with 0–3 $R^{41}$; cyclobutyl substituted with 0–3 $R^{41}$; cyclopentyl substituted with 0–3 $R^{41}$; cyclohexyl substituted with 0–3 $R^{41}$; pyridyl substituted with 0–3 $R^{41}$; indolyl substituted with 0–3 $R^{41}$; indolinyl substituted with 0–3 $R^{41}$; benzimidazolyl substituted with 0–3 $R^{41}$; benzotriazolyl substituted with 0–3 $R^{41}$; benzothienyl substituted with 0–3 $R^{41}$; benzofuranyl substituted with 0–3 $R^{41}$; phthalimid-1-yl substituted with 0–3 $R^{41}$; inden-2-yl substituted with 0–3 $R^{41}$; 2,3-dihydro-1H-inden-2-yl substituted 0–3 $R^{41}$; indazolyl substituted with 0–3 $R^{41}$; tetrahydroquinolinyl substituted with 0–3 $R^{41}$; and tetrahydro-isoquinolinyl substituted with 0–3 $R^{41}$;

$R^3$, at each occurrence, is independently selected from H, methyl, and ethyl;

$R^5$ is H;

$R^{6a}$ is selected from H, —OH, methyl, and methoxy;

$R^{6b}$ is H;

$R^7$, $R^8$, and $R^9$, at each occurrence, are independently selected from H, F, Cl, methyl, ethyl, methoxy, —$CF_3$, and —$OCF_3$, $R^{41}$, at each occurrence, is independently selected from H, F, Cl, Br, OH, $CF_3$, $NO_2$, CN, =O, methyl, ethyl, propyl, butyl, methoxy, and ethoxy;

$R^{42}$, at each occurrence, is independently selected from H, F, Cl, Br, OH, $CF_3$, $SO_2R^{45}$, $SR^{45}$, $NR^{46}R^{47}$, $OR^{48}$, $NO_2$, CN, =O, methyl, ethyl, propyl, butyl, methoxy, and ethoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from H, methyl, ethyl, n-propyl, i-propyl, n-butyl, i-butyl, —(C=O)NH(methyl), —C(=O)NH(ethyl), —$SO_2$(methyl), —$SO_2$(ethyl), —$SO_2$(phenyl), —C(=O)O(methyl), —C(=O)O(ethyl), —C(=O)(methyl), —C(=O)(ethyl), and —C(=O)H;

$R^{48}$, at each occurrence, is independently selected from H, methyl, ethyl, n-propyl, i-propyl, —C(=O)NH(methyl), —C(=O)H(ethyl), —C(=O)O(methyl), —C(=O)O(ethyl), —C(=O)(methyl), —C(=O)(ethyl), and —C(=O)H;

k is 1;

m is 0, 1, or 2; and n is 1 or 2.

18. A compound of claim 12 of Formula (I-a)

(I-a)

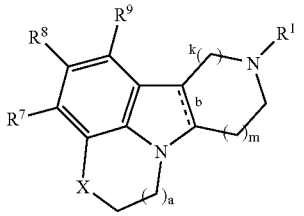

wherein:

b is a single bond;

X is —S— or —O—;

$R^1$ is selected from

—$C(CH_2)_3C(=O)$(4-fluoro-phenyl),
—$(CH_2)_3C(=O)$(4-bromo-phenyl),
—$(CH_2)_3C(=O)$(4-methyl-phenyl),
—$(CH_2)_3C(=O)$(4-methoxy-phenyl),
—$(CH_2)_3C(=O)$(4-(3,4-dichloro-phenyl)phenyl),
—$(CH_2)_3C(=O)$(3-methyl-4-fluoro-phenyl),
—$(CH_2)_3C(=O)$(2,3-dimethoxy-phenyl),
—$(CH_2)_3C(=O)$(phenyl),
—$(CH_2)_3C(=O)$(4-chloro-phenyl),
—$(CH_2)_3C(=O)$(3-methyl-phenyl),
—$(CH_2)_3C(=O)$(4-t-butyl-phenyl),
—$(CH_2)_3C(=O)$(3,4-difluoro-phenyl),
—$(CH_2)_3C(=O)$(2-methoxy-5-fluoro-phenyl),
—$(CH_2)_3C(=O)$(4-fluoro-1-naphthyl),
—$(CH_2)_3C(=O)$(benzyl),
—$(CH_2)_3C(=O)$(4-pyridyl),
—$(CH_2)_3C(=O)$(3-pyridyl),
—$(CH_2)_3CH(OH)$(4-fluoro-phenyl),
—$(CH_2)_3CH(OH)$(4-pyridyl),
—$(CH_2)_3CH(OH)$(2,3-dimethoxy-phenyl),
—$(CH_2)_3S$(3-fluoro-phenyl),
—$(CH_2)_3S$(4-fluoro-phenyl),
—$(CH_2)_3S(=O)$(4-fluoro-phenyl),
—$(CH_2)_3SO_2$(3-fluoro-phenyl),
—$(CH_2)_3SO_2$(4-fluoro-phenyl),
—$(CH_2)_3O$(4-fluoro-phenyl),
—$(CH_2)_3O$(phenyl),
—$(CH_2)_3O$(3-pyridyl),
—$(CH_2)_3O$(4-pyridyl),
—$(CH_2)_3O$(2-$NH_2$-phenyl),
—$(CH_2)_2O$(2-$NH_2$-5-F-phenyl),
—$(CH_2)_3O$(2-$NH_2$-4-F-phenyl),
—$(CH_2)_3O$(2-$NH_2$-3-F-phenyl),
—$(CH_2)_3O$(2-$NH_2$-4-Cl-phenyl),
—$(CH_2)_3O$(2-$NH_2$-4-OH-phenyl),
—$(CH_2)_3O$(2-$NH_2$-4-Br-phenyl),
—$(CH_2)_3O$(2-NHC(=O)Me-4-phenyl),
—$(CH_2)_3O$(2-NHC(=O)Me-phenyl),
—$(CH_2)_3NH$(4-fluoro-phenyl),
—$(CH_2)_3N$(methyl)(4-fluoro-phenyl),
—$(CH_2)_3CO_2$(ethyl),
—$(CH_2)_3C(=O)N$(methyl)(methoxy),
—$(CH_2)_3C(=O)NH$(4-fluoro-phenyl),
—$(CH_2)_3NHC(=O)$(phenyl),
—$(CH_2)_2$(NMeC(=O)(phenyl),
—$(CH_2)_2NHC(=O)$(2-fluoro-phenyl),
—$(CH_2)_2NMeC(=O)$(2-fluoro-phenyl),
—$(CH_2)_2NHC(=O)$(4-fluoro-phenyl),
—$(CH_2)_2NMeC(=O)$(4-fluoro-phenyl),
—$(CH_2)_2NHC(=O)$(2,4-difluoro-phenyl),
—$(CH_2)_2NMeC(=O)$(2,4-difluoro-phenyl),
—$(CH_2)_3$(3-indolyl),
—$(CH_2)_3$(1-methyl-3-indolyl),
—$(CH_2)_3$(1-indolyl),
—$(CH_2)_3$(1-indolinyl),
—$(CH_2)_3$(1-benzimidazolyl),
—$(CH_2)_3$(1H-1,2,3-benzotriazol-1-yl),
—$(CH_2)_3$(1H-1,2,3-benzotriazol-2-yl),
—$(CH_2)_2$(1H-1,2,3-benzotriazol-1-yl),
—$(CH_2)_2$(1H-1,2,3-benzotriazol-2-yl),
—$(CH_2)_3$(3,4 dihydro-1(2H)-quinolinyl),
—$(CH_2)_2C(=O)$(4-fluoro-phenyl),
—$(CH_2)_2C(=O)NH$(4-fluoro-phenyl),
—$CH_2CH_2$(3-indolyl),
—$CH_2CH_2$(1-phthalimidyl),
—$(CH_2)_4C(=O)N$(methyl)(methoxy),
—$(CH_2)_4CO_2$(ethyl),
—$(CH_2)_4C(=O)$(phenyl),
—$(CH_2)_3CH(phenyl)_2$,
—$CH_2CH_2CH=C(phenyl)_2$, —$CH_2CH_2CH{=}CMe$(4-F-phenyl),
—$(CH_2)_3CH$(4-fluoro-phenyl)$_2$,
—$CH_2CH_2CH{=}C$(4-fluoro-phenyl)$_2$,
—$(CH_2)_2$(2,3-dihydro-1H-inden-2-yl), —$(CH_2)_3C(=O)$(2-$NH_2$-phenyl),
—$(CH_2)_3C(=O)$(2-$NH_2$-5-F-phenyl),
—$(CH_2)_3C(=O)$(2-$NH_4$-4-F-phenyl),
—$(CH_2)_3C(=O)$(2-$NH_2$-3-F-phenyl),
—$(CH_2)_3C(=O((2\text{-}NH_2\text{-}4\text{-}Cl\text{-}phenyl)$,
—$(CH_2)_3C(=O)$(2-$NH_2$-4-OH-phenyl),
—$(CH_2)_3C(=O)$(2-$NH_2$-4-Br-phenyl),
—$(CH_2)_3$(1H-indazol-3-yl),
—$(CH_2)_3$(5-F-1H-indazol-3-yl),
—$(CH_2)_3$(7-F-1H-indazol-3-yl),
—$(CH_2)_3$(6-Cl-1H-indazol-3-yl),
—$(CH_2)_3$(6-Br-1H-indazol-3-yl),
—$(CH_2)_3C(=O)$(2-NHMe-phenyl),
—$(CH_2)_3$(1-benzothien-3-yl),
—$(CH_2)_3$(6-F-1H-indazol-1-yl),
—$(CH_2)_3$(5-F-1H-indazol-1-yl),
—$(CH_2)_3$(6-F-2,3-dihydro-1H-indol-1-yl),
—$(CH_2)_3$(5-F-2,3-dihydro-1H-indol-1-yl),
—$(CH_2)_3$(6-F-1H-indol-3-yl),
—$(CH_2)_3$(5-F-1H-indol-3-yl),
—$(CH_2)_3$(5-F-1H-indol-3-yl),
—$(CH_2)_3$(9H-purin-9-yl),
—$(CH_2)_3$(7H-purin-7-yl),
—$(CH_2)_3$(6-F-1H-indazol-3-yl),
—$(CH_2)_3C(=O)$(2-$NHSO_2Me$-4-F-phenyl),
—$(CH_2)_3C(=O)$(2-NHC(=O)Me-4-phenyl),
—$(CH_2)_3C(=O)$(2-NHC(=O)Me-phenyl),
—$(CH_2)_3C(=O)$(2-$NHCO_2Et$-4-F-phenyl),
—$(CH_2)_3C(=O)$ (2-NHC(=O)NHEt-4-F-phenyl),
—$(CH_2)_3C(=O)$(2-NHCHO-4-F-phenyl),
—$(CH_2)_3C(=O)$(2-OH-4-F-phenyl),
—$(CH_2)_3C(=O)$(2-MeS-4-F-phenyl),
—$(CH_2)_3C(=O)$(2-$NHSO_2Me$-4-F-phenyl),
—$(CH_2)_2C(Me)CO_2Me$,
—$(CH_2)_2C(Me)CH(OH)$(4-F-phenyl)$_2$,
—$(CH_2)_2C(Me)C(OH)$(4-Cl-phenyl)$_2$,
—$(CH_2)_2C(Me)C(=O)$(4-F-phenyl),
—$(CH_2)_2C(Me)C(=O)$(2-MeO-4-F-phenyl),
—$(CH_2)_2C(Me)C(=O)$(3-Me-4-F-phenyl),
—$(CH_2)_2C(Me)C(=O)$(2-Me-phenyl),
—$(CH_2)_2C(Me)C(=O)$phenyl,

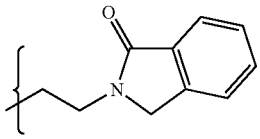
,
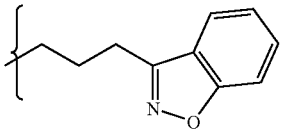
,
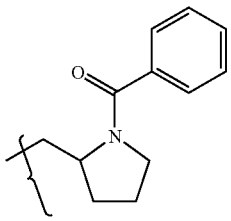
,
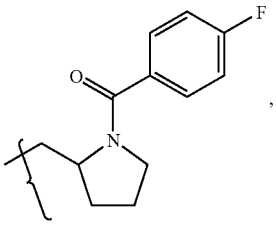
,
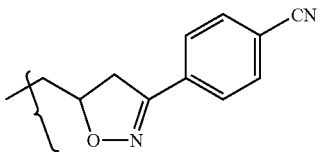
, and

-continued

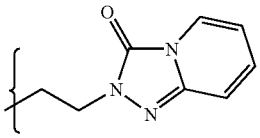
;

$R^7$, $R^8$, and $R^9$, at each occurrence, are independently selected from
hydrogen, fluoro, chloro, bromo, cyano, methyl, ethyl, propyl, isopropyl, butyl, t-butyl, nitro, trifluromethyl, methoxy, ethoxy, isopropoxy, trifluoromethoxy, phenyl, benzyl,
HC(=O)—, methylC(=O)—, ethylC(=O)—, propylC(=O)—, isopropylC(=O)—, n-butylC(=O)—, isobutylC(=O)—, secbutylC(=O)—, tertbutylC(=O)—, phenylC(=O)—,
methylC(=O)NH—, ethylC(=O)NH—, propylC(=O)NH—, isopropylC(=O)NH—, n-butylC(=O)NH—, isobutylC(=O)NH—, secbutylC(=O)NH—, tertbutylC(=O)NH—, phenylC(=O)NH—,
methylamino-, ethylamino-, propylamino-, isopropylamino-, n-butylamino-, isobutylamino-, secbutylamino-, tertbutylamino-, phenylamino-, p2 provided that two of substituents $R^7$, $R^8$, and $R^9$, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy;

k is 1 or 2;

m is 1 or 2; and n is 1 or 2.

19. A compound of claim 18 of Formula (II-a)

(II-a)

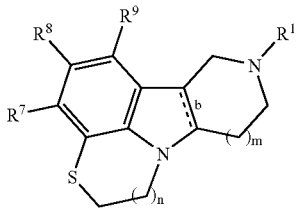

wherein:

b is a single bond, wherein the bridge hydrogens are in a cis position;

$R^1$ is selected from
—$(CH_2)_3C(=O)$(4-fluoro-phenyl),
—$(CH_2)_3C(=O)$(4-bromo-phenyl),
—$(CH_2)_3C(=O)$(4-methyl-phenyl),
—$(CH_2)_3C(=O)$(4-methoxy-phenyl),
—$(CH_2)_3C(=O)$(4-(4-dichloro-phenyl)phenyl),
—$(CH_2)_3C(=O)$(3-methyl-4-fluoro-phenyl),
—$(CH_2)_3C(=O)$(2,3-dimethoxy-phenyl),
—$(CH_2)_3C(=O)$(phenyl),
—$(CH_2)_3C(=O)$(4-chloro-phenyl),
—$(CH_2)_3C(=O)$(3-methyl-phenyl),
—$(CH_2)_3C(=O)$(4-t-butyl-phenyl),
—$(CH_2)_3C(=O)$(3,4-difluoro-phenyl),
—$(CH_2)_3C(=O)$(2-methoxy-5-fluoro-phenyl),
—$(CH_2)_3C(=O)$(4-fluoro-1-naphthyl),
—$(CH_2)_3C(=O)$(benzyl),
—$(CH_2)_3C(=O)$(4-pyridyl),
—$(CH_2)_3C(=O)$(3-pyridyl),
—$(CH_2)_3CH(OH)$(4-fluoro-phenyl),
—$(CH_2)_3CH(OH)$(4-pyridyl),
—$(CH_2)_3CH(OH)$(2,3-dimethoxy-phenyl), —$(CH_2)_3$S(3-fluoro-phenyl),
—$(CH_2)_3$S(4-fluoro-phenyl),
—$(CH_2)_3$S(═O)(4-fluoro-phenyl),
—$(CH_2)_3SO_2$(3-fluoro-phenyl),
—$(CH_2)_3SO_2$(4-fluoro-phenyl),
—$(CH_2)_3$O(4-fluoro-phenyl),
—$(CH_2)_3$O(phenyl),
—$(CH_2)_3$NH(4-pyridyl),
—$(CH_2)_3$N(methyl)(4-fluoro-phenyl),
—$(CH_2)_3CO_2$(ethyl),
—$(CH_2)_3$C(═O)N(methyl)(methoxy),
—$(CH_2)_3$C(═O)NH(4-fluoro-phenyl),
—$(CH_2)_2$NHC(═O)(phenyl),
—$(CH_2)_2$NMeC(═O)(phenyl),
—$(CH_2)_2$NHC(═O)(2-fluoro-phenyl),
—$(CH_2)_2$NMeC(═O)(2-fluoro-phenyl),
—$(CH_2)_2$NHC(═O)4-fluoro-phenyl),
—$(CH_2)_2$NMeC(═O)(4-fluoro-phenyl),
—$(CH_2)_2$NHC(═O)(2,4-difluoro-phenyl),
—$(CH_2)_2$NMeC(═O)(2,4-difluoro-phenyl),
—$(CH_2)_3$(3-indolyl),
—$(CH_2)_3$(1-methyl-3-indolyl),
—$(CH_2)_3$(1-indolyl),
—$(CH_2)_3$(1-indolinyl),
—$(CH_2)_3$(1-benzimidazolyl),
—$(CH_2)_3$(1H-1,2,3-benzotriazol-1-yl),
—$(CH_2)_3$(1H-1,2,3-benzotriazol-2-yl),
—$(CH_2)_2$(1H-1,2,3-benzotriazol-1-yl),
—$(CH_2)_2$(1H-1,2,3-benzotriazol-2-yl),
—$(CH_2)_3$(3,4 dihydro-1(2H)-quinolinyl),
—$(CH_2)_2$C(═)(4-fluoro-phenyl),
—$(CH_2)_2$C(═O)NH(4-fluoro-phenyl),
—$CH_2CH_2$(3-indolyl),
—$CH_2CH_2$(1-phthalimidyl),
—$(CH_2)_4$C(═O)N(methyl)(methoxy),
—$(CH_2)_4CO_2$(ethyl),
—$(CH_2)_4$C(═O)(phenyl),
—$(CH_2)_3$CH(phenyl)$_2$,
—$CH_2CH_2$CH═C(phenyl)$_2$,
—$CH_2CH_2$CH═CMe(4-F-phenyl),
—$(CH_2)_3$CH(4-fluoro-phenyl)$_2$,
—$CH_2CH_2$CH═C(4-fluoro-phenyl)$_2$,
—$(CH_2)_2$(2,3-dihydro-1H-inden-2-yl),
—$(CH_2)_3$C(═O)(2-$NH_2$-phenyl),
—$(CH_2)_3$C(═O)(2-$NH_2$-5-F-phenyl),
—$(CH_2)_3$C(═O)(2-$NH_2$-4-F-phenyl),
—$(CH_2)_3$C(═O)(2-$NH_2$-3-F-phenyl),
—$(CH_2)_3$C(═O)(2-$NH_2$-4-Cl-phenyl),
—$(CH_2)_3$C(═O)(2-$NH_2$-4-OH-phenyl),
—$(CH_2)_3$C(═O)(2-$NH_2$-4-Br-phenyl),
—$(CH_2)_3$(1H-indazol-3-yl),
—$(CH_2)_3$(5-F-1H-indazol-3-yl),
—$(CH_2)_3$(7-F-1H-indazol-3-yl),
—$(CH_2)_3$(6-Cl-1H-indazol-3-yl),
—$(CH_2)_3$(6-Br-1H-indazol-3-yl),
—$(CH_2)_3$C(═O)(2-NHMe-phenyl),
—$(CH_2)_3$(1-benzothien-3-yl),
—$(CH_2)_3$(6-F-1H-indol-1-yl),
—$(CH_2)_3$(5-F-1H-indol-1-yl),
—$(CH_2)_3$(6-F-2,3-dihydro-1H-indol-1-yl),
—$(CH_2)_3$(5-F-2,3-dihydro-1H-indol-1-yl),
—$(CH_2)_3$(6-F-1H-indol-3-yl),
—$(CH_2)_3$(5-F-1H-indol-3-yl),
—$(CH_2)_3$(5-F-1H-indol-3-yl),
—$(CH_2)_3$(9H-purin-9-yl),
—$(CH_2)_3$(7H-purin-7-yl),
—$(CH_2)_3$(6-F-1H-indazol-3-yl),
—$(CH_2)_3$C(═O)(2-$NHSO_2$Me-4-F-phenyl),
—$(CH_2)_3$C(═O)(2-NHC(═O)Me-4-F-phenyl),
—$(CH_2)_3$C(═O)(2-NHC(═O)Me-4-F-phenyl),
—$(CH_2)_3$C(═O)(2-$NHCO_2$Et-4-F-phenyl),
—$(CH_2)_3$C(═O)(2-NHC(═O)NHEt-4-F-phenyl),
—$(CH_2)_3$C(═O)(2-NHCHO-4-F-phenyl),
—$(CH_2)_3$C(═O)(2-OH-4-F-phenyl),
—$(CH_2)_3$C(═O)(2-MeS-4-phenyl),
—$(CH_2)_3$C(═O)(2-$NHSO_2$Me-4-F-phenyl),
—$(CH_2)_2$C(Me)$CO_2$Me,
—$(CH_2)_2$C(Me)CH(OH)(4-F-phenyl)$_2$,
—$(CH_2)_2$C(ME)CH(OH)(4-Cl-phenyl)$_2$,
—$(CH_2)_2$C(Me)C(═O)(4-F-phenyl),
—$(CH_2)_2$C(Me)C(═O)(2-MeO-4-F-phenyl),
—$(CH_2)_2$C(Me)C(═O)(3-Me-4-F-phenyl),
—$(CH_2)_2$C(Me)C(═O)(2-Me-phenyl),
—$(CH_2)_2$C(Me)C(═O)phenyl,

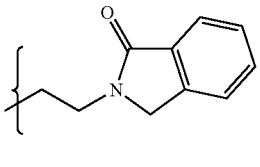
,
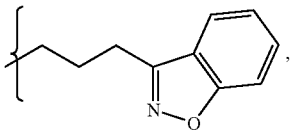
,
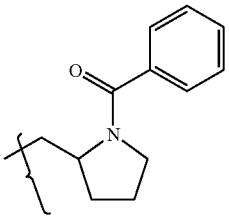
,
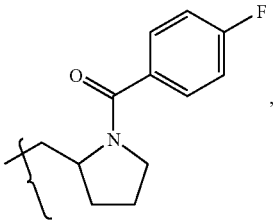
,
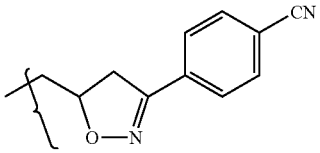
, and
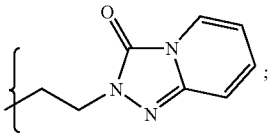
;

$R^7$, $R^8$, and $R^9$, at each occurrence, are independently selected from hydrogen, fluoro, chloro, bromo, cyano, methyl, ethyl, propyl, isopropyl, butyl, t-butyl, nitro, trifluoromethyl, methoxy, ethoxy, isopropyoxy, trifluoromethoxy, methylC(═O)—, ethylC(═O)—, propylC(═O)—, isopropylC(═O)—, methylC(═O)NH—, ethylC(═O)NH—, propylC(═O)NH—, isopropylC(═O)NH, methylamino-, ethylamino-, propylamino-, and isopropylamino-, provided that two of substituents $R^7$, $R^8$, and $R^9$, are independently selected from hydrogen, fluoro, chloro, methyl, trifluoromethyl, methoxy, and trifluoromethoxy;

m is 1 or 2; and n is 1 or 2.

20. A compound of claim 18 of Formula (III-a)

(III-a)

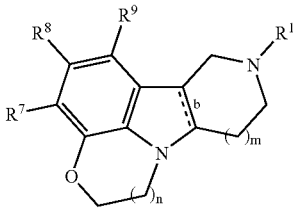

wherein:

b is a single bond, wherein the bridge hydrogens are in a cis position;

$R^1$ is selected from

—$(CH_2)_3C(=O)$(4-fluoro-phenyl),
—$(CH_2)_3C(=O)$(4-bromo-phenyl),
—$(CH_2)_3C(=O)$(4-methyl-phenyl),
—$(CH_2)_3C(=O)$(4-methoxy-phenyl),
—$(CH_2)_3C(=O)$(4-(3,4-dichloro-phenyl)phenyl),
—$(CH_2)_3C(=O)$(3-methyl-4-fluoro-phenyl),
—$(CH_2)_3C(=O)$(2,3-dimethoxy-phenyl),
—$(CH_2)_3C(=O)$(phenyl),
—$(CH_2)_3C(=O)$(4-chloro-phenyl),
—$(CH_2)_3C(=O)$(3-methyl-phenyl),
—$(CH_2)_3C(=O)$(4-t-butyl-phenyl),
—$(CH_2)_3C(=O)$(3,4-difluoro-phenyl),
—$(CH_2)_3C(=O)$(2-methoxy-5-fluoro-phenyl),
—$(CH_2)_3C(=O)$(4-fluoro-1-naphthyl),
—$(CH_2)_3C(=O)$(benzyl),
—$(CH_2)_3C(=O)$(pyridyl),
—$(CH_2)_3C(=O)$(3-pyridyl),
—$(CH_2)_3CH(OH)$(4-fluoro-phenyl),
—$(CH_2)_3CH(OH)$(4-pyridyl),
—$(CH_2)_3CH(OH)$(2,3-dimethoxy-phenyl),
—$(CH_2)_3S$(3-fluoro-phenyl),
—$(CH_2)_3S$(4-fluoro-phenyl),
—$(CH_2)_3S(=O)$(4-fluoro-phenyl),
—$(CH_2)_3SO_2$(3-fluoro-phenyl),
—$(CH_2)_3SO_2$(4-fluoro-phenyl),
—$(CH_2)_3O$(4-fluoro-phenyl),
—$(CH_2)_3O$(phenyl),
—$(CH_2)_3NH$(4-fluoro-phenyl),
—$(CH_2)_3N$(methyl)(4-fluoro-phenyl),
—$(CH_2)_3CO_2$(ethyl),
—$(CH_2)_3C(=O)N$(methyl)(methoxy),
—$(CH_2)_3C(=O)NH$(4-fluoro-phenyl),
—$(CH_2)_2NHC(=O)$(phenyl),
—$(CH_2)_2NMeC(=O)$(phenyl),
—$(CH_2)_2NHC(=O)$(2-fluorophenyl),
—$(CH_2)_2NMeC(=O)$(2-fluoro-phenyl),
—$(CH_2)_2NHC(=O)$(4-fluoro-phenyl),
—$(CH_2)_2NMeC(=O)$(4-fluoro-phenyl),
—$(CH_2)_2NHC(=O)$(2,4-difluoro-phenyl),
—$(CH_2)_2NMeC(=O)$(2,4-difluoro-phenyl),
—$(CH_2)_3$(3-incolyl),
—$(CH_2)_3$(1-methyl-3-indolyl),
—$(CH_2)_3$(1-indolyl),
—$(CH_2)_3$(1-indolinyl),
—$(CH_2)_3$(1-benzimidazolyl),
—$(CH_2)_3$(1H-1,2,3-benzotriazol-1-yl),
—$(CH_2)_3$(1H-1,2,3-benzotriazol-2-yl),
—$(CH_2)_2$(1H-1,2,3-benzotriazol-1-yl),
—$(CH_2)_2$(1H-1,2,3-benzotriazol-2-yl),
—$(CH_2)_3$(3,4-dihydro-1(2H)-quinolinyl),
–$(CH_2)_2C(=O)$(4-fluoro-phenyl),
—$(CH_2)_2C(=O)NH$(4-fluoro-phenyl),
—$CH_2CH_2$(3-indolyl),
—$CH_2CH_2$(1-phthalimidyl),
—$(CH_2)_4C(=O)N$(methyl)(methoxy),
—$(CH_2)_4CO_2$(ethyl),
—$(CH_2)_4C(=O)$(phenyl),
—$(CH_2)_3CH(phenyl)_2$,
—$CH_2CH_2CH{=}C(phenyl)_2$,
—$CH_2CH_2CH{=}CMe$(4-F-phenyl),
—$(CH_2)_3CH$(4-fluoro-phenyl)$_2$,
—$CH_2CH_2CH{=}C$(4-fluoro-phenyl)$_2$,
—$(CH_2)_2$(2,3-dihydro-1H-inden-2-yl),
—$(CH_2)_3C(=O)$(2-$NH_2$-phenyl),
—$(CH_2)_3C(=O)$(2-$NH_2$-5-F-phenyl),
—$(CH_2)_3C(=O)$(2-$NH_2$-4-F-phenyl),
—$(CH_2)_3C(=O)$(2-$NH_2$-3-F-phenyl),
—$(CH_2)_3C(=O)$(2-$NH_2$-4-Cl-phenyl),
—$(CH_2)_3C(=O)$(2-$NH_2$-4-OH-phenyl),
—$(CH_2)_3C(=O)$(2-$NH_2$-4-Br-phenyl),
—$(CH_2)_3$(1H-indazol-3-yl),
—$(CH_2)_3$(5-F-1H-indazol-3-yl),
—$(CH_2)_3$(7-F-1H-indazol-3-yl),
—$(CH_2)_3$(6-Cl-1H-indazol-3-yl),
—$(CH_2)_3$(6-Br-1H-indazol-3-yl),
—$(CH_2)_3C(=O)$(2-NHMe-phenyl),
—$(CH_2)_3$(1-benzothien-3-yl),
—$(CH_2)_3$(6-F-1H-indol-1-yl),
—$(CH_2)_3$(5-F-1H-indol-1-yl),
—$(CH_2)_3$(6-F-2,3-dihydro-1H-indol-1-yl),
—$(CH_2)_3$(5-F-2,3-dihydro-1H-indol-1-yl),
—$(CH_2)_3$(6-F-1H-indol-3-yl),
—$(CH_2)_3$(5-F-1H-indol-3-yl),
—$(CH_2)_3$(5-F-1H-indol-3-yl),
—$(CH_2)_3$(9H-purin-9-yl),
—$(CH_2)_3$(7H-purin-7-yl),
—$(CH_2)_3$(6-F-1H-indazol-3-yl),
—$(CH_2)_3C(=O)$(2-$NHSO_2$Me-4-F-phenyl),
—$(CH_2)_3C(=O)$(2-NHC(=O)Me-4-F-phenyl),
—$(CH_2)_3C(=O)$(2-NHC(=O)Me-4-F-phenyl),
—$(CH_2)_3C(=O)$(2-$NHCO_2$-Et-4-F-phenyl),
—$(CH_2)_3C(=O)$(2-NHC(=O)NHEt-4-F-phenyl),
—$(CH_2)_3C(=O)$(2-NHCHO-4-F-phenyl),
—$(CH_2)_3C(=O)$(2-OH-4-F-phenyl),
—$(CH_2)_3C(=O)$(2-MeS-4-F-phenyl),
—$(CH_2)_3C(=O)$(2-$NHSO_2$Me-4-F-phenyl),
—$(CH_2)_2C(Me)CO_2Me$,
—$(CH_2)_2C(Me)CH(OH)$(4-F-phenyl)$_2$,
—$(CH_2)_2C(Me)CH(OH)$(4-Cl-phenyl)$_2$,
—$(CH_2)_2C(Me)C(=O)$(4-F-phenyl),
—$(CH_2)_2C(Me)C(=O)$(2-MeO-4-F-phenyl),
—$(CH_2)_2C(Me)C(=O)$(3-Me-4-F-phenyl),
—$(CH_2)_2C(Me)C(=O)$(2-Me-phenyl),
—$(CH_2)_2C(Me)C(=O)$phenyl,

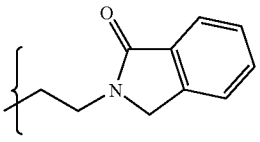
,
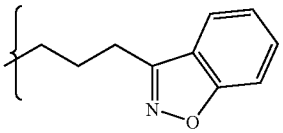
,
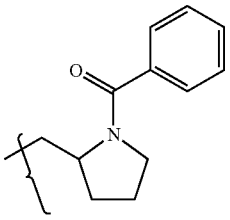
,
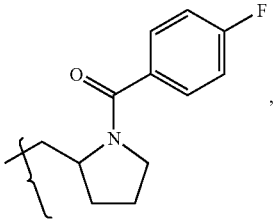
,
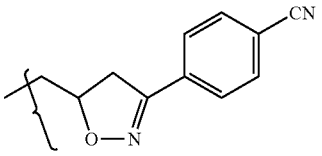
, and
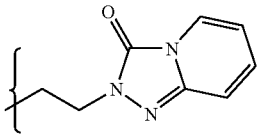
; and $R^7$, $R^8$, $R^9$, at each occurrence, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, methylC(=O)—, ethylC(=O)—, propylC(=O)—, isopropylC(=O)—, methylC(=O)NH—, ethylC(=O)NH—, propylC(=O)NH—, isopropyl-C(═O)NH, methylamino-, ethylamino-, propylamino-, and isopropylamino-, provided that two of substituents $R^7$, $R^8$, and $R^9$, are independently selected from hydrogen, fluoro, chloro, methyl, trifluoromethyl, methoxy, and trifluoromethoxy;

m is 1 or 2; and n is 1 or 2.

21. A pharmaceutical composition comprising a pharmaceutically acceptable carrier and a therapeutically effective amount of a compound of claims 1–20 or a pharmaceutically acceptable salt thereof.

22. A method for treating a human suffering from a disorder associated with 5HT2C receptor modulation selected from obesity, anorexia, bulemia, depression, anxiety, psychosis, schizophrenia, migraine, addictive behavior, obsessive-compulsive disorder, and sexual disorders; comprising administering to a patient in need thereof a therapeutically effective amount of a compound of claims 1–11 or a pharmaceutically acceptable salt thereof.

23. A method for treating a human suffering from a disorder associated with 5HT2A receptor modulation selected from depression, psychosis, schizophrenia, migraine, attention deficit disorder, attention deficit hyperactivity disorder, obsessive-compulsive disorder, and sleep disorders; comprising administering to a patient in need thereof a therapeutically effective amount of a compound of claims 12–20, or a pharmaceutically acceptable salt thereof.

24. A method for treating obesity comprising administering to a patient in need thereof a therapeutically effective amount of a compound of claims 1–11, or a pharmaceutically acceptable salt thereof.

25. A method for treating schizophrenia comprising administering to a patient in need thereof a therapeutically effective amount of a compound of claims 12–20 or a pharmaceutically acceptable salt thereof.

26. A method for treating depression comprising administering to a patient in need thereof a therapeutically effective amount of a compound of claims 12–20 or a pharmaceutically acceptable salt thereof.

27. A compound of claim 12 selected from the compounds disclosed in Table 1:

TABLE 1

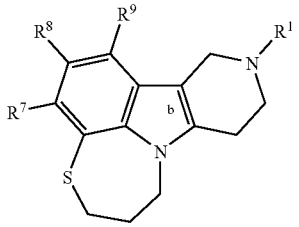

| Ex # | $R^7$ | $R^8$ | $R^9$ | b | $R^1$ |
|---|---|---|---|---|---|
| 25 | H | H | H | sgl | —C(═O)(3,4-diMeO-phenyl) |
| 26 | H | H | H | sgl | —C(═O)(2,5-diMeO-phenyl) |
| 27 | H | H | H | sgl | —C(═O)(3,5-diMeO-phenyl) |
| 28 | H | H | H | sgl | 2,6-diMeO-benzyl |
| 29 | H | H | H | sgl | 2,4-diMeO-benzyl |
| 30 | H | H | H | sgl | 2,4,6-triMeO-benzyl |
| 31 | H | H | H | sgl | 2,3-diMeO-benzyl |
| 32 | H | H | H | sgl | 2,4,5-triMeO-benzyl |
| 33 | H | H | H | sgl | cyclohexylmethyl |
| 34 | H | H | H | sgl | 2,3,4-triMeO-benzyl |
| 35 | H | H | H | sgl | 3,4-diMeO-benzyl |
| 36 | H | H | H | sgl | 3,4,5-triMeO-benzyl |
| 39 | H | H | H | sgl | —$CO_2$Et |
| 40 | H | —C(═O)$CH_3$ | H | sgl | —$CO_2$Et |
| 41 | H | —NHC(═O)$CH_3$ | H | sgl | —$CO_2$Et |
| 42 | H | H | H | sgl | —$CH_2CH_2$(4-F-phenyl) |
| 46 | H | H | H | sgl | pentyl |
| 47 | H | H | H | sgl | hexyl |
| 50 | H | H | H | sgl | 2-pentyl |
| 51 | H | H | H | sgl | 2-hexyl |
| 53 | H | H | H | sgl | 2-Me-butyl |
| 54 | H | H | H | sgl | 2-Me-pentyl |
| 55 | H | H | H | sgl | 2-Et-butyl |
| 56 | H | H | H | sgl | 3-Me-pentyl |
| 57 | H | H | H | sgl | 3-Me-butyl |
| 58 | H | H | H | sgl | 4-Me-pentyl |
| 59 | H | H | H | sgl | cyclopropylmethyl |
| 60 | H | H | H | sgl | cyclobutylmethyl |
| 61 | H | H | H | sgl | cyclohexylmethyl |
| 62 | H | H | H | sgl | 2-propenyl |
| 63 | H | H | H | sgl | 2-Me-2-propenyl |
| 64 | H | H | H | sgl | trans-2-butenyl |
| 65 | H | H | H | sgl | 3-Me-butenyl |
| 66 | H | H | H | sgl | 3-butenyl |
| 67 | H | H | H | sgl | trans-2-pentenyl |
| 68 | H | H | H | sgl | cis-2-pentenyl |

TABLE 1-continued

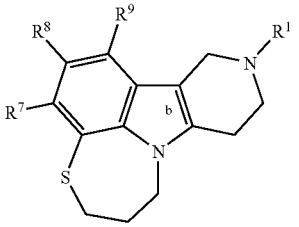

| Ex # | $R^7$ | $R^8$ | $R^9$ | b | $R^1$ |
|---|---|---|---|---|---|
| 69 | H | H | H | sgl | 4-pentenyl |
| 70 | H | H | H | sgl | 4-Me-3-pentenyl |
| 71 | H | H | H | sgl | 3,3-diCl-2-propenyl |
| 72 | H | H | H | sgl | benzyl |
| 73 | H | H | H | sgl | 2-Me-benzyl |
| 74 | H | H | H | sgl | 3-Me-benzyl |
| 75 | H | H | H | sgl | 4-Me-benzyl |
| 76 | H | H | H | sgl | 2,5-diMe-benzyl |
| 77 | H | H | H | sgl | 2,4-diMe-benzyl |
| 78 | H | H | H | sgl | 3,5-diMe-benzyl |
| 79 | H | H | H | sgl | 2,4,6-triMe-benzyl |
| 80 | H | H | H | sgl | 3-MeO-benzyl |
| 81 | H | H | H | sgl | 3,5-diMeO-benzyl |
| 82 | H | H | H | sgl | pentafluorobenzyl |
| 83 | H | H | H | sgl | 2-phenylethyl |
| 84 | H | H | H | sgl | 1-phenyl-2-propyl |
| 85 | H | H | H | sgl | trans-3-phenyl-2-propenyl |
| 86 | H | H | H | sgl | 4-phenylbutyl |
| 87 | H | H | H | sgl | 4-phenylbenzyl |
| 88 | H | H | H | sgl | 2-phenylbenzyl |
| 178 | Cl | H | H | sgl | —$(CH_2)_3C(=O)$(4-F-phenyl) |
| 179 | Me | H | H | sgl | —$(CH_2)_3C(=O)$(4-F-phenyl) |
| 180 | H | H | H | sgl | —$(CH_2)_3S$(3-F-phenyl) |
| 181 | H | H | H | sgl | —$(CH_2)_3CH(OH)$(4-F-phenyl) |
| 186 | H | H | H | sgl | —$(CH_2)_3C(=O)$(4-F-phenyl) |
| 187 | H | MeO | H | sgl | —$(CH_2)_3C(=O)$(4-F-phenyl) |
| 192 | H | H | H | sgl | —$(CH_2)_3(=O)$(4-Br-phenyl) |
| 193 | H | H | H | sgl | —$(CH_2)_3SO_2$(3-F-phenyl) |
| 194 | H | H | H | sgl | —$(CH_2)_3C(=O)$(4-(3,4-diCl-phenyl)phenyl) |
| 197 | H | H | H | sgl | —$(CH_2)_3C(=O)$(4-Me-phenyl) |
| 198 | H | H | H | sgl | —$(CH_2)_3C(=O)$(4-F-phenyl) |
| 199 | H | H | H | sgl | —$(CH_2)_3C(=O)$(4-MeO-phenyl) |
| 200 | H | H | H | sgl | —$(CH_2)_2C(=O)$(4-F-phenyl) |
| 201 | H | H | H | sgl | —$(CH_2)_3SO_2$(4-F-phenyl) |
| 202 | H | H | H | sgl | —$(CH_2)_3S(=O)$(4-F-phenyl) |
| 203 | H | H | H | sgl | —$(CH_2)_3O$(4-F-phenyl) |
| 204 | H | H | H | sgl | —$(CH_2)_3O$(phenyl) |
| 205 | H | H | H | sgl | —$(CH_2)_3S$(4-F-phenyl) |
| 206 | H | H | H | sgl | —$(CH_2)_3NH$(4-F-phenyl) |
| 207 | H | H | H | sgl | —$(CH_2)_3N(CH_3)$(4-F-phenyl) |
| 208 | H | H | H | sgl | —$(CH_2)_3C(=O)$(4-pyridyl) |
| 209 | H | H | H | sgl | —$(CH_2)_3C(=O)$(3-pyridyl) |
| 214 | H | H | H | sgl | 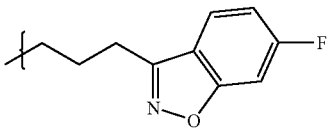 |
| 215 | H | H | H | sgl | 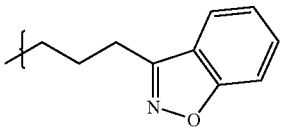 |
| 219 | H | H | H | sgl | —$(CH_2)_3CO_2Et$ |
| 220 | H | H | H | sgl | —$(CH_2)_4CO_2Et$ |
| 221 | H | H | H | sgl | —$(CH_2)_3C(=O)N(CH_3)(OCH_3)$ |
| 222 | H | H | H | sgl | —$(CH_2)_4C(=O)N(CH_3)(OCH_3)$ |
| 223 | H | H | H | sgl | —$(CH_2)_3C(=O)$(3-Me-4-F-phenyl) |
| 224 | H | H | H | sgl | —$(CH_2)_3C(=O)$(phenyl) |
| 225 | H | H | H | sgl | —$(CH_2)_3C(=O)$(4-Cl-phenyl) |
| 226 | H | H | H | sgl | —$(CH_2)_3C(=O)$(3-Me-phenyl) |

TABLE 1-continued

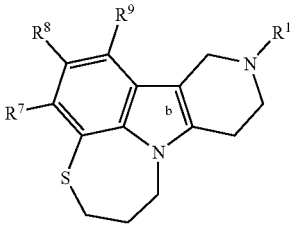

| Ex # | $R^7$ | $R^8$ | $R^9$ | b | $R^1$ |
|---|---|---|---|---|---|
| 227 | H | H | H | sgl | —$(CH_2)_3C(=O)$(4-tBu-phenyl) |
| 228 | H | H | H | sgl | —$(CH_2)_3C(=O)$(3,4-diF-phenyl) |
| 229 | H | H | H | sgl | —$(CH_2)_3C(=O)$(2-MeO-5-F-phenyl) |
| 230 | H | H | H | sgl | —$(CH_2)_4C(=O)$(phenyl) |
| 231 | H | H | H | sgl | —$(CH_2)_3C(=O)$(4-F-1-naphthyl) |
| 232 | H | H | H | sgl | —$(CH_2)_3C(=O)$(benzyl) |
| 233 | H | H | H | sgl | —$(CH_2)_2C(=O)NH$(4-F-phenyl) |
| 234 | H | H | H | sgl | —$(CH_2)_3C(=O)NH$(4-F-phenyl) |
| 235 | H | H | H | sgl | —$(CH_2)_3CH(OH)$(4-F-phenyl) |
| 236 | H | H | H | sgl | —$(CH_2)_3CH(OH)$(4-pyridyl) |
| 237 | H | H | H | sgl | —$(CH_2)_3CH(OH)$(2,3-diMeO-phenyl) |
| 238 | H | H | H | sgl | —$(CH_2)_3C(=O)$(2,3-diMeO-phenyl) |
| 239 | H | H | H | sgl | —$(CH_2)_4$(cyclohexyl) |
| 240 | H | H | H | sgl | —$(CH_2)_3CH(phenyl)_2$ |
| 241 | H | H | H | sgl | —$CH_2CH_2CH{=}C(phenyl)_2$ |
| 242 | H | H | H | sgl | —$(CH_2)_3CH(4\text{-}F\text{-}phenyl)_2$ |
| 243 | H | H | H | sgl | —$CH_2CH_2CH{=}C(4\text{-}F\text{-}phenyl)_2$ |
| 244 | H | H | H | sgl | —$(CH_2)_2NHC(=O)$(phenyl) |
| 245 | H | H | H | sgl | —$(CH_2)_2NHC(=O)$(2-F-phenyl) |
| 246 | H | H | H | sgl | —$(CH_2)_2NHC(=O)$(4-F-phenyl) |
| 247 | H | H | H | sgl | —$(CH_2)_3$(3-indolyl) |
| 248 | H | H | H | sgl | —$(CH_2)_3$(1-Me-3-indolyl) |
| 249 | H | H | H | sgl | —$CH_2CH_2$(3-indolyl) |
| 250 | H | H | H | sgl | —$(CH_2)_3$(1-indolyl) |
| 251 | H | H | H | sgl | —$(CH_2)_3$(1-indolinyl) |
| 252 | H | H | H | sgl | —$(CH_2)_3$(1-benzimidazolyl) |
| 253 | H | H | H | sgl | 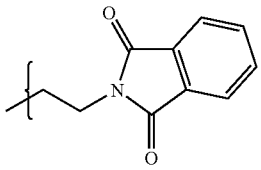 |
| 254 | H | H | H | sgl | 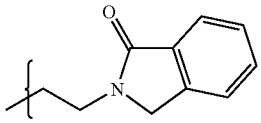 |
| 268 | H | F | H | sgl | —$(CH_2)_3C(=O)$(4-F-phenyl) |
| 286 | H | H | H | sgl | —$(CH_2)_2NHO(=O)$(2,4-diF-phenyl) |
| 287 | H | H | H | sgl | —$(CH_2)_2NMeO(=O)$-phenyl |
| 288 | H | H | H | sgl | —$(CH_2)_2NMeO(=O)$(2-F-phenyl) |
| 289 | H | H | H | sgl | —$(CH_2)_2NMeO(=O)$(2,4-diF-phenyl) |
| 290 | H | H | H | sgl | —$(CH_2)_2NMeO(=O)$(4-F-phenyl) |
| 291 | H | H | H | sgl | —$(CH_2)_3$(1H-1,2,3-benzotriazol-1-yl) |
| 292 | H | H | H | sgl | —$(CH_2)_3$(1H-1,2,3-benzotriazol-2-yl) |
| 293 | H | H | H | sgl | 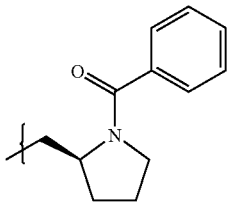 |

TABLE 1-continued

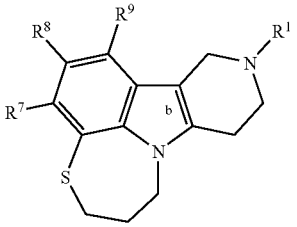

| Ex # | $R^7$ | $R^8$ | $R^9$ | b | $R^1$ |
|---|---|---|---|---|---|
| 294 | H | H | H | sgl | 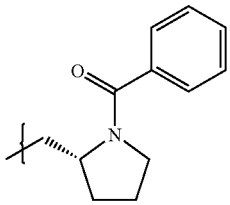 |
| 295 | H | H | H | sgl | 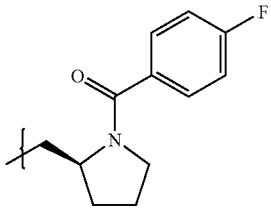 |
| 296 | H | H | H | sgl | 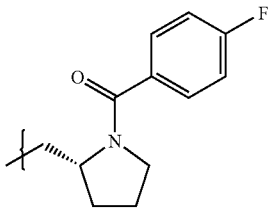 |
| 297 | H | H | H | sgl | —$(CH_2)_2$(1H-1,2,3-benzotriazol-1-yl) |
| 298 | H | H | H | sgl | —$(CH_2)_2$(1H-1,2,3-benzotriazol-2-yl) |
| 299 | H | H | H | sgl | —$(CH_2)_3$(3,4-dihydro-1(2H)-quinolyl) |
| 300 | H | H | H | sgl | —$CH_2CH_2CH{=}CMe$(4-F-phenyl) |
| 301 | H | H | H | sgl | —$(CH_2)_2$(2,3-dihydro-1H-inden-2-yl) |
| 302 | H | H | H | sgl | —$(CH_2)_3C(=O)$(2-$NH_2$-phenyl) |
| 303 | H | H | H | sgl | —$(CH_2)_3C(=O)$(2-$NH_2$-phenyl) |
| 304 | H | H | H | sgl | —$(CH_2)_3C(=O)$(2-$NH_2$-5-F-phenyl) |
| 305 | H | H | H | sgl | —$(CH_2)_3C(=O)$(2-$NH_2$-3-F-phenyl) |
| 306 | H | H | H | sgl | —$(CH_2)_3C(=O)$(2-$NH_2$-4-Cl-phenyl) |
| 307 | H | H | H | sgl | —$(CH_2)_3C(=O)$(2-$NH_2$-4-OH-phenyl) |
| 308 | H | H | H | sgl | —$(CH_2)_3C(=O)$(2-$NH_2$-4-Br-phenyl) |
| 309 | H | H | H | sgl | —$(CH_2)_3$(1H-indazol-3-yl) |
| 310 | H | H | H | sgl | —$(CH_2)_3$(5-F-1H-indazol-3-yl) |
| 311 | H | H | H | sgl | —$(CH_2)_3$(7-F-1H-indazol-3-yl) |
| 312 | H | H | H | sgl | —$(CH_2)_3$(6-Cl-1H-indazol-3-yl) |
| 313 | H | H | H | sgl | —$(CH_2)_3$(6-Br-1H-indazol-3-yl) |
| 314 | H | H | H | sgl | —$(CH_2)_3C(=O)$(2-NHMe-phenyl) |
| 315 | H | H | H | sgl | —$(CH_2)_3$(1-benzothien-3-yl) |
| 355 | H | H | H | sgl | 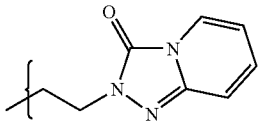 |
| 356 | H | H | H | sgl | —$(CH_2)_3$(6-F-1H-indol-1-yl) |
| 357 | H | H | H | sgl | —$(CH_2)_3$(5-F-1H-indol-1-yl) |
| 358 | H | H | H | sgl | —$(CH_2)_3$(6-F-2,3-dihydro-1H-indol-1-yl) |
| 359 | H | H | H | sgl | —$(CH_2)_3$(5-F-2,3-dihydro-1H-indol-1-yl) |
| 360 | H | H | H | sgl | —$(CH_2)_3$(6-F-1H-indol-3-yl) |
| 361 | H | H | H | sgl | —$(CH_2)_3$(6-F-1H-indol-3-yl) |

TABLE 1-continued

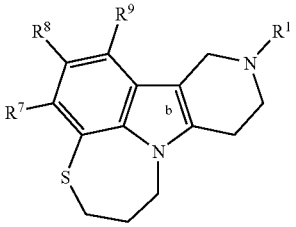

| Ex # | $R^7$ | $R^8$ | $R^9$ | b | $R^1$ |
|---|---|---|---|---|---|
| 362 | H | H | H | sgl | —$(CH_2)_3$(5-F-1H-indol-3-yl) |
| 363 | H | H | H | sgl | —$(CH_2)_3$(5-F-1H-indol-3-yl) |
| 364 | H | H | H | sgl | —$(CH_2)_3$(9H-purin-9-yl) |
| 365 | H | H | H | sgl | —$(CH_2)_3$(7H-purin-7-yl) |
| 366 | H | H | H | sgl | 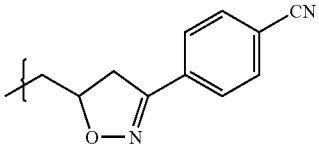 |
| 367 | H | H | H | sgl | —$(CH_2)_3$(6-F-1H-indazol-3-yl) |
| 368 | H | H | H | sgl | —$(CH_2)_3$(6-F-1H-indazol-3-yl) |
| 369 | H | H | H | sgl | —$(CH_2)_3$(6-F-1H-indazol-3-yl) |
| 370 | H | H | H | sgl | —$(CH_2)_3C(=O)$(2-$NH_2$-4-F-phenyl) |
| 371 | H | H | H | sgl | —$(CH_2)_3C(=O)$(2-$NH_2$-4-F-phenyl) |
| 372 | H | H | H | sgl | —$(CH_2)_3C(=O)$(2-$NHSO_2$Me-4-F-phenyl) |
| 373 | H | H | H | sgl | —$(CH_2)_3C(=O)$(2-NHO(=O)Me-4-F-phenyl) |
| 374 | H | H | H | sgl | —$(CH_2)_3C(=O)$(2-NHO(=O)Me-4-F-phenyl) |
| 375 | H | H | H | sgl | —$(CH_2)_3C(=O)$(2-$NHCO_2$Et-4-F-phenyl) |
| 376 | H | H | H | sgl | —$(CH_2)_3C(=O)$(2-NHO(=O)NHEt-4-F-phenyl) |
| 377 | H | H | H | sgl | —$(CH_2)_3C(=O)$(2-NHCHO-4-F-phenyl) |
| 378 | H | H | H | sgl | —$(CH_2)_3C(=O)$(2-OH-4-F-phenyl) |
| 379 | H | H | H | sgl | —$(CH_2)_3C(=O)$(2-MeS-4-F-phenyl) |
| 442 | H | H | H | sgl | —$(CH_2)_3C(=O)$(2-$NHSO_2$Me-4-F-phenyl) |
| 485 | H | H | H | sgl | —$(CH_2)_2C(Me)CO_2Me$ |
| 486 | H | H | H | sgl | —$(CH_2)_2C(Me)C(OH)$(4-F-phenyl)$_2$ |
| 487 | H | H | H | sgl | —$(CH_2)_2C(Me)C(OH)$(4-Cl-phenyl)$_2$ |
| 489 | H | H | H | sgl | —$(CH_2)_2C(Me)C(=O)$(4-F-phenyl) |
| 490 | H | H | H | sgl | —$(CH_2)_2C(Me)C(=O)$(2-MeO-4-F-phenyl) |
| 491 | H | H | H | sgl | —$(CH_2)_2C(Me)C(=O)$(3-Me-4-F-phenyl) |
| 492 | H | H | H | sgl | —$(CH_2)_2C(Me)C(=O)$(2-Me-phenyl) |
| 493 | H | H | H | sgl | —$(CH_2)_2C(Me)C(=O)$phenyl |
| 591 | Cl | H | H | sgl | —$(CH_2)_3C(=O)$(2-$NH_2$-4-phenyl |

or pharmaceutically acceptable salt forms thereof.

28. A compound of claim 12 selected from the compounds closed in Table 2:

TABLE 2

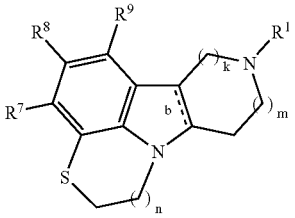

| Ex # | n | k | m | $R^7$ | $R^8$ | $R^9$ | b | $R^1$ |
|---|---|---|---|---|---|---|---|---|
| 472 | 2 | 2 | 1 | H | H | H | sgl | —$(CH_2)_3C(=O)$(4-F-phenyl) |
| 473 | 2 | 2 | 1 | H | H | H | sgl | —$(CH_2)_3O$(4-F-phenyl) |
| 474 | 2 | 2 | 1 | H | H | H | sgl | —$(CH_2)_3$(6-F-benzisoxazol-3-yl) |
| 475 | 2 | 2 | 1 | H | H | H | sgl | —$(CH_2)_3C(=O)$(4-pyridyl) |

TABLE 2-continued

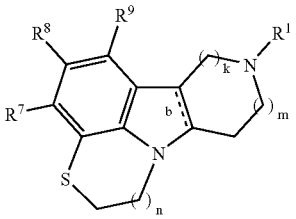

| Ex # | n | k | m | $R^7$ | $R^8$ | $R^9$ | b | $R^1$ |
|---|---|---|---|---|---|---|---|---|
| 483 | 2 | 2 | 1 | H | Br | H | sgl | —$(CH_2)_3C(=O)$(4-F-phenyl) |
| 484 | 2 | 2 | 1 | H | Br | H | sgl | —$(CH_2)_3O$(4-F-phenyl) |
| 488 | 1 | 2 | 1 | H | Br | H | sgl | —$CO_2$—tBu |

or pharmaceutically acceptable salt forms thereof.

29. A compound of claim 12 selected from the compounds closed in Table 3:

TABLE 3

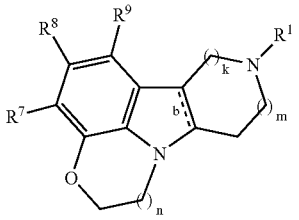

| Ex # | n | k | m | R7 | R8 | R9 | b | R1 |
|---|---|---|---|---|---|---|---|---|
| 182 | 1 | 1 | 1 | H | H | H | sgl | —$(CH_2)_3C(=O)$(4-F-phenyl) |
| 266 | 1 | 1 | 1 | H | H | Me | sgl | —$(CH_2)_3C(=O)$(4-F-phenyl) |
| 270 | 1 | 1 | 1 | H | H | H | sgl | —$(CH_2)_3O$(4-F-phenyl) |
| 272 | 1 | 1 | 1 | H | H | H | sgl | H |
| 494 | 1 | 1 | 1 | H | H | H | sgl | —$(CH_2)_3C(=O)$(2-$NH_2$-phenyl) |
| 495 | 1 | 1 | 1 | H | H | H | sgl | —$(CH_2)_3C(=O)$(2-$NH_2$-phenyl) |
| 496 | 1 | 1 | 1 | H | H | H | sgl | —$(CH_2)_3$(1H-indazol-3-yl) |
| 528 | 1 | 1 | 1 | H | H | H | sgl | —$(CH_2)_3$(6-F-1H-indazol-3-yl) |
| 529 | 1 | 1 | 1 | H | H | H | sgl | —$(CH_2)_3C(=O)$(2-$NH_2$-4-F-phenyl) |
| 530 | 1 | 1 | 1 | H | H | H | sgl | —$(CH_2)_3C(=O)$(2-$NH_2$-4-F-phenyl) |
| 531 | 1 | 1 | 1 | H | H | H | sgl | —$(CH_2)_3C(=O)$(2-OH-4-F-phenyl) |
| 539 | 1 | 2 | 1 | H | H | H | sgl | —$(CH_2)_3O$(4-F-phenyl) |
| 540 | 1 | 2 | 1 | H | H | H | sgl | —$(CH_2)_3$(6-F-1,2-benzisoxazol-3-yl) |
| 544 | 2 | 1 | 1 | H | H | H | sgl | —$(CH_2)_3C(=O)$(4-F-phenyl) |

TABLE 3-continued

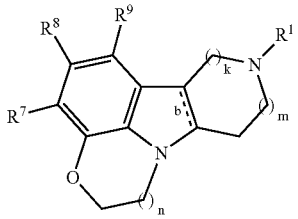

| Ex # | n | k | m | R7 | R8 | R9 | b | R1 |
|---|---|---|---|---|---|---|---|---|
| 546 | 1 | 2 | 1 | H | H | H | sgl | —$(CH_2)_3C(=O)$(4-F-phenyl |

or pharmaceutically acceptable salt forms thereof.

30. A compound of claim 12 selected from the compounds closed in Table 4:

TABLE 4

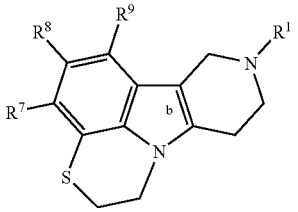

| Ex # | $R^7$ | $R^8$ | $R^9$ | b | $R^1$ |
|---|---|---|---|---|---|
| 185 | H | H | $CF_3$ | sgl | —$(CH_2)_4$(4-F-phenyl) |
| 188 | H | H | H | sgl | —$(CH_2)_3C(=O)$(4-F-phenyl) |
| 213 | H | $CH_3$ | H | sgl | —$(CH_2)_3C(=O)$(4-F-phenyl) |
| 438 | H | H | H | sgl | —$(CH_2)_3C(=O)$((2-$NH_2$-phenyl) |
| 439 | H | H | H | sgl | —$(CH_2)_3C(=O)$((2-$NH_2$-phenyl) |
| 440 | H | H | H | sgl | —$(CH_2)_3C(=O)$(2-$NH_2$-4-F-phenyl) |
| 441 | H | H | H | sgl | —$(CH_2)_3C(=O)$(2-$NH_2$-4-F-phenyl) |
| 456 | H | H | H | sgl | —$(CH_2)_3C(=O)$(4-F-phenyl) |
| 457 | H | H | H | sgl | —$(CH_2)_3C(=O)$(4-F-phenyl) |

or pharmaceutically acceptable salt forms thereof.

31. A compound of claim 1 selected from the compounds disclosed in Table 1A:

TABLE 1A

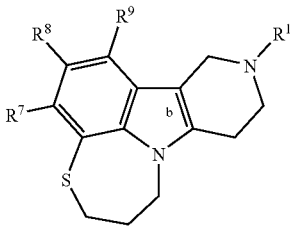

| Ex # | $R^7$ | $R^8$ | $R^9$ | b | $R^1$ |
|---|---|---|---|---|---|
| 125 | H | H | Br | sgl | —$CO_2$—tBu |
| 126 | H | H | 2,6-diF-phenyl | sgl | —$CO_2$—tBu |
| 128 | H | 2,4-diCl-phenyl | H | sgl | H |
| 129 | H | phenyl | H | sgl | H |
| 130 | H | 4-F-phenyl | H | sgl | H |
| 131 | H | 4-Cl-phenyl | H | sgl | H |

TABLE 1A-continued

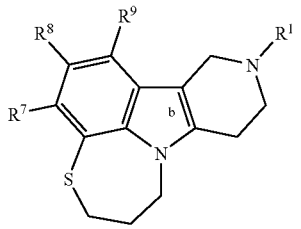

| Ex # | $R^7$ | $R^8$ | $R^9$ | b | $R^1$ |
|---|---|---|---|---|---|
| 132 | H | 2-Cl-phenyl | H | sgl | H |
| 133 | H | 2-MeO-phenyl | H | sgl | H |
| 134 | H | 2-Cl-4-$CF_3$-phenyl | H | sgl | H |
| 135 | H | 2,4-diMe-phenyl | H | sgl | H |
| 136 | H | 2-Cl-4-MeO-phenyl | H | sgl | H |
| 137 | H | 4-iPr-phenyl | H | sgl | H |
| 138 | H | 4-Bu-phenyl | H | sgl | H |
| 139 | H | 2-Me-4-MeO-5-F-phenyl | H | sgl | H |
| 140 | H | 2-Me-4-MeO-phenyl | H | sgl | H |
| 141 | H | 2-Cl-4-$CF_3O$-phenyl | H | sgl | H |
| 142 | H | 2,4,5-triMe-phenyl | H | sgl | H |
| 143 | H | 3-Cl-phenyl | H | sgl | H |
| 144 | H | 4-Me-phenyl | H | sgl | H |
| 145 | H | 2-Me-4-Cl-phenyl | H | sgl | H |
| 146 | H | 2,5-diCl-phenyl | H | sgl | H |
| 147 | H | 2-MeO-4-iPr-phenyl | H | sgl | H |
| 148 | H | 2,6-diCl-phenyl | H | sgl | H |
| 149 | H | 2,6-diF-phenyl | H | sgl | H |
| 150 | H | 2-$CF_3$-4-MeO-phenyl | H | sgl | H |
| 151 | H | 2-$CF_3$-phenyl | H | sgl | H |
| 152 | H | 4-pyridyl | H | sgl | H |
| 153 | H | 2-furanyl | H | sgl | H |
| 154 | H | 2-thiophenyl | H | sgl | H |
| 155 | H | 4-F-phenyl | H | sgl | H |
| 156 | H | 2,3-diCl-phenyl | H | sgl | H |
| 157 | H | 4-Et-phenyl | H | sgl | H |
| 158 | H | 2,4-diMeO-phenyl | H | sgl | H |
| 159 | H | 2-F-3-Cl-phenyl | H | sgl | H |
| 160 | H | 4-MeO-phenyl | H | sgl | H |
| 161 | H | 4-MeS-phenyl | H | sgl | H |
| 162 | H | 4-CN-phenyl | H | sgl | H |
| 163 | H | 3-$CF_3$-phenyl | H | sgl | H |
| 164 | H | 2-MeO-phenyl | H | sgl | H |
| 165 | H | 2-naphthyl | H | sgl | H |
| 166 | H | 4-acetylphenyl | H | sgl | H |
| 167 | H | 3-acetamidophenyl | H | sgl | H |
| 168 | H | 2,4-diCl-phenyl | H | sgl | Me |
| 316 | H | 2,3-diMe-phenyl | H | sgl | H |
| 317 | H | 2-Me-5-F-phenyl | H | sgl | H |
| 318 | H | 2-F-5-Me-phenyl | H | sgl | H |
| 319 | H | 2-MeO-5-F-phenyl | H | sgl | H |
| 320 | H | 2-Me-3-Cl-phenyl | H | sgl | H |
| 321 | H | 3-$NO_2$-phenyl | H | sgl | H |
| 322 | H | 2-$NO_2$-phenyl | H | sgl | H |
| 323 | H | 2-Cl-3-Me-phenyl | H | sgl | H |
| 324 | H | 2-MeO-phenyl | H | sgl | H |
| 325 | H | 2,3-diCl-phenyl | H | sgl | H |
| 326 | H | 2-Cl-4-$CF_3$-phenyl | H | sgl | H |
| 327 | H | 2-Me-4-EtO-phenyl | H | sgl | H |
| 328 | H | 2-Me-4-F-phenyl | H | sgl | H |
| 329 | H | 4-Bu-phenyl | H | sgl | H |
| 330 | H | 2-$CF_3$-phenyl | H | sgl | H |
| 331 | H | 2-Cl-6-F-phenyl | H | sgl | H |
| 332 | H | 2-Cl-4-($CHF_3$)O-phenyl | H | sgl | H |
| 333 | H | 4-$CF_3$-phenyl | H | sgl | H |
| 334 | H | 4-Me-phenyl | H | sgl | H |
| 335 | H | 4-$CF_3O$-phenyl | H | sgl | H |
| 336 | H | 2,4-diMeO-6-F-phenyl | H | sgl | H |
| 337 | H | 2-Me-phenyl | H | sgl | H |
| 338 | H | 2-$CF_3$-6-F-phenyl | H | sgl | H |
| 339 | H | 2-MeS-phenyl | H | sgl | H |
| 340 | H | 2,4,6-triF-phenyl | H | sgl | H |
| 341 | H | 2,4,6-triCl-phenyl | H | sgl | H |
| 342 | H | 2,6-diCl-4-MeO-phenyl | H | sgl | H |
| 343 | H | 2,3,4-triF-phenyl | H | sgl | H |

TABLE 1A-continued

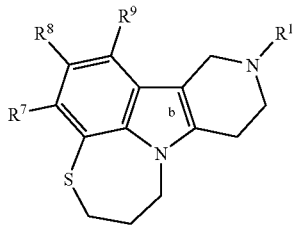

| Ex # | $R^7$ | $R^8$ | $R^9$ | b | $R^1$ |
|---|---|---|---|---|---|
| 344 | H | 2,6-diF-4-Cl-phenyl | H | sgl | H |
| 345 | H | 2,3,4,6-tetraF-phenyl | H | sgl | H |
| 346 | H | 2,3,4,5,6-pentaF-phenyl | H | sgl | H |
| 347 | H | 2,6-di$CF_3$-phenyl | H | sgl | H |
| 348 | H | 2-$CF_3O$-phenyl | H | sgl | H |
| 349 | H | 2-$CF_3$-4-EtO-phenyl | H | sgl | H |
| 350 | H | 2-$CF_3$-4-iPrO-phenyl | H | sgl | H |
| 351 | H | 2-naphtyl | H | sgl | H |
| 352 | H | 2-$CF_3$-4-Cl-phenyl | H | sgl | H |
| 353 | H | 2-$CF_3$-4-F-phenyl | H | sgl | H |
| 354 | H | 2,4-diF-phenyl | H | sgl | Me |
| 380 | H | 2-Cl-4-EtO-phenyl | H | sgl | H |
| 381 | H | 2-Cl-4-iPrO-phenyl | H | sgl | H |
| 382 | H | 2-Et-4-MeO-phenyl | H | sgl | H |
| 383 | H | 2-CHO-4-MeO-phenyl | H | sgl | H |
| 384 | H | 2-CH(OH)Me-4-MeO-phenyl | H | sgl | H |
| 385 | H | 2-CH(OMe)Me-4-MeO-phenyl | H | sgl | H |
| 386 | H | 2-C(═O)Me-4-MeO-phenyl | H | sgl | H |
| 387 | H | 2-$CH_2$(OH)Me-4-MeO-phenyl | H | sgl | H |
| 388 | H | 2-$CH_2$(OMe)Me-4-MeO-phenyl | H | sgl | H |
| 389 | H | 2-CH(OH)Et-4-MeO-phenyl | H | sgl | H |
| 390 | H | 2-C(═O)Et-4-MeO-phenyl | H | sgl | H |
| 391 | H | (Z)-2-CH═CH$CO_2$Me-4-MeO-phenyl | H | sgl | H |
| 392 | H | 2-$CH_2CH_2CO_2$Me-4-MeO-phenyl | H | sgl | H |
| 393 | H | (Z)-2-CH═CH$CH_2$(OH)-4-MeO-phenyl | H | sgl | H |
| 394 | H | (E)-2-CH═CH$CO_2$Me-4-MeO-phenyl | H | sgl | H |
| 395 | H | (E)-2-CH═CH$CH_2$(OH)-4-MeO-phenyl | H | sgl | H |
| 396 | H | 2-$CH_2CH_2$OMe-4-MeO-phenyl | H | sgl | H |
| 397 | H | 2-F-4-MeO-phenyl | H | sgl | H |
| 403 | H | 2-Cl-4-phenyl | H | sgl | H |
| 405 | H | (2-Cl-phenyl)-CH═CH— | H | sgl | H |
| 406 | H | (3-Cl-phenyl)-CH═CH— | H | sgl | H |
| 407 | H | (2,6-diF-phenyl)-CH═CH— | H | sgl | H |
| 410 | H | cyclohexyl | H | sgl | H |
| 411 | H | cyclopentyl | H | sgl | H |
| 412 | H | cyclohexylmethyl | H | sgl | H |
| 413 | H | —$CH_2CH_2CO_2$Et | H | sgl | H |
| 414 | H | —$(CH_2)_3CO_2$Et | H | sgl | H |
| 415 | H | —$(CH_2)_4CO_2$Et | H | sgl | H |
| 416 | H | —$CH_2CH$═$CH_2$ | H | sgl | H |
| 417 | H | Pr | H | sgl | H |
| 418 | H | benzyl | H | sgl | H |
| 419 | H | 2-F-benzyl | H | sgl | H |
| 420 | H | 3-F-benzyl | H | sgl | H |
| 421 | H | 4-F-benzyl | H | sgl | H |
| 422 | H | 3-MeO-benzyl | H | sgl | H |
| 423 | H | 3-OH-benzyl | H | sgl | H |
| 424 | H | 2-MeO-benzyl | H | sgl | H |
| 425 | H | 2-OH-benzyl | H | sgl | H |
| 426 | H | 2-$CO_2$Me-3-MeO-phenyl | H | sgl | H |
| 427 | H | 2,6-diF-phenyl | H | sgl | H |
| 428 | H | phenyl-CH═CH— | H | sgl | H |
| 429 | H | (2-Me-4-MeO-phenyl)-CH═CH— | H | sgl | H |
| 430 | H | —$NMe_2$ | H | sgl | H |
| 431 | H | 1-pyrrolidinyl | H | sgl | H |
| 432 | H | —$NTa_2$ | H | sgl | H |
| 433 | H | MeO | H | sgl | H |
| 445 | H | 2-Me-4-MeO-phenyl | Me | sgl | H |
| 446 | H | 2-$CF_3$-4-MeO-phenyl | Me | sgl | H |
| 458 | Me | 2-$CF_3$-4-MeO-phenyl | H | sgl | H |
| 459 | Me | 2,4-diCl-phenyl | H | sgl | H |
| 460 | H | 3-CN-phenyl | H | sgl | H |
| 461 | H | 2-Me-4-CN-phenyl | H | sgl | H |
| 462 | H | 2-Me-3-CN-phenyl | H | sgl | H |
| 463 | H | 2-CN-phenyl | H | sgl | H |

TABLE 1A-continued

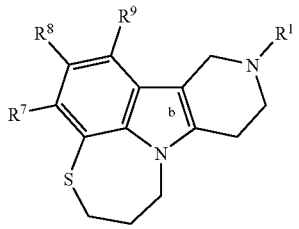

| Ex # | $R^7$ | $R^8$ | $R^9$ | b | $R^1$ |
|---|---|---|---|---|---|
| 464 | H | 2-$CF_3$-4-CN-phenyl | Me | sgl | H |
| 465 | H | 3-CHO-phenyl | Me | sgl | H |
| 466 | H | 3-$CH_2$(OH)-phenyl | Me | sgl | H |
| 467 | H | 3-$CH_2$(OMe)-phenyl | Me | sgl | H |
| 468 | H | 3-$CH_2$($NMe_2$)-phenyl | Me | sgl | H |
| 469 | H | 3-CN-4-F-phenyl | Me | sgl | H |
| 470 | H | 3-$CONH_2$-4-F-phenyl | Me | sgl | H |
| 581 | H | phenyl-NH— | H | sgl | H |
| 583 | H | (4-F-phenyl)-NH— | H | sgl | H |
| 584 | H | (2,4-diCl-phenyl)-NH— | H | sgl | H |
| 585 | H | phenyl-C(═O)NH— | H | sgl | H |
| 586 | H | benzyl-NH— | H | sgl | H |
| 587 | H | phenyl-S— | H | sgl | H |
| 589 | H | 2-$CH_2$($NH_2$)4-MeO-phenyl- | H | sgl | H |
| 590 | H | 2-Me-4-MeO-phenyl- | H | sgl | H |
| 592 | H | (2-Me-4-MeO-phenyl)-NH— | H | sgl | H |
| 593 | H | (2-F-4-MeO-phenyl)-NH— | H | sgl | H |
| 595 | H | (2-Me-4-F-phenyl)-NH— | H | sgl | H |
| 596 | H | 2-CH(OH)Me-4-F-phenyl | H | sgl | H |

or pharmaceutically acceptable salt forms thereof.

32. A compound of claim 1 selected from the compounds closed in Table 2A:

TABLE 2A

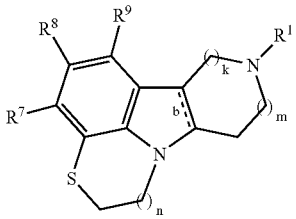

| Ex # | n | k | m | R7 | R8 | R9 | b | R1 |
|---|---|---|---|---|---|---|---|---|
| 479 | 2 | 2 | 1 | H | 2,4-diCl-phenyl | H | sgl | H |
| 480 | 2 | 2 | 1 | H | 2-Cl-4-MeO-phenyl | H | sgl | H |
| 481 | 2 | 2 | 1 | H | 2-Me-4-MeO-phenyl | H | sgl | H |
| 482 | 2 | 2 | 1 | H | Br | H | sgl | H |
| 497 | 1 | 1 | 1 | H | 2-Cl-phenyl | H | sgl | H |
| 498 | 1 | 1 | 1 | H | 3-Cl-phenyl | H | sgl | H |
| 499 | 1 | 1 | 1 | H | 3-F-phenyl | H | sgl | H |
| 500 | 1 | 1 | 1 | H | 4-Cl-phenyl | H | sgl | H |
| 501 | 1 | 1 | 1 | H | 4-F-phenyl | H | sgl | H |
| 502 | 1 | 1 | 1 | H | 2,3-diCl-phenyl | H | sgl | H |
| 503 | 1 | 1 | 1 | H | 2,4-diF-phenyl | H | sgl | H |
| 504 | 1 | 1 | 1 | H | 3,5-diCl-phenyl | H | sgl | H |
| 505 | 1 | 1 | 1 | H | 3,5-diF-phenyl | H | sgl | H |
| 506 | 1 | 1 | 1 | H | 3,4-diCl-phenyl | H | sgl | H |
| 507 | 1 | 1 | 1 | H | 3,4-diF-phenyl | H | sgl | H |
| 508 | 1 | 1 | 1 | H | 3-Cl-4-F-phenyl | H | sgl | H |
| 509 | 1 | 1 | 1 | H | 2-F-4-Cl-phenyl | H | sgl | H |

or pharmaceutically acceptable salt forms thereof.

33. A compound of claim 1 selected from the compounds disclosed in Table 3A:

TABLE 3A

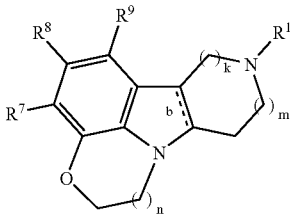

| Ex # | n | k | m | $R^7$ | $R^8$ | $R^9$ | b | $R^1$ |
|---|---|---|---|---|---|---|---|---|
| 173 | 1 | 1 | 1 | H | 2,4-diCl-phenyl | H | sgl | H |
| 174 | 1 | 1 | 1 | H | 2-Cl-4-MeO-phenyl | H | sgl | H |
| 436 | 1 | 1 | 1 | H | 2-Cl-phenyl | H | sgl | H |
| 497 | 1 | 1 | 1 | H | 2-Cl-phenyl | H | sgl | H |
| 498 | 1 | 1 | 1 | H | 3-Cl-phenyl | H | sgl | H |
| 499 | 1 | 1 | 1 | H | 3-F-phenyl | H | sgl | H |
| 500 | 1 | 1 | 1 | H | 4-Cl-phenyl | H | sgl | H |
| 501 | 1 | 1 | 1 | H | 4-F-phenyl | H | sgl | H |
| 502 | 1 | 1 | 1 | H | 2,3-diCl-phenyl | H | sgl | H |
| 503 | 1 | 1 | 1 | H | 2,3-diF-phenyl | H | sgl | H |
| 504 | 1 | 1 | 1 | H | 3,5-diCl-phenyl | H | sgl | H |
| 505 | 1 | 1 | 1 | H | 3,5-diF-phenyl | H | sgl | H |
| 506 | 1 | 1 | 1 | H | 3,4-diCl-phenyl | H | sgl | H |
| 507 | 1 | 1 | 1 | H | 3,4-diF-phenyl | H | sgl | H |
| 508 | 1 | 1 | 1 | H | 3-Cl-4-F-phenyl | H | sgl | H |
| 509 | 1 | 1 | 1 | H | 2-F-4-Cl-phenyl | H | sgl | H |
| 510 | 1 | 1 | 1 | H | 2-Cl-4-F-phenyl | H | sgl | H |
| 511 | 1 | 1 | 1 | H | 2,5-diCl-phenyl | H | sgl | H |
| 512 | 1 | 1 | 1 | H | 2,6-diCl-phenyl | H | sgl | H |
| 513 | 1 | 1 | 1 | H | 2-$CF_3$-phenyl | H | sgl | H |
| 514 | 1 | 1 | 1 | H | 4-$CF_3$-phenyl | H | sgl | H |
| 515 | 1 | 1 | 1 | H | 2,4-di$CF_3$-phenyl | H | sgl | H |
| 516 | 1 | 1 | 1 | H | 2-Cl-4-$CF_3$-phenyl | H | sgl | H |
| 517 | 1 | 1 | 1 | H | 2-MeO-phenyl | H | sgl | H |
| 518 | 1 | 1 | 1 | H | 2,4-diMeO-phenyl | H | sgl | H |
| 519 | 1 | 1 | 1 | H | 2-MeO-5-iPr-phenyl | H | sgl | H |

TABLE 3A-continued

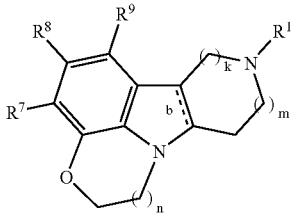

| Ex # | n | k | m | $R^7$ | $R^8$ | $R^9$ | b | $R^1$ |
|---|---|---|---|---|---|---|---|---|
| 520 | 1 | 1 | 1 | H | 3-$NO_2$-phenyl | H | sgl | H |
| 521 | 1 | 1 | 1 | H | 2-CHO-phenyl | H | sgl | H |
| 522 | 1 | 1 | 1 | H | 2-CH(Me)(OH)-phenyl | H | sgl | H |
| 523 | 1 | 1 | 1 | H | 2-$CH_2$(OH)-phenyl | H | sgl | H |
| 524 | 1 | 1 | 1 | H | 2-CHO-4-MeO-phenyl | H | sgl | H |
| 525 | 1 | 1 | 1 | H | 2-OH-phenyl | H | sgl | H |
| 526 | 1 | 1 | 1 | H | 2-$CF_3$-4-EtO-phenyl | H | sgl | H |
| 527 | 1 | 1 | 1 | H | 2-$CF_3$-4-iPrO-phenyl | H | sgl | H |
| 532 | 1 | 1 | 1 | H | 2-Me-4-MeO-phenyl | H | sgl | H |
| 533 | 1 | 1 | 1 | H | 2-$CF_3$-4-MeO-phenyl | H | sgl | H |
| 534 | 1 | 2 | 1 | H | 3,4,5-triMeo-phenyl | H | sgl | H |
| 535 | 1 | 2 | 1 | H | 1-naphthyl | H | sgl | H |
| 536 | 1 | 2 | 1 | H | 3-MeO-phenyl | H | sgl | H |
| 537 | 1 | 2 | 1 | H | 2,4-diCl-phenyl | H | sgl | H |
| 543 | 2 | 1 | 1 | H | 2,6-diF-phenyl | H | sgl | H |
| 547 | 2 | 1 | 1 | H | 2-$CF_3$-4-MeO-phenyl | H | sgl | H |
| 548 | 2 | 1 | 1 | H | 2-Me-4-MeO-phenyl | H | sgl | H |
| 549 | 2 | 1 | 1 | H | 2-Cl-4-$CF_3$-phenyl | H | sgl | H |
| 550 | 2 | 1 | 1 | H | 2,3-diCl-phenyl | H | sgl | H |
| 551 | 2 | 1 | 1 | H | 2,4-diMeO-phenyl | H | sgl | H |
| 552 | 2 | 1 | 1 | H | 3,4-diMeO-phenyl | H | sgl | H |
| 553 | 2 | 1 | 1 | H | 2,4-diCl-phenyl | H | sgl | H |
| 554 | 2 | 1 | 1 | H | 3,4-diCl-phenyl | H | sgl | H |
| 555 | 2 | 1 | 1 | H | 2,5-diCl-phenyl | H | sgl | H |
| 556 | 2 | 1 | 1 | H | 2-$CF_3$-phenyl | H | sgl | H |
| 557 | 2 | 1 | 1 | H | 2-Me-phenyl | H | sgl | H |
| 558 | 2 | 1 | 1 | H | 2-Cl-phenyl | H | sgl | H |
| 559 | 2 | 1 | 1 | H | 3-F-phenyl | H | sgl | H |

TABLE 3A-continued

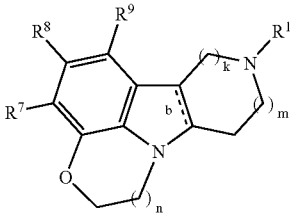

| Ex # | n | k | m | $R^7$ | $R^8$ | $R^9$ | b | $R^1$ |
|---|---|---|---|---|---|---|---|---|
| 560 | 2 | 1 | 1 | H | phenyl | H | sgl | H |
| 561 | 2 | 1 | 1 | H | 2-$CF_3$-4-EtO-phenyl | H | sgl | H |
| 562 | 2 | 1 | 1 | H | 2-$CF_3$-4-iPrO-phenyl | H | sgl | H |
| 563 | 2 | 1 | 1 | H | 2-MeO-4-iPr-phenyl | H | sgl | H |
| 564 | 2 | 1 | 1 | H | 2-F-4-Cl-phenyl | H | sgl | H |
| 565 | 2 | 1 | 1 | H | 2-Cl-4-MeO-phenyl | H | sgl | H |
| 566 | 2 | 1 | 1 | H | 2-CHO-phenyl | H | sgl | H |
| 567 | 2 | 1 | 1 | H | 2-CHO-4-MeO-phenyl | H | sgl | H |
| 568 | 2 | 1 | 1 | H | 2-$CH_2$(OH)-4-MeO-phenyl | H | sgl | H |
| 569 | 2 | 1 | 1 | H | 2-$CH_2$(OH)-phenyl | H | sgl | H |
| 570 | 2 | 1 | 1 | H | 2-$CF_3$-4-NHMe-phenyl | H | sgl | H |
| 571 | 2 | 1 | 1 | H | 2-$CF_3$-4-$NH_2$-phenyl | H | sgl | H |
| 572 | 2 | 1 | 1 | H | 2-C(=O)Me-phenyl | H | sgl | H |
| 573 | 2 | 1 | 1 | H | 2-C(=O)Me-4-MeO-phenyl | H | sgl | H |
| 574 | 2 | 1 | 1 | H | 2-CH(Me)(OH)-phenyl | H | sgl | H |
| 575 | 2 | 1 | 1 | H | 2-CH(Me)(OH)-4-MeO-phenyl | H | sgl | H |
| 576 | 2 | 1 | 1 | H | 2-$CF_3$-4-OH-phenyl | H | sgl | H |
| 577 | 2 | 1 | 1 | H | 2-$CF_3$-4-O(C=O)Me-phenyl | H | sgl | H |

or pharmaceutically acceptable salt forms thereof.

* * * * *